US009856534B2

(12) United States Patent
Bernal-Mizrachi

(10) Patent No.: US 9,856,534 B2

(45) Date of Patent: Jan. 2, 2018

(54) SELECTING USE OF PROTEASOME INHIBITORS BASED ON NF-κB2 SEQUENCE

(75) Inventor: Leon Bernal-Mizrachi, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/114,605

(22) PCT Filed: Apr. 27, 2012

(86) PCT No.: PCT/US2012/035590

§ 371 (c)(1), (2), (4) Date: Jan. 24, 2014

(87) PCT Pub. No.: WO2012/149419

PCT Pub. Date: Nov. 1, 2012

(65) Prior Publication Data

US 2014/0135288 A1 May 15, 2014

Related U.S. Application Data

(60) Provisional application No. 61/480,640, filed on Apr. 29, 2011, provisional application No. 61/556,591, filed on Nov. 7, 2011.

(51) Int. Cl.

| | |
|---|---|
| ***C12Q 1/68*** | (2006.01) |
| ***A61K 31/145*** | (2006.01) |
| ***A61K 31/336*** | (2006.01) |
| ***A61K 31/351*** | (2006.01) |
| ***A61K 31/4015*** | (2006.01) |
| ***A61K 31/4965*** | (2006.01) |
| ***A61K 31/69*** | (2006.01) |

(52) U.S. Cl.

CPC .......... *C12Q 1/6886* (2013.01); *A61K 31/145* (2013.01); *A61K 31/336* (2013.01); *A61K 31/351* (2013.01); *A61K 31/4015* (2013.01); *A61K 31/4965* (2013.01); *A61K 31/69* (2013.01)

(58) Field of Classification Search

None

See application file for complete search history.

(56) References Cited

U.S. PATENT DOCUMENTS

2008/0227096 A1* 9/2008 Ling .................... C12Q 1/6883 435/5

FOREIGN PATENT DOCUMENTS

| | | |
|---|---|---|
| RU | 2261248 C2 | 9/2005 |
| WO | 2009053038 A2 | 4/2009 |

OTHER PUBLICATIONS

Migliazza (Blood 1994 vol. 84 pp. 3850-3860).*

Nair (Blood May 27, 2010 vol. 115 No. 21 pp. 4168-4173).*

Evans (Science 1999 vol. 286 pp. 487-491).*

Mummidi et al (Journal of Biological Chemistry 2000 vol. 275 No. 25 pp. 18946-18961).*

Chauhan (Cancer Cell Nov. 2005 vol. 8 pp. 407-419).*

Jagannath (British Journal of Haematology 2005 vol. 129 pp. 776-783).*

Crawford (J. Cell Commun. Signal 2011 5:101-110).*

Cuenin, S., et al., p53-induced protein with a death domain (PIDD) isoforms differentially activate nuclear factor-kappaB and caspase-2 in response to genotoxic stress, Oncogene, 27(3):387-96 (2008).

Hwang, et al., Various patterns of IgH deletion identified by FISH using combined IgH and IgH/CCND1 probes in multiple myeloma and chronic lymphocytic leukemia, Int. J. Lab. Hematol. 33(3):299-304 (2011).

Kyoung-Eun Kim, et al., Transcriptional regulatory effects of lymphoma-associated NFKB2/lyt 10 protooncogenes, Oncogene, 19(10):1334-1345 (2000).

International Search Report for PCT/US2012/035590, dated Aug. 16, 2012.

International Preliminary Report on Patentability for PCT/US2012/035590, dated Nov. 7, 2013.

Extended European Search Report for European Patent Application No. 12776352.2 dated Mar. 6, 2015 (11 pages).

Betts et al., "Differential Regulation of NF-κB2(p100) Processing and Control by Amino-Terminal Sequences", Molecular and Cellular Biology, Nov. 1, 1996, pp. 6363-6371.

Coope et al., "CD40 regulates the processing of NF-κB2 p100 to p52", The EMBO Journal, vol. 21, No. 20, pp. 5375-5385 (2002).

Jost et al., "Aberrant NF-κb signaling in lumphoma: mechanisms, consequences, and therapeutic implications", Blood, Nov. 21, 2006, vol. 109, No. 7, pp. 2700-2707.

Nencioni et al., "Proteasome inhibitors: antitumor effects and beyond", Leukemia (2007), 21(1), pp. 30-36.

van Rijk et al., "Translocation detection in lymphoma diagnosis by split-signal FISH: a standardised approach," J. Hematop (2008) 1(2): 119-26.

Partial Supplementary Search Report for European Application No. 12776352.2 dated Nov. 14, 2014.

Communication pursuant to Article 94(3) EPC for EP Application No. 12776352.2 dated Feb. 25, 2016.

Takashi Narihiro et al., "Oligonucleotide primers, probes and molecular methods for the environmental monitoring of methanogenic archaea", Microbial Biotechnology (2011), 4(5), pp. 585-602.

Communication pursuant to Article 94(3) EPC for European Patent Application No. 12 776 352.2 dated Oct. 27, 2016.

* cited by examiner

*Primary Examiner* — Amanda Haney

(74) *Attorney, Agent, or Firm* — Kilpatrick Townsend & Stockton, LLP

(57) ABSTRACT

Provided herein are methods for selecting use of proteasome inhibitors.

7 Claims, 17 Drawing Sheets

| | BD* | | BTD or BRD** | |
|---|---|---|---|---|
| NF-κB2 3' end mRNA (CD 138(+) / CD138(-) | Low | High | Low | High |
| > Very Good Partial Response | 7 (25) | 12 (48) | 1(11) | 4(50) |
| Partial Response | 6 (21.7) | 12(48) | 7(78) | 4(50) |
| Stable Disease | 6(21.7) | 1(4) | 0(0) | 0(0) |
| Progressive disease | 9(32.1) | 0 (0) | 2(12) | 0(0) |
| Overall Response | 13(46.7) | 24(96) | 8(88) | 8(100) |

RNA-seq of three cell lines

| | KMS11 | MM1S | 8226 |
|---|---|---|---|
| NM_001077493.1 | 7.47 | 8.66 | 3.74 |
| NM_002502.3 | 31.03 | 18.56 | 2.14 |
| NM_001077494.1 | 38.85 | 26.38 | 2.98 |

FIGURE 12B

| Protein | Control | P100 |
|---|---|---|
| keratin 1 | 1 | 232 |
| NF-kB2 | 1 | 175 |
| keratin 9 [Homo sapiens] | 1 | 160 |
| nuclear factor kappa-B, subunit 1 | 1 | 58 |
| reticuloendotheliosis viral oncogene homolog B | 1 | 43 |
| PREDICTED: hypothetical protein | 1 | 23 |
| ribosomal protein S16 | 1 | 12 |
| RAS protein activator like-3 | 1 | 11 |
| eukaryotic translation initiation factor 4A isoform 1 | 1 | 11 |
| ribosomal protein S4, X-linked X isoform | 1 | 11 |
| GDP dissociation inhibitor 2 isoform 1 | 1 | 11 |
| profilin 1 | 1 | 11 |
| peroxiredoxin 1 | 1 | 10 |
| T-complex protein 1 isoform a | 1 | 9 |

FIGURE 12B (cont.)

| Protein | Control | P100 |
|---|---|---|
| aldolase A [Homo sapiens] | 1 | 9 |
| protein disulfide isomerase-associated 3 precursor | 1 | 7 |
| 5-aminoimidazole-4-carboxamide ribonucleotide formyltransferase/IMP cyclohydrolase | 1 | 7 |
| TIP120 protein | 1 | 7 |
| ribosomal protein S19 | 1 | 7 |
| v-rel reticuloendotheliosis viral oncogene homolog A, nuclear factor of kappa light polypeptide gene enhancer in B-cells 3, p65 [ | 1 | 7 |
| chaperonin containing TCP1, subunit 7 isoform a | 1 | 7 |
| deoxycytidine kinase | 1 | 7 |
| Ezrin | 4 | 24 |
| heat shock 70kDa protein 4 | 1 | 6 |
| ribosomal protein S9 | 1 | 6 |
| Na+/K+ -ATPase alpha 1 subunit isoform a proprotein | 1 | 6 |
| ubiquitin-activating enzyme E1 | 1 | 6 |
| importin 5 | 1 | 6 |

SELECTING USE OF PROTEASOME INHIBITORS BASED ON NF-κB2 SEQUENCE

This application claims the benefit of U.S. Provisional Application No. 61/480,640, filed Apr. 29, 2011, and U.S. Provisional Application No. 61/556,591, filed Nov. 7, 2011, both of which are hereby incorporated herein in their entireties.

BACKGROUND

Proteasome inhibitors are utilized to treat cancer. However, not all patients respond to proteasome inhibitors and the underlying mechanism for this is not well understood.

SUMMARY

Provided herein is a method for treating cancer in a subject comprising detecting the presence of a 3' end of a NF-κB2 gene in a subject with cancer, wherein the sequence of the 3' end is indicative of responsiveness to proteasome inhibitors, and administering an effective amount of a proteasome inhibitor to the subject.

Further provided is a method for treating cancer in a subject comprising detecting a truncated NF-κB2 gene in a subject with cancer, wherein the truncated NF-κB2 gene lacks a ankyrin or a death domain, and administering an effective amount of an immunomodulator or a DNA damaging agent to the subject.

Further provided is a method for treating cancer in a subject comprising detecting the absence of an NF-κB2 gene translocation in a subject with cancer, and administering an effective amount of a proteasome inhibitor.

Also provided is a method of treating cancer in a subject comprising detecting an NF-κB2 gene translocation in a subject with cancer, and administering an effective amount of an immunomodulator or a DNA damaging agent.

DETAILED DESCRIPTION

Provided herein is a method for treating cancer in a subject comprising detecting the presence of a 3' end of a NF-κB2 gene in a subject with cancer, wherein the sequence of the 3' end is indicative of responsiveness to proteasome inhibitors, and administering an effective amount of a proteasome inhibitor to the subject.

In the methods set forth herein, cancers can be, but are not limited to, neoplasms, which include solid and non-solid tumors. A neoplasm can include, but is not limited to, pancreatic cancer, breast cancer, head and neck cancer, melanoma, bladder cancer, bone cancer, brain cancer, lung cancer, prostate cancer, colon cancer, cervical cancer, esophageal cancer, endometrial cancer, central nervous system cancer, gastric cancer, colorectal cancer, thyroid cancer, renal cancer, oral cancer, Hodgkin lymphoma, skin cancer, adrenal cancer, liver cancer, neurofibromatosis 1, and leukemia. Cancers also include cancers that affect the hematopoietic system, for example, B-cell cancers, such as multiple myeloma or lymphoma. Also included are cancers that can be treated with a proteasome inhibitor.

As used throughout, NF-κB2 (p100) is a member of the NF-kappaB family of transcription factors, which are characterized by a Rel homology domain (RHD) in the N-terminal region. These transcription factors play roles in regulating immunity, stress responses, apoptosis, and differentiation. The NF-κB2 gene is located on human chromosome 10q and its genomic sequence is set forth herein as SEQ ID NO: 1. One of skill in the art can utilize the genomic sequence of NF-κB2 to design primers and probes for detection of full-length and truncated NF-κB2 genes and transcripts. Nucleic acid sequences encoding the wild-type NF-κB2 protein, include the nucleic acid sequences set forth under GenBank Accession Nos. NM_001077493.1 (SEQ ID NO: 2), NM_001077494.1 (SEQ ID NO: 3) and NM_002502.3 (SEQ ID NO: 4), which encode the protein sequences for NF-κB2 set forth under GenBank Accession Nos. NP_001070961.1 (SEQ ID NO: 5), NP_001070962.1 (SEQ ID NO: 6) and NP_002493.3 (SEQ ID NO: 7), respectively. These sequences can also be utilized to design primers and probes for detection of full-length and truncated NF-κB2 genes and transcripts. All of the information set forth under the GenBank Accession Nos. set forth herein is incorporated herein by reference.

Figure 3:
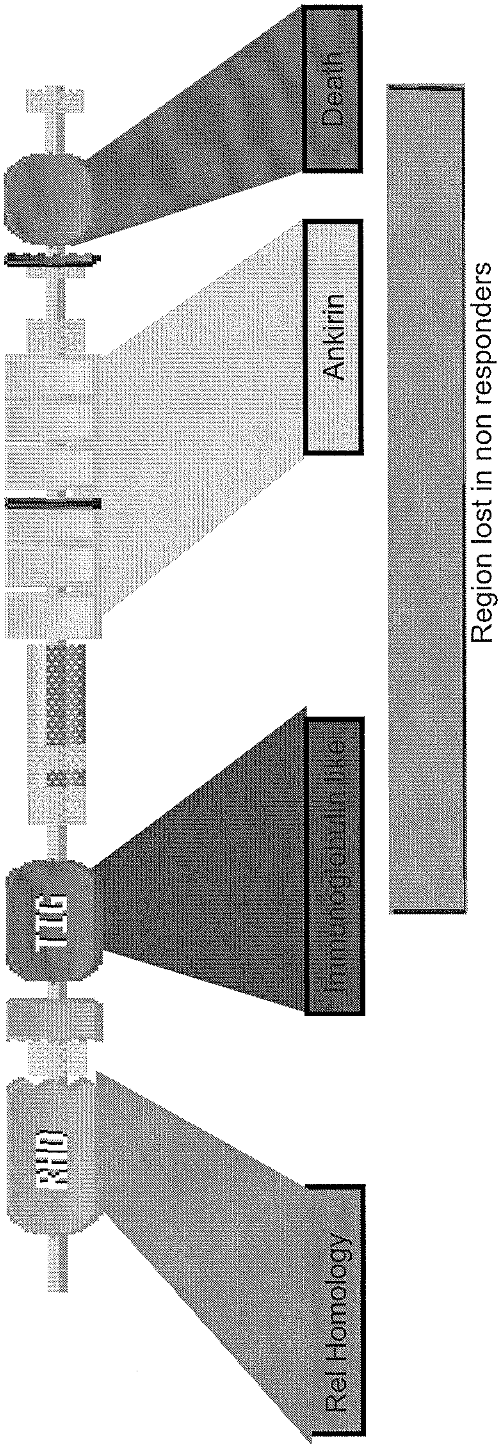
FIG. 3 illustrates the domain distribution within the NF-κB2 and the NF-κB2 regions that can be lost in non-bortezomib responders. In this illustration the Rel homology domain (RHD) and the TIG Immunoglobulin-like domain are also illustrated. Non-bortezomib responders can have a truncated NF-ϵB2 that has lost the death domain or a truncated NF-κB2 that has lost both the death domain and the ankirin domain as compared to wild-type NF-κB2.

As shown in FIG. 3, the NF-κB2 gene encodes an NF-κB2 protein comprising a Rel homology domain, an immunoglobulin-like domain, an ankirin domain comprising several ankirin repeats, and a death domain. The death domain and the ankirin domain are located at the 3' end of the wild-type NF-κB2 protein. More specifically, the death domain is located at about amino acids 754-851 of the wild-type NF-κB2. The ankirin domain comprises ankirin repeats that are located at about amino acids 605-696 of the wild-type NF-κB2 and at about amino acids 488-547 of the wild-type NF-κB2 protein. The ankirin domain comprising 7 ankirin repeats is located at about amino acids 487-758.

As provided herein, a subject's responsiveness to proteasome inhibitors was attributed to the presence of an NF-κB2 gene that comprises a nucleic acid sequence encoding the ankirin domain and the death domain, i.e., an NF-κB2 gene that comprises a nucleic acid that encodes an NF-κB2 protein having at least amino acids 1-849 of the full-length wild-type NF-κB2 protein. Loss of the death domain or loss of the death domain and the ankirin domain results in a truncated NF-κB2 that causes reduced responsiveness to proteasome inhibitors in the subject. If the 3' end of the NF-κB2 gene or transcript from a subject comprises an NF-κB2 nucleic acid sequence encoding the ankirin domain and the death domain, this indicates that the subject is responsive to a proteasome inhibitor.

An NF-κB2 transcript comprising a nucleic acid sequence encoding the death domain, a truncated NF-κB2 transcript that does not encode the death domain or a truncated NF-κB2 transcript that does not encode the death domain or the ankirin domain can be detected by utilizing polymerase chain reaction (PCR) methods known to one of skill in the art. For example, primers can be utilized to amplify nucleic acid sequences, such as a gene transcript of NF-κB2 by standard amplification techniques. Primers can be selected to amplify a full-length NF-κB2 transcript or a truncated NF-κB2 transcript. A variety of PCR techniques are familiar to those skilled in the art. For a review of PCR technology, see White (1997) and the publication entitled "PCR Methods and Applications" (1991, Cold Spring Harbor Laboratory Press), which is incorporated herein by reference in its entirety for amplification methods. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188. Each of these publications is incorporated herein by reference in its entirety for PCR methods.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g., $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product. Gene expression levels can also be measured using quantitative reverse transcriptase (rt-PCR) as set forth in the Examples.

As set forth in the Examples, fluorescence in situ hybridization (FISH) can be utilized to detect a full-length or non-truncated NF-κB2 gene. In other words, FISH can be utilized to detect an NF-κB2 gene that comprises a death domain and an ankirin domain. FISH can also be utilized to detect a break in the NF-κB2 gene that results in loss of the death domain or loss of the death domain and the ankirin domain at the 3' end of the NF-κB2 gene. Rearrangement or translocation detection by FISH is standard in the art. See, for example, van Rijk et al. "Translocation detection in lymphoma diagnosis by split-signal FISH: a standardized approach," *J. Hematopathol.* 1: 119-126 (2008 or Hwang et al. "Various patterns of IgH deletion identified by FISH using combined IgH and IgH/CCND1 probes in multiple myeloma and chronic lymphocytic leukemia," *Int. J. Lab. Hematol.* 33(3): 299-304 (2011)). Briefly, to detect an NF-κB2 translocation in a tumor cell, one of skill in the art can use different colored probes to detect nucleic acid sequences on either side of a known breakpoint region in the NF-κB2 gene. If a translocation is not present, each probe will hybridize to genomic sequences on either side of the breakpoint in the NF-κB2 gene and elicit a fused signal. If a translocation is present, one probe will hybridize to a genomic sequence on one side of the breakpoint and the other probe will hybridize to a genomic sequence on another chromosome where the portion of the NF-κB2 gene on the other side of the breakpoint has translocated.

Full-length and truncated NF-κB2 proteins can also be detected via protein detection methods such as Western blotting, ELISA, ELISPOT, immunoprecipitation, immunofluorescence (e.g., FACS), immunohistochemistry, immunocytochemistry, etc., as well as any other method now known or later developed for quantitating protein in or produced by a cell.

Any proteasome inhibitor can be utilized in the methods set forth throughout this application. These include, but are not limited to, bortezomib, disulfiram, carfilzomib, Atazanavir, epigallocatechin-3-gallate, salinosporamide A, lactacystin or synthetic analogs such as eponemycin, epoxomycin, aclacinomycin A, MLN 2238, MLN9708, CEP-1612 or derivatives derived from CEP-1612, ONX 0912, CEP-18770, MG132, CVT-63417 and a dipeptide boronic inhibitor (for example, PS-341, vinyl sulfone tripeptide proteasome or ritonavir).

One of skill in the art would know how to assess response to treatment for multiple myeloma. For example, response to treatment can be assessed using international Uniform Response Criteria for Multiple Myeloma. Blood and 24-hour urine samples are collected every 3 weeks during the 4 week treatment phase. Investigators can assess response based on the analyses of the monoclonal protein in serum and urine and other factors described below. Other efficacy assessments include a skeletal survey as required by the European Group for Blood and Marrow Transplant (EBMT) criteria. In the assessment, bone marrow examination is encouraged, but not required. Complete Response (CR) is defined by the disappearance of M-protein assessed by serum and/or urine electrophoresis, negative immunofixation and ≤5% plasma cells in the bone marrow. Very Good Response (VGPR) is defined as serum and urine M-protein detectable by immunofixation but not on electrophoresis or as a ≥90% reduction of serum M-protein. Partial Response (PR) is defined as ≥50% reduction of the serum M-protein or ≥90% reduction of the urinary M-protein. Immunofixation is not mandatory for the assessment of CR. The designation of SD is reserved for patients who fail to meet the criteria for CR, PR, or Progression of the disease (PD). PD is defined as a >25% increase in M-protein, a reappearance of an abnormal serum kappa/lambda ratio on two separate measurements at 4-week intervals or the appearance of new plasmocytomas or lytic lesions.

When treating multiple myeloma, the proteasome inhibitor can be administered to a subject with high risk multiple myeloma or low risk multiple myeloma. Genetic factors for high risk multiple myeloma include a translocation between chromosome 4 and 14 (t(4;14)). Fifteen percent of patients exhibit the t(4;14). This patient population is also present in premalignant monoclonal gammopathy of undetermined significance (MGUS), but is more common in smoldering and active multiple myeloma (MM). The t(4;14) population is enriched in IgA isotype MM and in cohorts of patients with relapsed disease. A large percentage (50-80%) of these patients will have a coexistent deletion of chromosome 13 and are frequently hypodiploid (loss of chromosomes) on conventional cytogenetics.

Other translocations include t(14;16) and t(14;20). The t(14;16), t(14;20) and rare t(8;20) are detectable in 6-8% of patients. The MAF transcription factor family is transcriptionally upregulated as a result of these translocations. As with the cyclins, the MAF translocations share a gene expression signature and, as such, may be considered together for the purposes of disease biology and clinical outcome. In at least two series of patients, this patient cohort was associated with a shorter survival among patients treated with conventional or tandem transplant-based chemotherapy. Again this population is enriched for IgA isotype, deletion of chromosome 13 and hypodiploidy.

Another high risk factor is inactivation of p53(17p13). Deletions of 17p13 are detectable in 10% of patients at diagnosis and are associated with a shorter survival after both conventional and high-dose therapy. This deletion is generally considered to be a progression event and is prevalent in plasma cell leukemia and multiple myeloma involving the central nervous system. This is not specifically correlated with other high-risk groups particularly t(4;14) that seems almost mutually exclusive.

Chromosome 13 deletion on metaphase is another high risk factor. One particularly common genetic marker in MM is deletion of chromosome 13 which is detected in nearly 50% of patients with abnormal karyotypes so that it was detectable in 10-20% of all patients overall. Independent of the mode of treatment (standard versus high-dose chemotherapy) and the mode of detection (karyotype versus FISH), MM cases with deletion 13 are associated with shorter survival and lower response rate to treatment. The net effect of deletion 13 on prognosis is, however, greater when deletion 13 is detected by karyotype than when it is detected by interphase FISH. Nevertheless, when deletion of chromosome 13 is found during metaphase analysis the prognosis is very poor.

Amplification of chromosome 1 is also a high risk factor. Amplification of chromosome 1 in a region that includes the cks1b gene is common as it is found in around 35% of patients and is considered a progression event. CKS1B expression is associated with a proliferation signature in MM patients and by both gene expression profiles and by FISH, it confers a poor prognosis.

Low risk factors such as t(11;14) and t(6;14) are associated with a neutral prognosis. The t(11;14) and t(6;14) upregulate cyclin D1 and D3, respectively. They share a gene expression signature and, as such, may be considered together as a molecular entity. Together they represent approximately 20% of all MM patients. Hyperdiploidy is also a low risk factor and likely to be associated with a favorable prognosis. The presence of hyperdiploidy is generally considered favorable. Determination of high risk myeloma or low risk myeloma can be performed prior to, concurrently with or after determination of the status of the 3' end of the NF-κB2 gene in the subject. The methods set forth herein can further comprise, diagnosing a subject with multiple myeloma, diagnosing a subject with a particular stage of multiple myeloma or detecting a particular genetic determinant in a subject with multiple myeloma (for example, a high risk or a low risk genetic factor).

In the methods set forth herein, the proteasome inhibitor can be administered with a second therapeutic agent, for example, an immunomodulator or a DNA damaging agent. As used throughout, examples of immunomodulators include, but are not limited to, thalidomide, lenalidomide and pomalidomide. Examples of DNA damaging agents include, but are not limited to, adriamycin, dexamethasone, doxorubicin, liposomal doxorubicin, cyclophosphamide, etoposide, vincristine and cisplatin. Wherein the first therapeutic agent is a proteasome inhibitor, the second therapeutic agent can be administered prior to, concurrently with or after administration of the proteasome inhibitor.

Other therapeutic agents that can be administered with a proteasome inhibitor include, but are not limited to, melphalan, bendamustine, taxol, cytarabine, methotrexate, steroids (for example, prednisone), hypomethylating agents such as, for example, decitabine and azacitidine, histone deacetylase inhibitors such as, for example, Panobinostat or vorinostat, HSP inhibitors such as, for example, geldanamycin or 17AAG. Any of the compositions set forth herein can be administered in combination with one or more therapies such as, radiation therapy, immunotherapy, surgery or chemotherapy.

Also provided herein is a method for treating cancer in a subject comprising detecting a truncated NF-κB2 gene in a subject with cancer, wherein the truncated NF-κB2 gene lacks a death domain, and administering an effective amount of an immunomodulator or a DNA damaging agent to the subject. In this method, the truncated NF-κB2 can lack a death domain and an ankirin domain. For example, the truncated NF-κB2 gene can be a truncated NF-κB2 gene that lacks a nucleic acid sequence encoding amino acids 754-851, or a truncated NF-κB2 gene that lacks a nucleic acid sequence encoding amino acids 774-851, or a truncated NF-κB2 gene that lacks a nucleic acid sequence encoding amino acids 487-851. The truncated NF-κB2 can also be a truncated NF-κB2 gene that lacks a nucleic acid sequence encoding amino acids 450-851, amino acids 475-851, amino acids 500-851, amino acids 525-851, amino acids 550-851, amino acids 575-851, amino acids 600-851, amino acids 625-851, amino acids 650-851, amino acids 675-851, amino acids 700-851, amino acids 725-851, amino acids 750-851 or amino acids 775-851, amino acids 450-899, amino acids 475-899, amino acids 500-899, amino acids 525-899, amino acids 550-899, amino acids 575-899, amino acids 600-899, amino acids 625-899, amino acids 650-899, amino acids 675-899, amino acids 700-899, amino acids 725-899, amino acids 750-899 or amino acids 775-899. The truncated NF-κB2 gene can also comprise a nucleic acid sequence encoding amino acids 1-475, amino acids 1-480, amino acids 1-485, amino acids 1-487 or amino acids 1-490, wherein the truncated NF-κB2 gene lacks a nucleic acid sequence encoding a death domain, or the truncated NF-κB2 gene lacks a nucleic acid sequence encoding a death domain and an ankirin domain, and does not comprise a nucleic acid encoding the full-length NF-κB2 sequence. The truncated NF-κB2 gene can also comprise a nucleic acid sequence encoding amino acids 1-475, wherein the truncated NF-κB2 gene does not comprise a nucleic acid sequence encoding amino acids 487-899 of wild-type NF-κB2. Truncated products of these truncated NF-κB2 genes, for example, truncated NF-κB2 mRNA transcripts and truncated NF-κB2 proteins can also be detected As set forth above, a truncated NF-κB2 gene can be detected by utilizing PCR or FISH. Upon detection of a truncated NF-κB2 gene in a subject with cancer, for example, and not to be limiting, multiple myeloma, an immunomodulator or a DNA damaging agent can be administered to a subject. The subject can have high risk multiple myeloma or low risk multiple myeloma. Detection of a truncated NF-κB2 gene or the absence of a 3' end of the wild-type NF-κB2 indicates that the subject will have a reduced response to proteasome inhibitor treatment. However, a proteasome inhibitor may be administered to a subject diagnosed with a low risk multiple myeloma.

An immunomodulator can be administered in combination with a DNA damaging agent. Further, an immunomodulator or DNA damaging agent can be administered with a second therapeutic agent. These agents include, but are not limited to: melphalan, bendamustine, taxol, cytarabine, methotrexate, steroids (for example, prednisone), hypomethylating agents such as, for example, decitabine and azacitidine, histone deacetylase inhibitors such as, for example, Panobinostat or vorinostat, HSP inhibitors such as, for example, geldanamycin or 17AAG. Where the first therapeutic agent is a DNA damaging agent or an immunomodulator, the second therapeutic agent can be administered prior to, concurrently with or after administration of the immunomodulator or DNA damaging agent. As set forth above, these compositions can be administered in combination with one or more therapies such as radiation therapy, immunotherapy, surgery or chemotherapy.

Also provided herein is a method for treating cancer in a subject comprising detecting the absence of an NF-κB2 gene translocation in a subject with cancer, and administering an effective amount of a proteasome inhibitor.

Further provided is a method of treating cancer in a subject comprising detecting an NF-κB2 gene translocation in a subject with cancer, and administering an effective amount of an immunomodulator or a DNA damaging agent. Detection of an NF-κB2 gene translocation indicates that the subject will have a reduced response to proteasome inhibitor treatment. However, a proteasome inhibitor can be administered to a subject with an NF-κB2 gene translocation that is diagnosed with a low risk multiple myeloma.

The NF-κB2 gene translocation can be, for example, a translocation between chromosome 10 and chromosome 18 or a translocation between chromosome 10 and 17. However the translocation site is not limited to these translocations as a translocation can occur between chromosome 10 and chromosome 1, 2, 3, 4, 5, 6, 7, 8, 9, 10, 11, 12, 13, 14, 15, 16, 17, 18, 29, 20, 21, 22, X or Y. By utilizing the break apart FISH assay described herein, one of skill in the art can readily determine the presence or absence of an NF-κB2 gene translocation. The breakpoint for the NF-κB2 gene occurs on chromosome 10q, between exons 7 and 13 of the NF-κB2 gene. As set forth above and in the Examples, the translocation can be detected by PCR or FISH.

As used herein, the term subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, whether male or female, are intended to be covered. As used herein, patient or subject may be used interchangeably and can refer to a subject afflicted with a disease or disorder. The term patient or subject includes human and veterinary subjects.

As used herein the terms treatment, treat or treating refers to a method of reducing the effects of a disease or condition or symptom of the disease or condition. Thus in the disclosed method treatment can refer to a 10%, 20%, 30%, 40%, 50%, 60%, 70%, 80%, 90% or 100% reduction or amelioration in the severity of an established disease or condition or symptom of the disease or condition. For example, the method for treating cancer is considered to be a treatment if there is a 10% reduction in one or more symptoms of the disease in a subject as compared to control. Thus the reduction can be a 10, 20, 30, 40, 50, 60, 70, 80, 90, 100% or any percent reduction in between 10 and 100 as compared to native or control levels. It is understood that treatment does not necessarily refer to a cure or complete ablation of the disease, condition or symptoms of the disease or condition.

The therapeutic agents described herein can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Administration can be carried out using therapeutically effective amounts of the agents described herein for periods of time effective to treat or reduce recurrence of cancer. The effective amount may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Administration can also be carried out in multiple doses, for example, hourly, daily, weekly, monthly etc.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

Any appropriate route of administration may be employed, for example, parenteral, intravenous, subcutaneous, intramuscular, intraventricular, intracorporeal, intraperitoneal, rectal, or oral administration. Administration can be systemic or local. Pharmaceutical compositions can be delivered locally to the area in need of treatment, for example by topical application or local injection. Multiple administrations and/or dosages can also be used. Effective doses can be extrapolated from dose-response curves derived from in vitro or animal model test systems.

Further provided is a kit for detecting the presence or absence of an NF-κB2 translocation comprising primers or probes that hybridize on either side of a breakpoint in the NF-κB2 gene. Examples of sequences that can be utilized as probes include, but are not limited to, a nucleic acid sequence comprising SEQ ID NO: 10 and a nucleic acid sequence comprising SEQ ID NO: 11. These probes are merely exemplary as one of skill in the art can utilize publicly available NF-κB2 genomic sequences to design probes suitable for identifying the presence or absence of an NF-κB2 translocation.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

EXAMPLES

Multiple myeloma is a B-cell malignancy of the plasma cell. The course of multiple myeloma is characterized by an asymptomatic or subclinical phase before diagnosis (possibly for several years), a chronic phase lasting several years, and an aggressive terminal phase. Multiple myeloma leads to progressive morbidity and eventual mortality by lowering resistance to infection and causing significant skeletal destruction (with bone pain, pathological fractures, and hypercalcemia), anemia, renal failure, and, less commonly, neurological complications and hyperviscosity.

The proteasome inhibitor, bortezomib, is utilized for the treatment of Multiple Myeloma (MM). However, may patients fail to achieve an optimal response. To identify biomarkers that could predict an optimal response to bortezomib, the role of the noncanonical NF-KB pathway in the response to bortezomib was assessed.

Clinical Specimens

Bone marrow aspirates were collected from 82 MM patients from 2 countries (USA and France). Eighty two patients were recruited from June 2009 to October 2011. Sixty patients received 4 cycles of Bortezomib (1.4 mg/$m^2$) by intravenous bolus on days 1, 4, 8 and 11 and dexamethasone (40 mg) orally on days 1-4 and 8-11. A second group of 22 patients was treated with a similar regimen of bortezomib and dexamethasone with the addition of lenalidomide (15 mg) or tallidomide (150 mg) orally on days 1-21. In addition 23 paraffin-embedded specimens of tumors were obtained for comparison of FISH analysis with the bone marrow aspirates. All patients provided written informed consent approving the use of their samples under Institutional Review Board approval. The primary end point was response rate at 4 cycles of treatment. Prespecified secondary end points included the duration of response, toxicity and overall survival (OS).

Assessment

Response to treatment was assessed using international Uniform Response Criteria for Multiple Myeloma. Blood and 24-hour urine samples were collected every 3 weeks during the 4 week treatment phase. Investigators assessed response based on the analyses of the monoclonal protein in serum and urine and other factors described below. Other efficacy assessments included a skeletal survey as required by EBMT criteria. In the assessment, bone marrow examination was encouraged but not required. Complete Response (CR) was defined by the disappearance of M-protein assessed by serum and/or urine electrophoresis, negative immunofixation and ≤5% plasma cells in the bone marrow. Very Good Response (VGPR) is defined as serum and urine M-protein detectable by immunofixation but not on electrophoresis or as a ≥90% reduction of serum M-protein. Partial Response (PR) is defined as ≥50% reduction of the serum M-protein or ≥90% reduction of the urinary M-protein. Immunofixation is not mandatory for the assessment of CR. The designation of SD is reserved for patients who failed to meet the criteria for CR, PR, or Progression of the disease (PD). PD is defined as a >25% increase in M-protein, a reappearance of an abnormal serum kappa/lambda ration on two separate measurements at 4-week intervals or the appearance of new plasmocytomas or lytic lesions.

Sample Preparation and Cell Sorting

The bone marrow aspirates were treated with RBC lysis buffer (150 mM $NH_4CL$, 10 mM KHCO3, 1 mM EDTA 10 mM Tris base, PH7.4) to remove red blood cells and plasma cells were isolated using immunomagnetic sorting on a big EASYsep magnet following the EASYsep human whole blood CD138 selection kit protocol (Stem Cell Technologies, Vancouver, British Columbia, Canada). Briefly, 3 mL of heparinized bone marrow specimen were spun down and passed over a 200-μm preseparation filter (Miltenyi Biotec, Auburn, Calif.) to remove cell clumps and bone fractions. Then, 75 μL of CD138 primary antibody were added to the cell suspension and incubated for 15 minutes at 4° C. Subsequently, 75 μL of microbeads were added to the mix and incubated for 15 minutes at 4° C. The mix was placed on a magnetic field for selection for 15 minutes. Unlabeled cells were eluted from the tube and placed through a second passage of CD38/beads mix for further purification. After removal from the magnetic field, the immunomagnetic-labeled cells were eluted from the walls of the tube. Purity of sorting was assessed by flow cytometry using CD38-phycoerythrin (PE) staining to determine the purity of the sorts. It was found that the mean plasma cell purity was 90%. Isolated cells were suspended in TRIzol (Invitrogen) and stored at −80° C. for long-term storage. Nucleic acids were isolated from TRIzol following the protocol supplied by the manufacturer and RNA was cleaned using the QIAGEN RNeasy kit (Qiagen, Valencia, Calif.), while the DNA used was cleaned up by phenol-chloroform extractions after RNase and proteinase K treatments.

Quantitative Reverse Transcriptase PCR.

Single strand cDNA was synthesized using 5 μg of total RNA, random hexamers and Taq Man reverse transcription reagents (Applied Biosystems, Carlsbad, Calif.). Relative gene expression levels were measured using power SYBR green master mix (Bio-Rad, Hercules, Calif.) and ABI PRISM 7000 sequence detection system (Applied Biosystems, Carlsbad, Calif.). Primers were obtained from Integrated DNA Technologies (Coralville, Iowa) (Forward primer: CCACACGCCTCTTGACCTCACTT (SEQ ID NO: 8); Reverse primer: TTTGGGCTCTGTTCGACGGGT (SEQ ID NO: 9). Amplification efficiency of individual primers was determined before QPCR. The relative expression level of each gene was measured by QPCR. GAPDH was used as the reference gene in all calculations.

RNA Sequencing Processing and Analysis

RNA sequencing in 2 non-responder patients identified to carry a translocated NF-κB2 and a responder patient is performed to validate candidate partners for whole genome sequencing. In brief, total RNA was isolated from tumor cells and an RNA-Seq sample library was generated using the Illumina TruSeq (Illumina, San Diego, Calif.) kit with assisted automation using Beckman Coulter's SPRIworks HT system (Beckman, Brea, Calif.). All isolates were individually barcoded, and no more than 4 barcoded samples were run at one time in a single lane of an Illumina flow cell. The RNA-Seq data was generated using 100×100 paired end reads for each sample using an Illumina HISeq2000 instrument. Data was analyzed using a variety of open source sequence alignment (TopHat, Bowtie, etc.) and analysis (Cufflinks, TopHat fusion, CloudBurst, etc.) tools for RNA sequencing. In addition, data summary and visualization tools using Galaxy (http://main.g2.bx.psu.edu/), IGV (http://www.broadinstitute.org/igv/) and CLC-Bio Genomics Workbench (Toronto, Ontario, Canada) were also used for RNA-seq analysis.

Whole Genome Sequencing

Whole genome sequencing for 22 multiple myeloma patients was provided by the NIH in order to explore potential partners translocated with NF-κB2. Unidirectional and paired end sequence fragments were aligned to the most recent human reference genome build (February 2009, hg19) using CLC Genomics Workbench software to parse only those sequences that partially align to NF-κB2 gene and any other fusion partner. Based on the amplification method set forth herein, there will be a preponderance of NF-κB2 gene sequences and other sequences spanning the fusion breakpoint.

FISH Procedure and Manual FISH Analysis

Based on the variability of genetic events causative of loss of 3' end break apart fluorescent in situ hybridization (FISH) methodology was designed to detect NF-κB2 rearrangement. Briefly, probes specific for the breakpoints in chromosome arms 10q were delineated using UCSC genome browser and the specific positions. Breakpoints were identified using a bacterial artificial chromosome (BAC) and fosmid clones (RP11-2F13 and BAC-RP11-946k20) purchased from Empire Genomics (Buffalo, N.Y.). Nucleus was identified using whole chromosome pairs with DAPI staining. The specificity of each probe was confirmed by hybridization to normal metaphase preparations to confirm chromosome and band specificity.

Thirty bone marrow aspirates with a known monoclonal plasma population ranging from 10% to 100% were determined by 2 independent reviews. Sorted plasma cells were resuspended in a fresh fixative (3:1 methanol:acetic acid) and 5 μL were dropped every 5 minutes ×3 on a cleaned slide. Slides incubated for 5-minutes in a series of ethanol solutions (70%, 80% and 100%). Subsequently, 5 μL of each denature probe were drop into the attached cells and slides were hybridized overnight. After several washings, the nucleus of the cells were marked using DAPI staining Hybridization of the probes were analyzed by two technicians and 100 cells were evaluated using an Olympus Reflected Fluorescence System, model No. BX41TF with a 100× objective (Olympus, Center Valley, Pa.). Touching and overlapping cells were excluded, and cells were analyzed regardless of their shape and size. The specimens were considered "abnormal" if scores from both technicians independently exceeded the sensitivity cutoff values for 1 or more signal patterns. In cases of discrepant analysis results, analysis was performed by a third technician.

Cell Lines and Apoptosis Studies

The RPMI, OPM, KMS11 and MM1S myeloma cell lines and the Burkitt's lymphoma cell line Daudi were grown in RPMI medium supplemented with 10% fetal bovine serum, 1% L-glutamine, 1 mM sodium pyruvate, and 50 μg/ml penicillin-streptomycin.

For apoptosis studies, $10^4$ cells were treated with titrating doses of doxorubicin (doses: 0.15, 0.25, 0.5, 0.750, 1, 1.5 and 2.5 mg/mL, Sigma) or rituximab (titrating doses: 1.5, 2.5, 5, 10 and 20 μg/mL, Biogen Idec Inc). Twenty four hours later cells were stained with Yo-pro-1 and Propidium Iodide (Invitrogen). Live cells were measured using a ImageXpress 5000A Automated Acquisition and Analysis System (Molecular Devices, Sunnyvale, Calif.), quantitating for Yo-pro-1 or PI negative cells.

Plasmids

Sequences of NF-κB2-shRNA are known. The sense shRNA oligonucleotide probes were as follows: p100, GCTGCTAAATGCTGCTCAGAA (SEQ ID NO: 12). Luciferase (Luc) shRNA plasmid was provided by S. Stewart. Short interfering hairpin RNA were expressed under U6 human promoter and were generated using PLKopuro.1. NF-κB2, NF-κB2-ankirin repeats region, NF-κB2-death domain and LcZ (control) were expressed under a CMV promoter and generated using a pLenti6/V5-DEST (Invitrogen Life Technologies). Recombinant lentiviruses were generated in 293T cells, for infection of all MM cell lines. Stable cell lines expressing shRNAs or the protein of interest were obtained after selecting cells with 2 μg/mL puromycin or 10 μg/mL, respectively. Cells were used for experiments two weeks after infection.

Statistical Analysis

Standard Kaplan-Meier mortality curves and their significance levels were generated for the cohort of patients with low or normal/high peripheral blood lymphocytes/plasma cell 3' end mRNA level. For the Kaplan-Meier survival analyses, the survival curves are compared using the log rank test. The mRNA peripheral blood lymphocytes/plasma cell 3' end mRNA level of responder and non-responder populations was compared using Student's-t test.

Results

Figure 1:
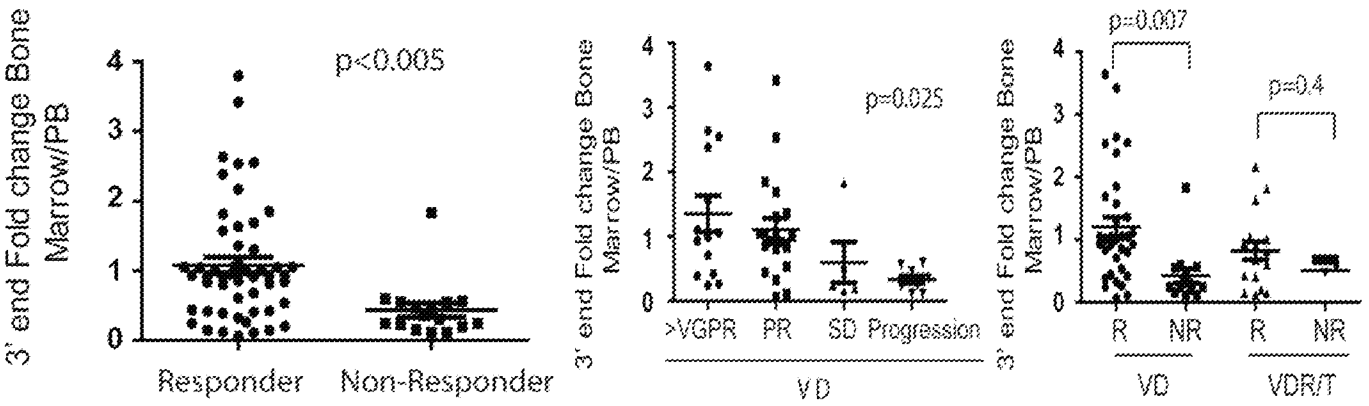
FIG. 1 shows that reduced levels of NF-κB2 are associated with a suboptimal bortezomib response. The possibility that abnormalities in NF-κB2, a common downstream target of the NF-κB pathway, can be found in MM patients was explored. To this end, the mRNA levels of different regions of NF-κB2 in 86 patients with multiple myeloma were detected by quantitative PCR (qPCR). Interestingly, it was found that ~45% of the cases characteristically lack the NF-κB2 3' end normally found in wild-type NF-κB2.

Loss of NF-κB2 death domain predicts a poor response to proteasome inhibitors. In vitro studies identified that NF-κB2/p100 protein levels correlated directly with bortezomib activity. Based on this finding, mRNA levels of different NF-κB2 regions in 64 patients scheduled to receive bortezomib-based regimens were measured at diagnosis. While no difference in expression of the 5' end regions was found between the CD138(+) and CD138(−) cells in these patients, half of them demonstrated low or absent 3' end expression levels in the CD138(+) cells. Among forty-seven patients treated with four cycles of bortezomib and dexamethasone, it was found that low plasma cell NF-κB2 3' end levels were associated with a lower overall response rate (low: 47.8% vs. high: 96%, see FIG. 1). In contrast, low plasma cell NF-κB2 3' end levels failed to predict bortezomib response when lenalidomide or thalidomide was added to the therapeutic regimen. To further understand the cause for NF-κB2 truncation, RNA sequencing in 3 non-responder patients and whole genome sequencing of 38 MM patients to determine causative mechanisms for the truncation were performed. Results suggest that NF-κB2 truncation results from multiple genetic alterations, including but not limited to, premature stop codons produced by ALU insertions, inversions and splicing variants. Overall, this study substantiates the basis for the use of bortezomib and dexmethasone in patients with high NF-κB2 3' end plasma cells levels and immunomodulators or DNA damaging agents in patients with low NF-κB2 3' end plasma cell levels.

Figure 5A:
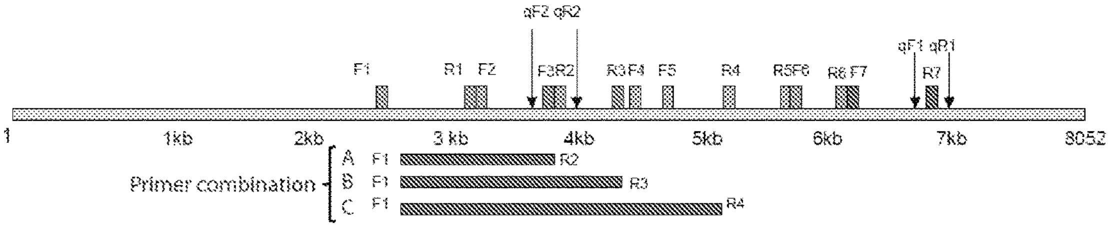
FIG. 5 shows that the NF-κB2 gene is broken apart and the break point occurs after the rel homology domain region. A) Diagrammatic representation of the primer locations across the NF-κB2 gene. B) Gradient temperature PCR of somatic DNA demonstrated that both bortezomib responder and non-responders have the Rel homology domain of NF-κB2. In contrast, only non-responders lack the distal 3' end domains. C) Break apart FISH pictures exemplifying that NF-κB2 is translocated only in non-bortezomib responders.
Figure 5B:
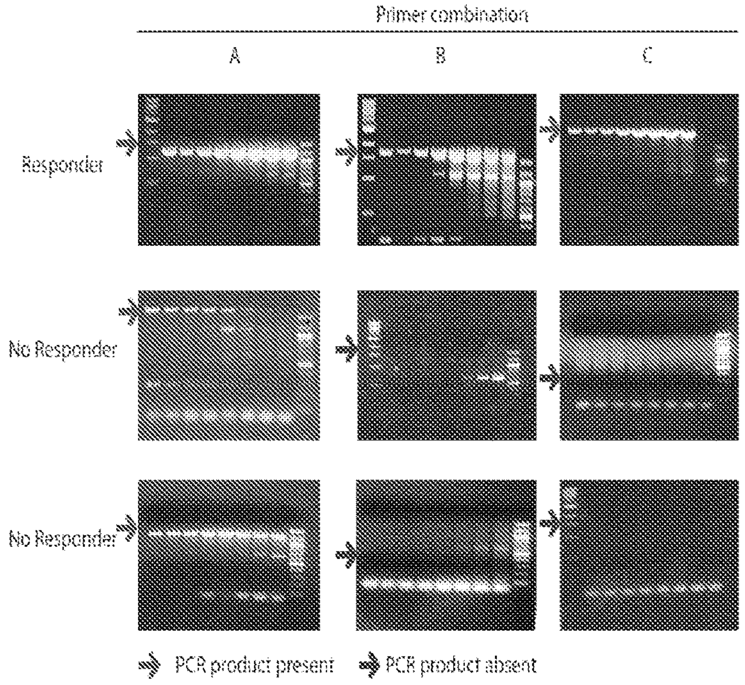
Figure 5C:
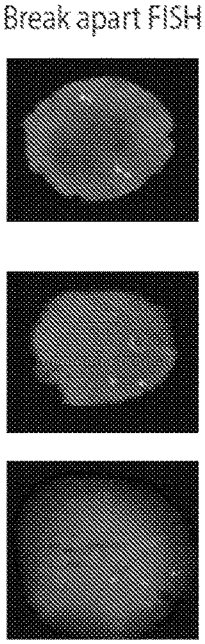

The break apart fluorescent in situ hybridization (FISH) methodology disclosed herein delineated breakpoints in chromosome arms 10q. Abnormal cells were identified using whole chromosome pairs with DAPI staining FISH confirmed that plasma cells from a patient with loss of the NF-κB2 3' end were associated with an abnormal NF-κB2 break (See FIG. 5).

Figure 2:
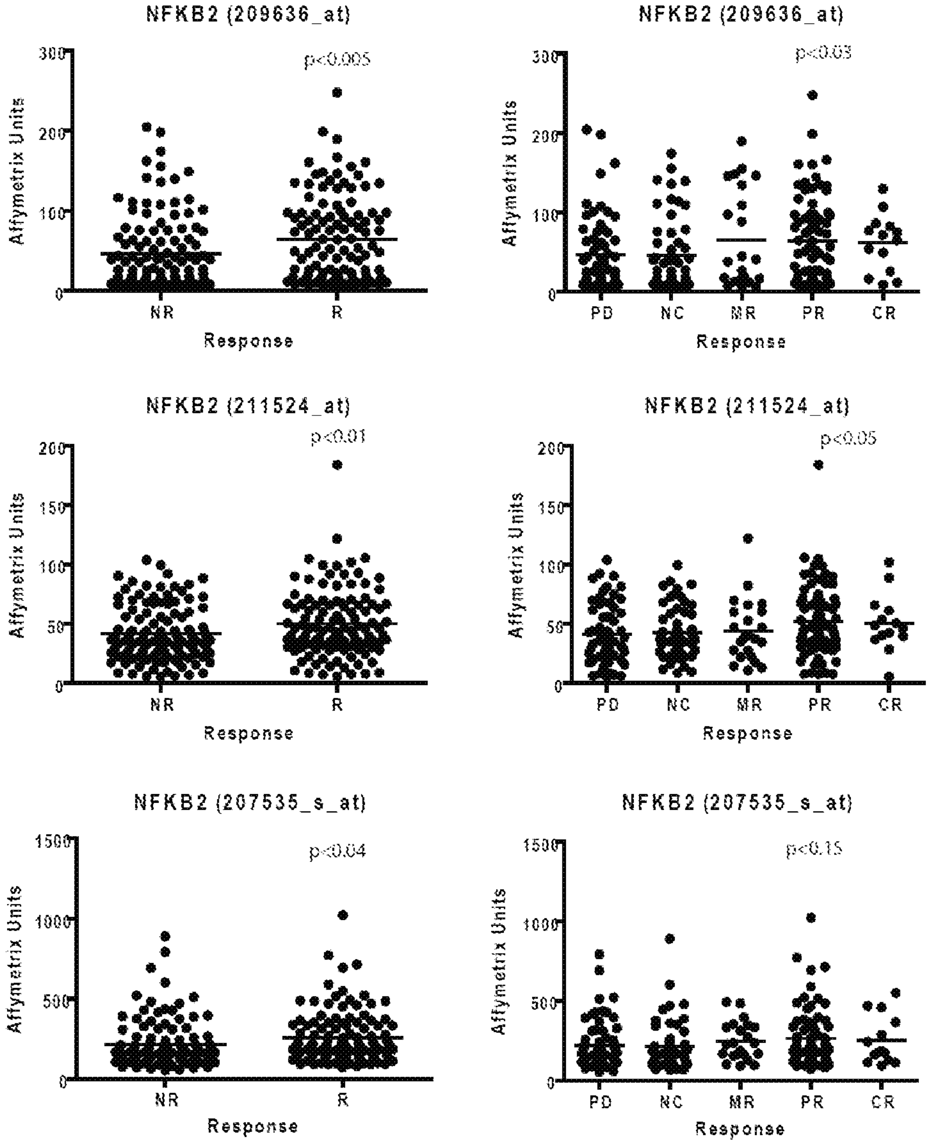
FIG. 2 shows that low levels of NF-κB2 mRNA are associated with a lower clinical response to bortezomib. Values of the Affymetrix units from 3 different probes of the mRNA levels of patients treated with bortezomib were obtained from a published gene expression dataset. The dataset was log 2 transformed and quantile normalized prior to selecting for the corresponding NF-κB2 probes. Then, patients were treated with bortezomib. Subsequently patients were sorted according to their clinical response. Response was defined as a patient that obtained a partial or better response (complete response, CR, very good partial response, VGPR, or minimal response, MR) and no response was defined as patients that fail to obtain a partial response or better (stable disease, SD, or progression PD) in patients treated with bortezomib alone.
Figure 4A:
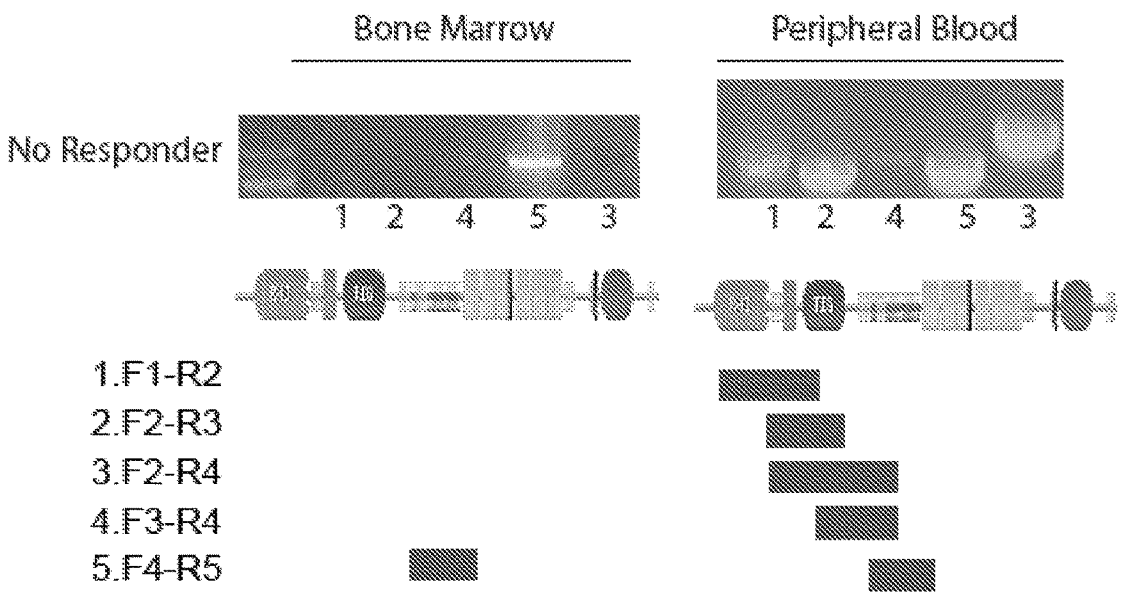
FIG. 4 shows the results of long range PCR demonstrating that the 3' end of NF-κB2 is somatic and present only in bortezomib responders. A) DNA from bone marrow plasma cells and peripheral blood lymphocytes (as controls) were used for long range PCR. Results demonstrated that only peripheral blood lymphocytes and the segment between the ankirin repeats in the plasma cells was present. B) Comparison of the fragments between the immunoglobulin like fold (TIG) and the first ankirin domain in a bortezomib responder and two non-responder patients.
Figure 4B:
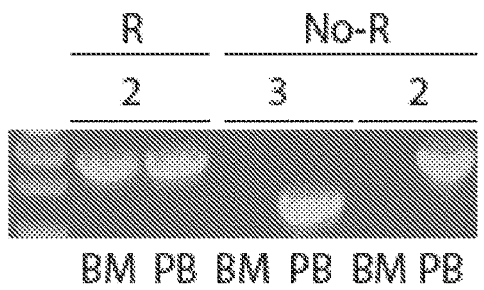
Figures 6A, 6B:
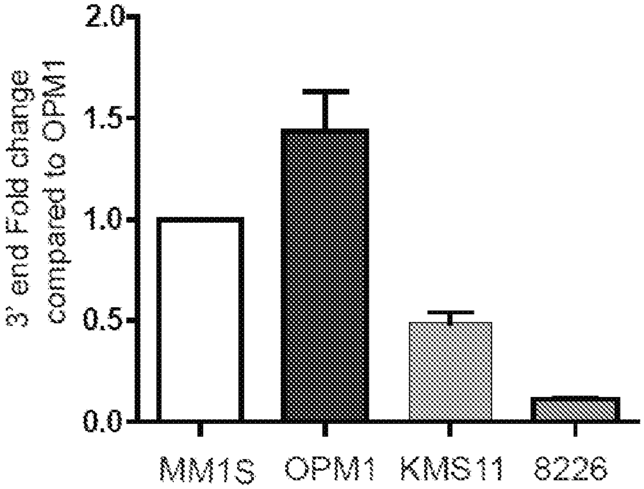
FIG. 6 shows the expression of the NF-κB2 3' end and different NF-κB2 transcripts in different MM cell lines. A) Quantitative PCR measuring the mRNA level of the NF-κB2 3' end in 4 different cell lines. B) RNA from 3 MM cell lines (MM1s, KMS11 and RPMI-8226 cells was obtained and subjected to gene expression analysis using an Illumina HumanHT-12 Expression BeadChip platform. Data was log 2 and quantile normalized prior to selection of the NF-κB2 probes. This analysis revealed that the second highest transcript expressed in KMS11 and RPMI (both bortezomib resistant) is NM_002502.3. This transcript was characterized for losing the 3' end at the level of exon 12.

Studies also showed that low levels of NF-κB2 mRNA are associated with a lower clinical response to bortezomib (see FIG. 2). Utilizing PCR, it was demonstrated that the 3' end of NF-κB2 is present only in bortezomib responders (see FIG. 4). Further studies showed that the NF-κB2 regions that are lost in non-bortezomib responders are the death domain and the ankirin domain (See FIG. 3). A non-bortezomib responder can have a truncated NF-κB2 that has lost a 3' death domain or a truncated NF-κB2 that has lost a 3' death domain and ankirin domain, as compared to wild-type NF-κB2, When expression of the NF-κB2 3' end and different NF-κB2 transcripts was assessed in different MM cell lines, a transcript expressed in both KMS11 and RPMI (both bortezomib resistant cell lines), was characterized as having lost the 3' end at exon 12 (see FIG. 6).

Figure 7A:
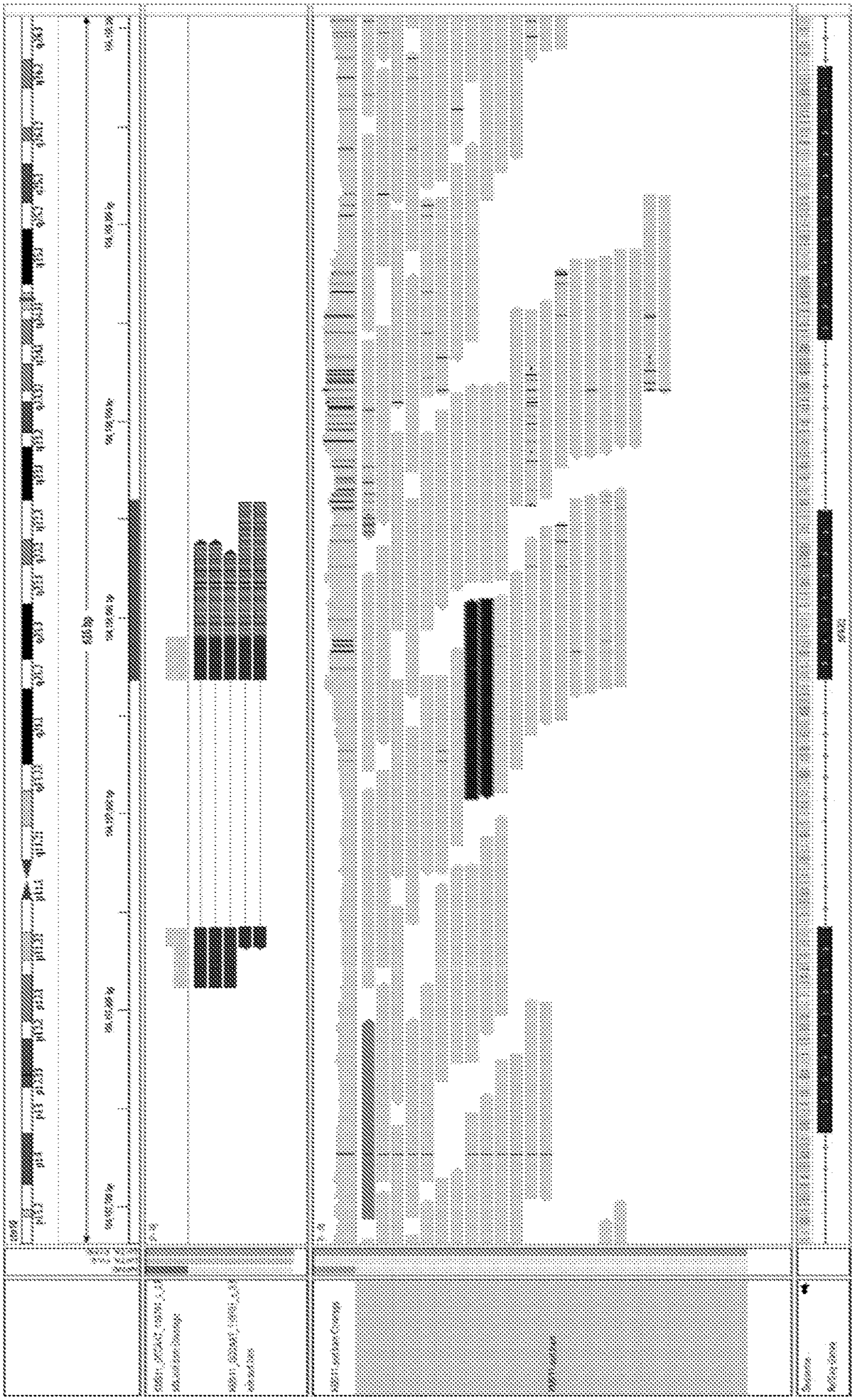
FIG. 7 shows RNA sequencing from KMS11 cells. The results suggest a balance translocation between chromosome 10 and 17. This is an example of a translocation that can occur. A) Five reads that are partially complementary to NF-κB2. B) Similarly, the 3' end of the read matches a region of chromosome 17 corresponding to UBTF (upstream binding transcription factor, RNA polymerase I) gene.
Figure 7B:
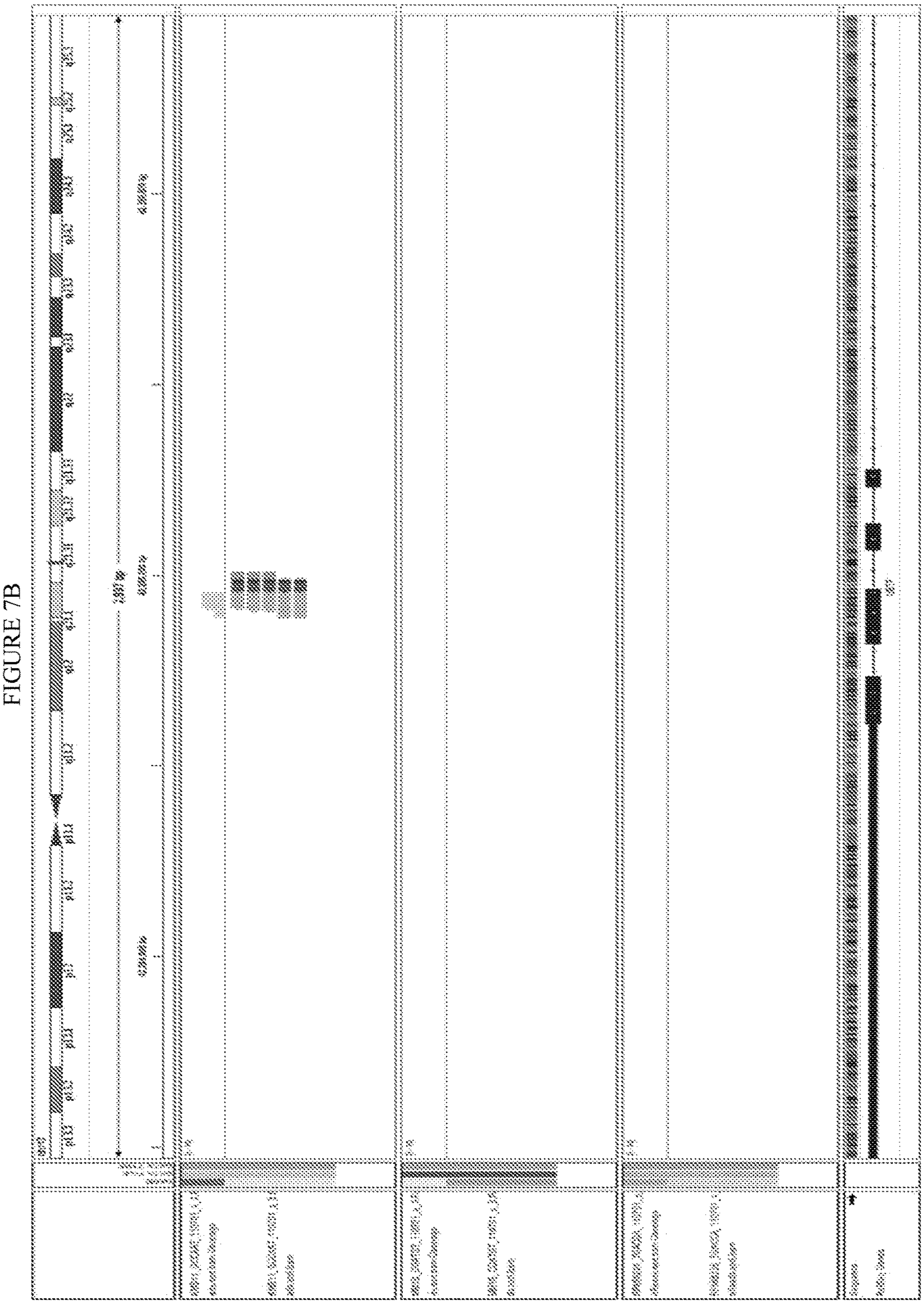
Figure 14:
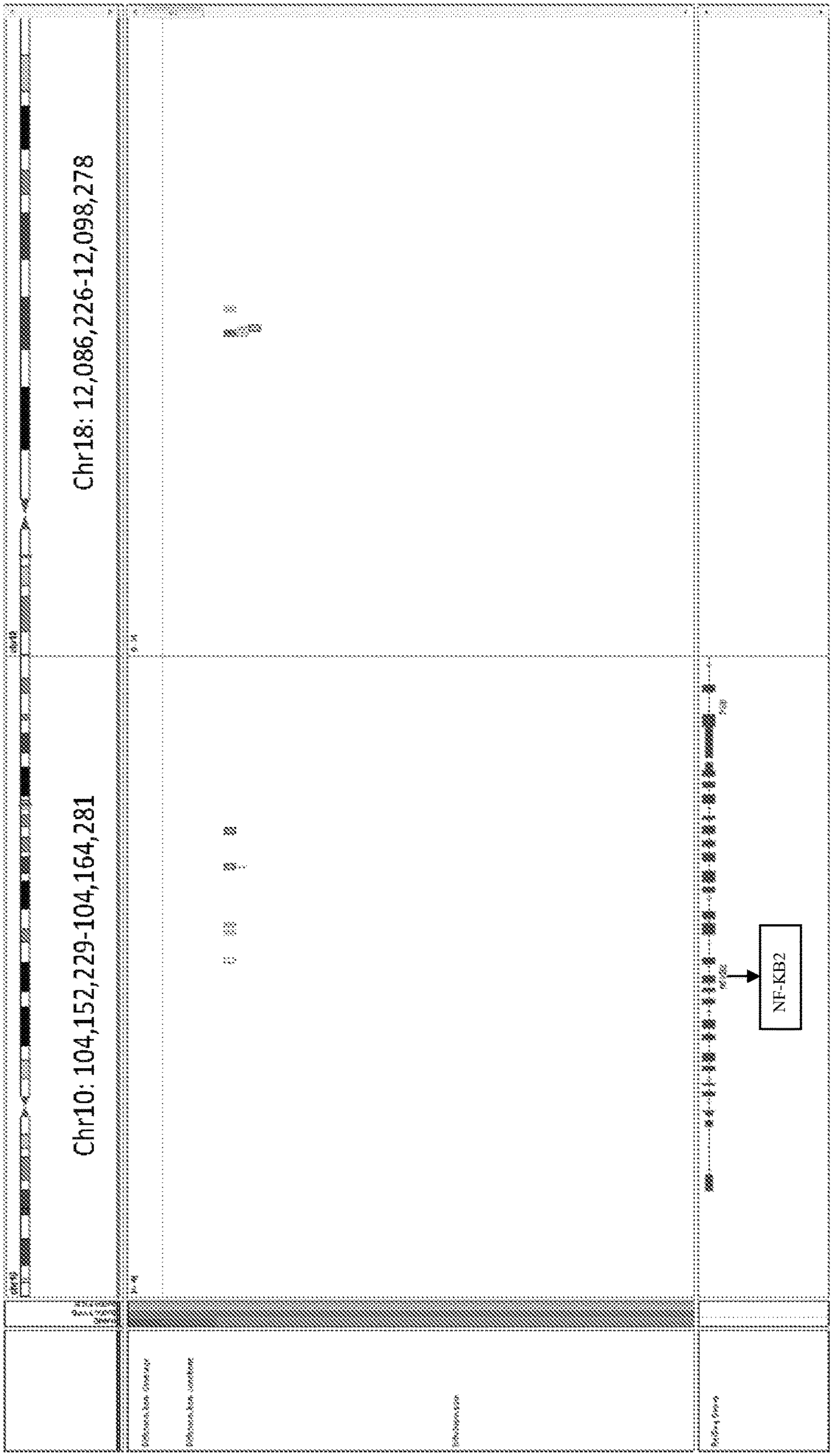
FIG. 14 shows RNA sequencing results from a bortezomib non-responder patient. Sequences were separated in pairs to different files. Sequences were mapped to a reference using Bowtie2 results. Duplicate files (sequences) were removed and pairs that map to different chromosomes were selected to further evaluation. To identify candidate gene fusions TopHatFusion/and FusionSeq tools were used. The results showed translocation between chromosome 10 and 18.

RNA sequencing results from KMS11 cells suggest a balance translocation between chromosome 10 and 17 (See FIG. 7). RNA sequencing results also showed a translocation between 10 and 18 (See FIG. 14).

Figure 8:
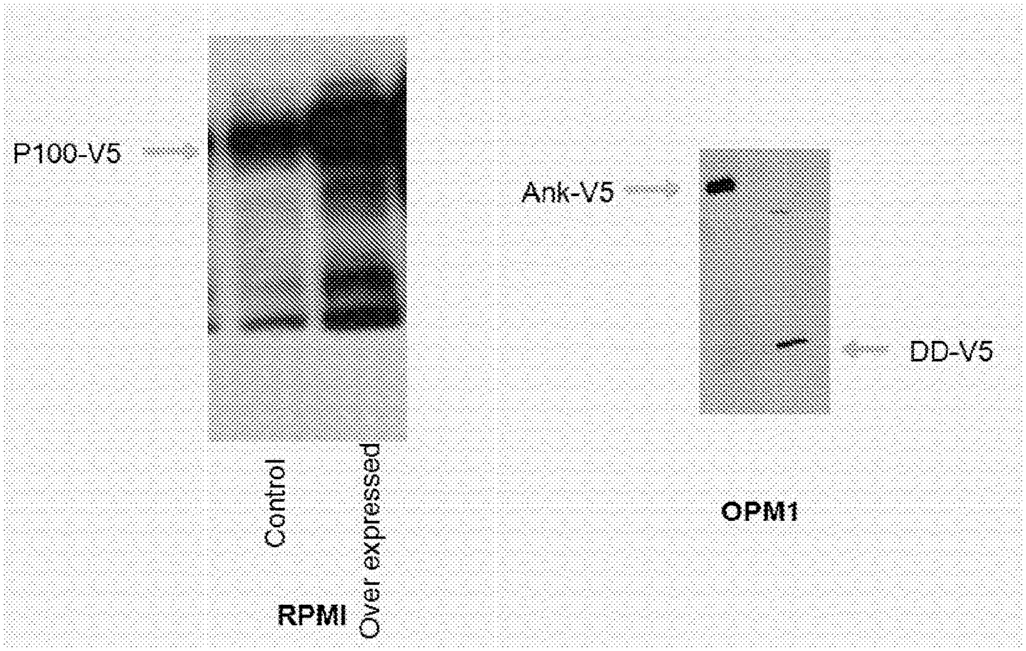
FIG. 8 shows expression of NF-κB2 (p100), NF-κB2-ankyrin domains and NF-κB2-death domain in RPMI cells and OPM1 cells stably expressing NF-κB2 (p100), NF-κB2-ankyrin domains and NF-κB2-death domain.
Figure 9A:
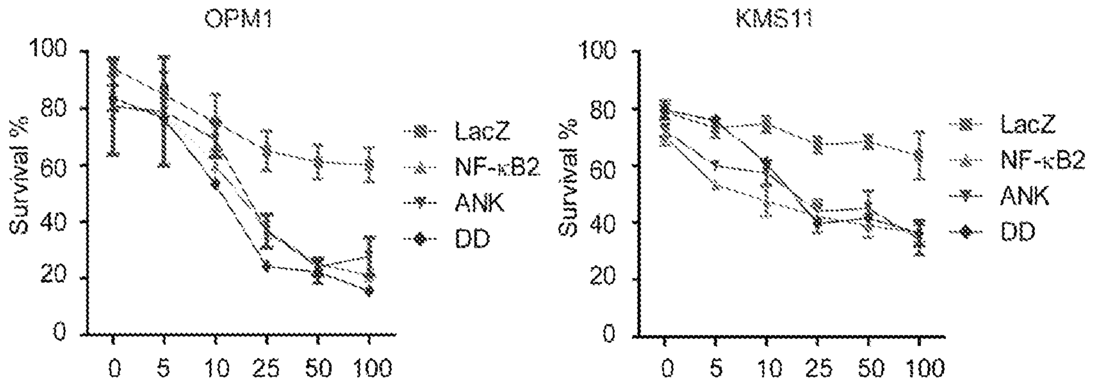
FIG. 9 shows that expression of p100(NF-κB2), NF-κB2-ankyrin domains, NF-κB2-death domain restores sensitivity to bortezomib. A) Two multiple myeloma cell lines, OPM and KMS11, stably expressing the full length NF-κB2 (p100), NF-κB2-ankyrin domains, NF-κB2-death domain were generated using a pLenti6.2/V5-DEST lentivirus. Cells were then treated at titrating doses of bortezomib. After 24 hours the cells were harvested and stained with Yo-pro-1 iodide and propidium Iodide (PI, both from Invitrogen, Grand Island, N.Y.). Live cells were measured using a ImageXpress 5000A Automated Acquisition and Analysis System (Molecular Devices, Sunnyvale, Calif.), quantitating for Yo-pro-1 iodide and PI negative cells. B) OPM1 and RPMI cells stably expressing NF-κB2 (p100), NF-κB2-ankyrin domains or control vector (LacZ) were treated with 10 nM of bortezomib for 24 hours. Cells were harvested and Western blot was performed to assay for caspase 9, cleaved caspase 9 and 3 and actin.
Figure 9B:
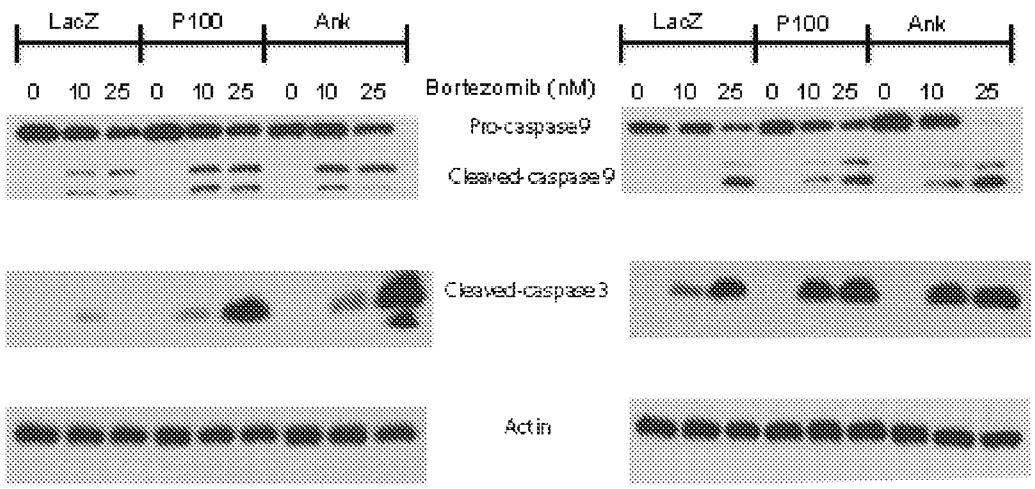

Expression of NF-κB2 (p100), NF-κB2-ankyrin domains and NF-κB2-death domain in RPMI and OPM1 stably expressing NF-κB2 (p100), NF-κB2-ankyrin domains and NF-κB2-death domain was investigated (see FIG. 8). FIG. 9 shows that expression of p100(NF-κB2), NF-κB2-ankyrin domains and NF-κB2-death domain restores sensitivity to bortezomib.

Figure 10A:
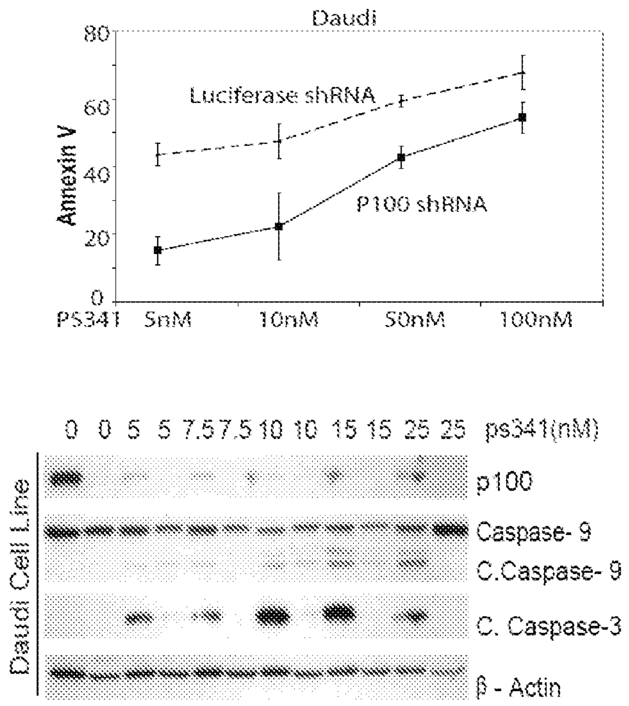
FIG. 10 shows that p100 siRNA expression reduces bortezomib-induced apoptosis in bortezomib sensitive lymphoma cells. (A) Two lymphoma cell lines, Daudi and Raji, expressing a p100 or a p105 siRNA were treated with titrating doses of bortezomib for 24 hours. Apoptosis was measured by flow cytometry using Annexin V staining B) shows that p100 siRNA expression reduces bortezomib-induced caspase activation. Expression of p100 siRNA in two lymphoma cell lines, Daudi and Raji, reduce the protein levels of cleaved caspase 3 and 9. Western blot of Daudi and Raji cell lines expression p100 siRNA or luciferase were performed after 24 hours of treatment with titrating does of bortezomib.
Figure 10B:
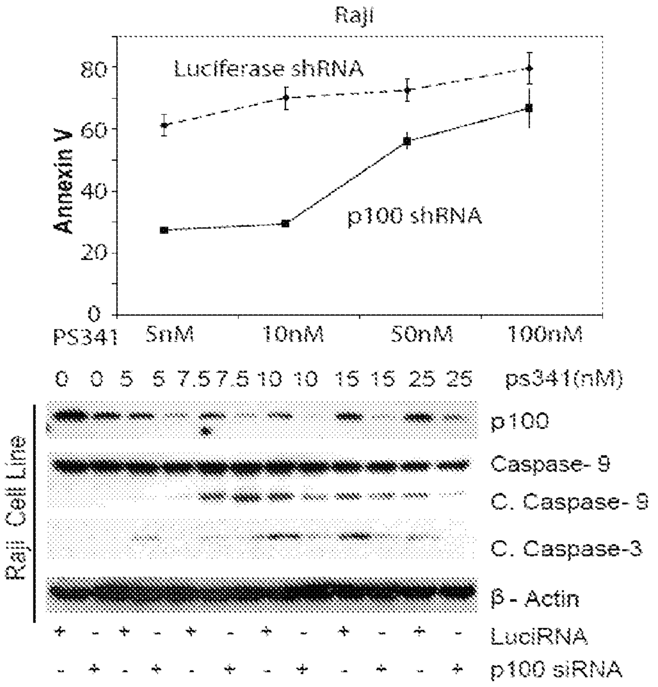

Further studies on bortezomib sensitivity were performed. FIG. 10 shows that p100 siRNA expression reduces Bortezomib-induced apoptosis in bortezomib sensitive lymphoma cells.

Figure 11:
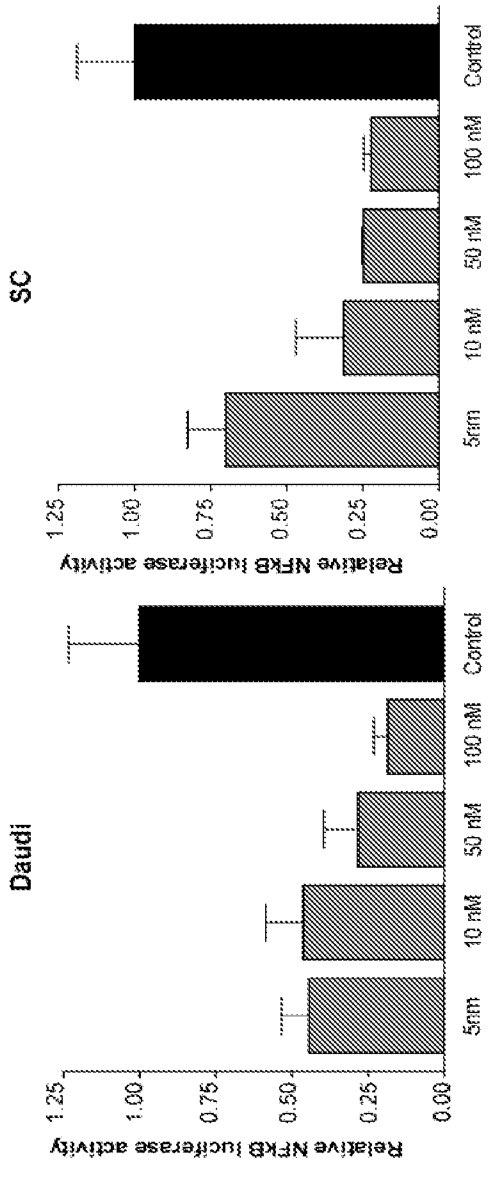
FIG. 11 shows a luciferase reporter assay demonstrating the NF-kB inhibitory effects of different doses of bortezomib in two different lymphoma cell lines. Daudi and SC cell lines were transfected with a NF-κB-luciferase reporter construct (1 μg of DNA). Twenty four hours post-transfection, cells were treated with titrating doses of bortezomib. After 24 hours of treatment, cells were harvested and lysed with RIPA buffer. Twenty microliters of the lysate were mixed with Luciferase assay substrate (Promega, Madison, Wis.) followed by Stop & Glo reagent. Luciferase activity was then measured in a luminometer.

FIG. 11 shows a luciferase reporter assay demonstrating the NF-kB inhibitory effects of different doses of bortezomib in two different lymphoma cell lines.

Figure 12A:
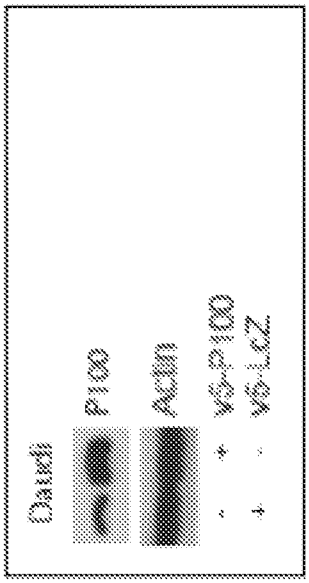
FIG. 12 shows the results of mass spectrometry experiments evaluating candidate binding proteins of NF-κB2 during bortezomib treatment. Daudi cells stably expressing NFκB2-V5 tagged (A) were treated for 12 hours with bortezomib treatment (10 nM). Cells were harvested and immunoprecipitated using a V5 antibody. Immunoprecipitated lysate was used for electrophoresis. Bands were cut and subjected to mass spectrometry (ITRAQ). B) Table demonstrating candidate binding partners if NF-κB2 during bortezomib induced apoptosis.

Mass spectroscopy was utilized to identify candidate binding proteins of NF-κB2 during bortezomib treatment. FIG. 12 identifies several candidate binding partners of NF-κB2 during bortezomib induced apoptosis.

Figure 13A:
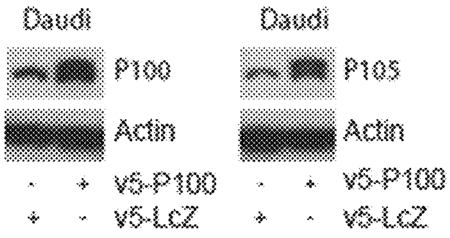
FIG. 13 shows that NF-κB2 (p100) and NF-κB1 (P105) binds to heat shock protein (HSP) 70 and 90 during bortezomib treatment and inhibition of HSP leads to cytochrome release from the mitochondria. A) Expression of NF-κB2 (p100) and NF-κB1 (P105) in Daudi cells expressing NF-κB2 (p100)- and NF-κB1 (P105)-V5 tagged protein. B) Cell lysates from Daudi cells expressing NF-κB2 (p100)- and NF-κB1 (P105)-V5 tagged protein were immunoprecipitated with a V5 antibody. Western blot for HSP70 and HSP 90 was performed. C) OPM1 cells were treated for 24 hours with bortezomib, geldanamycin (HSP inhibitor), or with bortezomib and geldanamycin. After harvesting, nuclear and cytoplasmic fractionation was performed. Western blot was performed to detect HSP 70, Cytochrome C, prohibiting (nuclear protein marker) and actin (cytoplasmic protein marker).
Figure 13B:
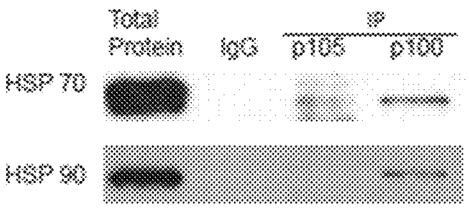
Figure 13C:
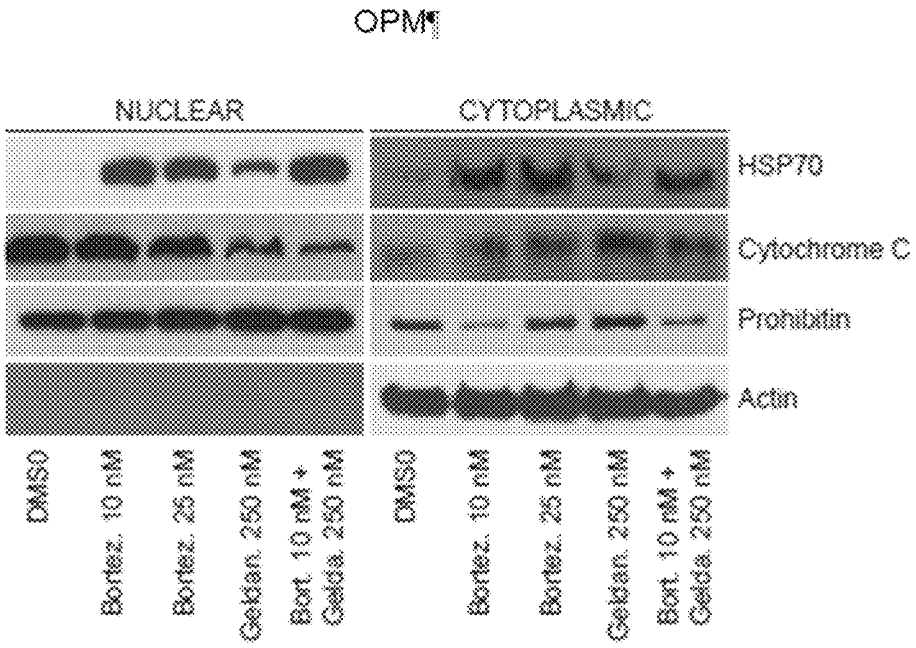

It was also shown that that NF-κB2 (p100) and NF-κB1 (P105) bind to heat shock protein (HSP) 70 and 90 during bortezomib treatment and inhibition of HSP leads to cytochrome release from the mitochondria (see FIG. 13).

What is claimed is:

1. A method for diagnosing and treating a human subject with multiple myeloma that is responsive to treatment with a proteasome inhibitor comprising:

a) obtaining a biological sample from a human subject with multiple myeloma;

b) detecting the nucleic acid sequence at the 3' end of the NF-KB2 gene by fluorescence in situ hybridization (FISH) or polymerase chain reaction (PCR) in the biological sample from the human subject with multiple myeloma;

c) diagnosing the human subject with multiple myeloma that is responsive to treatment with a proteasome inhibitor when (i) a death domain or (ii) a death domain and an ankyrin domain is detected at the 3' end of the NF-KB2 gene; and d) administering an effective amount of a proteasome inhibitor to the human subject diagnosed as responsive to treatment with a proteasome inhibitor.

2. The method of claim 1, wherein the proteasome inhibitor is selected from the group consisting of bortezomib, disulfiram, Atazanavir, epigallocatechin-3-gallate, salinosporamide A, lactacystin, eponemycin, epoxomycin, aclacinomycin A, MLN 2238, MLN9708, CEP-1612, MG132, CVT-63417 and a dipeptide boronic inhibitor.

3. The method of claim 1, wherein the multiple myeloma is a high risk multiple myeloma.

4. The method of claim 1, wherein the multiple myeloma is a low risk multiple myeloma.

5. The method of claim 1, further comprising administering a second therapeutic agent to the human subject diagnosed with multiple myeloma that is responsive to a proteasome inhibitor.

6. The method of claim 5, wherein the second therapeutic agent is administered prior to, concurrently with or after administration of the proteasome inhibitor.

7. The method of claim 1, wherein said diagnosing occurs when a death domain and an ankyrin domain are detected at the 3' end of the NF-KB2 gene.

* * * * *

SEQUENCE LISTING

```
<160> NUMBER OF SEQ ID NOS: 12

<210> SEQ ID NO 1
<211> LENGTH: 8017
<212> TYPE: DNA
<213> ORGANISM: Homo sapiens
<220> FEATURE:
<221> NAME/KEY: misc_feature
<222> LOCATION: (7533)..(7552)
<223> OTHER INFORMATION: n is a, c, g, or t

<400> SEQUENCE: 1

ggaattcccc cctccggggg gccgagaagg ggctttcccg gccctgagcc ctgctggcag     60

gcgaggtgtc gcgaccggtc ccaggtgggt cgggcgcgga gagaagccgc aaccagagcc    120

gccgccacgg tgagtggctg gattcagacc cctgggtggc cgggacaaga gaaaagaggg    180

aggagggcct ttagcggaca gcgcctgggg ctggagagca gcagctgcac acagccggaa    240

agggcgcgca ggcgacgaca ctcggatcca cgtcgacacc gttgtacaaa gatacgcgga    300

cccgtacgta cacctgtacc tgtgctggcg cacacacggc agcgtccgtg cagtcgcact    360

cgcacacaca tgcacacgga gacgtgccca ccggtgcact ggtgcctgca cccacaccct    420

tcacgcacaa actcaagata cgctcacccg tgtctgtaca tcaagacagg cgctgacaca    480

cacccacact gagaagctcg ggattcacct atctacacac atgctcgctt gcacactcat    540

gttgacgcca tggacacaca acatgcaacc aagcactaca gccgaaacac acttgtggag    600

ctgtgatgga gacacactct tgtattaggt gggggggggg ggggggagcg tgcagagatc    660

tccctgtcgc ctgcgcgccc agaaccggtg cggtgtggga ccagctgctg ttgtgaggtt    720

tgggagagag agaaaagagc ccactccgag gaggagacac ttttcccgca gccccagaat    780

cgcgttctcg gggcagaacc ccggggcctc ccacaggaaa gagcccccgc ctacaggctg    840

ttcgaagggg aggccgtccg acagcaggaa tgtcccccca aaagcccccg gggtttatca    900

gccgtggcct ccctcctggc agaaaatccc aaggttgctc cagaccgggg gaggggagcg    960

ggaggcggac ttggccccag actgccagcc tcctcccggc cgtgaaagac cctcctgttc   1020

cctgccctgg agggaggagg gggcttaacc cccaccgggg cttcccggat tctcctagac   1080

ctctgcccgc tgaaaagcag cgggagcccg tagactgtcg agggcctccc gcccctcccg   1140

tcgcgagggc ggggccagtg gcgtcatttc caggcccgcc ccctccggcc ccgcctcccc   1200

ttggtatttt cgggactttc ctaagctgct ctaactttcc tgccccttcc ccggccaagc   1260

ccaactccgg atctcgctct ccaccggatc tcacccgcca cacccggaca ggcggctgga   1320

ggaggtcgga ccctccccca aatctgggcc cccatctccc gcccaccccc atttagatct   1380
```

-continued

```
gaccccctcc cccacgccac tcctcccaac tttaggcggg cgtctaaaat tctgggaagc   1440
agaacctggc cggagccact agacagagcc gggcctagcc cagagacatg gagagttgct   1500
acaacccagt gagtcatgcc gcctgcccct gacccggccg gctgcccctc gtgtctgtcc   1560
acctgtctgc ccgagccccc tctgctgcct tacacctgta tgctcgcaga tgctctcagc   1620
ctgccagtct gtccatctgt ctgcaactct gcctccaaaa ggagctttct cttgggtctg   1680
aggaggaggg gggagtgacc actgaagact tggagatggg aggtggggct gtgggggtg    1740
ctgagagtcg gatgccaccc ccagtctgtc tccaaaccag ggtctggatg gtattattga   1800
atatgatgat ttcaaattga actcctccat tgtggaaccc aaggagccag ccccagaaac   1860
aggtcagcaa gttcactaac ctcccctagt cctaaagcgg gggagggaga gcatgtgccc   1920
tctctctggg ggaggggctg ggagatcgtg gctcagcaag gtctctctgt ccccagctga   1980
tggcccctac ctggtgatcg tggaacagcc taagcaggtg agtgagcaaa agggagggtg   2040
tggaatggct tcagctttgg ggacaaatgg ggtagtggta gctggctggc catggaggag   2100
ccattgccga aggaggccac aggggattgg atggtcactg ctgctgatca gagtgctgta   2160
gtttggttca gggctactac caggcactgc ggtcactgct ggcctgggtg gtcttccctg   2220
atcacaatgc tactatgccc ttggaccttc agagaggctt ccgatttcga tatggctgtg   2280
aaggcccctc ccatggagga ctgcccggtg cctccagtga gaagggccga aagacctatc   2340
ccactgtcaa ggtgagccag gatggtgctg gagggtgggc taagtggaca gcatgcccaa   2400
ggccctgact gacagtccct gcctctccta gatctgtaac tacgagggac cagccaagat   2460
cgaggtggac ctggtaacac acagtgaccc acctcgtgct catgcccaca gtctggtggg   2520
caagcaatgc tcggagctgg ggatctgcgc cgtttctgtg gggcccaagg acatgactgc   2580
ccagtaggtg ccctctacgc ctggccccca ctggtatgcc cgtctgccag tcccaggccc   2640
cagcccacct ccatgagctt agcatctgac caaggggaaa ggtgtaggtt ggccccaaac   2700
ccaagggcct aagtagaaac tccaatggct tccttgagga agtaaggctg agctgagccc   2760
tggcaatggg aaaggtgcct caggaagaaa gaactgcatg gccaaaggcc tccgattctc   2820
tcttctcaga tttaacaacc tgggtgtcct gcatgtgact aagaagaaca tgatggggac   2880
tatgatacaa aaacttcaga ggcagcggct ccgctctagg ccccagggcc ttacgggtat   2940
gggtgcaggg ggtgggtcgg gtatgggtgc agggggtggg tgggtcatgg gaggtgctca   3000
tggaaggagc agggagggag aagcccaggg gtcacacatg tacctactgc ccagaggccg   3060
agcagcggga gctggagcaa gaggccaaag aactgaagaa ggtgatggat ctgagtatag   3120
tgcggctgcg cttctctgcc ttccttagag ccagtgatgg ctccttctcc ctgcccctga   3180
agccagtcat ctcccagccc atccatgaca gcagtgagta tcctgattgc ctggggtgcc   3240
aggcctggtg gcagaggtgg catgaggggt gacctcaagc tgtgcagtca aacagaccca   3300
ggtttcagaa cctggccctg ccacatatga gctgagtgat cctgagcaag tcatttcccc   3360
cccgaagctt ctgtctttag taaatgtgta tattgggtgt ttcctgcagc tccaggggtt   3420
gctgagataa ggaatacaaa gcccccagct tcttaaatgt ggccttggct attgcatcat   3480
ctcaactaat ccatatctca ctccatagaa tctccggggg catcaaacct gaagatttct   3540
cgaatggaca agacagcagg ctctgtgcgg ggtggagatg aagtttatct gctttgtgac   3600
aaggtgcaga aaggtgagac tggagcccac tttgggcacc aaggacatcg agtataagac   3660
tggggccagg gaagctctag ggtaaatggc cccagagatt ccaccgggag ctgtggccaa   3720
```

-continued

```
gcttccgttt tccttgtaga tgacattgag gttcggttct atgaggatga tgagaatgga   3780
tggcaggcct ttggggactt ctctcccaca gatgtgcata aacaggtacc cagggctagg   3840
gcccgggccc gggctggggg ctaaattagg ctaaggactc actgacaccc tgtgtctccc   3900
tgcacccccc agtatgccat tgtgttccgg acaccccccct atcacaagat gaagattgag   3960
cggcctgtaa cagtgtttct gcaactgaaa cgcaagcgag gaggggacgt gtctgattcc   4020
aaacagttca cctattaccc tctggtggaa ggtggagctg ggctgaggac ctcagggtgc   4080
tggcgggggg ccaggctggg ctagaagaag gtcccaagag ctagatgtgg ggatgcatga   4140
gccaagtcag aagtgcgagg gtcccaggag gtgcttccta ggagccggcc ctgagggctc   4200
ttctgggaag ggcccctgag gcatgacaca ataactgggc tcaatctcat tttcctctgc   4260
ccccagacaa ggaagaggtg cagcggaagc ggaggaaggc cttgcccacc ttctcccagc   4320
ccttcggggg tggctcccac atgggtggag gctctggggg tgcagccggg ggctacggag   4380
gagctggagg aggtgagggg gtactgatgg agggaggggt aaaggtaaga gaagctgtgg   4440
aggaaaaaaa tctgggggag gccgggcgtg gtggctcacg cctgtaatcc agccctttgg   4500
gaggccaagg caggcagatt acctgagatc aggagttcaa gaccagcttg gccaacagcg   4560
tgaaacctcg tctctactaa aaatacaaac attagctggg catggtggca ggcgcctgta   4620
atcccagcta ctcgggaggc tgaggcagga gaatcgcttg aaccctggga gacaagaggt   4680
tgcagtaagc tgagatcaca ccactgcact ccaggctggg caataagagc gaaactccgt   4740
ctcaaaaaaa aaaaaaaaaa atctgggaga gtcatggctg gtgcccgctt cccacagccc   4800
tgcctgtatc cacaggtggc agcctcggtt tcttcccctc ctccctggcc tacagcccct   4860
accagtccgg cgcgggcccc atgggctgct acccgggagg cgggggcggg gcgcagatgg   4920
ccgccacggt gcccagcagg gactccgggg aggaagccgc ggagccgagc gccccctcca   4980
ggaccccccca gtgcgagccg caggccccgg agatgctgca gcgaggtatg gactccgggg   5040
cacgggcggt cggggcgccg gggctgagga cctagccctg acccacgccc tctgtggccc   5100
gtagctcgag agtacaacgc gcgcctgttc ggcctggcgc agcgcagcgc ccgagcccta   5160
ctcgactacg gcgtcaccgc ggacgcgcgc gcgctgctgg cgggacagcg ccacctgctg   5220
acggcgcagg acgagaacgg agacacgtag gcaacagagg gcctggcgga cgaggcgcgg   5280
ggtgggggca ggaaagggac cggcacggag gcgggctctg cagttttcgg acacgccagg   5340
cttcaagtcc ggcctcggtg ttcacaagct ctgttcaagc tgcttggtct ctccaaactt   5400
cagtttggtc gaccgtgcaa ggggtacagt catagcactt acctacctca aaaggtgctg   5460
cgaaacgtta agtgcaggca cagcgatgcc ctgggccacg tgctgggttc catgggcccc   5520
agcgagggag actatgaggg cggtggggcc ttgaaagcga aggatgctct gagtggctgg   5580
gccagactct cgctccccaa cccccagacc actgcaccta gccatcatcc acgggcagac   5640
cagtgtcatt gagcagatag tctatgtcat ccaccacgcc caggacctcg gcgttgtcaa   5700
cctcaccaac cacctgcacc aggtgcgggg gcgcctactg ggaggtggg aggggttgga   5760
aggcaagtgg gtctcgggcc tggctcaccc tgctttcatc cccagacgcc cctgcacctg   5820
gcggtgatca cggggcagac gagtgtggtg agctttctgc tgcgggtagg tgcagaccca   5880
gctctgctgg atcggcatgg agactcagcc atgcatctgg cgctgcgggc aggcgctggt   5940
gctcctgagc tgctgcgtgc actgcttcag agtggagctc ctgctgtgcc ccagctgttg   6000
catatgcctg actttgaggg tgagctcccc atctcacctg actaaggggg caggcgggga   6060
ccagggaggg tatctggcca gtgcccagaa tggactatga ggtgtcgaga ttgaatggtc   6120
```

-continued

```
agggctggtc caggggctgc cttaagggtc acagctgcag gttgagcatc ctgcatcctt   6180

aggactgtat ccagtacacc tggcggtccg agcccgaagc cctgagtgcc tggatctgct   6240

ggtggacagt ggggctgaag tggaggccac agagcggcag gggggacgaa cagccttgca   6300

tctagccaca gagatggagg agctggggtt ggtcacccat ctggtcacca aggtgggact   6360

gaggattgtg gaaggagtgg ggccaagggt ggtggagggg ccaaagatgg tgaagggggg   6420

ggctggccaa ggggaccatg ctgtggtgtc aactctcgct gctcgcaccc ccagctccgg   6480

gccaacgtga acgctcgcac ctttgcggga aacacacccc tgcacctggc agctggactg   6540

gggtacccga ccctcacccg cctccttctg aaggctggtc agtctcaccc tcaggggcac   6600

ttgaacaggg tgggggaag ggagagaggt gcctcccagt cccccgactt tgcagtcctt    6660

aatgtaggcc cccaccatac cgccccatga cggcctccct ctcccaggtg ctgacatcca   6720

tgctgaaaac gaggagcccc tgtgcccact gccttcaccc cctacctctg atagcgactc   6780

ggactctgaa gggcctgaga aggacacccg aagcagcttc cggggccaca cgcctcttga   6840

cctcacttgc agcaccaagg tgaggccagc ccgggactag aagtgctctg agtgacgggg   6900

tccagagtat ctggacttaa agacacaggc ttaaggacga ggtgggaggt agtcagaact   6960

gcggctgtct ccccaggtga agaccttgct gctaaatgct gctcagaaca ccatggagcc   7020

acccctgacc ccgcccagcc cagcaggtga gaagcatcag gcatccccag cccgactcct   7080

ctgactcctc acagaggtct cttctccttc aggacctctg aaggaggcct ccctttctct   7140

accctcagcc ccgtccatca cccctcatgg tcctgtctgt cgcttacctt gggagaaagg   7200

cagtgttcag gtgtccatgt ccccacccaa ctctggaggt aaatgacatg tctgtatgtg   7260

tgtcccccta agggccggga ctgtcacttg gtgatacagc tctgcagaac ctggagcagc   7320

tgctagacgg gccagaagcc cagggcagct gggcagagct ggcagagcgt ctggggctgc   7380

gcagcctggt agacacgtac cgacagacaa cctcacccag tggcagcctc ctgcgcagct   7440

acgaggtggg ttggcctgtg ccctgccccc tccccagcct tctttcccga tctgagtcca   7500

ggtgccttct tggccccagg gctcccgagc acnnnnnnnn nnnnnnnnnn nngacctggc   7560

aggtctactg gaggccctgt ctgacatggg cctagaggag ggagtgaggc tgctgagggg   7620

tccagaaacc cgagacaagc tgcccagcac aggtaaaggg gcctccctgg aaggtggatc   7680

tggacctgga gggccggagg cccgaggctt tgactatccc attcctgtcc ccatttaccc   7740

ccagcagagg tgaaggaaga cagtgcgtac gggagccagt cagtggagca ggaggcagag   7800

aagctgggcc cacccccctga gccaccagga gggctctgcc acgggcaccc ccagcctcag   7860

gtgcactgac ctgctgcctg cccccagccc ccttcccgga ccccctgtac agcgtcccca   7920

cctatttcaa atcttattta acaccccaca cccacccctc agttgggaca aataaaggat   7980

tctcatggga aggggaggac ccctccttcc caactta                            8017
```

```
<210> SEQ ID NO 2
<211> LENGTH: 3061
<212> TYPE: DNA
<213> ORGANISM: homo sapiens

<400> SEQUENCE: 2

ggaattcccc cctccggggg gccgagaagg ggctttcccg gccctgagcc ctgctggcag     60

gcgaggtgtc gcgaccggtc ccaggtgggt cgggcgcgga gagaagccgc aaccagagcc    120

gccgccacgg cgggcgtcta aaattctggg aagcagaacc tggccggagc cactagacag    180
```

-continued

```
agccgggcct agcccagaga catggagagt tgctacaacc caggtctgga tggtattatt    240
gaatatgatg atttcaaatt gaactcctcc attgtggaac ccaaggagcc agccccagaa    300
acagctgatg gcccctacct ggtgatcgtg gaacagccta agcagagagg cttccgattt    360
cgatatggct gtgaaggccc ctcccatgga ggactgcccg gtgcctccag tgagaagggc    420
cgaaagacct atcccactgt caagatctgt aactacgagg gaccagccaa gatcgaggtg    480
gacctggtaa cacacagtga cccacctcgt gctcatgccc acagtctggt gggcaagcaa    540
tgctcggagc tggggatctg cgccgtttct gtggggccca aggacatgac tgcccaattt    600
aacaacctgg gtgtcctgca tgtgactaag aagaacatga tggggactat gatacaaaaa    660
cttcagaggc agcggctccg ctctaggccc cagggcctta cggaggccga gcagcgggag    720
ctggagcaag aggccaaaga actgaagaag gtgatggatc tgagtatagt gcggctgcgc    780
ttctctgcct tccttagagc cagtgatggc tccttctccc tgcccctgaa gccagtcatc    840
tcccagccca tccatgacag caaatctccg gggcatcaa acctgaagat ttctcgaatg    900
gacaagacag caggctctgt gcggggtgga gatgaagttt atctgctttg tgacaaggtg    960
cagaaagatg acattgaggt tcggttctat gaggatgatg agaatggatg gcaggccttt   1020
ggggacttct ctcccacaga tgtgcataaa cagtatgcca ttgtgttccg gacaccccc   1080
tatcacaaga tgaagattga gcggcctgta acagtgtttc tgcaactgaa acgcaagcga   1140
ggagggacg tgtctgattc caaacagttc acctattacc ctctggtgga agacaaggaa   1200
gaggtgcagc ggaagcggag gaaggccttg cccaccttct cccagccctt cgggggtggc   1260
tcccacatgg gtggaggctc tgggggtgca gccgggggct acggaggagc tggaggaggt   1320
ggcagcctcg gtttcttccc ctcctccctg gcctacagcc cctaccagtc cggcgcgggc   1380
cccatgggct gctacccggg aggcgggggc ggggcgcaga tggccgccac ggtgcccagc   1440
agggactccg gggaggaagc cgcggagccg agcgcccct ccaggacccc ccagtgcgag   1500
ccgcaggccc cggagatgct gcagcgagct cgagagtaca acgcgcgcct gttcggcctg   1560
gcgcagcgca gcgcccgagc cctactcgac tacggcgtca ccgcggacgc gcgcgcgctg   1620
ctggcgggac agcgccacct gctgacggcg caggacgaga acggagacac accactgcac   1680
ctagccatca tccacgggca gaccagtgtc attgagcaga tagtctatgt catccaccac   1740
gcccaggacc tcggcgttgt caacctcacc aaccacctgc accagacgcc cctgcacctg   1800
gcggtgatca cggggcagac gagtgtggtg agctttctgc tgcgggtagg tgcagaccca   1860
gctctgctgg atcggcatgg agactcagcc atgcatctgg cgctgcgggc aggcgctggt   1920
gctcctgagc tgctgcgtgc actgcttcag agtggagctc ctgctgtgcc ccagctgttg   1980
catatgcctg actttgaggg actgtatcca gtacacctgg cggtccgagc ccgaagccct   2040
gagtgcctgg atctgctggt ggacagtggg gctgaagtgg aggccacaga gcggcagggg   2100
ggacgaacag ccttgcatct agccacagag atggaggagc tggggttggt cacccatctg   2160
gtcaccaagc tccgggccaa cgtgaacgct cgcacctttg cgggaaacac acccctgcac   2220
ctggcagctg gactggggta cccgaccctc acccgcctcc ttctgaaggc tggtgctgac   2280
atccatgctg aaaacgagga gcccctgtgc ccactgcctt caccccctac ctctgatagc   2340
gactcggact ctgaagggcc tgagaaggac acccgaagca gcttccgggg ccacacgcct   2400
cttgacctca cttgcagcac caaggtgaag accttgctgc taaatgctgc tcagaacacc   2460
atggagccac ccctgacccc gcccagccca gcagggccgg gactgtcact tggtgataca   2520
gctctgcaga acctggagca gctgctagac gggccagaag cccagggcag ctgggcagag   2580
```

```
ctggcagagc gtctggggct gcgcagcctg gtagacacgt accgacagac aacctcaccc   2640

agtggcagcc tcctgcgcag ctacgagctg gctggcgggg acctggcagg tctactggag   2700

gccctgtctg acatgggcct agaggaggga gtgaggctgc tgaggggtcc agaaacccga   2760

gacaagctgc ccagcacaga ggtgaaggaa gacagtgcgt acgggagcca gtcagtggag   2820

caggaggcag agaagctggg cccacccccct gagccaccag gagggctctg ccacgggcac   2880

ccccagcctc aggtgcactg acctgctgcc tgcccccagc cccctttcccg gacccccctgt   2940

acagcgtccc cacctatttc aaatcttatt taacacccca cacccacccc tcagttggga   3000

caaataaagg attctcatgg gaaggggagg acccctcctt cccaacttaa aaaaaaaaaa   3060

a                                                                   3061
```

<210> SEQ ID NO 3
<211> LENGTH: 3128
<212> TYPE: DNA
<213> ORGANISM: Homo sapiens

<400> SEQUENCE: 3

```
aaccagagcc gccgccacgg tgagtggctg gattcagacc cctgggtggc cgggacaaga     60

gaaaagaggg aggagggcct ttagcggaca gcgcctgggg ctggagagca gcagctgcac    120

acagccggaa agggcgcgca ggcgacgaca ctcggatcca cgtcgacacc gttgtacaaa    180

gatacgcgga cccgcgggcg tctaaaattc tgggaagcag aacctggccg gagccactag    240

acagagccgg gcctagccca gagacatgga gagttgctac aacccaggtc tggatggtat    300

tattgaatat gatgatttca aattgaactc ctccattgtg gaacccaagg agccagcccc    360

agaaacagct gatggcccct acctggtgat cgtggaacag cctaagcaga gaggcttccg    420

atttcgatat ggctgtgaag gcccctccca tggaggactg cccggtgcct ccagtgagaa    480

gggccgaaag acctatccca ctgtcaagat ctgtaactac gagggaccag ccaagatcga    540

ggtggacctg gtaacacaca gtgacccacc tcgtgctcat gcccacagtc tggtgggcaa    600

gcaatgctcg gagctgggga tctgcgccgt ttctgtgggg cccaaggaca tgactgccca    660

atttaacaac ctgggtgtcc tgcatgtgac taagaagaac atgatgggga ctatgataca    720

aaaacttcag aggcagcggc tccgctctag gccccagggc cttacggagg ccgagcagcg    780

ggagctggag caagaggcca aagaactgaa gaaggtgatg gatctgagta tagtgcggct    840

gcgcttctct gccttcctta gagccagtga tggctccttc tccctgcccc tgaagccagt    900

catctcccag cccatccatg acagcaaatc tccgggggca tcaaacctga agatttctcg    960

aatggacaag acagcaggct ctgtgcgggg tggagatgaa gtttatctgc tttgtgacaa   1020

ggtgcagaaa gatgacattg aggttcggtt ctatgaggat gatgagaatg gatggcaggc   1080

ctttggggac ttctctccca cagatgtgca taaacagtat gccattgtgt tccggacacc   1140

cccctatcac aagatgaaga ttgagcggcc tgtaacagtg tttctgcaac tgaaacgcaa   1200

gcgaggaggg gacgtgtctg attccaaaca gttcacctat taccctctgg tggaagacaa   1260

ggaagaggtg cagcggaagc ggaggaaggc cttgcccacc ttctcccagc ccttcggggg   1320

tggctcccac atgggtggag gctctggggg tgcagccggg ggctacggag gagctggagg   1380

aggtggcagc ctcggtttct tcccctcctc cctggcctac agcccctacc agtccggcgc   1440

gggccccatg ggctgctacc cgggaggcgg gggcggggcg cagatggccg ccacggtgcc   1500

cagcagggac tccggggagg aagccgcgga gccgagcgcc ccctccagga ccccccagtg   1560
```

```
cgagccgcag gccccggaga tgctgcagcg agctcgagag tacaacgcgc gcctgttcgg   1620
cctggcgcag cgcagcgccc gagccctact cgactacggc gtcaccgcgg acgcgcgcgc   1680
gctgctggcg ggacagcgcc acctgctgac ggcgcaggac gagaacggag acacaccact   1740
gcacctagcc atcatccacg ggcagaccag tgtcattgag cagatagtct atgtcatcca   1800
ccacgcccag gacctcggcg ttgtcaacct caccaaccac ctgcaccaga cgcccctgca   1860
cctggcggtg atcacggggc agacgagtgt ggtgagcttt ctgctgcggg taggtgcaga   1920
cccagctctg ctggatcggc atggagactc agccatgcat ctggcgctgc gggcaggcgc   1980
tggtgctcct gagctgctgc gtgcactgct tcagagtgga gctcctgctg tgccccagct   2040
gttgcatatg cctgactttg agggactgta tccagtacac ctggcggtcc gagcccgaag   2100
ccctgagtgc ctggatctgc tggtggacag tggggctgaa gtggaggcca cagagcggca   2160
ggggggacga acagccttgc atctagccac agagatggag gagctggggt tggtcaccca   2220
tctggtcacc aagctccggg ccaacgtgaa cgctcgcacc tttgcgggaa acacacccct   2280
gcacctggca gctggactgg ggtacccgac cctcacccgc ctccttctga aggctggtgc   2340
tgacatccat gctgaaaacg aggagcccct gtgcccactg ccttcacccc ctacctctga   2400
tagcgactcg gactctgaag ggcctgagaa ggacacccga agcagcttcc ggggccacac   2460
gcctcttgac ctcacttgca gcaccaaggt gaagaccttg ctgctaaatg ctgctcagaa   2520
caccatggag ccacccctga ccccgcccag cccagcaggg ccgggactgt cacttggtga   2580
tacagctctg cagaacctgg agcagctgct agacgggcca gaagcccagg gcagctgggc   2640
agagctggca gagcgtctgg ggctgcgcag cctggtagac acgtaccgac agacaacctc   2700
acccagtggc agcctcctgc gcagctacga gctggctggc ggggacctgg caggtctact   2760
ggaggccctg tctgacatgg gcctagagga gggagtgagg ctgctgaggg gtccagaaac   2820
ccgagacaag ctgcccagca cagcagaggt gaaggaagac agtgcgtacg ggagccagtc   2880
agtggagcag gaggcagaga agctgggccc acccccctgag ccaccaggag ggctctgcca   2940
cgggcacccc cagcctcagg tgcactgacc tgctgcctgc ccccagcccc cttcccggac   3000
cccctgtaca gcgtccccac ctatttcaaa tcttatttaa caccccacac ccacccctca   3060
gttgggacaa ataaaggatt ctcatgggaa ggggaggacc cctccttccc aacttaaaaa   3120
aaaaaaaa                                                            3128
```

<210> SEQ ID NO 4
<211> LENGTH: 3054
<212> TYPE: DNA
<213> ORGANISM: Homo sapiens

<400> SEQUENCE: 4

```
ggtattttcg ggactttcct aagctgctct aactttcctg ccccttcccc ggccaagccc     60
aactccggat ctcgctctcc accggatctc acccgccaca cccggacagg cggctggagg    120
aggcgggcgt ctaaaattct gggaagcaga acctggccgg agccactaga cagagccggg    180
cctagcccag agacatggag agttgctaca acccaggtct ggatggtatt attgaatatg    240
atgatttcaa attgaactcc tccattgtgg aacccaagga gccagcccca gaaacagctg    300
atggccccta cctggtgatc gtggaacagc ctaagcagag aggcttccga tttcgatatg    360
gctgtgaagg cccctcccat ggaggactgc ccggtgcctc cagtgagaag ggccgaaaga    420
cctatcccac tgtcaagatc tgtaactacg agggaccagc caagatcgag gtggacctgg    480
taacacacag tgacccacct cgtgctcatg cccacagtct ggtgggcaag caatgctcgg    540
```

-continued

```
agctggggat ctgcgccgtt tctgtggggc ccaaggacat gactgcccaa tttaacaacc    600
tgggtgtcct gcatgtgact aagaagaaca tgatggggac tatgatacaa aaacttcaga    660
ggcagcggct ccgctctagg ccccagggcc ttacggaggc cgagcagcgg gagctggagc    720
aagaggccaa agaactgaag aaggtgatgg atctgagtat agtgcggctg cgcttctctg    780
ccttccttag agccagtgat ggctccttct ccctgcccct gaagccagtc atctcccagc    840
ccatccatga cagcaaatct ccgggggcat caaacctgaa gatttctcga atggacaaga    900
cagcaggctc tgtgcggggt ggagatgaag tttatctgct ttgtgacaag gtgcagaaag    960
atgacattga ggttcggttc tatgaggatg atgagaatgg atggcaggcc tttggggact   1020
tctctcccac agatgtgcat aaacagtatg ccattgtgtt ccggacaccc ccctatcaca   1080
agatgaagat tgagcggcct gtaacagtgt ttctgcaact gaaacgcaag cgaggagggg   1140
acgtgtctga ttccaaacag ttcacctatt accctctggt ggaagacaag gaagaggtgc   1200
agcggaagcg gaggaaggcc ttgcccacct tctcccagcc cttcgggggt ggctcccaca   1260
tgggtggagg ctctgggggt gcagccgggg gctacggagg agctggagga ggtggcagcc   1320
tcggtttctt cccctcctcc ctggcctaca gcccctacca gtccggcgcg ggccccatgg   1380
gctgctaccc gggaggcggg ggcggggcgc agatggccgc cacggtgccc agcagggact   1440
ccggggagga agccgcggag ccgagcgccc cctccaggac cccccagtgc gagccgcagg   1500
ccccggagat gctgcagcga gctcgagagt acaacgcgcg cctgttcggc ctggcgcagc   1560
gcagcgcccg agccctactc gactacggcg tcaccgcgga cgcgcgcgcg ctgctggcgg   1620
gacagcgcca cctgctgacg gcgcaggacg agaacggaga cacaccactg cacctagcca   1680
tcatccacgg gcagaccagt gtcattgagc agatagtcta tgtcatccac cacgcccagg   1740
acctcggcgt tgtcaacctc accaaccacc tgcaccagac gcccctgcac ctggcggtga   1800
tcacggggca gacgagtgtg gtgagctttc tgctgcgggt aggtgcagac ccagctctgc   1860
tggatcggca tggagactca gccatgcatc tggcgctgcg ggcaggcgct ggtgctcctg   1920
agctgctgcg tgcactgctt cagagtggag ctcctgctgt gccccagctg ttgcatatgc   1980
ctgactttga gggactgtat ccagtacacc tggcggtccg agcccgaagc cctgagtgcc   2040
tggatctgct ggtggacagt ggggctgaag tggaggccac agagcggcag gggggacgaa   2100
cagccttgca tctagccaca gagatggagg agctggggtt ggtcacccat ctggtcacca   2160
agctccgggc caacgtgaac gctcgcacct ttgcgggaaa cacacccctg cacctggcag   2220
ctggactggg gtacccgacc ctcacccgcc tccttctgaa ggctggtgct gacatccatg   2280
ctgaaaacga ggagcccctg tgcccactgc cttcaccccc tacctctgat agcgactcgg   2340
actctgaagg gcctgagaag gacacccgaa gcagcttccg gggccacacg cctcttgacc   2400
tcacttgcag caccaaggtg aagaccttgc tgctaaatgc tgctcagaac accatggagc   2460
cacccctgac cccgcccagc ccagcagggc cgggactgtc acttggtgat acagctctgc   2520
agaacctgga gcagctgcta gacgggccag aagcccaggg cagctgggca gagctggcag   2580
agcgtctggg gctgcgcagc ctggtagaca cgtaccgaca gacaacctca cccagtggca   2640
gcctcctgcg cagctacgag ctggctggcg gggacctggc aggtctactg gaggccctgt   2700
ctgacatggg cctagaggag ggagtgaggc tgctgagggg tccagaaacc cgagacaagc   2760
tgcccagcac agaggtgaag gaagacagtg cgtacgggag ccagtcagtg gagcaggagg   2820
cagagaagct gggcccaccc cctgagccac caggagggct ctgccacggg cacccccagc   2880
```

```
ctcaggtgca ctgacctgct gcctgccccc agcccccttc ccggaccccc tgtacagcgt   2940

ccccacctat ttcaaatctt atttaacacc ccacacccac ccctcagttg ggacaaataa   3000

aggattctca tgggaagggg aggacccctc cttcccaact taaaaaaaaa aaaa         3054


<210> SEQ ID NO 5
<211> LENGTH: 899
<212> TYPE: PRT
<213> ORGANISM: Homo sapiens

<400> SEQUENCE: 5

Met Glu Ser Cys Tyr Asn Pro Gly Leu Asp Gly Ile Ile Glu Tyr Asp
1               5                   10                  15

Asp Phe Lys Leu Asn Ser Ser Ile Val Glu Pro Lys Glu Pro Ala Pro
            20                  25                  30

Glu Thr Ala Asp Gly Pro Tyr Leu Val Ile Val Glu Gln Pro Lys Gln
        35                  40                  45

Arg Gly Phe Arg Phe Arg Tyr Gly Cys Glu Gly Pro Ser His Gly Gly
    50                  55                  60

Leu Pro Gly Ala Ser Ser Glu Lys Gly Arg Lys Thr Tyr Pro Thr Val
65                  70                  75                  80

Lys Ile Cys Asn Tyr Glu Gly Pro Ala Lys Ile Glu Val Asp Leu Val
                85                  90                  95

Thr His Ser Asp Pro Pro Arg Ala His Ala His Ser Leu Val Gly Lys
            100                 105                 110

Gln Cys Ser Glu Leu Gly Ile Cys Ala Val Ser Val Gly Pro Lys Asp
        115                 120                 125

Met Thr Ala Gln Phe Asn Asn Leu Gly Val Leu His Val Thr Lys Lys
    130                 135                 140

Asn Met Met Gly Thr Met Ile Gln Lys Leu Gln Arg Gln Arg Leu Arg
145                 150                 155                 160

Ser Arg Pro Gln Gly Leu Thr Glu Ala Glu Gln Arg Glu Leu Glu Gln
                165                 170                 175

Glu Ala Lys Glu Leu Lys Lys Val Met Asp Leu Ser Ile Val Arg Leu
            180                 185                 190

Arg Phe Ser Ala Phe Leu Arg Ala Ser Asp Gly Ser Phe Ser Leu Pro
        195                 200                 205

Leu Lys Pro Val Ile Ser Gln Pro Ile His Asp Ser Lys Ser Pro Gly
    210                 215                 220

Ala Ser Asn Leu Lys Ile Ser Arg Met Asp Lys Thr Ala Gly Ser Val
225                 230                 235                 240

Arg Gly Gly Asp Glu Val Tyr Leu Leu Cys Asp Lys Val Gln Lys Asp
                245                 250                 255

Asp Ile Glu Val Arg Phe Tyr Glu Asp Asp Glu Asn Gly Trp Gln Ala
            260                 265                 270

Phe Gly Asp Phe Ser Pro Thr Asp Val His Lys Gln Tyr Ala Ile Val
        275                 280                 285

Phe Arg Thr Pro Pro Tyr His Lys Met Lys Ile Glu Arg Pro Val Thr
    290                 295                 300

Val Phe Leu Gln Leu Lys Arg Lys Arg Gly Gly Asp Val Ser Asp Ser
305                 310                 315                 320

Lys Gln Phe Thr Tyr Tyr Pro Leu Val Glu Asp Lys Glu Glu Val Gln
                325                 330                 335

Arg Lys Arg Arg Lys Ala Leu Pro Thr Phe Ser Gln Pro Phe Gly Gly
            340                 345                 350
```

-continued

```
Gly Ser His Met Gly Gly Gly Ser Gly Gly Ala Ala Gly Gly Tyr Gly
        355                 360                 365

Gly Ala Gly Gly Gly Gly Ser Leu Gly Phe Phe Pro Ser Ser Leu Ala
    370                 375                 380

Tyr Ser Pro Tyr Gln Ser Gly Ala Gly Pro Met Gly Cys Tyr Pro Gly
385                 390                 395                 400

Gly Gly Gly Gly Ala Gln Met Ala Ala Thr Val Pro Ser Arg Asp Ser
                405                 410                 415

Gly Glu Glu Ala Ala Glu Pro Ser Ala Pro Ser Arg Thr Pro Gln Cys
            420                 425                 430

Glu Pro Gln Ala Pro Glu Met Leu Gln Arg Ala Arg Glu Tyr Asn Ala
        435                 440                 445

Arg Leu Phe Gly Leu Ala Gln Arg Ser Ala Arg Ala Leu Leu Asp Tyr
    450                 455                 460

Gly Val Thr Ala Asp Ala Arg Ala Leu Leu Ala Gly Gln Arg His Leu
465                 470                 475                 480

Leu Thr Ala Gln Asp Glu Asn Gly Asp Thr Pro Leu His Leu Ala Ile
                485                 490                 495

Ile His Gly Gln Thr Ser Val Ile Glu Gln Ile Val Tyr Val Ile His
            500                 505                 510

His Ala Gln Asp Leu Gly Val Val Asn Leu Thr Asn His Leu His Gln
        515                 520                 525

Thr Pro Leu His Leu Ala Val Ile Thr Gly Gln Thr Ser Val Val Ser
    530                 535                 540

Phe Leu Leu Arg Val Gly Ala Asp Pro Ala Leu Leu Asp Arg His Gly
545                 550                 555                 560

Asp Ser Ala Met His Leu Ala Leu Arg Ala Gly Ala Gly Ala Pro Glu
                565                 570                 575

Leu Leu Arg Ala Leu Leu Gln Ser Gly Ala Pro Ala Val Pro Gln Leu
            580                 585                 590

Leu His Met Pro Asp Phe Glu Gly Leu Tyr Pro Val His Leu Ala Val
        595                 600                 605

Arg Ala Arg Ser Pro Glu Cys Leu Asp Leu Leu Val Asp Ser Gly Ala
    610                 615                 620

Glu Val Glu Ala Thr Glu Arg Gln Gly Gly Arg Thr Ala Leu His Leu
625                 630                 635                 640

Ala Thr Glu Met Glu Glu Leu Gly Leu Val Thr His Leu Val Thr Lys
                645                 650                 655

Leu Arg Ala Asn Val Asn Ala Arg Thr Phe Ala Gly Asn Thr Pro Leu
            660                 665                 670

His Leu Ala Ala Gly Leu Gly Tyr Pro Thr Leu Thr Arg Leu Leu Leu
        675                 680                 685

Lys Ala Gly Ala Asp Ile His Ala Glu Asn Glu Glu Pro Leu Cys Pro
    690                 695                 700

Leu Pro Ser Pro Pro Thr Ser Asp Ser Asp Ser Asp Ser Glu Gly Pro
705                 710                 715                 720

Glu Lys Asp Thr Arg Ser Ser Phe Arg Gly His Thr Pro Leu Asp Leu
                725                 730                 735

Thr Cys Ser Thr Lys Val Lys Thr Leu Leu Leu Asn Ala Ala Gln Asn
            740                 745                 750

Thr Met Glu Pro Pro Leu Thr Pro Pro Ser Pro Ala Gly Pro Gly Leu
        755                 760                 765
```

Ser Leu Gly Asp Thr Ala Leu Gln Asn Leu Glu Gln Leu Leu Asp Gly
770 775 780

Pro Glu Ala Gln Gly Ser Trp Ala Glu Leu Ala Glu Arg Leu Gly Leu
785 790 795 800

Arg Ser Leu Val Asp Thr Tyr Arg Gln Thr Thr Ser Pro Ser Gly Ser
805 810 815

Leu Leu Arg Ser Tyr Glu Leu Ala Gly Gly Asp Leu Ala Gly Leu Leu
820 825 830

Glu Ala Leu Ser Asp Met Gly Leu Glu Glu Gly Val Arg Leu Leu Arg
835 840 845

Gly Pro Glu Thr Arg Asp Lys Leu Pro Ser Thr Glu Val Lys Glu Asp
850 855 860

Ser Ala Tyr Gly Ser Gln Ser Val Glu Gln Glu Ala Glu Lys Leu Gly
865 870 875 880

Pro Pro Pro Glu Pro Pro Gly Gly Leu Cys His Gly His Pro Gln Pro
885 890 895

Gln Val His

<210> SEQ ID NO 6
<211> LENGTH: 900
<212> TYPE: PRT
<213> ORGANISM: Homo sapiens

<400> SEQUENCE: 6

Met Glu Ser Cys Tyr Asn Pro Gly Leu Asp Gly Ile Ile Glu Tyr Asp
1 5 10 15

Asp Phe Lys Leu Asn Ser Ser Ile Val Glu Pro Lys Glu Pro Ala Pro
20 25 30

Glu Thr Ala Asp Gly Pro Tyr Leu Val Ile Val Glu Gln Pro Lys Gln
35 40 45

Arg Gly Phe Arg Phe Arg Tyr Gly Cys Glu Gly Pro Ser His Gly Gly
50 55 60

Leu Pro Gly Ala Ser Ser Glu Lys Gly Arg Lys Thr Tyr Pro Thr Val
65 70 75 80

Lys Ile Cys Asn Tyr Glu Gly Pro Ala Lys Ile Glu Val Asp Leu Val
85 90 95

Thr His Ser Asp Pro Pro Arg Ala His Ala His Ser Leu Val Gly Lys
100 105 110

Gln Cys Ser Glu Leu Gly Ile Cys Ala Val Ser Val Gly Pro Lys Asp
115 120 125

Met Thr Ala Gln Phe Asn Asn Leu Gly Val Leu His Val Thr Lys Lys
130 135 140

Asn Met Met Gly Thr Met Ile Gln Lys Leu Gln Arg Gln Arg Leu Arg
145 150 155 160

Ser Arg Pro Gln Gly Leu Thr Glu Ala Glu Gln Arg Glu Leu Glu Gln
165 170 175

Glu Ala Lys Glu Leu Lys Lys Val Met Asp Leu Ser Ile Val Arg Leu
180 185 190

Arg Phe Ser Ala Phe Leu Arg Ala Ser Asp Gly Ser Phe Ser Leu Pro
195 200 205

Leu Lys Pro Val Ile Ser Gln Pro Ile His Asp Ser Lys Ser Pro Gly
210 215 220

Ala Ser Asn Leu Lys Ile Ser Arg Met Asp Lys Thr Ala Gly Ser Val
225 230 235 240

-continued

Arg Gly Gly Asp Glu Val Tyr Leu Leu Cys Asp Lys Val Gln Lys Asp
245 250 255

Asp Ile Glu Val Arg Phe Tyr Glu Asp Asp Glu Asn Gly Trp Gln Ala
260 265 270

Phe Gly Asp Phe Ser Pro Thr Asp Val His Lys Gln Tyr Ala Ile Val
275 280 285

Phe Arg Thr Pro Pro Tyr His Lys Met Lys Ile Glu Arg Pro Val Thr
290 295 300

Val Phe Leu Gln Leu Lys Arg Lys Arg Gly Gly Asp Val Ser Asp Ser
305 310 315 320

Lys Gln Phe Thr Tyr Tyr Pro Leu Val Glu Asp Lys Glu Glu Val Gln
325 330 335

Arg Lys Arg Arg Lys Ala Leu Pro Thr Phe Ser Gln Pro Phe Gly Gly
340 345 350

Gly Ser His Met Gly Gly Gly Ser Gly Gly Ala Ala Gly Gly Tyr Gly
355 360 365

Gly Ala Gly Gly Gly Gly Ser Leu Gly Phe Phe Pro Ser Ser Leu Ala
370 375 380

Tyr Ser Pro Tyr Gln Ser Gly Ala Gly Pro Met Gly Cys Tyr Pro Gly
385 390 395 400

Gly Gly Gly Gly Ala Gln Met Ala Ala Thr Val Pro Ser Arg Asp Ser
405 410 415

Gly Glu Glu Ala Ala Glu Pro Ser Ala Pro Ser Arg Thr Pro Gln Cys
420 425 430

Glu Pro Gln Ala Pro Glu Met Leu Gln Arg Ala Arg Glu Tyr Asn Ala
435 440 445

Arg Leu Phe Gly Leu Ala Gln Arg Ser Ala Arg Ala Leu Leu Asp Tyr
450 455 460

Gly Val Thr Ala Asp Ala Arg Ala Leu Leu Ala Gly Gln Arg His Leu
465 470 475 480

Leu Thr Ala Gln Asp Glu Asn Gly Asp Thr Pro Leu His Leu Ala Ile
485 490 495

Ile His Gly Gln Thr Ser Val Ile Glu Gln Ile Val Tyr Val Ile His
500 505 510

His Ala Gln Asp Leu Gly Val Val Asn Leu Thr Asn His Leu His Gln
515 520 525

Thr Pro Leu His Leu Ala Val Ile Thr Gly Gln Thr Ser Val Val Ser
530 535 540

Phe Leu Leu Arg Val Gly Ala Asp Pro Ala Leu Leu Asp Arg His Gly
545 550 555 560

Asp Ser Ala Met His Leu Ala Leu Arg Ala Gly Ala Gly Ala Pro Glu
565 570 575

Leu Leu Arg Ala Leu Leu Gln Ser Gly Ala Pro Ala Val Pro Gln Leu
580 585 590

Leu His Met Pro Asp Phe Glu Gly Leu Tyr Pro Val His Leu Ala Val
595 600 605

Arg Ala Arg Ser Pro Glu Cys Leu Asp Leu Leu Val Asp Ser Gly Ala
610 615 620

Glu Val Glu Ala Thr Glu Arg Gln Gly Gly Arg Thr Ala Leu His Leu
625 630 635 640

Ala Thr Glu Met Glu Glu Leu Gly Leu Val Thr His Leu Val Thr Lys
645 650 655

Leu Arg Ala Asn Val Asn Ala Arg Thr Phe Ala Gly Asn Thr Pro Leu

```
            660                 665                 670

His Leu Ala Ala Gly Leu Gly Tyr Pro Thr Leu Thr Arg Leu Leu Leu
        675                 680                 685

Lys Ala Gly Ala Asp Ile His Ala Glu Asn Glu Glu Pro Leu Cys Pro
    690                 695                 700

Leu Pro Ser Pro Pro Thr Ser Asp Ser Asp Ser Asp Ser Glu Gly Pro
705                 710                 715                 720

Glu Lys Asp Thr Arg Ser Ser Phe Arg Gly His Thr Pro Leu Asp Leu
                725                 730                 735

Thr Cys Ser Thr Lys Val Lys Thr Leu Leu Leu Asn Ala Ala Gln Asn
            740                 745                 750

Thr Met Glu Pro Pro Leu Thr Pro Pro Ser Pro Ala Gly Pro Gly Leu
        755                 760                 765

Ser Leu Gly Asp Thr Ala Leu Gln Asn Leu Glu Gln Leu Leu Asp Gly
    770                 775                 780

Pro Glu Ala Gln Gly Ser Trp Ala Glu Leu Ala Glu Arg Leu Gly Leu
785                 790                 795                 800

Arg Ser Leu Val Asp Thr Tyr Arg Gln Thr Thr Ser Pro Ser Gly Ser
                805                 810                 815

Leu Leu Arg Ser Tyr Glu Leu Ala Gly Gly Asp Leu Ala Gly Leu Leu
            820                 825                 830

Glu Ala Leu Ser Asp Met Gly Leu Glu Glu Gly Val Arg Leu Leu Arg
        835                 840                 845

Gly Pro Glu Thr Arg Asp Lys Leu Pro Ser Thr Ala Glu Val Lys Glu
    850                 855                 860

Asp Ser Ala Tyr Gly Ser Gln Ser Val Glu Gln Glu Ala Glu Lys Leu
865                 870                 875                 880

Gly Pro Pro Pro Glu Pro Pro Gly Gly Leu Cys His Gly His Pro Gln
                885                 890                 895

Pro Gln Val His
            900


<210> SEQ ID NO 7
<211> LENGTH: 899
<212> TYPE: PRT
<213> ORGANISM: Homo sapiens

<400> SEQUENCE: 7

Met Glu Ser Cys Tyr Asn Pro Gly Leu Asp Gly Ile Ile Glu Tyr Asp
1               5                   10                  15

Asp Phe Lys Leu Asn Ser Ser Ile Val Glu Pro Lys Glu Pro Ala Pro
            20                  25                  30

Glu Thr Ala Asp Gly Pro Tyr Leu Val Ile Val Glu Gln Pro Lys Gln
        35                  40                  45

Arg Gly Phe Arg Phe Arg Tyr Gly Cys Glu Gly Pro Ser His Gly Gly
    50                  55                  60

Leu Pro Gly Ala Ser Ser Glu Lys Gly Arg Lys Thr Tyr Pro Thr Val
65                  70                  75                  80

Lys Ile Cys Asn Tyr Glu Gly Pro Ala Lys Ile Glu Val Asp Leu Val
                85                  90                  95

Thr His Ser Asp Pro Pro Arg Ala His Ala His Ser Leu Val Gly Lys
            100                 105                 110

Gln Cys Ser Glu Leu Gly Ile Cys Ala Val Ser Val Gly Pro Lys Asp
        115                 120                 125
```

-continued

```
Met Thr Ala Gln Phe Asn Asn Leu Gly Val Leu His Val Thr Lys Lys
    130                 135                 140

Asn Met Met Gly Thr Met Ile Gln Lys Leu Gln Arg Gln Arg Leu Arg
145                 150                 155                 160

Ser Arg Pro Gln Gly Leu Thr Glu Ala Glu Gln Arg Glu Leu Glu Gln
                165                 170                 175

Glu Ala Lys Glu Leu Lys Lys Val Met Asp Leu Ser Ile Val Arg Leu
            180                 185                 190

Arg Phe Ser Ala Phe Leu Arg Ala Ser Asp Gly Ser Phe Ser Leu Pro
        195                 200                 205

Leu Lys Pro Val Ile Ser Gln Pro Ile His Asp Ser Lys Ser Pro Gly
    210                 215                 220

Ala Ser Asn Leu Lys Ile Ser Arg Met Asp Lys Thr Ala Gly Ser Val
225                 230                 235                 240

Arg Gly Gly Asp Glu Val Tyr Leu Leu Cys Asp Lys Val Gln Lys Asp
                245                 250                 255

Asp Ile Glu Val Arg Phe Tyr Glu Asp Asp Glu Asn Gly Trp Gln Ala
            260                 265                 270

Phe Gly Asp Phe Ser Pro Thr Asp Val His Lys Gln Tyr Ala Ile Val
        275                 280                 285

Phe Arg Thr Pro Pro Tyr His Lys Met Lys Ile Glu Arg Pro Val Thr
    290                 295                 300

Val Phe Leu Gln Leu Lys Arg Lys Arg Gly Gly Asp Val Ser Asp Ser
305                 310                 315                 320

Lys Gln Phe Thr Tyr Tyr Pro Leu Val Glu Asp Lys Glu Glu Val Gln
                325                 330                 335

Arg Lys Arg Arg Lys Ala Leu Pro Thr Phe Ser Gln Pro Phe Gly Gly
            340                 345                 350

Gly Ser His Met Gly Gly Gly Ser Gly Gly Ala Ala Gly Gly Tyr Gly
        355                 360                 365

Gly Ala Gly Gly Gly Gly Ser Leu Gly Phe Phe Pro Ser Ser Leu Ala
    370                 375                 380

Tyr Ser Pro Tyr Gln Ser Gly Ala Gly Pro Met Gly Cys Tyr Pro Gly
385                 390                 395                 400

Gly Gly Gly Gly Ala Gln Met Ala Ala Thr Val Pro Ser Arg Asp Ser
                405                 410                 415

Gly Glu Glu Ala Ala Glu Pro Ser Ala Pro Ser Arg Thr Pro Gln Cys
            420                 425                 430

Glu Pro Gln Ala Pro Glu Met Leu Gln Arg Ala Arg Glu Tyr Asn Ala
        435                 440                 445

Arg Leu Phe Gly Leu Ala Gln Arg Ser Ala Arg Ala Leu Leu Asp Tyr
    450                 455                 460

Gly Val Thr Ala Asp Ala Arg Ala Leu Leu Ala Gly Gln Arg His Leu
465                 470                 475                 480

Leu Thr Ala Gln Asp Glu Asn Gly Asp Thr Pro Leu His Leu Ala Ile
                485                 490                 495

Ile His Gly Gln Thr Ser Val Ile Glu Gln Ile Val Tyr Val Ile His
            500                 505                 510

His Ala Gln Asp Leu Gly Val Val Asn Leu Thr Asn His Leu His Gln
        515                 520                 525

Thr Pro Leu His Leu Ala Val Ile Thr Gly Gln Thr Ser Val Val Ser
    530                 535                 540

Phe Leu Leu Arg Val Gly Ala Asp Pro Ala Leu Leu Asp Arg His Gly
```

-continued

```
545                 550                 555                 560

Asp Ser Ala Met His Leu Ala Leu Arg Ala Gly Ala Gly Ala Pro Glu
                565                 570                 575

Leu Leu Arg Ala Leu Leu Gln Ser Gly Ala Pro Ala Val Pro Gln Leu
            580                 585                 590

Leu His Met Pro Asp Phe Glu Gly Leu Tyr Pro Val His Leu Ala Val
        595                 600                 605

Arg Ala Arg Ser Pro Glu Cys Leu Asp Leu Leu Val Asp Ser Gly Ala
    610                 615                 620

Glu Val Glu Ala Thr Glu Arg Gln Gly Gly Arg Thr Ala Leu His Leu
625                 630                 635                 640

Ala Thr Glu Met Glu Glu Leu Gly Leu Val Thr His Leu Val Thr Lys
                645                 650                 655

Leu Arg Ala Asn Val Asn Ala Arg Thr Phe Ala Gly Asn Thr Pro Leu
            660                 665                 670

His Leu Ala Ala Gly Leu Gly Tyr Pro Thr Leu Thr Arg Leu Leu Leu
        675                 680                 685

Lys Ala Gly Ala Asp Ile His Ala Glu Asn Glu Glu Pro Leu Cys Pro
    690                 695                 700

Leu Pro Ser Pro Pro Thr Ser Asp Ser Asp Ser Asp Ser Glu Gly Pro
705                 710                 715                 720

Glu Lys Asp Thr Arg Ser Ser Phe Arg Gly His Thr Pro Leu Asp Leu
                725                 730                 735

Thr Cys Ser Thr Lys Val Lys Thr Leu Leu Leu Asn Ala Ala Gln Asn
            740                 745                 750

Thr Met Glu Pro Pro Leu Thr Pro Pro Ser Pro Ala Gly Pro Gly Leu
        755                 760                 765

Ser Leu Gly Asp Thr Ala Leu Gln Asn Leu Glu Gln Leu Leu Asp Gly
    770                 775                 780

Pro Glu Ala Gln Gly Ser Trp Ala Glu Leu Ala Glu Arg Leu Gly Leu
785                 790                 795                 800

Arg Ser Leu Val Asp Thr Tyr Arg Gln Thr Thr Ser Pro Ser Gly Ser
                805                 810                 815

Leu Leu Arg Ser Tyr Glu Leu Ala Gly Gly Asp Leu Ala Gly Leu Leu
            820                 825                 830

Glu Ala Leu Ser Asp Met Gly Leu Glu Glu Gly Val Arg Leu Leu Arg
        835                 840                 845

Gly Pro Glu Thr Arg Asp Lys Leu Pro Ser Thr Glu Val Lys Glu Asp
    850                 855                 860

Ser Ala Tyr Gly Ser Gln Ser Val Glu Gln Glu Ala Glu Lys Leu Gly
865                 870                 875                 880

Pro Pro Pro Glu Pro Pro Gly Gly Leu Cys His Gly His Pro Gln Pro
                885                 890                 895

Gln Val His
```

<210> SEQ ID NO 8
<211> LENGTH: 23
<212> TYPE: DNA
<213> ORGANISM: Artificial Sequence
<220> FEATURE:
<223> OTHER INFORMATION: Synthetic Construct

<400> SEQUENCE: 8
ccacacgcct cttgacctca ctt 23

-continued

<210> SEQ ID NO 9
<211> LENGTH: 21
<212> TYPE: DNA
<213> ORGANISM: Artificial Sequence
<220> FEATURE:
<223> OTHER INFORMATION: Synthetic construct

<400> SEQUENCE: 9
tttgggctct gttcgacggg t 21

<210> SEQ ID NO 10
<211> LENGTH: 181695
<212> TYPE: DNA
<213> ORGANISM: Artificial Sequence
<220> FEATURE:
<223> OTHER INFORMATION: Synthetic construct

<400> SEQUENCE: 10
ggttgggccc agagcttttg tggacctaag gggaccgaag aaagaaggca ggccacctac 60
ctcaatggtg ctgccatcag gcaggtagta ctgagctttc tctgtctcta gcgtctcatc 120
cttttggggg tttatggata ggtaacaggc tctctgcaga tccaagcaag acagtcaggc 180
tggcaggaaa tctggtgcac atccagtcaa aggcccaggg gaggaatgtg ctgctgcaca 240
aacctgtcta aacgttgtga tggccccaat ggtcactata gctgctgccc agaagcaggg 300
gcagtgaggt ctctgttggc cttcactggg tggcatttag catatgagtt cttaaccgct 360
ccaccttcct gatgggcaag cttggaaact tggcccctgg atcctaggtc tgagaccaca 420
acctaagttc agcccaggcc caggcatctt tctccttcta ccactcatat ggttctggtc 480
ctacccagct cgagttttcc ctatagccac aggtggcagg aggtttcagt ttacttacaa 540
agacaaatgt tttaaatgta ttatgacttc ttcaaggatg ttaaaaaaat aaaaataaaa 600
aaaccaggag tgggcgcggt agctcatgct gcaattctag cactttggga ggctgaggcg 660
ggcagatcac ttgtggtcag gagtttgaga ccagcctgat caacatggtg aaaccatgtc 720
tctgctaaaa atacaaaaat tagtggggtg tggtggcagg cacctataat cccagctact 780
tgggaggctg aggcaggatt caagcgattg cttgaacccg ggaggcagag gttacagtga 840
gccgagatca caccattgca ctgcagcctg ggcgacagag cgagactcca tctcagaaac 900
aaaacaaaat gaaacaaaac caaaccctat gtaatttgca tataaggtat aaaaaacata 960
ctgagcccct atgtagccat cacccaactg aagaaatgga agcagctccc tttcccccaa 1020
caagatggca gcacgtcagg aaggcgaatc tgtcagtgtg acgtagggga gacctggctg 1080
ggaagaacaa ggcctcacca gggacccccca ggcaggtgct ttgcctggct tcactggcag 1140
gtcaccaagg tcctgggtgc tatgctccca acccccactc catccctagg cccagggggc 1200
agcacttact tcttttatgg ccttgacaat ctcaaactca gaggatgagt ggaagtcgta 1260
gccctcctta cgcaggtaga ggcgcaggaa gcgagagacg tcccggcccg cgatgtcgat 1320
gcgcatgatg gagtggggca tggcaaagcc ctcatagatg ggcacagcat gggtgactcc 1380
atccccagaa tccagcacca cccctgtggt cctgcctgta gcgtaactga agcaaagggg 1440
caaaccgtca ctcagcactg cctcctcacg ctgggaagaa atacacttct ttatttaggg 1500
ttcaatgtca gctaaactaa agcttgggcc tgcctctctc cagggtctgt agaatggact 1560
gggtactaag gaagcccagg tgttggagca agccatgaaa tacctgaacg gaagttgctg 1620
atcttctcca agttccctcc ccgtacccag aagagcaggc cttcctgtct gagatggcct 1680
ggccttcagc tgcttcagag acccagccta ggggccagtt ttaactctct agacaaaagg 1740
caaaaaccct caaatgtcaa caggggccag gcaggaaaag taagagtaaa gaaaaataag 1800
aatatttttc acttccataa aaaacaaagg caggagaaga ccctgcttta ctggtttgag 1860
agcccgggga cctttgtcag cctccctcca aaaaaaggca agtgaggcaa ctgacccccct 1920
gcttcagtgc ggagaggcca acagagcatg gacaggctgt ggggagggtg ggcttgccag 1980
ccccatctca agtggcagcc gctcttcagc tccagctgat ttttgccctg tgggaatgtg 2040
tgcccgacct tcccagatct tcccattttt tcagagaagc caaaaatttg ggttttgatg 2100
ggacacctct tgatttttaa atgctggctc acagtttgtt aatggggtca aataaatccc 2160
acgtgtaggt cacttgtgga taatctctgc cgtagacctc actctggtgt gaggtggggt 2220
aggagtgtga caggagccac gggggatggg aacaaggact gtggtggcat tcggatcatg 2280
gttgtctcac agcctggcag agcagctggc cacagtaagt gctgaataat aagtggacac 2340
attacggggg cctccgggaa gagctgctgc agcatgtggc tgcctcggca ggcccagcca 2400
aggccttggg gaccaaaccc actaggagtc ctgacactgg gatatggtca atagcagcca 2460
catgtccttc tttgctttca actacgaagc ctcagtgctc agtttcagca aaagcctctc 2520
tctctttccc accatcttta acctttccct agcagagggg gctcaagtta ctctgaacca 2580
ttccagagga gagccagcct cagctgtgcc aaaggactgc tttccccgca ggggccgggc 2640
tagccagctg ctactcacag gctgagtaca gcttgcatgg agatgaaaag agcgggcaca 2700
ttgaaggtct cgaagaaaac ttcggcagct cgttcccggt tttttcgtgg gtttaaaggc 2760
gcctcagtca ggagcacagg atgctggtga aaggagcccg ggagacaatg aggccaaggc 2820
cagatttcca tcttcattag tcttagggga gaagaccctg ccttgctggt ttgagagccc 2880
ggggacttca gtcagcctca ctccaaaaaa aggcaagctg tgcctgtcaa ctatccctgc 2940
ccaagtagtt ttctcaactt ttcaagttaa tgcccacttt aaaatttcat tctgtcctca 3000
gctgtgcccc ccaactcccc tccttgtcct ccaagattgt tatacaggcc cctgtgtcta 3060
ctgtgtatct ccaactgtca agaagatttt gtgaaactct aaattcctgc cgcagaccag 3120
ttctagtctg tgacctgtta ggaaccaggc tgcacagcag gaggtgaatg gcaggtaagc 3180
gagcattatt gtctgagctc cacctcccat cagatcatcc aaggcactag attctcatag 3240
gagtgtgaac cctactgtga actgcgcatg tgagggatct aggttgggca ctccttatga 3300
gaattgaatg cctgatgatc agaggtggaa cagcttcatc ctgaaactat ctggccaccc 3360
caaacccccca cccccatgga aaaactgtct tccaagaaac tagtccctgg tgccagaaag 3420
gttggggacc actgctttaa aaaaactgtc tgaaaacagc cgggcgtggt ggctcacacc 3480
tgtaatccca gcaccttggg aggctgaggc gtgcggatca tctgaggtcg ggagttcgag 3540
accagcctga ccaacatgga gaaaccccgt ctctactaaa aatacaaaat tagccgggct 3600
tggtggtggt gcatgcctgt aatcccagct actcaggaag gctcaggcag gagaatcgct 3660
tgaacctggg aggcagaggt tgcggtgagc cgagattgcg ccattgcact ctagcctagg 3720
ccacaagagc gaaactccat ctcaaaaaag caaacaaaaa aaacccaaaa ctgaaaacat 3780
cccacctgca cctggaaatt gatacaccta gtctgcacct ctctgcattt tctttctttc 3840
ttttttttt tttgagacaa ggtctcactc tgtcaccagg ctgcgagttc agtggtgcga 3900
tcttggctta ctgcaacctc gatgccccca ggctcaagca gtcctcccac ctcatcattt 3960
caagtagctg ggactacagg cacgcaccac tgtacccggc tattttttt tttttcatat 4020
ttttagtaga ggtggtgttt cgccatgctg cccaacttgg tctcaaactc ctgagctcaa 4080

-continued

```
gagatccacc caaagtgctg ggattacagg catgacccac agtgaccagc ctccctttac   4140
atttttgaat ggagagttac ttccttacaa gttaataagc acaggctgca caaggtggct   4200
cacgcctgta atcccagcac tttgagaggt ggaggcggat agattgcctg aacccaggag   4260
ttcgagacca gcctgggcaa catggcaaaa ccttgtctct acaaaaaata caaaatttgc   4320
caggtgccat ggctcatgct gtaatcccag ctacttggga agctgaggca ggagaatcat   4380
ttgaatccgg gaggcagagg ttgcagtgag cctagatcac gccattgcac tccagcctgg   4440
ccaacaagag caaaacccca ccacacacac acacacaaaa ttagccgggc atggtggggg   4500
gtggggctga gatgggagga ttacttgagc ccaggaggtc gaggctgcag tgagctattg   4560
cactccagtc tgggtgaaag aagttaatga gcacaggctt tgaattctaa aagacatagg   4620
tttgaattcc atctctaccc tttgttcact tggtgacctt ggaaatacca cttggctttt   4680
cttttttttt tttttttttg ggacggagtc tcactctgtc acccaggctg gagcacagtg   4740
gcgcaatctc ggctcactgc aagctccgcc tcccgggttc acgccattct cctgcctcag   4800
cctccggagt agctgggact acaggcgccc gccaccacgc ccggagaatt ttttgtattt   4860
ttagtggaga cagggtttca ccgtgttagc caggatggtc tcgatctcct gacctcgtga   4920
tccacccgcc tcggcctccc aaagtgctgg gattacaggt gtgagccacc gcgcccggcc   4980
acgacttggc ttttctgaac ttgttccctt gtttgtaaaa tgagataata ctacctatat   5040
ctcataggaa tggtgttaag attaaatctg aatatgcctg aaaatcaaat ggctccagca   5100
ctcttggcag tgatcatcgt cctcctcatc atctctaggg taggagtttg acacagcttt   5160
gcatacccta caggagtgcc ctacacacag gatcctcacc tcctctgaga aagtctgcag   5220
ctggtcctta gaatagacat attgccaaat gcgttccatg tcgttccaat ccttgacgat   5280
gccatgctcc atgggatagc ggattgaaag cagccctcgg tgctcctggg aaaagagaac   5340
aggacttacg actgcagtca ggctccaccc aggaccctgt tctcccaaga ctaagcagtg   5400
caagctgaat cccttgcaaa gaagcctcag cttcctgagc ttccaccctg ctgtccttgc   5460
ccagggctaa gggtgggcac tcattctcca aggctaaata ctgtttgctg caaactgccc   5520
tcattcccga ggagccggca aagcaggggc ttctgcattt ccatggcccc tcaggtgcct   5580
ctagggcaag tggcaggagg catcttcctc attgcctggt tccaggacac aatctcctgg   5640
ctcccacctc tgggcctcag cacttgaagc caaggatggc aacagcgatt ctgctatctg   5700
cttacaagag gctgcatgag ggctctgaca aagctgtgtg aattaactca tccctagggt   5760
accccagcca ggatctcccc actgaatatt ttttgtgaaa aaaataataa acacagtaaa   5820
tttgatcact gacaaggcag tgacaggatg cagaagacaa cagccctgtt tcctagactg   5880
gtctcagtgt gtcccaaagt gaggtcccag gtattttctt ctccaagacc acaggctgtt   5940
cctgggaaaa ataaaccacc taagcctagg atgagagaat caaaaaggag attttcagag   6000
aaagttgccc cttttactta tgggtatgtc caaatgttgg gacatgttcc atgtggtgaa   6060
taatgaaggt cctctgctgg cttaaggctt gttctgtagg cctgggaatt acctcagctt   6120
tggggccaat gaagatgtcg ccttcaaggg ctcctgccat gacacgaacg tgcttgggtc   6180
ggcccacact agaaaagaca gtgaggagga ccatcatttt tcatttcatg acagaacaca   6240
ggaaggatgt atagatgtac atacacactc aaattctact gagattatct tcaaggagtg   6300
aagtcacagt tgattttgat tttcttcttt atacttttct gtattttcca caatttctaa   6360
aatgaacatg tattatttat atattatttc atattttata tttattataa attatgaaaa   6420
caaattttta gagtatttaa tacctctagt tcttctcttt ctgcagtgta tgaacagacc   6480
```

-continued

```
aagaaagatg aggaaatgag aatttctaaa ggagtgatta actcaaaaca ttttagtgtc   6540
cttagtcccc ttcccaggac ctctaagtaa aactgatgct gggctgggct cgatggctca   6600
cacctataat cccagcactt tgggaggctg aggcaggtgg atcatttgag gtcaagagtt   6660
tgagaccagc ctggccaaca tggtgaaacc ccatctctac taaaaataca aacattagct   6720
gggcgtgatg gcacatgcct ataatcccag ctacttggga ggctgaggca cgagaatcgc   6780
ttgaacctgc aaggcaggag ttgcagtgag ccgagattgc gccactgcac tccagcctgg   6840
gctacagaat gagactccat ctcagaaaac aaaaaaaact gtgatgctat agatcggaca   6900
gatagcctct tcctttcctc cccctttaag cccttcctgt aagcctctgt gctcttctcc   6960
tgcctgcagt ctctctgtct taggaggaaa gttctgagaa actcctcatt aagatggtag   7020
aagggctgta atcccagcac tttgggaggc cgaggcaggc agaccatgag gtcaggagat   7080
caagaccatc ctggctaata cggtgaaatc ccatctctac taaaaataca aaaaaattag   7140
ccaggcacgg tggcaggcgc ctgtagtccc agctactcgg gaggctgagg cagaatggtg   7200
tgaacccggg atgcagagct tgcagtaagc caagatcaca ccactgcact ccagcctggg   7260
caacacagcg agactccgtc tcaaaaaaaa aaaaaaaaaa aaaaagatgg tagatgggtt   7320
aaatgttaat ccccagcctg ggtgatagga gaattttaaa aggagggctc caccaagagg   7380
caatcctcca aagcaataag ttaccaatga taaaattttt tagcatcaga taaaattgga   7440
tttttaaaaa gaggcctctt atctgtgcct ctcaaattgt accatgtaga caactgtttt   7500
cctttgttga ctccaaactc ggctcctgtc ccttataggg ctgggcctgt aacaaagctg   7560
atgagcctcc aaaacgtcta agctacagaa tgacttacta gtttggaaag cagtatttgg   7620
ggatctgatc accagcaaaa ccagctttaa tcacaccgga tccctgagga aagaggagag   7680
agaatgagga gtcagaacta tcacaaatac aaaaggaaaa atacattata tggtaccatt   7740
tttatttaag aaaagaaagc ggccgggcgc agtggctcac acttgtaatc ccaacacttt   7800
gggaggcaga ggcaggcgga tcacttgagg tcaggagttt gagaccagcc tagccaccat   7860
ggtgaaagcc tgtctctagt aaaaatgcaa caattagctg ggcatgttgg caggcacctg   7920
tagttccagc tacttgggag gctgaggtgg gagaatcact tgaatctggg aggcagaggt   7980
tgcagtgagc caagattgtg ccactgcact ccagcctggg tgacagactc tgtctcacag   8040
gaaaaaaaaa acaaaactaa tatttgtata taatatatac atttatttga acctagaaaa   8100
aggtaaatgc acaccaaaag aagggaagtg gaaataggat ggtgaggagg attctcactg   8160
tatacacaac cgtatgtgtg atttttctgt agtctctgac ttttctacat tgaacatgtt   8220
ttgctttggg aattaaaaat actagtaata aagggaagaa aaagacagaa aacctgggga   8280
aagaagaaag tacctagaag catcaaagca gccaagttca ggaacataag gtaggaaaag   8340
cacatgactc cttgttacgc caccctgggg tgcttttaac ctactttccc agctcaggcc   8400
tgaactctcc cagcttccag ggcctctgtg acagacaccg ccatgagcac tgtcatgctt   8460
gaaatggact cccatggaac acgtgctgtc tggttcttat tgcaagggca gagcacgatg   8520
ctttgggaga tttttgttgt tgttttcttt ttaactatgc tttcctttta ctccttggtc   8580
tcctgatggt aaagagaagc aaagactaaa gcctactctg agaatagaag agaaccacag   8640
tcctgctgct ccaacacttg gtatgtcgag tgaggtgtcc agaaaagaat ctgagttctc   8700
ccagcatctc aggtaccacc cagggcccaa tcaatgtaaa cagtgactct ggacacagag   8760
accaaccctg tgcaggacag atgtcaaggc ttagtattgc ttgtagatac accctgtcct   8820
```

```
cttccttttt tttgagatgg agtctcgctc tgtcgcccag gctggagtgc agtggtgcaa   8880
tctgggctca ctgcaagctc tgcctcccag gttcatgcca ttctcctgcc tcagcctcct   8940
gagtagctgg gactacaggt gcccaccagc atgcctggct aatttttttt tttttttttt   9000
agtagagaca gggtttcacc gtgttagcca ggatgatctc gatctcctga cctcgtgatc   9060
cgcccgcctt ggcctcccaa agtgctggga ttataggcgt gagcccaccg tgcccggcct   9120
tttttttttt ttttttttga gacagaatct cggtctgtca cccaggctgg agtgtggtgg   9180
cacaatctca gctcactgca acctccacct cctgggttca agcgattctc ctgcctcagc   9240
ctcctgaata gctgggatta caggcgcgca ccaccatgcc tggctaattt ttgtattttt   9300
agtggagatg agggttcacc gtgttggtca ggctggtctc gaactcctga ccttgtgatc   9360
cacctgcctc ggcctcccaa agtgctggga ttacaggcat gaaccaccgc gcctggcctc   9420
ttcttccttc ttaactcttc taccaccaca cctgataccc tcacctttct aacccaacat   9480
ggtttgcagc tgcacccgta gctggggcaa gccttttcct gctgcctgtt gaccactctc   9540
ctggggtgga gtgtggtatt tactgacctc attctacaag cactgaacac acctggagac   9600
tctaagtagc caaggttatc tgcaccaaag gcttcccagc aacatgcctg cttccctcct   9660
tgactctctt attcctgctc ttctgcagga agagggggag tgagactggc catctggtgc   9720
ttgcctttgg caagacagag gttggtggag gaagcaagtg gttgaaggaa gccaggtgtg   9780
gtggctcacg cctgtaatcc cagcactgtg ggaggccgaa gcggggcaga tcacatgagg   9840
ccagggagtt caaggccagc ctggccaaca tggcaaaaca ctgtctttac tacaaataca   9900
aaaattagcc aggtgtgcta cacgtctgta atcccagcta ctcagggagg ctgaggcagg   9960
agaatcactt gaacccagga ggtggaggtt gcagtgagcc aagatcgcac cactgcactc  10020
tagccaggga gacagagtga gactccacct caaaaaaaaa aaaaaaaaaa aaaagaagtg  10080
gttgaagggc agagaaagtg gtatgagagg agagcagggc agccagttct ctaagggagc  10140
aggaatcttt gccaacagaa gagagtgaaa acagaagaca atgtgcaaac tcattggact  10200
gggcagtaca acaaggagcc tggaaaaggt gcagctgtca agtgagctga aagactggga  10260
aggaggggca atttgcctac aaacccaagg gctctgagag caaggcacgg acaggcaagg  10320
ggggaactcc tagaacttgt ttgctcaggc ttccaatgat tgctcactgc cttcatctgg  10380
gtgtggtgat gccaacagac taattgggtc tcccggcaga ggttaaaaac aagagaggat  10440
gagatctgtc cttcagaccc tggatatttt taagagatga ttttcctggg tattttattt  10500
ttagtttact agcaaaagga ctagagtctg ggtaaacagg cagattatga agtcagattt  10560
gtttttctt ctctgtcctt cctagcaaag agtataaaaa gcccagttca aatatcatca  10620
ccttcctcct gaagaaacat ccccagttgg aatgaatgat catcttccta ttatctcaca  10680
gcaaatttcc attacctgta ccacgaggtg gcatgcactt cattctgctt tttattacaa  10740
tgtaaggttt ccactttcgt ctcttttcag ttgaagttcc ttaaggctaa aatacatttt  10800
ggcagtatct ggcatttgct gggtactcaa cagatgctgg ctgagtaaaa ttaaaatcaa  10860
gtgcaaatga ctggcagata gaacctaaag tatggaacct gaatgaccag ctgaaatgac  10920
agaagcccca ggcagaggcg gttcagcaaa ggggaaagca gcactgggag tgatgcacaa  10980
ggtggaacca gacccagcgt gtccttgcag cccccaagca ggcctgccat gccagtcata  11040
gggtgaagaa tcagtggaga atgaggagca gctgagctgc ctcaattctg ctcaagccac  11100
acaaattctg ctcaagagca tacaaaaggg ttatgtccat ttctttaaca gtatttacaa  11160
ctaggaactg tgtacctggc aaataagctg ccactgtctt tgttattcac tctggcaagg  11220
```

```
ccaaatgaaa aaatgcctgg tagaggcttc ttgagtagtc ttggctgggt gtggtaactc  11280
atgcctataa tccaagcact taggaaggcc gaggcacgca aatcactttg aggccaggag  11340
tttgagacca gcctggccaa aatggagaaa ccccatcact acaaaaaata ccaaaaagtt  11400
agccaggcat ggtgatgtgt gcctgtactc ctagctactt gggaggctga gctaggaaga  11460
ctgcctgagc ccgggaggtc gagaccagcc tgcacatggc gaaaccccgt ctctacaaaa  11520
atacaaaaat tagctgggca tggtggttgt gtgcctgtgg tcccagctac tcaggaggct  11580
gaggttggag gatcacttga gtctgggagg tcaaggctgc agcaagctgt aattgcactg  11640
ctgcactcca ggctggatga cagagtaaga taagaccctg tctcaaaacc aaccaaccaa  11700
ccaaccaaac aaacaaaaag tatggctggg tgcggtggcc cacgcctgtc accccatcac  11760
tttggaaggc agatgaggga ggattgcttg aggccaagag ttcgagagac cagcctgggc  11820
aacatggcaa aacgctgtct ctacaaaata ttaattttaa ttttaatttt aatttttttg  11880
agatggagtc tggctctgtc acccacctag agtgcggtgg cacaatctcg gctcactgta  11940
acctccgcct cctggattta agcgatagtc ctgtctcaga ctcctgagta gttgttgtta  12000
caggtgtgcg ccaccacgcc cggctaattt ttgtattttt agtgtagagg gggtttcacc  12060
atgttggcca ggctggtctc gaactcctga tctcaagtga tccacccgcc ttggcctccc  12120
aaagtgctag gattacaggc atgtgccacc acaccaggcc tacaaaatat ttaaaaatta  12180
ctcgggtgtg gtggtgcggg tccatagtcc ttgctacttg ggaggctgag cccaagaggt  12240
cagggctgca gtgagctgtg atcttgccac tgcactccag actgggcgat agagtgagcc  12300
tctgcctcaa aaaatatata caaaaaattc aaaataaggc caggcgcagt agctcacacc  12360
tgtaatccca gcattttgcg aggccaaggc gggcagatca cgaggtcagg agattgagac  12420
catcctggct aacacggtga aaccccgtct tcactaaaag tacaaaaaat tagccgggtg  12480
aagtggtggg cgcctgtagt cccagctact ctggaggctg aggcaggaga atggcgtgaa  12540
cccaggaggc ggagcttgta gtgagcagac attgcgcgac tgcactccag cctggacgac  12600
agtgcgagac tccatctaaa aaaaaaaaaa ttagccgggt gtggtggcac gtgcctatag  12660
tcccagtact cgggaggctg aggcaggaga atctcttgaa cccacaaggg ggaggttgca  12720
gtgagccgag attgcgccac tgcaatttag cctgggcgac agagacagcc tccgtctcaa  12780
aataaataaa taaataaata cacaattttt tttttttttt tttttttga tacggactct  12840
tgctctgtcg cccaggctgg agtgcagtgg cgtgatctcg gctcactgca agctccgcct  12900
cccgggtcca aagccattct cctgcctcag cctcccgagt agctgggacc acaggcgcct  12960
gccaccacac ctggctaatt tttttgtatt tttattttat tttgtttttg tttgagacgc  13020
agtctcgctc tgttgcccag gctggagtcc agtggcgaga tctcggctca ctgcaagttc  13080
cgcctcccgg gttcatgcca ttctcctgcc tcagcctcct gcatagctgg gactacaggt  13140
gcccgccacc acgcctggct aattttttgt atttttaata aagacggggt ttcaccatgt  13200
tagccaggat ggtctcgatc tcctgacctc gataaataca caaatttttta aaaatcagaa  13260
tatctggcaa cactaggccg gtattcctgc atggggacaa ttggatagaa aggagaatca  13320
gttaacattt tggtcaggca tgctcaattc aatgcacctt tcagatttcc cagcctggaa  13380
gaggtgcctt tcaggctatt ctctctcttc tcttttgagt atatttccat tcctgcttgg  13440
cctctgcagg cattgaattt gaaatcccta ttctaggcat ttgcagccac taattggtga  13500
cgtttcttct tccacatggt atctgatttc tttttaccc tcagaggact tagctcagtg  13560
```

-continued

```
tgaagcacat ccttggcttg caaaatatac ataattgaac agtgaaaata tctttataag  13620
tcacctcttc ttcacctttt ctgtcaagct agggatggat tcttgctgaa gctgtacaac  13680
caacagcctg aatatcacac tgcaagtgac agtgttagat aaatacattg acttcatttc  13740
ctcagctaat tctagtgtcc ctaaaaactt aagtgaatca gcattagtag gatcagaaaa  13800
gctgataaca aattgtaaaa gaaaaatttt tttagacaat tagtgaaatc tgaacattga  13860
ctagataact gataagatta aggggttctt gttgatttga ttaggcatga taatagtata  13920
ttgattatgt ttttaaatga gtgtggggct gggcgtggtg gctcacgcct ataatcctag  13980
cacattggga ggctgaggcg ggtggatcct ttgaggccag aagttcgaga ccagcctggc  14040
caacatggca aaaccccgtc tctactaaaa atacaaaaat tagctgggca tggtggtgca  14100
tgcctgtagt cccaactact cgggaggctg aagcaggaga atcgcttgag ccacggaggt  14160
ggaggttgca gtgagcatca ctgcactcca gcctgggcca cacagcagac tccatctcag  14220
gaaaaaaaaa aaaaaaaaaa aaagaatgtg ggagagggaa atgggcagga atgtagttga  14280
aaagattggc caagagtttg ataactgtta cagctaggtg aacgtatgga tgttccttac  14340
actattcctt ctcctttgta tgtttgaaat tgctataata aaaagagata acagtaggat  14400
gatagcactt aagtaaactt tcaaaacaca aacagcacac tcccctgcca aacttaaaat  14460
gcatatgcac ataaaatcat ggatggatct aggcatggtg gcttgctcct cctatactcc  14520
cagctacttg ggaggctgag gcaggaggtt tgctcgagct caggagtttg aggctgcagt  14580
gagctacgac tgcagcactg cactctaatc tgggtgatag agtgagacct catctctaaa  14640
aaaaatttaa aaacaaataa taattaaaaa ttaaaaaaaa tcataggtgg aaaggagcac  14700
aatttttttt tttaaagaga tgggggtctt gctgtattgc ccaggctggc cttgaacaac  14760
acaattctcc tgacttatct tccagagtat aaaaggagga caattttatg atgatggttg  14820
ttttgcggat tatttgtaaa acagagagaa aggatagggt tgccaggcac agtggctcat  14880
gcctgtaata ccagcacttt gggaagctga ggtgggagga ctgcttcagc ccaggagttc  14940
tagatcagcc tggggaacac agggagaccc catttctaca aaaaaaaaaa aaaaggctga  15000
gcaggtggta cacggctgta gtcccagcta cttgggaggc tgaggtggga ggattgctta  15060
agcttggcaa gctgaggctg cagtgagctt tgattgtgcc aatgagcccc aacctgggca  15120
acagagtgag accttgtctc aaaaaaaaaa aaaagatagg gttgtggagg ggtacaaaga  15180
gtcttcaatt atatctgtaa tgttttattt ccttaaaaca tgaaggtgga tgggaacact  15240
aaagcaaaaa aaatactgaa gcaaatatgg caacatcaat atttactaaa tctgggtagt  15300
agacacatgc tacctgggtg cttgttatat accacaccga atttttctgt gtgtttaaag  15360
tatctctctc tctctttttt ttttttaaa gggggctgaa gcagcacaac atccaaagca  15420
aaacaaacaa atgcttagct tattgttgaa cttctgaaga gcctgcattt aggtccatat  15480
agtcacaaag acagttttaa gtttgacagg aatgttgatc cattttaggt tcaggcaaaa  15540
ctgtaaactt agagtttttt tgtttttgtt tttaaatagg ctggagtgag gtgcacgatc  15600
tcactgcagc ctcaaactcc tgggctcaag tgattctccc atctcagcct cctacaggtg  15660
catgccacca agcaagcctg gctaattttt tttttttttt aaagtagaga tgaagtctca  15720
ctatgttgcc caggctggtc tccaattcct gggctcaaac gatcttccag ccttggcttt  15780
ccaaaatgct ggaattacag gagtaagcca ccacatttgg cctggatctt aggaaaaatt  15840
tgagtttcag aataaacata gtattctgat caaagtgtag tcctcaaaat gtggcctagg  15900
agctgctcct atcttacact attctctatg tctttgggaa gaaatgactt atatttggtt  15960
```

ttaaaaaata tctatcatca taaagcttct tgggtgatta aaaaaatacc tatcacttta 16020
ttgttgtcat taaagcacac acctacctgc ccctccattt tcctcattaa attctgatga 16080
aatgacttga tgccagagta agatgaaaga cgtggtcaca attgtcttat gattgggaaa 16140
ggctgtgaac ttaatggggc tctttccctg ctttctttct cctgcattct tttgattata 16200
ctcttctgcc cataaataaa gtgtagcaac atgttaagct atggagttaa catagctagt 16260
gatacattat tctcattata tgtaataagt tgtctcaggt atttcaaata atgtttccta 16320
tacatctacc atcttgaaaa taataaaaac aaaatgaccc cccaaatgtt aaacaacaag 16380
gactacctga gaccgcacat gtaaaaatgt ggcagatttt cagcaaatac taataggaaa 16440
atgacttaag tttctcctac ttcacctttt ggcagaaata ctggcataat aaaggacatg 16500
ttttcccaga gggggaaaaa aaagacaagt caattcttta aatcttgaaa ctaaaaatgc 16560
atcactgctg taatgcattt cgaaacatac taccaggaaa gagaaagaaa aaaattaaga 16620
cgcattagtg taagtgatat taaagaaaat ggccggagat ggaactcctg cctagcaatt 16680
caagaagcaa aggagctggt gggatagaca ggttgttcct tctgcattgc tgatgaaaac 16740
aggaaattga atttctatat atttttcctt tttacaacta agaaaaaggc agaagaagca 16800
caaagagcct ggctaaagac agaaatcgta gtgctctctg aaaatcaaca tcaagaacaa 16860
aaagtcctac tcaattatct gcagtaacta actagagaaa actccccatc ttttctttat 16920
ttaggaatat ctttgttact ttgatagaga tattcagtca ttcatccaat cacccatcaa 16980
tccaatgaaa aaacatttat tgagcacaca gaggtgccag accctaggta tactgtgtgt 17040
gtgtggagag aagtgggtga agtgagacta aaggaatatc atctttctta aatttttttt 17100
cccaacacca ctaaacctgt gggagaatat catctttttc cacaaggatt taatagtcta 17160
gtgagggaga caaaaagatc ctctcaaaaa tgaagtatct gggctgggtg tggtggctca 17220
tgcttgtaat cccagcactt tgggaggcca aggcgggtgg atcatttgag gtcaggagtt 17280
caggacaagt ctggccaata tggtgaaacc ccatctctac taaaaataca aaaattaggc 17340
cgggcgcggt ggctgacgcc tgtaatacca gcactttggg aggccgaggt gggcggatca 17400
cgaggtcagg agatcgagac catcctggct aacacggtga aaccccatct ctactaaaaa 17460
tacaaaaaat tagccgggcg aggtgacggg cgcctgtagt cccagctact cgggaggctg 17520
aggcaggaga atggcgtgaa cccgggaggc ggagcttgca gtgagccgag atcgcgccac 17580
tgcactccag cctgggcgac agtgagactc cgtctcaaaa acaaacaaac aaacaaacaa 17640
acaaacaaac aaacaaaaat tagccaggcg tggtggtgca catctgtaat cccagctact 17700
tgggagtcta ggctggagaa tctcttgaac ctggaggcgg aggctgcagt gagctgagat 17760
cgcacaattg cactccagcc tgggtgacaa agcgagatcc tgttccctcc acccccccac 17820
accaaaaaaa gaggcgtctc tgccaggcac ggtggctcag gcctataatc ccagcacttt 17880
gggaggccaa ggtaggagaa tcgcaacagc ccaggagttt gagaccagcc tggacaacat 17940
ggtgaaaccc ttcctacaaa aaatacaaaa attagccagg ggtggtggcg cgtgcctgca 18000
gccccagcta ctcgggaggc ttaagcggga ggatcacttg agcccaggag gttgaggctg 18060
cagtgagctg tgatcgcgcc actgcatttc agactcagca acagagcgag accctgtctc 18120
caaaaaaaaa aaagaaaaaa aaaatgagct gtctcattga gctcaatcct gccccttttct 18180
aagggggaat aataaaaaca aaatacccat ggagagaagg aaaatttaat gaaaacaaca 18240
acaaaaatat attggaaaaa gcaagcaact tggaactgga tcttagtctg atgactggct 18300

-continued

```
cctcaattcc taaactggat ggtttgaaat ctgttattta acatccctgc atacactggg  18360
gatagtaatt cctatctacc taacagagct gaagcttaaa cgagaacatt gtaatatgcc  18420
taaggtccca agagctgaat caacaaaggg aatctgacag agtcagctta caacagaggg  18480
aactggtagt tttgcctcaa tggagggacc tacaagggac acagacaggg atcaatctct  18540
gtgggaccaa agctttgaat cgaaggcaga aatgcagtcg ttttacaatt ttctcctttc  18600
cccccaaaat aagagcagta tttagattct ttctattggt caatattgat gcttctgcat  18660
ggtggtgctg gcaaaaggga tgacggataa agtactggat ttagggcacc tctgctatgt  18720
gaccttgggc tcacgttacg tcttcgcgct tcagttttct catcggtaac acgaagatca  18780
aagttccttt taaactatgc gtccagtttt tgtgaggatc caactcgaat gtatgtgaaa  18840
acgccctgga agcgctagag cgccaggcaa atattaagtt tggtaatttt ttccccgtaa  18900
gaactaggcg ttccaaagag gaggacaacc tctctgcttc ctttgtcact ctcctttctt  18960
ctcgaccttt accaactttg taatttataa tcacagtaat agctgacatc ctacagcggt  19020
ttctggcacc agattctcgg gccccaccca gatccacacc accaagccgc agcgccggct  19080
gagaccgaag gaaaacttag ccgttctcca cccgcgggcg ggcactcgcc tctaggcccc  19140
accacccaga gtcccggaag ccaatcccca cagccctgga gcactgcccc gccccttcaa  19200
gagggaaaac aatatggcgg caaggaagaa tggcaggggc gtgagccaat caccgcagag  19260
gcctagcctc atccggcaag gctaagaggc ggtatcattg gctaagatgg acagccagag  19320
caaccaatag agcgatcgga aatgggggag agggcgggcg acgggaatct cacacagcgg  19380
ttaaggcccc tagagccaag ggcccaagga ctggcttgga ctataactct ttcctttatc  19440
cactccagag ttctccatcc cacttttgct ggctggccgc cttgcctgcg gactatgtga  19500
taaggggagg aaggaggcgg cggtggctga acgcgcctga caggccgggc cagtgacaaa  19560
gagccggcgg ctcaggctga accccgggaa gcgatccttt cgaggaggag agcccaagtc  19620
cccttataga taggaaagac gcaactcacg ttgtcgatca cgacaggctg gttggcgatc  19680
acatcgtagg actccatggc agaggaatct ctccttctgg ggaaggaact gcccagccgg  19740
gtccgccgct agcgccactg acacgcatgc gcagtctagc cgccggttca gggcggcgag  19800
ggagcggccc gacctcgcct ctgaagaact acaatcccca gcaagctttg cgcctgggtt  19860
agcgatctag cttgctttgt tgcccgccta gtttaagatt gggagtcgca tttccaatgc  19920
gcagtaccct gggatttgtg gtctccctag attaaacagc cagagacaca ggttgatggt  19980
catgttgcat gcctggatct gtagtccctt tgaaggagtt cgcagtgcat gctgaggtat  20040
gtagtcttct cgagtacttg tctgtagttc ggtttggatt ggtcgtaatt catggatgtt  20100
tggattttgc agatcagccc tgccactccc cccgacgttc ccttagacaa tataaggttc  20160
tcatgttttt atttgggtct gtaagacttt aataaacatc tcctagcacc tcacactcta  20220
acaaaaagga aatgttaaca cacgtacgcg agaggacata ttcctacaac aaaggaaaac  20280
aatttaaatt gcataaaatt agctttaagt ttaaaaacct gtacattgtc gttgcctttt  20340
gcattttctt tttttctgca taacaggcta acattgatcc gaagattggc aattggaact  20400
actggtatag gtaatctttt ggtcattaaa acatcatcta agggtttcag aaactgctcg  20460
agtatctctt taattttcat aacgagctag aattgacact gatggttgag aaaatggagg  20520
tgaagagagg ttatgtgtca ctgctttcaa atgagcccag tgcatttttt tctctggatt  20580
atgttctccc ccagccccct tgaaatttca gggacctttt tgtcaatagc cctagaaaac  20640
attagattta ttatcatcta ttaatactaa cgccccatgg atgaatgaat caatccattg  20700
```

-continued

```
tcagatttat gtttaaatcc tagttagcag cgcgtcagca aaacagtaac aaatcctttg  20760
ttggcgcact tctcgctgct ttcgtgggac cttagcacct cagagggtgc tcagcatctc  20820
taaacttggg ttcctcctaa cactaggggg agaccaagag ccttgggaca ctcccaacac  20880
agggagggga ggcggggcct attgtcaagt cacaccttcc ctgcctgtga ctggcacaga  20940
cattagccaa tgggtgcttg gatagggtgc gccggcgccc cgcccccctt agcgccccgc  21000
cgccccgagg caccctctgg cagactcggc ggcggcgaca gcctgggcgg acagtgcgcc  21060
gtgcgcaggc gcggagctag acctcgctgc agcccccatc gcctcgggga gtctcaccca  21120
ccgagtccgc ccgctggccc gtcagtgctc tccccgtcgt ttgccctctc cagttccccc  21180
agtgcctgcc ctacgcaccc cgatggcgga gctgcggcct agcggcgccc ccggccccac  21240
cgcgcccccg gcccctggcc cgactgcccc cccggccttc gcttcgctct ttcccccggg  21300
actgcacgcc atctacggag agtgccgccg cctttaccct gaccagccga acccgctcca  21360
ggttaccgct atcgtcaagt actggtatgc tctgggccgc ggggagacgg acaggcgcgg  21420
gctggaaagg gttaaagcgc cgagggcgaa gtaatttgtg ggaggtggga ggaggggtag  21480
agaatggtta aagcactcag aaggagggct tcttgctgcg agggaaggag ttaaggctca  21540
agttgggaat ggggacaaag gggttaacgg agcccgtggg tactgagggg ttaaccggga  21600
ttaggagaat agagtgagga ctgggggtgt gtgtaggagc agagggggga acggcaggag  21660
cgagggaact gtaaacgtgg tgaaaagagg gggcgcctgt agggggtcat tagtgggcga  21720
ggggaagcca agcgggggcg gccgaagtgg gatgggagag gcgaggcggg gcctggggag  21780
catttgagag ggctttggag gagcgaagcc gaagaagctc agagggcacg agactgcata  21840
gaatgggggg ttcgggggc ccagggctct cctgtggtgg gtaggagggc caaagatgag  21900
ggcctggtgc ttgtggagag aggaggaggt ctccttttga taccttcccg attagctcag  21960
acgtcgtatc agggcaaagc ttttgctttt gaagtttgac ggagcagctc ttcctgataa  22020
actttttgct tactctgcac tgttctcttt ctccgtgcag agcttcctcc tagctctgca  22080
gttgcttcgc tttagggcat taggtagaga gaaccatggt ttggcttagg attgaagggg  22140
ccgacagctt cccacctcca gttggaaata aatggtggag actctgggac cccagcaggg  22200
aggaattgtg cagtgggaca ttaagaggag cttctcggcc atggcctgca gtttctccgg  22260
ggagctgaga gtaaccctca agtagcttta gggtaggaat ggtcttttct aatttcccat  22320
tcctgtttgc agcctgtttc ttccttcagc atttgggcag aacagatgtt ctggggactc  22380
tggaaaagaa cctgtcctca aagtcttgct ggaccaaaaa ctgagatatt ggttgaaact  22440
gtccaggacc acattcatgc aggcattgtg taagatgatc ttcaatgagt cttgaaagac  22500
tgttctgcag ctgcttgggg gtgtagccaa agggtagacc tgaaggggca agtggacatc  22560
tttgctggtt acctctcctt ttaggactga gtcttcctcc tggtgaaaac ctgttgcttc  22620
ccctggacat cggtgtcagt aggctgtgca gggctgaggc cagctgcccg catcaatggg  22680
aggatgccaa gaggccaaca gcgtggagag cctggggacc agccacctgc tgtctaggga  22740
ggattgtagg gaacagcctc ctctgtcaga gtagacggga ggaggtggaa ctggtgtcgc  22800
agtcctctct cactggcgaa ctgttctctg gttgagagga gttgttgaag agcgcttctg  22860
agtggaaagc agctcttgct agcttaatga cccattctca ttgtgccttt atatttaact  22920
atgtgttgtg atgaacttgt tgtcatgtgt caggagaaaa gtgggcctgg gctgggcaca  22980
gtggctcatg catgtattcc caccactttg ggaggccttg aggatccctt gaggccagga  23040
```

```
gttcgagacc agtgtgggga gcgtagccag accctaactc tgttatttga aaaaaaaaaa  23100
aaaaaaaaaa aaaaaagaag tgggcctggc tctgccacgc tgtttgttca ggcctcattt  23160
gagtgtgagg agaaatccct acacagattc aggcaactat ttttatgtca cccaagtagc  23220
cataaaggat agaattgtat gtaaaaggta tgaaagcatg tgcaaaggac taagggcaat  23280
ttttttttcc ttcctgctgc aagcttgtta acagccatat cttcagagat gggccaacat  23340
gtgataatga agaaaaggga ttatacagca ctttgtgaaa gcccttccta gatgcagaaa  23400
agtataaaga gaaacagcac agtgactggt actttctttt ttttttgaga cagagttttg  23460
ctctgtcacc caggctggag tgcagtggca cgatcttggc ttactgcaac ctctgtctcc  23520
cggtttcaag cgattctcgt gcctcagcct cccaagtagc tgatattaca ggcacacgcc  23580
accttgccca gctaattttt gtatttttag tagaggcaga gtttcaccat gttggccagg  23640
ctggtctcga actcctgacc tcaagtgatc aacccacctc ggcctcccaa agtgctagga  23700
ttacaggcgt gagccagtgc gaccagccat cagtgactgg tactttctaa gatgtggagg  23760
ggtttgcaaa aataagatcc tgaaattcat ttatattcct cacatttggg atcccacgag  23820
gtttctagca ggatgactga cccaggctgt ctgggtctgt ctgtggccca gggtagcttg  23880
ggattcattt tgcaatagca gtgtggctct gtgactggtg atccctgagt agtggggaca  23940
ttctaactga aagctgagac tttggtgagc aaggatcaaa gcagagaggc agaacctgta  24000
ctcatggccc acttcagtcc tgcaactgcc ctgcagagag aagttgggtg ttcaaggaat  24060
taagttgagg gatgccctgg gaccttggat aacatcattt gctaagtgta aaatgcgatt  24120
tttttccaca tactcatctg gcctctgagt agtaagtaaa cagaatactc tgtgcttggg  24180
gacagggtta attttatctg actcttggta gttccttgca gttggagttt gaaggttaag  24240
cttctctcct tgatgtgaca ccttgtggga gacttggtga gaaagagggc tgcagggatg  24300
ctgcagatgg agcagagaat ggtaaacaca gttttgcagc ttggtgcagg atggacctag  24360
gctgtagcgg ggcaggtttg gaaatttgca gcaggaaact ggagcaggta tggggcctgt  24420
agtggctctc atctgctctg gagttctgta gctctaatgg ggtctttcca gggatctcta  24480
ctcttttctt tcttcccttg ccccacaaac ttttctaaat ccaacctgtt gtagaattag  24540
tcaagtgatt tgttgaaatc agttaaggca gacatggaga gttgtccctc ttcctctgtt  24600
gagatgctaa gctatttgta gcaactttct taaaagttct ataaataact tagcatttcc  24660
taacagagaa tagggatttc tatccacaaa ggcaaataat atcctggtga aagaggacga  24720
aacaagacca actggtttta aatagtgttt aaattgcctg gtgctggcac cattgactgg  24780
gatcacttgt aacatgtctt ttatttggtt gttagctttc caccagcatg ctatcccagt  24840
tgcaaagtgt actccatcga tgtcccaggg gcaggtgaag cttttgcagt ctgtggaatg  24900
gtcagatgtt tgaggcagct caaatgccgt gtttgtgggc taaatgcaga cttccttcca  24960
ctgatggttt ctatttggtc tatttctcta gctaccaaaa tttcttatcc attttttttt  25020
tttttttttt ttttagacaa agtctcactc tgtcacccag gctggagtgc agtggcgcaa  25080
tcttggctcc ctgcaacctc tgcctctgtt gtccaggcga ttctcctgcc tcagcctctc  25140
aaatagcaaa tagctgggat tacaggcacc tgccaccaca cctggctaat tttttgtatc  25200
tttagtagag atggggtttc accatgttgg ccaggctggt ctcaaactcc tgacctcaag  25260
taatccaccc acttcggcct cccaaagtgc agagattaca ggtgtgagcc accgtgcccg  25320
gccaaaacag gatttttttt aaaaagcact gattactaaa gggaactctt attgtattaa  25380
atcctcagag tgagataata actgaatctc ttccgcaact ccttctcagt tgaatggtgg  25440
```

gggaaattta atgtggtcct gagaggcccc aaatcattta ccatcccagc tctacctttg 25500
atgtggcagt ctctcctggg atcattttct gggtgcagat gctcacaggg cgcagtttga 25560
ctccttctgc agttctctgt gcagaactaa gttaagccta agtttggcct ttgtcacttg 25620
caatgataag agaccagctt tggtctatgg ggtgcaggct ggtgtcagca cagactagag 25680
gctttgggtt tgtttagaac aaactgtaat taacataggg cacaatatag tctttcagga 25740
attagctgtc taagaggctg gagtggagca gagcctctgc ttccaggaac aatgcccatt 25800
ggggatgctt gggatggtct ttcaacagag gccaattgat tgactgatgt acctcttgcc 25860
ttgaagcttg gcatgtatac aggcaccaca gaagagagac aatccctgcc aatctcattt 25920
gggatcggta atttgaaaca ggagaaagca aaatgggtaa ccatccagtc tgttttattt 25980
ctaaaagagg cccagtcttt caggggtagg agaagggagc ctcttgggct tgcagagttg 26040
ggcagcctta gctgtccatc ccttagtctc attctggaga gatgtggcct ctgtttagtt 26100
acctttcacc caggttcctc caggatgggt cctttaggtt tacaaagtag agcgccttag 26160
cttgacattg tctgatttcc aggcttacac taacacccct gtgttttgtt ttttgcaggt 26220
tgggtggccc agaccccttg gactatgtta gcatgtacag gaatgtgggg agcccttctg 26280
ctaacatccc cgagcactgg cactacatca gcttcggcct gagtgatctc tatggtgaca 26340
acagagtcca tgagtgagta tatgccacct gttctttatc cagagcctta ttcctgaggt 26400
cttcctgagc aggggtgaca atgtcatagt gctgtgagca tggtacttct ccgtggaacc 26460
tctgcatttc tgccctctga ctatatctac tcatgccaag gtggtcctcg ttaacacctg 26520
attcctgctt atctagtgca ggaaagtctt gatgagcagg attcccaaat caggtttttc 26580
taagcttgcc ctggagtttg ggctcatagg acaggaaggt agcatggtta tgactcagaa 26640
cttgggctga tgcctctgtg tctacttcct tttattcccc tagcttatta tgaaacattt 26700
taaacataaa gcaaagttgg aaggatttta tagtgaacac tcatataccc acaacccaga 26760
ttctactgtt aactttatac ttgctttatc acaaatctgt tcatctctta tcctttatct 26820
atcttaccta cttcctttta acctgtattt atttattttt ttatcttagt ctgcttccgt 26880
ttgttgccct atatgctttt ttttggagat agggtctcac tctgtcatcc aggctagagt 26940
gcagtggtat gatcatggtt cactgcagcc tcgacctccc taggctcagg tgatcctcca 27000
acctcagcct cccgagtagc tgggacgaca ggcaagcacc accatgccca gctaattttt 27060
gtaatttttt tgtagagaca gggtttcacc atgttgccca ggctggtctc aaactcctgg 27120
gcttaagcag ttcttccacc tcagcttccc aaagtgtcgg gattatgggt gtgagccact 27180
gtgcccaact cagagttcat actgttaatg actgtattct cttgcctttt gagcaattat 27240
atcatgtact ccaataagct accaactatt ttttttagaa acagagtctc gctttgttgc 27300
ccaggctgga gtgcagtggg gtgatcttgg ctcactgcaa gctccacctg ccgggttcac 27360
gccattctcc tgtctcagcc tcctgagtac ctgggactat aggcacccac caccacgccc 27420
agctaatttt tgtattttta gtagagacgg ggtttcacca tgttagccag gatggtcttg 27480
atctcctgac ctcgtgatct gcctgcctcg gcctcccaaa gtgctgggat tacaggcgtg 27540
acgactgtgc ccggcctgct accatctata ttttaaaaag attttttttg gctgggcaca 27600
gtggctcatg cctgtaatcc cagcactttg tggggctgag gcaggtggct cacttgaggt 27660
caggagttcg agaccagccc ggccaacatg gtgaaacctt gtctctacta aaaatacaaa 27720
aaattagcca ggcatggtag catgtgcctg tactcccaac taccccggag gctgaggcac 27780

-continued

```
gagaatcact tgaacctggg aggcagaggt tgcagtgagc tgagatcgtg ccactgtgct  27840
ccagcctggg caacagagtg aaactgtgtc ttaaaaaaat aataattagg ctgggtgtgg  27900
tggctcacgc ctataatccc agcactttgg gaggtcgagg caggcggatc acctgaggtt  27960
gggagtttga gacaagcctg accaacatgg agaaaccctg tctctactaa aaataataaa  28020
attagccggg cgtggtggca catgcctgta atcccagcta ctagggaggc tgaggcagga  28080
taattgcttg aacctgggag gagtaggttg cagtgagcca agattgtgcc attgtactcc  28140
agcctgggca acaagagtga aactccatct caaaaaaaaa aaaaaaagta ataataataa  28200
taataataat gaaaataaac aaagtttttt ttatttatat tcttttgatg gagagtttct  28260
tttcttcaat ttaaatgtaa tctttctatg tttgtattct gtcaattaaa aataaaataa  28320
atagtcttcc ctcaacctca ttagcatggt taatcaagag ctgattttat ttgtattgtc  28380
atatcctctt ctggtttttg ccttttgtac tttttttgccc cttataccat gtcttttcta  28440
tcttggtggt ggctgcttaa cctgggcagg ttgaaagagt agcaggactc gtcctgtcct  28500
gcctttgcat agcgaccaat tctggagatg atgatggtat cataaagaag atgatgatag  28560
ccttttttcc ctttgtttag tacttactgt cttccgtgtc attgtgttaa atgctttaca  28620
atcttatcag ggtctcgtta ttcctatttt atagataaga aaaatgagtc tcttgagggg  28680
ttaaatgaat tgctaaagtt acagatctag gggtaaaaga gctgggattg aattgggctg  28740
tttgagtcca aagtttgagc ttttttgttt tgttttttga gacagggtca cgctctgtca  28800
cccaggcagg agtgtagtgg ctcagtcatg gctcactgca gcctcaacct cctgggctca  28860
agcaattatc ccaccttaac ctgccaagga gctgggacta caggcatgca ccaccacacc  28920
tggctaattt ttcaaatttt ctgtagagtt gaggtctcac tatgttgccc aggctggtct  28980
cagatgcctg ggctgaagcg atcttcctgc cttggcctcc cagagtgttg ggattacagg  29040
cgtgaaccac tgtattcagc ctcagagttt gagcttttaa ccactgggct attccacctc  29100
tctgaacaca ggcctaaccc aacttcctct tctctcttgt taagctcaga ggcccaggtt  29160
tcatctcttc gctggtcacg tgttgggagc aatgtctgca gctgccttta cagccttcca  29220
aatggattca ttgcagtgtc agcagaagga tttgggaaga gggaattaat cttgcctgaa  29280
tggggaccca gcattacagt attaataatg gagatagaat agcaaacaga tgtggggagt  29340
aaagagacta tgctggacct taatttatat ttttaataag aacctgcaga gagtatttag  29400
tgcagctagc ctgtaccttt ttgttgacag atttattctg gttaaaagaa tatcatttcc  29460
tatgtggctt aaggattctt ccagtctacc tgctaggtat aggcccaagg cccaaaataa  29520
catgaagaat gtgattgagc aagcctcata tttcagaagg ggcaacctct taatttgaaa  29580
taggaccttt cttattgttt ttttctggtt taatactatc ctcttacatg tgtttcattt  29640
ctacatggta cagcactttg tattcatatg tcatttatga caagagtgaa acctctattt  29700
gggttttcat gtcaccaatc aagcctagta ttttccagta ttacatcctg gcactagaag  29760
aatgtggaag gaatgttctc agatatttac ccagttctgg tctatgttgc agaagtcaaa  29820
agtacttcta taggctgcgc atggtgcctc atgcctatag tcctagcact ttggaggtca  29880
aggcaggagg atcgcttgag cccaggagtt tgacaccagc ctggggaaca tagtgagacc  29940
ctcccccatc tctacagaaa atacagaaat tagccagaca tggtggtgtg catcgtagcc  30000
ctagctgctt ggggggctga ggtgggagga tcactggagc ctgggagttt gaagctgcag  30060
taagccataa ttgcactact gcgctccagt ttgggtaaca gagcgagacc ctatctcaaa  30120
aaataaataa agaaagaaaa ataataaaac acgaataggt acctttataa ttggctttgt  30180
```

```
actgggatga ctggtttctt tttgatcctg ttaagtttct tgaagaaaaa tgtgattttc  30240
cacacatttc gtaatggtgg ggcctcttta aaatgactta atgaatcctc atttaaatta  30300
gtactcaaag ctaggccaga aaggcaagtg ttctgccatc cagcttaagt gctaaggggc  30360
gctgggttgg aatgatggca aatggatctc tggcaacaat tcttccactg tctgtgtctt  30420
ctcttcagca aaaaaggagc agaagcattg attcattttt tcagcacaca ttcatcaagc  30480
acctactttg tatcagacac agaacatcgt aatagatgtc ttgggggata aaatagcaag  30540
acataattct tgtctgaagg agctcatgtt ctagagggga gataaacatg taaagatggt  30600
tataatattg agtaataaat gctacagtcc atgggtgtaa aacacggtct gggagcagag  30660
cagagggagt aacttctagt gaggctgctg aattgctaga ggctgcagtg aggaggtagc  30720
gtttgagagg aaccctgtag gaaggggcct gggatgccat ctgcagcctg acgcggtacc  30780
aacaacgctt ttaggagtga gagggacttg aaaaaccttc tagctcagta tttcaaaaac  30840
ttctagtgcc actttcataa ttgttgccac ttgtagtatt atttacttca tgttcctttt  30900
aagttatcct ctcctttttt aaactgatat gaatttattt ttatttttat ttttgagatg  30960
gtctcgctct gttgcctagg ctggagggca gtggcgaggt cacggctcac tgcagcctca  31020
accactctgg ctcaaacgat cctcctacct cagcctccca agtagctggg accacaggca  31080
tgcaccacca cacccggcaa attttttttt ttttattgtt gacacgaggt cttgctatgt  31140
tgcccaggct ggtctcgaac tactggactc aagcaatcct cctgccttgg cctctcaaag  31200
tgctggaatt gcaggcaaga gccagtgctc ctggcaacgg catttattaa atgcctgctg  31260
tgtacctcct cctattatga tctttccttc tcctcacagc ctgttgaggg tagggacagg  31320
cagaagcgag gggtcctctg catttcttct tgctcctggc aggcatgctt cagggtcagg  31380
aggggatgcc caccctggta accctaaaag ggatgaagag tatgatgatt tgataagcct  31440
tgggatggcc attttcattc aagttctttc cttattcaca ttcactaaag gaaaccaggc  31500
aagagagcac ttgttttgat caagattctt aagaagccat ttctgaagtt ggagagatgg  31560
aacaagttcc aggtctgggc agccacagga gagaacagag tgcttttcta ggaaccccaa  31620
ggctgctccc aactgacctg agtggagaaa ttgtcctgtg ggactcttcc ctgggacttg  31680
ggaggtgtca gacagctgag cctcagctgc caagtgctgt cggagcttgc agctctggcc  31740
ttccccttca tggccagcta gctgtggact ggaatgtggg gatctatgcg gctgtagaag  31800
tggtttcagc atcactctgt gaggatttct ggctgtccct ggtaccacca acagctctgg  31860
ctagacagag cctatggggc cctaaccgag gctggaaggc tgggtagttg gagagtgcat  31920
ttgagaactc aggcagactt ccctggtggg attttcccag ggcaggtcat ctgctgtaca  31980
agtcgggctg gttccaaaga cagcctttgt gtggagttgg cccaaaagca tgggtcatgc  32040
ccatgcctca ccaccatggg tgatctaggc tctgtctcac aaatgtgact tcttggcgca  32100
catgtccagt ggagtttgga gcagttctgc accccccgtg gggtctggaa ctgccgctga  32160
ccggctttct ggggctgcct ccacccggtt ggtggagagc ctccctttcc cttgtgttct  32220
tcttagctgg gctctgcacc cgcatgagtt atttattaaa acactggata cagattaact  32280
tttccacttg ttgtttagtg tggcctccgt ctcctgcagt tgagaaatgc taatttttcc  32340
tcctcaaagc ttagtttgcc ggaacttttt tttttttttt ttttgagacg gagtcttgct  32400
ctgtcaccca ggctggagtg caatggtgtg atctcactca ctgcaacctc cacctccctg  32460
gttcaagtga ttcacctgcc tcagcctccc aagtagctgg gactacaggc gcatgccacc  32520
```

atgcctggct aattcttgta tttttagtag agacggggtt tcaccatgtt ggccgggctg 32580
gtctcgaact cctgacctca ggtgatccac ccacctcagc ctcccaaagt gctgggatta 32640
caggtgtgag ccatcccgcc tggcctgcag gaacttttta acatgtcgtt tccaagagag 32700
atcctttctt cgccatacac atctgtactg ggagcttggt ccctcctctg gttggacctt 32760
tgccctcctc ctagagctct catgaggctg gcaaccagaa tgcctcccta agccactgga 32820
cccaccccctg gctaagttta gcaggctaaa agaagtgttc tgcaggctca ttggggggca 32880
cacctccctg aagcctggtc cctctgcctt tcctctcagg gatgttcagt gtcaggatga 32940
ctatttgcat gagatggtgg agttccctgc taagaacagg tgatctggac caccaagcaa 33000
gcgtgaggcg tcctttgtca cggcccagtg tggggcaggg cccaacaggg actctccaga 33060
gcccttcctg aggccaaagc tttcacttag ggttggagtt caggccccaa atctctgaat 33120
ttgtgaattt ttaaatgttg aggagaattt cttttctttt tctttctttc ttttcttttt 33180
tttttttttt tttgagatag agtcttcctt tgttgccgag gctggagtgc agtgacacga 33240
cctcgactct gctgagatta tttataggtg tgcgccacca tgcccggcta atttttttatt 33300
tttattagag atggggtttt actatgttgg ccaggctggt ctcagactcc tgacctcaag 33360
tgatctaccc gtctcagcct cccaaagtgc tgggatttct tttcttttgt agctacagga 33420
agacctgtat tgtgggggtt cccagcagat gtctgtgggt gcatggcttc atcctttata 33480
aagcatttca tttgcagcat ggattgtttc ttccttcatg ggtaagggt tacaaattct 33540
ccaattcaga gagtccctca acagttggga aaaaacttgt ccagctggcc cagttaaact 33600
caattttctt ttttttgaga cagagtctcg ctctgttgcc aggctggagt gcagtggcac 33660
gatctcggct cactgcaacc tccacctccc gggttcaagc gattgtcctg cttcagcctc 33720
ccaagtagct gggattacag gtgcccgcca acacgcccag ctaatttttg tattttttagt 33780
agagatgagg tttcaccatg ttggccagga tggtctcgat ctcttgacct tgtgctggga 33840
ttacaggtgt aagcctctgt actggcctaa actcacttct aaaaagcctg tagctgggca 33900
tggtggctca catctgtaat cccagcattt tgggaggctg aggtgggcgg atcacctgag 33960
gtcaggagtt cgagaccagc ctggccaaca tggtgaaacc tgtctctact aaaaatacaa 34020
aaattagccg ggtgtggtgg tgggcacctg taatcccagc tactggggag gctgagacag 34080
gagaatcgct tgaatccagg aggtggaggt tgcagtgagc cgagactgca tcattgcact 34140
ctagcctggg caataagagt gaaactccat ctcaaaaaaa aaaaaaaatt agctgggcat 34200
ggtggcacac acctgtaaac caagctactt gggaggctga ggcaggagaa tcgcttggac 34260
tcgggggcca gagattacac tgagccgaga tctcgccact gcactccagt ctgggttaag 34320
gagtgagact ctgtccaaaa aaacaaaaca aagcaaaaca aacaaacaaa aagaacaact 34380
gagtggtgtg gtattgtaag tgactaccag gccagagtgg tgccaggtag gtcagcgctg 34440
ggaaagttcc ttctcttcct caagagactt ggaagccttt atgggtttga tgcaatctga 34500
tctctcagtc ccgggatttt tccctgttca gcccaccctt ttgggctctc ctcttccaag 34560
ctgtgctgtt atctattttg aatgctattc cccatacctc tcatgtcctg ggtctgagtt 34620
tgctagcctc tcccttatcc acctttctga ttcaggggtc ccaactctgg cctttggccc 34680
ttgactcctg aattcattca tgtatcttgc ctctgaggta ttcagtgcag cttcatttct 34740
tgtttcagtt ctgatgttgt tcctgagatg tgtctggtgg gatcttatcc tctatgacct 34800
cagccctgag gaatggtatc ctcacccgtc caactaactt tgcagcttgc tgtcctgcct 34860
accaagctct tgagaaccag gctgtgcagc acactcacca gcagagctat cttgagtccc 34920

```
ctgtacaggc agaacattgg acaagatgat gtgtttgagt gtggagacaa tgaagaatct  34980
gaccgagcgc ctgcccttaa aaatgcagca tgtgcttggt aggagatggt gaggtccttg  35040
agaaagaaga tgacagtgag gattgggact gggagcagct tcctgtctcc ctgtgacttt  35100
gaggctctct cccctcatcc tgtgatcttc agtgttccaa gaaactttaa acatataatt  35160
attattacaa acaattatag cccttacttt gtataaggca cttttctaag tgctttatat  35220
aaactcattt aatcctcaga acaactctat ggtgtaggac ttattatcct tattttacac  35280
ataaggaaac tgagatgcag aaatgttaag gaactcatcc acccagccag tgaatgctgg  35340
aactgggata taaacccagg cagtctggat ccagtagtca ccacctcctt tttctacctc  35400
ctgcagagag ctggagaatt ctattcagaa ttatgctgct aaattcaaag ttatcttgga  35460
ttaatggaat gaaatgatca agactgagta gagttaacca gaaagtgctt tgtgggggga  35520
aatgttgagc tggatgtaga agctatctat ctaactgtct gtctgtctgt ctatctatct  35580
atctatctat ctatctattt atttatttat ttttgacaca gggcctggcc ctctcgccca  35640
ggctggagtg cactggctcc atcttggctc actgcaacct ctgcttccca ggcttaagtc  35700
atcctcctac ctcaacctcc tgagtagctg gtactgcagg catgcaccat catgcctggc  35760
taatttttat actttttgta gagattgggt tttgccatgt tgcccaggct ggtctcaaac  35820
tcatgagctc aagccatccc aaagtgctgg gattatagac gtgagtcacc gcacccggcc  35880
tggaagcagc ttttaaagaa agggtctggc cgggtgcggt ggctcacact tgtaatccca  35940
gcactttggg aggccgaggc aggcggatca tgaggtcagg agatcgagac catcctggct  36000
aacaccctga aaccccgtct ctactaaaaa aatagaaaaa attagccagg cgtggtggca  36060
ggcgcctgta gtcccagcta ggcgggaggc tgaggcagga gaatggcatg aacccggggg  36120
gcggagcttg cagtgagtgg agatgcgcca ctgcactcca gcctgggaga cagcgagact  36180
ctgtctcaaa aaaaaaaaaa aaaaagaaag agtccttcag ggcaatggca ggagggtaaa  36240
atgggacagc aggtgacagg tgtcatctct caagtcaaga cttcaccaac caggctgggc  36300
atggtggctc actcgtgtaa tcccagcact ttgggaggct gaggcaggtg gatcacctga  36360
ggtcgggagt tcgagaccga cctggccaac atggtgaaac cgtctctact aaaaaaaacc  36420
acgaaaatta gccgggcctg ttggcgggca cctgtaatct cagctcttca ggaggctgag  36480
gcaggagaat ggcttgaacc cacgaggcag aggttgcagt gagctgagat catgccattg  36540
cactccagct ttggcaacaa gagagaaact ctgtctcaaa aaaaaaaaaa aaaagtcttc  36600
tgcaacctta tcgtagtcat ttacagtaag ttgccaggaa agtctgcaac ttttaaaaac  36660
ataaaaattt ctggcttaga tggcaagttc ccatggtcat gctgctgctt ctgtggtcag  36720
ggatgtgccc agcatctcag tgatccttat atcaatgcag atagtcattt aaaatttttt  36780
aaattccttt aatgatttat ttttaatcaa tagactttat atttttgtgg ggtttttttg  36840
agatggagtc tcgctctgtc gctcaggctg gaatgcggtg gcatgatctc agctcactgc  36900
aacctccgtt tcctgggttc aagcaattct cctgcctcag cctcccgagt agctgggatt  36960
acagatgccc accaccacgc ccagctaatt tttgtatttt tagtagagag ggggtttcgc  37020
catgttggcc aggctggtct tgaactcctg acctcaggtg atctgcccac ctcggcctcc  37080
caaagtgctg ggattacagg tgtgagccac cgcgcctggc cagtttcccc tattattaac  37140
accttgcatt attgtggttt atttgttatc attggggaac caatattgat acttattact  37200
accttaagtc catagtttac cttaggcttc actctttgtg ttgtacagtt ctttttctt  37260
```

```
tctttttttt tttttttttt ttttgaggca gagtttcact cttgttgccc aggctggagc  37320
acaatggtgc gatctcagct cactgcagcc tccgcctcct gggttcaagt gattctcctg  37380
cctcagcctc ctgagtagct gggactacag gcacccgcca ccacgcccgg ctaatttttt  37440
tgtatgttta gtagagatgg ggttctacca tgttggccag gctggtctcg aactcctgac  37500
ctcaggtgat ccaaccacct cggcctccca aagtgctggg attacaggcg tgagccaccg  37560
tgcctggcca gttcttgggt tttgacaaat gcatgtcatg tatataccat cacagcacca  37620
tacaaactag tttcactgct ctaaaaattc cttgtgctcc acctgttcat tcctccctcc  37680
cccgaaaccc ctggcaacaa ctgtttggtt ttttttacta tctctgtagt ttttgccttt  37740
tccaaaaggt catagagttg gaatcaaata gtatgtaact tttgcagact agcttctttc  37800
actgagtaat atacagttaa gattccgccg tgccttttgg tgacttgata gctcctttct  37860
ttttatcact tgatactatt ccattgtttg ttatgtacca cagtttattc tttcaccttt  37920
tgaaaaatat cttgattgct tccagtattt tttggcgatt tttaattaag cttctataaa  37980
catttgtata caggtttttg tgtggacata cgttttcaac tcatctgggt aaatccctag  38040
gaatgtaatg ctagatcgta tgttaagact atgtttagct ttatgagaag ctgccaaacc  38100
attttccata gtggctatac cattttttcat tcccactagc aatgaatgag agttcctatt  38160
gtttcatgtc ctcaccagca tttggtattg tctgtttttt ggattttagc cattccaata  38220
ggtgtggagt ggtatctaat tgttttaatt tgcagttctc tcatgacata tgctgttgag  38280
cgtcttttca tatgcttgtc tgtcatctgt atatcttctt tggtgacata tctttgtttt  38340
tcttcctaac ctccagccac tccccattct acctctgccc atacatacct ttttctcaca  38400
tcatgggttc agaccatggg gctaattatg ctttctggca tatttttcttt ttggtcactt  38460
ctcaagccgt taaatgagtt agatccgctg agtaggtgct gggcctacct ctgaattcct  38520
aagttgctgt tggttttaac tggggctggc tcatgagttc tccaccttat attctccaat  38580
gatggtgtct tccataaagt gtagctgcta ctgagatttg caacctcaat cctaaggttt  38640
gagattgatt ctgccctcca gtacagactg tagagagact ggtatgcaga tttgtccatt  38700
ccataccccta ttgggcttaa ccttgccttt gatgagaaat gcatatacca tgctcctttg  38760
aagccccaac cagatctcaa actctcatag ttgaaccagc atcaagaaga caaagtctaa  38820
aactttcctg gcctggcctt ttgctgttaa attcgttatt gttatccaat gtcttagttg  38880
taattttgct ttttttcact tataaaaaca gttgaaccat tttactaaaa atgttgggaa  38940
ttagaaatgg gagaaaacaa ttactgataa tcctatcacc ttttgtttac aattctatgt  39000
ctgttcttat gatgatttct gtaaatgatt ctataaataa ctgggagtga cgctgtccca  39060
gttgtgcaca gggcttttgc tttgcgtgca tctcatcttc ttagtgagga cttaacatct  39120
tctgaggctt ccctgctacc tgcttaacgc tgttgtctga attcagcttg cccactgttg  39180
ctagggtttc tagattctga aaacagcaca tttgcttggg aagatagctc ttacccactg  39240
ccatgttaca ttaacgatat tcccattttt cctccttgac gtctcacagc agtgaagagt  39300
ggtttaggta gtatatgtat gaactgtgct gtttgcctac ttctcagatc acagctttac  39360
tatcacaaat ggtggtagct gtcctgaggg gttgtgttct tccagttgtt gcttttattg  39420
ttattttccc cttagaacag tcaagatttg gtgatcagtg tcacctggaa taaataccac  39480
acgcctcctc ctttctctct ttcttgggtg cgtggtacag aagactgaga ttggcttaca  39540
gagtgcccca gggtccttgt actcgaggga cacagaaggt tcacaggcat aagcacaaat  39600
gcctagagct ccttttcagg taattgcctg aaacaaatgg gctaccattt agggcttctg  39660
```

-continued

```
tcacacagga agtcagataa cttaatacta ctgtatgttt gcagcaggac tagatctaga  39720
gatctagaga aggagtggcc cactgtcctt tcctagcact gggttgtggg taagcagaca  39780
cacttagttc ccatccagcg ttgatcgctg tcctctcttc tttggaaggc cagacgttaa  39840
tctgctccgt agattgtcat cgttgggaca cagttctggg catgaggctt gtagtaacaa  39900
gcaacataaa cctggtcctg gtcctcattg ggctgaaggg tccttgagct agaagacatt  39960
gtggggaggt gggcctgata cagtttcaca gccttaggtt atcacctggt gcctctttgt  40020
ctcctcttca gcagtccatg gcttgaggcc tagtggaggg ctcttggcaa gcaggagtcc  40080
tgaggctcag aaatgatgtg accaggcctg agtttgaggc tgagacagtt gtccatttgt  40140
cagcgagatc atagcttcac agcagcttct cagagaggta tggttcactg gactccaggc  40200
ccctagcatg ttagtaaaag atagtggccc tcacagatcc ctttccttcc tactcctatg  40260
ttactcagtc tcttggagtc cctggtcata gaatcagctt agccacagga aggccaatca  40320
aagagatgtc ttgtttttct agtactaacc ctcatgtgat acctggggcc tcttggagcc  40380
ctgcctccga ccaccagttt ctcttactct gacctcaggc ctttcaacat gatgtcaggc  40440
tgcccacggc catggctgta gggaagagta actgctagag aatgggactt ggcccaggct  40500
accagtccca ggggggtcga gctggctggc tgtgcttttg gcctgtgatg gatttgactc  40560
ttcaaggctt ctgacaaagc ttggttggtt agaggaaaaa tgtagtgaaa acctacaggc  40620
aacaccatgg cttgccctaa ccctctcgtc ttcctgttct agcttttccc atatatcagg  40680
ttgcagacat gctgaattcc caccctcctg gagccaagct gccaatttct cattcctgta  40740
accagtggtt ttgtgtagat aaaaggccca gaaggaagat ggtcgctgag cagggagcct  40800
tcggagttag accttcttta gccagggcca gtggacactc atctcatgaa tcatgctcag  40860
aaccatccag tggcttcatg tctcacttga gtaaaggcca aaggccatca cctttaaggt  40920
cctttgtact ctacttcaat cggccttctc tctgactgct ctgctcttcc tattctgccc  40980
cccttgcttt tcctctgaag tgccaggcat tcttctacct cagggccttt gcacttactc  41040
tccctatgcc tgcaaagttc tgcctgcaga tagcttcata ccttacctca cttccttaga  41100
ccctttcgca aataacttct ctcagttagg ccttccctga cctccttatt taaaaaggaa  41160
atcctgcacc ctcctcccac aaagcagtat ccccctttcc tgcctaattc ttctttttaa  41220
aaagttatat atatttgtat agtcagggtc tcactatgtt acccaggctg gtctcggact  41280
cctggactca agcgatcctt ctgtcttgcc tcctaaagtg ctgagattac agacatgagc  41340
caccgcaccc agcctaattt ttcttttttct tttcttttct ttttttttt tttgagatga  41400
agtctagctc tgttgcccag gctggagtgc agtggtgcaa tctcggctca ctgtaacctc  41460
cgcctcctgg gatcaagcga ttctcctgcc tcaccctccc aagtagctgg gactacaggc  41520
acgtgccacc acacctggct aatttttata ttttttgtag agacggggtt tcaccatgtt  41580
ggccaggctg gtctcaaact cctcaagtga tctgcctgcc tcagcctccc aaagttctgg  41640
gattacaggc gtgagccacc gtgcccagcc tatttcttct ttaaaacact tatcacttct  41700
gcgatgtcta ttatgcttta agaaattttt ttttaaatta ccatctagct tattttactt  41760
acttacttat ttgtcttgtt tattgtctgt cccccctcct tcccactaga acataagctc  41820
cctgaagata aggatggaaa tgtgctttat ccattaatgt ttctccagta catcagtaaa  41880
tatttgttga acaaatgaat aaaatggagg aagctcttgc tttggggttt ttccgactgt  41940
tggaaaaata ttctcaccac tggagacgga gaattctcct ggcccagcac caagcccgag  42000
```

-continued

```
cttttagctc attcaagagc acttcttcag tttggaccct tattcccata ggagaggaga  42060
cattccaagg gcattttcat aggagtcaga acccttctgt gggaggaggt atgtgatttt  42120
ggaaaaattg tctgaacctt gctttatttt attttatttt attttatttt ttatttttga  42180
gacggagtct ctctctgtcg cccaggctgg agtgcggtag tgtaatctcg gctcactgca  42240
acctccacct cctgggttca agtgatcctc ctgcctcagc ctcccaagta gctgggatta  42300
cagggcacgc taccacgcct ggctaatttt tgtattttta gtagagatgg ggttttgcca  42360
tgttggccag gctggcctca aactcccggc cttaagtgat ctgcccacat cagcctccca  42420
aagtgctgag attataagca tgagccaccg tatctggcct gaaccttgct ttatgaggtg  42480
agggagtacc tccatcccag caactggcac agtgcttagt atgtgtcaag cacttaattt  42540
attttctttt tttgtttggt ttgagatgga cccttgctct gtcgcccagg ctggagtgta  42600
gtggtgcgat cttgcgatct cagttcactg caacctctgc ctcctaggtt ccagcgattc  42660
tcctgcctca gtctcctgag tagctgggat tacaggcacg cagtaccatg cccaactagt  42720
ttcttgtatt tttagtaaag atggggtttt gccatgttgg ccaggctggt cttgaactcc  42780
tgacctcagg tgatccacct gcctcggtgt cccaaagtgc taggattaca tgcatgagcc  42840
actgcacctg gcctattttc ataaattttt agagcacatt acctaaatat ccagtgcttt  42900
cttagtgctg aggataccat ggaaagcaaa gcaggcaagg tttctgctct catgaatctt  42960
atattcttat tggagaaaca tgaaaaattt tatatagttt tagatagtac aagtgctgtg  43020
ttgaaaataa agcagggccc cagctactca ggaggctgag gtgggaggat cacttgagct  43080
caggagttct gggctattat gcactatgcc agtcaggtgt ccacactaag ttcagcatca  43140
atatggtgac ctcccaggag catgggacca ccaggttgcc taaggagggg tgacctggcc  43200
cagtaggtca aaactcctgt gctgatcagt agtgggattg tgcctgtgaa tagccactgc  43260
acgccagcct gggcaacatg gggagaccct gtctcttaaa aaaatgaaag taaagcaggg  43320
cgccaagtgt ggtgactcat gcctctaatc ccagcacttt gggaggccac ggggggggtgg  43380
atcacttgag ccaggagttc gagagcagcc tgggcaatgt ggtgaaaccc catctctaca  43440
aaaaatacaa aaattagtca ggcatggtgg tgcgtgcctg tagtcccagc tacttgggag  43500
gctgaggtgg gaggatcgct tgagcccagg aggcagaggc tgcagtgagc caagatcgtg  43560
ccactgcact ccagcctagg tgacagagtg agaccctgtc ttaaaaaaat aaataaaatt  43620
aaaaaagcag ggatggtact ctggagctta catgggtaga agtagtggtt gaggtgggtg  43680
gggaggatgc tgttagcagt aatcagtgat ggcttccttg aagatttgaa ctgagacctc  43740
aaagaccggt ggcagccagg gctgtcacat tgtacaactc tagggccacc gttcacatta  43800
ttctgtgcaa ttgctgcccc ctggagttgt acaatgctgg gagtcctgat gaaggtccta  43860
ggcagtgaaa cagctagtat aaaggccctg agggcagcac ggacctcgaa gtgtttaagg  43920
aaaagaaaga aggccagtgc atctgaggct tggtaagaga gaacagtgga acaagatgag  43980
gttgcagagt ttgaagacaa tgtaaagaat gtgacattca ataaattata attattatta  44040
ttgttttttt tttttttttt ttttgagatg gagtctcgct ctgtcgccca ggctggagtg  44100
cagtggcagt ggtgcgatct cagctcactg caagctccgc cttctggtgt catgccattc  44160
tcctgcctca gcctcccaag tagctgggac cacaggcacc caccaccacg cctggctaac  44220
tttttgtatt tttagtagag acagggtttc accgtgttag ccaggatggt ctcgatctcc  44280
tgaccttgtg atccgcccac cttggcctcc cagagtgctg ggattacagg cgtgagccac  44340
cgcgcccggc cgacattcaa taaattattt gttgactgat gaggaaagaa aaaggatgat  44400
```

-continued

```
atgatggagg ctggagtggg gttttaggaa gcattccagt gtgggacctc agctttagta  44460
tgaagacagg agaactgagt tgagtgacgg ttttatttcc ccaaaaagga aatagtagca  44520
aaagtggctc aaaggaaata ccattaagat atatatatat atatgtatat ttatagtaca  44580
tcatgacatt caaagccatg aagatatttg aatctacttt gatagtgact aagagggagg  44640
cacattgctt tttaatacca tcttatcttg ttgaatgtct cggcttgatt atctctttgg  44700
gtggcagtgg gaatattatt accatttagc attgctcagc catgacatga tgtattcatg  44760
tacagaacac acaaaaagta cagtccttgc ccttggggaa ctgaaatgcc aaaaagattt  44820
gtttcttccc attgccctgt ttaggtttct tgatcttctg ggatggctgg cttcccagag  44880
ttctggagga gagtgggtgg acaaaaggcc cttgggtaga tgccttgcct cttgggtcag  44940
taagaagtcc ccaagctgca tacttaggca cagagggcac ctcgcttccc aaatcagact  45000
gtgatcttgt cgccattggc ctagcctgtc ttttttatt tttaagaaga cctttgtaaa  45060
ggtgttgctt taagccaaag ccaagagtgg gagctaccat attgatgcca agaaacccaa  45120
gcactgggct tcttccttgg cccagaattc ctgtagcgct ccaggctggc ttaggagtcc  45180
cctgggggct ggctgacctt tgagtttggg ggtggttggg agtagatgga agaaggtgca  45240
acagatgtcc agcaggggat ggttgaatgt gagcttttac caccctgcaa gaaagggtct  45300
ggtgcccttg gcttagaatt tctaaaattc agtatcttgg ctggtacaat ggctcacacc  45360
tgtaatccta acactttggg aggccgaggt aggagaactg cttgagccca ggagttcaag  45420
accagcctgg gcaacatagt gaggcctcat ttctacaaat aataaaaaaa attagccagg  45480
catggtggca tgtgtctgta gtctcagcta ctcagtggct gaggtgggag gattacttga  45540
gcccaggaga tcaaggctgt agtgagctgt gatcacggca ctacactcta gcttgggcaa  45600
cagagtgaga ccctgtctca aaaaataaat aaaaataaaa ttcagtgtct tattccagga  45660
aacccttt gc tcactgaaag cccaggacag agttaagctg cctgaagtgt tgggagccgg  45720
aagagtttat ttgactggat tctcagccga atcagtgctg ggagccactg tttttgaact  45780
tgaggaatgc tgtgggaaca tggtctttgg ctcccagcaa aatgtctcag gaaccatcta  45840
cttgagtggg gcaaatgcat tccatgaatc tggttggttg gggtatagcg caaagaaagc  45900
ttctataacc cagagttgca actcaaaggt ggctgctgca ctgtagcctt attggactcc  45960
caggtcagag tatgagagtg cagtcttcgc tgatgtggct tttttccttt ctttttttt  46020
tttttttaa gattatataa aattgattaa atataacgag atttatgggt tttttttcta  46080
ttattttgtt tttataactg gaggcttaaa agcttagcta tatcagaata ttatcatata  46140
aacatatttc aaaagttatt tttacaaagt tttgctacat acagtagtat ttgtgttgtc  46200
acccaacacc attttcaaat gtctaataaa gtatcagtaa ttttgaatta taaataaaaa  46260
ataatctctg cagttgttta tttagtagtt gttgactgaa ttctgttgta atggctgtga  46320
ctcaaagcat ctcacaaagg aaatctcagg tctggttaga aggttctggg agggacccaa  46380
ggtcaggaaa ttgggtgaag ctgaaagcag cttttgaagg actgggctga ttaagatcca  46440
gagcccagaa gttagggaag ctggaggcat ctgctgatat tttaaaggat aaatgatgag  46500
cagagtttgc tttgagtgag tactaagaaa aggaaagttg cagccaggct cagtggctca  46560
cgcctgtaat cgcagcactt tgggaggcct aggcgggtgg atcacgaggt caggagttcg  46620
agaccagcct ggccaatatg gaaggctgag gcagcagtga gccatgatca tgccactgca  46680
ctccagcctg ggcaacagag tgagacttta tctctactaa aaccccatct ctactaaaaa  46740
```

tacaaatatt agccgggagg ccaaggcggg cagatcacaa gatcaagaga tcaagaccat 46800
cctggccaac atggtgaaac cccatctcta ctaaaaatac aaaaattagc tgggcatggt 46860
ggcatgcacc tatagtccca gctactcggg aggctgaggc aggagaatcg cttgaacccg 46920
ggaggcagag gttgcagtga gccgagatcg cgccactgca ctccagccta gcgacagagt 46980
gagactccgt ctcaaaaaaa aaaaaagaaa agaaaaagga aagttgcaca ctaactgccg 47040
tggaagggca cttgctaggt gccagacact gtgctgtcac actaaaacct cccaccctat 47100
gagatgagtg ttcttctccc agttttacag atgaggagcc ttgcacacat ggaagttaac 47160
ttgcccacca gtcagctaga gaaaggtgga gctggggttt gatgggctca gttgcttcca 47220
cagcgtgtat tctcgtccac tttgctgggc tcctctctgg catcttattg ggatgctgga 47280
gtaatatgtt aataatttca tgcagtttcc acctaagtcc acccagagac ctccaaaggg 47340
tccaaagatc gtgagactaa gaatgtctga cacctgcctt cctcacttcc caacttccct 47400
gtctctaagc caggctcaac actctgccta agtccttcag cccataacct tgggctggca 47460
tttagtttct ctttaccttt gtccactatt ttaaatcttt tttttttttt ttttttttaa 47520
tggagacagg gactcactct gttgcccagc ctgagtgcag tggcacagtc atagctcact 47580
acagcctcaa actcctgggc tcaagtggtc ctcatgcctc agcctcttga gtagatagga 47640
cttcaagttt gtgccaccat gcttggttaa tttttaaatt ttttatagag atggggtctc 47700
actatgttgc ccagactggt cttgaactcc tgggctaaag caatcctact gcctcggcct 47760
cccaaagtac tgggattaca ggtgtgagcc accatgtctg gccttctgtg actcttaatc 47820
ccaaggaaat aacccaaata tgggaaggaa acgaggtaat atgcacaaaa atattttcca 47880
aggcatagct ttggaagcaa ccttatgtcc aacaagaaag cagtggtcaa atagaggact 47940
atatatggtt ttcctggttt tgtaataaat gataatagta attatcaaga aaattgtagt 48000
ttcttggctg tgcatggtgg ttcacacctg tagtcccagc gctttgggag gctgagtcag 48060
gaggattgct tgagcccaga agtttgagac cagtccaggc aacatagcaa taccccataa 48120
cccatttcta ccaaaaaaaa aaaaaaaaaa aaaatgtaat caggtgtagt ggtgcacaca 48180
tgtagtccca gctactcagg agactgaggc aggaggatca cttgagcctg gaaggctgag 48240
gcagcagtga gtcacgatca tgccactgca ctccagcctg ggcaacagag tgagacttta 48300
tctctaaaag aataaaaaat aaaaatagta atttcttaat tgtgtaaact gacagatcaa 48360
aaattggaga gccttggagt cttaaccaag gggccaggca cccccagagt caacatcaga 48420
agctcaaaat tgcaggactg gttcagcctc attactccca tcgcccagcc tttgtagtcc 48480
caactggctt tgctggacag gtcacctttc ttgttgagct gatgcccatt cctttgttcg 48540
gctgctttca ctgagcactc ctgtgccagt cagtggggtg tacaaagggg taaatcctgt 48600
cctgatggga gagataggca gctgcaatac agcaaggaga gtcctgtgat ggaggtttgc 48660
acaggggtaa ggaagaagtg atgagagccc tctcttggtc agggtcccaa ataagggatt 48720
ggtgccttca aagtaagata ttggaggaag gtatatttat aaaggaatag catagggat 48780 agtgatgtaa cccagggcta gtggttggcc tggctgtcac tctcctaagg ctgaagggac 48840
cagaagaggg agtgggatcc aagaacctag aggagaaagt tgtgttgagt gttcttgaga 48900
gtgactgtta gcagtgacct tcaatcaagg ggcatagcac ctcgggcaat cccaaaggga 48960
gggaactcta gcctcactct cctcccttct gctgatttcc tgtgagaact tttttttttt 49020
ttgagataga gtcttgctct gttgcccagg ctggagtgca gtggcatagt ggcatgatct 49080
tggctcactg cagcctctgc ctcccgagtt caagcaattc tcctgcctcg gcctcctgag 49140
tagctgggat tacaggtgca tgctactatg ctcagctatt ttattattat tatttttggt 49200
agaaacaggg tttcaccatg ctggccaggc tggtctggaa ctcctgaccc tctagtgatt 49260
ctcccatctc tgccacccaa agtgctggga ttgcaggcgt gagccaccat gctcctgtta 49320
gaactttcac tggcttaacc caattagatg ccagagggcc caggagcccc acacaggcca 49380
gccctctagg gcagggagca gggtggacat actggttttc tgttgctgca aatcagcagc 49440
ttacaacaca catttgttct ctcacatctc ctttgcacca ggagtccagg aatagctcat 49500
ctgagtgcta tgcttaggtc ctcctaaggc tgtggtcaga gtgtcaggcg ggctgcatcc 49560
tcatctgggg ctccagtggg gaaggatctg cttcccagct ccctcaggtt tgtgttggca 49620
gaattccttt ccttggagct gtcagggatc tgtcttgcac agtggggaat ggaagggcaa 49680
acagaagata ctcagagaag gtgacacctg agccttcctg aagatgagca gagggcaaag 49740
aagagaacac ctgcgcagag tttcggaggc aagggagtca tcagtgtgtc cacagatctg 49800
ccagtccatt catttggcct agagtataag gcagaggagg tataggacct gtttcacggt 49860
ggcctagtga gacttactga gaagtctgga ctttgttctg cagattgggg atagggatgg 49920
gctttggagg atttttaagc aggagaaagg tgtatcgttt ccattttggg aacaacactg 49980
aacagcagga ggcaggagat cagtgaggaa gaggttgttg gccacccaag tgaaggatgc 50040
agaaggctaa cgcatggtgt ggcagttgag atggagagaa gaggacagat tgagggccac 50100
tgagaaggga gggggcagag ttgccagaac tcactgactg tctgaccagc tgcacatggg 50160
gagagggagg actggaggat aactcttggg attctggcct ggtggatttt ttagttccta 50220
ttgctgccat aaaaaattac cacaaaatta gtgtcttgga acaatataca cttattgtgt 50280
tataattctg gaggtcagaa gtctaacatg tatctcactg ggtcaaaatc aaggtgccag 50340
gctgggtgcg gtggctcaca cctgtaatcc cagcaccttg ggaggctgag gcaggaggat 50400
ggcttgagcc caggagttcg ggaccagcct gggcaacatg gtggaacccc atctctacaa 50460
aaaaaaaaaa aaaattagcc aagcatggtg gcctgtgctt gtggtcccag ctatttggga 50520
ggttgaggtg agaggatcac ctgagcccaa gaggctgagg caacagtgag ccgtgatcat 50580
gccactgcac tgcagcctgg gcaacagagc aagaccctgt cttgaaaaaa agcaaagtgc 50640
ctgagggaga attcgtttcc ttgctgtttc cagcttctag aggccatgtc cattccttag 50700
ctcacggcca ctccctccat cttcaaagtg agcaacaaca gacaaattct cacgtcacat 50760
ctctctgatc ttttacctgt ctctttcatt aaggattcat ggattagatt gagcccaccg 50820
aggtaattca ctgtaagatc atccccatct caagatccct aactgaatta catttgcaaa 50880
gtccctttttg ccatttaagg tagcatatca caagttccag ggattcaaat gtgggcatta 50940
gggaacattt attcaggcta ccacagtggt gctcttcttc aagctaggta aagatggaaa 51000
gatcaggttt ggtaagatac tgagtttgga tttgtgtaga ctgaactaga agtatctagg 51060
tctggttctt tgcttgggta tagatttggg aatcctcaac agaggtgtgg tggctgaagc 51120
catttcatga ggttgctgaa ggagaccgtg tggtgaggag gggcggagac tgagtcctgg 51180
agaaagtgga actctgggcc aggcgcggtg gctcacgcct gtaatcccag cactttggga 51240
ggctgaggcg ggtggatcac taggtcagga gatcgagacc accctggcta acacagtgaa 51300
accccgtctc tactaaaaat acaaaaaata agccggtgtg gtggcaggtg cctatagtcc 51360
cagctacttg ggaggcggag gcaggagaat ggcgtgaacc cgggaagcgg agcttgtggt 51420
gagccaagat cgtgccactg cactctggcc tgggctacag agcgagactc tgtctcaaaa 51480
aaaaagaaag tggaactctg actttgtccc tctttcccca cctaggaagt cccctagggg 51540
acaggcggag gccacgcaag gggaaatgtt cacgttctgc tttcctagtg aagaggtttc 51600
caatgacggc ctcccttcgc cagactgtcg ttcatcctct gcgtaggtgt aaggggcaga 51660
gcagtggcta gtcctggggc atcatggggc ttgggccagc actgaaggtc ttagagcaga 51720
ttgacaggaa acggtacaaa taggaaaggc agctggcatt ccaagcatgt gctggagttt 51780
gggtgagtgg tccttggact tgcttggcat tgccctggga tacagagaga ttgtagagaa 51840
gctgcaggca gcctctgtaa agccctagag caacaggagg tctgcggttt aggtttctct 51900
atagtctctg ggtccagctg ggcctaaggc tgggcttgtc cctatgcctg ttggagacat 51960
gcatgggaga tgtgtatgtg tgtgcactta gagggaggcc actgaaggaa aaggtctgca 52020
ggtctatacc acccatgccc acctccaccc cctacccct gcacaggatc taggtccatt 52080
cttctggagg gaatagctag cccagtaagg tgagaactca gcctgattcc caaggagaag 52140
ggctggttgg aaaggaggac taaccccagg ataaaggatg ggtctgccca gttctccatc 52200
cagcctggga ccaggaggaa ggggaagagg aagggggaaa gaaagagaca acagggccgg 52260
gcgcggtggc tcacgcctgt aatcccaaca ctctgggagg ctgaggcagg cggatcatga 52320
ggtctggagt tcgagaccat cctggccaac atggagaaac ctcgtctcta ctaaaaatac 52380
aaaaaatgag ccgggcatgg tggcacacgc ctgtagtccc agctactcag gaggctgaag 52440
caggagaatc tcttgaacct gggaggtgga ggttgcagtg agcccagatt gcaccactgc 52500
acttcaacct ggtgacagcg tgagactccg tctcaaaaaa aaaaaaaaga gaaagaaaag 52560
aaagaaaaaa gaaagaaata agagcttttg taggggaaga agtgacatca cccctggttc 52620
tggagttgga ctgggctggc ctcctatgcc atgtgtttcc ggaggcacat ggtcccctct 52680
tccctttctt ctgataccat cactgggctt gagactgagc cataatgcct aaccctggta 52740
cctttgcagg gtcagtagcc accgtggctg gcctggcatt ccttgcttca aagaccaatg 52800
gaagcatcca ggccaccccc agaggaaggg gcctgacctt gggcctctct tgccatgtcc 52860
ttggcatatg catatgaaca cttagcaaca gactatgtga agccttgcac gctagacctg 52920
cagatacagt agtgaccaag atacaaccct gcccttgtgg ggtttatagt ctaggctgga 52980
gatgatgatg atgatgatga tgatgatgat gatgatgatg ttgttgatga ttttaagaca 53040
gagtcttgct ctgtctcgct tcggttagag tgcagtggca ccatctcagc tcactagagc 53100
ctctgtttcc tgggttcaag agattctcct gtctcagcct cctaagtagc tgggactaca 53160
ggcgcccacc aacacacccg gtaattttgt atttttagtg gagacggttt caccatgttg 53220
gccaggctgg tctgaaactc ctgacctcag gtgatccacc tgcctcggcc tcccaaagtg 53280
ctgggattac aggcgtgagc gtgagccact gtgcctggcc aggagattat aaatggtaga 53340
aaattttgga aaatacaaag aagtttgaaa aacaaaaatt atactgtagt agccactata 53400
ataattttat tgcttttttt tttttttttt ttgagacaga acctcactct gttgccaggc 53460
tggagtgcag tggtgcaatc tcggcgcact gcaacctccg cctcccgggt tcaagcaatt 53520
ctcctgcctc agcatcccga gtagctggga ctacaggcgc ctgccactac acctggctaa 53580
tttttgtatt tttagtagag acagggtttc accatgttgg ccaggatggt ctcgatctct 53640
tgacctcgtg atccacctgc ctcggcctcc caaagtgttg agatttcagg cgtgagccac 53700
catgcctggc ctgcattttc tttttccctt atatatttta ctcacattta aaatttcgta 53760
tttacatcaa cattttgaat catactttat gttgaatttt gttttgtgtt ttttcataac 53820
tacttatttg tggcataatg tacataactt atcttttttct taaattatta tactttttga 53880

```
gatggagtct tactctgttg cccaggctag agtgcagtgg tgtgatctta gctcacggca  53940
acttctgcct cctgggctcc actgatcctc ctgcctcagc ctcccgaata gctgggactg  54000
caggcatgtg ccaccaaacc cagctaattt ttgtattttt agcagagaga gggtttcact  54060
gtgttggcca ggctggtctt gaattcctga cctcaggtga tctgcccgcg ttggtctctc  54120
aaagtgctgg gattacaggc atgagccact gcacccagcc tacataattt aaatttacct  54180
ttttttttt ttttttttt gagtcaaggt cttgctctgt cactcaggct gcagtgcagt  54240
ggtgcagcca caacttactg cagcctggac ctcccagact cagtgattct tctgctacag  54300
actccgagta gctgggacca cagctgcaca ccaccatggc cagctaattt ttaaattgct  54360
tgtagagatg ggatgtcctt atgttgccca ggttggtcgc agactcctgg gctcaagcag  54420
tcctcccacc ttggactcct atagtgctgg gattataggc atgatccact gcacccagcc  54480
caaaatttac cattttaacc atttttagat ttacagttca gtggaattaa gtacatttac  54540
cttgttgtgc aaccataacc accttccact ttcagaaaca ctctgtaccc cttaaacaat  54600
aactccccct tctcacttcc tccaaaccct ggcaaccacc atcttatttc tgtctctatg  54660
aatgtgacta ctctgggtac ttcatataag tggaatcata tgacatttgt ccctttgtgc  54720
ctggcttatt tcacttagca taatgtcttc agggttcatc catgttgtag cagatgtcag  54780
aattttcttc ctttttaaag gctaatattc cattatatgt gtataccaat ttggcttgtc  54840
catccatcta ttgactgact cttgggttgc ttctaccttt tgactattgc taataatgct  54900
actctgaaca tcagtataca aatttctatt caagaccctg ctttcagttc ttttggatat  54960
atacctggaa gtagaattgc tggatcatgt ggcaattcta tgtttaattt ttgaggaacc  55020
gccatactgt tttccatagc agctgtatca tcttacattt ccaccagcaa tgtgtaaggg  55080
tcctaatttc atgaccattg tgaaaggagt ttatttttat gctatagtga ataataggtg  55140
aacagaaaac attagaggct atagagtggg gttctgatgt aaagttcctg ttcctcttta  55200
ccagtaagag gtggaaagag aacccctcac ctctcaaaga ttagtccctc tgctttcaga  55260
accattgttt ttagtgactt gtaatgtcct accacataat gtgccagaac tcatataata  55320
ccgctacttg tagaacagtt agattgtttc tagatttttt attcttataa atactactga  55380
atatacttat gcaagaggct tttttttttc caaatgtaag attattccct taggtaaatt  55440
agcagaactg gaaactgcta ctgtaagtaa tcactgacac taagatctac tgtgttccag  55500
gtgctgttct aagtgttttc tatattatat gttaactcat tttagtagct accatatgga  55560
aactacaatt atcttcgttt ttgaaaaaag actttttttag agccgtttta ggttctcagc  55620
aaaattgagc agaaagtaca gagagctacc acacaccctc tgcttaccac acgcatgcat  55680
gcacacacac acatgtatgc agcctctccc gctgtcaaca tccttaccca gattggtaca  55740
tttgttacag tcagtgaacc tacgttgaca catcatcacc acccaaagtt catagtttac  55800
attagaagtg agaaggtata taagtgaaat gtagataaga agagaagtaa actcttctta  55860
tctacatttt acagatgaag aaactgaggt acagagaggc taagtgattt gccaagggtc  55920
acacagccag gaagggtggc agagctagga tttgggcata ggcagcctgg cttcagagac  55980
tgtgctctgg cactgctgac attttggtgg ctcttgatgc atattcagtg ctttttaagt  56040
gtggcagtgt tttgctttgt gcgggtcaga cagtggacac ttcaggatcg gttgaccaac  56100
tgtccccatt tgcctgggct tttcctggta tgtggggctt tcagttctaa agccagaaaa  56160
gtcctgggca aacaagacaa gttggtcacc ctgcttcagt gactccagag tctttttag  56220
```

taacttaatt gtcacatctc ttagatgcct tcaaatgttt cctcaatctt tctgtttttc 56280
atgacctttt gaagagtaca ggtcagttat tttatagaat gtccttcaat ttggatttat 56340
ctgatgtttc ctcatgcgta ggatcagtgt atgtatttct ccataggaat atcacagaca 56400
tgttgtgccc ttcttagtga tcatatcagg aggcacttga tgttgatttg tctaattact 56460
gttgatgatg tctaattact ttgattgttt ggttaaggtg gtgtctgcta ggtttctctt 56520
ctgtatagtt actgcttttc cattaataat taataagtaa cttgtgggaa ggcattttga 56580
ggctatgtca gtatcttgtt tctcatcaga ttttttaccc actattttta ccacccgttg 56640
atgattcttg cctgaattat tattacaata gttgtcaaat ggtgacttct catttgataa 56700
ttgtttctac attcattcat tgatattgag attttactgt aaggaagagt cttctccata 56760
tttacttact tattcattta tttatatcaa tgtattaggg ctctctagga aaaacaattg 56820
gagatgcaca tccacatatc tatatattat ctatacacat aatataaata caaatctata 56880
aagagattta ggagaaagaa ttagctcatg cgattacaga tgctggcaag tccaaaatct 56940
ttagagccag tgtcactagg tccattacaa tcagtgtgga ctcatagatt tttattttaa 57000
ttaatagatt ataatttgtt aggatgcttt aatttaatgc tcagattgtt gttgatttgg 57060
ccagtgagaa ccttgagttt ggcttctctc tacttttggc atgttcccat cattctctga 57120
accacttcct tactttctgg cacagtagga aatttcagaa tcattttgta ctttgccagc 57180
ccaggaatca gccatttatc caggaagccc tggttttatt tagtggagaa tggtatatag 57240
aagccatgat ccggaggcta ggtattatca ttgctcttgg agtgtcactg ctcccagtgg 57300
ccagaactag gaaacacaca tgcacatata cacataccac tctatttcca tattggtttc 57360
tctcttaaat accatgaatt catactgata cctccaattc taaagctata cctatggggg 57420
cctggtgcag tgactcatgc ctgtaatccc agcactttgg gaggcccaag tgggtggatc 57480
acttgaggtc agtagttcaa gaccagcctg gccaacatgg tgaaaccccg tctctaccaa 57540
aaatacaaaa attagccagg tgtgttggtg cacacctgta gtcccagctg ctcaggaggc 57600
tgaggcagga gaatcacttg aacctgggag gcagaagttg cagtgagcca agatcacacc 57660
actgcactcc agcctgggca acagagcaag actctgtctc aaaaaataat aactaactaa 57720
ctaaataaat actatacccg tggcattcat tcctgcctgc ctttaaaata tatatatata 57780
tatatttcag accaggcaca gtggctcaca cctacaatcc tagcgctctg ggaggccaag 57840
gtgggtggat cacttgaggt caggagctcg agaccagcct ggccaacatg gtgaaaccct 57900
gtctctacta aaaatacaaa aattagctgg ccgtgatggt gtgcgcctgt aatcccagct 57960
actcgggagg ctgaggcagg tgaatcactt gaacccggga ggcggaggtt gcagtgatca 58020
gagatcgcgc cattgcactc cagactgggt gacagagcaa gactccatct cgaaaaaaaa 58080
aagttacttg ggttatatct tttcttcccc ctttcagtgt ggttatatgg ttgatttgaa 58140
atactgttag gttcattaat ttctgtttgt attatatttt agcattttct ccctcctcat 58200
tgattctgtt tcatttattt tgagtatgtg aaagcattat cacggatcca aaaccaaaag 58260
tgagaactat acaaaaaggt atattcaaat aaatgttacc cacctccaca ccctgcagtg 58320
ctttctaccg ccttcccacc tactgtatgt aagaatccat ctcattcatt tttggtttat 58380
ccttcccaca tggctttcta cagaaatgag taggtaatgt atattttcct acttttcttt 58440
ctttctttct ttctttcttt ttttttgaga tggagtctcg ctctgtcacc caggctggag 58500
tgcagtggtg cgatctcggc tcactgcaac ctctgccttc tgggttcaag cgattcccct 58560
gcctcagcct ccctagtagc tggaactaca ggcatgtgcc accacgcctg gcaaattttt 58620
gtatttttag tagagacgag gtttcaccat gttggccagg ctggtctcca actcctgacc 58680
tcaggtgatc tgcctgcctc ggcctcccaa agtgctagga ttgcaggcgt gagccaccgc 58740
gcccggcttt tttttttttt tttttttttt tccttttgag acagttttgc tcttggtgcc 58800
caagctggag tataatggtg tgatctcggc tcaccgcaac ctccacctcc caggttcaaa 58860
caattctcct gcctcagctt ccctagcagc tgggattgca ggtgtacacc gccatgcccg 58920
gctaattttt tttttttttt ttttttttga gacagagttt cgctcttgtt gcccaggctg 58980
gagggcaatg atggtgcgat cttggctcac tgcaacctct gcctcctggg ttcaagcagt 59040
tctcctgcct cagtctcccg agtagctgag attacaggca tgcgccacca tgcccgacta 59100
attttgtatt tttggtagag atggggtttc tccatgttgg tcaggctgga cttgaactcc 59160
cgacctcaag tgatccaccc accttggcgt tttttttttt gagatggagt ctcactctgt 59220
tgcctgggct ggagtgcagt ggcgtgatct cggctcactg ccacctctgc ctcccggatt 59280
caagcgattc tcctgcctca gcctcctgag tagctgggat tacaggtgca cgccaccact 59340
cccagctagt tttgtatttt ttagtagaga cagggtttct ccatgttggt caggcaggtc 59400
ttgaactcct gacctcatga tccgcccacc tcggcctccc aaagtgctgg gattacagat 59460
gtgagccact gcgcccggcc tatatatata tatatttttt tttaagtaga gatggggttt 59520
catcatgttg gccaggctgg tcttgaactc ctgaactcag gtgatccacc tgctttggcc 59580
tcccaaagtt ctgggattac agatgtcagc caccatgcct ggctcctatc ttcctttctt 59640
tcttcctcaa aaacatacta taatatcctt ttgctctttt tttttttttt ttgagactga 59700
gtctccctct gtcacccagg ctggagtgca gtggcgtaat cacagctcac tgtaccttct 59760
gcttcctgga ttcaagcaat cctcctgcct tagcctcctg agtagctggg actacaggca 59820
cgtgccacca tgcccagcta atttttgtac tttttgtgga ggcaaggctt cgccatgttg 59880
cccagcctgg tgtcgaattc ctgggctcaa gcaatctacc ggctttggcc tcccaaagtg 59940
ctggaattac aggcatgaac caccgtgccc agcctctttt gctttttttcg cctaacagtg 60000
tttataccaa tttgtagagt tcttcattct ttcttacagc agcattttct tacagcactt 60060
tgagtcattc tcctataaat gggcatttag gtgatttcca gtattttgca attataagtt 60120
cttagaagtg ggattgctgg atccaaaggt ataaacctat acgtagtttt attaggtact 60180
gcctaattct cctccatata agttgtacta atttatatcc ataccggcaa catatgagag 60240
tgtctcttcc cccacaacct cagcaacaga atatgatgtc atacttacta atttttgcca 60300
atctgatagg tgagaatggt atctcattgt tttcatttgc atttctttta ttatgtgtga 60360
ggtcaaacat cttgtcttat gcttaaggga tatctgtata tctcgtttgt gaatttttttc 60420
tatcaggttt ttgagttttt tccaaattaa aaaataaatg aataaagcat ttattgatat 60480
aattaatgta gcatacagtt cacccattta aaatgtacgc tttcatggtt ttttgcatat 60540
ttatagttat gtaaccttca ctacaatcta attttagaac tttttcttta ccctgaaaag 60600
aaactccatc catattcatt agcagttact cccaattcat ccccactacc ccagtcctag 60660
gcaaccatta atccactttc cccatagatt tgtccattct ggacatttga tgtaagtata 60720
atttatatta tatattacga attatacaat ttttcctgta atataaataa aatcatacaa 60780
catatggtct tttgtgactg gctttcttca cttaatgtaa gtgatataat gcttatagtg 60840
ttctgagtac tgtttccaaa tgtttaatcc ccaataacaa ctctatgaaa cagttactgt 60900
tattatcccc attttataga tgaggaaact gacacacaga agaggttaaa tagcttgcct 60960
ctggtcacac agccataaga agatagactt aattaggcaa aaatagatta attaggcaca 61020
cacttgtaat ttcagctact cgggaggctg aggtgagagg atctcttgaa cccaggaggt 61080
catggctgtg atgagccctg attgtgcagc tatactccag cctgggcagc agagtgagac 61140
cctgtctcac aaaaaaaaga tgagctttgg agttatacag acttcaagtt ctagctctat 61200
cacttgttct gtgatttatg gactattaca caaactccat cagtgtttct catttgtttg 61260
ttaaatgagt ataacaatgg ctgagtccta gagttataga gagttaaacg atatgacatc 61320
aggtatacct gagatgccag ctttttaaaa ataaatcata taccatgaaa ttcaccctgt 61380
taaagtgtgt aattcattgg tttttaagta tatttataag gttacacaac cagtacatta 61440
tctaattcca gaacatttcc atctcccagg ccaggcacgg tggctgacgc ctataatccc 61500
agcactttgg gaggccgaga cgggcagatc acttgagatc aggagtttga gaccaacctg 61560
gccaacatgg tgaaacccta tttctagtaa aaatacaaaa attaatggtg tggtggcacg 61620
cgcctgtagt cccaactact tgggaggctg aggcaggaga atcgcttgaa cccaggaggc 61680
agaggttgca gtgagccaag attgtgccac tgcactccag cctgggcaac ggagtgagac 61740
tctgtttcaa aaacaacaac aacaaaaaag aatttccatc atcccaaaaa gaaattctgt 61800
acccatcagc agtcactccc cattctgtcc tcaccctagt ttctggcaac caccaaccta 61860
ttttctgtct ctatagattt gtctattatg gacatttcat aaaaatagaa tcatacaata 61920
ggtagtcttt tgtatctggc ttctttcact tagcatgatg ttttcaaggt catccatgtt 61980
atagcgtatg catacttcat tctttttat ttccaagtta tatttcattg tacaggtata 62040
ccatattttg tttatccatt cctcagttga tggacatttg ggttgtttct actttttggc 62100
tactatgaat aatgctacta tgaacattga tgtatacgtt ttcatgtgaa caggttttct 62160
tttttctttt ttttttaga caaggtctta ctctgtcacc cagggtggag tgcagtggca 62220
ccatcaaggc tcactgctgc cttgacctcc ctcggctcag atgattttcc cactgcctca 62280 gcaccccac cctgggtagc tgggactaca ggtgtgagcc accatgcctg gctaattttt 62340
gtattttttt tttttttttt ttttgtagaa acggggtttg gccatgttgc ctaaggtggc 62400
ctcaaactcc tcggctcaag tggtccatcc acctcggtcc cccaaagtgc tggtattaca 62460
ggcatgagcc actgcatcca gccaggtttt cagttctctt gggcatatac ttaggagtgg 62520
aattgctgga tcatatggtg actctgttta acttttttag gaactgccaa actcttttc 62580 caaagtagct ccatcatttt atattccccc taatgatgtg caagtattcc tatttctcca 62640
cgtcctctct aacacttact atctcttagt tatgatagag ggtgtggagg ggcagtagct 62700
cactgtggtt ttgatttgca tttccttagt aataaataat gggctgggca cagtggctca 62760
cgcctgtaat cccagcactt tgagaggtag aggcgggcag atcatctgag gtcagaagtt 62820
cgagaccagc ctgggcaaca taatgaaacc ctgtctctac taaaaataca aaagtcagct 62880
gggtgtggtg gcacacacct gtaatcccag ctactcagga ggctgaggca ggagaatcac 62940
ttgagcccag gaggcagagg ctgcagtgag ctgtgatcgc accactgcac tccagcctgg 63000
gagacagagt gaggctcggt ctcacatata aataaataat ggtgttgagc atgagatgct 63060
gactttcagc agtcattttg ggctcttgga tgctcactga taccttctta gtgaggtact 63120
ctgggggaga cctttgggtg agttctgatg gtcaggctgt tgtgtgtcta ggattcaagg 63180
catgtgttct tgtctttggt ttgatgttac tcttggggct ggcacagcca tcaggcagac 63240
ttgccaaact gctgggacaa agccagcctt cccccggaca cccccgtgaa caggatccag 63300
ggttcttgag caggaaacaa tcttgagagt cttatctcat ccttcctttt gcaataagac 63360
agttagaacc ccttaccccc actctgccag cctgggaaga attttttct ttctttcttt 63420
aatttctata ggaagaaatt ccactggccc cagttaccac cagccagtat tttagtagac 63480
ttctgtgtta gaaaaatgct ttgctctgac ccagatccca ccttctgcag cacatgccaa 63540
tttcccctta tactttcctt tcttggaaga tgtgagagac agccgctccc taggaggggc 63600
ttcattctct gttcagacaa aaccactttg gctagagaag ccctcatgtg aggaagtcca 63660
gaccaagcca ggcccctcca ggagacttta aagatggaat gaccttgtca cttggtgatt 63720
gcttgggcag cctgctttga aaaagagaac ttctgacaga cttcaggtcg tgtgtttatc 63780
ctgaggctgg gccattccaa actcatgttt cagggtttag aggttgcgtc cagccagccc 63840
gtgggtggta atcaaatgca ggtggagacc atctggccgg gcctgtccct cccacccagc 63900
caagtaaggg ctggcctgcc caccacagaa ctggcccaga aagcaccctg cgtggaggca 63960
gatggtggac acatgcgtgt gcacgcatgc acacctctag gcgcgtgtgc acggaccctc 64020
cttagtgaag tggtgctgtg tggatgcatc tgatccagtg atttctttct ctgcatttga 64080
gggttcttcc cattgtgcag ccgaagagga acaagtttct tttagtctgt ttctcaagtt 64140
tttgtggtta gaaatcatgt acgtttcttg gcccaagatg aaagccctgg agtaatagtc 64200
taatacattt tacaaagctg cctctaattg gtggctgctt aaaatcttcc ctttgcccta 64260
ctgacccatc tccctttaca gagttttaac tctagtcaat cttgcattac tccatgtttt 64320
cacacccctc ccaaacctgc agctccaggg aggtagctct tccaacttca gtttgatagc 64380
tgttccctca gcctgcctgc actgaattga cctcaaacag ggtaattcag caaggaaata 64440
aaatagctta caatgtgttg tccaagcatc ttctgctggc ctggtctcca aaattccacg 64500
tgtgtaccct caaaatggat tctgtttccc acattgctat agatacctgg ggaaaatgaa 64560
accgtggata cttcatttaa acatagttgg gccaggtgct gtggctcttg cctgtgttcc 64620
tagcactttg ggaggccaag gcgggaggat tacttgagcc tgggagttca aggactagcc 64680
taggcaatgt gttgagacct gtctctacaa aagttttaaa aattagctgg acatggtggt 64740
gcacacctgt ggttccagct acttgggagg ttgaggtgga aggattgcct aagaccggga 64800
ggtcaaggct acagtgagcc atgttcacac cattgtatag agcaagatgc tgtctcggaa 64860
agaaagagag agaggcgggg gggagagaga gagagaaaga aagagagaaa gaaagagagg 64920
ctgggcatgg tggctcatat ctgtaatccc aatactttga gaggctgagg ccaaaggatt 64980
gcttgagccc aggaatttga aaccagtctg ggcaacatag ggagacttta tctctactaa 65040
aaaaaaagaa agaaattagc caggtgctag gtgccatgat gtgccagcta ctcgggaggc 65100
tgagacaaga ggatcgcttg agcccccagg agttcacaca tgcagtgagc tgaagatcac 65160
gccactgcac tccagcctga gtaacagagc gagaccctgt ctcaaaaaaa tacatagatg 65220
atagagagat agagagatag atagatagat acatacatac atagagtttg atcatgatgg 65280
tttctaatga taccttttca gtccattgga gaacttagct tctcagaggt gatctttccc 65340
tgcaaagtgc aggaggtctg ggttcaccca ggcacagaaa actaggacag atgtcagctt 65400
ctgagacttg ggaatctctt tctatcccat ctcctggcct tgcctctcgg ggtgatgatg 65460
atcatgatga agaaaagatg ccacgtggaa ttctagggtt gggcattgac tgcatcatca 65520
gcccttgaga attctcacct ctgatcacct gtttcaggag cttggttggc tgtcatctta 65580
gtttatggtt tgtgtttgta tgctgacgag tttacaggtg tataatcatt gtggctcatg 65640
tttgtacaag atataattac tgaaaattat atcatgaatg tattttaatt ttaaccttcc 65700

-continued catgctggca agcctcatgt agctctccct ggatgcttcc cttacctggg gaggtgtggc 65760
accccaccag ccaggcccag ctctctgatc cacatcactg ccctctctga tggaagtccc 65820
tttcagggac ttccctgaga cttggggctc ctgagtgttt cctacaaaca gggaggcagg 65880
gattcctgct ttctctcatt gtcactttaa tgaattgtgg ccacagaagc agtcatcctc 65940
attattctgg gtcactgagg gatgggaagg gagggcaacc catgcatctc tagggttcca 66000
gcaattgaag agtacatgtg gagtgccagg tttcaggaag agcttgtgct aattgaggag 66060
tgtgtgttgg gtgctgagtt tcaggaagaa tatgggccca cccagtattt ggaatctgcc 66120
ttaggacctg tccacaaatg ctgagtctgg aggccagcca gtgccaccca aggttgtacc 66180
cttgtgggca gagtggaggt gggagtggag aaagggtctc atcctcacag agtgtattaa 66240
tccattctca cactgatata aagacatacc tgagattggg taatttataa aggaaaatag 66300
gtttaattga ctcacagttc cacatgactg ggaagacctc aggaaactta caatgttggt 66360
ggaaggagaa gagggtggca ggcacaagag agtgggcaaa agcagagaaa actgccctat 66420
aaacccatca gatcttgtga gaactcactc actatgacaa gaacactgtg gaggaaacca 66480
cccctgtgat ccagttatct cccacctggt tcctcccttt acacgtggag actatgggga 66540
ttacaattca agatgagatt tgggtgggga cacagagcca aaccatatca cagagcatat 66600
agccttgtgg ctcacaggac atgtatcctt agcaaacaaa gtagatgcct attaatagct 66660
tgaaggaata aggagcatga acaagggaga ttttcagcag tgttgcctca atcatccagg 66720
aaggaatgtt ccagagccac aaaatttgga actcataatt cagagtgcca gcagtagaat 66780
ttggccaggc caaggtcaca tccacatacc cgcagctggc aggaggatga ggcaagagtt 66840
ctggttcctt atgggcttct caggttccct ccccacaagg ctcacatcct gggatactcc 66900
tctgaatgga ggatttggat actgaggcca ccataaaaag ggggagaact ttagactttc 66960
aagagagtgt ttttcctaag gtaattgagc ttaaaacact tgctttttat gtctttcagg 67020
tttacaggaa cagatggacc tagtggtttt ggctttgagt tgacctttcg tctgaagaga 67080
gaaactgggg agtctgcccc accaacatgg cccgcagagt taatgcaggg cttggcacga 67140
tacgtgttcc agtcaggtag gaggccaggg ctggctgctg tgctggtcct tttgccatga 67200
gcctggttga ctttgagtac tagcagctat attttgatgt ttgtggagtg gcctttcctg 67260
ggagtactat gccccaattc taccatgagg atggcttgtt ttgcctggtg tttcctggtt 67320
ggaaaaccaa ctgggccatg gcagagaggg gtactcccct gtgccctcca gcagcaagtt 67380
ctgtgttatg ttgtgccacc ctgcaccctt gtcgtgtttc atggagggtt tctttcatgt 67440
catctgatat atgtttctct gtggctaatt gctcagaagc atttcccatc tgatctcaga 67500
ttttgtttct ttgtttttgt aagtagcctt caaatgaagg ccaagatact tttcccaacc 67560
ttttgctctt gaaatatcac agataaagtt cagagcaagc catggtctct caaagcatgg 67620
ttcttatacc acctgcctct gaactacctg gagagcttgt tgcaaataca tattcctagg 67680
ccccattgca gatgtctgac tcagaatctt tgagggtgat gttccttggt gcttctggta 67740
gagactaaat ttggagaacc atagatctgg tagcttctgt agttacagtg acttttttttt 67800
tttttttga gatggagttt tgctcttgtt gcccaggctg gagtgcaatg gcgcaatctc 67860
gactcactgc aacctatgcc tcccaggttc aagtggttct cctgcctcag cctcctgtgt 67920
agctgagatt ataggaatgc gccaccacac ccagctaatt tttttgtttt tttagtagag 67980
atgggatttt tccatgttgg tcaggctgct atcgaactcc tgacctcagg tgatctgccc 68040
gcctcgcctc ccaaagtgct gggattgtag gcatgggcca ccgcgcctgg ccagtgactt 68100

```
cttttttaa accttgagta ggttatacat ttggggtaca atagacctgt ctaggttgaa  68160
cccctctgcc cgcatttcac acctgtggga gccagttgtt ggcacatgag gcagatccat  68220
aactaccacc taccattgta tgccctgtgg aacagtcccc tcatggaggc tacaatgggt  68280
cttctctaag caggagttcc taaatctggc tgcccatcaa cctcttcgag gagcttgtca  68340
acacactgat ttccaaacct tcctgtgggg ctccagttga gttggccaga agtgggacta  68400
gggcaggcca ggcacagtgg ctcacgcctg taatcccagc actttgggag gccgaggtgg  68460
ttggatcacc tgaggtcagg agttcgagac cagcctggct aacatggtga aaccctgtgt  68520
ctactgaaaa tacaaaaatt agccaggcat ggtggtgggc acctgtaatc ccagctactc  68580
gggaggctga ggcaggagaa tcgcttgaac gcgggaggca gatgttactg tgagccaaga  68640
tcgcaccact gtactccagc ctgggcaaca gagcaagact ccgtatcaaa aaaaaaaaag  68700
taacaatcac agtagttgtg aaacagaaca gcactaataa tggaacaaat tattattatg  68760
tgccttcttt tttttttttt tttttttttt tggagatgga gtctcactct gtcccccagg  68820
ctggagtgca gtggtgcgat ctcggctcac tacaagctcc gccttctggg ttcaggccat  68880
tctcctgctt gagcctcccg agtagctgcg actacaggtg cccgccacca cgcctggcta  68940
atttttgta tattttagta gagacggggt ttcaccttgt tagccaggac ggtctcgatc  69000
tcctgacctc gtgatccacc cgcctcagcc tcccaaagtg ttgggattac aggcgtgagc  69060
cactgtgccc gaccttatta tgtaccttct tatgtgttgc agtgtgaggt atgtaacatc  69120
aactatgtag cattttccca aaaatgttta acctgaatca agttataagc agacaaatac  69180
agattgtgag acactttaca agacaaatgc ctatattctt caaaaatgtc aatgctctaa  69240
tcccagcagt ttgagaggct gaagcaggag gatcacttga gctcaggagt ttgagaccag  69300
cctgggcaat gaagcaagac cctgtaaatt aaagattagc caggtgtggt ggcatgccta  69360
tagtcccagc tacttgggag gctgaggtag gaggaccatt tgagcccaag aggttgaggc  69420
tgcagtgagc catgattgtg ccaccacatt ccaggctggg cgacacagtg agacccccacc 69480
taaaaaaaaa atacacacac acacacacgc accccagtgc tatgaaagac ataaaaaggc  69540
aaggggcagg gactgttcta cattaaagga aacatggcag tttaaatgca ttgttgatcc  69600
ttgattagat cctgaattga aaaaaaaggg tcattttta aggacaattg gaaaaatgtg  69660
aatttacact gtgtattagt taatagtact gtatgtgaaa ttccctggat gtgattatgg  69720
tattatggtt atacaggata atgtccctgt tgctagagat aaaggctaaa gtattaacgg  69780
ataaaaggac ctgatgtctt taacttaatt gtcaaatgac tcaaatgatt taacttaatt  69840
gtcaaaaaat aaaacatctg tgtatgaaga gaagctaaag caaatgaggc gaaatgttaa  69900
caacttgtga agctgggtga atggtatttg gttattcatt gtatcattct tttaactttt  69960
ctgtaggatt ggaaattttc aaaataaaat aaaagttgtg gctgtttgtt gagtatacat  70020
tgactaatat gtgctctgag gccctttctg tacctgatgg ccccacttat ggtcgttata  70080
atgtgcctgc tgtagtttgt gtctgcagat cactttaggg acgtcagaac gggacagggt  70140
gactacactc ctaaaagtgt aatacttgac tttctatttt ccagatttct tgtgatatga  70200
ttgtattatt taaataacag gtaaaacaaa tctactttaa atttttttta gaacatggta  70260
ggaaataata gtaaattgtt taaataatgg gaaaatgata aagaaaagta aatggtaact  70320
gatttaagat aggagaccat ggctatgggc ctaaatggtg atgggaatga ctaacattta  70380
gacttgtgct ctgtgtgcca ttgaatatgt gaggttaggg actgtgatat accagctttt  70440
```

-continued

```
cagttgcagc aagcaagaca acacaggttg agctgcatgt tcaagatcac acatctagtg  70500
ggtacaaagg caaatttttt tttttttttt tgagatggag tctcgctcta ttgcccaggc  70560
tggagtgcag tggtgtgatc ttggctcact gcaagctccg cctcccagat tcacgccatt  70620
ctcctgcctc agcctcccaa gtagctggga ctacaggcgc ccgccaccgc gcccagctaa  70680
ttttttgcgt ttttagtaga gatggggctt cactgtgtta gctagaatgg tctccatctc  70740
ctgacctcgt gatccgcccg cctcagcctc ccaaagtgct gggattacag gcgtgagcca  70800
ccgcgcccgg ccacaaaggc aaattttaac ccagacagtg tagctctgaa tggcagctct  70860
tggccagaca cggtggctca tgtctgtaat tctagcactt caggaggcca aggtgggagg  70920
ttggcctaag cccaggagtt caggaccagc gtaggcaaca taaggatatt ctgtctctac  70980
aaaaatttta aaaattagcc attgtggtga cgcgtgcttg tggtcccagc tactcaggag  71040
gctgaggtgg gaggattacg cataagcctg gaaggtacag gcagcagtga atggtgattg  71100
caccattgca ctccagcctg aatgacagag tgaaaccctg tctcaaaaaa caaaaacaaa  71160
aacaaaaaca ggtcaggcgc agtggctcat gcctgtaatc ccagcactct gggaggccga  71220
ggtggttgga tcacctgagg tcaggagttc gagaccagcc tggccagcat ggtgaaacct  71280
cgtctctact aaacatagaa aatttagctg ggcatggtgg tggacacctg taatcccagc  71340
tacacgggag gctgaggcag gagaatcact tgaacctggg aggcagaggt tgtagtgagc  71400
tgagatcacg ccattgcact ccagcttggg caacaagagc aaaactctgt ctcaaaacaa  71460
aacaaagcaa aaaaaagtac acataactgt acagcttgat gagttttcac aaaccacata  71520
cacccatgta accagcacct aaattgagaa acagaccagt tctctagaaa cctcccttac  71580
gtctcctttt agtcaatact cttaccgtct cctgacttcc aacatcattc ttttcttttg  71640
tttgatttca ctgcatagtt agatccttag cactgtgtgt ctgaactcat tgctaatagc  71700
ttaagtagct ccgcatcccc actcctcttg cctgaactgt tctccatctg cctgtgactg  71760
ccagatcaag gcagcagcat ggtgtggtgg tttaagagtg tggcctcctg acccagatag  71820
cctgcattca tattggctct gccagttact gccttcttgg gcaacatgta catccatttg  71880
ctcagctata aagcagggat aatagtaacc gcatgaagtt atcgagaggt gaattaatac  71940
ctgtaaaaca cttagaatgt gcctggtacg cagtaagtac tatgttttac ctgcaatcat  72000
tatcattatt cagtctttaa aaactttata tggattggcc gggcgcagtg gctcatgcct  72060
gtaatcccag tactctggga ggccgaggcg ggcgaatcac aaggtcagga gatcaagacc  72120
atcctggcta acacagtgaa accccgtctc tactaaaaat aaaaaaaatt agccggacgt  72180
ggtggtgggc gcctgtggtc ccagctactt gggaggctga ggcaggagaa tggcatgaac  72240
ccaagagatg gagcttgcag tgagctgaga ctgcgccact gcactccagc ctgggcgtca  72300
gagtgagact ccgtctcaca aaaaaaaaaa aaaaaaaaaa ctttatatgg atcaagatgg  72360
acaccttggt cttttttttt tttttttcct caatgacaga ccctacttaa cagcaaaact  72420
gtattaggaa atgtcttgct cgtccctgaa tcagatatgc agcctcagct gacatgatga  72480
catttggagg cattatctta ctcacacgga aaatcagtaa tattgataca aataaaatta  72540
cctcgttttg tacatcatat tatatagctg aaaacattca gttcaggtgt ggctccttgg  72600
tttttgtag ttgatttatg tagttgcctg tgaagtctta ggcaaatcaa accctattct  72660
aagtccggta gagcctatgc agtttagtgg gaccttgtag taaatccttt aataaggtga  72720
agaatctttc tatagtgtaa gtaattgccc cttattgtaa atattttgta agattgggtg  72780
taggtctatc aggttttctc agagcagatc actcagctgc tgctgcagag cacctccttt  72840
```

```
gtgacttgta ggcattactc taccccctgtg tggttacacg ctacaagagt tacatgcata  72900
tgtactgtac agaacgtgtg tcatttatgt ttgatgtgta cacagatata cctgcctacg  72960
tacatagtgt tgtaattctg tttgatggtc ttgcctcact tgtgctgtcc accttaaact  73020
tagtgagttt atggggagca ctccacccac ccatttgcac gtgagaacat gctcagcagt  73080
gtaatcaagc aagtgaactg tttagacctg cttttccaga tctaagtgac atccgcagtc  73140
ctacaaccca gccttggaaa tagcatcaag gcagtgggag gcgaatgaaa ggggaacgat  73200
gaggctccgg tgggtgtggg ggcgggggcg gagatgccca cagccagcca tggagctgta  73260
tgaggcagcc ttggaagcct gctctgaagc atgactcaga tggcttctat aacagccctg  73320
acctgctggc agacagctac cctctgggag gtttgcgcag aggtggaagc tgagctggag  73380
agaaaaggaa gtagaaatgg gagagatctg agaatgaaga gcatccagag gcagtgaagg  73440
cttccagata tggctagata tagacagatt agggtgattt agttaggatt cttctagtta  73500
taagaaaatg ggccaggcat ggtgcctcag gcctgtaatc ccagcacttt gggaggccga  73560
ggcatgtgga tcacctgagg tcaggagttt gagactagcc tgaccaacat ggagaaaccg  73620
tgtctctact aaaaactcaa aaattagccg ggagtgctgg cacgtgcctg taatcccagc  73680
tactcaggag gctgaggcag gagaatcgct tgaacccggg aggcggagat tgcagtgagc  73740
ccagatcgtg ccactgcact tcagcctgga tgacagagtg agactcaaaa aaaaaaaaaa  73800
ggaagggagg gaggaaggaa gggaagaagg aagggaggaa ggaaggaagg aagatgggtg  73860
gggcacagtg gctcattact tgtaatccca gcactttggg agcccgagac aggcagatca  73920
cttcaggtta ggagttcgaa accagcctgg ccaacatggt gaaaccctgt ctctactaaa  73980
aatacaaaaa attagctgga tggtggtgca catctgtaat cacagctact caggaggctg  74040
aggcaggaga atggagaatc actttgaacc tgggaggcgg aggttgcact actgcactcc  74100
agtctgagca atagagcgag actccctctc aaaaaaaaag aaattagctt gatgtggtgg  74160
tatgcacttg tggtctcagc tacttgggag gctgagtttg agcccaggag gtcaaggcta  74220
cagttagctg tgatcatgcc actgcactca gcctgggtga tagagcaaga ccctgcctct  74280
aaaaaaaaaa aaaaagaaaa agaaaatggc agaaacccaa ctgaaactac cttaaacaat  74340
aacagggcca ggcgtggtgg ctcacatctg taatcccaat actttgggag gctgaggcag  74400
tgaggcgggc agattgcttg agcccaggag tttgagacca gcctgggcaa catggtgaaa  74460
ccccacaggg gtagagtgaa aagattgaaa aaattagcta ggcatggtgg catgcatctg  74520
tagtcccagc tattcaggag gctgaggtag gaggattact tgagccaggg aggtcgaggc  74580
tgccttgagc cagggaggtc gaggctgcag tgagccatga tcacacaact ggacactcca  74640
ccctggacag cagagcaaga ccctgtctca aaaacaaaaa acaaagaaaa acaataacag  74700
acttcattgg ctcaggtgac tgggacaaca agggtttcag gtgtggcttg atctgtatgt  74760
tcaaatgggg tcctctgggc tatgactata gctatgactc tctgtatgtt gatcttgttc  74820
tgcagactct ccccatgtgc caccactggg gagatgagca ccatcattcc tagtttcagt  74880
ttctctcagt ttgtagtccc agcaggcaca gggctttgtg cttttaactt cggtgttttg  74940
tttgtttttt actgattttt ttttttttga gacggagtct tgttctgttg cccaagctgg  75000
agtgcagtga cacaattcca gctcactgca cctccgcctc ctgagttcaa gcagttctcc  75060
ttcctcagcc tcccgagtag ctgggaccat aggcatgcac caacatgcct ggctaacttt  75120
tgtattttta gtagagatac agggtttcac catgttggcc aggctggtct cgaactcctg  75180
```

```
acttcaggtg atccacccgc catggcctcc caaagtgttg ggattacagg cacaagcccc  75240
aacacctggc ctgtttttta attgattttt gagacagggt tcttgctttg tcacccagac  75300
tagaggctag agtaccatag caccttttta gttcactgca gcctcaaatt tctgggctca  75360
agtgatcttc ccatttcagc ctcctgagta gctacgacta caggtgcaca ccaccaccct  75420
cagctaattt ttaaactttt tgtagagaca gggtctcgct gttgcccagg ttttagtctt  75480
gaactcctgg gctcaagtgc tctacccact ttggccaccc aaagtgctag gactacacat  75540
gcgagccact gcgcccagcc aaggctttaa actttggaca tttctacatc agttctgggg  75600
taggacacag attagttctg tctggccatg tgaccacctt ggttggtggc agtggtccag  75660
atggaccacc aggatttacg ttgaaagtct tccctctgct catcacttcc aagcacatgg  75720
aataggaggg aagtcctcta aagcaaaggc taaccaccag cagaagaata gcacggcttt  75780
gcataggcaa aatcagttgc tgccacggga ctggagggac atgtcttacc tcagtaatca  75840
tggtgtacag ttaacacttg gaagtcagat tattagagga gatgtcgatg gagcgggcac  75900
tttctgttct gtcttgtatg tgttgggatg gttttgacta caagtaatag aacaccctga  75960
ccagagtggc ctaacaataa gggcacttac cttacatggc aagccatctg gaggaggggc  76020
aattccaggg ttggctgcca tctgttcagc gatgttctca aggacctgag ttgttcttaa  76080
cttctctgcc ttccttagca cttggcttgt ctttttaaat tggtttcctc atattccaga  76140
gatggctgcc atgatcctag cgtcctgatc acccttgaca gagtctacag gcagtaagag  76200
agacatttct gtcctatgtc ctttaaagat gaaccaaaac ctccacagaa ccgccctcat  76260
tggtgtcccc tttgcatctc attggctaga gttaggtcaa ggatgatatt ggctgggaat  76320
gggcctggct cgcagaaggg aatggccagg aaaaggcaga aaaccaaaat tggggttctg  76380
ttagtaagga ggggaatgcc catcgtgtgg gcaaaacact ccccacctaa gaagccccag  76440
ccctgcctgg gatcagagga accttgccta ttgatcagga cactgggcct gggaagagaa  76500
tgttccagtc acgaggacag gatggctgtc atttcacctg ctatggcaga tttacaaaca  76560
aatctagcct gtggcatgag tcgtttggaa agttttgcaa taaatgtatc agtaacttca  76620
ccagtagaca catccatgtc tgtctgtcct actttgcagc cagtttttct tacttccctg  76680
ttcccctttc attttacgat cagtttattc ttttcagatt gccagttact cttcccctgc  76740
cccccatcct ctgggtttca ttagaaagaa accattcccc aactcaacag ggcttgattt  76800
ctgaactgtg ctttagaatt ctgctggaga ggctatctgc tctcagttct gccattggta  76860
ggctttaacc acaaattcca aggcaatttc atttgcgttt ttaggaaaaa cgtatctccc  76920
caaccttgta actgacactg gaaattgaag tgccttcact tgctgctgtt taatggcaac  76980
ctcatgacat gtgctcagtt ggctcgattt gtgagtggct cgatttctga gtgctgggat  77040
ggcactgcat gagtagggat ctctcccagg ccatcagagc tcatggctga tccaaccctg  77100
tggtactgac agactctaat gctaacagag attttttttt gttttcacat tttcttccct  77160
ttcccctgtt tacaaaagaa atacttgctc attataaaat tgaaacttag aaatttaaaa  77220
tctgacacag aaggtgaaag tccttcataa ttcattccct cacagagaaa actttggtgt  77280
tcctctttcc aggttttgtt tgccatgcgt atgtctggat agaatttgca gtattttgac  77340
caggcgcagt ggctcacacc tgtaatccca gcactttggg aggctgagat gggtggatca  77400
cttgaggtca ggagtttgag accagcctgg ccaacatgat gaaaccccat ctctgctaaa  77460
aaaaaaatac aaaaattagc caggtgtggt ggtacatgcc tgtagtccca gctacttggg  77520
aggctgaggc acgagaattg cttgaacctg ggaggcggag gttgcagtga gctgggagca  77580
```

cgccactgca ctccagcatg ggtgatagag caagactcag tctcaaaaaa aaagaacttg 77640
cagtattttg taaaaatgga ctatgctttt catactgttt ttcaccttgc ttttttaact 77700
tactatcatt tggacatctg tcaggatgtt ctttttaacg cgacactttt ttaataccta 77760
catatactgt actttattta accagtcttc tattgttaga catttgggtc atttctaatt 77820
ttttcctttc acaaagctgc agtgagcgtc ctcgtatatg tacatctttg tattcttacc 77880
gaagtatttc tttttttttt tgatgagatg gagatttact cttgttgccc aggctggagt 77940
gcaatggcgc gatctcggct caccgcatcc tccgcctccc aggttctcct cccagcgatt 78000
ttcctgcctc agcctcccga gtagctggga ttataggcat gtgccaccac acccggctaa 78060
ttttgtattt ttagtagaga cggggtttca ccgtgttgcc caggctgatc tcgaactcct 78120
gacctcaggt gatccgcccg ccttggcctc ccaaagtgct gggattacag gcataagcaa 78180
ctgcacccag ccttaccgga gtatttcttc aggataaatt cctttaaatg ggatcactta 78240
gccaggtgtg gagaaattaa cctttacatg ttaataacca ttgctaaagg atttttaaag 78300
tgaggaggaa ttagataaat taatatgtta ttaaaataat actattgggg ccatccagta 78360
aatgttatcg ttattttcaa caaacaatag aaggatcatt atataaaagt ggttgttttt 78420
gtttgtgtgt tttgtttgag acagagtctc gctctgtcac ccaggctgga gtgcagtggt 78480
atgatcttgg ctcactgcaa gctccacctc ccaggctcaa gtgattctcc tgcctcagcc 78540
tcctgagtag ctgggattac agatgtgagc cactgcaccg agcctagtgt ttttatagca 78600
acaaaatact ttactgagtc cttgagaata ggtcccccct cttaggttcc ttggccagag 78660
agattggttc atacacacta tgtggcatgc atttagggtt aggaaagacc agcaagcttt 78720
tttttttttt ttttttgaga tgggatctca ctctgttgct cagaccggag tccagtggta 78780
cgattatggc tcactgcagc tttgacctcc cgagctcagt tgatcctctt atctcagcct 78840
cccaagtagc tgggactaca ggtgcatgcc accacacccg gctaattttt aaattttttg 78900
tggagacagg atttcgccat gttgcccagg ctggtcttga actcctgggc tcaagtgatc 78960
tgcccatgtt ggcctcccaa agtggaggga ttataggcat gacccactgc gcctggctag 79020
caaaccttat acagtgtgtt gcacagttta gagttccagg aatccatcca tcatgcttcc 79080
tgtctctgaa gttggaagtg ctgagggaca cagcctgcct ctgtaagtca gagagacttt 79140
tccagatatt gacagcaagt catgttttac ataaggaacc tcaatgcatt gtagagtttt 79200
cttggggttt gcctcctctt gccttcccaa aagttaacag atgtgattca gtcttttcct 79260
gttgaggccc tttttttaaaa cttgcttttc tatgccaggt gcggtggctc acgcctgtaa 79320
tcccagcact ttgggaggcc caggtgggtg gatcacgagg tcaagaggtt gagatcatcc 79380
tggccaacat ggtggaacca cgtctctact aaaaatataa aaatttagct gggtgtggtg 79440
gcacgcacct gtagtcccag ctatcgggag gctgaggcag gagaattgct tgaacctggg 79500
aggcagaggt tgcagtgagc cgagatcgcg ccgctacagt ctagcctggg caacagagcg 79560
agactctgtc tcaaaaacaa caacaacaac aacaacaaca gcaacaacaa aacttgcttt 79620
tctatagtta aaagtaagta aataaaacag taggtattgg ctggctgtgg tggctcacac 79680
ctgtaatccc agcactttgg gaggctgaag cagttggatc acttgaggcc aggagttcaa 79740
gaccaggctg gacaacatgg tgaaacctca tctctactga aaatacaaaa attagctgag 79800
aatgatggtg catatctgta atcccagcta ctcaggaggc tgaggcatga gaattgcttg 79860
aacctaggag gcggaggttg cagtgagctg agatcgtgcc attgcactct agcctgggcg 79920

-continued

```
acagagtgag actccgtctc aaaaaaacaa aacagtagat attgagcacc aatatcatag  79980
gtacttacct tctcttattt aacctgtgcg gtgggtagcg tggtgaggaa gatactggtt  80040
catattgccc cttttcagat gaggcgatag ggaggtgatg ggccctggag aacttcctat  80100
agctgctgag tggcaagagc aagcctccag ggacagtcta accagcctgc tctgcgtgct  80160
ccagcctctc agccgccaag ggtccatttt agatgaagag agaggacttg gggaaaagga  80220
gctttttcat cagttatatt tattttattt aagtgcctgc gacataccag aggctctgtc  80280
aaatgctagg taagctgtgt ggaacaaact ttccactgcc gttagctagt agagacagac  80340
attgaaaaaa taagcaaata aatatttgat tccataagat cactaaaagg gaaaggtgag  80400
gaactgaaag aaggcttatg tagctggagg gaggtgaggg agaggcgagg gctcaggaaa  80460
agctggaggc ctggcaagaa taggaaagtg ctgggcttga ggcaagtcat ggtgcatttg  80520
cctcaataga gtcttgattc taagggtaat ggaaagctac gaaagcatgt taagggctgg  80580
gtgtggtggc ttatacgtgt actcccagat acttgggagg ttgagtgggg aggatagatt  80640
gagtccggga ggttgaggct gcagtgagcc aggatcatgc cactgcagtg agccaggatc  80700
atgccactgc actccagcct aggcaacaga gcaagaccct gcctcaaaaa acaaaaaaag  80760
aaaagaaaat gaaagcatgt taaggaggaa ggtgaaatgg ccagtttggg gagtgaagtc  80820
cttttttttt tgttgttaaa ttaagatgta cttggatttg aagtatttga gactctagct  80880
gcattttgag agtggctctt acgcagaagg gacaggggct gctgcagcag ttggagcgca  80940
gccctcaggg tcatggatac ttctcagctc tgccattcca gtccctgggg tcttgaactc  81000
agcagaatcc tgtctcaagc ctgctctatc ctgaggctct ccagcctaag aaggggaccc  81060
tcttatcttg gggtgttag cagcctcagc attgctgtgc tcagcagcac accacagggc  81120
tgtcttctca gatccaagag ggagatcagg ctttgcctcc tcttccctgc cctgcaggtg  81180
agtaaaggaa gtcaggaagg ttgagtgagg agttcagagt acgtccccag gtaagatgtt  81240
actaggctgc aggcagcttc tcatctacag ctcacctggc tttcttctct catgtcccaa  81300
atgtatgtgg tcttaatatc ttttcctcag gtaaagcttt ctggaaagag gtgctccatc  81360
attaccaatg agagctgtca agctgtatct ctctttttg gagacagagt ctcactctgt  81420
cacccaagct ggagtgcagt ggtgtgatct cggcttactg cagcctccac ctcctaggtt  81480
catactgttc tcatgcctca gattcctgag tagctgggat tacaggcgtg caccaccaca  81540
cccggctaat ttttgtattt ttagtagaga tgaggtttcg ccatgttggc cacgctggtc  81600
tccaactctt ggggtcaagt gatccacccg ccttggcctc ccaaagtact ggggttacaa  81660
gcatgagccg tcgcacccaa cctcaagctc tcgtttcctg gtttcgctaa gctgcctatt  81720
gccccagtca gctaactaaa gccaaatgga gctgcctggt tatattcata tcatttttct  81780
ccctcacact ctttttaatt ttcctgacat tttctttgcc tcaacctgat tcatcctctt  81840
ttctggttgc tgtggatctg tgaaatattt tcacttttat cagttagtaa tactgaccaa  81900
ctgtaagaca aaacaactct tgatttctct gcactttcct aagattttag attaatagtt  81960
gaaagattgt gttcctactg cactgaagaa aaacaggtca gtccctcaga aatgagtttg  82020
tgccctaaaa tttaagtgat ttagccaata tataaatctg ggtattttta gggaaaactt  82080
aaaccctgag agcagaggtt ggcaagtaca gcctgcaggc caaatcctga taatcacctg  82140
tttttataag taaaattata ttggaacata gccataccca tcatggatta cctgggcttc  82200
ttttgtgcca cagcagtgga gttgactagt tgtaacaaga atgatatggc cctcaaagcc  82260
tgaaatattt tatctctggc cgttcactgc aaaagtcggc cgacaactga cttagagaat  82320
```

gttttccact tctgaataac aactcaggtg gagaggtagc catctctgtg agatttcaga 82380
ggtcccgaga aatgagttgc cttagctggg tcctgtgctc tgtggcctgt ggtagaggaa 82440
tcaattacag tacctagagt ttgttggggt tggggggtat gcatctcctg ctgtgttgct 82500
gaaggatttt ctttagcaag ttcctttagc ttctataggt ctgtatccta cattggagaa 82560
ctacattaaa tgacttgaaa ctcttagtag aaagagtcta tttattgttt ttgagacgga 82620
gtctcgctct gtcgcccagg ctggagtgca gtggcgcgat ctcggctcac tgcaagctcc 82680
gccttccagg ttcacggcat tctcctgcct tagcctcccg agtagctggg actacaggtg 82740
cccgccacca cgcacggcta attttttttg tatttttagt agagatgggg tttcaccttg 82800
ttagccagga tggtctctat ctcctgacct cgtgatctac ccgcctcggc ctcccaaagt 82860
gctgggatta caagcgtgag ccaccacgcc tggccgaaag catttatttg atacaggcat 82920
tcagctagga taattcaccc tcggacaagg tctctcatct ctggacccct gtggagtttt 82980
aattggttgg ctctttcagc ggaatgtggc ccttttgtct ctagcacttg caattcaggg 83040
atgctttctg cagagggcag tgaagcccac tggcaagcag agattgccgc tggagagtta 83100
ggacagtaga actagcatct ctgcaggagg taaagcactt tgatgactgg aaactgctca 83160
tgatagagtg ttcagcgaag agggctggaa aagaacatgg ctgagagcag gaatccaaat 83220
ggcaggttgc ctgggttcaa atcctagttg ggccatgtag gaccaaaatt gaacatctct 83280
aacagttggt tacttcatct gtgaaacaca ggtaatagta atatctactt cataatatag 83340
gtagtgttcc taatgcagac cctagcatta tacatagaaa caatcaatat tatttatggc 83400
tgggtgcagt gtctcacgcc tgtaacccca ttactttggg aggctgagat gggtggatca 83460
cctgaggtca ggaattcgag accagcgggg ccaacatggt gaaaccacgt ctctattaaa 83520
agtacaaaaa ttaggtcagg cgcggtagct cacgcctata atcccagcac tttgggaggc 83580
caagggggcg gctcacaggg tcaggagttc tagaccagcc tggccaacat agtgaaaccc 83640
cgtctctact aaaaaataca aaaaataaac caggcgtggt ggcgggcgcc tgtaatccca 83700
gctacttggg aggctgaggc aggagaatcg cctgaacttg ggaggcggag gttgcagtga 83760
gccgagatta tgccattgca ctccagccca ggcaataatg tgagactctg tctcaaaaaa 83820
aaaaaaaaaa aaaagtacag aaattagccg ggcatggtgg tgggcacctg tatagtccca 83880
gctactcagg aggctgaggc aggagaatca cttgaacccg gaaggcggag gttgcagtga 83940
gccgagattg tgccactgca ctccagcctg ggtgacagag cgactccatc tcaaaaaaaa 84000
aaaaagttta tgttgttgtt taagaagcac attgcaaaag aaaaggaaac aggctctttt 84060
tttttttttt tttttttttg agacagagtc tcgctgtgtt gctcaggctg gagtgcagtg 84120
acacaatctc ggctcactgc aacctctgcc tcccgggttc atgccattct cctgcctcag 84180
cctccctagt agctggaatt acaggtgccc accaccatgc cctgctaatt ttttgtattt 84240
ttattagaga cggggtttca ctgtgttagc caggagggtc tcgatctcct gacctcgtga 84300
tccgcctgcc tcggcctccc aaagtgctgg gattacaggc gtgagccact gcgcccccatc 84360 caaaacctgt caagaaaaaa aaaggccagg gcagtggctt tcttactcag tttcttcata 84420
gctctctcag tggaaaatga ctggcacccg taagccatac acagtactgc ttgagattcc 84480
ctgggagtgg gtctccaccg ccaggcctgt cttcttgcct tgcagggcag acatgaggac 84540
aagcttgttg tttaggttct tcccaggact caaggaccaa gagaacagaa tggccctccc 84600
tcgagggttc tgatgaggtt caagcagcat ttctgactcc tcacagagcc ctctctctgg 84660

-continued

```
acagatgaca gttggagctt gagccagggg aggaagagaa aagggaggga attcgggtgc  84720
ttttaaagag ggattgcagc acacccaggc agtggattgt tgttttgctg gcatgcagca  84780
ggtagactct gaaacagcag tgggggtcct tctctgcctt gtcctgcttg gcccagtgga  84840
agctgcatac ctggggcact gtgctgggca gggaacacat ctctgggaga ggctatagcc  84900
caatatcccc tagccccagg cctagctcca gcagcctatg tttggctttg aagatttagg  84960
aagaacagga cactatcaac ctcctgggcc aaccgggcat gtctaggtcc tcctgtattg  85020
agtaccgtgg tgatctgaac acaggaaaac cttgtccttt gcttctcttt actgggccac  85080
tcacatcaca cattcattgt cttctgtcct tggctggtac acttttattc ccccaaacaa  85140
atataacatt attgttttcc ctaattacaa aaaggacatt aaaaaaatcc aggcaacact  85200
gaaaacataa agaaaccttg tcgcagaaca atgggtagag tggagtttca tttttactta  85260
aaaaaaaaaa aaagtatgac tttgattata catgctgaaa agaaagtctt aaagactgca  85320
tatcagatgt taacagcaaa tgttaatagc tgagaaatgg gactgatggg aaaagagatt  85380
ttcatgtttt actttataca tttctttgtt gtttgactct cttataataa gcctatgtta  85440
ctttgtaact taaataaata tatgttgaaa acaaaaataa atattatgct gctgagacag  85500
ccatttttat ttggttacta tccttctaga tatgtctcta tacaaaaaat aggcagttgt  85560
actaagtact gtatatatta acatgcttta ttcacacagc atcatgtcat ggaagtcttt  85620
ctagctaagt aactatagtt cagccgggca cagtggctca cgcctgtaat cccagcactt  85680
tggaaggcca aggcaggtgg atcacctgag gtcaggagtt caagaccagc ttggccaatg  85740
tgatgaaacc ctgtctctgc taaaaataca aaaattatct gggtgaggtg gcgggcgcct  85800
gtaatcccag ctacttggga ggctgaggca ggagaatcac ttgaacctgg gaggcggagg  85860
ttgcagtgag ccaagattgc actattgcac tccagcctgg gcgacaagag caaaactctg  85920
tctcaaaaaa aaaaaaaaaa aaaaaaaata tatatatata tatatatata cacatatata  85980
tatatatata tatatatata tatatatata tatctatagc agtgcttgta attgtatggc  86040
atttcattgt atgatactaa cataacaggc ccctctagga taaatagacc cctctggatg  86100
aacttgcaga tagtttccag ttttccctat tttaaacaac actataagat tgttgcccat  86160
atatgaacat cttggcaact gcgtccaatt atctcaggat cagtttctaa agtgggattg  86220
tgggtcacaa ggtccgcaga ttttacagtt tggcacatat gcccagctct ccttttgaag  86280
gtgattccac taggcagggt ggcccctgcc gcggctgcca ctgtgttctc acctgtagtc  86340
atggccattt ggcagtccag gcactgagga agcactgtgt agtctttcaa gtccgtaaaa  86400
taagacacag gactcttccc actcttgata gctttaaagc tggccgtatt ccaacattaa  86460
ggaagttctt tgaggctgga ggcccacagg ctactcagac tctgtggctc ttggaaagcc  86520
ctgcactacc tgagttcacc ctcacaactc agtcccttct ctatctctcc aagcaggtag  86580
aaatgtcctg gaagagtctg gcctgaacac caaaagggtt cactaatgat ttattgctat  86640
ctcttcctat aatcaaatca cccaaaattg gttatctaaa ccccttttcct gtatctgatt  86700
ggtagggaaa ctttgaaatt tgggcaggta catagacggc tgaggggctg ttctttatac  86760
agatactcag aggtaagtgc ctgcctcatg tccgtctctg acccaacagc cccttctggg  86820
tgcaacattc aacaagggat ttaaaccaat cagagtgtgt ccagagaatg gtggcattca  86880
aactggcaaa acctttcaaa actgtccatc tatgaggaat gactataaaa gtgaggtaac  86940
tggaaatatt ctagtttgaa gacgaaaaga ctttgagatg gaatatgtag ggagttgaac  87000
tatgacccac aacaggtatt taaaaatagc tgaggtcttc ccatatggaa aagggatttg  87060
```

```
actttttgtt actcagaata gagagctaga aagctgttaa ctcttcattg ggatgtagaa  87120
gaatttccaa atgtggatag gcactgggag gcagtaaact caccatccct gaagttttcc  87180
tagtcgtctg ggcagttgct ggcccaggcg cttgtagagg ggatttaagc gctgggtgtg  87240
cagttggtga tttgggaatc tagattgccg aaccgagaga atatttattt atttatttat  87300
ttatttattg agacggagtc ttgttctgtt gcccaggctg gagtgcagtg gtgcaatctc  87360
ggctcactgc aacctccgcc tcccaggttc aagcaattct cttgcctcag cctctcaagt  87420
agctgggact acaggcacac gccaccacgc ctggctaatt cttatatttt ttagtagaga  87480
cggagtttca ccatgttgac caggctggtc tcgaactcct gactttgtga tccgcctgcc  87540
tcggtctccc aaaggagacc atttattaat gctggggttt ttttagtttt ttgtttgttt  87600
gttttctaat cggtattttt gtgacccctt cttctgtgtt ccagtctggt ttcttgcaaa  87660
caagtccttc ccccttcctc ttctcgatgc ttcccaggtc ctccaggtct gacccagctg  87720
ggtgacttct gagaacatcc ataagtacta tagctgtgct tcttggtgta aactaaggca  87780
ggaagaaggg agttagtttc ctaagctgaa aattagaatc gtggctcctc gaagaaaaca  87840
tctgctcttc ctatgtgggt ggattctatg tctgtgtctc agttctactg gatccttctg  87900
tcttcatttc tttttgtgta aatagtggcc atattttcca gtggtcagat ctttcaaatg  87960
aatagcaact gtttaatttg tacagtattt tcagtacaca aggcaatttt tacatatttt  88020
gttttcttgg attctaaaaa aaaaaccaaa accttcaagg tgtacagtat atcatcacat  88080
catgttttgg taggtgaaaa aacagatgca gagaagttaa gtggcttctt caaggttaca  88140
cagtaagaaa atcgtatcag agaataaagc taagagagga gactcttaac tagaggatct  88200
gattttgtct tgaacaggag ggtatacata atacattttg ggtgactatt tgcacccatg  88260
acctgataga agaaaaatag tcagtactaa taagtaacgg tttcacctta cactaagatg  88320
gccagtgact gagctaaaga gaagttagtg tttcattaat ttatcttttt ttgggttgct  88380
ggggatgagg ccaaccaaaa ttctctctgg gttaaaagtt gatgtttaag gaggccgggc  88440
acagtggctg acgcctgtaa tcccagcact ttgggaggct gaggtgggtg gatcacttga  88500
ggccaggatt tcaagaccag cctgggcaac atgccgaaac cctgtctcta ctaaaaaaca  88560
aacaaacaaa acaaacaaac aaacaaaaaa ttagccaggc atggtggtgc acacctgtaa  88620
ttccagctac ttgggagact aaggcaggag aatcatttga acctgggaga cagaggttgc  88680
agtgagtcaa gattgcgcca ctgcactcta gcctgggcga cagagcaaga ctctgtttca  88740
aaaaacaaaa caacaacaaa aaattagtgg cttaaaaccc aatttctgtg tgtctcaagt  88800
ttggacacag cttatctcta ggtcctctgg ccagggcctt gcaaggctac aattaaggtg  88860
tttaccatgc tgcattcttt tcttttcttt tttttccttg ttcatataca ggctgcattc  88920
ttatttgagg ctcccctgga gaagaatatg cttccaagtt ccgtcaggtt gttgacagaa  88980
ttcctttcct tgcaacttta ggattcaagg cagcttgctt ctttaaagca gcaatggagg  89040
aagagtctga cgtttgtgta ggggtacagt tccctttttaa agggctttta cctgtttcag  89100
tcaagtccac ccaggagaat ctcttttttt ctgagatgga gtttcactct tgttgcccag  89160
gctggagtgc aatgatatga tcttggctca ttgcaaactc cgcctcccag gttcaagcca  89220
ttctcctgcc tcagcctccc gagtagctgg gattacaggc accggccacc acgcctggat  89280
aatttttttt tttttttgta attttagtag aggacgggtt tcatcatgtt ggtcaggctg  89340
gtctggaact cctgacctca ggtgatccgt ctgcctcggc ctcccaaagt gctgggatta  89400
```

caggtgtgag ccaccgtgac cggcctctcc cctttttctt tctttttttt ttttttgag 89460 acagagtctc actctattgc ccaggttgga gtgtagtggc gcgatcttgg ctcactacaa 89520
cctctgccac ccgggttcaa gcaattctcc tgccccagcc tcctgagtag ctgggattac 89580
aggcacctgc caccacaccc ggctactttt tgtattttta gtacagatgg ggttttgcca 89640
tcttgcccag gctgatcttg aacccctgac ctcgtgatcc accctccttg gcctcccaaa 89700
ctgctgagat tacaggtgtg agtgagccac catgcccagc cttttttttg ttgttgttat 89760
ggtgaaaaga tatacatata tttagaatta cccagctgga ctcagtttaa atgatcccaa 89820
ttttgttggc aacatccaaa gcatcgtaat caggagccag tccaacatat gccttcttct 89880
ctccatcacg ctgaatcagg gtgttgacct tggtcacatc agtgtcatag agcttcttca 89940
cagcctattt gatctggtgc ttgttggctt taacatccac agtgaacaca agtgtgttgt 90000
tgtcttctat cttcttcatg gcagactcag tggtcagtgg aaacttgatg atagcatagt 90060
ggtcaagctt gttctccggg gttggtcttc tgagggtact tgggctgcct ccagaatcgc 90120
agtgtcttgg gccgctggaa ggtaggtgac gtgcggatct tcttttttt gtggctgtgg 90180 acacctttca acactgcctt cttggccttc aaagcctttg ctttggcttc ggctttagga 90240
ggagcaggag cttccttctt tgctttcggc accgtcttgt gaaaagggcc tccattttaa 90300
ttaacacaaa atcatctact ttggcctcac agccgttaga atggctacta tcaaaaaaag 90360
aaaaaacaaa acaaaacaga aaatagtatg ttagcaagca tgtgaagaaa ttggcaccct 90420
tgtacactgt tgataggaat gtaaaatggt gcagctgctg tggaaaatgg tctggtgctt 90480
cttcagaaag ttcaaaatgg aattactgta tgatccagca atctcacctc tgggtatgtg 90540
tccaaaagaa ttgaaagcag ggacttgaac agatatttgt gcaccagttt tcatagcatc 90600
caaaaagtgg aagtaactca agtgtccatc aacagatgaa tgggtaaaca aagtatggta 90660
tatacatata atggaatatt actcagcctt aataaaagga aggaaattct gccacatgct 90720
gcaggctaca acatggatga acccaggaga cattatggca agtgaaataa gccagacaca 90780
aaaagacaaa tattgtatga ttccacttac ataaggtact tagagtagtt aggttcatag 90840
agacagaagg caaaatgttg gtttccaggg gttggaagca gtggaatggg gagttactgt 90900
ttactgtata gagtttcagt tggggaagat gaaaaaaagt cctggaaatg gaagcttctt 90960
atggttgcac aacaatatga atgtacttaa tgccacttaa aaatggctaa attggtgaat 91020
tttatgttga tgtattttac tacaactaaa actgaaaaaa aaattaataa atgatttggg 91080
atgttacttt acatctttaa aatatcttta cttttgccat attctgttag caagaagcaa 91140
gttataggtc tcgcccacac ttgggggaaa gtattagaca gggcttgagt accaagggga 91200
ttggggacca tgggggcacc ttagagtctg tctgccacat ttcctaaaac tcagaagcaa 91260
aataaaacaa gtgaaattca cagcatacca aattggtgtc aaaacaatat acagagatct 91320
taaactatag taatttgtct gtatatccct aatatataca caaagacaga aaaaactgtt 91380
ttcagtaatc atgttgttaa taaaaatatt gactttaacc taaaactagt atatggatat 91440
aataggataa agcaaataag taattatgtt agaaagcaag atgttcagca taagattaga 91500
aagatacaaa tatatggcca ggcgttgtgg ctcacatttg tagtgccagc tgtttgagag 91560
gctaagacga gaggattgct tgagcccagg aatttgagcc tgcagtgagc tgtaattgtg 91620
ccactacact ctagcctgag tgacacagtg agaccttgtc tctaaaacag taataaaata 91680
aataaaagat acaaatataa aatcaaataa gtaaaaatgt tatattctta aatttggatt 91740
ctaattagca agatgaacaa aagatgtgtt ttctctttct tttaaaaaaa atgtatttta 91800
tcttcgtcac taaaaaagcc ttgaaacagg ccgggcacag tggctcctgt aatcccagca 91860
ctttgggagg ccaaggcagg cggatcatga ggtcaggagt tcaagaccag cctagccaat 91920
atggtgaaac cctgtctgta ctaaaaatac aaaaaattag cccggcatgg tggcatgcac 91980
ctgtagtccc agctactcag gaggctgagg caggagaatc acttgaaccc gggaggcgga 92040
ggttgcagtg agctgagatt gagccactgc actccagcct gggtgacaga gcaagactct 92100
gtctcaaaaa aaaaaaaaaa ttaggcatgg tggtgtgcct gtagtcttag ctactcggga 92160
agctgaggtg gaaggattgc ttgagcctag gaggttaagg ctacagtgag ccataatggt 92220
gccaccacac tccagcctgg gaaacagagc aagaccttgt ctcaaaattt ttttaaaaag 92280
ctagcctggt tgaaaatgcc agtggtgcca ttttagttgc cagccaagga tggctcctaa 92340
tgttctagtc cattttctgc tgcttataac agaatatctg aaactgctaa tttataaaga 92400
aaaggaattt atttcttaca gttatggagg ctgagaagtc caaggttaaa gggccccatc 92460
tgatgaaggc cttcttgctg gtgaggagtc cctgcagagt cccagggaca tcacatggca 92520
aggaggctga acttgctagc tcaggtctct attctgataa acccaccagt ttctaccccc 92580
attgtccacc tctgtgataa tccattaact tattaatcta tatatgaggg cagggcccac 92640
atgacccaat cacctcttaa aggccccacc tctcaatact gctagattgg agactgagtt 92700
tcaacatacc ttttgaagga ggcagacatt caaatcatac cacctagctt cctggcatgt 92760
ccagattagt gccactgcat ttggagtgat gccacagtag ccagtgtgat ggctgctggt 92820
gccacatagc agaggggtca aggaggagga tcatctttcc aacattaagt atatagataa 92880
tacataaata aatttcagat tttttttgg aaacggggtc tctgttggcc aggctggagt 92940
gcagaggcgt gatcttggct cactgcagcc tcaacctccc gggctcaagt gatcctccca 93000
ccttagcctc tgagtggctg ggtctactgg cacatgccac catacccccgc taatttttct 93060
gtgttttttt ttttttgtag agatggggtc ttggtatgtt gtccaggctg gtcttgaact 93120
tctggactga agtgatccac ccacctcagc ctcccaaagt gctgggatta caggcatgag 93180
gtactgcaac tgacctcaga tgttaaaaac ttagactata cagataaagt caaagttctc 93240
tgtgaccacc ccacccaatc tcagggccct cgctaaagaa accctcttta tccatttggt 93300
gtgcgtcctt gcagcttgcc agattttttt ctatgtattc accttcttct gggtacctat 93360
gaaatggttt gggtttctat gtttttttt ctttctttaa tgtaaatgaa actgtactgc 93420
ccttcacaat tggattttc agttgacggt atgtcttgaa gatctttatt taattttttt 93480
tactgttgtc tgtgatttta ttgtatgaat aaaccataat ttaactattc ccctggtgat 93540
gcacctttag gttgttgcca tttttgcagt attacaaaca gtacaaagat gcagtgacca 93600
tccttattca ttcctccttg tgacatgttt tgctctaggg tagatattta taagtagaat 93660
gattgggtca aagggaagtt accttttata ttaatagatt ctgccatttg gtcctccaaa 93720
gtgaccatac tagtttatag gtccatggca actaaatgtt ttgttttgtt ttgcagtgac 93780
agggtctttc tctgttgccc aggttggagt gcaatggtac aattatagct cactgtaacc 93840
tggaatgctt tggctcaaat gatcctcaag cctcagcctc ccaagtagct gtggaactac 93900
aagtgtgcac caccatgcct gactaatttt taaatttttt tgtagagaca gggtctcact 93960
gtgttgccca ggctggtctt gaactcctgg tctgaagcga ccttcctgcc tcagctgtgg 94020
gattgcaggt gtgaatcact gtacccagtc taaatgggtt ttcattcctg atttaactgg 94080
tctcttcagg aagaagatgg gaggagtaga agcatgtcct ggattttttc ttttcttttt 94140

-continued

```
ttttttttt tgagatggag tctcaccctg ttgcccagtc tggagtgcag tggcaccatc  94200
ttggctcact gcaacctccg cctcccaggt tcaaacgatt ctcctgcctc agcctcctga  94260
gtagctggca ttataggcgt ccactaacac gccaagctaa tttttgtatt tttagtagag  94320
acagggtttc accatgttgg ccaggctagt cttggatttt aaagcttcaa aggatttcct  94380
gggatttttt tttcttgttt cttttttttt ggaaatggag tctcacgtct tactctgtca  94440
cccaggagtg cagtggtgtg atcatgggtc actgcagcct ccctctccca gggcttaagt  94500
gatcctccca cttcagcctc tgggaccaca ggcatgtgcc accacacctg gctaaatttt  94560
gtatttttg cagaggcagg gttttgccat gttgccaagg atggtatcaa actcctgtgc  94620
tcaagtgatc cacctacctc agcctcccaa agtgctagga ttacaggcgt gagccactgc  94680
acccagccct cctggcattc tttggttgaa atgtatatag gactacgagt tgtttttttt  94740
ttttttttga gacgtagtct cgctctgttg cccaggctgg agtgcagtgg cacgatcccg  94800
gctcactgca agctccgcct cccggattca cgccattctc ctgtttgagc ctcctgagta  94860
gctgggacta caggtgccca ccaccatgcc cggctaattt ttttgtattt ttagtagaga  94920
tggggtttca ccatgttagc caggatggtc tccatctcct gacctcgtga tctgcccgcc  94980
tcggcctccc aaagtgctgg gattacaggc gtgagccacc gtgcctggcc aggactacga  95040
gtttaaaacc tccttagtcc ctttggcttt aagaacaaag aggctggtgg ctcatgcctg  95100
taatcccagt actttgggag gccgaggcgg gtgaatcacg aggtcaggag atcgagacca  95160
tcctggctaa catggtgaaa ccccgtctct actaaaaata caaaaaaatt agctgggcgt  95220
ggtggtgggc gcttgtaatc ccagctactc gggatcgcgc cactgcactc cagcctgggc  95280
gacaaagcga gactccgtct caaaaaaaaa aacaaaaaca aaaaacaaag aacaaagagg  95340
cttggggcca ggcatgatgg ctcatgcctg taattccaga actttgggag gccgaggtgg  95400
gtggatcact tgaagtcagg agttcgagac cagcctggcc aacatggtga aaccccatct  95460
ctactaaaaa tacaaaaatt agtctgggtg cagtggcacc tgtaacccca gcactttggg  95520
aggctgaggc gggtggatca taaggtcaag agattgagaa catcctggcc aacatggtga  95580
aaccctgtct gtactaaaag tacaaacatt agctggtcat ggtggcgcgt gcctatagtc  95640
ccaggtactc ggtaggctga ggcaggagaa ctgcttggac ctgtgaggca gaggttgccg  95700
tgagctgaga tcatgtcacc gcactccagc ctggcgacag agcaagactc cgtttcaaaa  95760
aaaaaaaaaa attagatgga catgatggtg cgcgcctgta atcccagctg ctcgggaggc  95820
tgaggcacga gacttgcctg aacctgggag gcagaggttg cagtgagctg agatggcacc  95880
actgcactcc agtttgggca acagagtgag actctgtctc aaagggagaa aaaaaaaaaa  95940
gagcaaagag gcttgggctc tgccttgtgt gtaggtggca ggccctcgtg ctggtgaagg  96000
agagaggaac aagggcaggt cttgctcagt tacaagcttg tgggcagaag attctgcctt  96060
ctcatgctga caggtgtcta aacagatgga gctgcttaaa aagaaaagtg aaggcatctg  96120
ctagattagg acttcaggct ctctctaagg ggtaagcaag gacctgtgta ctttacaggt  96180
gggcatagca tatatgggtg agtaaatgag gtttgactag tgacagctac aagctgtggc  96240
caggtgaacc ctcctgagct ctgtgggcag tcagggtcct caccctcatt ggggggagaa  96300
tgaggctgtc tgctgtgtgc cctgcccatg tgggcacagg gtgagtgtca ggtccacagt  96360
ctatctctag ctagcgaaac tgcatcagtc cagttctgaa aggtttgcag ccccctacac  96420
tcgctttggg gtgagaacct gcagggtctc tggcagcccg ccagcctccc acctcccctg  96480
ctgtgacttg tattccagtt tactgagcat ctctgcttat aaagggattt tccttacact  96540
```

tcactgtttg cctttatgat tgcggctttg agggacagga aggaagctga agagcgggcg 96600
gttctggaga aaatgcatag ggaagcagtt ttgagtctcc tttggctagc tgtgcgattc 96660
ctttgattcc aggcaaaacc tggaaggaat agcctttaca tttcctttca gttttgcaag 96720
agcaaatatg tcttctctca gtcttcttta atcaagtggg actgcgtatt catttcccgt 96780
ctccatgtct tgcaaccaca tttagccaaa ttaatatcag acagagctag ctgagggaag 96840
ctctcaaacc aaacactcaa atgaactttt caagtgataa aactgcatcc agaactttga 96900
aaaggtaggt gggtgagggt aggggttaat tcttgcttct accacatgac caagttggga 96960
aactctacaa ctggtcacca tctgcgccat ttgaccagct atgaagaact ttaccttcta 97020
gccccaagag ctcctcagcc acatgtacag agaatctgtt ttgggtctcc tcccccgcac 97080
cccccccccg cccccagttt gtttgctttg ttgtttttttc tttcttaaag agagtttctg 97140
tctttcccct tctttggagt ttgattggaa gccctgcaga ggggctgttg agcagtcagc 97200
catgttcctg ggattatcct tcctttggag catctgtctg ctgtgcactg tgttgggaga 97260
aaggcagggg tgcgaaattc tgttggtttg taacaaattg tagcttctga gctggggagt 97320
atcccatctt ttcctctcct tgcaggaggt ccactgttaa aggggaatta cgcaggatgt 97380
gtttattttt tttgctccta cgctgtttat acatcattgt attcaatttc tgtcccagtt 97440
cctagtgtgg gccttgtctc aagactctgc tgcaaggttt ctgtcctagt tcttagtgtg 97500
ggtcttgcgt cattactctg ctgtaaggtt ctttggcttg gggagggggt atggagccgg 97560
gtaggcaggg aagtggaggg aggtgctcac tctcagcttt atttggattc ctggaggaag 97620
gagagttgct gttaccagga aaagtcagtg ttgatcagac aagaagagga tctgctgcct 97680
tcctttggtg ggtgggtact gttaggttga gggagaattt gcctggagga ggctctgtgt 97740
cttcctgagg gcagtgccct ctgtacagtg cctggggtta ctcctcccta aaatgagggt 97800
agcattgtgc gggtgtgcta agggctccag aaatgtcatt tgtggctgtg ctacaccctg 97860
tggcctaaaa ctttgtaggc ttttcatttc tggcaataga ctaggcacac acatccctat 97920
tctcctctct ggtctagaaa ttaggcttgg gctgggcgtg gtggctcaca cctgtaatcc 97980
cagcactctg ggaggccgag acaggtggat cacttgaggt caggagttca agactagcct 98040
ggccaacatg gcaaaactcc atctctacta aatacaaaaa ttagctgggc atggtggtgt 98100
gtacctgtgg tcccagctac ttgagaggct gaggcacgag aatcacttga acccaggaag 98160
tggaggttgc agtgagccga gattgtgtca ttgcactcca gcctgggcga cagagagaga 98220
ctctgtctcc aaaaaaaaaa aaaaaaaaaa aaaaaaaaaa agaagaagaa gaaattaggc 98280
atgggtttta gaaattagta tgggcttaca gagagatcca gtgggggcag taggcagact 98340
gagtggcccc cattaggagc atctgggctg ggcagaagcc aacaggacta actttgaact 98400
ttatttcctt cactgcctca gccagagatg ttttgttcaa caaaaactcc agattttctc 98460
ctcctctcac tggggagtca tgaagctccc aggcctgtgt ggacctgtag ttctgccccc 98520
gtaaatatat ttctgctcgt gggccttctg ttgacttgag aaggagctgt cttccaatct 98580
cagaggaagc ctcctctggg cccagctccg ctgcgcagtc caccatggcc gcagcagtag 98640
cagcttgagc cttctcagga aggagggcgg gttaggcagt tgccagtctc cccacaggtg 98700
tcggcttcat cctgggactt ccagatatgg ggcataggct aactgaacct ttcctcctca 98760
gcagtctgtg ttactgggga catgtctggc acatctgaca ttttgggaaa gaactgctaa 98820
gcccccctag gaccagctcc gggtgttcac agaagacact taagccctgg ttatcagaat 98880
gatttgtgaa caccagaaat gcaagaggag tggagatttt ttcttgagag attatgatgg 98940
ctgtgccatt gtcaaatatt tgacctccaa gttgacagac ctgagtctcc cagcctgctt 99000
tgggtcacct cccattttcc tgctctctca aaaacacctc ttgcagacta gccactcctg 99060
tgacacctgg cacagtccag ctgcgtttcc tgcccttgtt ctctgtccct ggaaagcacg 99120
gaataatctc agagcacgca gaagagcacc tggagaaaag gggcatttgg ctttcacagc 99180
gccaagcttc acgctcctgg gctcccaaag ggaacattag tccccgctcc acagaccaag 99240
catgttaatt ctgaccctgg gttggggtgt tagtttccag gctattatgt agaacatcac 99300
ggggcctgta cttttgcaca gaagggaggc aggctggcac tgtctagagt taggatgaat 99360
taagaactct tgaagaatgt atttgtaaga actcaaggaa tgtatttgct tctatgtttc 99420
aaaggcagca ctattttaca aacaatagct gttttcttct gcaacccctc tccctagatt 99480
ttgctaactt attatatccg ggacagtcca acttcaaacc accataactg aagctggatg 99540
tcagggaggt gggggtgggg tgatggccaa ttggaggagc cagtaggatt ctgtgcgcct 99600
gttcagcacc ccccacgttt tcagagttct tgcccaggag ttgtttgtta atggggaatg 99660
agacgtggag gaatgaaatc tttctcccaa gtgagcaagg tgtagaactg taactagcat 99720
ttttggcggg gaggggagag actccttttg ctatcctgga gtggtatttc ccttccagtg 99780
aatttgccaa acaacataaa agtcgggtag ctgagggagg tttctcctgg tacctggggg 99840
caaagctcca aggagggaag ggaatagaaa gtgtctaccc agcccttacc tggaatggcg 99900
acgttctttc agacactggg tgcgggggag cctctgctgt gtggtttaag tggaggtctc 99960
tgggattttc accctgactt ttcaatgagg ataccttggg gagcaagaga gaggaagcca 100020
gctcctgtaa ccgctggact gaacagctgg gcctctaact gagacattat tagcatttga 100080
aagcccctct gaaggggcca agagcttccc agggtgggcg caggggcctg agtgctgaga 100140
ccccacagtg gctccaacag aatgggtctg agcatccagg gcataaagac cagaccggac 100200
tcaagaatga actcattgtg gctttgtccc atgcttgaaa actgtgacca gggctctttc 100260
attgttaaga aagaccattt cttgtccaca gaagagctca taagtctagt tccttcatca 100320
ggcagagctg cggaagaccc tgcccctcac tagaagtttc tgttagtgtc ctgctctcca 100380
agcatttctg atggaagttg cactttctgc tccccacttt aactcaggag tacctttggc 100440
caaagcctga tcacacatgc tcagggtgga acgtgttgat cctagagcaa cacctgggcc 100500
cgactccctt ttcttgcctt agagtctccc tttcccagct gcctaaatta agcctcttcc 100560
caagttatta agcctgcaca aagtgctttt tggtcattct ggttcaaaca gtttgggttt 100620
gcacagtatt ttaaaatcat gttaattctg gttaataaaa ggtcaaaggt catggctcca 100680
aatctttcca gccttttccc tgtttccagc ctaaataaat ccccacccgg tttggggtat 100740
gtttcttttt ctttttcttt ttttttaat tgtactttaa gttttagggt acatgtgcac 100800
aacgtgcagg tttgttgcat atgtatacat gtgccatgtt ggtgtgctgc accgattaac 100860
tcgtcattta acattaggta tatctcctaa tgctatccct ccccccctctc cccaccccac 100920
aacaggccct ggtgtgtgat gttcggtttg gggtatgttt ctacagacta gacatcagat 100980
agggatgcag agctccaggg aactggccca tctgtttctt aaaccaggag caatggtgcc 101040
acctactggg cacttgctgg tagcgacaag ctctgtggcc agtcctgttt tctggtgact 101100
tgggtgagag tatctgtact gtattccagt acacgagtaa taacatactg cagtagaaag 101160
catattgagt aggcacgcta tttcctgtta acaggcttag atactgtgtt tgggcaagtt 101220
gcccagggtc acatccagtt agggatggag gcaaatagaa acagggcctt cccaactccg 101280
aagttcacca ctaagccagg gtttgccaaa accagcaggc gatttcagct ggtaactgca 101340
caagagtggt aactggtagc atgaatagtg aagccacttt tctctctttg gttctctttg 101400 tcttttttt aatttaagat ggggtcttac tatgttgccc aggctggttt tgaactcctg 101460
ggctcaagag atcctctcac tgggcctccc aaaatgctag gattacaggc atgagccacc 101520
atgcccggcc cagtttgttc tctctcagtc ttggtgattt tgtctcagct ctatatgact 101580
ctttaaacct tgaacagctc tttgaccctt gtttatttca ttttttaaac aattttaggt 101640
aggcaacaat atcagttaga aattaataac attttgttat attatcctga agttaccact 101700
tgaggtaagc aacgctaatt tgccattaat tttccttatt tagtatagtg atatgaagtt 101760
gccttttcag agtaagtttg tttaggttaa aaaaaaaagg caagtcaatt ttagggggaa 101820
aaatacaggt aagtaatggt acagatggtg cacagatatg gcaaacatgc tgatgggtgt 101880
tgtggatgag cccaaagttt ggaaagtgtt gggccatgcc catcatcact gacgtactgt 101940
gagactgtgg gcaatctcaa gcatcctttt ctcatttgta gaaaagaaca tgttagtagg 102000
tgattgttca ggtcatgtag acatacacag tgctgtgatg tctcagcatt atgggtcagg 102060
tttctcccag gccaggctgc tgtgcctggg gtggtgggaa caaggaattt aaaggcttgg 102120
ccttgcttcc cctactttgc ctgtgcctca agattccttc cttttgcctg ctatattttc 102180
ttttttaata acagatttat tgacatacga ttcacatacc atgtaatcca cagttgtgaa 102240
accatcacca taaaaaaaga acctcatatt ggtcactccc tattccctcc aaccatcaca 102300
gccctagaca accactaatc tactatctgt ttccatagat ttgcctattc tggacattcc 102360
atatggatgg aatcatataa ggtctattat gactggcttt tttcacttag cataatgtct 102420
ttaaggttca tgttatagta tatattagta ttttgttcct ttttattgcc agataatact 102480
tgtaattgcc atcttttttg ttttaaacat tctagtggat atgaagtggt ggtgtctcat 102540
tgtgggtttt ctgttttctt ttcttttgtt ttttgagaca gggtctcact ctgtcatcca 102600
ggctggaata ctatggtgcg accaaagctc actgcagcct ccacatcccg ggctcaaaca 102660
atcctcccac ttcaacctcc cgagtacctg ggactacagg cttgggccac cacacccagc 102720 taatttttttg tttgtttgtt tgttttttat agagatgggg ttttgccatg gttgccctgg 102780
ctggtctcaa actcctggcc tcaagcgatc ctctcacctt ggcctcccaa cactttggga 102840
ggccactgca ctggcctcat tgtggttttg atttgcattc ctctgatggt taatggcatt 102900
gaggatcttt ttatgtgctt attagctatt tgtatatctt tttttttttt ttttgacaga 102960
gtctcactct gttgcccagg ctggaaggca atggcacgat cctggctcac tgcaacctct 103020
gccttccggg ttcaaacaat tctcctgtct caacctccct agtagctggg attacaggct 103080
catgccacca cacctggcta atatttgtat ttttagtaga gacggggttt caccatgttg 103140
gccaggctgg tcttgaactt ctgacctcag gtgatctgcc cgccttggcc tcccaaagtg 103200
ctgggattac aggtgtgagc caccatgccc ggccagctat ttgtatgtct tctttggaga 103260
aatatattca gatcctttgc tcatttttaa attgaattat ttatctttta ttattgagtt 103320
gtaagaactc tttatatatt ctggatacaa aatacttaat atatgctgga tacttattag 103380
atatatgatt tgcaaatatt ttctctcatt ctctgggttt tttcttttaa aatgtgatta 103440
agcctgggca cggtggctta cgcctgtaat cccagcactt tgggaggccg aggcgggtgg 103500
atcatgaggt caggagatcg agaccatcct ggctaacacg gtgaaaccct gtctctacta 103560
aaaatactaa aaattagccg ggcatggtgg cgggtgcctg tagtcccagc tactcgggag 103620

-continued gctgaggcag gagaatggcc agaactcggg aggcggagct tgcagtgagc cgagatcacg 103680
ccaccgcact ctagcctggg cgacagagcg agactccgtc tcaaaaaaaa agaaattgtg 103740
attaaatata tgtaacataa aatttatcat tttaacaatt tctaagtgta cagttctgtg 103800
acattattaa gtacattcac attgttttgc agacattacc accatccatc tctagaagtt 103860
tttcatcttc cccaacttaa actctgtacc cactaagcaa taactcccca ctcgcttctc 103920
ccccagcctc tgacaaccac cattctattt tctgtctcta taaatttgcc taccctaggt 103980
acttcatgta agtgaaatca tgcagtattt gtccttttgt gtctagctta tttcacttaa 104040
cataatatta tcaagtttca cccatgtttt agcatttgcc agaatttctt ttttatggct 104100
gaatagtatt ccattgtgtg taaatactac attttgttaa tccattcatc tcttgatgga 104160
catttgggtt gtttccacct tctggcaatt gtgaataatg ctgctgtgaa cataggtata 104220
caaatatctg tttgagacca tgctttcagt tattttggct atatacccag atgtgagctt 104280
gctggatcat atggtaattc tgtgtttaaa ttttttttgc agaaccgccg tactgttttg 104340
cacagcggct gcttcatttt atattccacc agcaatgcac acggattcca aattctttgc 104400
atcctcacca acacttgtgc acttattttc tgttttcttt tttttattaa tagtcaccct 104460
aatgggtata aagtgatatc tcaaaagtga ttttgctttg catttctttt tactttcttg 104520
atggtattgt ttacagcaca aacagtttgt tttgttttga gacgaagtct tggtcttgtc 104580
acccaggctg gagtgcagta gcgtgatctc ggctcactgc aacctcctcc tcccgggttc 104640
aagcaattct cctgccatag cctcccgagt agctgggatt acaggtgccc accactacgc 104700
ccggcaaatt tttttgtatt tttagtggag acggggtttc accatgttgg ccaggctggt 104760
cttgaactcc tgacctcagg tgatctgccc acctcagcct cccaaagtgc tgggattaca 104820
ggcatgagcc actgcgccca gccagcacaa aaggttttaa ttttgatgaa gtctaattta 104880
cctatccttt gttacttatg cttttgatat tgtatggaag aaacctttgc ctaatccaag 104940
gtcaaaagat ttactccaat gtttgcttct aaaagtttta tagttttagc tattacagtt 105000
aggtctgtga tccattttga attgactttt gtttgtgata taagaaagag ctccaacttt 105060
atccttttgc gtgtgagtat ccagttcttt tagcagcatt tgctgaaaag actatttcct 105120
ttatcgaatt gttttggccc ccttgttgaa aattaatgcc cacaggctgg gcgcagtggc 105180
tcacgcctgt aatcccagca ctttgggagg ccgaggcacg cggatcacga ggtcaggaga 105240
tcgagaccct ggctaacatg gtgaaacccc atctctacta aaaatacaaa aaattagctg 105300
ggcgtggtgg cgggcacctg tagttccagc tactcgggag gctgaggcag gagaacggcg 105360
tgaacctggg aggtggagtt ggcagtgagc cgagatcgtg ccactacact ccagcctggg 105420
cgacagagca agactctgtc tcaaaaaaaa aaaaaaaaga aaagtaaatt aatgccccaca 105480
aatgtgagag tttatttcag gcctctcaat tctattacat tgatcaaatg tctgtcctta 105540
tgccagtgcc gcactgactt ggtgactata tctttgtagc aagttttgaa atcaggaaaa 105600
ttaagacctt caactttgct cgtcttcttt aagaatgttt tggctattct gggtgtcttg 105660
catttccacg tgaagttttg aatccgtttg tgaattactg caaacagcat acctggcatt 105720
ttcataggga ttgcactgaa cccgtagatg gatttgggga tactgccatc tcaacaacac 105780
taagtcttcc gatccatgaa tgttggatat ttttccgttt atgtaggtct tctcgaattt 105840
ctttcaatga tgttttgtag ttttcagagt ataagttttc atttcctttg ttaaatgaag 105900
cattgtatta tatttgatgc tactgtgaaa gaattgtttt tcttactttc atttttttatt 105960
ttgtttattt atttatttat ttattttttt gagacacagt ctcactctgt tgcccaggct 106020
ggaatgcagt gatgtgatca tagctcactg caaccttcaa cttctgggct caagccatcc 106080
tcctgctcca gcctcccaga tagctgcagc tacaggtgtg cactaccatg cctggctaat 106140
ttgtgtgtgt gtgtgtatgg agatgggtgt tcttgctctg ttgcctaggc tggtctctaa 106200
ctgccaggct caagcaatcc tcctacctcg gcctctgaaa gtgctgggat tagaggcatg 106260
agccaccatg catggcctta gttttgtttt tggattgttc cttgctagta tatacaaata 106320
caaataactt ttgcatattg tttttgtacc ctacaacctt gctgaacttg tttaatagtt 106380
ctagtaattt ttagcacatt ccttaaggtt ttctgtatac aatatcatgc tatccatgaa 106440
tagaggcagt tttacttctt cctttccaat ctggaagtat tttctttctt tcttttttt 106500
ttttttttt tttgagacag tgtcttactc tgtcacccag gctggaatgc agtggcatga 106560
tctcggctca ctgcaacctc tgcctcccag attcaagcaa tcctcctgtc ttggcctccc 106620
gagtagctgg gactacaggt gcacgccacc acgcctggct aatttttgta tttttagtag 106680
agacagggtt tcaccatatt ggtcaggctg gtctcagact cctgacctca ggtggtccac 106740
ctgcctcgac ctcccaaagt gctgggatta gaggcgtgag ccaccacacc tggcctttta 106800
ttttgtactt ctttttcttg cctaattgtc ctggcttgca ctctaataca gtgttgaata 106860
gaagtggtga gagtaagcac ctctgtcgtg ttcctgatcg tagaaggaat tagttcagtc 106920
acttaccatt aatcaagtat gatgttagct gtggggtttt ttgttaatgt cctttatcaa 106980
gatgaggaag ttccatctat tccaaatctg agtttttttt tttatcatga aaaggatctt 107040
gtcaaatgct ttttctgtgt ctattgacat gatcatgtag taatttttat aatctgtatt 107100
acattgattt tcttgtgtat aactaacctt gcatttctgg gatagattct acttggtcat 107160
tgtgtataac cacctccccc ccgacttttt cttttttttt ttctttttttc ttttttttt 107220
tttttgaga cagagtacag agtctcacac tgtcacccag gctagagtgc agtggcgcaa 107280
tctctgctca ctgcaacctc cacctcccag gttcaagtga ttctcctgcc tcagcctccc 107340
gagtagctgg gattacaggc gccttctacc acgccctgct aatttttttgt atttttagta 107400
gagacggggt ttcactttgt tggccaggct agtcttgaac tcctgacctc gtgatccgcg 107460
tgcctcggcc tcccaaagtg ctgggattac aggcatgagc caccacgcca ggcctgtata 107520
accctttta tatgttgctg ggttctgttt gctggtattt tgttgaggat ttttgtttgt 107580
atatgcataa agtatattgg tctatagttg ttttttttct tgtcttacct ttgcttttca 107640
tatcatggta atactggttt catagaatga attagaaatt atttctttta ttttttggaa 107700
gagtttgcga aaagttgata ttaattcttc tctaaatctt tggcagaatt taccagtgga 107760
gtcatctggt ggacctggac tgtttgtatt gtgtatgttg ttggtggggg ttaattactt 107820
attcattcct tttacctgtt gcattgtttc ttgcttgcag aacatgcagg ttgcttgtag 107880
aaacacactt acgtaaaagg agagagattc tgggaagagt gggcctagca ggaatttgga 107940
aatttagggg tttctagttg gctctacctg aagctgtgcc ttctcctctc ccctgtatta 108000
tcacatctca gatgaagcag tcttccttct cctgcctgaa tgaacactat tgaggttagg 108060
accaataact gaagccgtat cttggatgga aaaggtgtgt ctgtgtgtgt atgtgtgtgt 108120
tctgccttac cttaaatatt gataaaaagt gaagaaagat acctcaactg ttgagattcc 108180
gagatcgtga atgacagacc atagtgaact ctggaacagc catttaaaga atgagatagc 108240
tctccatatg ctgagaagca gtgatctctg ctgggtgctg tggctcatac ttgtaatccc 108300
cgcactttgg gaggccgagg agggcggatc acgaggtcag gagatcgagg ccatcctggc 108360

-continued

```
taacaccgtg aaatcccacc tctactaaaa atacaaaaaa ttagccaggt gtggtggcac 108420
atgccagtaa tcccagctac tcaggaggct gaggcaggag aatcgcttga acccaggagg 108480
cggaggttgc agtgagcaga gatcgcgcca ctgcactgca gcctggcaac agagcgagac 108540
tccatctcaa aaaaaaaaaa aaaaggtgat ctcgtgctca cttcagcagc acatatacta 108600
aaattggaac gatacagaga agattagtat ggcccctgcg caaggatgac atgcaaattc 108660
gtgaagtgtt ccatattaaa aaaaaaaagg tgctgtctaa gatatataat taagtgaaat 108720
ctgcagaata gtgtgcttcc atttgtgtaa ggacaaaaca tggaagggag cctgtggatg 108780
cataggctgg acatatagag caccttggca cccacgatga gagtcagagc tggtgagaga 108840
cttagtaccc tgtggggttg ttttcccttg tggttatgtg gccttaaaca aaactctctc 108900
taaagtaacg tacctgcttg aagtgcagtg gtgagcctgt gtgtgaggag gctatgccct 108960
catggcaaca gctacccttg gcagaatctg aacatctcag agacatggcc tgaggatcct 109020
catgagttgt ctctgccacg gtgtgggagg cactatttag acctccattt acttgaagcc 109080
tagtgttcct caggaattcc tacatctgcc tgtgggaaaa tggtgataga tttcaaaggc 109140
tctccaaggt tcgatgtttc cttctgagtg ccatttcagc aacataggaa tttcggtctg 109200
tttctccaag gtgaagggct ttcattgccc tgttgcctct ctgtggactt ctggccaggt 109260
ggccctacag aaaagcacct tattctttct tggcagatcc agtcatggct cctgcctccc 109320
accatgagtc gggatattgg ggaagcgaag cagatgccag aagtctttct ggtttcccag 109380
gccgaaggag ctttcacact aatagcctgt ccttttcaag tctgacagaa ctggcaagca 109440
ggaacaattt aggtttttgg aaatatccac aaactctttg cttccatccg gagtgaatgc 109500
ttctcttcct tcacaggggc taccctaaga ggctgggaag cctcccagcc tgggctagtg 109560
agatcccagc ccagattcca ggcctggatc tggggccttg aacaatgagg atccttgtat 109620
ctctcccaca gagaacacct tctgcagtgg ggaccatgtg tcctggcaca gccctttgga 109680
taacagtgag tcaagaattc agcacatgct gctgacagag gacccacaga tgcagcccgt 109740
gcagacaccc tttggggtag ttaccttcct ccaggtgagg cacaggttgg acgctggctc 109800
aagccttcct gtgggaaggg tcctgggagg acaaggaggc ttgaggaggg ggagtgaagg 109860
gagtgggagg tttcctttgg cctcgtcctg atttctgttt cctctgatgg tttgtcaggt 109920
agattcagat ggtctgattt aacctgctga gatgggagag gggagaaagg gaagggggca 109980
tttggttggg agagaatggc tgtagctgag agggagtaat ggggtggcgg gtattctttg 110040
aacagtgaag acccagtctc aggaacagga ctttccagcg ggaagccagc tctgggtcgt 110100
ccttgctctt tgccagaagc tgtgggaacc tgcccagctt tgaccagtgc ttgtttttgg 110160
tcacgaagtc tatgtgaagg ttccactgat tcccttgata tttacacaaa ggcctatccc 110220
ctaataagga agggaggagt ttctctgcag gctgctatga cctattggtg gtggttccaa 110280
gcctgatagg tctcaaagtc tcttgtttac attccccatg ataccagact gggtaggaat 110340
ggctccctga acctccccta cttccagaga catggcctga ggacacatct tgagttgctc 110400
aggccttggt tttctccttt gtagctaaga gctagacttg gtgtcatcca gacacagcaa 110460
gggcaagggt caggcctcag ggcccacatg tggacccagc catttcccag ccaggcagcc 110520
actccctcct aagggaatca tccaatcttg gctgcaccag ctcctgagca cagatcctgc 110580
ctgtggtctc ccaactggag gtgactcaga gagcctgggt agctgacctt cttggggtgg 110640
ggggtggcca ttaacacaca atgggctttc tatcctgggc ctcagatcgt tggtgtctgc 110700
actgaagagc tacactcagc ccagcagtgg aacgggcagg gcatcctgga gctgctgcgg 110760
```

-continued

```
acagtgccta tgtgagtacc catgcaaggt gggagcgcgg ctccctgggc ctgggggtgg 110820
gagtccctcc actaccctcc atgtggggct ccctcttgcg ttgttatttc agaccctggt 110880
ttttcacatc agggcttcct gacgactcac tccctgacag tccctgacca cgaactattc 110940
ccctgtgtcc taggcctggg gcagcaaaca gggcaggctg taggcccagc ccatcagccc 111000
cagaccctca gttaccattg tatccccttt ccttgtccac agtgctggcg gcccctggct 111060
gataactgac atgcggaggg gagagaccat atttgagatc gatccacacc tgcaagtatg 111120
tcttgagtga ggaaaacctt tctagcaccc tgtgcctagg cctcttccaa ataacactgg 111180
ctttcatcct gggaaaacag aggaccttta tgtgtgagtg agtagaaata tggcatcact 111240
tggaacttgt cccctgaatt ctgcagagca cgtagggagc agaggtttca gcccaggaaa 111300
gctagtcctc agacatatgt attttggcat tttaaaagga tatttttatt gtatgtaaat 111360
tatatattgg cttaaaaaat tagattgcca gcaataaaag ataagtgtag tggatattgc 111420
ttgcttgccc agtattcatt ctcctgcctc ccagactttc ttttagggag ccaccacggc 111480
caccaccgcc ctgtaccaga cagtagtgta ggtgatactg actccatggc tcagctgcag 111540
gagtgagggc tgattggtct aatggtccta tccccatttt cgccacattt tctatcttgg 111600
acagtcagat gcagagctcc tagcctggaa agattggcac cttagacaca caggctggca 111660
gctgcccact ccctgtggcc cacctggaca ttgtttcagt gtcatctttg ctgttttaga 111720
agcattcctt tgtcatgcag gtaaagtttg aaagccacaa gaacgtaact gccttttctt 111780
tttttgagac ggagtttcgc tcttctcacc cagcctggag tgcagtggca caatctcggc 111840
ttactgcagc ctccgcctcc cagggtcaag cagttctcct gcctcagcct cccgagtagc 111900
tgagattaca ggcgcccacc accacgccca gataattttt tgtattttta gtagagacag 111960
ggtttcacca tgttggccag gctggtctcg aactcttgac ctcagatgat ccgcccgcct 112020
cggcctccca aagtgctggg attacaggtt tgagctagtg cgcctggccc ataactgcct 112080
ttcttatggg cttctcttga agcaggagcc acagacagct aataatgtta cctgcctggt 112140
gtctggctcc ttctactccc ctgaccaaat gcaggtcatt gccatctcta aacctgccat 112200
gcttctgtaa aatatctggt aggccacagg cagttgccgg gagttccatg tgttagagca 112260
agagaaaggt ggcagatgga catgtagcca gcagcccctg agttcttcac tgtagacttg 112320
tgagttcttg ggcataaatc ctcttcattc acagatgatg ctcctctgtt ttcctagtgc 112380
ctttaacact gaacatttca aactgctgcc aggatcctct gttctctctg ctttaaactt 112440
ggtttccttg tatcttctgc atatgcaaga accaggaacc aggaaggcta tctttcccta 112500
agcccttgtt ctgtagccac actgggatcc agcatggggc actgtgggcc gttgtttggc 112560
ccctgtcata agtgccaagt actaagaaag aacctggtcc tttgcactag tagggtaaac 112620
agctgtcctt ccatgccaag ggctgttctt cctagtctgc aggatcccct gagagcagcc 112680
cacaggaccc ggagcaccta gtggtctttg aaagcaagcc agggtcccac aggaacaaag 112740
gacagctttc tttcctggtg gctctgtgca ccaagtgtga actcctctgt attcactgtg 112800
cctttctggg gcctgcttgc tatcagtctc tttagagctg gcatatattc ctgtgattca 112860
agctctacac taaccagctg tgtgcccaaa taagtccctc gccttctggg tcttaacttt 112920
ttctttttac ttataaagta aatagcccag acaagttgag ccaagaattg tctgtctgca 112980
actctttacc taagtgaggg accccagggc agccagtgca gaggaaaaag ctcagactat 113040
cccctgagca caccagggta tacatgctcc ctgcccagag tacacagagc gcttccctgc 113100
```

ttagcctctt cctgctcgga acccacagct ttgcccaggc cagcattagc acttgaaagg 113160
aggagatgac tgatgggaag gaggcgtctg gggcagagcc acttgctgac tggtcccagg 113220
aaataaggac agtacctgta cttctcccac atggggcttc tgggctgatc agcaggccag 113280
tgtggtacct gtggagccgg gaagcacaga ttattgttga gatgctcagt cacaagcttg 113340
atttggccca catggacata gagccttcca gatgactttt aattcaaggt ccagcatcaa 113400
tgaactgtgt tttaccagaa aatccaggga tgttttgagt acaactcttc cttgaagcca 113460
tttggagagt gtttgtactc agcagtacca aggcctgcac aaaggcaggg tctcgatggg 113520
gagagaaggg tgtctgcaga tagtcactgc actctaggcc cccatttcag tctaagaaat 113580
gggaaggaat ctccatccag agtcctttgc taaacaaggg aaccaatgca tctagggaag 113640
tccagccttt gttctccagt ggctcttccc tgtgtgacca caccctctag ctgttagaag 113700
gggaaactgc aggtgtggcc tgttgcctgt ggcaggcttc caccctgttt tctatagcag 113760
tgactgggag gttctgcctg aagatcggga ggagaggaag gatcacacct ctcctcagag 113820
aagtaggctc tctcatggcc acatcagccc caccagccag cgtggcgggg acaggtttgg 113880
ggctctgaaa caggtagagg ccattgtgct ggaaggctga tggtagaaga gatgtttccc 113940
ttgggatttg cattcctcct ggcttcccct aatccctggt tcccctggag gagtccagga 114000
gctggcagag accatcatgc attggtaacc agggcagaac aaggtcagag atcctgctct 114060
ccagcatttg tcccatgctc agcaccacaa gggctcagta aatactgtaa gagcagtggc 114120
tgaaagggtg gtcaccttgg gtcaccagtt ctctgaaaga actctggctc tttggttctt 114180
ttcaagcagg agagagttga caaaggcatc gagacagatg gctccaacct gagtggtgtc 114240
agtgccaagt gtgcctggga tgacctgagc cggcccccccg aggatgacga ggacagccgg 114300
agcatctgca tcggcacaca gccccggcga ctctctggca aaggtgggag ccatcactca 114360
gcattccacc agccttcctc cttccttttc cccagggcct ggtttccagt ctctctagga 114420
tgggtctcta acaaaaacaa cccattcaat agtttatttc ctggcatgat ttaaacagca 114480
agtgaagtct tccagcaggg cggaattaag ggagctttat tggcccattc ctagttgtgt 114540
ttcctgtgtg tatttcaaat gcatcaccag caggcaccgt tgtgttttag atatgccctt 114600
tgcaatctga ggtcatggag gtgagtggaa gcctcagaac agttacagga aaagtccata 114660
gtccacccaa gtgcaagaga aaagtgtcgg ccacccacgg aattgacaca gggcccagct 114720
ctggcctgaa ggccatgcca gatccaagga tcactctggc ctcgggccct cccaggcctt 114780
caacaaatga ggcctgagtg tgaggctggc ttgcaaattg cccacctcct gtcatataga 114840
tacagggtta ggggctgtgg gcagggcctc tggacccacc gtgttccgga tggggtcttt 114900
gggaaggagg atgtggctgt cctgttggaa tctccctgtg ctgatcttgg ctacagaaac 114960
agttgtggtt tttagtagag ggcgtcccca gctaactgca aaggagaagc agccacttac 115020
atatacatgt gttgacagct tctttgtcta cttcctttct tcattcttcc atcttttctt 115080
tttttgaaga ataagatgtc tacagccctg aataaaatcc ttacatatat gataacactt 115140
ataaaaggtt tttgttcgtt ctgtaaagga caaacttaaa ctcctagtgc aaatatttga 115200
gccctttctt tttttttttc tttgaaacag gggtctctgt tgcccaggct ggagtacagt 115260
gggttgatct tggctcactg caacctctgc ttcccaggct gaagtgattc tccagcctca 115320
gcatcccaag tagctgggac tacaggcgtg agccaccaac gcccagctaa tttttgtatt 115380
tttttgtaga gtcagggctt cgctgtgttg cccacgctgg tcttaaactc ctgagctcaa 115440
aacaatccac ccgcctcagc ctcccgaagt gctgggatta cagatgtgag ccaccgcacc 115500

-continued

```
cggccaagcc ctttctttcc ttcctgtttg ttctaatggc atgccaagcc tattggaggc 115560
tcaaagagag ggtatacagt tattggaatc atttggttgc ttttgacaaa agaggtgatt 115620
taaagaggga gtcatagtct tgtctaaaat ttcagtcatt actggctatt tttaaaaatt 115680
gtaaaagtaa tccattccac tgtaacaagt caaatagtta gaaaagttag taatcatctc 115740
cttcccactc taaggccact ctttgagcaa ctaattttaa tttgcttttt tgtatctgtt 115800
tacagtttgc agaggtaaat ttagatccaa atctcaatac aggggaccag actagtaagc 115860
ttcatcccaa agaccagcaa agcaccttac aaagaaataa tcccaccaag ggaactcttt 115920
cacttcctgg cccttgcctc tccatggaga ggcagagttt cctgggatag accaaggtgg 115980
agagatgatc ttagcatctc actgacttga atgcaagggg aaggagtggc gggaccagat 116040
gctagttgac tacccagaac ccagaaaggt gtgttagagg cacctgccca ttcatggcag 116100
ggtgcttgca gccttaactc acatccattt cagtgggcag aatccccagt agtcagtcac 116160
tgtgtggagc catgttaagg gtaaacctcg ggcctgtgac acaggaaaga aaaggatggt 116220
ggagagcgct cttctgaact ctagaggctg cccctggctt ctacaagaat ggtactcttc 116280
caacccagag cttcttaaga gcgcggttgt cccctcgcaa tctgtactca ctcagcgctt 116340
acatctggat gcgtagagtg ggctcaggac tggccagcgt ggtagttttt cttagcacct 116400
ctgctgagcc aggtttcaag agcggggtga gaattgctgg gagcccactg ggccactggg 116460
caacttagtg gtgtcgttgc agacacagag cagatccggg agaccctgag gagaggactc 116520
gagatcaaca gcaaacctgt ccttccacca atcaaccctc agcggcagaa tggcctcgcc 116580
cacgaccggg ccccgtaagt tccccagtgt ccctgggctg gaacaagagg acgacttttt 116640
tctgaagggc ctgtccctgt ggattgcatg agagagaaca atgcacatag cccttgctgg 116700
atgggcccag gatctctagg cttaagggca ggcatggtct ggggcacaca gatctatctg 116760
tgggtcatag gagagggcct cagaggggac ccagcagacc gtgaatatta acatcagtaa 116820
atatttacat gagccgtgtg aacagacagg aggccaggtt ggggagaaat ctgacttggg 116880
gcctcccagc cttgtgggag cccattgtgc tgagcacggt tccctcctta tctcagtctt 116940
ggccagagtt gcccttcctt ccttcctgga gcctggtctc cggctgatag ctgcaaccct 117000
gggggcctcc ctctctggcc agccccatac tggatgcctg tggctgaggc ccttcttcct 117060
gcctctcttc cctggggccc agggaaggga aaggaagtct tttgcaggcc tctgctgcct 117120
gtccaggggc ccctgtagcc ctccggagag actgtggcca ccctagaggt cagatccgct 117180
tcctgccaac ctctcttcct ctgatagagg ggatgagtga taggcagggc tgaagctggg 117240
caccccccctc tgcccttagt cccagggcag ctctagggaa tagctgctgg caggagatac 117300
ctgggggctg gcagcccaaa gcaggaacct tgcctgccag ggaggaaatt gctgtgcctt 117360
gggctgaaag ggaggttgat catcctgcaa gaccagggtg atctagcctt cttctatgaa 117420
gtctttatta cacatttgct gtctgacaag ctcggaccta gggggccatc tggggtgcac 117480
aggctcttcc tttgggagaa catgagtgaa acagttacct tttaatggtg tgcatctggc 117540
tgtcgatgtg atttgttgga aatggctgct tctctggatt ctagctctag ttgctgatcg 117600
tgtttcccag aagtagtaat gcttcagtgc actacagaaa agacaggtcc acaggatctg 117660
gggtagttag ggagggcatc ttggaggagg aagaacatag catcgacctt gagggcacct 117720
tagaatttta ataagcaggg gaaggaactc aagaggatag cacaggggag gcctggctgg 117780
ttaaagttga ggctgcctgc tgggacctga ctggaactag agttactctg ggaacagggc 117840
```

-continued tgtactgaga gttgagctct ttggcaaaag cctggagaag cctccaccgc cacctcagag 117900
cagcttttaa ctccggcctg taggtttctc cagccagctg ccctgaagta gctggctgga 117960
ggcatcctga tcatcccctg gcagcagcag atggccacac caggtcatac gacatatgga 118020
agctctctac ctgtgagtct ggaccctgtc ccgggtctac actccttccc attccctgag 118080
cttggcttct cgctttgggc ctccttggca ctgttggcag gccagaggta ctggaaggcc 118140
tataacatgg acacagtctc agtccagatg gctctctgcc tctggaagcc tggggtttct 118200
aggcagaagg gcacaagctc ctgcagagat acaaccttct tgccccgctt gtgtatctgg 118260
aacaggcctg agatctcact ccctggcttg ggggcacttc cagctactgc acccctggac 118320
attgcaatgg ggcacaaggc tctgtgctcc tagatataca cataagccga gactctcagc 118380
ctacacccta actgggcagt cggtattgg ttctggccca agggttctct gtaaacataa 118440
ggcagagagg ctgcagcttc taccctttgg cttgagttgg ctgagataca gagagatggg 118500
tgagaataga ttcgaggtgc cggggttgtc tccccttcct gaaggtttag tgcccagtaa 118560
ggtctctaaa gcaccaggac ctgtagtctg aggggaatag aatgtttcct ctgaggctgt 118620
cagtattggt taccaatttg ttagcaattg gttgagaaat ggtttctcct cctcctttgc 118680
caagaacatt ctccaacaca cccctcaagc ctgtcagact caagtttcct gttatctcag 118740
gatcgatgat gatggactca gttcagatca gtgagcgtga cggtaatatc tgtgctgccc 118800
actctgggac ctgaccccat ttcacataca ccacatggat tgcaactgag aaagctgacc 118860
caaaatgtgc tggcaccagt gtttgctcct ctccctgttg gggggcagcc agcgtgggcc 118920
atattttgtc tgcgggtctg atttcccctt agtcaggact tctgggccag ggagctctta 118980
tgcatgggtc ttcgcgggtt tgtctgtggt ctaaggaaga tacagagcta aatcagaggc 119040
tcagagcagc tgatcaagcc tgggcaatag cagccgggtg ccggcctact tgggggtgtc 119100
aagcacttgc tcttttcaca cttcagcagc agctaaaacc ttattagtgc tcattctgtg 119160
ctaggtaatg tgccagctac tatgtgctgc cattcattta tcttatcctc atagccatcc 119220
tgtggtcgat aatcttacat attccccttt aatggatgag gtacagagag gctaataagt 119280
atcttttcca aggttggaaa ggggtagagc ttagttacag ccatctatca gccattaaaa 119340
tggatgtaat cttccttacc ccattctcag ggaccccatg gggacacat cagactgtgt 119400 ctctgagaaa ataatgacct ttactggtag aattcatcta actagttgca gcatgaatca 119460
ggacctctca catggcacca aggacaaggc caaagcctca tattagaagc ttattgggct 119520
tatttaacta aactctaggg gagttaaata actcctatga gatgccatga gccttgatga 119580
ttccaaatcc cagaaataac aagctatgtc ataattggct catttatacc aaaattattt 119640
tgtgacacaa ggccttactt tcttcatgtg cagaaactaa aacaaccctc tctctggtcc 119700
ctctaccacc tcagggctag gggatttctt tccattttga gggtctattt cttcctttcc 119760
agaaaggcag gccccctggg taacccgctc ctctcctact cttcattgcc agccctcctc 119820
ccactgcctt cccggaagga gagtccttgg ccctctttgg ggcttcttca gcatttcaca 119880
acccttgcat tccagccatg aaatctgtat ctggcttttc ccaagatgat cagttgagaa 119940
aagcctcctt cagcttgctg gcgcctccct tcccactgcc tgctcgggtg agtttgggaa 120000
ggatgggaag cagttccttt gtgccacatg aggacagcct ggcttaaaga ctgtgcctgc 120060
caatatctgt agagatttga ggagggaaaa gttcctgggc atcctctctg tctgaggtca 120120
cctggtcaga catggtctac ggagtctggt ctctctacag tgcacagaag atacgtgtgg 120180
tcaggtgaat tgtgtgtaga ggttttcttt tatttatttc tttttttag acacagggtc 120240 tccttctgtc acccaggctg gaatgtggtg gcaagatcat agctcactgc agcctcgagc 120300
tcctggcctc aagtgatcct cctaccttgg cctcccaaaa tgctgggact acaggcatga 120360
gccaccacac ctggcctgta tttctctaaa ctgttgctca gatgctggga acctgcacca 120420
gtattctagg gccacctcct ccctcagcca gtgacttacc acctgaggct gggaactctt 120480
aggaagctct ctgagttgtg tgccctccca gagagggaca gggcacatgc aggtgtgcac 120540
acttatgtta gaggggaaaa gttcctgact atgggagaag cactttgtag ttgaggcacc 120600
tctaaaaagc gaactcacca tcactgctga gtttctcagt cttctagaat cacaccagca 120660
gcttttaaga cctttaaaaa attttttttg ccttaatttc atggagaatt aagattctgt 120720
accatgaatt cctctgctgt aacattcaca tttgcaacac ctccccaaca tacacacaca 120780
cacatataca tagatttctc tctactctta ggagtgtctc tgcacttgtc tgtttggcct 120840
ttgattgggg tgactttgct ccctctaatt cccatcttga ataccttgta acctggccag 120900
ggagtcatcc tttagagaaa attgtgtttt gttttgctca gcttgtgagg tccatgaaga 120960
ttaattagag gaagaaaata tcttgtttgc atccaactta ccagtgaatt ggggtgaagg 121020
aaggtgagtt tccatctggg gaaacagctg ggctgtggct ggtgccgctc gcacgaaggg 121080
cagtgttggg taaccctgct tcaaggggtc tctcctgtca gcgcagtggc cagcctggag 121140
ccctctctgt cacgttggct tccctcacac tcccacgctg gggaagtaca gttgcttgca 121200
ctggaaagaa agcccagaaa gaaacagccc ttctcttagg gccccagcca gactctgcag 121260
ggctgatgag aggaacagcc caggcctctc tgctccctgc gtcctggaca gcaggctcct 121320
ttttgcctcc ctcactgtga tccatgttgt catgccaagt gcctttacag gcctttctca 121380
gaaatacata tttgaaaggg cagagcaagg ggctccacag caagtctggc atgggtaaat 121440
ttctgtttta actccgttct ttgctccgct tccccaaaga gatgaagtca cggccattgt 121500
taacacctca acttcagaat tccttgctgg tgcttgaatt ctcagtccaa acgctgcatc 121560
cccctccctc gagttgcaca atcaggggta tttttatcgc ccatccttga tcctcggtgt 121620
cacccaacac ttcagcagtg agtcacttct ccagggaagg gaaaaggaag gctcaaaggt 121680
aagagctaga gaaaggaaat gactcagtgt ctcagaaaaa ggaaagctgg ggttctggct 121740
agagtaagct cattcaggag agtaggggtc ctaatctccc acccaagtca gagggtaggg 121800
ctggggatgg cggcccctgg tgcccagagg agttaatagt tgactaggaa atcccctaac 121860
cttgatgcag attttactca ccctgacttc tttagccata ctctgtccca ccatttcatg 121920
atttcatgat cacattttac ctttgggata ttcccgatga aaatattgcc ttttttttt 121980
tttttttttt ttttaacacg aggtgaagtc tcactctgtc acctagactg gagtgcagtg 122040
gcacaatctc ggcttactgc aacccctgcc tcctgtgttc aagcgattct cctgagtagc 122100
tgggattata agcacacacc accacgtcca gctaattttt gtatttttag tacagatggg 122160
ttttcaccat gttggtcagg ctggtctcga actcctgacc ttatgatctg cccgcctcag 122220
cctcccaaag tgctgggatt acaggcatga gccactgtgc cctgccaaat attgcatttt 122280
taaactgggt gtggtggctc atacctgtaa tcccagcact ctgggaggct gaggcagaaa 122340
gagctcttga gtccaggagt tcgagaccag cctgggcaac atggcaaaac cccatctcta 122400
caaaacatta gccaggtgtg gtggcacatg cctgtagtcc cagctactca ggaggctgag 122460
gtgggaggat tgcctgggcc tgggaggttg aggctgcagt gaaccgtgat cacaccactg 122520
cactccagcc tgagaccctg tctcaaagca aaaaaagaaa atactgcatt ttgtcatttg 122580

-continued gttattggtg tttactattc accttttgtg gccttttact cctatattgt ccttataaga 122640
aaatttgtca gaataaccag gttatacagc cttgtgctta ataagaactt cagaggtgag 122700
ctggtcccct ctccctcgat cccacagcca caccctttc cagttctgcc ttaaagggag 122760
acctgcaggt ggttctttct ctggaaagtt cagagctttc gtcagcaatc agaaagcaaa 122820
aggaagaatc tcccaggcaa ggggcagaag ccagaggttg ggctgggctc agcaggccaa 122880
atccacttca cttgtgaata gttgccaagc ttgatgccct ggttcctgtt cctgggcatc 122940
cccaaggaga aggccccaag tcgtgtgtcc actgcagacg tcatgactca caggactggg 123000
attgtggcta aaaggagtct caatggttca gctcctctcc tttccaccca tgctgccact 123060
gactgaatgg gaccaatgcc ctttaggcga atgtgaaaaa ttaagacttt tccgttcaga 123120
gagaccaggg tggaggggaa gcatggttga gactctgttg gtctgttatg tgtaggtagg 123180
gtgatcaagg catgtactat gaactgtaca ctgctagaaa tcaggaatct accttgacac 123240
tggaaggaga gggtatatta ggatctataa aaagtcacct tatgcagtga gaaatacaag 123300
tatagaatgt gttatataga caggtggtta aagatgaaat agatcagttt agatcaattg 123360
cacctctaag ccatcccata aaccacccct tggtgtggtg ctctcaatat agaaggaatc 123420
ctgggctggt cctcgcggct gagtgggcag tttttattgc gcatcacctt gtgccaggcc 123480
ttgcgtcgtg ggatgccctt gttcctgtct tgtgacttag aacactgaga cttagccagg 123540
ttgtagaact tatctagcat cagactgcag ggattaagtg tcagccagga tttgaacctg 123600
agtggtgtga ctctagatct gagcctcttc actgagtatt gcctgtaaaa gaggataaag 123660
gtggagggat acatgccagt tcaccagaaa acataactgg aaacagggtc tttgatgcct 123720
gcatgccggt gcacagagga aagctggtat tttagtttgc ctggaaaccc ctgaaggtgg 123780
cagttcagga gagaccattt agctgagaga ggcatactaa aaaaataaag tgaaatcagc 123840
tagaggatac actccatcca aatctaagtg aggaagacat atgggggtag gaaatggatt 123900
caacatgaga aagagacaag gagaatccgg ggtgaatggg agagtgatcc cagatgacaa 123960
cggtatagca ggaatgaaag gcagccaact caggtgggag cgggttggaa ggatcctctg 124020
gagaaatgtc tccaagaaaa taaaattgat aaatacctga tgtatttgaa tgtcctggga 124080
ggaggatgtg tggaccattg gtaagagtaa tttttttttt tttttgaga cggcgtctga 124140
ctctgtcgcc ttggctggag tgcagtggtg tgatctcaac ctctgcctcc tgagctcaag 124200
tgatcttccc tcctcagcct cctgagtatc tggtaccaca ggcacatgcc accatgcctg 124260
gctaattttt tgtacttttg gtagaggtgg ggttttactg cgttgcccag gctggccttg 124320
aactcctgag ctcaatcgat tttcccaccc ggcctcccaa agtgctggga ttacgggcat 124380
gagccgccac gcccagccaa taatagtaat tctgatttaa ttggtgataa gcacatagaa 124440
aactaagaca ggtattaaat ccaaggaaaa tagaaaatta tgacagaaag gaaaagtata 124500
ttaatataat acatggctca actgtaaaca gcattgatat agtcataaaa tttaaacaca 124560
ccagtccaca caaactgatg gtgcagttat cctgaaaagg tgggaaggtg catggaagag 124620
agctaaaagc tcatcttccc tagtggggag tcagtaggta aagcctgaaa aggaaatacc 124680
aggccaggtg tggtgactca cgcctgtaat cccagcactt tgagaggcca aggcgtgcag 124740
atcacttgag gtcaggagtt ggagactggc ctggccaaca tggtgaaacc ccgtctctac 124800
taaaatacaa aaattagctg gaaacggttg cgtgcctgta gtcccagcta ctcgggaggc 124860
cgaggcagga gaatcgcttg aacccaggag gtggaggttg cagtgagccg agatcttgcc 124920
actgcactcc agcctgggcg acagagcaag attccatctc aaacaaaaaa aaaaagaaaa 124980
gaaagaaaag aaaaggaaac accggggaaa gtttatttaa aatatcaagg atgggaggct 125040
gaggtgggtg gatcacctga ggtcaggagt tcaagaccag cctggccaac atgataaaac 125100
cccatctcta caaaaatata aaaatcagcc aggcgtgatg gtgggtgcct ataatcccag 125160
ctcttcggga ggctgaggtg ggagaatcgc ttgaacccag gagttggggg ttgtagtgaa 125220
ccaagatagc accattgcac tccagcctgg gcaacagagc gagactctgt ctaaaaaaac 125280
aaaaaaaaaa tttaaggaaa atgcgaaaga atcatctaca gaggtgacag ttgtctccga 125340
ggaggggagc atgggaaaac agtgactatt gtaatgaccc tcatgaaacc gtttgactaa 125400
acactaaaaa agaaaaaaga aaaagatatt gtatgagctg ttacagttta ccctgcccag 125460
tgaaaagaaa ggatgatgtg tgccaggtaa aaagcacaca gttagtgcca aggcaagccc 125520
aggggaactt cagcttcccc agcctcaggc tgagagttga gggtgagcca tggagaatca 125580
tctgacagcc ccctgaaaag tgtctgtctc aggggcacag aagataatgg ggggaacttg 125640
gctgtggacc caattctgac cagcagggag tgtgagtcct gtgagaaagc agcttgggca 125700
ggcagagttc aggagggaaa accctgggcc agtagtccct agaggaggtc cccacagcgt 125760
tttaggggat tttcttgggt gttcagccag aagagggttc tctggctaca gttggaaaat 125820
gctggcttac acaaaatgaa accggtacat tttccctctg tcctcctcag agtccaaaat 125880
gccaacattt tgtgaatctc taatctgaga tgggacatat tccatccacc tttgccacac 125940
ctgtttttct agaggcttct cttaaattaa aattccatcg aataccottt gggaagtcct 126000 gccctgtctt ccaggaaggc agttctttta agaattcaag gaaaagatag atatgtcttc 126060
atagtcttga aaccccggaa gaaaagacca ctcaaaagag atgggagttt cttaaggaga 126120
aatgtagaaa tattatagtt acttttgggg ttttatctca gctctttact cattgtgcga 126180
tcttgggcta gttatttaag tttctgagtt tcagtgtctt tatctgtaaa atggggaaaa 126240
taatgcctct ttatagagtt gtgatggaaa tgaaaggaag caaagtacac aaaggattag 126300
catgggaccc agcaccatag tctgtgctca ataaagatgt ctcttattat tgtgaatagt 126360
cccctgaaaa ccaaaaggag gtctattacc tccagggacc aatataggtc tgtagagaat 126420
acttcacaca actcaatttg gaagaatttg aacaaatgct ggaaggagag agatgttatg 126480
tcagcataga ctttaaagaa cagggtcaag aaaagctgaa actcaagaac tgagtcttgc 126540
aaaaaaagtg caatgaccag caaaaaggac attatttttg tacttctctt tggagcaaga 126600
agaagaaaac ctagacccaa ttgtttggac agagtaacat ttatcagtgg cagagagaaa 126660
gcaaaatttg cttaagttct gttatggttc catattaaag caaatggtta tcagaccagg 126720
aagggtccca caggcattga caagagggtt gaatctatta tttcagctct cctggctcac 126780
atgtattgtg cctccagaac accagaattg gcaggcgaga gtcatgaagc tggtgtcagc 126840
aatctttgag ggaatgggag agaggtgttg gcagactgga agtactcgga agtttcagga 126900
tgcaaaaagc atcttgcact ctctagacta gtgagcttgg tgtcactctc agtgaaaatt 126960
ctggactaga ttattcagca agtaggctgt gaacactcca agggaaagag cgagtcctga 127020
gagtcagaaa cagccaggct tgccagacca tcctcattgc ctttttattt atttattttt 127080 aatttttttcc aaagaccgct aagtggactc aacatcgtcg ttgccttttt agaaatgcct 127140
acctggctgg gcgcggtgac tcacacctgt aatcccagca ctttgggagg ctgaggcggg 127200
cagatcactt gaggtcagga tcacttgagg tcaggagttc gagaccagcc tggccaatat 127260
ggtgaaaccc cgtctctact aaaaatacaa aaattagcca ggtgtggtgg tgggcaccta 127320

-continued taatcctagc tgctcggtag gctgaggcag gagaattgct tgaacctggg aggcggaggt 127380
tgcagtgagc cgagatcaca ccattgcact ccagcctggg cgtcgcagca agactctgtc 127440
tcaaaaaaaa aaagaaaaag agaaaagaaa tgcttacctg cccaagtaga caaaggaagt 127500
gctgtagacc ttatataggc ggggtttagc aagatgtttt gagaacattc tgacagcatt 127560
ataggcaaaa cagaaatgtc cagagaacat ccagaagggt gagggccgtg gcgatgggaa 127620
ggttgggttg atttataact ggttggatga gcatacccaa agagtaatga tgtcagtccg 127680
tcagcctgtc tgcctagccc tttcctgttt actttttaat caaagcctgg gatgagaaca 127740
tcgatgacga atttatcagt tttgtcagtg atctgaagtc aggaaggaat gccaatatga 127800
tggatgccag agtcaggttt cagaaatacc cgaactgccg gaacactagc cagatagcgc 127860
agagttcttc tgctcctagc tccatgtaat cagccagaca tatgggggag aacgggtccc 127920
agggcatccc atgggagaaa gcccgaggga gatttcgttg acagagggag tgcagtgtga 127980
gttggtagta tgaggaggtt acaaagagta gataattcga tgacagtttt aatagaaata 128040
aaatgtcctg gacaagagag atcatagtcc ctctgtgatc tgcactggtg aggtcacata 128100
ctatgtttat tgccacacac gacacttcac ttctggatgg gacatcaaac tttgacaggt 128160
tagaatgagc ccaggggagg tgacttgaat ggatggagga tttcagaacc ttgtcaagaa 128220
tctagttaaa agttagagcc acagatagta gaaaaagaaa cttggtggga tgtgagagca 128280
gcctcaggga ttggaaagtc tgttatggga agatggattc agctcgctct gggcaacttg 128340
aagaacagtg gtttgagaat tgcaggaagg cagcttgtgc tctgtagaag gaagagagcc 128400
ctggcgtcac ctccctcagt agagcaaagg cctcagtgtt tctgttggac tgtagttggg 128460
cctttccaga gcaccagtgg ttgaccaaag cctgcagggt ccactcaagg agtcaggagc 128520
tctttcaagc cccatctcag aagtaccctc tcccaagctc caggcaagaa cctttgttca 128580
gcagggaact ggcctggcca gaggcagttg taaaggcaaa caagttttgg ttaagccatt 128640
gacattttta caggaggagc agatagactt ttagaggcag ccagctaacg tcaacacatt 128700
aatgcacttg tcagatatat tgtgagcacc tactacatcc caggcactat tggccttatc 128760
tgagtcatcc catttagtca taatgaccta ttgttattta ttcttgttaa gaggatacca 128820
aagcccagag agaagttaag cccaatgtca cataaaactg gaacccagaa cttaagctgt 128880
tagccactct gcctcctgga gcacagcctt ggccccatgc ccctggcagt ccccagcggg 128940
tatgagctgt gcctccctga gagcccctct cccttccagc cccaaagcc atgccttccc 129000 ctccactggg aactcaggga gaaaacagcc cagctgaaaa attaggccat gctgccgagc 129060
acactactta ttttttatga ctaagattaa gctgacaacc atgcaaaaca ttgcaaacct 129120
gtgtcggctg cagatttaat acctcaccta gcccacacaa ataattcatg cttctgcatc 129180
gatgtccaga agaaacaaat cagcagaaaa ctgggttctt gtgtgtgtgt gtgtgtgtgt 129240
gtgtgtgtgt gtgtgtgtgc acgcgcatgt gtgtgtgtgt gtatagcagc cgcgtttcca 129300
tcgaagcagc atgccggaaa tacccaagct ccaggactgc aaatcttgca ttttgcaatt 129360
tttttttctc ttaaaagatt aaagtacagt ttcaaatgat tgaaggttgg tgggaggtgt 129420
aaatgtgggc acttgtcaca ttaattcttc agatgattaa gttcttttcc atttctttaa 129480
ggctgtttgc agttgggttt gatgtcctgg ttctgggtga gtgtgttgtg gcagttacca 129540
aggtgacttt agctgacttt caacaattta tttttccctc cagcttgaga cgtctctagc 129600
cctgtgtgct gttgattctt ttctgcaagc ccccacccca cctcccattg ctattcatga 129660
gcatttttgc ctgcaccata gaggctggga ttctctagca cgccctgcct ggacaagcta 129720

-continued ggcctcagcc cctctcagga ggacagtagt gtgtctggag gcaggaaccg gtggtcaaag 129780
atggcacagg ggagtgattg tgagagtcac cccctggtcc tttcgcttaa actcactctg 129840
agcccttcgg ctcgtcacct cacctcccta agcctcagtt acctcctctg tgaaagaagg 129900
cttgacaaca gagcctacct cgtgcttgct gggaggaatc agcgagtgaa cctatggcct 129960
tagcagaggg ttggcgcaga gtaagggctc aggaaacatg gctcaggaaa cactgcttcc 130020
tgagttctgc tcttgtttgg gccctgaggg caccctatgt ctccactgag ccctcacctg 130080
tgactgctgc ctccctcaga aggaagggag gtgcagtggc cctggtggaa gggaaagaga 130140
gttggtcgga agtctgaggc ttcgatcaga agtctgacgc acggtgaggg gggacgcgtc 130200
acccactctc ttttgtaaag gaaagaggga gattaaacaa cctcagagtt tccttccagt 130260
cctgaatact gtgaccctct tggccatagc atttgtctcc ttcacaggtc ttgcgcaaag 130320
gcgaagccag gggaaaaggc agttttagag ctggctttag gaaagcagag gaagggaccg 130380
ctttgtgaag gaacagtcag atccaggagt gagtcctcac aaggagaagg ccagcaggca 130440
ggcacggccc atgacctcag gggcacgtct aacccactgc cgccacaggg ccatcctctg 130500
tctttggcct gcggacccta caccttcccc tggggaggtg ccctgcctgt tggggtgcca 130560
ccctggctgc aggccccagc acctagcccc gcaacgtgtg aggaggttgg gcctgcccct 130620
cagtggctgt ctggctgtca tcctgggtgg ctcctgcctg ccacttgaat gataaataac 130680
tagagcttct cacccagttt ttgatggaca cttggggaat tgttctgaga ttcacagccc 130740
aaaccaggat ccggcctttt gaatgggatc agtgggtaac tcttatttct ggctgaggca 130800
gatttgagag gttgtcagtg ggggcagctg aatttgaaag agcaaatctt agaatgcaaa 130860
gggaccctgt gtcccagccg tgggccgcac ttttggtggg gagcaggcag gagggagtgt 130920
ggggcagcag tgacagctca ccgtgccaag gccacagtca ggaggaatct ggtacaggct 130980
cctggggcct taaagcccag cagggcgggg gcccggttct gctttccagc caagcccact 131040
ggtctgactc gtaagagccc agcttgtact cagcagtaca gattgtatca tcatctggtt 131100
agatgaaggg tgtgaatgtc cctgcagctc ctggctgttg gcggaatgtg catcctcaga 131160
gccttcaggg tcagctggac agaaactctt ggagccgcat ctcatggtgc tcagagctag 131220
ggctcagagg ctccagggca ggagaggaag ggctcccaga agctcctgct gatcacaggg 131280
aaagacaagc cactgtgcca taaactttaa tatagaatgt tggggccagg cacggtggct 131340
catgcctata atcccagcac tttgggaggc cgaggtaggc agatcacctg aggtcaggag 131400
tttgaaacca gccttgccaa catggtgaaa ccctgtctct actaaaaata caaaaaaatt 131460
agctggacat gatggcaggt ccctgtaatc ccagctactt gggaggctga ggcaggagaa 131520
ttgcttgaac ctgggaggcg gaggttgcag tgagccaaga tcgtgccact gcactccagc 131580
ctgggtgaca cggcgagatg ctatctcaaa aaaaaaaaac gaaacaaaaa aacaaaaacc 131640
aaaggctggg tgcagtggct cacgcctata atcccagcac tttgggaggc caggacgggc 131700
agatcacctg aggtcaggag ttcgagacca gcctggccaa catggtgaaa ccccgtctct 131760
actaaaaaga caaaaattag ctgggtgtag tggtggatgc ctgtgatccc agctactcgg 131820
gaggctaagg cgggagaatt gcttgaaccc aggaggcgga ggttgcagtg agctgaaatc 131880
gcaccactgt gctccagcct gggtaataga acgagacacc atctcaatta aaaaaaaaaa 131940
aaaaatagaa tgttggccaa agatgcaggc tttatagaat cagacctgcc cgagactgga 132000
tctcaactct gcccactccc tggctgtgca acctgtgcaa attacttagc ctccctgtcc 132060
ccagttcctc ctctgtaaaa agagacaatg gtggcagcca cctcttgggg gcattgtgag 132120
gagtagccag tcagtgagaa gtgcttggtg cagtggctgg cgctcgccag gcatatacag 132180
aatgatggct gtcaccatca ttatcatcag tcaccattat tgtctttatt actcaggagc 132240
ccagctggag actcccatct tgctcctccc tgagcttttc accttgtgcc gaaccttttc 132300
ctgtgcttgc ttcacaggag ccgcaaagac agcctggaaa gtgacagctc cacggccatc 132360
attccccatg agctgattcg cacgcggcag cttgagagcg tacatctgaa attcaaccag 132420
gagtccggag ccctcattcc tctctgccta aggtgagcga gacagccctg ccacacagtt 132480
taccccacag cacccagctc agcctccagg gggcacttca gagcctcccc agccccctcc 132540
cccagcaggc gtcctccagg gcctccaagg agccaccagg cccgtgcttc ccgtctccct 132600
gtctccctga tgagggtgag gtgcctgttg gcagcctaca cacctaagca ggctgggtct 132660
cagggaggga ggagagctac tccacatggg gcctgtttag gagcctgggg actgtgaacc 132720
agccagtcgc ccccatgtca ctgggccatg cggtgttctc cttgcccaac cctctggctg 132780
gcctaggtgg tgagaagtct gccatgcttc ctagagcggg gctctcttat ctgcatctcc 132840
tgtctagccc agagcagcaa cagtccccaa tgcgcccagc actgtgacca gagagcccca 132900
ctggtctcct attgcttgtt tgacagacct tcctcgttcg caagttctgg agtcagaatc 132960
cacagggaga agtattcctc agccctgctc cccttaggaa ggctctgtga cccagggagt 133020
ctcaggtgcc cccagccacc gacaagccca gggcagggat ggcagggtcc ccagtagcac 133080
tggtttgtca gggtggggtt gggtgggttg ggctctattt tctcctgctt gctgcttttc 133140
ccatgcaaaa cactcagttc taaaacctag tggccagccc agcaaactcc ttgagggacc 133200
aggaagccca gctgtgtccc ttctgcttct gtccacagtg ccaaaagccc agccctatgg 133260
ccagaactca gctctgtgct cagggctgct gcacggctgc atctgctaca gctggctacc 133320
ccacagccca ggggctccac ccacactttg agcagcagag tcaccaagag taattctaaa 133380
ctcacagaac agtgacaggg aagaagaact tgcacacttg gggactcccc actgtcccca 133440
gcacctggga gtgagtttga agggtaacta gccttggcca gccaccctgg gcagcagaca 133500
gagagcaaat ggccagaatg aacaggacct ggaggggccc actgccatcc cacagccaca 133560
tcctccccag ccacttctct ggcccaggcc cagggccttt caactggtga agggttaatt 133620
ggaggcagcc tgagaaggca gagggcaggt tccacttcct ttgctgatga gtggctctgc 133680
ccattagctg cccctgcctg cccctccccc aggtgtattt ccagactagg gattaacagt 133740
aacttctgtg gctccctgag tgaccccact tggcttcagc ttgcttgctt gcttttttt 133800
taaagatgtg ctgtggcctt tgggccagcc acttgaatgt tatgggaaag cccaggagca 133860
ggtggaagat tctgccctgg acactgaagg gtcccactgc ggaggcacta tcccatcgtc 133920
ccagggaaac ttgtctagac gctacttcac ctccgtcccc taaggggga tgtgaccccc 133980
ctcttacctc tgggcatgac cttcagcaca ttgctacctt ccctctctgc cctcaatttt 134040
cctaagggag gtgagctcca ggatctctgc agggcttttg aactcagtgt tttctgctag 134100
ctttgagcac tttggaagga tgatgttaga gaacttgtga gaggagcttc tctttgaagg 134160
tgttgaaatg agcgtgtttg gatacagtcc cctgttgatg ggcaggtggg cagccaggag 134220
ggcatgttac ctggcccgcg gaccatagtc cccactgtcc cagagccttg gccaggcctg 134280
ctgtgcttgg aactgtttcc aagcccagct cctcactgtc tccatgttcc catctccagg 134340
ggcaggctcc tgcatggacg gcactttaca tataaaagta tcacaggtga catggccatc 134400
acgtttgtct ccacgggagt ggaaggcgcc tttgccactg aggagcatcc ttacgcggct 134460

-continued

```
catggaccct ggttacaagt gagaaggccc tttttcttct ccctccttcc tttcatagac 134520
ttccttgccc accccctcctc ttctcccttg gcagctcttg atggcacccc ttcctggggg 134580
gctggtcatg aatgcctcat ggattcaggg cctggggcct gtgtgtaggt atggagtgtg 134640
gatgctgcta cccactccag cagcttagga gcacttcctg accttctccc cctgtcacct 134700
gagacacaag tgttaactct ccaggccctg gctcttggta attctggttc cccgtggaaa 134760
tccaggttgg agggatataa gactttctgc accttgggta aaccaaggta caagaactca 134820
aggatgaagc aagatgggag gatgtgtgga ggccactctc caatggctac atggaaatcc 134880
caccagaatt cagacagtgg catgtgtgcc tggaccaggg ctgggcaggc ctcagtggga 134940
agagcctccc cttcttagcc tacccccatc tgacagccct cccgttcctc ctgagtttgt 135000
gtgaccagag acctgctggc ttatccggag cactttgtcc ttcctttgct cttctggctg 135060
gagcgagctt cagagctgtt gccaagcagg gtaccagggc ctcagagcca taggcctcct 135120
tccagtcccc accccgtccc gggtctctaa caggtgctca acctactcca ccacactccc 135180
gagtgtcttg gagggacagc atcctttttt ggcatttgtt tgttgcgggt ggggagagga 135240
ttgaaccctt aacctcacct cgctcgcaag tatcaagaaa gggaacctga ccctaaacct 135300
aaaggtggcc atacctggtt tgtgaatgta ttggagaggc atgcagcatt acagtagagg 135360
ggaagagaat gatgctaggt ttgtgagttt cacccagtct ggggagtctg tgaagcatat 135420
gtagtcaata cagacacact ttttgtccct gcatgtctac agaatttctc ctccttcagg 135480
ccaggcccct cttctcccgc caccaccaaa atacaaccct taattaaaac aaacagcaaa 135540
caaaggacac caaccacact ccccagacta agccgagata gaaatggaag ctagtgcttt 135600
agggatattg tgttccataa attatcttgc ctttttccac tgttgttatt atatcgtttc 135660
ataacaaaat tactttgaac cataaagtta taaatacatt ttaaaagtcc cacttggtaa 135720
cattagattt ctgtccatgt ggtgttggta gttactgtaa caaaagctct gaagtgtaat 135780
atttgaaatt agcccagcac aagtggaaag ggcctccctc cattccctac ccccagccat 135840
gtcccgggct gctgcgtctg cccctgtgga gaacagggag ggagcaggcc tgtctcctgg 135900
gcggagctgc tgaggaggct ggaggtaagg acaagcccct gagagttcac aggtcatcat 135960
tcccaagtgt cctcaggtag cgtgtgtgtg tgtgtgtgtg tgtgtgtgtg tgtgtgtgtg 136020
tgtgtgtgta atgttcaagc acgttttcct gggacagtcg ggactggggc ctccccaaac 136080
tgcagaatct acccagttat gtttgacatc ctcagctctg aacctatcct cggagctctg 136140
ccctcccgtc ctggaacgtc tttctgccct gaggagaggg tagtcagcat ctccaatttt 136200
cagcagctca agaaccttgg cccccacagg acttcgcaga tgtcacattg cccctcagtc 136260
ccctgaatgc ccttcggacc caaccccaat tccccaagcc cctgaccccc tagctgccgg 136320
ggttcccact cccagtgcca caaccccctc acctccctgg cagcccctca gcgagcctga 136380
ggcccagcac ccgctggctc cccagcacat ggtcccctcc catgggctgt tgcccaggga 136440
accggggcgc ggtgggaacg agctgctggc ctcggcatgt ttcaataaag ttgctgtgct 136500
gggagctact caatcaaagg cctgtgttat gggctcatta gtgtggtcca ccacggggcc 136560
ggctcacagg agagctcctg ggaaggctgg cggaggcccc acaccccaag cacccaccct 136620
tgatcaccga ggggtttctc aggccctttc caaggagccc tgggaaaccc tctgaccctg 136680
cccccagccg gattctcagc agtggagcca acacccacac cagccctcct ccccctgcca 136740
ggcagtcagc actttctccc tctgactgcc agccagccgc ccctgttagg gtcctgccac 136800
```

tgtggtcaca ggcagctccc ttgcttgtgg gaacctgggc ttgtaattac ttgtgggcct 136860
ctagatctcc ctctggggct ggctgtctcc ctgggagtct gcaggacctc ctagaggcct 136920
ggggttagac ttgcagtcgc cagtgagggc cactccactg ggccaaggag agccataggt 136980
ccctcaggag gggaccccag cacaaagagg cccacccttg ctccctgcag gcatctcttg 137040
ctcgcacccc cagggttccg aggtgtcttc ttgggccttg tgtgcccagg cctattggag 137100
gcagaggagt aggaaggagt gaaatccaat agacccagga catgacgaga cccagtctta 137160
tgttctctta actgctgccg gaactctccc attggtccca gctgaaatgg aggggctggg 137220
atgactttgt tacagcagcc ttggaagccc tcactcccag ccttggcacc ttgttctggc 137280
caccagccca gcccaggcct gttatctctt gggagaaagc gtggcagaga catcctgcag 137340
ggggaagagt gacaaggaga ggccgagagg aaaaggcaga aggtttagga acccgagccc 137400
ctttccggag cctgtggaat ggccccagac aggcctccac acccacctgc tccacagcct 137460
tcccccatca gtccagaccc aggagagtca gggccccagc atgtggcaaa gcagggcttg 137520
tctgcagcac caggtggagc acagtggaca ctccctgctt tatggaggat ctgggggtgc 137580
aggaagccag ctccagttcc acaggctttc actttctgga gaacagcacc ttgactccgt 137640
ctgccctgcc atttgctgtt ttcatccttg ctgagactgt aaagcttatc agccaattcc 137700
ggggctgtgc aggaggctct tcagaccctg ggagggggcc tgccaaggtc tgctcctgca 137760
cctccttccc ccagcattcc tcatcctggt ggctttaaca agcctctctc ccttgagcct 137820
gtcaacactg ggctgttagt cttctgagcg ggagcccggc ccagagctga gttgttcatc 137880
cgtccccagc cagggttgat ctgaaggggg ataagtctca gccccagcgg tcacataggg 137940
gtcacatcac caaatatgag aatattgttt taggccccgc aatgctttct cagctgtgtg 138000
gtgtctgaca gctcacccag gttgcgcccc tagtcccagc cattctctgc cagtcctgat 138060
gggaagcccc aggcgtggga gaagacgccc agcagctgtt ccaagtgggc tctgctgctc 138120
caggccaggc ttgggaaggt gctgccgagc tctcctctgg gcaagccctg ccttctgcta 138180
cccatttgga tattgtgtag aagatgactt gggaatcccc agcccatgcc ctgggcacct 138240
cctctttggt gcctctactg ttcctccttc cacgggtgaa cccaggcata cttattctcc 138300
ctggagacct ttgcttggac tgccccgaga ccttgttgtc caggggggaca cccattaagg 138360
tttagagccc agcaatgcgc ctggggaagt accctccctt gtaggaaagg actgtgatgc 138420
cgccctgtgt ccctggcagc ccacagccag agcaggagtc tgagcccgct tctggccacc 138480
agagccaact tttcaccgcc cactaagaac aggaaatgag cgagacctgt gccccaactg 138540
cagcccgcta cctgccgcac cacacgcctc tgtccctgac ctgggttggg ggtgttctcc 138600
aggctgtttt ctggcttttg tctggcctgt ggagtggggg tgggagggaa gggatgcaga 138660
caggactgct tccccgtccc tgcctcctcc actgccatcg tgggtgccag agcagctcct 138720
tggcaggctc ttccactgta aacaacacat ttccttccct gagaggagga aagggaggga 138780
aaagaaagcc aaatttgttg ggaagcaagt acaacgtgtc aacatgaaga acaaacaatg 138840
ccctggacaa agtgtggatt gtcataccaa agggaaggag tgggcattgt cagccactct 138900
ttgcagactc agaaatatca ttgaccacag acatctgaat cggcgtcaga tctgcagcag 138960
ctgggcccct gcctgcagtg cagcctggct tgcccagggc aggcactgac acaagatcac 139020
ttttcgggtt cctttctgga acttgctggg gcctggggaa ttgggaggtt gttgacagtc 139080
ctccctcacc accacccagc caagctggtt aaggcagctg gtgtgagccc actggagtag 139140
ctgctggcct agattccaag ccccctccc tggccaaagg tgggaactgg gggtaaccaa 139200
gatccattgc ccccctcgca gctcagcccg tttgatggtg gtgaagctac agccaccaac 139260
tcacccctgt tggttaagcc tgtgcccaaa ccccctttcc ctgtgggcct gagtatttcc 139320
ccagcagccc ctcaccatga tctcctgggg caccacttaa gaatacaagt gctggccagg 139380
tgcggtggct cacgcctgta atcagtccca gcactttggg aggctgaggt gggtggatca 139440
tctgaggtcg ggagttcgag accagcctga ccaatgtgga gaaaccccat ctctactaaa 139500
aatacaaaat tgccaggcac ggtggctcac acctgtaatc ctagcacttt gggaggccga 139560
ggcgggcgga tcatgaggtc aggagatcga gaccatcctg gctaacacag taaaaccccg 139620
tctctactaa aaatacaaaa aattagccgg gcatggcggc gggcgcctgt agtcccagct 139680
tgtttgtctg ctgttaaaca gcagacaaaa ctccagcccc tggccgggcc cagtggctca 139740
cgcctgtaat cccaacactt tgggaggctg aggcaggaga atggcatgaa cccaggaggc 139800
ggagcttgca gtgagccaag atcatgctac tgcactccag cctgggtgac agagtgagac 139860
tccgtctcag aagaaaaaaa aaaaaaaaaa attagctggg catggtggca catgcctgta 139920
atcccagcta cttgagagac tgaggcagga gaatcacttg aacccaggag gcagaggttg 139980
cggtgagttg agatcgtgcc attgcactcc agcctggaaa acaagagcaa aactccgtct 140040
caaaaaaaaa aaaaaaaaaa aaaaaagcat gggccttggc cttaccccag agtattctga 140100
ttcaggaagt gtgaatgggg cctagcatcg ccatattttc agaagcttcc caggggagtg 140160
tgctgctcag attggttgag ggtcttcctc tcttactaga gggtctcctc cctctgaggg 140220
ctgtttgtgt acaaacataa gtgttttctg cctggctctt ggtaagtgca aatatcagtg 140280
agtgctgtta tcaatattat ttctactgct actttctggg ctagagaact gtcaagatat 140340
atgtattcac taggctggcc tgggaatttg ccccaccgtc cccacttggg aaccatctct 140400
gggcattggt ttgccttcct tttcattggc cagtctggtt ttttagcagt gtctgtgact 140460
ctcaggcttc tagccctctt aagttgagca ggtggccagg aaatgtgtgg ctggtggagg 140520
ttgggactgc tgattttcca ggtcattggt aaaaaccaaa gctaccttca cctccctcat 140580
cagaagacag agaagttatc cccatctata taggcttcta cagttggggt gtcttcccca 140640
gacaggaaaa gagcatcctc tatcaccatg agatcagata gccgttcctc taaagtccag 140700
agccttgagc caggcgtggt ggctcttgcc tgtgatccca gcactttggg aggccaaggc 140760
ggatggatca tttgaggtca ggagttcaag accagcctgg ccaacatggc aaaaccccat 140820
ctctactaaa aatacaaaaa ttagccggac atggtgatgg tcacctgtaa tcccagctac 140880
tcgggaggct gaggcaggag aatcgcttga acccaggagg cggaggttgc aatgagccaa 140940
gattgtacca ctgcactcca gcctgggcga tagggcaaga gattccatct aaaaaataaa 141000
aagaaaagtc cagagccttg tctcctctgg gtacctaccc ttgggcaaag tggggatgat 141060
agtcacctcc ctagcagaac tgccataagg attcaatgaa atgacactga tcaagctctt 141120
agcacagcgc ctagcacatg gtggaggtac tgcttctgct attggccatt tttactgtca 141180
tttttatcat caccattccc attattattc gtgacagagc caagcagctc tgtagggacc 141240
cagtgagcct caggagtgcc aagccccaga actgcacagg cttttcccac agttgcatca 141300
caagggcaag tctgttactc gggagagctc ccaggagctg ccccatctta gctgtctatc 141360
tccagtgtcc tgttgataag atctgttaac attctcagct ccaggtctga aatatacaaa 141420
gaacagggcc tgtttgttca atccaacctt ctaaggttta actcccaaag gaaattaaat 141480
taggtgcctg gagctatgac agtctgtcgt gtttctttgc agagaatgtc acctttaata 141540
tcatgtagat ctcatgtata atttttcccc tttaattctt ttaaaataac gtgaagtttc 141600
cagcgggaac cagcaaatca ccaaaagcaa aaatggagga gcagctaggg tttgtcctca 141660
tttttgatct ggccatcccc tcccccaacc gagtccaaaa taagtccaca cacagatggt 141720
gccgcgcatg gtcgttgctc tactaaaagc caccataact caccctctcc ttagcaccag 141780
ttccagacct ttgtcagggg aaccagctta gaattgaact cagtgttggt ggcattacgt 141840
ttccttgaag aataactctg gcgtctcact gggtggccac agcctctgtg aacccttgcc 141900
cctcttcctg tcctccctcc accccatctc acccccagca cttgttatag tcccacatct 141960
atttactgat ctggcagaaa gcccctccct ccaagttatt tgtgagttag aaattagccc 142020
agcccggccc agactggagc cattgtaata taattgggtt ttaggtatgc ttgtgtttgt 142080
gctagcattt gcagagatgg caacgagccc cggaaatgcc aaaaatatga atgtaacttt 142140
tgtattgctt gagcagactg gtgataactg gtggggaaac tgaacttttg gggaggacac 142200
ccctgggata agagagtagg aggagcaagg gcttaggctg tgagagggag tacgtgtatg 142260
gctggagtct gtgggcagag tcggccagtc ccactttggg gaattaggaa gaactgtagg 142320
ggtgcacctc cccgaacttt gccaactttg cctctcctgc tctgtctcta agccttgtct 142380
ctgtccttgg tcggggccct agctcctaga acagagagtt tggtgaggag acgtggacca 142440
gtggtcagag ttattttgtt cctgctatgg gcttggagcc tgggaaggct gggtctcttg 142500
tctccttgcc agccaaaaga gggtgcttgt cctggtggga aatgagctgc cttcatgcct 142560
gtgtccctgg aaggatgaat ggatgagtta gtgtcctggg ggtgagagtt cagcattcgg 142620
gagcagtact ccaggcacta aattgagagt ccagacatga tcaggatatg gtcttaacca 142680
ctcacaagcc gtgtgacact gagcaaatta cataacctgc ctgtgcctgt ttcctccact 142740
gtaaggagac atggagatga gcagttagca tgcccggtat gatggcggct tttctgctca 142800
cttgggggta gtgttcttat ttctcactcc ctcctccacc ccgtccactt cttgctttag 142860
agacctccgt cctgtgagct cccgagccgt cctgtgtgct caccttcctg tgtgcactcc 142920
ttccttgtta tctcacagcg tggaaacttt tgttcttggc agctgacaat tcccagggga 142980
aacctggtgg gtatttttttc aagttctcaa ttctcctcct cacagggagg gtttcccctc 143040
agaggagccc ctcacctgga tcttcacccc attatctttc ttcctttgtg ccctacctgg 143100
gtgctcaagg tgtacgggag aagacaggta gagctgtggc ctgggggtac agaagggtct 143160
gcagtggagg gaggctggga ggccctgggg acaaggacag ggagggggag gggtgaagga 143220
aggggtcaca gttggaagag gaaagacacc ctcacccagg gcgtggtggg gtgcagacct 143280
gggatcagct tggcctggct ctgcctagca gcctgacgag aggggtgggt ggggaagaat 143340
ggcccagcag attgaggaag gccggtttta gagggcctga gagcccttgg acgttggtat 143400
tggctgtgaa aacttcttta gcggatgaag ttggtgtttg tgccagccaa atagtggggc 143460
cagactcagc atcaaagcga gaggcaatga ggtgtcagac tagaacagca acgtggaatg 143520
ctgggaggtg acctagagaa gaggaacctc aaagaaggct ggaggaactc agtggctgat 143580
cgagcacagc aggtcagggg cttgggagct tccagcctgg gaggatgtgg ctactgtgaa 143640
tgggaatgga agttgggagt ccctttgtca tctgtaaaat gagacgttgg tccacaatct 143700
ccagattctc cagctcagac attcttggat gtaccttcca gggcacttcc agattccaga 143760
tagggcttgt attccaaatc caaacagttt ccttttgtcc ttctacggtg aggggcagag 143820
ggggacacta gagcctgact gggcagcagc tttaatttaa ttttttttcc ttttaatttt 143880
tcttttctgt tcctttttct tcctgagatt cctttttacc ggccccacca gtgttcatct 143940
cccttctggg agcagcattc ccagctctcc cagtgtcctc cctcccctcc ccattgtccc 144000
ctgacccctt tccttctatg cctcagtctg atattgcagg gaggtgaggg tgtgggggga 144060
atgacagctg gggacaggcc tcaaacactt ccctgtgtcc cttgaacaga tcacagtgag 144120
ctcatctctc ctccatggtc agaagagagg tataacgctt ggtggttggc aaaaagatca 144180
tacatttaaa aataataata aaagcctgcc ttgtgccttc acagattctg ttgaccgaag 144240
agtttgtaga gaaaatgttg gaggatttag aagatttgac ttctccagag gaagtaagct 144300
tgtttgactt ttcctgacaa caggtcccgt ctctgggacc atgtgtgtgc gtgcgtgtgc 144360
acgtctgtgc atgcatgtgt gcgtgtgtac ctgtggtgcg tgtgtgcttg catgtatctg 144420
tgtggctgca tctgtgggct cctccccaag gtgcagggat aggctggaga ggagactgta 144480
gatttctctt ctgtttctat gcaccctcac catcccctgc cctaccccca gcccttgtaa 144540
ggacacccag caaatcgtct gaattgccag ctcctgagag cctcattgaa gaggaagcca 144600
gggccttcag gctagtacga gttctcccca gcccctgctg ttccctggca gattctgaac 144660
agaacgccca tgtctgttgc cagagaacat tccgctgggg agttctggtg ggcagcaagg 144720
gactcctgct ctcgcctcgg gccacccagg agccactctc ccttcttcgt cctccagcca 144780
tgagctgtgc ctcttagtct ccctcttcca gccctggctc agagctggag gagctggcag 144840
gccagctgtg gctgtgcctt ctttagctgc tcctctgggg tagaggaatg gagtccataa 144900 tccccttgt tttttctccc ttgttcccgg catccttatt tgcgagggct tacctcatcc 144960
tggaaaatcc cttcccctcc cccgctcctg cccgcagcac cccagtggga tgggagcttt 145020
cctggcccca gtgccccatg ggttagtgaa ctctagcagg ctggccgggc ctctggagag 145080
ctctcctggg ccctgccctg cctgtggcag aggcagaccc ttcccttgtc ctgtctgcca 145140
ggaaatgtgc ttgggggaga actccttcgc ctcccagggg ccaggctttc taccaagagg 145200
gaggccaggc gggagctagg ttccagccag ggctggagct tccagcttcc agggctccct 145260
gggctgcaac agccaggaca caggcctctg gtgtttagga agctgagggg agtgcacagg 145320
gcgggaccgt ccagtccagg tctccagttg gacaggaact ccccagagcc agggtcacct 145380
caatagagca gggtctcctc tgtcctctgg gatgcagctt gagaaatttg ttcatttata 145440
tattccaaag ccatcaagca cccagtccat gccagccaat caaccccccac aagtcactgg 145500 tccctgagtc ccagctcccc attcagtcag accagagcca gctgcccaga agcgcttccg 145560
gagaggcctt gtcgcactgg gatggcgctg tgccaggctg ctgctttgag cttgggggta 145620
ggagggggac agtccaggca agagggacag aagcctgggg gagcagagga aagtaggtca 145680
ctaaaaatga cttttttctt tttttccttt tctgtccaga ggctgtccct acaccctgcc 145740
tcactcgcca ctttggtcct ggcagagaca gtcccccagc agagggagcg aagagggagg 145800
cagccaggaa gggtcaggct cgtctgcctc cagccccaga ccgaggcagg ctgagaacac 145860
tgttctctcc tttccaccct gccctgactt ccggcctagc caaattagaa aagacagacc 145920
ctgggccggg cgcagtgact catgtctgta atcccagcac tttgggaggc cgaggcaggt 145980
ggatcacctg aggtcgggaa tttgagacca gcctgaccaa catggagaaa acccatctct 146040
actaataata caataattag ccgggcttgg tggtgcatgc ctgtaatctc agctactcgg 146100
gaggctgagg cacgagaatc gcttgaaccc gggaagcaaa agttgcagtg agccgagatc 146160
gcgccattgc actccagcct gggcaacaag agcgaaactc cgtctcaaaa gaaaaagaaa 146220
agacagaccc tgtgtctaag ttccggtatc agtcccaggc agtgagcatt tattgagctc 146280
catctgtgtg ccagactgca tgcaaagttc tacagtaaag agggaataag aggcatcagc 146340
ctcttcccct tcccctacca gaaactccca ggtgaatggg agaaacagaa ctgtaggcaa 146400
atcagtgtat cctgggatgg ggtgggagac atttggctct ccttggccac cactgggacc 146460
actctgaggc tggtaaccct gggaagtggt gcgaatgaat acagggagca gggtggggat 146520
tggcccctct caggcccaag ggatcacctc aaaccacact tgtcccactc ttctgctccc 146580
accaaggccg caagtgtggt tctgactttg ggccgaactt ggggcctcct tccctttgga 146640
gcctttggcc aagtatacag aggacaggtt ccagggttct tcctgcacta gcctctgaaa 146700
gagaggccat ggcagtgaca gagctcaggc cacttcccca tagcctccag accctccccc 146760
agcccccatc ctccagcccc agggcctcag ggagcagatt ctttacatgc ctgtggccag 146820
aggcagaacc aaggaagtga gcaagaggga ggtcagctta gtggagaaag gaggagaaaa 146880
cgccctcctc caacctgcct cattattgac aggccgtggg gaaagaaggg gtcaccaact 146940
ccagccgttt gagcccagcc tgccacctgg gtctagcatt tgagaatgaa gccacgcctc 147000
ccgcggcctg tcctatccct agctccccgg ggacaggcct gggcaatctc tggaaagacc 147060
acggtgtatt ctgctaacca ctcacactcc tggtctgtgc ttgctccctc cacagttcaa 147120
acttcccaaa gagtacagct ggcctgaaaa gaagctgaag gtctccatcc tgcctgacgt 147180
ggtgttcgac agtccgctac actagcctgg gctgggccct gcagtggcca gcagggagcc 147240
cagctgctcc ccagtgactt ccagtgtaac agttgtgtca acgagatctc cacaaataaa 147300
aggacaagtg tgaggaagac tgcgcagtgc caccccgcag cccagtgggg tgccatgcac 147360
aggccacagg ccctccacct cacctccagc tcaggggccg caccccgccg ctggctaagc 147420
cttgtgaccc atcaggccag tgagtgggca aatgcggacc ctccctgcct gcagcctgca 147480
cagattctgg tttgaggttt gactctggac cctggctgtg cccctaggtg gagacagccc 147540
tctttctcac ctaccccctg ccgcacagcc cagcaggagg gaggcggaca gccagatgca 147600
gagcgagtgg atgcacttcc cagctcatct ctggaagcct ttgctactca agctcctctg 147660
gccgcggaac aattcctctg atcatgtttg gttttcttct tccttatttt attttgtaga 147720
aaccgggtgg tattttattg ctctgcaaag atgtccagaa gccatgtata taatgttttt 147780
taaacagaac ttcattcccc gttgaacttt cgcattctct gacagaggcc tagggctgta 147840
tctctccctg ggctgccacc agagaaggtg cttggtgttc gcctgccagc ccagagccct 147900
ggaggagccg gctgcacaga gaggcttttc ttcccagctg ggcctggtgg agcccggggc 147960
agggggagag tagagacact cccttgtgca gctttgagcc tagtttagct ggggccaggg 148020
aggggtgcta ctgttttcca agtgaatggg tctcaaagac ttggtgaccc cagcctcatc 148080
ttctaggcct tttccaccca accaggccta cctgggagag ggtgaggttc agcacatcac 148140
acaccatccc cactgtcatt cagggcctgg gtctccagct ctgtaaccag tcctgtccca 148200
tttcctcagt ccctgggcct cccagccttc aggctgtagg gctgccttac taaaattgaa 148260
aaatccacct cttaacatct ctttcacttt ggttttgcta acactgctct ctgctgccct 148320
cccatcctcc ctgtatccat tcatgcccta tctttcattc tccactccta atccctctcc 148380
tttctggcat cctggcctct cgtggtcctc agcccctcac ccccagtact gcagatctca 148440
cagtttgcct tccagaagcc agcctatctc tagcccatgg ttttggagtt cctctcgggt 148500
tatctcccac gcctgacctg gaaccagcaa gccccttcc tgccttctta cccccaactc 148560
tagggatggg actgttacaa tacttcaaga tcactcttta cacctcttca aagcaaagtc 148620
atgacaatgc agggctcctc attgctccca tctgcctctg ctgcacacac aggcaccagc 148680
agggatgcca caggagtgcc cacagggtgc aggactccac tgatgagaga tccagccaaa 148740
gagctgcccc caggggtatg agggcaccag ctgggttctc cagggagcag gagttggacc 148800
tccatggagc cactaggcct ggcctcctct acacatcccc agggctatct ggttaattcc 148860
atcaagctca gagttaaaag gcatatcagc ctggagtatt tgggagagac tggctgcaga 148920
tccccgccag ccaagatgca agccactcgg gacctgatgt cggcagctgt gcctctactg 148980
ccctgaggac ttaccagagg gagccctact ggccttcccc caccacagca gccctgcctg 149040
tgaagctctt gtttctgaca tttcacaggc agagaggtgc catcagttcg cctccattcc 149100
ttgccaccat gaccagcctc tccctgaact ctctcttgct cgggacctgc ctgagggctc 149160
cctgctgcag ttcgccgtac ttccatctgc tgggtgcctc catcgttggt tgggtgggga 149220
tggggcattt tctgagctaa gctttgtcat tagtttgtga agcacctggt cagcaacctg 149280
ccccagacct ggagggtctt tgtggactga aggtagacac cagccagcat ggtggccctg 149340
ttctggggga gcagggtaag gcaggaggaa gtgggtgagc tccgagatga tgagcacatg 149400
aagcctgtgg ccccttcgta cctgcaatat gtcaggagcc tcacgctcac ccaagatcct 149460
gcaggggcca ggctccatct cactggctct gagggcagga cagggtatca cacatttctc 149520
accaggcctc ctttcctatg ggcattggtg cctcccagag gtttcttggg ctgctggctg 149580
gtgagagagg acccttaaag aagatcaagc caagctgacc ttggaccctg tccagcacag 149640
cttctggcac aggatgcttg gtgaatgtac cctttctttc cctccctgca gctctgaggg 149700
agcccctgac cttgtagtgg gtggaggagg taaggggcct ccctccctaa atctgcctct 149760
tctgcaagct acttggagac ttgcctagtt gtacccaccc ctccaggtcc ctggtgctag 149820
agcttctgag aagggccttt ccctttcctc tttgcctgct atataaggca ggctcctgtg 149880
gctctgctgg ctcagtgtgg gctgcaggag gactgcagac tcagctgcaa ttctgagggg 149940
ggtttgggag gcttgtgcga ggtctcaggc ctgtgtgggg agctggtgcc tcttcctgcc 150000
cgtatctttc tcttccaagg gcagtgctcc aaggcaggga ctggagaagc caaggggaga 150060
gtctaaaagg gctagagcat ttttaaaaat agacacaggg tcttgggact ggggtttcgg 150120
attgagttgc aagcagggag aaaacctgaa ggtcggtgcc cctatggggc tgaccagtag 150180
agaatttcct ttactgtatt tttgtgtctg gtcttccctt tctggcttct aggacatcca 150240
tgccaggtga ggtgcctggg tccctgttac aagtcaggag ccctgtaggg agacccctcc 150300
ttttgtacaa gtacctgaat gctgcgacaa gcagattttt gtaaaatttt atattagttt 150360
ttaatgtcag tggcgactcg gttcctgggg ctgcagccag cctgggactt ttgtaagaat 150420
ttttgggtga ctcacttaga tgtcgtttcc ttcttgcccc ctcttcctct ctgtaatcta 150480
agtgcattaa acatctttgc agaagtgcct gggttgtgtg ctcatttctg gctgcctgaa 150540
gtagtggagc cggaagcccg gggccctggc agagggagtg ggttgttgtt agccacttag 150600
aagccaggat ggagggaggc cccaggatt gttgtcgaga gtggaggagg tgccagagag 150660
tgggatcaca cagctggtgg ctcttcagtc ttgaagaaat gaccttgcaa ggacaggctc 150720
tccctcactg gtcctgaatt cctctaaggt caagggggtg ggagcgagga gcagtctggg 150780
gagatgaggc ggtgggaaaa gaccctctcc ctgccactac atccctcttc tatcctcctc 150840
tcaccaaaaa cccctttgc cttaggaaga ggggcccaga caggtgagga gggcaggccc 150900
tcctcatctc ctttggagtc cttgcccggc ttccagctcc tctcacatga catctaaatt 150960
ccacctccta atccagggcc caggggcagg atccagatag aagggcaatt cagaaccggt 151020
ggcacccact gggtgacaca gaggccagcc cacccgccct agcaactcca ctgggcctgg 151080
cagtggaggg aggtatcagg tatatcttcc tttcctggac tgcccagctc ctgcctctcc 151140
agggctgggg ggcagcaaaa cagcccaacg cccagtgtgg ggaggcactg agctggggga 151200
gaaggcacta gcctggcagg caggataagg gctgcgccca gacagagttc ttggaacctg 151260
tgaccacctg ggccctcaca tattcattcc cttctggttt tctatcctgg atagtggcag 151320
gggatttggc tggggctggg ggctggggcg gaggtcctag gacatcataa gcaagggaga 151380
gggggtgtca gctcctatga gggggttctt atgtcctgtc ccttctgtga gacctagcca 151440
tgtggggggc ctttgctgag aggtccgcac tccttcccct gcagcctctt actgaactct 151500
ccaacggagc agtgcagcag gtcctgtctg gggccctcat gccctttccc ttttctcccc 151560
ggagactggg ggctggggga ggtatcctca tctgacttta gcctacaagg acacagtatc 151620
agggtgaagt tcttgcccca gagaatgcag aatagcaaga tcctctgctt aggtggttct 151680
gcaagatacc aggctgacgc tgtttctgga aagagaagga ctcctgggcc tagggcagag 151740
accctagccc tagaattagg gaggagagag atctgccatg ccatctgtaa tatctcctac 151800
agaaagtcat gtgccttcct cccaggtgtc tgctttgcct catctggggg ccttggggag 151860
ggagtcccac aggtttcagg ggggctgggg agcctgagag gtttgccaaa ctggcctgac 151920
cagaagaaga atgcaaacta caagtgactc aacccagcct gccaggcacg gaggcagcag 151980
cagggtgcaa gggggtaggt ggtggggagg ccggggtggg gtgatctgct gcgcaggaga 152040
agggggaagc ctgcaggggc aggtctggat gtggtctgag aggggcagcc atctccaggc 152100
cccttccagg ggacatggtg ggactgaccc gttccctcct ttcctcctta ttgccaacaa 152160
gtctgggagg tgaggacacc atgagggaag aagcagctga ctgctggtgg gtgtccatgg 152220
cttgaatgag cttaactctc caagtaactc gtaggacgag ggaaactttg agggggttat 152280
gatgagagta gtggtcttac tggggccaga gaactggtct tactggggca gagaccctct 152340
tccttgtttt tccaatttca cccacaccca ccccacaccc atttcagtac cacgagagca 152400
ctgcaaggac ggagaatgga gttttgagtc ttaaccttta caagacagat gaaggccaac 152460
catgcattgt ccagcctcta caataacact gtgggaatga actagaaaac attccgttgt 152520
tctttcaaca agtgtgtgcc aggcactctg taatatactg ggacgctgga ctcaggccct 152580
gccttaagag gctcagagtg tggtgagggg aaatagacga ggaaacagat acttatgagg 152640
aagaaccatc aaagaggaag gcagtaagct gcttcctgtc ctaccccagc tccaccactt 152700
atcagggtga cttcagacag gtgcctaacc ccatctgcgg agattcaaaa aaactccctg 152760
aagaagtgac atctaagcta aaacctaaag gatgcttaag gatgagttga gcaaaacaag 152820
aggaaacttt actttcataa gctctccagg cagtcaaaaa aacaagggta gaagccttaa 152880
aactgcttgg gaactagagt gcaaattgcc tggagtatat ggtttaaggc atcaaacttt 152940
cattttagga tcatctcctt gtctgctgga tggagaatgt tttgaaaggg agtaagagtg 153000
aaggcaaggt gaccagtgat gcttggatta gggtagaagc agtagggatg gagagaatgg 153060
gattcattta ttgattcgac aaatatttat tggggatcta caatgtgcta ggtcccattc 153120
taggcaccag ggatacagca ttaaagaaaa tacctccttt gacagatctt actttttttt 153180
tttttgagac agggtctcac tctgtcgccc aggctggagt gtggtagcgc gatctcagct 153240
cactgcaacc tcccaggctg gagtgcactg gcgcgatctc agttcactgt aacctctgtc 153300
tcccgggttc aagagattct cctgcctcag cttcccgaac agctgggact acaggcacgt 153360
gccaccacgc ccagctcatt ttttattttt agtagagaca gggtttcacc atgttggcca 153420
ggctggtctc gaactcttga cctcaggtga tccacctgcc tcggcctccc aaagcgctgg 153480
gattacaggc ataagccacc gcgcccggcc tcacagatct tatattttaa tgatgggtga 153540
cagataataa tttcttttc tttttttga gacagagatt tgctcttatt gcccaggctg 153600
gagtgcagtg gcgcaatctc ggcttactgc aacctccgcc tcccaggttc aagcaattct 153660
gccacctcag cctcccgagt agctgggatt acaggcgcct gccaccacgc ccagctaatt 153720
tttgtacttt tagtagagat ggggtttcac tacgttggcc aagctggtct tgaactcctg 153780
acctcaggtg atccacctgc cttggactcc caaagtggtg ggattacagg cgtgagccac 153840
catgcctggt cagataataa ttttcaaaag gaggatatat cttacataga gacccatgct 153900
atggagaaac agaggaggag ggatagtggg gctggaggga gggatgcatt ttaaatagag 153960
aagtcaggga cggcatcaca gcataggtga catttgaaca aaggataagg atctcaatta 154020
ctggaagaag tgtgccatag ggctatctgg gggaagatgg gccagggaaa ctgaagagca 154080
cctgcaaagg atgagggagt caagaataaa cacaccgggt gtctttgaga agcaccaagg 154140
aagccagtgt aggtgcagca gagtgggaga agagaaggct agaaaattat gcagaggcca 154200
gactgtgcag gacctcggag ggaattctaa aactttcacc tttattctgg ttgaattgag 154260
aaggcattgg aagattctga gcagaggagt gacattttct gatatatata tatataatat 154320
atatattata tattatataa ctatatatta tatataatat atatattata tattatataa 154380
ctatatatta tatataatat atatattata tattatataa ctatatatta tatataatat 154440
ataattatat attatataac tatatattat atataatata tatattatat attatataac 154500
tatatattat atataatata tatattatat attatataac tatatattat atataatata 154560
taattatata ttatataact atatattata tattatataa ctatatatta tatacgatta 154620
taaaatataa tcatatataa tatatgatta taaaatataa ttatatataa tatatgatta 154680
taaaatataa ttatatataa tatatgatga ttataaaata taattatata tattatacat 154740
gatcatataa aatatataat atacatgatc atataaaata tataatatac atgatcatat 154800
aaaatatata atatacatga tcatataaaa tatataatat acatgatcat ataaaatata 154860
taatatatta tacatgatca tataaaatat ataatataca tgatcatata aaatatgtat 154920
tatacatgat catataaaat atataatata ttatacatga tcatataaaa tatataatat 154980
attatacatg atcatataaa atatataata tacatgatca tataaaatat ataatataat 155040
atacatgatc atataaaata tataatatac atgatcatat aaaatatata ttatacatga 155100
tcatataaaa atatataata tattatatat gatcatataa aatatataat atattatata 155160
tgatcatata aatatataat atattatata tgatcatata aatatataat atattatata 155220
tgatcatata aaatatataa tatattatat ataatatatt atcccaaagt gctgggatta 155280
taggcatgag ccaccatgcc cagccattct gacttatgtc tttaaaaaac tggccggggc 155340
ctggtgtgct ggctcacacc tgtaatccca gcactctgag tccaaggtgg gcagatcact 155400
tgaggccagg agttcgaaaa cagcttggcc aacatggcaa aacccagtct ctactaaaga 155460
tacaaaaatc agctgggtgt ggtggtgcac acctgtaatc ccagctactt gggaggctga 155520
ggcaggagaa tcacttgaac ccaggagaca gaggttacaa tgagccaagt tcgtgccaca 155580
aaaaagatta ccctggctac tacattgaga attgactcca ggagttaagg gcagaagcat 155640
ggaaaccagt taggatacac tgaaataatc taggcaagag attatggtga agtaatggag 155700
aggttaagaa gtagtcaaga tttgctggct ggacacagtg gctcacacct gtaatcccag 155760
cactttggga ggccaaggca ggtggatcac ttgagctcgg tagttcaaga ccagcctggg 155820
caacatagca agactccatc tccacaaaaa gtacaaaaat tggctgggtg tggtggcata 155880
cacctgttgt cccagccact ctggaggctg aggcaggaaa tcacttcagg ccaggaagca 155940
gacattgcag tgagccatga tcgcaccact gcactccagc ctgggcacta cagagaccct 156000
gtctcaaaaa aaaaaaaaaa agatctgctg aagggttggt tcaccaaaaa gcagaatacg 156060
gcaacaagaa caggtttaag agggagcaga gattagtatc cttttggaca tgctgagttt 156120
gagatgtttg ttctaaccac atgaggatgt catgtgagca atagatatac aagtggatga 156180
tcggagagat ttaagagaag gacctatagg accggatacc tgattgaatg gataaggggt 156240
cagggagggc agtaagggac agacagctgt caaggttgtc ttcttcatcc tcagcttggt 156300
aatacatttt tgaagtccag gcgcggtggc tcacgtctgt aatcccagca ctttgggagg 156360
ccgaggaagg cagatcacct gaggtgagga gtttgagatt agcctggcta acatgggcaa 156420
aatcctgtct ctaccaaaaa tacaaaaatt agccaggcat ggtggcgcgc acttgtattc 156480
ccagatattt gggaggctga ggcaggagaa tcgctttaac ttgggaggca gaggttgcag 156540
cgcgccacta gcactccagc ctgagtgaca gagcaagact gtctcaaaaa aaaaacaaaa 156600
aacaaaaaac aagttgttga taggtccacc aatagagatg gggaatgcag gaggaagaac 156660
aggctggaat gtgaagataa tgagtttggc ttccaataca ttgaattcaa cgtgcctgtg 156720
ggacatctgt gcagacagca tagccagtta cacagatctg caaccaggag gtgaggattt 156780
agcctggaga tactgactgg ggagtcatca gcatgtagat ggtaataaag ctcaggagta 156840
aatgagatag ccccagggtg tagattggta agagaagagg atggaaagca gaactctgaa 156900
gactgccaac atttatgaga tggaaattgg agacatctat gattagaaga taagaagaaa 156960
acgacaagca tatgatatct tacaagttaa ggggagtgtt caaaaaagac aagaagtgag 157020
gaattgttta gattgtttat cctggaggtc actggtgagg aggtcagaaa gggccctcca 157080
actgcttcca agctagacct tctttctttg caccatcctt acagcatgga attgaggatt 157140
agggcttaga agccactttc tccttgtttg ttcattcatt catttattca catattcact 157200
tgccctgcat ataacccccc atgtgaagag atacaaaaca ctaaagacag gctctgtcat 157260
cagaggatca gggacccagg ggtcatactg aactagattt caatctcagt tctaccattt 157320
agaacataat ctttgatgac tccaaaatcc ctatctccag gacaaacatc cccactgggc 157380
ctgtatatac aattgtctcc tcaatatttc cattgggata tgagccaact caacttagaa 157440
aatcccttta ctcaccagcc tggcaacat ggtgaaaccc tcactctaca aaaaaataca 157500
aaaatttagc tgggctgttt tgtgagcttg tagtcctagc tactcaggtg gctgaggagg 157560
taggatcacc tgagcctggg aagttgaggc tgcagtgagc catgattgcg ccactgcact 157620
caagccaggg caacagggtg aaaccctgtc tcaaaaaaaa agaaaagaaa agaaaagaaa 157680
agagaaaata gagaagaaaa gaaaataccc ttactcaaat aatctaatcc tgttcaattt 157740
tccccttttt agtaaatggt gctaccatca gccttttgtt gagatccaaa tcctaggaat 157800
catttttaaa acatttttgg aggatagaag ggaaaaatat agagtataaa tattatagta 157860
tagcctggca tggaggctga cgcctgtaat cctagcactt tgggaggcca acgcagctgg 157920
attacctgag gtcaggagtt tgagaccagg cttaccaata tagtgaaacc ttgtctctac 157980
taaaaataca aaattagcca agcgtggtgg tgcatgcctg taaccccagc tactcaggag 158040
gctgaggcag gagaatcact tgaaccctgg aggcggaggt tggagtgagc cgagatcacg 158100
ccattgcact ccagcccgag caacaagagt gaaacttgtc tcaaaaaaca ataattatag 158160

-continued tatatataat atatggtata ttatagtata tatatggtat agtatatatg gtatattata 158220
gtatataata tatggtatag tatatatatg gtatattata gtatatataa tatatggtat 158280
ggtatatata acatggtata ttatagcata tataatatac actataaata catataatac 158340
atatagtata tttatactat atacttatca ccatatactg tatatcctat actagatata 158400
atatgtacta tatataatag tatactatac ttttatagtg tacttataat atatagtatc 158460
ttatactata cttatatagc acacttataa taagcgtact attatataat atataataga 158520
tatataagga aggccctgtg tgttctggcc cctacctttc ttcctggaca catggccttc 158580
tttctgtcct ggaacctgcc tgttctattg cttttgcatt tgttttttct tccgactgga 158640
tcgctcctcc cccaggtttc acctatctga ctctttgtgt gcattcaggt cccagctcaa 158700
atgtcacttt ttcagaaagc ctttgtgtga gcctgttatt ctctatcacg taaattgtcc 158760
tccgtgtatt tacgttaaat tttttgtacg tttttctggg aattctcagg gcctagaaaa 158820
atattttgtt aaagatttat tgactgacca ttgaccttgg cagatttctg cagttcttta 158880
agccatggtt tccttattaa tagaggaata aatgcctatc ttgctaggta gtttaaagtg 158940
ccagggatga agttaaaagt attaaggaca tcgggaaatc tccccacact gaacctttgc 159000
atttccctgc tcagttccac cggactgctg agcagaccga caaacgctcc tttccctctg 159060
ggtaaaaaga gccacgggtc ttcacttcag gcccaggaag aggtggtccc actacgccgt 159120
ggcatcatcg ctttttttaac aagcgcggaa aaccccctcc catcccaatg tttaatgtac 159180
cgaagtttgt gagagtcacg tgagactctc gggtctgccc cgccttaggg aggtggagcc 159240
tcagcttgtg ggccaatagc aggagcagcc tccggaacag ccccaacgcg acagggaaag 159300
ggggaggagc cgggcgcccg gccctgtaac tgtacttccg gaaagcacgc cccgcccctt 159360
cccccccacc gcgcccgttt ctttcgccag tgccgggtgg gccgaaccgg cgggtgccga 159420
ttaaaggcgc cgcctgccgc tttctcctcg ccccccagcg ccgcagctct ccgccccctt 159480
cccgagtagc gggaccggcc ttgatgtagg gacaccaccc cccgtctcct tccgccccag 159540
cccgggagct cggctcgctg cagcccctgg ccctcccgtt tccccaccct gcctgccccg 159600
ctctgctccg aacccattgt atacggccgg ctgcggactc ccaggccggg ccgtggcggg 159660
ggccccggga cccccgagtg cccctccggc tggtcccgcg ggccgcggca tctccgccgc 159720
cgccttcctc gcggcggcgg cgagggcgcc ctttcctccc cgcgcgggtg acggggacgc 159780
acccccaccc cggggcgccc cttcgcgggg ggagagccgg gcccgagcaa gtcgaggcag 159840
gaaagggccg ccacggactg cccggcccgc cgatcgtttt tattatcgag attattatta 159900
aaagggggcg gggaccccag gacgcggggg aggggctgga tacgcaggta tttttattaa 159960
acagattatt cctgaaataa taatacgcgc aagatggctg aaggtggctg tgatgagagt 160020
gttggggttg ggattttttt cttcctgttt tttcttttt gatctgagga taaagctctg 160080
aggcgacagc ggctgcggag accctgcccg aagcgccctc ccctcccttg agaagccgcg 160140
ggcagacaga cggacctcgg accgagcaac gggtgcgggc ccgcccccgga cgcgtcgcct 160200 gggcagcagc cggggaccgc gggctctcgc ctttctgccg acttcttcca attctcatct 160260
tcttttattt tttggacagg accggggtgg gtggagcaga ggtggagaga aatcgggact 160320
tggcattttc tccctctctc tctcctaatt tgttggaggc cgccagccct ccccttggaa 160380
aaaaaaaaat cccaccaaaa aaaaaaaaaa aagaatcagg agcgagagga cgccgcgggg 160440
ccctcagcga gcgcgcccag accccggccg ccgccgcgga gcccaagatg gctgggcgct 160500
gagggtggcg gctcggcctg gccccgccgc cgcaggctgg ctccgaccgc agccccgagc 160560
cttccaggcc ccagcagagg ccgagaagaa aagaaagtgg ggaggagggg gccggggggg 160620
cgaaggggga gggccggggg aggggagggg agggccggga gccgagcctc ctgttcatta 160680
gcagttgaga aaaattcctt tctagtttga tcaatccttg ttttcctcgg cagagcccgg 160740
gcgcccgccc agcgcggaga cgggcgcgcg gggtctctcc gcggcggggg cgccgggcct 160800
cgggggagcg cagaagtagc cgcccggggg tcaggccgga gcgccgccgg ggcttctccc 160860
tccctccctc gccggttgcc tttttttcca cttctctccc tccccccttcc gtttctattt 160920 gtgaagggag gaggaaggca gaggcgggct ggtgtctctg gccggggact ggaatttcat 160980
ctgaatgact gcccctgcgc gcacgcagcg ccccggagtc ggcccgcccg cgccccgcag 161040
cccgcgcccg gccagccagc cgggggacgc ctgcaccgtg gcccggggac cgccggcctg 161100
cccctcccgc cccgtccgga tctagcagcc ctcggcgcgg ccgccctcgc ctcctggccc 161160
cgcagacccc gggctccggc ccctgcgagg gaggtgcggc gccgacgagc caggcaggag 161220
ccgccgctgc cgccgccgcc ggaagaagtg tgctgctccc aagctccgtc tgccgcgggg 161280
cgcgccccaa tgtcagccgc ggggacgagc gcaggccgcg ggccgccact gccctagccg 161340
cgccgacggg gaggcggcct cttatatgga atttggaccc cggcgctccc ctccaaggct 161400
ggagtcccgg ccgcggccct ggcgcagtcc gccgcctccc gctaggcgct cgggaggagg 161460
aggagacgca gcccgctgcg cgcgcggcgt gaggaccgcg gctccctcct ccggggggcg 161520
ggcacgcgga aggcgctgct gactgagcga ccgtcggggc cggctggggc cggagctcgg 161580
ggctcggtgg gcctacagcg gctccggacg gacccccggg gctggggagt cggggaggcc 161640
tgccccggcc ccctgcccgc ggccgccatg gcggagaatt ggaagaactg cttcgaggag 161700
gagctcatct gccctatctg cctgcacgtt ttcgtggagc cagtgcagct gccgtgcaaa 161760
cacaacttct gccggggctg catcggcgag gcgtgggcca aggacagcgg cctcgtacgc 161820
tgcccagagt gcaaccaggc ctacaaccag aagccgggcc tggagaagaa cctgaagctc 161880
accaacatcg tggagaagtt caatgccctg cacgtggaga agccgccggc ggcgctgcac 161940
tgcgtgttct gccgccgcgg ccccccgctg cccgcgcaga aggtctgcct gcgctgcgag 162000
gcgccctgct gccagtccca cgtgcagacg cacctgcagc agccctccac cgcccgcggg 162060
cacctcctgg tggaggcgga cgacgtgcgg gcctggagct gcccgcagca caacgcctac 162120
cgcctctacc actgcgaggc cgagcaggtg gccgtgtgcc agtactgctg ctactacagc 162180
ggcgcgcatc agggacactc ggtgtgcgac gtggagatcc gaaggaatga aatccgggca 162240
agtaccctac gcgcgcgcgc gcacacacac acacacagac acacagtccc ttcctctctc 162300
ccgccccggg accacccatc ccgacaggct gactcttgtg acatcaggcc agtggcccct 162360
ggccaaactc ttctctgaaa gtttggggac agggtcctgg gaagaagggc cccgggtcgc 162420
tacttggtac attctcgcac ctgtgcgcac agggtccgtc ttctgagtgc tttatgggat 162480
tggggtgtgg gaccgtcagg ggtagagtct gggtgttgct tttctgtggt gcgcagctcc 162540
ctcccccagt cttgttgctg taggccctac gggaagtcac cgaggcagtg accccggtcc 162600
tgcctctcca gctgctgttt atgtaatgag tgtcccggtg ccgctgctgt ggctgacatg 162660
atccatgatg ctggcatacc aatgaggaag taaacaaaag cagccatgtt agttttcagc 162720
gctattggaa acacactggg gggggagtgg ggggagtttc cagagggaga gcagaactcc 162780
ggccgtctct ctggacaggg cctgggcagc cagcgaggcc ccgacagcgg ctccgctatt 162840
tggattcctc ccgagagccg gctctccctg tgtgagaatc gctgccctgt gtgcctgtgt 162900
gtcgcacggg ccgcatgaac aagccttcaa gtatctgtct tcatcatcct ggccctttcg 162960
cctagcacag ccctctcgcc gccctcccac atttggggag gggaagtgga agacggaaaa 163020
agaatcctgt gggtttaagg ttgagccgcc ttgaaatctg gtttcaggca gctggctccc 163080
ctgggctgcc ggctgggtga ttacggaacc gcgtcccctc ccattgtata caccctgcgg 163140
ccgcggccaa tgtcaaaccg cctccccct caggcctctg ggcctggttt tggagctgga 163200
ctgaggcaat acttccgtcc ccttcagtgg agggggctcc tcctaggtcc ctccccagtc 163260
ctctggcttt cagggttgag tcataccaaa atgaaggggt tggcctgaca ccgaggagtc 163320
ctctctgaag ccccaccttg gggcctgggg cctgggtgtg atatctgggg gctaggctgc 163380
actctggtgg gactgggagt gtctctgggt ggggatccct ggaggttagt ggaggccagt 163440
gcggaggctg gctatgagga agctctgttc agggcatgat tggagatggg gctgtttcct 163500
gtgtgggggg accagtcaga atgagtcact gtttagcaat taaaaaacat acacatacaa 163560
ccaacaaaag gcaggagggc caccacaggc tggggcgggg gcagcaaata cgatttgctg 163620
tataattagt ttccaatcgg atggactagc cctgggtttg tgtgccagga taggcctctg 163680
gtttcttaaa ggaagtgtgt cctccacccc ctgtgtcctc catccccgtt cagggcaggc 163740
acagcccaca ctttccccag tattgggaag ctgctgctat taataaagat ggaagggctg 163800
ggggaggagg ccgggaaaag tgcagaggca ggagaaagga gggctgtcca gttctgtcct 163860
gggattggca gtggaaaatg agaggagggg aaaggagatg tggctgaaag gaacagggga 163920
ggggcagcaa cctgggcgat gggcggatgc ctgcccgcac ccacagtgct gctgtagctg 163980
gtctgagttc tagggatgtc tttaattggg gtgggggaga aaacgtcatt atacctgact 164040
tggtgtagga ggatagcttt aggtgtctgt gtttttgaat gtctttgaga ctgtgtgctt 164100
cgccctccaa tgcacctgtc tcctgtctct acagttcagg gcacaggcag gggtgggtgg 164160
gtggcatgtg catgcagagt attccctggg gtgcccccca gcaggcccct catttccaga 164220
ctcgtggatt ggatggaagc aggcactgaa ctttgtcggc aactccgcag ggtgtgtgtg 164280
tgcgtgtgtg cgtgtgtgtg cgtgcgcgtg catgcgcgtg ctttcttgtg cctggtgtgg 164340
gcaggctcag aagtagtggg ttgcatcagg gccagatgtg caattctgtg cgttcagcag 164400
ctgtgccctg cagtggcagc ctgagcctca tccttctcca ggttccccct ccccaggccc 164460
ctgattcttt ctggtgcccc aggccactgg ggttggaaac ccttcagtag cccagtgtca 164520
ctcaagtatg agtttgactt attgaatgtg gaggaatagg ggccctgcct gccctcccag 164580
gagggagagg agggggtgaa ccataggaac ctaaatggaa gaaccctctg cactctctgt 164640
aggccaaaca gggggagtgg gtggagcgct cttccttggc cccttttctc ttcccggagg 164700
gagtctgcct taaagggcct ttgctggtgt tgtgggcgag ggccacagaa ttccccagga 164760
tacaggggca gaagcacaga gacctggcac ctgccttaaa atctaggctc tgcttcttgt 164820
gcgtcctctt ctgccctccc agggggattg ctgacatgcc tgtcaactgg ctagaaatag 164880
gaaactctga ttaacccctc cctggtggcc tcaccctcat atacttacag catccacagg 164940
tgcacatggg ccatagccta gagcagggac ccagcaggag agcaaacagg tcctccatcc 165000
atcctgggga actacaaggg ggactctcag aatcaggccc aagcaggttg ttgccctaat 165060
cttcccttgg gaagccagtg tgtcggccac attgccgagg cctggatact cactggatga 165120
tcccgagacc attgtctagg atgtgcctag atcctaaatg tgctctccca tgaggctgtg 165180
gggaagctaa gggcccaaga tttggacatc caggtgggct caggcctggc agtcctgagt 165240
ggtcagaccc ctcctagccc ccaggttcag gggttcatct aagcattgaa ggactggtgg 165300
gagctggggg gcatccttat ctcatgaccc cccatgacat ggaaagaaga cccaagagca 165360
ggcccggttg catgtgtgag gggcctgcag gtatgtggtg cgtatgtgtc tatgcaggtg 165420
tatctgcttg agtcttgtgc agttacggtt gtgtttctgc atcgtccctg gtgtcccaga 165480
gcaaggccag acatgttgct agggccctgt tccttgcatt ttcagaggtt cagagtcaag 165540
aagaggttct ctgggggagg agatcccact gcttgggcca gtgtggggtt tgcccctgct 165600
tggagtgagg gtatcctgtg cacattgccg gtggctggag gggtcaccct gagaccctgg 165660
agggaatcct gggtttcctc tccatttatc tgtctctgag tacgcagtga gagtgagggc 165720
tggctctact ggggctggtg ctgaggctgg ggctgcagcc tgactccagc agtgcaaacc 165780
tcactgctcc ctctccctac agcagaccat actcctgcag ggtgtgtgt gtttgtgtgc 165840
acgcacgtgt gtttgtggtg tgacggtcat gtggcccctt ctttggccac ccccgagtct 165900
tcgtggaagg aggccctggc ttggctttct ccgttgcccg tgaaagggag cctcaggcag 165960
aggcccagct gcccacccct accccaggat cctgctgaca tggccaggca cctgtcatgc 166020
acacactatt attactctgc cttctgcggc cctgggtggc tgcacatctg tgtctgtctg 166080
caggtgtgtg tgtgtgtgtg tgtgcgtgca tgtgtagcca gcacgtctgg gtcgtgtatc 166140
ttggatgtga ctgatctttt tgcatctcac atgggtgtct ctgagaaggc gcagcctgcc 166200
tgacttcagt ccctagttgc gcagccgtgt ctgcctgccg ggcttgctga gcgcctgcga 166260
gttgaagttg agtgtgcctt cctgacagtt ggcagcacta ctgtgctgct gtgtgagtgc 166320
ccgctcaggt gatccttgct tggtggctgt gagtttgtca ggggtcctgg gacttccccc 166380
tgtggtgggg ttgttgggga aaggagggaa agatgggctt ccccttgggg tgagcctgtg 166440
gcgggtattg gaggcaggag ctgaaagggt cctgcgctgt tgtgttgggt gcagtctggc 166500
gaggcggagc aagcccggct tgggcccctg ccccgggccg agcaggctgg cctggctggc 166560
ctcctccctg gctctgggaa agccttcctt tcccggctgg cctggcattc aaagccagac 166620
aaagggggc tttctctctc gcctctttgt tctgctgccc cagagcgctg ctctctgcat 166680
ggcaaaagct aattccactc tgcagctggg aagccctctc tggggtctgc cgggctcgca 166740
tctgaggtgc tgcctctctc cttgccctgg cgcctgccct ggagcccctt ccctctgcag 166800
cttgtggttt ccccagcctg gggttcagtt cacatgatag cccaaggcag tggcttgagg 166860
catggaaagg gggtttaggg caggcagaag cttttctgag gaaaggggag agtgctatga 166920
gcgcagagac ccagggagag atggggacag ggaccagggg gaggagtagg ggagggttag 166980
gatggggtgg ctctgagaag ggggctggag ccagaactgg agctggccgg gcagggacct 167040
aagcaggaag aggctgccca gccccctctt cttgcccctc ccaccaccac aggggcttct 167100
ggagctagcc atggtcttgt ctgaaaacct agggactgcc tctgtcccag tccctggggc 167160
cctgtttcct cctgaccttg tttctcttca aggttgactt gagggtttta ttattattat 167220
ttattaactt ttatacagcc cagagtcccc aagcctcacc cgtctgccca gtctagtctg 167280
gcatcaaaaa tggcagctgg cctggccagt cagtctccag agggacatga ggctttcctg 167340
gggcaggaat gtaggggctc agggttcgct gctccaggcc gggaggggag tcagaggaag 167400
cagcggcaaa gctgaggagt gggggcccag gtggtggagg gtgggaatgg cggctcctga 167460
ttcttcatgc ttttgtcctc ataggccccg ggcagatcac caaaggcctg aggcccgaca 167520
ggcagggctg ggggtgtgaa ggtcctccct gggccccacc tagtcccagt ctccctggtg 167580
gcctggggcc tccagagctt ctagcccagg ccacgttcca ctctgctctg ctcctgcatg 167640
ctccagtgta cgcagtccag gccatgcact gctgtggggg gatggggcgg tggcatgtgt 167700
aaggtgcctc cagcccacct gcctgcgcag agagtacttg ctctgaactg agctgggaaa 167760
tctggtcgga tctcagctat gggtttttcc caggtgggaa gtggggcctt ggctcttagc 167820
cattccctgg ggaggcaggt gggggttggg atggaaagga ggctgctggt ggtggggggt 167880
ctgggccttg cttcctctgc tccctgtttt ccagcatttt ccagtgtctt ggcaacctga 167940
tttgctcatt cggtgaactg gggtggggtc gtgaagggga cggcaggcag gtatttccca 168000
tcttccttcc agtttcccag gcttgaagcg gcagcagctc ccactgttct cccaggcgct 168060
gtctgtagca ggagttggcc ctgagggaga gcaggccaga ccagtgcagc cccccggact 168120
cctccctggc tggcaccccc tggccagcct ccttcctctt cctgctctca ctccaacccc 168180
tgcagcagag acaggagccc agtggcctca gcagcaggag ggggaaatga aaccctccca 168240
cctgctaggg actgtgtggc ctgggctggt gtcccaccca gattgcctgg gacagacaga 168300
agcttgggaa gaccctgccg gctcccaggg tagaagtgct gtcaggggag gctgaggaaa 168360
gcccggaaga agagggaagg ggctgagccc caccccccca ggactggaca ggaaggccct 168420
ccctctgctg tgccctgagg ggtcactccc tgggcatcag caagggatgg ggcaaagggg 168480
cacccaccag cctgcggggt gggtgtggac agctcagttc ctgtccccaa ggaagctgcg 168540
ctgggacctt ggagctgcct ctttcctacc cctcccctgg gactcacctg aatcctccct 168600
gaaccagctc ctggtgggtt tggtcgtgga gaagcagcca tgcagtaagc ctgtggtgtg 168660
agatgtgtgg ggccagcagg gcctttcaga tgtcctgggc actggatgga gggatcagcc 168720
tggactctga agagcacctg gggggccctg tcctcctgag ggtgggcttg gggcaaccag 168780
caggcaagaa tttgagggcc aattgttcca ggggaggtca gtgggcctga tgttcccaga 168840
gtgtcctggc cacctcgcca tcgtgccagg cctcttgcca ttgtctgggg cctccaggag 168900
gtccagcctt ccctgtgagg gggttgggtc aagtgccttt gcacctctgg ctgtgcccgc 168960
cagcatacct gaggcgggct cggggctcag gtggcaaggt attcccatgt gcgtgcgcag 169020
ctttgtgcca ggtgcccctg cgcctgccca ctcatgctgt gtgtgctgtc gggctctgac 169080
ccttgggctg gcagcagatt cctgtgcctc ttggtgcttc tgggggcagg gcaaggtctc 169140
ccaggcctga ttcttttaga ggtcctgtcc tgggtcactg aaaggttaag ttgtgtgtgg 169200
gccccctgca cccagcttat aaggtgaaag cctcaccccc acacttcctc ctgctcccag 169260
ggttctggtt ttttccacag tagcctccaa cacaaaatag ggtcaggctg aagtctgtgg 169320
tgggccttgg tttgccccta cgtaaaatgg gctggcgggg tgaggaaggg attgatggca 169380
gcttgtcttc ggggagccag ctgggagtgg ctgggatggg agtcatgggg ttgaactgga 169440
gggttacttt gaggccccca cagaggaaga aagagaacca ctccttgcag catgacagtt 169500
actgtgaatg tctgtggtta cacagagctg ctttgcaaat tttagtttgt gtatggaacc 169560
catgggctta ttgagtgaat ttgttatgca tctcaggccg cccaggcctt tgtgtggcct 169620
gcctctgaag gaaggtggag aaagacagca gcaaatcccc attcttaaga ggccctgtgt 169680
cttgtaggga gatgagacca tggtttgtga ggcaattaga agactccaga atagtgctgt 169740
ctaatagaac ttctgcatga tggtaacatt ttataacttt agtatctgag actagtgata 169800
cgtaggtact gggcacttga aatgaggttg gtgcatgagg aaccgatact taactttttt 169860
tttttttttt gagacagact ttcgctcttg ttgcccaggc tggagtgcaa tggcgcgatc 169920
ttggctcgct acagccttcg tctcccgggt tcaagtgatt ctcctgcctc agcctcctga 169980
gtagttgcga ttacaggcat gcaccacctt gcccagctaa ttttgtattt ttaggagaga 170040
tggggtttct ccatgttagg ctggtctcga actcccgacc tcaggtgatc cgcctgcctc 170100
ggcctcccaa agtgctggga ttacaggcat gagccacagc acctgacctt attttttatt 170160
ttttgttaac ttggatttaa atagccacat atgactagtg gctaccatat tggacagcac 170220
aacctgagag ggagggcaga atgggacagc cccaccccgt agccaggaca gggagggacc 170280
tgcacaggct cagagcaggg gtcatggaaa gtttcctaga ggagtgggga cttcagttgg 170340
gccttgaaga atagacaggg gagggaggag gcactgtggg ctgcagaaga atgtacctag 170400
agctacaggg agtttccatg tgtggagggc tggggacagg ataccagccc agctggctgg 170460
aagagtcagg gtgtaaaaga gccttcattg ccatgctaaa gtagttgata ggacggagtc 170520
acggagagtt tttgagcagg ggagagagcc tgtctaaaga ggcatatctg gtgagaggag 170580
ggcaggagag atggagtgac tggcaggaaa ggggttgtgg ggacaggaga ttatgagctg 170640
agaagagcac tttggtccag caccttccag cagcctggcc tcaggtctta ggagacctca 170700
aatctccttt ctgcctgggt cccactgagg gggctgaggg agctagccag gactccagag 170760
tcctagctct cagtcttaag aacaagggag ggggtgactg gcctgatgcc ccctaatgta 170820
aggcgagggt aaagtgagat ctttggactg ggacagaggt tcacgtggct atggaaggga 170880
atttgacccc ctgcatctta gggtactcat ctcttagagg atgctcccca gggagaggca 170940
gcacagcctg ggtaagaacg gaccctgctg ccagatcacc tgtgtttgtg cccaagctct 171000
gctatttaca agctgtgtga ctgtggacaa attacttaac ctctctaggc ctcagtttcc 171060
tcttctgtga aatgagaata atgatagtac ttatctcatg acattactgg gatgattaga 171120
taaatctgta caggaaaagt gtttagaaca gaggttggtg tagccctgcc ctcagaaagc 171180
tcagggttta aatatgcatg ggggctgggc atggtggctc acgcccataa tccccgcact 171240
ttgggaggcc gaggcgggca gatcatttga ggtcagtagt ttgagaccag cctggccaac 171300
atggtgaaac cccgtctcta ctaaaactac aaaaaaatta gctgggcgtt gtggcgcacg 171360
cctgtaatcc cagctactcg ggaggctaag acaggagaat cacttgaacc ggggaggcgg 171420
aggttacagt gagccgagat cgcaccactg cactccagcc tgggcaacag agtgagaatc 171480
catctaaaaa aataataaga taaataaata tgcatgggaa gctattctgg ggagagctgg 171540
gaataggccc ctgggattgg agggggccaa aggggctggg tagcagaggc ttggtgccat 171600
cgggtcaaag gatccatagg atgcatgtgt tgtgtagagg gaagcatggg tcagggttgg 171660
agccacagtc cctctgatac tcccacccaa atgtccctgc agaagatgct catgaagcag 171720
caggaccggc tggaggagcg agagcaggac attgaggacc agctgtacaa actcgagtca 171780
gacaagcgcc tggtggaggt agctaagccc aaggccatgc tgcggggtgg gggtggcttg 171840
agcgcagggc tttgggtgag ttccttacta aggattgatt gtgtagccct atgccagaac 171900
cactccatca gtcattcaat caactgcccg tggatgccca ctggtgccag gggatgctgg 171960
cccagagccc tgtgctacca gtggggaact ggcaggtcag accttgccct tgggagcctg 172020
gggcagcctg gtgacttagg gttctaggat gtgagaaggg taagaggggg ggaaaccaaa 172080
ggtttccagt gcttacctgc ctgcccactc ctgccctctg tactcgcagg agaaagtgaa 172140
ccaactgaag gaggaagttc ggctgcagta cgagaagctg caccagctgc tggacgagga 172200
cctgcggcag acagtggagg tcctagacaa ggcccaggcc aagttctgca gcgagaacgc 172260
agcgcaggcg ctgcacctcg gggagcgcat gcaggaggcc aagaagctgc tgggctccct 172320
gcagctgctc tttgataaga cggaggatgt cagcttcatg aaggtgggct gggctcagga 172380
ccaggctggt ggcacccaga gggccatttc caaattgaga tctgcagttt cctgcacctg 172440
tagctcacat gcccttacct ttggagccag catgcatggg ttcaaatcca cctgcctgct 172500
ctttctagca ctgtgacctt gggcaagtca taggtacatc ccgggccttg ttccctcacc 172560
tacgaagtgg tgttgatgat acaggtctac tattctttat ccacaattcc acatttataa 172620
acatctctgg aaactaaaca aattttggca tctaatttaa cagcaaaaat tgacctaaac 172680
tgatgttagg caatttatgg tctttatctt gcttagtatg aaaattcaaa cattttgctg 172740
cagaaatgtt gctgtattag attgttgtgt cttgctgggg atgataatgt aatatatgat 172800
acaggcactg tattctccgt ctaaaatcca aaaaattcca aattccaaaa cacatctggc 172860
cccaaagact tgagctaaaa cagtgtgggc ctgcagagcc cttctcctcg ggtatggatg 172920
aagttatgga tgcacagaaa gcacttacaa tgcctgggtc acgtggcaag agctcagtaa 172980
atgttagctc ttcttccgca aatggccacc cctacccctg ccactttctg tccagaatga 173040
gaggatccac ccagcctggg ggaggctcag ggggggcagc ttttgtcttc ccctctcccc 173100
gggctctccc tggactgcct tttccactga cttgactctt ttctctcccc aacagaacac 173160
caagtctgtg aaaatcctga tggacaggta agctgagggc cctagccctc ccgggggcac 173220
atcctgggga gggcaggggg gccaggccca tggcggggag gtagggcggg ctcaccggtg 173280
atgcctcctc acagcagatg ccccgtccac tgcccccagg acccagacct gcacgagcag 173340
cagcctttcc cccactaaga tcggccacct gaactccaag ctcttcctga acgaagtggc 173400
caagaaggag aagcagctgc ggaaaatgct agaaggtgag ggtggggtgt tccgccgaag 173460
ggagacaggg acctttgggg aggggttcag cgccacagcc ttccctccaa gaggcagtgt 173520
ggcccagtct gggagacctg tcctcatatc caggctttgc cacttgtagc tgtgggacag 173580
tgggtaagca acatgacctc cccagcctcc atttcttcag cttaaagtgg ggatataact 173640
attctgtacc tcctaatggt agaggagcaa gcatcacctg agatgtaaca ttcttgggcc 173700
tctaggtgtc aatggtcccc aggtccaacc cagggagagg aggcctgggt tgcttggggt 173760
gggagctttg gcgacttttg ccccaactct ccacaggccc cttcagcacg ccggtgccct 173820
tcctgcagag tgtccccctg tacccttgcg gcgtgagcag ctctggggcg gaaaagcgca 173880
agcactcaac ggccttccca gaggccagtt tcctagagac gtcgtcgggc cctgtgggcg 173940
gccagtacgg ggcggcgggc acagccagcg gtgagggcca gtctgggcag cccctggggc 174000
cctgcagctc cacgcagcac ttggtggccc tgccgggcgg cgcccaacca gtgcactcaa 174060
gccccgtgtt ccccccatcg cagtatccca atggctccgc cgcccagcag cccatgctcc 174120
cccagtatgg cggccgcaag attctcgtct gttctgtgga caactgttac tgttcttccg 174180
tggccaacca tggcggccac cagccctacc cccgctccgg ccactttccc tggacagtgc 174240
cctcgcagga gtactcacac ccgctcccgc ccacaccctc cgtcccccag tcccttccca 174300
gcctggcggt cagagactgg cttgacgcct cccagcagcc cggccaccag gatttctaca 174360
gggtgtatgg gcagccgtcc accaaacact acgtgacgag ctaacgccac gcaggcggcg 174420
gggcgctggg gaatcttcct ccccagcccc cgggctcggg agttatgcat ccagagacct 174480
gcccttctac cttcctcgcc tcccctcttc ctcattccat tgccccaggt cttttccttt 174540
tggattttgt tttggttttg gctttgtttt tgattttttt ttattatgaa tctcctggac 174600
gcagaggtga cagtgggagc tggcctgggc caggacggca ggtggccctg gagatgggaa 174660
agtgtctgtg tcgaggcgct gagctctctc tctgtttctc ctttttttcct ctactccttc 174720 cccttcacac ccccgtggct ggaaggaacc tcggcttccc tgaaagcttg ggggtcccac 174780
ccttcttacc ccacccggga ggaacgccca gggccccggg cttgtttctc ctcttgtttt 174840
ccttttgggc agtttgatca ctgatcgagt aaggaatgac ctttagattg tgcgactttt 174900
gtttttgttt ttttaaattt ttttaaacca agaatgattt ctcctgcttc cttctcctca 174960
ccatcttccc agacggagtt caaaggccac ttctcaagca gcttttggca ccttcagcct 175020
cagagtggaa tcttttaaag acaggacccc tatgtccagg aaaggggaaa aggaactttg 175080
ccaatgatag tgaccacagc aaaagcaaat aataataata ttaataataa taaagagaaa 175140
taaaataata aaataaaaaa caatagcaca gcccttgttg aggtcagcag ggaggagggg 175200
ctgcccggag ttgggtcctt gcctggattt tgacacagca acttcctgta gtgagcactt 175260
tgtatgaatc gtggacttcc tgttctcaag gcgcaggtat ttattctgta tctgtctaga 175320
gcacacacca aaatccaacc ttctaataaa catgatggcg cagtcccact ccctgcctcg 175380
cctgttcccc tatccccccc aggcctggga tcttcaggcg tcggtgtggg gaggggcccc 175440
tgccctcctt gccttgattt tgctcccctg ggtccagctg gttccaggcc tgtgaatgtc 175500
agttcgtcgg gcactgactc cgtctgctct tggccttggg ttcatttgac aaatatttgc 175560
ccagggcctc ccaggcccag ccccatgcca cctgggcccc ggcatctctt tgaggttctg 175620
ccaatgtgct cttagctgag gacgaaggag gaacaccttt ctatgagtct tgcaaagttt 175680
acctccttca ggccacaaat atttgagtgc acactacgtg ccaggcactg tgcagggctg 175740
caggcataga gacagaatgt aatctagctg ggccttggac cccataggga gaggggacca 175800
ctcaggtcca tacttccttt ggacttgggg ctttggcctt gggaggggtg gaggtggggt 175860
ggcaagatga aaaagacatc ctgcccccat ccacttcggc agagcttctc aaagtctcaa 175920
gcatgtcttg ggagcttgtt aaaagggccg attccttgct gtggctcacg cctgtaatcc 175980
tgacattttg ggaggccaag gcaaattgcc tgagctcagg ggtttgagac cagcctgggc 176040
aacatgtcgg aaccctgttt ctacaaaaaa tacaagaatt agttgggcgt ggtggggcac 176100
accacacctg tggtcccagc tactctggga ctgaggtggg agaactgctt gagcctggga 176160
ggcagaggtt gcagtaggtc tagatcaagt cactgcactc cagcctgtgc aacaaaacaa 176220
cagagcaaga ccctgtctca aaaaaaaaaa aaaaaaaagg gtaagggtgc tgattcctga 176280
ggcctagctt agactcatcg ggaatctctg agagcccagg aatttgcatt tttaactcta 176340
ttctcccata tcctgggttt agagaagtgc tgccattgtg gtggtcaggg tcctccctgc 176400
tgcttgtcac agaggccact gcggggagag gaagctggga cacccccaag gcccttctct 176460
ggagaggggc ctcaccttca aaaaggctcc ggttgttgcc tgatgctctg cacagagctg 176520
taagtccgca gcccatgcac ttctgtaatc tgctgggtgc ctagttatct ttcttcttgt 176580
ttgggcagaa tccgggcctg aatgccaccc accccaggaa gcccaggaca aggcagacag 176640
ccttgtaaag tcccattcct gccaggcgcg gtggctcatg cctgtaatcc cagcactttg 176700
ggaggctgag atgggcggat cacctgaggt cgggagttcg agaccagcct ggtcaacgtg 176760
gtgaaatttc atctctatta aaaatacaaa aattagccgg catggtggtg ggcgcctgta 176820
gtcccagcta ctcaggaggc tgaggcagga gaatcgcttg aacctgggag gcagaggttg 176880
cagtgagccg agatcgtgcc actgcactgc agcctgggtg acagagccag actccatctc 176940
aaaaaaaaaa aaaaaaagtc ccatgccagt ggtccaagcc tcactgaccc ctagccaccc 177000
ctcccctcag aaaaataaag gcttgccgag cacgttggct catgcctgga atcccagcag 177060
tttgaaggtg gatggatcac ttgagttcag gagttcaaaa ccagcctggg ccacatggtg 177120
aaaccccatc tctactaaaa cgaaaaatta gccaggcgtg gtgccacggg cctgtggtcc 177180
tagctactct ggaggctgaa gtgggaggat tgcttgattg aggctgggag gtggaggttg 177240
cagtgagctg agatcttgcc actgcactcc aacctgggca acagagcaag atcctgtctc 177300
aaagaaaaaa aagaaaaata aagactttgg ggctggccag accaaaccat agccttggtc 177360
ttgctaactg cctccgcctt cctgccctga gggagtagag gatgactcgg gtggggtggt 177420
ggacccttgc ttcattgttc ccctccccag tgtggcaggg agccaggagc agtatgacaa 177480
cagctggcct accccttccc tccccgtgca cctgtttggg gctaaaggga gtggggaaat 177540
gactggagca cagtgcccct ccagcccagg gtgcaggatg cctgggggca ggtgccggtg 177600
gacagtcact tcactccact caaatctgct tctgtctcac tgtccctttc tccagttctc 177660
aggagccctg agacatcccc cgtgccaaga gttgggagcc aagataaaaa gctgcctaat 177720
ttctttccca cttggcctag ttttgttttg gctgagggga gaggcccttt ccccaggtgc 177780
gtcaatccac tgagatgtgg aggggacatt ctggtgggaa tgggatgggc ttgagcccct 177840
ccatgtccca gctttgaagc ccactccaga caatgacacg ctcaggcaca catctatagg 177900
tgaagcagca gctgcccaga gttggcttgg ggggggttcc ctaggcagcc agggaagcag 177960
ggagacgcta acccacccag ctgtccccag ccacccagct gtccctggct ttgtaggagc 178020
agctgtcacc cagctcccaa aagggtcggg gcagaggagg cccagaaaga gctggggctg 178080
ccccagggaa caggcttatt cagaagtcat cggaggggcc ttctctgccc tgaactggtg 178140
gccccttgga gggctggctg cagccacagg tgccccagtg cccagccctc ccctcctgcc 178200
ttcccccaaa ggccatcacg cctccccttt ccgggaaggg ttggggatct gaccacgtct 178260
ccctacccca cagactgggg ccgacagctc ctgtggccca gatgtgctga gcccgcagcg 178320
aggccaccgc gagggagtgg gtgggggtgg tttcctctgc tgcctgccgg ccccagctct 178380
ttcatgttgc cgccctcccc atcccagccc ggagccaagc agctgggccg ctcctgcccc 178440
ctccctcggc ctcgctccca gctgtctttg gggtggggca gggcagctgg ggaacagctg 178500
caaggcagga gcctgggggg tgatgggtgc cccctgcaac tgccggaaac ggtctttggg 178560
ccaagaaggg agtctgaagg gtgggggtgg agagggcgag gcctagggga tgatcggctc 178620 cacccccttct cccagcgcat ctggccagga gaccccagct caaagccccc tccagcttca 178680
aagggcaccc tggggtggga ggcaggagac gagggtggat gccctgaccc actgagtccg 178740
caccccaggg cccctctctc caagctgtga cctcacctca gggttcttaa caggccttgc 178800
taacactctc ccactcagat cctgtcattg tcaccatggc cttcctaaga caccctcatc 178860
ttctcccatc cgagggtggg ggagaaccaa ttcgattcgc aacttcagga cccaggaccc 178920
atctagccgc ctggggggatt ccctacccca cctctgcagc ctgtaaattc tgggggagga 178980
ggccctggag ggaggatcag aggcatgtcc ttccccaacc tcccactctg gcctactaag 179040
aaatgggagc agggctgacc ctatgaaagt gtgggaggtg aaggagctgg agtcgtgatt 179100
cctgggtatc cccagacaga catcaccaca ctacagcccc tcttctaagg tgatcccagc 179160
actttgggag gctgaagcag gaggatccct tgatgagacc agcatgggca gtataaggag 179220
atcctgtctc tataaaaaat taaaatatta ggctgggcgc ggtggctcat gcctgtaatc 179280
ccaacacttt gggaggccaa ggcaagcaga tcacttgagg tcaggagttc gagaccagcc 179340
tggccaacat ggtgaaagcc caactctact aaaaataaaa aaaattatct gggccgggca 179400
cggttgttca cacctgtaat cccagcactt tgggaggctg aggcaggcgg attacgaggt 179460

-continued

```
caggagatgg agaccatctt ggccaacatg gtgaaaccct gtctctacta aaatacaaaa 179520
acttagctgg gcgtgaaggc acatgcctgt aattccagct acttggaagg ctgaggcagg 179580
ggaatcgctt gaaactggga ggcggaggtt gcactgagca gagatcgtgc cactgcattc 179640
cagcctcggg acagagcaag acttcctctc aaaaaaaaaa aattatctgg gtgtggtggt 179700
gggcacctgc aatcacagct actggggagc ctgaggcagg agaatcgctt gaacagggga 179760
ggcggaggtt gcagtgagcc gagatggcgc cattgcactc caactggggt gacagcgcga 179820
gactccatat caaaaaaaaa aaaaaaaaaa aaaggccggc acggtggctc acgcctgtaa 179880
tcccagcact ttgggaggct gaggcgggag gatcatgagg tcaggagatc gagactatcc 179940
tagctaacac agtgaaaccc cgtctctact aaaaatacaa ataattagct gggcgtggtg 180000
gcctgcactt gtagtcctgg ctactcggga ggcagaggca ggagaatggt gtgaacccag 180060
gaggcagagc ttgcagtgag ccgagatcgt gtcactgcac tccagcctgg gccacagagc 180120
aagactctgt ctcaaaaaca aaacaaaaca aaacaaaaac ccacaaaaaa ttaaaaattt 180180
aacctgacgt gctggcatgt gtggtctcag ctactcagga ggctgaggca agaggatcac 180240
ttgagtgctg gaggatccct tgagcctggg aggtcaaggc tgcagtgagc tgtgattgca 180300
ccactgaact ccagcctgga cgacagagcg agaccctgtc tcaagtaaat aaaataaaat 180360
aaaataaata aaataaaata aataaaataa aataaaataa aataaataaa ataaaaaata 180420
aaataaaata aaataaaata aaataaataa aataaaataa aataaataaa ataaaataaa 180480
taaaatgcct ggcatggtgt cttatgcctg taatcccagc actttgggag gccgaggcag 180540
gtggattgcc tgaggtcagg agttggagac cagccaggcc aacatggtga aaccctgtct 180600
ctagtaagaa tacaaaaatt agcagggcat gttggtgggt gcctgtaatc ccagctactt 180660
gggagactga ggcaggagaa ttgcttgaac ctgggaggtg gaggttgctg tgagccgaga 180720
ttgcgccact gcactccagc ctgggtgaca gagcaagact ccgtctcaaa ataaataaaa 180780
taaaataaaa taaaatataa aataaaataa aataaaataa aataaataaa ataaaataaa 180840
attaaaataa aataaaataa aataaaatat aaaataaaat aaaataaaat aaaataaata 180900
aaataaaata agtctccctg cgtgtttttg gaaaattctt ccttggagga gctttagaaa 180960
cagtggtctc cagaacccgg attctggtgc tggttctaga atcctctggg tcctgtttgt 181020
ttttgttaag agggcaagga aggaaattga gagcactctt agacggcctt tgtctttttt 181080
tttttttttt tttggggaga cggagtctcg ctctgttgcc caggctggag tgcagtgacg 181140
atctcggctc actgcaagct ccgcctccca ggttcacgcc attctcctgc ctcaggctcc 181200
ccagtagctg ggactatagg cgcctgccac cacgcccggc taattttgcc cggctaattt 181260
ttttgtattt ttagtagaga cggggtttca ctgtgttagc caggatggtc tcgatctcct 181320
gaccttgtga tctgcccacc tcggcctccc aaagtgctgg gattacaggc gtgagccacc 181380
acgcccggcc ctagattgcc tctgtcttat actctgtgca gaagagctgg ggcagggcct 181440
ggggttcagg cttttccagg gctaagcttc cagaatcttc tttggaggct gggagaaatg 181500
ggaaatactt cacagtatgg ggcagaggct gctagggttg aggggcttat ggtgagaagg 181560
gatccgcctg gaccaggaag gggctggccc caagaacatg agcttcttcc ttcagcttta 181620
gcttccgtct ttctttccta acactgtgtc cttccacctg aatcccaaag tctgtcttcc 181680
tttccaggat agcat                                                  181695
```

<210> SEQ ID NO 11
<211> LENGTH: 210917

<212> TYPE: DNA
<213> ORGANISM: Artificial Sequence
<220> FEATURE:
<223> OTHER INFORMATION: Synthetic construct

<400> SEQUENCE: 11
agaatatgtg tggcaactaa aggcagaggg taggtatagg aagaatggca tatggcacat 60
ttgaaaggca atggatagct ggctttctta gtataaggcg tggatgtagg tgctatggag 120
gacactatct tcttctcaag gagcttatgg tctaactggg gagaagaatc tacagaaatg 180
attcctgagt tggtaacaag gcaaaataga aaatgtgatt tgtagaacaa gagtaggctg 240
tgaggccagg aagctagtta ggcagatcat agatcacctt gaacgctagg cttatacatt 300
tggactttat ctcagattca gtggaggaat gtgggtgttt ctgagcagaa aagagacatg 360
attaaaaata gtacttgggc atccactgga ggagactaga tctctttggg gagatcccaa 420
cagggaatat gtaggcaaag tggattttcc tcctttgggt ctcaaagcaa gcccttctgt 480
gccgcctcag tctagaacat ctggttgggc ttttaactag tatggtttct ttgcagccaa 540
aaaggagtgt cctcctccgg ctcctgctga cagcttggct gtaggaaact cagggtaagt 600
atggagacat gagcgagtta ccctacagct gttagtcagc agccggctga cactccagga 660
ctgtcaactg gatgcctctg ttgcagggac gctgtagtca gctctagagt ctttccctgt 720
ttccccaccc cttactctgc ctatcactac cgggcagtgt cttgggtggt gaggtgagaa 780
cggggcatgt tcactgccct ccagctgatt ccagtcgggc tccaaatgtc ctagaggtgc 840
cttttatctc ctggcaagtc atacctttgg ggatttcttt ctttcattta ataacacttc 900
aagtttgctc agtgctggta atggtgtaac ttaaagtgga ggaagatgtt aatggctagg 960
agtcattttt catgttcatg atcctccatc ctgttctgcc aagcatgttc ccctccacat 1020
tgatttcagg ttggtgtgag ctgggcaggt gagactcgat gtgaaggagg tggggggtat 1080
tcaaggtcat ggccagcctg cctcttggaa ttgggcaggg ctcagttgag atccaatttg 1140
tagttcagtc aataagaccc ttttgtgcag gaagaagatg atggaggcag tttgtgcatc 1200
ccattcttct ctgcacccac cccctcccat tgatttctga gaaaggcaaa tgtataagat 1260
attgagaagg caatgaatca ggctttccct tttccccccc cgccagcggc gttgacattc 1320
cccaggagaa gaggccccta gaccggttac aagccccaga actggccaac gtggcaggtg 1380
ggttcagggt ggggaattct gcctgtgatt agtctatgca gcaacacttg ctgagcctac 1440
tccaaatcca ttgtgtgtag gcgttaagga catagagatc tgatctccag ccttgagata 1500
ctcacagtct agggggcaga cttgtaaacg aatgagcatg ttgagtatca ggtgctatgt 1560
tacagcctat gggctaggcg cagtggctcg cgcctgtaat cccagcactt gtgggaggct 1620
gaggcaggcg gatcacttga ggtcaggagt tcgagaccag cctggccaac atggtgaaac 1680
cctatctcta ctaaaaaaaa tacaaaaatt agttgggcgt ggtggtacac gcctgtagtc 1740
ccagctactt gggaggctga ggcaggagaa ttgctaaaat ccaggaggtg gaggttgcag 1800
ggagctgaga tcgtgccact gcactccagc ctgggggaca gagcaagact atctaaaaaa 1860
aaaaaaaaat gtcgggcgcg gtggcccacg cctgtaatcc cagcacttgg ggaggccgag 1920
gcaggtggat cacgaggtca ggagatcgag accatcctgg ctaacatggt gaaaccccat 1980
ctctactaaa aatacaaaaa aattagccgg gcgtgatggc gggtgcctgt agtcccagct 2040
acttgggagg ctgaggcagg agaatagcgt gaacccagga ggttgagctt gcagtgagct 2100
gagattgcgc cactgccctc cagcctaggc gacagggcaa gactctgtct ttaaaaaaaa 2160

-continued

```
caaacaacaa aaaaaaacaa ccatggatta cagtgagatg tgaagaggga cagtcaggga   2220
agggttatat agaaactaat cccctaagct gaggcttgag aaactctatc aggtggtaga   2280
tttagggaac agggcattct aggaagacag agcatcttga atgaactgaa gaaacaaaac   2340
caactgggta tgttttgggg aattgtgaga ggcttggttt ggctggagtg tagtagctga   2400
tcagggcagt gggcagaggt aaagcgagag ataaaactgg agtggtaaat agaaggtcag   2460
attattggga cctcgaatgc catattaagc tctttggact ttatcctgtg cattgaagaa   2520
actttgccag attggttttt gggtgctcca tctagcagga atgtagaaga caggtggact   2580
ctgaagctgc aagtggggag acgatagatg atgactgcat gagtgcagga aagatgcagc   2640
ctagaagtca ggcagtactc gggggaaggg gcggatctga gaatggagag cttagactct   2700
aggacctggc tactaggttt gggtagtgag aggatgaggg cttcaggaag accctagctg   2760
gctggatttc tcttgctggt ccccaagttg gggaacatgg ggaaggggca gttgaagcag   2820
tgggaaaagt tgggctgctt accttgcttg gtgtactttg tgagatgagg tgggggtctc   2880
tggaggctat atacacggta tttggaagcg tagaatcgga tctcatcctg ctatctccat   2940
cctccctccc caccacaggg ctcacccctc cagctacccc tccccaccag ttatggaagc   3000
ccctggctgc tgtctcactg ctggccaaag ccaaatctcc taagtccacc gcccaggagg   3060
gaaccctgaa gcctgaagga gttacggagg ccaaacatcc agctgcagtt cgcctccaag   3120
aaggggtcca tggccctagt cgagtccatg tgggctctgg ggaccatgac tattgtgtcc   3180
ggagcaggac ccccccaaaa aagatgcctg ccctagtcat tccagaggtg ggctcccgat   3240
ggaatgtcaa gcgccatcag gacatcacca tcaaacctgt cttgtccttg ggcccagctg   3300
cccctccgcc cccatgcata gctgcctccc gggagccgct tgatcacagg actagcagtg   3360
agcaggcaga tccctcagca ccctgccttg ccccatccag cttgctgtcc cctgaggcct   3420
caccctgccg gaatgacatg aacactagga ctccccctga accctcagcc aagcagcggt   3480
caatgcgctg ttaccgaaaa gcctgcaggt cagccagccc ctcaagccag ggctggcagg   3540
gccgccgagg ccgcaacagc cgttctgtca gctctgggtc caaccggact agcgaagcat   3600
cttcctcatc ctcatcatcg tcttcctcat cccgatctcg gtccaggtcc ctctcccccc   3660
cacacaagag gtggcgaagg tgagctttga tggccctgta ggtcctctcc atttaggaag   3720
ttcacgtact tctgtggttt actttgaaag cttttacccg ttgactttgg tactttcagg   3780
cgctaaggct tctatttctg actttggctt ttgtgttttc ccttttcctg gattgttgaa   3840
ggaggcaagc tgtgagacaa ttgcttctgt cccctgttgg agcttggggt gtcaggtctc   3900
ctgcttcttt gagacctgcc ttggggagac ttttagggtt tgattttgac catgttgatt   3960
tttttcacat actgtatcag ccttcatttt tggtattctg ggcgctatgt gaggtagtgg   4020
gttacttgtt aatagaaaat agttcttccc ttaatcatct gctgaggaag gtgtctgggg   4080
cagttccttt gggtgtcact atggcctcat ctatttcctg gcagtatctt tttttctcag   4140
taaccaagtt ttcccactta atgaagaatt cttgggtttt ggagatgata tatgtcttca   4200
gaactggccc atactacaag tctagcagtt aacctctctc atggtcacag tatttcagtg   4260
agacctggta ggggagcaat agtaacccaa aagacccagg cttggcccca gcaccacaga   4320
tagctgggtg tgagacctag ggctcacccc tctccctgag tctccattta ttgttcttcc   4380
tctttctgat ttgttaaata tttttcaatt tttaagtgca caattgaaaa tgtgatctct   4440
tccaaaacac ttcacaacat tccaggtaca cctaaagttc catgaagggc ctcagtttgt   4500
tcatctctga atgaaaattg ttcttctaga cctcttctac tctgctttgt ctttggtcct   4560
```

-continued

```
gagcttccta aaagaaaggc aggactgggg cctgggtgag ataagcagag tatacctgaa   4620
ccactcccag cattcctgca tgccctctta tccttcaggt ccagctgtag ttcctctgga   4680
cgttctcgaa gatgctcttc ctcttcttcg tcatcatctt cctcttcgtc ttcctcatcc   4740
tcatcatcca gttctcgaag ccgctcacga tccccatccc cccgccggag aagtgacagg   4800
aggcggcggt gagcatgtgt tcagggagcg ccatgcacct gggatgcagg tgcctaagag   4860
ttgagtcttg aattgtctta tgtttggggg gctgatgaca ccctcttttg tcaggtacag   4920
ctcttatcgt tcacatgacc attaccaaag gcaaagagtg ctacaaaagg agcgtgcaat   4980
agtgagtaga ggaacagatc atgggaggat ggggcttacc ccctgagcct tgagctcaga   5040
gagctgcctg cagctgtagc cctggctaat ggtgtgttga tttttttca tttccaaaca   5100
taggaagaaa gaagggtggt cttcattgga aagatacctg gccgcatgac tcgatcagag   5160
ctgaaacaga ggttctccgt ttttggagag attgaggagt gcaccatcca cttccgtgtc   5220
caagggtaag cttgggcccc aggctcagga tgttctttct atcccattca tctaccttgg   5280
tgtttctttg tcttgcctcc ttgctctggt gtgctgagca atatggggca ccttcatttc   5340
tgcagtcaga gggttggcca ctgggaatga gaagaaccac ctctgtacct tgggatgctg   5400
tgtctcctct atggcatggg cccatatagc cactccagcc cctgcctcac tctcctccta   5460
ctagggacaa ctacggcttc gtcacttatc gctatgctga ggaggcattt gcagccattg   5520
agagtggcca caagctgcgg caggcagatg agcagccctt tgatctctgc tttgggggcc   5580
gaaggcagtt ctgcaagagg agctattctg atcttggtga gtggagggag ggcctaaagc   5640
tttggaatgc ttcatcccct ccccagaagg gttcctaacc ctttgtgagt ggggctaggc   5700
agacttacct tagtttgaca tacaaagaac ccaagggggc tgggcatggt ggctcacgcc   5760
tgtaatccca gcactttggg aggctgaggc aggcaaatca cgaggtcagg agttcgagac   5820
cagcctggcc aacatgatga aaccccatct ctaccaaaaa tagaaaaaat tagctagagg   5880
tggtggcacg cacctgtaat cccagctact cgggaagctg aggcaggaga attgcttgaa   5940
cccaggaggc ggaggttgca gtgagctgac atcacaacac tgcactccag cctgggctac   6000
agaacgagac tgtctcaaaa aaaaaaaaaa aaaagaccca aggggtggga cgagaggaga   6060
aatggggact ggggactctc ctatctcttt gacttaaaat tagagcagtt ttcactccat   6120
ccgtttttgg gatgggagat agctagccat ttgcagaccc tgtggttggg aagtgtggtc   6180
agagaccttg aagtttgtct ttacctttat agactccaac cgggaagact ttgacccagc   6240
acctgtaaag agcaaatttg attctcttga ctttgacaca ttgttgaaac aggcccagaa   6300
gaacctcagg aggtaacctt gggcccttcc ctgctatcct ttttctcctt tggaggtgcc   6360
caacctcctc cacccccttc ccctactcta ggggagagag ctgctagtga gatgactgtt   6420
ttataaagaa atggaaaaaa gtgaaataaa aaatatgttg aatcagattt tttaaaaggg   6480
gtatttgttt ttttataaca ggtattgaaa caagttaact tgcattccta tgtaagatag   6540
gaggggctga ggggatcccc agtgtttgga acataagtca ctatgcagac taataaacat   6600
caactagaga gaactcccaa ctgctgttgt gcgtctttat atggtgctaa tgccaaatgt   6660
attcactttt cctatctgaa catggtccag ggacatgcct ctccctggtc aggtgcaaaa   6720
atcccactgg atttgaacct tggttcctca gatgtattgt ctaaaatgag tcatttagga   6780
cagtgcttct caactttaaa gggaatttga atcatctagc gatcttttta gaatgtagat   6840
tctgacaatg ggatgatgat actggtccag gaagggattt tgataacaag gacctagaga   6900
```

-continued

```
agctcacact tgttccaaag aaaggttttc taaactgcga caggtgtata cattcatcat   6960
gtcagttatg ttcatcattt tataatagct tgagcacact gcatggcaca gcaggtgctc   7020
aaatgtttta aataatgcat gcatgtgggt agaacaggaa gcgtggggaa gagggaactg   7080
tggagttttt tgtttctgtt tttgaatttt tttgttttgt tttggagatg gagtcttgtt   7140
ctgtctccca ggctggagtg cagtggcacg attttggctt actgcaacct ctgcctcccg   7200
ggttcaagtg attctcctgc ctcagcttcc tgagtagctg ggattacagg cacccgccac   7260
catgcctggc taattttttt tgtattttta gtagagacag ggtttcacca tgttggccag   7320
ggctgttctt gaactcctga cctcaggtga tccacccacc ttagcctccc aaagtgctga   7380
gattacaggc atgaaccacc gtgcccagct ttgtttttga tttttgagat aggatctcac   7440
tctgtggccc aggctggatt gcagtggcag gatcatagct cattgcagct ttgacctccc   7500
tggctcagtt gatcctcctg ccccagcctc ccaagtagct gggaccacag gtgcatgcca   7560
ctacacctgg ctaattttaa aaattttttg tagagatagg ggggtttcac tgtgttgtcc   7620
aggctggcct cttaactcct gggctcaagg gatcctccca cctaggcctt ccaaagtgtt   7680
gagataacag ttgtgagcca ctatgcctgg ccaattttat ataggagagg ggggtgtgtt   7740
cccatgagga tccttatctt tcctgagcgg cattagtggg aggtagccaa ggggtagtgg   7800
gtaggattga agggattgct aactgctaat atctggaatg tggcagaact tggaattaac   7860
ttggtaggtc tgagcattga tactggagtt actcatgaca aaggcattga tactggagtt   7920
actcatgaca aaggcagagt gtgaactctg atcccggagg aagaagggtt attttcaaca   7980
atctcttcag cttgaataga ttgttgctgt gtgtgattca ggtttggtgc atgacacctt   8040
tcctcttcat ggagctgacc taaggcggaa tataagggag atgggagggg cagcttggga   8100
aatcaacacc tcccaccctc acgacggata acccgaagga tcttctgcag cagaggcagg   8160
agtctggagg ctgggatggt atcagaaagg gcctccctgg gtattggagg cagtgaagat   8220
gaagggcgag aatccattgg ccgtgccagt acgccatggg ggcggttggg agatcttgta   8280
gaacaactgt tcgagcccgc ttgtccactc attactctgg aatccgagtc ccagcagggg   8340
cgcgggaaac cgctgctctg agaaaaggta cctcccccag aaagactgcg cgggaagtcc   8400
cgagttttcc cgccacgccg agggcgtgat ccctgacgtc agagctccgc ctccacaagc   8460
tggcggccgg tgggctccgc ccttaaccaa gatggcgata cgcgtgggac cggaaagagt   8520
ttatagattt cccgtctacc ctacctctga ggtgaaggtg ggactgccct gtggagccca   8580
ccctttccgt tatgcgcccg cgcggcgcaa tgacgtaaca caggcccgcc cactgcccct   8640
gttgggttcc tgagtcgtgc tgcgtcgaca acggtagtga cgcgtattgc ctggaggatg   8700
gcggacgccg gcattcgccg cgtggttccc agcgacctgt atcccctcgt gctcggcttc   8760
ctgcgcgata accaactctc agaggtggcc aataagttcg ccaaagcgac aggagctgtg   8820
agttccgggc ttggggcggg gaccgggctg agatgaccac aaggcttcag gccctgacgt   8880
gcttaggttt ccaggtgggg aagtctgggg gtccgccagt ccagtgtctg caaggccttt   8940
acgccgaccc ctcggcagtg accagagaaa gcctgcggcc tcggtcgctt accttcctcc   9000
atgtctgagt agatatcgct gagtcttgtt gctttttttct tgtgacctgt gcagcggcgg   9060
cagcgtggga gcctcgtggc cccaagccac atggctggca gagtgcagcg gggaggtaga   9120
gtcttgttcc actgaggacg ttggttcttc ggcatcttct ggggggcttt tcgttgggtg   9180
aggcaaaccg tgatttgacc ttagcctcag tcacatttac tgggattcaa aagcaagtga   9240
aatttcttta gaatgaagtc tggattttc gtttgtaaag aagaaaatga atgaaagtag   9300
```

```
aagcagagtt ttgttttgag ttacactgag aattgagagt catcaacagc cctaccaagt   9360
aggcatagta gtgggcttgg agctttggct aattgaatca aacaaaccta ggtttgggac   9420
caggctctgc cactttttag atacgtgacc cgggcagttt atttaacctt tctgagtctt   9480
tctacaggga tgtcatcatc cactttatag gatttttgtg agtttcagta agatgatgtg   9540
taagagtagc aatctcagtg ctggtacaga ggaatcttgt aaaagtgaaa gctgtaccat   9600
agttatggca atttaggatg ctccaaacac atgtaagagt aagagaacca ggaatgtgaa   9660
aggtttgtaa tctacatcaa cggacattcc tgcatgggaa gacactttga gagaggagag   9720
aggggggg tc ttcagcaggg atgatagcat gactaggaag gatggcttgc acttttagca   9780
gaatcaggct gcgaaagcaa agaatcagat cagcctcaaa acttccttaa gctgggacag   9840
gctgccatgt gatctaactg ctttcttaat gaaactgttt agagttgact gttaaggaga   9900
ctgcggagag tgctttcaca gtggactgga tggaattgga catttcagaa ttaggattct   9960
tttttttttt tttttttttt tgagacggag tctctgttgc ccaggctgga gtgcaatggt  10020
gcgatctcgg ctcattgtaa cctccgcctc ccaagttcaa gtgattatcc tgcctcagcc  10080
tccccagtag ctgggattac aggcgcgtac caccacgccc ggctaatttt tgtattttta  10140
gtagagatga ggtttcacca tgttggccag gctggtcttg aactcctgac ctcaagaaat  10200
ccacttgcct cagcctctca aagtgctggg attacaggcg cgagccaccg tgcccggcct  10260
caggattagg attctgaaat ggttttatgt gagaaaagct aatctttgtg aagagctaac  10320
taagggtcag atgctacgcc cttcacatgc atttaatttt tttttttttt tttttgagg  10380
cggagtctgg ctctgtcgcc caggctggag tgcagtggca cgatctcagc tcactgcaac  10440
ctctgcctct caggctaaag tgattctcct gcctcagctt cccaagtagc tgggactaca  10500
ggtgtgcccc accatgcctg gctaattttt tttttttttt tttgtatttt tagtagagac  10560
ggggtttcac catgttggcc aggctgctct tgaactcctg acctcaagaa tctactgcct  10620
cggcttccca aagtgctggg attacaggtg tgagccaccg cacccggcca acatgcatta  10680
tgtcttatcc tctcaataac ttaatgagat gtgtagtatt atctccattt tatagaaaag  10740
aaaataatct cagggagata aggtaatttg tccaaaggtg agttcccatc tgtactgact  10800
ctgatcattt actctttttt ggaccacaga gtctcactgt tgcccaggcg ggagtgcagt  10860
ggtgcaatct cagctcactg caacctttgc ctcccaggtt gaagcgattc ttgtgcctca  10920
gcctcatgcc tcagcctccc aaatagctgg gattacaggc gcccgcctcc acgcccagct  10980
tatgtttgta tctttagtag agatggggtt tcaccatacc agccaggctg gtctcaaatt  11040
cctgatcagg tgatccaccc acctcagcct cccaaagtgt tgggattaca ggcccgtgag  11100
ccactgcacc tggcctgatc ctgtactctt ctgtgtattg ttttgtgttt gtttgtttct  11160
tttagagggt ctcactctgt cgcccaggct ggagtaaagt gatgcaatca tacttcgctg  11220
tagcatcgaa ctcctgggct caggcaatcc tcctgcctca gtcactgggg tagctaggac  11280
tacagacatg taccaccaca cctggctaat tttttttttt ttttttttgt gacagtttcg  11340
ctcttgttgc ccaggctgga gtgcaatggt gcaatctcgg ctcaccacaa cctccacctc  11400
ctgggttcaa gcgattctcc tgccttagcc tcctgagtag ctgggattat tacaggcatg  11460
cgccaccacg cccagctaat tttgtatttt tagtagagac ggggtttctc catgttggtc  11520
aggctggtct cgaactcccg atctcagatg atccacccgc ctcagcctca caaagtgttg  11580
ggattacagg cgtttagcca ccacaggcca agcaaccgca gtgccattgc aatccaacct  11640
```

-continued gggcgaccaa gagcgaaatt ccatttcaaa aaaaaaaaaa gagagagaga gagagatgga 11700
ggtctcactg tcttgcccag gctggtcttg aactcctgtc cttaagtgat cctcctgcct 11760
tggcctgcca aagtgttagc gtacctgcgc ccggcctgaa tgcatttttt tttttttttg 11820
agacttactc tgtcgcccag gctggagtac aatggtgtga tactggctca ctgcaacctc 11880
agcctcctgg gttaaagcga ttctcctgcc tcagcctcct gagtagctgg gattacaggt 11940
gtgcaccacc atgcccagtt aattttttgt gtttctggta gaaatggggt ttcaccatgt 12000
tggccaggct ggtctcaaac tcctgacatc atgatctgcc tacctcgacc tcccatagtg 12060
ctgggattac agcagacctg agccaccgtg cctggccctt aaatgcagtt ctttacattc 12120
aatacagtac ttactagtct tgtttctttc tttttttttt tgagacagag tcttggtctg 12180
tcgcacaggc tggagtgcag tggcgcgatc tcagcttact gcaccctccg cctctggggt 12240
tcaaacgatt cttctgcctc agcctcccga gtacctggga ttacaggcgc ctgccaccac 12300
acccggctaa gagacagggt ttctccatgt tggccaggct ggtcttgaac tcctggcctc 12360
aggcgatctg cccgccttgg cctcccagag tgttgggatt ataggcgtga gccactgcat 12420
cccgcctgga ggcttatttc taatgatttg gtattataat ccacattgca ggaaaaacct 12480
tcttgtatta gtgtttgtac cctcaagtaa tggataagat tacattctta gatagtacat 12540
tgctagagta aagagagagc cttttttttg gcagaggggt agagatgggg gtcttgctat 12600
gttgcttagg ctggtcttga actcctggca tccagtgatc ctcctgtctc agcttcccaa 12660
agtgctgaga taacatgaga taacaggcat aagccactgt gcccagtcaa aagtgatttt 12720
tttttttttt tgaaatggag tcttgctctt gttgctcagg ctggagtgca gtggcgcgat 12780
ctcctaggtt caagtgattc tcctgcttca gccttctagg ttcaagcaat tctcctgctt 12840
cagcctccca agtagctggg actacagaca tctgccatca tgctgggcta atttttgttt 12900
tagtagagat ggggtttcac catgttggcc aggctggtct tgaactcctg acctcttgat 12960
ctgcctgcct cggcctccca aagtgctggg attacaagca tgagccaccg tgactggctg 13020 atttttttgtt ttgttttgtt ttaggacttt gatcaatata gattggcagg caggggggtta 13080 gatggttaga tggtgccgca aacataggag tagcccgttt tttacatcag aaattgggaa 13140
atccacaaat agaatatttt tctcctgatt tatgcacgta gcaaaagttt tatgaagatg 13200
taacatttat accaaattta gtaattatgt atgtaacagg ccacatttaa tgaaagcata 13260
accaggataa aataatttcc ttacccagct ctttttcttc tacagacaca gcaggatgcc 13320
aatgcctctt ccctcttaga catctatagc ttctggctca agtaagcctt tcctgttcca 13380
ttttggctat tttctccccc aagataggct gggctgtgtt tcttggtttg ggaagattcc 13440
agtcccctag aaattggtcc aatctacctc agcaggtctg ccaaggtccc agagcgaaag 13500
ttacaggcaa atggaccagt ggctaagaaa gctaagaaga aggcctcatc cagtgacagt 13560
gaggacagca gcgaggagga ggaggaagtt caagggcctc cagcaaagaa ggctggtaag 13620
gcagagtagc aggtgggctt ggtggtgcca ggaaaagaat ttacagcctg cttgtttcac 13680
atggctgatt cttactggga cctgtgtgtt tgttcagctg tacctgccaa gcgagtcggt 13740
ctgcctcctg ggaaggctgc agccaaagca tcagagagta gcagcagtga agagtccagt 13800
gatgatgatg atgaggagga ccaaaagaaa cagcctgtcc aggtttgcag ctttgggaag 13860
aaaaaggggt ttaaggatta gaaaggaaga aacctaaaat cttggcctct agcttgtaac 13920
caaggggtga tggcggcaat acaataggtg attatgagga agaaaatctg ggattttca 13980 gggagctgat aaaagtatga ggtctggaag ggatgtgtga ggttgaggtc aggctccgaa 14040

```
tctagaggaa attaaaccca ttctgcttga ggagtttggg ttcttctggg acactattca  14100
gggctccaag aataagagag agtgttttcc tgggagcttt ggcaggataa ggcaggaaca  14160
gggccagtgt atcaagtggc tgaactttgt tgtttttttgc cctttccgta tcctgtcctt  14220
agctttcttt tgctcttact gctccattag gcccctaaaa ataaaaggaa cctaggatgc  14280
cctttgggta cccggaagct tttgctgatt tctctccttg tgtcttttct aacagaaggg  14340
agttaagccc caagccaagg cagccaaagc tcctcctaag aaggccaaga gctctgattc  14400
tgattctgac tcaagctccg aggatgagcc accaaagaac cagaagccaa agataacacc  14460
tgtgacagtt aaagctcaga ctaaagcccc tcccaaacca ggtactgttt ctgttcccaa  14520
gaggctgggc tggggaccag attgctctgg ggactggagt taaaattgcc gatttggcac  14580
aggggtgaaa tggtactgtt tgttgaactg gaggtgttga ttactggtct tttaatttta  14640
aaggttttac taataaataa caagatttca taggagctag taaatagaga aagttattgc  14700
agcaagaaaa aatgtgtatt ttttttaatg gtatccattt ggtattttgt gacatttcat  14760
agacatttta tgttttcaca catcccattc cactgtaatc acttaaatat ctatttgttg  14820
tgcttttcac tgccattttt actcttgtat gttcattcta tgagacaaat gagaattttt  14880
ctttttttct gtaacttgtg atgagggtta ggttatttct ctgaatggag gttgaagtga  14940
aagattttag agggcgtatt gagattattt atgtcatctt ttctaagaag acagttttat  15000
tcctgccatg ggataggaaa ggtatccttt gatgtggtaa accatggctg gcattctcct  15060
cgatggctgc tctaaagttg aaagaattgg tggactcctg gccaggcaca gtggctcaca  15120
cctataatcc cagcactttg ggaggctgag gcgggcggat tgcttgaggt caggagttca  15180
agaccagcct ggccaacatg gcgaaaccct gtgtctacta aaaatataaa aattagctgg  15240
gcatggtggt gggcacctgt aatcccagct actccagagg ctgaggcggg agagttgcct  15300
gaaccactgc acactagcct gtgcaacaga gccagagcca gactccgtct ccaaaaaaaa  15360
aaaaaaaaaa aaaaaaaaaa atggtggact cctaagttct ctgctcatag gaaggaggtt  15420
tttcatggtc ctgacttgcc ctaatactcc ttactctttc tttttcttgg gtattccagc  15480
tcgagcagca cctaaaatag ccaatggtaa agcagccagt agcagcagta gcagcagcag  15540
cagcagtagc agtgatgact cagaggagga gaaggcagca gccacccccca agaaggtctg  15600
gaccataact tctgtcaggg cagaggtgac cagggtgtga tgtgtgtgtg tcttccttcc  15660
ctggcaggat tggttgggtc agcattttcc tgtggtaatc aattttcttt ctaatgcaga  15720
ctgtacctaa aaagcaagtt gtggccaagg ccccagtgaa agcagctacc accccctaccc  15780
ggaagagttc tagcagtgag gattcctcca gtgacgagga agaggagcaa aaaaaaccca  15840
tgaaaaaataa accaggtgac tggacatggg gagcgaagct gtgtgactgt ggtcagggcc  15900
cagctgcagt aaccacatgg acctctccat agaggtgcat gagcgtcctc atgacatgac  15960
agctagcttc tccgagcact agtgatccag gaaagcaagg agaaatctcc agtgccttgt  16020
gtaacctaga ctcagaggtg acaccatgtt ctgttagaac tgagtcattg attctggccc  16080
atactcaagt gaaggggaat taagcttcat ttctacaaga aagtagtatc aaaaaaagtt  16140
gtagacatat cctaaaacca tcacactatc ctttttaaac aggtccctac agttcagtcc  16200
ccccgccttc tgctccccca ccaaagaagt ctctgggaac ccagcctccc aagaaggctg  16260
tggagaagca gcagcctgtg gaaagcagtg aagacagcag tgatgagtct ggtgagtcag  16320
agggatgcag cctcccctca gcgtgggtct ggaggagggg atgaggaata agggagagag  16380
```

```
aaagccttcc atccttcggt tgctttttgc ttaaagcaag acagagctaa ggctctgtgc  16440
gtgtctttgc attcttttta ttgctgtcct ggttgggttg ggactctgga cccagcataa  16500
tgctacaggt tctcctcaga ttcaagttct gaagaagaga agaaaccccc aactaaggca  16560
gtagtctcta aagcaaccac taaaccacct ccagcaaaga aagcagcaga gagctcttca  16620
gacagctcag gtaaggcata tggaggccct cagttcagtg agatgctctc aggcagctgc  16680
taagggctcc cctgaatcca atttggggag ctgttgattc catcccttct gtgtctagac  16740
tctgacagct ctgaggatga tgaagctcct tctaagccag ctggtaccac caagaattct  16800
tcaaataagc cagctgtcac caccaagtca cctgcagtga agccagctgc agcccccaag  16860
caacctgtgg gcggtggcca gaagcttctg acgagaaagg ctgacagcag ctccagtgag  16920
gaagagagca gctccagtga ggaggagaag acaaagaaga tggtggccac cactaagccc  16980
aaggcgactg ccaaagcagc tctatctctg cctgccaagc aggctcctca gggtagtagg  17040
gacagcagct ctgattcaga cagctccagc agtgaggagg aggaagagaa gacatctaag  17100
tctgcagtta agaagaagcc acagaaggta gcaggaggtg cagcccctte caagccagcc  17160
tctgcaaaga aaggaaaggc tgagagcagc aacagttctt cttctgatga ctccagtgag  17220
gaagaggaag agaagctcaa gggcaagggc tctccaagac cacaagcccc caaggccaat  17280
ggcacctctg cactgactgc ccagaatgga aaagcagcta agaacagtga ggaggaggaa  17340
gaagaaaaga aaaaggcggc agtggtagtt tccaaatcag gtctgtaccc aatgaacatg  17400
ccctctgggt tttgtccccc caaatcagga tgggatatac tctttgagag tagggtagtg  17460
agaggaggcc caccactggg cttccagttg tggaaactgg gaggaagaac aggaaactgg  17520
ttaccttttt ttttttttat tagagtctca ctgtgtcacc cagaccaggg tgcaatggca  17580
tgatcacggc ttgtgcagcc ttaacctcat ggactcaggt gatctttcca ccccagcctc  17640
ctgagtagcc gggactacaa gcatgcacca ccatgtctgg ctcatttttt taacttttta  17700
tagagacaga atctcactat attgcccagg ctgatctgaa tttcctgggc tcaagcgatc  17760
ctcctacctt ggactcccaa aatgctgggg ttacagttgt gagccactgt actcggcctg  17820
agtctggctt tttgttttgt aggttcatta aagaagcgga agcagaatga ggctgccaag  17880
gaggcagaga ctcctcaggc caagaagata aagcttcaga cccctaacac atttccaaaa  17940
aggaagaaag taagttgtct cactttcttc tcaggagcca gctctttaaa agtagaaaaa  18000
tctaggatca tcttgacagc tctgcctggc gtgacctggt acatgtgccc atgtgtatca  18060
ctcaggagaa ctgttacatg accactctgt ctttaatttc ctacttcatt cttctgtagg  18120
gagaaaaaag ggcatcatcc ccattccgaa gggtcaggga ggaggaaatt gaggtggatt  18180
cacgagttgc ggacaactcc tttgatgcca aggtgagaga gagatctgtg ccattcttgg  18240
gagggaggat gggtagtgtc agagaggaca attcttggtt caggttggtg ggaatcttct  18300
ctgggttcag gtttccttga gcagggagta gaaagaataa agtgacaggg ctccagcatg  18360
gtcctcctct gtgttaatct ccctctctac ttaccagcga ggtgcagccg gagactgggg  18420
agagcgagcc aatcaggttt tgaagttcac caaaggcaag tcctttcggc atgagaaaac  18480
caagaagaag cggggcagct accggggagg ctcaatctct gtccaggtca attctattaa  18540
gtttgacagc gagtgacctg aggccatctt cggtgaagca agggtgatga tcggagacta  18600
cttactttct ccagtggacc tgggaaccct caggtctcta ggtgagggtc ttgatgagga  18660
cagaagttta gagtaggtcc taagacttta cagtgtaaca tcctctctgg tccttttctg  18720
tgttcctagt tttgtacaga cttgtttttg agtgttgagt agcagggaca aaataaggga  18780
```

-continued

```
atgttatttt ttaagaaaat tcattttcat tgttgtctcc ttccttttct gtgaaagtcc  18840
tcatactgag aaatttgtat attttatatt aaatcactta ctattgattt ttgttgtgat  18900
tttcaaaggt ggattcccac agataaaatc ttggctattg cccaaaacat agtaaagggt  18960
cacgtgtgac tttttataat aggaagaaaa ttctgccttt gtgagtgcac atgtccacat  19020
ttcatccctc cttccctcaa aaccctagag aggggcatta aagaattgtt gatgtatatg  19080
caatgtctgt taagcatgca ctatgtattt catcctcatt tattgggtct gggactgaag  19140
tttttagcca gcatggacct aacctacttt ttgggataaa attctctgtt ttgttacagg  19200
caaaattctg gtatggcgtg aatgccatgg gtcattctga atatattttt ttctgtaatt  19260
ttatcattac acgatgtttg caatacgtgc tttgtttttt aatttgaaag caaacttttc  19320
tactgttgaa agacattttt tgacaacttg acccttccta gtattgagtt ctaagttgag  19380
gactgcatct tctcgttttt tacagtatag agaacaaaat gacatgagtt tgaaaaatac  19440
atatcacttg gtattgctgt cttggttgca gtggtgatac agaattggtt tcattaattc  19500
ctacatggtt gagaatcact gatcaagaaa gtggggggaa aaaaaacaaa cgttaaaacc  19560
tcaatcctca gtaggaaggt agattacatt aggtgaaatt ataggtaatc tatgtatgtg  19620
ctaatggggt tggaaagaac cttacagagc atattacctg ataaactgga gtgggtttgg  19680
gagaacaaac taataggatt attgtgtctc ctagttggta cctgggagca attgacatgc  19740
ccccttcaga accttaactg ttagtagcag tggctgtaac aacacaaacc agtgaccaga  19800
gataacagct tttaggccaa gctggcctga cggtatggct gcaggaagtg actgagcagt  19860
agcggtactc agccagacca agacggagag ggaagagtcc acagctttct ggaagctaag  19920
gcattctggt ggtagaaaag tgtgccccaa gccttcatgg acgagttata ggtcttaaga  19980
ttagtctcct cttgtttgga ttccatactt gctaaataac ctgataataa cctggttttc  20040
catgtaactg cctctaggaa gaaaatgtac tgttcatgct gacacagata tttcagtctg  20100
catggtaaaa gttctaaatc ttactacaaa ataataaact ggctggttta taatgtgtct  20160
tgggagtttt attattgtga gtctaaaccc ctcccacccc ctactcaaac cagaacaact  20220
ttggtgccag ttataggact ggggtccaga cctgtgattt cactgcagag gctttttggc  20280
agcagcttgt ctcacggtgc cttttccagg ctatattcta gcctacgcat agtccaaatt  20340
gggggttggc aaaatggcct atgggtcaaa tccagcccat ggtttgtttt tgtattacct  20400
aggagctaag aatggttttt acatttgtaa aggtctttta aaaagagaat gtgtgacaga  20460
gatcttatca atggcccaca aagcctaaga tatttaggat gcggcccttt acagaagaag  20520
tttgccaatc cctggtctaa atcagcgatt cctaagacat cagctgaaaa ttagaatcat  20580
ctgaggaact tagaagcacg gatactcgca aatcaaaacc acaatgagat accatctcac  20640
accagttaga atggcgatca ttaaaaagtc aggaaagaac aggtgctgga gaggatgtgg  20700
agaaatagga acacttttat actgttggtt ggactgtaaa ctagttcaac cattgtggta  20760
gacagtgtgg cgattcctca gggatctaga actagaaata ccatttgacc cagcaatccc  20820
attgctgagt atatacccaa aggattataa atcatgctgc tataaagaca catgcacacg  20880
tatgtttatt gtggcactat tcacaatagc aaagacttgg aaccaaccca aatgtccatc  20940
aatgatagac tggattaaga aaatgtggca catacacccc atggaatact acagccataa  21000
aaaaggatga gttcgtgtcc tttgtaggga catggatgaa gctggaaacc atcattctca  21060
gcaaactatc acaaagacag aaaaccaaac accgcatgtt ctcactcata ggtgggaatt  21120
```

-continued

```
gaacaatgag aacacttgca cacagggtgg ggaacatcac acaccagggc ctaatgtggg  21180
gtggggggag ggaagggata gcattaggag atagatatac ctaatgtaaa tgacagttaa  21240
tgggtgcagc aaaccaacat ggcacatgta tacatatgta acaaacctgc acattgtgca  21300
catgtaccct agaacttacc ctagtataat ataaaaaata aaaagaaaca cggatactca  21360
ggggcccatc ctgagatcta ttgagtcaga ccctggtgct gtctggtgag gcccgggcac  21420
tagggtattt ttaaagctcc cagatgattc taatgaacag gtagagttga aaaccgctta  21480
tctaaagagt atttgaaaag aagtgaattg gtatttccca ccttcatgct tccattttca  21540
aatatacttg ttaaaaataa tagtataaaa tgaaaatttc aggccaggta cagtggctta  21600
cgcatgtaat accagcactt tgggaggcca aggcagacgg atcacctgag gtcagtagtt  21660
cgagaccagc ctggtcaaca tggtgaaacc ccgtctctac taaaaaatac aaaaattagc  21720
tgggcgtggt ggcacgtgcc tgtaatccca gctactcggg aggctgaggc aggagaattg  21780
cttgaaccct ggaggtggag gttgcagtga gctgagatcg tgccactgca ctccagcctg  21840
gcgacacagt gagacgctgt ctcaaaaatt taaaaaaaaa aaaaaaaaat ttcatctcag  21900
ccctgtttcc tggaacctgc ttctgtgtct ccttccagac agtttctagg tatgtgctac  21960
tatatgcatc ctcccctcct ttttttcttg gcacaaatgg ggcagttcgt caagtgcaat  22020
gttttgcaac tttcagagct caattcatag cagaacacag cagctcattt ttaatggcta  22080
tatggtactc tgttttaagt tatttaaatt agtactttag gggcagaagt ttaagtattt  22140
tgctattaca aatagtgtta cactgggtag tcttatacat gagactgagt atctgtgtgt  22200
ttttatgtag gaaatattcc taaaaatgat ggctggttca aaggatattt gcatttatta  22260
ataacatttt gatcattatt gccctccaaa atcgttctac taatcgtata gttccagcaa  22320
cattttatca aagtgcctct ttgccctctt gccaacacta tttaccaaat tgatctttgc  22380
tacttggata aatgaaaatg ctctctcatt tttgtttgtt tttgttttat agtggtaaaa  22440
cacgacatta aatttaccac taaccatttt taattgtatg gtttagtagt gttaagtata  22500
ttccactgtg taacagatac ctaggacgtt ttcatcttgt aaaattgaaa ctatattcat  22560
taaacactaa tatcccctcc tccccagccc ttggcaacca tctttctact ttgtttttat  22620
gattttggct actttagata taacctcatg agtggaacag taatgatatt atctttttgt  22680
agctggctta ttttacttag ccaagccaat gtcctcaagg ttcatccatg ttatagcagg  22740
tgacaggatt cccttccttt ttaagactgc atgatattcc attgtacgtc tataccactt  22800
tcgcccagac tggagtgcag tggcgtgatc tcagcttact gcaacatccg cctcccaggt  22860
tcaagcaatt ctctgcctca gcctcctgag tagctgggat tataggcacc tgccaccatg  22920
cctggctaat ttttgtattt ttagtagaga cgggatttca ccatcttggc caggctggtc  22980
ttgaactcct gacctcgtga tctgcccacc tcggcctccc aaagtgctgg gattacaggt  23040
gtgagctacc acgcctggcc ttggcatttt tattttattt attttgagac agggtcttgc  23100
tctgtcaccc aggctggagt acagtggtgc aaacttggct cactacaacc tccacctccc  23160
aggctcaagc aatcctctca tcttagcctt ccgaatagct gggaccacag gtatgtgcca  23220
ccacacttgg ctaatttttg tgtttttgt agacagggtt ttgtcatgtt gcccaggctg  23280
gtctcgaact gagctcaagc tatctgcctg ccttggcctc ccacaagtgt tgggattaca  23340
gacgggagcc accgcgccca gcccgttttc atttttaagt tgaatatgac atacatccat  23400
taatttattc tccttaaaac ataaataatt tgtgaggttg ctgtttattg tttaaatcat  23460
gacttttctt ctgtattgta taacccttct cagtcttgtt tgcttttttc cgacagaact  23520
```

```
catttcctct taggccttgc aaagctgagt ctgctacgtt ttgcagctag tgtgttacac  23580
aaatgaggcg gtttagcaaa ttgcctaaca gtattcatta ggaaggttaa cctgagtctg  23640
cgtttgtttg tttgtttgtt tgtttttgag acagggtctt gctctgttgc acaggctgga  23700
gtgcagtggt gcgattacga tcaccgctca ctgcagcctc agcctctggg gctcaagcag  23760
atactctgat ctcagccccc tgagtagctg agatcctccc acctcagcct cctgagtagc  23820
tgggactaca gtagtcacta ggcttggcta gttgtttttt tgtttgtttt gtttttgttt  23880
ttgtttttaa ttttgttttg tagagacagg gtctccctgt gttgcccagg ctactctcaa  23940
acaatcctcc cacctcagcc tcccaaagtg ctgggattac aggcgtgagc cactgtgccc  24000
agcccagagt gtaccttctg atgtaaaatg agaatactgg ctgggcctgt aatcccagca  24060
ctttgggagt ccaaggcggg tggatcacga ggtcaggaga tcgagactat cctggctact  24120
tgcagtgagc tgagatcgca ccactgcact ccaggctggg tgacagagca aggctctgtc  24180
tcaaaaaaag agagaatact atctcaactc atttgtagat tcttgactct ctcagaggct  24240
tgttgtaagg actgagaatt taaagcactt agtacagtcc ctggcatatt ataagcactc  24300
cataactgcc tcttgctcaa caaaaaaagc tttggaaatg atgttctttg gtttccttgt  24360
gatgtgcaac atgccatttt ggcaaaggca tcaagcatat gttaatgatt atttccctgc  24420
aatggttttt tgttgtttca cgtttatcat ctttattcct gatacaaaaa tggatatgtg  24480
gaattggtcc tattagaaac ttcttagttt tgtgaagaat ctggaattcc taccccttgc  24540
tgatgggctc tggcactgaa atccgcaaat tcagtcaacc agacacatgg ctcatgcccc  24600
tctgcatcat gcttcatgga cacaggcagg agacttccta atgccctgtt gggggcttgc  24660
ccttcgcccg gtgtagcctt actgcaaccc tgttaggtgg gtatcgagta gatcattcca  24720
tttggggcca ggtaagtctt tgcttttgag gactgtcctg tgtgttgtag gatgtgtggc  24780
agcgtccctg gcctctaaca ctgcatgcca atagtttccc ctagttgtga caaccaaaaa  24840
cggctccagg cattgccaaa tattttctgg gaaggaaaat tgcccctagt tgaaaaccac  24900
tacggaaaca gccctgagta tcaaatgatt tacttagggt tgatgaaact gcaacttagt  24960
ggcacattga gacaagaaca caggtctctg tatgtccaaa catggagcta cctgtattca  25020
atagtctttg tgaacctgct atgtactcgt catagaactc ccagagagct cagtgtctaa  25080
tggggaaagt caggcatggg aatggtttct gtgcactgag ctgagttctg tcccaaactg  25140
aaggtcagag tagcacccct aagggtacaa gcaagaaaat acttggcttg gcccggtgtg  25200
gtggctcaca cctgtaatcc cagcactttg ggaggccgag gcaggcagat cacgaggtca  25260
ggagttcgag accagcctgg tcaacatagt gaaacctcgt ctctactaaa aatacaaaaa  25320
attagccagg tgtggtggca ggcgcctgta atcccagcta ctcaggaaac tgagacagga  25380
gaatcgcttg aaaccggaag gcggaggttg cagtgagcca agatcgtgcc actgcactcc  25440
agcctgggca acaaagtgaa actctgtctc aaaaaaaaaa aaaaaaaaaa agaagaagaa  25500
gaagaagaaa agacttggct gatggtggcc taggattctg aagacagctg cagtttgcca  25560
ggagcgagaa aagtgcatac cgtgtaagga agagtgcctt ttccagtggg agaagagggc  25620
tgttagaatg ggtcaagcag aggtgtgcgg gaggtggggg caagatactg cgaaatttca  25680
ctgagagttc aatgtcaatg gccttttgta cctaagttag gaattagtac tttattttgt  25740
ccacctgagt atgttaggag atttgatagt ctaatacaat actcctggca ctaatccggt  25800
tgcggtgaaa gcactatttc tgccggacca cgaagttctc aaatccctcc tgcagagcct  25860
```

-continued

```
gtctgcagtt accgatgggg ccagtaggtg gcgatgttgc ccccctgttt agggagctgg  25920
gctggactta aatagaagct taactcctta cttactccag tgctattcaa caaacttgaa  25980
gagccgggcg cagtggctca cgcctgtaat cccagcactt tgggaggcgg aggcgggcgg  26040
atcacgaggt cagccgatcg agaccaacct ggttaacaca gtgaaacccc gtctctacta  26100
aaaatacaaa aaattagcgg ggcgccgtgg cgggcgccta tatagtccca gctactcggg  26160
aggctgaggc aggagaatgg cgtgagcccg ggaggcggag cttgcagtga gccgagatag  26220
cgccactgca ctccagcctg ggcgacagag cgagactccg tctcaaaaaa aaaaaaaaac  26280
accttgaaga gcccactgtg agcctttgga tacacagatg aataagacac aggccctcat  26340
ctgaggctct ttagttttgg aaattagaga aggggttttt tgtttgtttg tttgtttgtt  26400
tgttttgaga cagagtctcg ctctgtcgcc caggctggag tgctgtggtg ccatctcggc  26460
tcactgcaag ctctgcctcc tgggttcacg ccattctcct gcctcagcct cccgagtagc  26520
tgggactaca ggcgcccgct acggcgccca gctaattttt ttgtattttt tagtagagac  26580
ggggtttcac cgtgctctcc atctcctgac ctcatgatct gcccgcctcg gtctcccaaa  26640
gtgctgggat tacaggcgtg aggcaccgcg cccggccgag aagggaggtt ttctggtctc  26700
tggtctgtac tggttatcca tgagaggtta cctgatacct gaaagccagt ggcaggcaac  26760
atggcttgta gaagattaat gttccccgtg gaaccccaac cctacctcca ggtcctggca  26820
gggccttcgg gctcctgcaa gggtgaccgg ctgcagatcc cactgctgat ggaaattgcg  26880
ggcctgtgtt cttcctaggt ctgggagctc agaggctttg atgccttctc ctctctcctc  26940
tctcttccct cctctcccag cataatctca aggagctcag gattgaggag aacaaatgcc  27000
aggcttccgc cttggaagtg gatacttcca agtggcagag gaagtacaga gtatttcaag  27060
aaattagcct gccaaacaga aatttatcca ttcagcaaaa attcatccat tcagaaaata  27120
tgagtggctg ccatgcgcca ggtacatgac atgtgatcct gtgtggtagc tgttgcagat  27180
acaatcctga atgaacaaaa aacacagttc cagcaatcaa agtttactca aaaaaagttt  27240
tgtttactca aaaaagacaa aaagtttgtc cgactagtga gggacaaaaa tattaatcct  27300
cacaaataaa tgtgtaaata caaacttcag tgtgtgaagg caggttgtac agagctatga  27360
gagcatgtaa taggggcagc tgacccatgt ggtggtggga cttcctcatg gatagcatga  27420
ccatgtaact tttttttttt tgagacggag tctggctctg tcgcccagtc tggagtgcag  27480
tggcctgatc tccgctcact gcaagctccg cctcccgggt tcacttcatt ctcctgcctc  27540
agcctcccga gtagctggga gtacaggcgc ccgccacgct aatttttgt atttttcata  27600
gagacgggat ttcaccgttt tagccaggat ggtctcgatc tcttgacctc gtgatctgcc  27660
cgcctcggcc tcccaaagtg ctgggattac aggcgtgagc caccgtgccc agcatgacca  27720
tgtaacttat tgtctgaact gggatgcttt tgagaggaag agggagggaa attagtctga  27780
gatgaatagg tgtaaagtga ggctatgcta gtcatgccag gacatatggt cactctagta  27840
atagaaatct aagaatagga agtgatgttt cagccaaaac ctgaagttaa gggttaatta  27900
ggggaagcta gagggttggg ggtgctagat atgtgagttt tccagttaga gggaatagca  27960
cgtgcaaaga cctttttgtg ccttgggagg atgatggaga ccccacactg aaaggtctat  28020
gcagctggaa tgcagagtga ggagagagag cagtgtaaca tgaagctaga gaggtaggca  28080
ggggtagagt aggcagaggc tttgtaaggc atgtttgaaa tgtcggtctt taataaggca  28140
gtaggggcca ggcttgatgg ctcatgcctg taatcccagc actttgggag gctgaggcgg  28200
gcagattccc tgaggccagg agtttgagac cagtctggcc aacatggcaa aaccccgtgt  28260
```

ctactaaaag tacaaaaaat tagccgggcg tggtggtggg cacctgtagt cccagctact 28320
cggaaagctg aggtaggaga attgcttgaa cccgggaggc ggaagctgca gtgagctgag 28380
attacaccat tgcactccag cctgggcaac aagagtgaaa ctctgtctca aaaaaaaaaa 28440
aaaaaaaaaa aaaaaaaaag gcaataggaa gccattcaag gtgtgagtgt cttagcttgg 28500
gctgcgataa ctaaatacta gactgggtgg cttaaacaac agaaattgat ctcttacatt 28560
ctagactctg ggaagtgaag catcaagggg ccgaccaatt cacttcctgg tgagggctgt 28620
cttcctggct tgcagatggc catcttgctg tggcctcaca tgatgggggc agaatggggc 28680
gaacaaattc tttggtgtct ctcttttttc ttttgtgttt gtttgtttta gagacagggt 28740
cttgctatgt tgtccaggcc atagtgcagt ggctattcac aggtgtgatc gcagcacact 28800
acagcctcga actcctgggc taaagtgatc ctcccacttc agcctcctga gtagctggga 28860
ctacagacac gtgccactgc acctgggtct tcggtctctc ttttttttta ttttttttgag 28920
acagagtctt gctctgtcgc ccaagctgga gtgcagtggc acgatctcag ctcactgcaa 28980
cctccacctc ctgggtttaa gtgattctcc tgcctcagcc tcccaagtag ctgggattac 29040
aggcacgtgc caccatgccc agctaatttt tgtactttta gtagagacgg ggtttcccca 29100
tgttggcaag gctggtctaa aactcctgac ctcaggtcgg gcacagtggc tcacgcttgt 29160
aatcccagta cttccggagg ctgaggcagg tggatcacga ggtcaggaga ttgagaccat 29220
tctggctaac acgtgaaacc ccgtctttag ggaatataca aaaacttagc caggcgtggg 29280
ggcgggtgcc tgtagtccca gctactcagg aggctgaggc aggagaatgg tgtgaatctg 29340
ggaggtggag cttgcagtga gccgagatcg caccactgca ctccagcctg ggcgacagag 29400
caagactccg tctcaaaaaa acaaaacaaa acaaaacaaa acaaaacaaa aaaaacactc 29460
cggaccttgt gatccgcccg ccttggcctc ctgaagtgtt gggattacag acgtgagcca 29520
ctgtgcccag gcaacgggct cttcttatga aggcactgat ctcacctggg tctgcaccat 29580
catgacctca tctaaaccta attaggtggt gattaaaggc cccatcttcc aacataccac 29640
actggggatt agggagtcaa tatatgaact tgaagacttc acaaatattc agtccataag 29700
agtgaatgtg tatgcgtgtg tggttttttt tttttaattt tttttaattt tttttttttt 29760
ttgaggcaga gtctcgctct gtcgcccagg ctggagtgca gtggcactat ctcggctcac 29820
tacaagctcc gcctcctggg tttgcgccac tctcctgcct tagcctcccg agtagctgag 29880
actacaggcg cgtgccacca cgcccggcta attttttgta tttttagtag agatggggtt 29940
tcaccgtgtt agccaggatg gtctcgctct cctgaccttg tgatccgccc accttggcct 30000
cccaaactgc tgggattaca ggcgtgagcc accctgtccg gcctttttat tttttttgaga 30060
cggagtctcg ctgtgtcacc caggctggag tgcagtggcg ccatctcggc tcacggcaag 30120
ctccacctcc tcgggttcac gccattctcc tgcctcagcc tcccgagtag ctgggactac 30180
aggtgcctgc caccacgccc agctaatgtt tgtattttta gtagagacgg gatttcactg 30240
tgttagccag gaaggtctcg atcacctgac ctcgtgatct gcccgcctca gcctcccaaa 30300
gtgctgggat tacaggcgtg agccactgcg cctggccttt tttttttttt tttcccctag 30360
aaacaaggtc tcactatgtt gcccaggctg gtctgaaact cctggcctca agtgattctc 30420
ctgtcttggc gtcccaaagt gctgtggtta caggcatgag ctactgtccc cagttgtgta 30480
tgtgtgtttt tttcttttct tttcttttct tttttttttt tttttgagat ggaatcttgc 30540
tctgtcgccc aggctggagt gcagtggtgc catctcggct cacggcaagc tccgcctccc 30600
gggttcacac cattctcctg cctcagcctc ccgagtagct gggactacag gcccccgcca 30660
ccacgcccgg ctcatttttt gtactttcag tagagacgag gtttccccat gttagccagg 30720
atggtctcga tctcctgacc tcgtgatccg cttgcttcgg cctcccaaag tgctgggatt 30780
acaggtgtga gccagcgcgc ccggccgtat gtgtgttttt aaaaaggatt ttattaggga 30840
aattttcaca tacttaccaa agtaggaaga acagtataat taagccccat cttcccatcc 30900
agctcttaac aatacacagc ccatcttatt tcatctctta ttagcccaac tcattcccct 30960
tcccacttcc cattggataa ttctgaagca aaaacaagac ttttttttt tctaagcagt 31020
ctcactctgt tccccaccct ggagtgcagt ggtgcaatct ggggtcactg caaccccaag 31080
cctgcaacct ccagccaggc tcaaatgatc ctcccatctc agcctcctga gtagctggga 31140
ctacaggtgc acaccaccat gcccagctaa tttttcatcc catcagaaca agtaaacatg 31200
tgggccccac ggctcttgtg ggtactgtct ccctcatggt gaacaagcct cctggtgttt 31260
cgtccaagaa aaggaagggt gtcagcggaa ccacagtcct ttttcattta taaactgcct 31320
cttcatgttg cctgctcaag tttccacgta gaattgctat cactgtggct ctttattttt 31380
ctttttcttt tttttttttt tgagacggag tcttgctctg ttgcccaggc tggagtgcag 31440
tggcgcgatc tcggctcact gcaagctccg cttcccgggt tcacgctatt ctcctgcctc 31500
agcctcccga gtagctggga ctacaggcgc ccgccacggc gcccggctaa tttttgtat 31560
ttttacaaaa tacaaagtag aaacggggtt tcaccatgtt agccaagatg gtctcgatct 31620
cctgacctcg tgatccaccc acctgggcct cccaaagtgc tgggattaca ggcgtaagcc 31680
tccgcccccg gcccactgtg gctctttcta aaaatccttc tatttaactg gctcactgaa 31740
attagtcata ggaaacttgt gatttggtga agaagcattc cttgtaataa ccaaatgatg 31800
ggacggtttg catagcaaca gtgttacact tatgggggcc gtctctagaa tccaggaagt 31860
ctctggatct gaaggatgaa cagttcttcc tgctctgaat gagagtggac tcttcccctc 31920
acctccaact gaaaccacga acacccagaa tcttctggga ttctgactta agagtccttg 31980
ttatagaaga ccttgttgct atggaacatg aaactgtgtg tgtcagatgg agagattccc 32040
ttaacttaag agccttaaat agccctgaaa gtacaccggg acagtttgcc atgtaattaa 32100
aattagaagt gaatattttt aggtgccctt gaagctttct ggggactcaa aattatcaag 32160
agtcagggac agtccgaagg aagaacgtct gtaaaagtgg gttcctggaa gtacagacag 32220
atgtggcttt ttgtagaact tggtggggag cggtgcctcg taagagcgga atggcctggc 32280
gtagccagtg cttcccggca acacgcagct ctgccagcct ccagaattcc cccgttctga 32340
gcttgatgcc cttagcctgt cccccacctc cttcttcccc tcccctctag ccctctcaca 32400
ggggtgattg ctaccactct tttcttgggc ctaggcaagt tttagaggag ttctcaacca 32460
ttgtcacgaa gcctgtgtgc tccctgggct ggatggcctg ggcttgcgtg tggcccgagg 32520
gctctcctgg ggtctttttc ccagtcaccg tccaagccac agtgcactca ttggatgtat 32580
gttcttaaca tagctcactg cttctctttc tacattaaaa aaaatcatta ttgcattttg 32640
gaaagcagtg cttatcaaaa gcaacttttt tttttttttt tttttgagaa acggagtctc 32700
tctcagacgc ccaggctgga gtgcagtgcc acgcccggcc caaaagcaac ttttaaaacc 32760
tattttattg ttcctttaaa tgttctctcc cgctgaaact gccttgggga ggctagcagc 32820
tgctcttcca tttccccaca tcagggtatt ctccacgtca ctgagtggag atgactccag 32880
gtatgtttaa agactggaca attcacctgt actgtgtagg aaattacctc cttaattacc 32940
tggtagaatt gtcagcagac atgttcatcc gatgatagta ctgcagtttt ctataaataa 33000

```
tttgctgact tttatctaac ctgcactcat gtacagatta ttaaaagttt taaaatgtaa  33060
ctgatcagta ttgatcaatc attatcttga cttttttttta ccgtgtatat ttcttttttc  33120
tttttatttt tttgagacgg agtctcgccc tgttgccctg gctggagtgc agtggtgcaa  33180
tctcggctca ctgcaagctc tgcctcccgg gttcacgcca ttcgcctgcc tcagcctccc  33240
gagtggctgg gactacaggc gcccaccacc acgcccagct aattttttgt atttttagta  33300
gagacggggt ttcaccgtgt tagccaggat ggtcttgatc tcctgacctc gtgatccgcc  33360
cacctcggcc tcccgaagtg ctaacaggcg taagccactg agcccacccc ctatagtgta  33420
tatttctaat catattcttt aaagccaaga gaactggttg aatgaatgtt tattttcctg  33480
aaggtatttt taggataaag ctgcctaatg gcctgtaaac tttgcatata tatgtagttt  33540
gatacatatt gtcacatttg aaaatcttgt gagttgtaac tggttttata caaaatatcg  33600
aatagtggaa attgtataat tacaatcatg taattaaact ccccccccaa aaaataccaa  33660
aattagtcgg gcgtggtggc atatgcctat aatccaagct actcgggggg gctgaggcag  33720
gagaaccgcc tgaacttggg aggtggaggt tgcagtgagc cgagatctca ccactgcatg  33780
ccaagctggg caacaagagt gagactccat ctcaaaaaaa ttaaagttaa gcctttaagg  33840
aaaaaggctt tacttttcac acttaaaaga attatcaggc cgggcgcagt ggcaggcgcc  33900
tgtagtccca gctactcggc aggagaatca cttgaaccca ggaggcggag gttgcagtga  33960
gctgagattg caccactgca ctcctgcctg gcgacagaat gagactctgc ctcaaaaaaa  34020
aaaaaagaat tatcagtata gtaattagtt ggtatcatta aacatccagt gagtatcacc  34080
atccagtcag tagagatggg atttcaccat gttgcccagc ctggtctcaa actcctgggt  34140
ccaagagatc tgcccacctc tgcctcccaa agtgctggga ttataggcat gagccaccac  34200
accaggactt taaaaaattt ttttcttgaa ttgagtagtg ctttagaatt atccattaag  34260
cttcatgttt atgtttgctg tatttcacac acacatacaa agtgttgttg ttgttttaaa  34320
gaagaatgct gtgtttcctt gggacaggtg aggtgagagg agaaacgtag aaggagaaaa  34380
gtagagagat ggaaaaaaga gggctctgag gaatacaaaa cctgcaagac aaaagggaaa  34440
agagtggctg tgggggccgt ggaccctgag aaggtgtttc caggttctcc acagagggac  34500
cccagacctt gcatctgcaa gcccacttga gctccaggct tctggagagg tctccagaga  34560
gcgggactag aaaggcagcc ccaggagtga tgatggtgag cctgcccggg ccagagcaac  34620
tccaggacaa aaagcaaagg ggcctgggaa gttggagaaa gtttcttttc attttctctt  34680
tttcatttga gaaaggcagc agagagcagt ggaaaggacc aaagggcccc gtgtctgaat  34740
tgtagcacta gtagttgtgt gatactgggt tatgatactc cattaaattt ttttttttta  34800
ctctcctcta atttctttta ccagactcca ttaattttta tctcagcttc attatacagg  34860
ttgagtatcc cttatccaga agggcttcag attttgtgtg tttttttgtt tttgtttttg  34920
gactttggaa tatttgcatg tacataatga gatatcttgg ggatgggacg aaagtctaaa  34980
caagaaattc atttgcgttt catatacatt ttatacacat agcctgaaga taattttatt  35040
atgtatttat gtatataaac ataaaaatat gtgtgtatat ttattttttt gagatggaat  35100
ctcactctat tgcaaggctg gagtgcagtg gcacgatttt ggctcactgc aacctccacc  35160
tcctgggttc aagcgattct cctgcctcag cctcctgagt agctgggact acaggagtgt  35220
gccaccacac ctggcaaatt tttgtatttt ttaatagaga cagggtttcg ccatgttggc  35280
caggttgatc tcgaactcct gacctcaggt gatccacccg cctaggcttc ccagagttct  35340
```

gggattacag gtgtgagcca ctacacctgg ccaattttat attatatttt aaaacaattt 35400
tgtggctggg cggagtggct cacacctgta attccagcac tttgggaggc tgaggtggag 35460
cccagcattt ggagaccagc ctggccaaca tgttgaaacc ccgtctctac taaaaataca 35520
aaaattagtc agtagtggta gctggtgcct gtaatcccag tttttcggga ggctgaggca 35580
ggagaatctc ttcagcctag gaagtgcagt ttgcagtgag cccagatcgt gacactgcac 35640
tccagcttgg gcaacagagt gagaccccat ctccaaaaat taaaaaaaaa aaaaagaagc 35700
tgaggtgggc ggatcacttg agcccaggag gtcaaggctt tggtgagctg agatcacgcc 35760
actgcactcc agcctgggtg acagagcaag accctgtctc aaaaaataaa ataattttgt 35820
gcatgaaaca aaatgttgac ttcatttgac tgagacctgt catatgaggt caggtgtgga 35880
atttttcact tgtggcatca tgttggcact taaaaagtat caaattttgg agtattttgg 35940
atttcaggtt ttggattaga gatgctcagc tcagcttgca tgtaaatagt aacaatagcc 36000
aagctttatt atatgcttac aataagccag gccctgtaaa ccttgaaaat acaactcatt 36060
tggccaggcg cggtggctca tgcctgtaat cccagcactt tgggaggcca aggcgggcgg 36120
atcacgaggc caggagatag agaacatctt ggccaacatg gtgaaacctc atctctacca 36180
aaaatactaa aaaaaattag ctgggcatgg tggcatgcac ctgtagtccc agctacctgg 36240
gaggctgagg caggagaatc gcttgaacct gggaggcaga ggttgctgtg agcaccacta 36300
ctccagcctg gcgacacagc gtgactgcat ctaaaaaaata tatatatata tatatgcaca 36360
tacatatata tatatgtctt atttactcct tacaacagcc ctcgaaggta ttatccacat 36420
tttacaggtg aggaaaataa ggcagacggg ttatgttact tgcccatatt cacacaggga 36480
aacgtagagc tgagacttga atccaggcaa ttggactcag aatccatgtc cttaccacta 36540
tattaccatt gccaagagat ataacattac agaattgttt tattggttat agataattaa 36600
tgcaaagtac ctggaactga gtaagtatag tcgtccttca gtatgggggga gattggttcc 36660
aacccccccaa tacaccagat atcaaaatct gcagatactg aagtccctta tataaaataa 36720
gcagtacttg catttaacct atgaacatct tcctgtatac attaaatcat tctagattac 36780
tcataatact taatacaatg taaactctat gcaagtagtt gttatactat tttttttattt 36840
gtttgttttt tgaaatggag tctcagtctg tcgcccaggc tggagtacag tggcgtgatc 36900
taggctcact gcaacctcca cctcctgggt ttaagcaatt cttctgcctc agtctcctga 36960
gtagctggga ttacaggcgc ttcccagaac gcccggctaa tttttgtaca tttagtcaag 37020
acagggtttc accatgttgg ccaggctggt ctcgaactcc tgacctcggg taatccacct 37080
gcctcggcct cccaaagtac tgggattaca ggcgtgagcc actccacctg ctcctgcctc 37140
ttttcttctt aaaaatctgt tggagaaagc attttagaag aaaatgagtc tctggtctca 37200
cgtttcatct gatctcttgt ggctatttta ggacacttta ttcctagacg ggtaggtcct 37260
ggaagctcat ttttagcagg ttgtgaagtc tcatgtccta tgaagagaaa atggggggag 37320
gaagaaagaa aaacaacaac aaacaaaaga ataatcctgg aaaaattgat ataggcaaca 37380
ttactctgaa gtccatacat tagtaggcag gtatgaaagt ggcttatgta tataaatagg 37440
tggctgttat tttcttctga cacttaaatt gtctggcttc agttcacagg gcattaagaa 37500
agcacagttt agttttcagt gaatccaaat taggaaaaat gggggaaaaa gaagaaaaaa 37560
aaatgaaaac agtattttga agtcttgtag ctaagaaaaa ttagaatttg gttcaaactg 37620
tagaaaacaa taaaaattgg ccgggcgcgg tggctcacgc ctgtaatccc agcactttgg 37680
gaggccgagg cgggcggatc acaaggttag gagatcgaga ccatcttggc taacacggtg 37740

```
aaatcccatc tctactaaaa atacaaaaaa ttagccgggc gcggtggcgg gcgtctgtaa  37800
tcccagctac tcgggaggct gaggcaggag aatggcatga acccgggagg tggagcttgc  37860
agtgagccga gatagcgcca ctgcagtccg gcctgggcga aagagcgaga ctccgtctct  37920
aaaaaaagaa aagaaaagaa aagaaaacaa taaaaattga aaaaatatta ggcaagacta  37980
gaatctaaca acaggtgtac tatagtttta aaacataatt tttctctctc cagtttccca  38040
tttttactaa agacaaatca tggtaggact ggtttgcttt attacacttg gcataattat  38100
ttgtatacag tgcagcaaga ataatcattt ttttaatgta ggcttttaaa ttggctttga  38160
tggaacttgt tccataggag gattctcaga taagactttt taaagccgaa cccagtcatg  38220
gattacaggc atgagccact gcactcggcc gctttttgag aaacttttac tataatggat  38280
tataaaaata accactttaa ggacagtatc aataatttaa ttttattatt atttttttgc  38340
cccacccccct ctgcctctta attatttatt tatttatttt ttgagaggga gtctcgctct  38400
gtcgcgaggc tggagttcag tagcgcaatc tcagctcact gcaacctctg cctcccaggt  38460
tcaagtgatt ctcctgcctc agcctcctga gtagctgaga ctacaggtgc acgccaccat  38520
gaccagctaa tttttgtatt tttagtagag acagggtttc accatgttgg ccaggctggt  38580
ctcaaactcc tgacttcaag tggatctgcc ttccttggcc tcccaaagtg ctgggattac  38640
aggcatgagt caccaagcct ggccaattta tttttttctc cccttaattt gaaatgctac  38700
agaatgaaag atttgtttgt ttgtttgttt gtttatttat tgagatggag tcttgctgtg  38760
ttgccgaggc tggagtgcag tggcgcgatc ttggctcact gcaacatccg cttccttggt  38820
tcaagcaatt ctctgcctca gcctcccgag tagctgggat tacaggcgct gccaccacac  38880
ccagctaatt tttgtatttt tagtagagac ggggtttcac catcttggcc aggctggtct  38940
tgaactcctg acctcgtgat ctgcctgcct cggcctccca aagtgctggg attacaggca  39000
tgagctacca cgcctggcct tggcattttt attttattta ttttgagaca gggtcttgct  39060
ctgtcaccca ggctggagtg cagtggcact atctcggctc actgcaagct ccgcctccca  39120
ggttcatgcc attctccttc ctcagcctcc tgagtagccg ggactacagg caccaccacc  39180
acgcctggct gatttttgta tttttagtaa agacggggtc tcaccatgtt agccaggatg  39240
gtctcgatct cctgacctcg cgatccacct gccttggcct cccaaagtgc tgggattaca  39300
ggcgtgagcc attgcttctg gccttgttta ttttttattt ttattttttt aaattgagac  39360
acagcccagg ctgaagtggt gagatctcgg gtcactgcaa cctttgcttc ctgggttcaa  39420
gtgattctcc tgcctcagcc tcccaagtag ctgggattac aggcactaag tccctatgct  39480
gcacacagca caggaaccct tggcccagcc cacaaaacta atttttcctc ctaggcctct  39540
tggcctgtga tgggaaggga tgctgtgaag acttctgaca tgcactggag acattttccc  39600
cattgtcttg gggattaaca ttcgggtcct cattactcat gcaaatttct gcagccagct  39660
tgaatttctc ctcagaaaat gggatttttt tttctatcgc attgtcaggc tgcacatttt  39720
ccaagctttt atgccctgtt tcccttttaa aactgaatgc cggctgggcg cggtggctca  39780
cgcctgtaat accagcactt tgggaggctg aggtgggcag atcacgaggt caggagatcg  39840
agaccatcct ggctaacacg gtgaaaccct gtctctacta aaaaatacaa aaaattagcc  39900
gggcgtggtg gtgggcgcct gtagtcccag ctactcggga ggctgaggca ggagaatgtg  39960
tgaacctggg aggtggagct tgcagtgagc cgagattgtg ctactgcact ccagcctggg  40020
caacagagca agactccgtc tgaaaaaaaa aaacaaaacc aaaactgaat gcctttaaca  40080
```

```
gcacccaagt cacctcttga atgctttgct acttagaaac ttttttccac cggataccct  40140
aaatcatctc tctcaagttc aaagttccat aaatctctag ggcaggggca aaatgctgcc  40200
agtctctttg ctaaaacata acaagagtca cctttgctcc agttcccaac aagttcctca  40260
tctccatctg agaccacctc agtctggacc ttattgttca tatcactatc aacatttttt  40320
tttttttgag acggagtttc gctcttgttg cccatgctgg aatgcaatgg tgtgatcttg  40380
gctcaccaca acctccacct cctaggtaag tgattcttct gcctcagcct cccgggtagc  40440
tgagattaca ggcatgcacc accacgcctg gctaattttg tatttttagt agagaagggg  40500
tttctccatg ttggtcaggc tggtcttgaa ctcccgatgt caggtcatct gcccgcctcg  40560
gccccccaaa gtgttgggat tacaggtgtg agccaccatg cctgacccat tatcagcatt  40620
tttgtcaaag ccactcaaca agtctctagg aagttccaat cttttccaca tttttctctc  40680
ttcttctgag ccctctaaat agtttcagcc tctccctgtt acccagttct gaagttgctt  40740
ccacattttc aggtatcttt tcagcaacac tccactcctg gtactaattt actgtattag  40800
tccattttca tgctgctgat aaagacatac ctgaagctgg gcaatttaca aaagaaagaa  40860
gtttaatggg cttacagttc cacatggctg ggaggccgca caatcacagt agaaagacaa  40920
ggaggagcaa gttacaactt acgtggatgg cagtaggcaa aaagagaact tgtgctgaga  40980
aactcccatt tttaaaacca tcagatcttt tgagacccat tcactatcac cagaacagca  41040
caggaaagac ccaccccat gattcagtca tctcccactg ggtccctccc acatcttatt  41100
ggagctacaa gatgagatct gggtggggac acagagccaa acatatcact gcatgttctc  41160
acttataagt gggaggtaaa tgatgagaac acattggcac aaagagggga acaacagaca  41220
ctggagccta ctggagggtg gaagatggga ggagagagag gatcagaaaa aataactaat  41280
actagacttt atacttgggt gaagaaataa tctgtacaac aaaccgctgt gacaagtaca  41340
aatttgctta tataacaaac ctgcacatgt acccctgaac ttaaaaggta aaaaacaaac  41400
aaatgaaatc aacccaatag ttccagagac tattgttttg gataaacata aaaatttatc  41460
tttctggtct taaagcttga aacttatatt tgctttattt gagttccttc attagtaaat  41520
gaccttcagg cttctccccc gcaaaaaaaa agtatcaatg aactgaaact caccagatca  41580
ctacatccag acaatgagac tttggacccc tcattcatca tgattacttc cttggccctc  41640
cctacttcct gttttcttac acattacatt tcttcccctc tgtataaaac ccttgtttta  41700
gttgatcagg gagatggatt tgaggttttg agctcccatc ttctcagctg cagcacccga  41760
ttaaagcctt cttccttggc aatacttgtc atctcagtca ttggctttct gtgcagcgag  41820
ctgtaggacc tagactgaac ccctgatgtt tcaataacat attttggttc cctgactggg  41880
aacatgttgc ttgtggctca gctgccatgg gtggagtctc agaagccctc ttatgcagct  41940
gcctgacaaa ttttatttta ttttattatt ttattttatt tcctttgaga tggagtctca  42000
cagtgtcacc caggctgtag tgcagtggca caatcttggc tcactgcaac ctctgcctcc  42060
cagtgctata ggagtcagaa gaaatcactt gggcagatag ccagggtacg ggaatcctca  42120
gtaaggcttt tctttttctt ttttaatgaa aagctgcccc aaatcatttt ctaacaaaga  42180
gcagcctgaa acctgggagt ttgcaagggt gaatgccagc aggaactaag gagtagacat  42240
gttcaagata gcgacttcat cttcccttct ctgccagtca tgtgtactgt aaggagcaga  42300
ccagatggtg tcgatcacct cgcctctact aaaaatataa aaattagctg ggcgtggtgg  42360
tgggcgccta tagtcccagc tgctcaggcg gctgaggcag gagaattgct tgaaccgggg  42420
agtcagaagt tgcagcgagc tgagatcgca ccattgcact ccagcctgga taacgagagc  42480
```

aaaactctgt ctcaaaaaaa aaaaaaaaaa aaaagaaaaa gaaaaaaaaa acagatggtg 42540
tcgatcaact ggaaaggcca tttgcgtaac aagattaggg tggggcaacc agcctttcct 42600
gagcactatg taaacgtcat agctgatcaa accaatctgt gagccctatg taaatcaaga 42660
cacattaaaa cagtccacac taaatcagac actgcctcct caaactggtg tcttcactac 42720
cagccagtcc tttccattcg gagacctctt cttctataga ggaagctatt tctcttttct 42780
cttctaccta ttaaacctct gctcctaaac cccttgtgtg tgtctgtgtc ctaaattttc 42840
ctggcctgtg acaatgataa atatatacct gagggcatat accccagaca atgtagccac 42900
ttcaccaggt tcaagttatt ctcctgcctc agcctcccca gtagctggac tacaggcatg 42960
caccatgccc atctattgac caatatcagc tggaagtgag tttcagtttc tctctggccc 43020
caccatggtc agccccaacc atcctcctga ttgccttgga agaatagcct tcgaaattgg 43080
acatctgcat ccagataggt gagtatcctt tgtgggccca gacagcagga tttgctcctc 43140
tcaatttggg aaatttttaa aagaatttc atttgcaggt tgaacaagcc caactgactg 43200
agggagggaa acaccctgac tgtttttatg tggacactct tgggggctag tttataattg 43260
tatgttgtgt ctgggcaagt gagtgcctcg tgtgtgtacc agacagcggg atcagttcct 43320
ctcaatttgg gaaatttcct aaggaatttt tgtttgcatt tgatcaagcc caaccaatga 43380
agagaggaag caccctgact gtttgagttt ggacactctt ggggcttgtt ttttgctgca 43440
gcagttggat tgtgttttgg tgatcatttg tgtgtgtttt atatagtcat gagaagttag 43500
aattcggtaa actgatattc atttgcaata ctgttggccc cagtgttgtt tggaatctgg 43560
cgtttgctgt ttggaatctg gagtttgctg ctgaatggga aagtgggatg gagttgtgtg 43620
tatccaggct tttgtgctgc tgttctaagc aaggttgggc ctggcaggta tgtgatgttc 43680
tcctttgttg ctgtttgacc ccaatgttct ttggagtctg aggaggtttg gcctttaaaa 43740
atcaaactgc catggaaact actataccca aaattttgat tcacagcctt cactgaatta 43800
cctactggga caaagtgtaa ccatgtaaaa ccagtaagct tgtattgcta tctcatagct 43860
atagttccaa ggtaaaagct attggatctt tgtttatgtg tgtatattca tgtttagatg 43920
tgtttatttg tatgtaccct tattggtata tgttgtgtct accaaattgg cttataagta 43980
aaacagcact cataaattaa ataagtcaaa gcaattttca agttcgtgtg agttaagtaa 44040
attttttcga aaccagctgg ctgtaaaatt attggtaaaa tgaaaataaa aatgtcttca 44100
aaattgtgag catacatttt tgtctggatt ttatatttgt ctctggtaga tattttgagg 44160
tttcagggtt tggcatagaa ggttataaaa ttataaaccc agccaaaaca aatgatcttc 44220
atgaaaattt tttgaaaagt agtattacgg gatcactgga tgtcaatttt tctggccaga 44280
aacctctgtg gccagtggtg ctttgcctga gttcttgtcc tgcgttcagg aagaatgagg 44340
tactcaggca agtgaaccag acaaagagga gctttattta gtattagagc agctcagggg 44400
agacgcacag tgggtagctc ctttctgtta ctcgttgtcc caacgtctgc tgctctcagc 44460
agagaggagg ccctggagag gacagctcct gtctgctact ggtcatcttg acgtatgctg 44520
ccctcagcag agaggaggcc ctggagagga tggctcctct ctgaagctgg tccacgcaat 44580
gtctcttctg gtctctgaag ctcttagcag agagggtagc tcctttctgc cagctggcca 44640
tcccattgtc tctagctatc agcaggggga atagctcctc tctgcatttg gtcctcttgt 44700
tgtctcccca acctctgccc tgctgtggct gagcccaggg cttttatgtg gctcggggaa 44760
gggagtgtgt gctgactggt ccacaggaaa aagcaccatg agttcctcct ccaatcagca 44820

```
ggaatggcag cctggccccc acacttcagg cctgtcctgg catgaaggtg gggcttcact  44880
ggggacttgc cccttccac ccaggagcct gtctgccttc cacagccatc catagtgccc  44940
aggctgctgg caccaagggg cacctgcagg ccagcaccag tcactctcag cccctctcaa  45000
cttcccttcc tgcactcctc agtgcccaaa gtccagaggg gggcagggca gcaggggact  45060
ggcgtgtcag cactgccctg agcttgcaca cacctggcag cactgtgaca gcccctggac  45120
ttggccccaa gcctggtcca agatcagagt gggcaccggg agcagggaaa ggccaagcag  45180
caagagcagg gagaggccaa gcagcaggag caggcaactc tgagcctaca agggcaagga  45240
gggggccttt tcaggccccc caagagtgca gggatgcctg ggtctgcagc cccaatttgg  45300
gcggctgcag caccccacag cggggtgggg ttcctgcctg ctctgtggaa ctggaggcct  45360
gtatctggag ctgtggacca agttgctgca gctgcaccca ggaagggatg gatcctgcct  45420
gctcctggcc ccaacaagag cacagggagg ctcagatctg cagcgaacac ctgtagtccc  45480
aggtactcag gagactgagg caggagaatt gcttgaacct aggaggcaga gattgcagtg  45540
agctgagatt gtgttactgt gctctaggcc agggaacaaa gcaagactct gtctcaaaaa  45600
aaaaaaaaag acttttgtca accacaatcg atgttttgct ttgattcttc tcaaaaagtg  45660
acttacaatc agctacagtc cagggcttgc ttctttggag gagttcatta aaaggacttt  45720
tgatttgcag gtttctgata actttggggt ttgtgccact gaattagaga gaaaacttcc  45780
aggactgtaa ttgaaaagct ggtgtgttca taaagattgc taactcaata tgaaacagag  45840
caagagttga ttgcatgaat tgaaactgaa actgaaatag tttttatggc tttttgtttg  45900
aaatattgct gattcttttg tttgtttgtt tgtttgagac ggagtttccc tcttgttgct  45960
caggctggag tgcagtggcg gatcttggct cactgcaacc tctgcctccc aggttcaagt  46020
gattctcctg cctcagcctc ctgagtagct ggcatttcag gcatgcatca ccatgcccag  46080
ctaattttgt atttttagta gagacagggt ttctctatgt tggtcaggct ggtctcgaac  46140
tcctgacctc aggtggtcca cccacctcag cctcccaaac tgctgggatt acaggtgtga  46200
gtgaccacgc ccagctatat tgctgattct tttgttttt tcagagtctg aataattttt  46260
ccttttgagc tgtttatagc ctttaagcat actttaagtg tattaagtgg agtatacttt  46320
tttttttttt ttgagatgga gtctcgctct gttgcccagg ctggagtgca atggtgtgat  46380
cttgactcac tgcaacctcc acctcctggg ttcaagcaat tatcctgcct cagcctactg  46440
agtagctggg attacaggtg tgcaccacca ctcccagcta atttttgtat tttcagtata  46500
gatgggattt tgccatgttg gccaggctgg tcttgaactc ctgacctcag ctgatctgct  46560
tgccttagcc tcccaaagtg ctagccactg cacccagcaa aagtgcagtg tactttttaa  46620
tttttttgag atggagtgtc actctgttgc ccaggctaga gtgcagtggc gtgatcttgg  46680
ctcactgcaa cctccgcctc ctggacccaa gtgattctcc tgccccagcc tcctgagtag  46740
ctgggattac aggcgtgcgc caccatgtct ggctaatttt tgtattttta gtggagacag  46800
ggtttcacca tgttggccag gctggtctca aactcctgac ctcaagtgat ccaccagcct  46860
cagcctccca aagtgctggg attacagacg tgagccatcg cacccagctg agtatacttt  46920
tgtaaacaga atttgagtca tatatctctc tctgcctaat ttctccaaaa tttgtaaact  46980
atttgtgaat attcttaatt catggcaatg tatatgtttg catatactta ataacaacat  47040
attttcagcc aggcgcggtg gctcactcct gtaatcccag cactctggga ggccgaggtg  47100
ggcggatcac gaggtcagga ggtcgagacc atcctggcta acacggtgaa accccatctc  47160
tactaaaaac acaaaaaatt agctgggcgt ggtggtgggc gtctgtagtc ccacctactc  47220
```

-continued

```
gcaaggctga ggcaggagaa tgacgtgaac ccaggaggca gagcttgcaa tgagccaaga  47280
ttgtgccact gcactccagc ctgggcaaca gagcgagtgt ccatctcaaa aaaaaaaaaa  47340
aaaaaaaaaa ccaacaacat attttctttt gtaacagggc acaattgaag gaactggttt  47400
tattatcatt attattatta ttattattat tattttgaga cagagccttg ctctgtcacc  47460
caggctggag tgcagtggca tgatcttggc tcactgcaag ctccgcctcc tgggttcacg  47520
ccattctcct gccttagcct cccgaatagc tgggaccaca ggtgcccacc accacgcctg  47580
gctaattttt ttttttgta tttttaggag agacagggtt tcaccatgtt agccaggatg  47640
gtctcgatct cctgacctca tgatccaccc acctcggcct cccaaagtgc tgggattaca  47700
ggtgtgagcc accacacctg gccaggaact ggttattttc tcagggcttt gactgaaatg  47760
gtcttgtgag atgttccagc aaagctgatt tgggagagtc tatatggaca atgattcttg  47820
ctgcactgtg tgtgggtaat caggtcgatt atatgggact gcagcttatt ttgcaggtag  47880
attggtcctg ctgtgatttg tctttggtgg aagcagtgga ctgtagagag aaatatcatg  47940
tgtcagaaga aactctacat tagattaacc tttgatccct ggatggctac atggtcaccc  48000
atggtatgga gctgcctatg acacccctcc tcattatgaa gcagccagaa agatagacaa  48060
ccagattcct catgattgag gaattgatca atagaaaggg ggcactgaaa ccaacccaat  48120
agtcccatag actgttcttt tggataaaca tagaaattga cctttctgat cttaaagctt  48180
gaaccttata tttgttctac ttgagttcct tcctcaggaa aggaccctta ggccttttaa  48240
aaaaaaaaag aaaactgaaa ctcatcagat cattacattt ggatagactt tggacccctc  48300
attcatcgcg attgctttct tacccttctc tagttcctgt ttgcctacac attgttacat  48360
ttcttccctg ctatataaac cctttgtttt agtcagtcag ggagatggat ttgaggctga  48420
gctcccatat cctgggctgc agcacccgat taaagccttc ttccttggca atacttgtcg  48480
tctcagtcat tggctttcag tgtggcgagc agcaggacct ggactgaacc cctcgtgttt  48540
tggtaacaca aaaagaagat ggctgactgg aggcatcttg cacttgcctc ctccacaaag  48600
aagaaccaaa atagcgaata gataataata ctttgaatca agcatctaag ggagaccact  48660
ggaactcaac agggaagtga caggaaacac ctgaggcaca ggaggagagg gaagcgagac  48720
agccagctct gcaggccagg attggctggg aggccaagga gtttccccag tgtgggaaag  48780
tgtaaatgag agatccctag tgatccacat tcccacctga aacccgagac atgggagaac  48840
ctcgtgatcc ttgcaggccc tgagaatagt gtaggagctg cctggagact gtgtgacgtc  48900
agtgctctag agagggagct cacactgggt cccacacccc tcctccatga cccctaagca  48960
gctgcagcat gggatcattt ttagagctaa gcacctatca gactgcattc tgtcctgggg  49020
cccaacagcc cttgcatctc cacatctctg gagcctcact gacatccacc tgtgtccacc  49080
tggagggctg aagcagcaga cgtggttgga cccagtagag gttccctctg atgtggttgc  49140
tctagcacac agtatcttgt accctaggga acaggtagta tagcacacca gggaagctgc  49200
ccctggggca aacagagcca aaacacaaag tccctagagc ctgagggaga tgggttaatg  49260
gacacaaaca tacagttaaa tagaaggaat aagttccaat attccacagc agagtagggt  49320
gactataatt tgcaacaata tattgtctat ttcaaaatag ctagaagaga ggactttaaa  49380
ggttcctaac acatagaaat gataaatact tgaagtgatt atgagaaacc ctcacctgtc  49440
caaaatcaaa gaatggactc agagacacga aatgcagcag aagcgagact taatggcggt  49500
cttgcaagat caggtgtccg gtaggcaggc atacccgggg cagttacaac aggtaattta  49560
```

-continued

```
tctcctagca cgcaaggccc tcccccagct cctcgttggt ctagtactat ggggttacaa  49620
tcttcccgga catcgcctaa gtttcattat ccccttataa ggttataccc cagtcccctt  49680
cctcacttaa gtttcaattt cccaataatg aaactttctt ccctttttatg ggctgacccc  49740
tcctctacat tctgttctct tatcgtgact ttctaggtgc atgagttgtt cggtttgtca  49800
catctgcagg ctggctgcca gtacacagat ttatcatgcc ttgaaaatag accatttaaa  49860
atattctctc acaaattccc tcctcttttc tatttacttt cctcagtctc atttttatct  49920
aaaccctttt ggtcctgaaa ttgctctaga agtcatttac tttcttcctc ataggagagt  49980
gagtttaatt tggtttctaa tagtagtagg ttatttttct ggtaaatcat gggcatttgt  50040
ttattaatag ctgtttcagg ccgggcgcgg tggctcatgc ctgtaatccc agcactttgg  50100
gaggctgagg caggcggatc acttgaggtc aggccaacat aacagcaccc catctctact  50160
aaaaatacaa aaatcagcct ggcatggtgg tgcacacctg taatcgtagc tactccagag  50220
gctgaggcag gagaattgct tgaacccgag aggcagaggt tgcagtgagc tgagatcgtg  50280
ctactgcact ccagcctggg cgatagaagg agactccaaa aaaaaaaaga aaagaaaaaa  50340
tagatgtttc agttaatctc tgtgctagtc ccctcacaca aaggataata caacatccca  50400
ctgctaagac ttctgctaca attatgagag atgtaaggat tgaagctacc atgtaccatg  50460
cctttccttt tttttttttt tttttttttt ttgagatgaa gtttcactgt agcccaggct  50520
ggagtgcagt ggtgcaaact cagctcattg caatctctgc ctcccaggtt caagcgattc  50580
tcctgcctca gccttccaag tacctgggtc tacaggcaca caccaccatg cctggctaat  50640
ttttgtattt ttaatagaga cagagtttca tcatattggc caggctggtc tcaaacttct  50700
gaacttatga tccgccccac tcggcctccc aaagtgctgg gattataggc gtgagccacc  50760
atgcccagcc acctttccat tttttttttt tttttttttt gagacagagt ctcattcagt  50820
cgcccaggct gaagtgcagt gacgcgatct cggctcactg caagctctgc ctcccgggtt  50880
caagccattc tcttcctgag tagctcctcc tctcctcagc ctcccgagta gctgggacta  50940
caggcacctg ccaccacgcc ctgctaattt ttttgtattt ttagtagaga cggggtttca  51000
ccatgttagg caggatggtc ttgatcgcct gacctcgtga tccacccgcc tcggcctccc  51060
aaagtgctgg gattacacgt gtgagccacc gggcctggcc cacctttcca ttttttaaac  51120
catctttcta gccagtctat aaatgggtca tcaatcccag cattttctgc cagtttgttg  51180
gctagggttg ttagcccttg taatgccttt gtgatagttc tatctggggc agtattattg  51240
ggaatgaaag tacaacattt tccacctagc ataacacata cacctccttt ttctgctaat  51300
atcatatcta atgcaaacct gttttcctag gctggtggca tctaactggc tagccacccc  51360
cttgagggca tcttgagtat aatgaatgtc tgttgattat aatagatgta attaatccaa  51420
tctacttttt tgttaatagt tgaccagcag aagagtgctg actcaaaccc cacagctatt  51480
tggttttggg ccttgaatta attaggcacc cccctgggga ctcactgtgt caatgtagat  51540
attgggatta aaggaatttg ttaaatgtct ccggttttgg tggccatgtg aattttcagg  51600
tatcttatgg aatgccaggg taaagggaac agccagttgg actaaagcac aagtaccggt  51660
ccaattggac cgtaacaggt tatggaggtt cctcttccca cagtaccacc agacatcagc  51720
ccagggtata tggagaactg agtaattgcc attgcctgac tcaccagtga cgtttaggat  51780
gtgggtacaa gtcaagagtt ctcccatgga cttattgaac tcagcctcct gcctggagag  51840
acaagaggag tggttcatac tccctataga gaatgagggg attgctgtgg gatccgacct  51900
ctgcaatgca ggaaagagta atgacagact cttacaagtc tcatctcccc atgcattctt  51960
```

gtcctggtat agagccaaca tgcaatgcat tccttcagga ttggtatccc gtcctagggg 52020
aaacggaacc acctgtgctt gtggtcatcc tgcagcacac atgtagcagt tactcttgtt 52080
gagggcttgt accaaaaatt tgacctattt gacccaggca ttcacatctg cttaccctgt 52140
ctcaatttct tttgcctttt tccccttct ttccttcctt ccttccttcc ttctgtcctt 52200
cctttttctt tcttttcttt ccttctttcc tttcttttt ttgagataga gtctcactct 52260
gttgcccagg ctggagtgca gtggcacaat cacggctcac tgcaacctcc gcctcccagg 52320
ttcaagctat tctcctgcct cagccccact agtagctggg attacaggca catgccacca 52380
tgccaggcta atttttgtat ttttaatagg gacgggtttt cgccatgttg gccaggctgg 52440
tctcaaactc cgggcctcag gtgatccacc cgccttagcc tcccaaagtg ctgggattac 52500
aggtgtgagc caccgcacat ggcccccgtc ccaatttcta aggtttgcct taaatccttc 52560
aattatttct attcttttag gattattgtt gggtgaacta gagtgtttgt tggggtctgg 52620
agttggagtg gtcccaggca aatgagaggt tgagttctcg actaacttga ggataaatct 52680
acctaaagga tccctcccaa taatatctgc ccctaactca tatactcaag atgctacctc 52740
tggcttttgg tttaaaatga ctgggttgtc aataaagatg agtatagcat tacattgtag 52800
attctgacaa ttatttggtg gggagccctt ggacagttgt attttattat ttagggccct 52860
ccaagatggg gttacccacc ccatattgac agtccaaccc tggtatttgg tggtccagca 52920
aacatcatcc cagctaggtc agggacttgc cctacggtag cctttgtctg gttcagggca 52980
gagatatact tatctgcctg tgaaagctgc ctctggtttt ctaaacttct acaggataaa 53040
atttggcagg catcaaacta tagtttgggg tgctattgtt ctagtcacat taatcaccaa 53100
tttgatcggg taggaagggg tctcctgcca atttccattt tgaccttcca ccctttgtat 53160
agtaagccat cccaaccaca ttaatttcca aaagtagggc cttcccatgg tcttctttgt 53220
taagtttttt ttcagactca actttaaaga tttctcgggt aactgataca ctttccactg 53280
gtctttcttc ctcccttctg gggtttcttt taccagtctc ttgactcatg tatagtgagt 53340
ccacccccgt tcagcttttc atacagctgt cttggtggtc aggagcactt gatagggaac 53400
ttcccagctg ggttggagca tatcttcttt ccaagtctta atcagcacca agtcattgga 53460
ttggaagtgg tgaactgtga actcaagagg cagggtttga gttagaagtc cttttaacct 53520
aagggatgac aaggtggagt atatggccag tatataattt cttaagaatt ggtccttggt 53580
tttcatagta ggaagatctg tagccctgcc caaatattgg agtctgtata ataactcata 53640
tggggacagt cccaagtctg tttttggggg ctgtccttac cctaaggagt gctactggaa 53700
gacatttggt ccaaggaatt ttagtttagt ttagtttttt ttttttgttt ttgagatgga 53760
gtctcactct gtcgccaagg ctggagtgca ttggcgctat ctcggctcac tgcaagctcc 53820
gcctcctggg ttcacgccat actcctgcct cagtctccca agtagctggg actacaggcg 53880
cccgccacca cgcgtggcta atttttttgta tttttttagta gagatagggt ttcaccgtgt 53940
tagccaggat ggtctcaatt tcctgacctt gtgatccacc tgcctcggct tcccaaagtg 54000
ctgggattac aggcatgaac caccgtgccc agccgaattt tagtttttaa gattagtttg 54060
gtaatatgct ttttgagagt ttgattcatt ctttctacgt ttccagagga agggggatgc 54120
caaagggtgt gataatccca tgtaatttgt aaaccttccg taattcccct taataccctt 54180
gaggtaaaat ggctcccatt gtctgaatca gtattttcta ccaagccaaa tcggggtata 54240
atctgctcta agattatttt gatcacattc gtggcagtag ctgttggaag gggaaaggct 54300

-continued

```
tccaccctgc tggaaaggta atctgctatc accagcaaat actttagttt tcctacttca  54360
ggcatttctg tgaaatctac ttgaatgctc tggaatggtc tcagtctggg aggtcttcct  54420
cctgtggcct gttttctaat tacctttttg tttgtccttt gacaagttac acaacttcca  54480
catatttgtt tagtgagggt gtggatccag ttattcctag gtattccatc acacagagcc  54540
tggggttccc aatgactccc tttgcgtaat atagacatta gttctgtcat caggggttta  54600
cttatcattt ctctcccatc aggaagtacc catttcccat ctttagttcg agtgaccctc  54660
tatcctgtct aattcttctt tcttctctct ggtaagctgg ggtcttcata ctaccttagg  54720
gatgtctggg atcaggctaa atagtctaat ttctttctcc agggaggctt gcttagcagt  54780
ttcatctgca agcctgtttt ctgcagcttc tatagtgttt cctttctgat gaccatttac  54840
ttttattttt atttatttat ttatttattt atttattttt gagatggagt ctctctcttg  54900
tctcccaggc tgaagtgcaa tggcgtgatc tcagctcact gcaacctcca cctcccaggt  54960
tcaagtgatt ctcctgcctc agtctcctga gtagctggga ttacagacac ctgccaccaa  55020
gcctggctaa tttttgtatt tttagtagag acagagtttt gccatgttgg ccaggctggt  55080
ctcgaactcc tgacctcagg tgatccaccc acctcggcct cccaaagtac tgggattaca  55140
ggtgtgagcc accacgccca gcctgtctga tgaccattta tatgaactat ggttacttct  55200
gctggaagaa ggaggtttct aaaacctgtc tgaccagttc cccaagtacc aattcttttc  55260
ccttgctatt tattaggccc tgctctgtcc agatttttcc aaaactgtgt accaccccat  55320
aggcatattt agaatcagta tatatagtgc cttcttggcc ttcaaggagc tttatggcct  55380
ggttaagagc atataattca caagtttggg ctgaccagcc attaggtaat ctaccttcct  55440
cacataagga gtgtttattt ttattaatga cagcatgact gttatgtttc ttggcatcta  55500
tcactctgga tgacacatcc acaaacaggc ttatcctacc atgtagggga gcttctctaa  55560
ggtctgggct aactttgatt tggtattcta tgatatctaa ggcagttatg gactgatgcc  55620
tctttgttct tctctccttt ccataagaaa ctggctggat tcaggcaagt atctgttgtt  55680
atgaccaaat catctttttc tagtaacatg gcttcatatt ttagaatcca agaatccatt  55740
aaccatctct tggctttttg atttaatata ttcctgaccc gatgtggggt gctcactgtt  55800
aggccccagc aaaggttaac ttttgactct catctgccag cagggctgtg gcagctacta  55860
cttgcacaca tttgggctat cctcaagaga caggattgag aagcttggag acaaaagcaa  55920
caggttgcct cttccctccc caggtttgag tgagcacccc aagagccaca ccctggtcta  55980
ctgttacaaa tagatggaat ggtttctcta aagatgggag ggccaggacc ggggctgtaa  56040
ggagggcctg ctttagctct tttgtgtctg gaattggtgg gttcttgatt tcactgactt  56100
caagaatgaa gccgcagacc cttgcggtga gtgttatagt tcttaaagcc agagtgtctg  56160
gagtttgttc attctgatgt ttggatgtgt ttggagtttc ttccttctgg tgggttcgtg  56220
gtctcgctgg ctcaggagtg aagctgcaga ccttcacagt gagtgttaca gttcacaaag  56280
gcagtgcgga cccaaagagt gagcagcagc aagatttatt gcaaagagca aaagaacaaa  56340
gcctccacag tgtgaaagga gacccgagca ggttgccact gctggctggg gcagcctgct  56400
tttatttcct tatctggccc cacctacatc ctgctgattg gtgcattttg acagggtgct  56460
gattggtgtg tttacaatcc ctgagctaga cacaaaagtt ctccaagtcc ccacagagca  56520
ctggttggtg catttacaaa ccttgagcta gacacagggt gctgactggt gtgtttacaa  56580
accttgagct agacacagag tgctattggt gtatttacaa tcccttagct agacataaag  56640
attctccaag tccccaccag attagctaga cacagggtgc tgattggtgt gtttacaaac  56700
```

cttgagctag gcacagagtc ctgattggtg tatttacaat cccttagcta gacataaaga 56760
ttctccaagt ccccaccaga ttagctagac acagggtact gattggcgca tttacaatcc 56820
tctagctaga cataaaagtt ctccaagtcc ccaccagatt aggtaggtac agagcactga 56880
ttggtgcatt tacaaacctt tagctagaca cagagtgctg attcgtgcgt ttacaatcct 56940
ttagctagat gtaaaagttc tccaagtccc caccagatta gctagataca gagtgctaat 57000
tggtgcatcc acgaactctg agccagacac agagtgctga ttggtgcata tacaatcctc 57060
ctgctagaca taaaagttct ccaagtcccc acccgactca ggagcccagc tggctttgcc 57120
tagtggatcc ctcgccgggg cagcgggtgt acgcctgcat tcctcagccc ttgggcggtc 57180
gatgggacca ggcactgtgg agcagggggt ggcacctgtc ggggaggctc aggccatgcg 57240
ggagactact gcagggtggg ggctcgggca tgacgggctg ccattcctga gccctgcctt 57300
gcggggaggc ggctgaggcc cagagagaat ttgagcatgg cacaggcggg ctagcagtgc 57360
tgggggaccc ggcgcccccct ctgcagctgc tggcccaggt gctaagcccc tcactgcctg 57420
gggccggcgg cgctggccgg ccgctcggag tgcggggcct gccaagcctg tgcccacctg 57480
gaactcgccc tggcccgtga gtgccacatg cagccccggt tcccgcccat gcctctccct 57540
ccacacctcc ctgcaagcag agggagctgg cttcggcctc ggccagccca gagaggggct 57600
cccatagtgc agctgcaggc tgaagggctc ctcaagcacg gccagtgagg ccgaggaggt 57660
gctgagagcc agcgagggct gcgagggctg ccagcacgct gtcacctctc actttcactg 57720
cctgaatttc ctctggggac tactgcaaag gatcaggttc ctcttcttgt gacttgagat 57780
acaggatctt tgtcttttga gcacatgagt caatccataa cctccagtag ccagttaaac 57840
ctaaaaattt tcagagttct ttctttgtct taggcagaag cccactattc ctggtattct 57900
ttctgggttt attctccacc tcccttcatt aatcaggtat cctaaatatt taacttattt 57960
ttctacaaac tgcaatttgt tcttagagat ttgcaacccc ctttctccta gggaattaag 58020
caagcttatg gtggtttctg atactttggt cttcctctcc ctagaaatta aaagatcatc 58080
tacatattgt aataactggt ttcccctgga aggttggaat tccttcagga ctttttctaa 58140
gatttgacca aataagtttg aggcatctgt gaagccttgt ggcagcacag tccagcagta 58200
ctgttgtttt ctgccagtta tgggattttc ccattcaaag gcaaagagat ccctactcct 58260
aaagtctagg ggacatcttt tctttcctgc tcctctgtta ggaggcccat cattactttt 58320
atttgtcctt cctctattcc taatcctaaa cccaatctca caatcaggtc tcaactcagg 58380
aggttagttg cctgcttcag gaacatataa gagtgacccc tctatttgtt ctggtcctaa 58440
tctaattacc attttcttga atatcagaac ctgaaatccc tccccttta ccccctgatac 58500
tgtcaatttt tccttcgagt cctgtacccc ttggttgatt aattaggaag gagagagaca 58560
gcccagtatc aagcaaaaat gttacttctt ccccatcggg tcccaccctc aaatttatca 58620
agagttcctg gtgggaccta cttacaagga acccctgact ccctaatctt catcaaaagt 58680
catacagtgg attacttctc ttcctttttc cattctggac attctctttt aaaatgtcct 58740
ggttttccac acttgtaaca tccacttaca gtcttaggag tttttccttg tatttctctt 58800
ctgtcttttt gctgaaacct agtattttct tgtctcctct gagaggggtc ttgatctaac 58860
ttcttcctga ctacctcctc tgcagtggaa accattattt tcgctttttg tttctgtttc 58920
tcctcttctc ttctcacaaa gatctttttg agcttccctc agtaattcct caattgattt 58980
ttcattccaa ccatcaatct tctgtaattt ttttgtaatg tcaggctagc tcttagttac 59040

```
aaagttaaca ttcaaaaggc cttgccctac tggggcctcc agatctaatc cagagtattt  59100
tctcatctga tctctgagcc tctgcaggaa tgcagaggga gtttcctctt tttcttgttg  59160
aatctttgag acatttgaga cattttgtgt cctagaagtc aattatttga tccctttaat  59220
tattagttcc ctgaggtcct gcatttgggc ctggtccctg ggatcattat tatcccattc  59280
gggattgaca tttggaaatt ttttgtttgg ctggcaagac tcctttcctc ggaggatgtt  59340
gcctcttcca gatggtcatt gccaccctcc taatcattcc tctttcttct cctgtgaata  59400
agatattcat gataggcatt atttcagtcc aggtataaaa gctggtccta ggaattggta  59460
caacttgtct gctaaatgaa ggggatcctc taggagtggt ttcattacct tcttgaaatt  59520
cctaacttca gtacttgtaa gaggagcgtt tacaaagcca atctctttct gtcctgtggg  59580
aacttcccta agagggaaca tgctagatgt ttgctgtttg gaggggatag ggaagttctc  59640
aatatctctt ttacattatt ctaattcttt tcttaaattt ggataagggt ctaaaggagc  59700
agttggttca gctcccccat ggtctccagg tctttctttc tctaactctc ctgctgcccc  59760
ttgatctccc tgtcccctat tttgtgagac atatggaggg ggctcccatg ataggggggtc  59820
ccagggcttt tcactgggca agggcttttt actaggctct ttttcttctt ctttgagggg  59880
ggaacatggg ggctaattcc ttgatcccac agacagcata acctatcttc tcctgtgcag  59940
atggggtttt atcattcaca tagagaatta aagcttggca cacccaatcc tcatctgagc  60000
caaccttagg ccaaaagact gaaggcttat gaatggggtc tttgggtcag gtaaaacagc  60060
aatactttat caacttttgc ttttccttgt ccctggctgc agggttgtcc ctccaaacct  60120
gcaacattca ttcaccccaa aggactatct gggggaatgt cagagggagt ctctttggct  60180
ccctctttcc tttgtcccta ggcctagaat ttctgtttcc catttttggc cagtctctgt  60240
gtctgggcct ttccctatgt actcaaccct cctactggag gtttcttgca caccctgaga  60300
atcgcttcat ctgtttcctg ccgattccct cgcaggagaa cggaactgtg gattgggact  60360
ccgtgcttgc ttcgtatcta gggtatgtct cagtcacaca cactcaacct ccaaaaaatgc  60420
ccaaccacca aggtggtact tacagtctgg ttttcctacc ttggctcatg cacaaggttg  60480
cctggttgcc atagtgtctg cttttctccc tatgtcacct ctgctgcctg ctgaataaca  60540
atctcaggtt tgtctatggc ctatgtgggg agctgggaca cctgcacaga gcgggccacc  60600
taaaattggg tgagatgtgt ctcccctctt ggctggagtc ccattccatg caggcacaga  60660
gatcctggat gagcccccaa gtttgtgaga aacgctcacc tgtccaaaat caaataatgg  60720
actcagagac aggaagtgca gcagaagcaa gacttttaat ggcaatcttg caagatcaga  60780
tgtctggtag gcaggcacac ctggggcagt tacagcaggt aatttatctc ctagcatgca  60840
agtctttccc ccagttcctt actggttgag tactacaggg ttacaatctt cccagacgtc  60900
acctaagttt cattatcccc ttataaggtt atactctggt ccccttccct gcctatgttt  60960
caacttccca ataatgaaac tttctcacct tttatgggct gacccttctt ctacatcttg  61020
ttctcttatg atgattttct aggtgcatga gccattcagt ttgtcacatc tgcagggtgg  61080
ctgctagtac atagatttat catgccctga aaatgaacca tttaaatgtt ttttcacaat  61140
ggcatatacc ctaaatgccc tgacttgatc attacatatg ctatgcatat aacaaaatac  61200
cacatgcacc ccataaaaat gtacaaatat tatatatcaa taaaaaattt aaaaaaaaag  61260
aaaaagggag aaagatgttg aatctacaac cacactttac aatctaagga agtagaaaaa  61320
gaaaaacaaa tggtagcaga aagaaagaaa tgaagactag agcagagata aatgaaataa  61380
gaaatagaga aaacaataga gagaatcaat aaaaaccaaa agttgtttgt ttgaaaagat  61440
```

```
caacaaaagg ctgggctcga tggctcacgc ctgtaatccc agcactttgg gaggctgagg  61500
tgggcggatc acgaggtcaa gagattgaga ccatcctagc caatatggtg aaaccccatc  61560
tccactaaaa atacaaaaat tagctgggca tggtggtgtg tgcctgtagt cccagctact  61620
tgggagggtg aggcaggaga atcacttgaa cccgggaggt ggaggttgca gtgagccaag  61680
atagtgccac tgcactccag cctggcgaca gagagggact ctgtctcaaa aaaaaaaaaa  61740
aatgttcaac aaaattaaca aaccttaggc cagatgcagt ggcttacatc tgtaatccca  61800
gcactttggg aggccaaggc aggcagatca cctgaactca ggagtttgat aacagcctga  61860
tcaacatggt gaaaccctgt ctctactaaa aatataaaaa ttagctgggc atggtggtgc  61920
atgcctgtaa tctcagctac tcaggaggct gaggcaggag aatcacttga acccaggagg  61980
tggaggttac agtgagctaa gatcgtgccg ttgactccac cctgggcaac aagagtgaaa  62040
ctctatctaa aaaaataaaa ataaaaataa aataaaatta gtggtggtcc acacctgtaa  62100
tcccagatac tcaagaggct gaggtgggag gatcgcttga gcctggctgg ttgaggctgc  62160
agtgaggtgt gccactgcac tacagccagg gtgacaagag tgagaccttg tctcaaaaaa  62220
aaaaaagaaa aaaaggccag gcgtggtggc tcatgcctgt aatcccagca ctttgggagg  62280
ccaagccggg tggatcacct gaggtcagga gttcgagatc agcctggcca acatggtgaa  62340
accccgtttc tactaaaaat acaaaaatta gccaggtgtg gtggcaggcg cctgtaatcc  62400
cagctacttg ggaagcctga ggcaggagaa tcacttgaac ccagaggtgg aggctgcact  62460
gagctgagat cacgcgattg cactctagcc tgggcaacaa gagtgaaact ccgtctcaaa  62520
aaaaaaaaaa aaaaaaaaag aaatgcctag aataggcaaa ttaatacaga cagaaagtgg  62580
atgagagctt accaggagcc agagggaagg tgcaatggtt agctgttgcc tcacaagtac  62640
agaatttctg tttggagtga tgaaaaagtt ttggaactag tcagtagtga tggttgtaca  62700
ttatgaatgt aattaatgcc acttaagaat ggttaatgtg cacatgtacc ctaaaactta  62760
aaatataatt taaaaaaaca acaaaaaaaa gaatggttaa aaggggccag gcatggtggc  62820
tcatgcttgt agtcccagca ctttgggagg ccgaggcaag tggattacga ggtcaggaga  62880
tcgagaccat cctggctaac atggtgaaac accgtctcta ctaaaaatac aaaaaaagtt  62940
agccaggcgt ggtggtgggt gcctgtagtc ccagctacta gagaggctga ggcaggagaa  63000
tggcgtgaac ctgggaggca gaggttgcat tgcgccgaga tcgtgccgct gcactccagc  63060
ctgggcgaca gtgctaggct ccgtctcaaa aaaaaaaaaa aaaaaaaaag aatggttaaa  63120
atggcaaatt ttatgttata cattttcatc acacaaaaca aagacacttt ggcagctgta  63180
aagaaacaag actagccggg cacagtggct cacacctgta atcccagcac tttgggaggc  63240
caaggcaggt ggatcacgag ttcaggagat tgagaccatc ctggctaaca cggtgaaacc  63300
ccgtctctac taaaaataca aaaaattagc caggcgtggt ggcgggcgcc tgtagtccca  63360
gctactcggg aggctgaggc aggagaatgg cgttaacccg ggaggtggag cttgcactga  63420
gccgagattg caccactgca ctccagcctg ggcgacagag cgagactccg tttcaaaaaa  63480
aaaaaaaaag aaactagact ctaggttaag gttactgaag taatccaggc taaagatcat  63540
cttctgtttg tccttccagg tgcacactgc cctcttcctt gctttgtgct ccaggatgct  63600
gacctgtgtt gactgattag cagattctta ggccctctgg cttctggttg aatttgacca  63660
atgtggagca ctggcaagtg atccaagagt gagaggaaag tgacagcagg gtagtcccct  63720
ggctcccaat cttcaggttg ctgtgggctg ctgtatccct tgaccaaagg tcacagctcc  63780
```

tgtcaggcag ccttctccac aaagctctgt ctctgtattg tattaatagt aatggcttgg 63840
ccgggcgcgg tggcccaagc ctgtaatccc tgcactttgg gaggccgagg tgggtggatc 63900
atctgaagtc aggagtttga gaccagctgg ccaacatgat gaaactccgt ctctactgaa 63960
aatacaaaaa aaattagcca ggcctggtgg ccggcacctg taatcccagc tacttgggag 64020
gctggggcag aagggtcgct tgaacccggg aggcagaagt tgcagtgagc caagatcatg 64080
ccactgtact ccagcctggg tgacaagagc gaaaatctgt gtcagaaaat aataataata 64140
ataataaaat agtaatggct ccctccgcca ttcctcctag gggaaaaatg gccccaacta 64200
gtctaaggca gggggtagac agcacggtcc atttgtgtgt tttcctttgt gtgttttcct 64260
acatgagttt attagtttaa taattccttt attaagcttt catcaaatta cccagtttga 64320
ccgtgctgtc tatttcctgc cttagactag gatggagaga gagcactaaa tctatgtgga 64380
ggtagagcct tgaggttttg gtagtttgga tggtttggca aacttggccc ctggctctca 64440
gaaaagttct cataaactgg gggagacaag acacatagct tagaaaaaac acaagattca 64500
cactcatagc aagtaatcat agtgaagtcc agtataggct caatttgcaa agtggctgat 64560
agcaggtact taatgcacta attcgtctgt tttcctatgt tggggacaga attgactctt 64620
cttcaagtat gagagaggtt ggaagtgttt ggctagtttc cacagaagac tcagaatact 64680
caagtgtccc gagaaacagt ggaaatagag gttcttggaa atgatcccag aaaacaggtc 64740
taatcaactg ggtgaagtgt caggatccag acagtgactt ataatggctc aacctccaaa 64800
ccagtgatcc tgagataaat gggaacaccc agctgtggat gtgtgccgac ttcagggttt 64860
ttgaagcaat accctgttac atccatcagc tgtcctcctg aacctgttcc ctccctgaag 64920
ccacgtatgg agcaaaaaga gtatatttct ccattacagg ccctgcctca cttatctcct 64980
ccatactact tccccacttt ccttgttttc cccaaaggcc tctctcccac tctggctctc 65040
ccagctacac atatcaaacc tacatctctg ccaggaggca gggtgtctgt ggtagaggag 65100
tgacccacac atttgagatt ttcccgggtc acactggaaa ccctggattc ctgcctggtt 65160
tatttccctt ggattcaatc cataaaaccc tgattggtgt gtaactccca taacatgatc 65220
cttatctctt gggcccagga cccatcatct gaggcctgcc agctgtttca gcccaggctt 65280
tcatgccaag ctctcgaatg gatgtggcca gtaaaataca gtctcctttt ttttttttta 65340
tttaaaggca aaactcaata aatgttagct attattatta ttactagatt taaaaagtac 65400
caatatgctc atataataaa tacgagctgg gcatggtggc tcacgcctgt aatcccagca 65460
ctttgggagg ccgaggcagg cggatcacct ggtcgggagt tcgagaccag cctgaccaac 65520
atggagaaac cccgtctcta ctaaaaatag aaaattagcc gggcatggtg gcgcatgcat 65580
gtagtcccag ctactcagga ggctgagaca ggagaatcgc ttgaacctgg gaggcgtaag 65640
ttgcagtgag ctgagatcgc accattgcac tccagcctgg gtgaaaagag tgaaactctg 65700
tctcaaaagt aaataaataa gtatgaccca cttcaccaaa tttgagtcta aaaggatggt 65760
cacatttctc ctctctcttt tttttgagat ggagtctcgc tgtgtcaccc aggctggaat 65820
acagtggtgc agtctcggct cactgcaacc tctgcttctt aggttcaaac gattctcctg 65880
cctcagcctc ctgagtagct gggattacag gcacgcacca ccacgctcag ctaatttttt 65940
tgtattttta gtagagatgg gttttcagca tgttggtcaa gctggtcttg aactcctgac 66000
ctgatgatct gcctgccttg gcctcccaaa gtgctgggat tacaggcgtg agccactgca 66060
cctgacctct cctctctctt tttaaaaaat tcaaagttca gtttattttt atacctgttt 66120
tactttattt attccttaca taagtaatat gtgcacccag aaaaattcta agaaagtcaa 66180
aaggcctgcc acttttccca acccccaagt ttccctctcc acagatgccc ctcttaccaa 66240
cttcttccat ggacttgaag agagtctatg caattacaga cactgatatg tttttccttg 66300
tacaaataca agttatatat tttggagagt gtcaattctt attgagttgc ctaattcttc 66360
cctttaatta ctcccaaacc tattgaggta tgtgtgtact atcctttttt ttcctttctt 66420
tctttttct cttttttga gacagagtct cactgtgtca cccaggctgg agtgcagtgg 66480
catgatcttg gctcactgca gccttgacct cctggactca agcagtccac ctgtgttggc 66540
ctcccaacag gcattagcca ccgcacctgg tgaggtatag ttttctttct ttttttttg 66600
agatggagtt tcgctcttgt tgcccaggct ggagtgcaat agaatgatct cggctcaccg 66660
caacctccac ctcccaggtt caagcgattc ttctgcctca gcctccctag tagctgggat 66720
tacaggcacc tgccaccatt cctggctaat ttttgtattt ttaatagaga cagggtttct 66780
cctttattgg tcaggctggt atcaaactcc cgacctcagg tgatctgccc gccttggcct 66840
cccaaagtgc tgggattata gacatgagcc accatgctca gggaagtata gttttcataa 66900
ggtaaaattc atccatttta actttacagt ttgatagatg ttggcaatcg tatactgtca 66960
tgcaactgtc actacaatta agatataaaa tgtttccatc accctaaaaa gttacctcct 67020
gccctattac aattcaatcc cctcacctaa cagctctagg caaccactga cctgctttct 67080
gacactgtag ttttgctttt cctagaattt cttataaatg gaatcccacg atatattttt 67140
ttatgcttga ctactttcac ttagcataac gtttttgaga ttcagccaca ttgttgtaca 67200
tatcaatgtc tcatttcttt ttagtacaga gtagtattcc ataataaaga aattgttcat 67260
tcacttacca gttgatggat atttggtttg tttccagttt ggccctatta tgaataatgc 67320
tgccgtaaaa atttgcatac caagtcttta agtaagcatg tgttctcttt tgttcttggg 67380
taaatacctg agagtaggat tgctgggtca tatggtaaat aaagtattgt tactttcata 67440
agacactgcc aaactatttc ccaagtgtct atactatttt gcaaatctca cctacaatgt 67500
tttggagctc tagtttgcct cattcattgt aacagctgga atgtaactgg tggtggaaaa 67560
gagcaataaa gcaaatgtgg caaatgctaa caattggtga atatagatag agtatgtgga 67620
tgttcatttt attattaatc ccatttcttt tttgagacaa gttctcattt tgttgcctag 67680
gctggagttc agtggtgtgg tcatggctcc ctgaagcctc aactgcccag gctcagagga 67740
tactcctgcc ttagcctctg aagtagctgg gactattgat gcataccacc atgcctggct 67800
aattttttgt acttttagta gagacggggt ttcaccatgt tggccaggct ggtctcgaac 67860
ccctcacctc aggtgatcag cccgccttgg cctcccaaac tgctgggatt acaggcgtga 67920
gccactgcac ctggcctaca ttactaattt aaaaattgtg gcaaaatata tataaaacat 67980
aaaatttatc attttaagtg tacaattcag tgcatcagtt acattcacaa tgttgtacaa 68040
tcatcactgc tatctagttt caaaactttt aatcacctca aacagaaact ctgtacttat 68100
taggcaataa ctctctattc acccccttgca ctaaccactt gcaagctgtg gtctactttc 68160
ggtatatgtg aatttgccta ttctagatat ttcatgtaac tggaatcata caatatttgt 68220
ccttttatgt ttgacttctt tcacttggaa taatgttttc aaggtttatc catgttgtaa 68280
catgtatcag agcttcattc atccctttgt atggctgagt aatattctgt tgttgagtat 68340
acaccacatt tggtttatcc agtcatctgg tgatggagac ttctgttgtt tccacttttt 68400
ggctattgtg agcaaagatg ctatgaatat tcacatacaa gtatctgact gaatctttgt 68460
ttttaattct tttgggtata tacataggag taaagttgct gggtcataag gtaattctat 68520
gttgagctct ttggggaacc atcagactgt tttcgatagc agttgcacca tttacatttc 68580
caccaacaat gcagaagggc tccaatttct ccacatcttt gctaacattt gtctttttcc 68640
tttaagaaaa aaaatagcta tcctagtagg cataaaatga cctctcactg tgtttttgat 68700
ttgtatttcc ctagactaag gatgttaaac acattgtgct tattggccag ttgtatatct 68760
tctttgaaaa aatgtttatt caagtcattt gcccttttta tttatttatt tttgagacgg 68820
agtcttgttc tgtcacccag gctggagtgc agtggcacga tctcaactca ctgcaagctc 68880
cacctcctgg gttcacgcca ttctcctgcc tcagcctcct gagtagctgg gactacaggc 68940
acccgccacc atgcccagct aatttttgt atttttcgta gagacagggt ttcaccgtgc 69000
tagccaggat ggtctcgacc tcctgacctc atgatccgct tgcctcggcc tcccaaagtg 69060
ctgggattac aggtgtgagc caccgcgctg ggccttcttt ttctttttct taagttatag 69120
gatatggtac attcatgtaa tgaaatagta cacagctatt caaaaaatgt actaatatgg 69180
tacactctct gagacaaatt taaaaagcaa ggtatagtct gggtacaatg gctcatacct 69240
gtaatcccaa cactttagga ggctgaagca ggaggattgc ttgagcccag gagttgaaga 69300
taagcctagg caacataatg gtatctcata cctatttaag aaaaaaaaaa gcaaggtata 69360
aaataatatg gaaacccaca cacctacagt gaacccattt tcgacaaagg tgccaagaac 69420
atacactggg aaaagacagt ctcttcaaca aacggtgctg aaaaaactga atatccatat 69480
gcagaagaag gaaactagac ctgtatctct caccatatat aaaaatcaaa ttaaaatgga 69540
ttaaaaactt aagtctaata cctcaaacta tgaaactact acaagaaaac attgggaaaa 69600
atatccagga cattgaactg ggcaaaaatt tcttaaatag caaccccaga agcacaggca 69660
accaaagcaa aaatggacaa atgggataat gtcaagttaa aaggcttttg cacagcaaag 69720
aatacactca acaaagttaa gagacaactt acagaatggg ataaaatatt ttcgaactac 69780
ccaggtgaca agggaataat aaccagaata tatatgaagc tccaacaact ctatagggaa 69840
aaaaatccaa taatctgatc aaaaaatggc aaaagatttg aatacacact tctcaaatta 69900
agacatacaa atggcagaca gccacatgaa aaggtgctca acatcactga tcatcagaga 69960
aatgcaaatc aaaactacaa tgagatataa tctcacccca gttgaaatgg cttatatcgg 70020
taaggccata acaaatacag gcaataacaa atgctggtga ggatgtggag aaaagggaac 70080
cactttacca ctgttggtgg gaatgtaaat tagtacaacc actatgggga acagtttgaa 70140
ggttcctcaa aacactaaaa attgagctac catatgaccc agcaatccca ctgctgggta 70200
cctgaaagaa aggaaatcag tgtatcaaag atatctgcac caggcgcggt ggctcatgcc 70260
tataatccta gcgctttggg aggccaagac aggtggatca cctgaggtca ggagtttgag 70320
accagcctgg ccaacatggt gaaaccctgt ctctactaaa aatacaaaaa ttagccaggc 70380
gtggtggtgg atgcctgcaa tccccgctac ttggcaggct gaggcaggga gaattgcttg 70440
aacctgggag gtggaggttg cagtgagcaa agatctcatg actgcactcc agcctgggag 70500
acagtgagac tccgtctcaa aaaaaaaaag gcgatatctg cactcctatg tttgttgcag 70560
cactctttat aatagccaag atttgcaagc aacctaagta tccatcaaca gatgaatgaa 70620
taaagaaaat gtggtacata tatacaatgg agtactattc agtcataaaa aagaataagg 70680
tcctgtcatt tgcaacaaca tgaatggaat gggagatcat tatgttaagt gaaataagcc 70740
atgcacagaa agacaaacat cacatgttct cacttatttg tggtataagt gagaacaaaa 70800
caattgaact cgtggacata aagagtagaa tggtggttat cagaggctgg gaagggtagt 70860
gaggggctgg ctaggggagg tggtgatggt tcatcagtac aacaaaacag aaagaatgaa 70920
taagacctat tatttgatag tacaacaggg tgcctatagt caataataac ttaattgcat 70980
attttaaaat aacataaaga gagtaattag attgttagta actcaaagga taaatgcttg 71040
aggggatgaa tacccatgtt ccatgaggta cttatttcac attgcatgct tgtattgaaa 71100
catttcatgt accccataaa aatatatgct tactatgtac ccacaaaaat taaaaatgaa 71160
attttaaaaa attttctttt ttcttttttc aagacaaggt ctcactctgt cacccaagct 71220
ggagtgcaat ggcatgatct tggctcactg ccatctctac atcctggact caaatgatcc 71280
tcctgcctca gcctcccaac tagctgggac tacaggcaag caccactatg cttggctaat 71340
ttttatattt ttgtagagac aggtcttgcc atgttggcca ggctggtctc gaactcctgg 71400
actcaagtaa tctgcctgcc tcagcccccc aaattgctgg gattacaggc gtgagccacc 71460
acgcccagcc cccaaaaaaa ttttaattaa aaaaaaatat gaaggccggg cacggtggct 71520
cacgcctgta atcccagcac tttaggaggc caagacaggt ggatcacgag gtcaggagat 71580
tgagaccatc ctggctaaca cggcgaaacc ccatctctac taaaaataca aaaaaattag 71640
ccgggcgtgg tggcaggcgc ctgtagtccc agctacttgg gaggctgagg caggagaatg 71700
gcgtgaaccc gggaggcgga gcttgcagtg agccaagatc acgccactgc actccaggct 71760
gggcaactga gcgagactct gtctcaaaaa aaaaaaaaat atatggaaac atgctaccac 71820
ttaagaagtt atatacaaac atacccttt atgcatagat gatattagaa agggtatgta 71880
gcagacaggt cattgcagtg cctctggaag gagaacactg aggacagcag tgggagacag 71940
ttaattttat cagtttacct cttcttcttc aaaaaaattt ttttttgggg ggacagaatt 72000
ttgctcttgt tgcctaggct ggagtgcaaa tggcgcagtc tcggctcact acaaactctg 72060
cctcctgggt tcaggcgatt ctccttcctc agcctcccaa gtagctggga ttacaggtgc 72120
cctccaccac gcctggctac ttttggtatt tttagtagag acggagtttc accatgttgg 72180
cctggctggt ctcgaactcc tgacctcaga tgatctgccc acctccgcct cccaaagtgc 72240
tgggattaca ggtgtgagcc accgcacctg gcctattctc tttaagtttt ttttaccatt 72300
cacttcaatt tcacgtgtat gcgtgtgtgt gtgtgcacat atatgttagt aatggaaaaa 72360
acaccatttt tcctttcttc tgattaattt cagaagactt tctggacaag gaaaggataa 72420
ttctaaagta ttcagaagag acaggttttt cctagctatg ggagagggga gaggcttagg 72480
acagggcttc agaataagtt ttgagggtca tcaaaaatgg tagaacaggc cgggcgcagt 72540
ggttcacgcc tgtaatccta gcactttggg aggccgacgc gggtggatca cctgaggtcg 72600
ggagtttgag accagcctga ccaacatgga gaaatcccat ctctactaaa aatacaaaat 72660
tagccgggtg tgtggcgcat gcctgtaatc ccagctactc gggaggctga ggtagaagaa 72720
tagcttgaac ctgggaggcg gaggttgtgg tgagctgaga tcgtgccatt gcactccagc 72780
ctgggcaaca agagtgaaac ttcgtctcaa aaaacaaaac aaaacaaaac aaaagtagaa 72840
caggcagctt caaaacccca tccctccatt agggcaatga ttaagctgca aaaactgtca 72900
gaatctactt ttttggaatt ctggaatcta ataataaaaa acctgacaac aaccagagga 72960
attcttttct tttctttctt tttctttttt tttttgagac agagttttgc tcttgttgcc 73020
caggctggag tgcaatggcg tgatgtcatc tcactgcaac ctctgcctcc tgggttcaag 73080
ctattctcct gtcttagcct cccgagtagc tgggattaca ggcatgcacc accacgccag 73140
gctaattttg tattttcagt agagacgggg tttctccatg ttggtcaggc tgatctcaaa 73200
ctcccaacct caggtgatcc tcccgcctcg gcctcccaaa gtgcttggat tacaggccgg 73260
gcgcggtggc tcacgcctgt aatcccagca ctttgggagg ccaaggcagg cggatcacga 73320
ggtcaggaga tcgagaccat cctggctaac atggtgaaac ctcacctcta ctaaaaatac 73380
aaaaaattag ccgggcgtgg tggcaggcgc ctgtaatccc agctaatcgg gaggctgagg 73440
taggggaatc acttgaaacc aggaggtgaa ggttgcagtg agccgagatt gtgccactgc 73500
actccagctg ggcaacagag cgagactctg tctcagaaaa aaaaaaaaag aagaagaaga 73560
agaaccagca ttaaagaggt ggaaagaagg ggaagaaaat ctcacaaagg cacagccaga 73620
aatatcaaga aaaaaacaag acagtaaaat accggggaaa cgatgagttt gggaggaatg 73680
caggatccca gggtagggaa ccggaagcag agaagtcaat tagtgacaga gcacatgtaa 73740
aaaaaaaaag acttcaagat atttcaatac atttattatt acttttaaac atttactcat 73800
tataagaata attttaaaat tctgccattc agagacaaat tccattagca tcttggtata 73860
tttccttcca atcttttttc tctatgtggt tttcttgcat attttttccc tacaaaaatt 73920
ttacaaacat tcttcccatc tgaattgcct ccacattttt agtcaacaaa tttgagacca 73980
tactatacat atcgtctcat atcctacatt ttgaaactta acataatatt ctgagcattt 74040
cttatgccat taaaaagcat tatttattgg atgcaaagca ttccaaaatg tatacatcag 74100
ttttaaaaca acatgagaga aaatttaaaa tacttctaag tttatgccta taatctcacc 74160
cacaccatca actgatttca cattttagtg cttcttttca acttcagtct ttaggaacat 74220
tattgctttt agataattga ggtaatagga aaggtatggt tttgaatatt gtttttcttt 74280
cacattattt tggaaacata gtttcacgtt tcttcatatt ctgatagatg caagctgttc 74340
tgtgatgtta gttaaatgtt tgttgcgatg ttaaattcag taattatcca tcagtgggtt 74400
gtttctagct gtcttttttt tctttttttt tttttttttt ttgagatgga gcctcactct 74460
gtcacccagg ctggagtgca gtggcttgat ctccactcat tgcaacctct gccccccagg 74520
ttcaagcaat tctcctacct cagcctccgg agtcgctggg attatgggcg cgcaccacca 74580
cgcccggcta atttttgtat ttttagtaga gacagggtct caacatgttg gccaagctgg 74640
tctcaaattc ctgacctcaa atgatccacc cacttcagcc tcccaaagtg ctgggattac 74700
aggcgtgagc caccgcccct agccttccag ctttctatta ttttaagtcc cactgactta 74760
atatgtgact taaaatatga ctttcaaata tatatatatt ttttgtttgt tttgttttgt 74820
tttcagatgg agtgtcactc tgtcccccag gctggagtgc aatggtgtta tctcggctca 74880
ctacaacatc tgcctcccag gttcaatcaa ttctcctgcc tcaacctccc gagtagctgg 74940
gaccacagga gcaggccacc acgttcagct gatttttgta tttttagtag agatggggtt 75000
tcaccatgtt ggccaggctg gtctcgaact cctgacttca agtgatccac ccacctcggc 75060
ctcctaaagt gttgggaata caggcatgag ccacctcacc tggcctaaaa tatacatttt 75120
aataatggtg acataatttg gtagccaaag aaactgcttt gaatgttcca ggctattggg 75180
ccattgatgg ggaattaaag taggttgaaa tttaatcagt tgatattact ttgtaaggct 75240
aatttttttc ctttttgaaa tgatttcatt aatagctgac atatttattt tgcaacaagc 75300
tacttacaat aaaggaataa tagtctattt atgtattact tgtgattggc cctttactgc 75360
aaataacaaa tgccactaaa tgcaagcatt tacaaaaggt ttacaatcca gtctacaatc 75420
atcagaaacc tgctctacaa atcactgctt tttttaaaaa gtatttaatc attttttttaa 75480
ttgacaagta aaattgtgaa tattcatggg gcaaatagtg atgttttgat acattataat 75540
gtatactgat cagattgggg caattaacat ccatcatctg gaacatttat catttctttg 75600
cattgggaac attcaatttt tttaaaaagc tggttttcat ggggaagaaa accacactta 75660

```
ttaatatttt ctgtgtctgg tcaagtactc tttatatata attaacagtc tcagctgggt  75720
gcagtggctc atccctataa ccctagcact ttgggaggcc aaagagggag gattatttga  75780
gccaggagtt caagaccagc cttggcaaca tagcgagaac ttatctcaaa aaaaaaaaaa  75840
aaaagctgat gtggtgacac atgcctgtca tcctaattac ttgagtgggt ggattgcttg  75900
agcccaggag gtcaaggttg cagtgagccg tggttgcacc actacactcc agcctaggct  75960
ggacagagtc ttgctctgtc gggatctcca ctcactgcag cctccacctg ccgggttcaa  76020
gtgattctcc tgcctcagcc tcccgagtag ctgagattac aggcatgtgc cgccacacct  76080
ggctgatttt tgtattttta gtagagatgg ggtttcacca cattgcccaa gctggtctcg  76140
aactcctgac ctcaggtgat ccacctgcct cggcctccca aagtgctagg attacaggct  76200
tgggccacct cacctggcct tttttttttt tttttttttt ttagtcttcc cagacactga  76260
taatagatag gcatctttca agctgatccc cactcgagtt tataggtggt ttgacagctg  76320
cctctcctca acgttgcatc tgttatgatg gtttaattgt tgagtcagag ccagtgaaca  76380
tttatatttc ctaccaacta ccttgaagta aatatcttgg gagctgctgg cctggaaagg  76440
ttgtgagaag gctcctggct tcttctttgt ctcacttaac atttatttta aggtcaaagc  76500
aatatctgca cactactttc tctttggtcc cccagataca gtgagcccct tggtccagtc  76560
ctctccatgt cctatatgta gtttcaccct agatcagatt ttgtgtcttg gttctcagac  76620
caaaacggga acactgcatg attgttttct ggagcccatc catcgtggat gccagccttg  76680
tatccacata ggagttgaag ctccttttgt attgtatttc ctgaatcacc actaagcgaa  76740
tacagtcttt tctcatctag gctggggatg ttgaaaatgc tcagccttct atagaaattc  76800
ttaagttctc attaacacat ttcacaaaag gaaatgagta ttatttgaca tggttcagat  76860
ggtgttttaa tggtcagcat ttgaataaat acttgcatta taatttgtcc ctttaaaaaa  76920
gttgtagctg aatgtaactt attaaatgtt cagtggaatg taaaaatata tatatattaa  76980
tacatacaga tttttttttc ttttggatta tttcactggg ttgaattcct aggtgagaca  77040
ctgggtcaaa gcataccagc tcttgctaag tgttgcctaa gtgtgtttct acaaggatta  77100
tatcagttta cttggccact agccaggtgt gattgcacct gtttcctaaa gctttgactg  77160
gcattaggta tttaattgct gcttagctat taattgggac cacactatac atacagtctt  77220
taatttgcat ttccttaatt actaagaaag ttgagtcttt taaaaaaatg tttattgttt  77280
gtatttcctc ttaggtgcct actcaattca aagcaacaga catattttga gtgcccacta  77340
tgtgccaggt agtatgtgct accctcaagg atgagtgacc tagtgaaaat gaccatttgg  77400
gatagggtga gggagccaga atagtacaga aaatatatga ctgactgtcc tccacaagta  77460
gaagcacaat actggcaggc agtttgggca aagtttttg aatgaaagac aaagaaggaa  77520
gggcctgact ctgaaatata ttaggctttt gcagggcaag tgactttaga gctagagcta  77580
gagttaagat ttgtccaggt gagaaaatga tgtatggggg gagagggaaa gatgcgtaga  77640
gaggtaaagg ggtaagtatg tagagttgtc cattatggct acaatgcgga atgctggggg  77700
gagagggaaa gatgcgtaga gaggtaaagg ggtaaaagta tgtagagttg tccattatgg  77760
ctacaatgcg gaatgctggg gctgagggat ggtgggattt tggctggaaa tgaatggtca  77820
gggctaaact caggaatctg atctttgtcc tgaggattat ttttgttctt aatgaggaat  77880
gacatgagct catgtgtttt agaaagacct ttctggcagc aaatgagagg cagatttgga  77940
gacactggag tgtatgaaat gagcttgttt gtatccttag ccatttacca agggtcgaag  78000
```

```
ataagactat gaataagatt tttgtgtagt atgcacatta accctttatc tgacctactt  78060
aaaacaacat ttcaggccag gcacagtggc tcacgcctgt aatcccagaa ctttgggagg  78120
ccgaggcgtg tggatcaact gaggtcggga gttcgagatc agcctggcca acatggcaaa  78180
accccgtctc tactaaaaat acaaaaatta gccgggcgtg gtgtcgcacg cctgtaatcc  78240
cagctactct ggaggctgag gaaggagaat cgcttgaagc cgggaggtgg aggttgcagt  78300
gagccgagat cgcgccactg tactccagcc tgtgcaacag gagcgagact ccatcgcaaa  78360
aaacaaacaa acaaacaaaa aaagaaggta aaaatgtcgc ttttttgta aataattact  78420
gatgcttact caactcttta cattgtataa tgctctttat ttatttattt ttaaattgag  78480
acagagtctc actctgttgc ccagactggt cttgaactcc tggcctcaag tgatcctcct  78540
gccttggcct cccaaagtgc taggattaca ggcataagcc atcatgcccc gccaatgctc  78600
tttaacatat attatttcat ttgatcctca taaacatcct tctgaagtag ttatctccat  78660
tgtacagatg agaaagctga ggccatgata tgtttgatga tgtcttcgcc aaggttacct  78720
aggtagtaag tggcagagat aaaatctgaa tataggcatt ctgatgacca tgccacctcc  78780
agaagaaatg acaggacctt gtgtcctata gaagaatata acttgacctc acaatttcta  78840
gcctgaaaaa ttatataaat agtggctgga aaaatcagcc tattttggag gtagataaca  78900
aattctgttt ggggtgtgta ttgctaagga tgctagcaga acataccggt agagatgtcc  78960
aacaggcagt tggaaatagg gagagaaaga agttgggttg agaactcata gacacagaag  79020
gcagctactt ggcaccaggt aatacaagtg attggtgttc tataaacttc caaagcctgc  79080
tcagttattc atctgctcac accatcccat gcttagcgct tcttcctcta tgttgaggct  79140
ttcaggaggg ctactgggga aaaaaaacaa aacaaaacca gtgaccacac aaaagatagg  79200
cttggagtat ttatcctgga gaataaataa tgtcactcag gtttacatgc caaggatttc  79260
atccattcaa tcacttgcgc aacaaatatt acctgggtta tgctcagggt taggagaatg  79320
atgaaaaaaa cagacatatt ccggcagtgg ctcatgtctg taatctcagc actttgggaa  79380
gctgaagtgg gcagatcact tgaggtcagg agttcaagac tagcctggcc aacatggcga  79440
aaactgtctc tactaaaagc acaaaaatta gcaaggcgtg gtggcacaca tctgtagtcc  79500
cagcactcag gggactgagg tacgagaatc gcttgaactc aggaggcaga ggttgcggtg  79560
agccaagatc aggccactgc actccagcct gggcgacaga gcaagactct gtctcataat  79620
aaaaaatttt aaaaaataga catagtccct gcattcatgg agctcaagaa ctagtaggaa  79680
aaacaggcat tgatcaagaa atcacaaaaa caactaatta taaactctca ctgaagaaaa  79740
gaaataccat gctctgagaa cagtttatat aaaataaggg taccagacca agtccaaggg  79800
tcaaggaatg tttcctctag aatataattt ctgaagattt ttcctcttct tttttctttt  79860
ttgagacaga gtctcgctct gttgcccagg ctggagtgca gtgacacaat ctctgctcag  79920
tgcaacccac gcctgccaga ttcaagcaat tctccctgcc tcagcctgcc aagtagctgg  79980
aattacaggt atccgccact acacctagct aatttttgta tttttagtgg agatggggtt  80040
tcaccatgtg ggccaggctg gtcttgaact cctgacctca ggtgatctgc ccacctcagc  80100
ctcccaaagt gctgggataa caggcgtgag ccactgcacc tagcttttt tttttttttt  80160
tgagacagag tctcactctg tcacccaggc tggagtgcag tggtgtgatc acagctcagt  80220
ggcacgatca cagctcactg cagccttgac ctccctggct caagtgatcc tccctcctca  80280
gtccctgagt agctgggacc acaggtgggc gctaccatgc ccagctaatt tttgtacttt  80340
ttgtagagat ggattttcac catgttgccc aggctggtct caaattcctg ggctcaagca  80400
```

-continued

```
atccccccac ctcagcttcc tacagtactg ggattacagg cgtgagccac cgtgcccagc  80460
cccgagtgtt cttctttccc tcttccacat acacctcctc caagcctcac cattaaacct  80520
cacagggaaa gacaatgtta aatatcttca cagagaaatc caggactgag tatatattct  80580
ccatatgcac ttgtaaacct cccataatga ttcaccttgc catttccatg tgtctagtcc  80640
acaatatcat tttatctaca ttatctggct tgcatactaa tcacaacctt gtgacataag  80700
caggcgagta tgactatatg catttttttc tgaagtagaa tgtgacaaag gctaggtaac  80760
ttgcctaaaa tcacatggct cattaatggg ggtgctggga cttgaacttg ggtcttgtaa  80820
gacctagatg gcattattct tgtaatattc attcttttat ttattcattc atccatagac  80880
atgtattgat cacctttgga ttagctgtca ggctatatat ggagccatca ggaaccactg  80940
aaggtttttt tttttttttt tttttttgag acggagtctc actctgtcac ccaggctgga  81000
gtgcagtggc acgatctctg ctcactgcaa gctctgcctc ccaggttcac gccattctcc  81060
tgcctcagcc tcccgagtag ctgggactac aggcgcctgc caccacgccc ggctaatttt  81120
ttgtattttt tagtagagac ggggtttgac ggtgttagcc aggatggtct cgatctcctg  81180
acctcatgat ctgcccgcct cggcctccca aggtgctggg attacaggcg tgaaccaccg  81240
tgcccggccg aaccactgaa ggtttttaag caggaaagca gagctgtttt ctggatgagc  81300
aaacagaaag tagtggtttt ccaagtacag tctgagacaa cctataggac cagaatctct  81360
gcagttgagg ctcaggaatc tggtaatcag ccaggtatag gaactctttt ctgattgcaa  81420
tgcagtgaag agcagaagca ctgtattaga gaaagaggca gtgcaaccag gtaacgtgac  81480
caggtgagaa gtgatgaggt acagagacaa agagatgcac ttttgagtca cttagatggc  81540
actgatagga cttccactac accctcgcat agacagtggc tgaggttcag gaaatagagc  81600
tggggttcct acttggatcc tctggctcta gagctttact gcacatagcc atttataccc  81660
acatcttgat tttaattatt ttatatctat gtttcttagc actttttgca aatttccacc  81720
ttatctcaaa ctgccctcaa gccttgtatt tctccttcgc tttcataaaa cctaggaaag  81780
aaataaggga cagccaagta aaacttttaa aagttttaga acatttattt ctttggggct  81840
ggttacacag gcgagaaaga agtagatttg gttagggaga gaaaacaaca ggccttgggg  81900
agatacactg gctctccccc tccctaaacc ctaagaggcc tccaggaaac ctgaagacaa  81960
taattccaga agcccagagg gtgaccccat ttcctctctc catggttatt actgtcagtc  82020
tggagcagtt caggaattca ggaaactata aagaaaccac aacagcctca acaacccaaa  82080
catcaacatc aacaacctca acaataaaac tccttaaaat tcatctcctt ccacccactc  82140
acaaccgcag actcgaagct aggaggtgga agggactaca gaagctctgc gttgcccagg  82200
ttagtatttg ctcatcacag gcctgggttt cccaggatct cagggagcct ggaaactgac  82260
gcctccattt ctgggtggga gcaccaaagc ctaaggacac ctttcctctc tcttcactgc  82320
taagcaggtc aagattaaag caaaccgagg caaaggccac ggttgacagt tccaagggaa  82380
cccgcaaggc cgcacaggat ggggtggacg ttttacggga gaaaaggctg ggggaagtggg  82440
cgggcgatgg cctacgacgg gacttggggc ggggtgtgcg aaacgcctgg caggcgggcc  82500
cttgagtatg accaatcaga atgcggactg cgtcccaggg gcggagcaga ggcgtatctt  82560
ggtcgagatt ggatagcggc ggggcgcagg aaagaggtcg cgccagcccg ggcaggcagc  82620
tttgcaagtc cgcgttatat atcgcagtgg ctgcgcccgg gatagctggc tgcgccgccg  82680
cgcacatgcc taggttcgac gccctcctcc ctttgcccag gagttccttc tgtcccggct  82740
```

ctgttccgtc tcgccccgag gttcacgcca tcctcggagc cccagccttt cacccagcgc 82800
ctccaagctt tggaccttga cttctgcaaa actagatggt cacagccatg aatgtctcac 82860
atgaagtaaa tcagctgttc cagccctata acttcgagct gtccaaggac atgaggccct 82920
ttttcgagga gtattggtga gactttggga gagggaaagg ccatgccagg gccccggggc 82980
cggggcgcga gggggtggca ttgaatgccc acaatgattt tcttacagag cagagttatg 83040
ggactccctt gtactggctt cacactacct ttgtccgagg tgcaggtagt atgtggcacc 83100
tcaaagagat tagagctgaa agcaagcaag cagaaataag aggatgaggg agaacgtgga 83160
aatatacaga agtcaaagag agcgtgtagt gagaagggtc ttggaggcgt gaggttgatc 83220
tgaagcctta ctagatgact tccccgtcct ttgtggctgt gtgtgcgcgc gtgtgtgcac 83280
agtgcagggc ccgggggaca gcctgccctt tacaattatc ccatcgttcc ccaggtgctc 83340
caccgttcct gctgtggaga aggaggcgaa gtcagagagc tcttccaagc tttccccagg 83400
aagagctctc tggctttgcc ttaaagctcc ccagaggttt tggaggctga ctttatgctc 83460
caaccaattt gccatacccc agccagggag aagctattgc cacattcttc ttacgccaca 83520
gccctggtat gcttctagga gccccaacca gggagaagct attgccacac ttcttacacc 83580
acagccctgg gctgcttcta ggcgcgggcc agacagccgt cacccacctc taaccccact 83640
gagagagcaa taatcacaga aaccttggac atagctcctg ccctgtgcta gatactttgt 83700
atacgttaat acccccagga gagatgtagt attcgcgctc tacaaatgag gaagccaagg 83760
ctcagagaat taagttggtt tttccaatgt cacatagcta gtaagtggca gaactgggac 83820
tccaacccag agcactcacc tggagagatg agtgggcatt tctctaatca gcacccaccc 83880
atgagcccat ccctctgcct tctgcttgcc agggcaacct cattccccat agccctgatc 83940
tacctggttc tcatcgctgt ggggcagaac tacatgaagg aacgcaaggg cttcaacctg 84000
caagggcctc tcatcctctg gtccttctgc cttgcaatct tcaggtaaga ccccatccca 84060
ctccctgcct cttctctaga tcttagacca ccattctatc ccttgaagct ttcccgattg 84120
catcaacctc catcctgtcc ccaagttgcc ttgtaacact ctccccatct cattctcggc 84180
tttagttccc ctcccagcct tcaccctctt ctgttatatt atcctgtttt ccttctcttt 84240
tagaccccta cctggtggtc tctgctttgt ccctcttgcc ttcgtagagt ctgtactcgc 84300
aactaatttc tccagcctct aatagtgtca cctcctaaca ccctctctca agaccctcca 84360
ataacttccc catattttct cccccaaact ccttcagtct tcccctatcc ctctacacat 84420
ctcctcccag gctcctaacc cctcccaaga accccattcc ttaactcaac tttcagtccc 84480
atccccctgc attccctgat ctttctccag ccctcgtctc ctctagacta ctgattggat 84540
ctaccagatt ggcttcagga tctcaggagc tttgacccac cccctgtgga caggtgggga 84600
ggtggtagag cttggaacac agtaacctgg ccaagccggg ggaagggtgg attattggtg 84660
cctggggatg acacttacac catcttcctt tgtcccattt cagtatcctg ggggcagtga 84720
ggatgtgggg cattatgggg actgtgctac ttaccggggg cctaaagcaa accgtgtgct 84780
tcatcaactt catcgataat tccacagtca aattctggtc ctgggtcttt cttctcagca 84840
aggtcataga actcggtgag tggcaaagct ttgtctttct ggtgccttgt gaactgcatc 84900
cttcctcagg gccctccctt cacccatccc atggagggtc tctttcctac ccttgggtcc 84960
caataatacc tctcacccaa gcccctctac agattctctg ccacaaagac ccccttccct 85020
cccctgagaa tttctcccgt gtccctacat ccagtgcaga gggtggtccc agcactgggt 85080
ggtatgccaa ctatgactct ccatctccca ggagacacag ccttcatcat cctgcgtaag 85140

```
cggccactca tctttattca ctggtaccac cacagcacag tgctcgtgta cacaagcttt  85200
ggatacaaga acaaagtgcc tgcaggaggc tggttcgtca ccatgaactt tggtgttcat  85260
gccatcatgt acacctacta cactctgaag gctgccaacg tgaagccccc caagatgctg  85320
cccatgctca tcaccagcct gcagatcttg cagatgtttg taggagccat cgtcagcatc  85380
ctcacgtaca tctggaggca ggatcaggga tgccacacca cgatggaaca cttattctgg  85440
tccttcatct tgtatatgac ctatttcatc ctctttgccc acttcttctg ccagacctac  85500
atcaggccca aggtcaaagc caagaccaag agccagtgaa ggtttggaga gaacaatgaa  85560
gctccaggct ctctcttctc cagggcacca agaggctggg cttagttttg ggagaatgat  85620
taggttgcct tacctgcatg gtttccccag aggatgtgtg ccccaaggtg gctggaattt  85680
ttgacagaca agaagggtga ccttgggatg gggtgtggt ctgttacttt aatgtttctg  85740
tttttaatgt gaaggccaag caggccctgg gatgggagtg gggcggagga gggtcctaag  85800
agctgattat ttaatttcta tccagaaatc tttcttcttc ttgctctgtt tttttaaatt  85860
aaagatttca acaaaatttt gagagttggg ggatttgggg ggaaagaggg ctgctgtgat  85920
ggcaggaggc tgctaccaag gggatgatct gcaggtggga cgcctgaggg tgtgtggaag  85980
ggtgagaggc acacacacag acactgaaag aatcctaggc ctggtaggca cttaacaaat  86040
gtctgttaca gaccagaatt ttattgctgt tagagaccca agcccctcat aggaacagtg  86100
agaaacaggt gcagaaaggc ggagtaactt tatctaaagt cataggctcc ctgaatagca  86160
gagctgacac ctacaaggaa gcgttggaga ccagatctac cagctagcct ccctgagacc  86220
acgaggtggc gccgcagcac cggctgtggc cgatgccagc caggtagccg gtttcccacg  86280
tccccgcac gcacgcacct ctttgctgca ggaatcccgg gctgccccga cctggagtag  86340
ggggggtggt gagtgggact gagtccctag aagcctggac cctcacttcg ttcctgtaca  86400
tccagctcgc ctgtagacag tgggggagga tgaagggaag aggactcaag cgcaactttg  86460
aatcatcacg ccttcgacag tccgcgcacg tttatttcat ttatctttga aaacgaggga  86520
ggggaagcct ggagaaggcg ggatgggcca agggtgagtt ggcccccggg gagctggtcc  86580
ctgttcctgg ctttagtccc aggggcgcgg tctgtgtgta gggcctagtc cacccctcag  86640
ggctgggagg ggaaggccct ctcctgagcc ggtgcccccc agctgcccaa acacccccttt  86700
cagaccctgg ggcgggagca agccagtcaa aatgacccca gtccgcggag gctgtgaatc  86760
gttgccccccg ccctcgggga tgatctacgg gcggggccgc tcatacgggc ctttccacgg  86820
cgtactggca cggactaagg ttggctgccg ggggcggccc gtgcacagcg gggtagctga  86880
aggaggcgtg ctgtttggct ttgagccgca ggctggccag gctcgagtta cacgggtccc  86940
gatagacgta gggggaagag gcggcagccg cggcggcggc ggcggccgag gcataagggc  87000
aggacacggc cccggaggac acggcggccg gagccagccc ggggggcccc ccgcccaggc  87060
cctgcagggc cccaggccct ggcacggtgc ccggggcagc cgcggcggag ggcaccatgg  87120
aggcggcgat ggagctgggt ggcgagaaga cgggctgcga agccagaggc cccacgttga  87180
ccgagttgaa ggcgaatgga aaggtcttgg cggcgagcgg cggggcaaga gccttgggcg  87240
gccagttgcc gtacgagtag ccggggtaca cctcctcgta gggcggcacc agccccccga  87300
gcggcgccgc gaagctgcct ttgcatagct cggcctgctg gctgcgctcg cgcttccgcc  87360
atttggcgcg ccggttcttg aaccacacct gcgggcacgg gagaaaggcg gtcagggccc  87420
ggggccgggt cccagcggct gaagggcggg ccaccccgac ggggcttcca gccggggccc  87480
```

-continued

```
tgcggtcaat aaacgagatg aggtggctag agacggggtg ggagggaagg agcgcacgga  87540
gtccggggtc ggagaacaga aggcgcgggc ggctggaccg agtcatcggc gccagggtct  87600
ggcgggacag taggatgggg ttgaggaggg gtggtgaggg gaaggagaga cggtgtcagg  87660
gccgaagaag cgcgcggtcc gagtagtagg gagcagtggg agcagaggct ggaggttggc  87720
gggcaagaga ccgcgtgggg ctgcggccgg gagccagggt ccggggtccg gggtccgagg  87780
gagggggcag gtggggtgga accgctggcc tccgggtcgc aggctgagcg cggagggccc  87840
gcgcgggtgc gagtcgcggg tctggagagc atacccgcac gcgggcctcg gtgaggttgg  87900
tccacacggc gatctcctcg cgcgtgctca tgtcggggta gcggttcctc tggaaggtcg  87960
cctctagctc ctgtagctgc tggctggtga agtgcgtgcg ctgccgccgc tgcttctttt  88020
tcagcgaacc gtcctctggg gagccgccgg gcagcgaagc cgaggccttt tctgagtctg  88080
ggggccaggg tgggggcagg tcacagagcg cccaagccag cgcatattct ccggctcggg  88140
gacctcctaa gccactcgct ggctcccacc ggggctgccc agccggggtc ccacccgcac  88200
tggggatgaa gctgttatgt cctgcacccc cggaaggggg cgcgcttacc gctgtgctcc  88260
tggcccttgc agccgtgctc tgggagctgg gggtgcggag tgccagcgtc tgacagcgac  88320
agggcagggc tccgggcctc tgcctcgctg agcaggccga actccatgga gggagggctc  88380
tggaggcgag agaagacaca gaccagggta atgggggtaa aatctccggc ttagctaggt  88440
cccagcagcg tttcctcgta aattccctgg cgcctttctc aaccccagcc gtaaagctgg  88500
ggctgcgtgg ggctccttag gatagaatcg ggaaatagca tcctaaggac gcagaggtgc  88560
atgctgagag gttctctgca tagatatata aactagactt cgtttcgttt actgctggga  88620
actagaactg tgccaggtat acagttgggg ttcaatattt attgaattaa taaaaatgta  88680
gactataggc cgggcgcagt ggctcacgcc tgtaatccca gcactttggg aggccaaggc  88740
gggtggatca cctgaggtca ggagttcgag accagcctgg ccaacatggt aaaatcccgt  88800
ccctactaaa aatacaaaaa ttgctgggcg gggtggcacg tgcctgtaat ctcagctact  88860
cgggaggctg aggcaggaga atcgcttgaa cctgggaggc ggaggttgca gcgagccgag  88920
atggtgctac tgcactccag cctgggtgac agagcaagat gctgtctcaa aaaacaacaa  88980
caacaaaatc tacactatag cacgctacat accctatact acatctgcaa aaacttaaaa  89040
tccttctcac ctgaatgctt agtatccccc tatactcata catggtcctc agccaatcat  89100
acctgagaca cagaccagat gtctgttacc cattctcctt aggacagatt gtattttgaa  89160
ccagacctga tatttctccc ttaagaataa tgtatactta ctgtgagcct ttacctcatt  89220
ctctctcccc tcacaagaat acctcaagta tgatcatcct ttttctgctg aggaaaccgt  89280
aacttgaagg aacttgatga ggctcacaga gcttgtaagc agtgggattg agatctgaac  89340
taggtctgtg agactcctaa tgctttttct ttgtttgctt tttatttttc ttttattatt  89400
attttatttt tctgatccag tcaactcaga acgcttgttt tctcacactg tgctttctgg  89460
ggccttccct cgagattcgc tcagggactc agctgcggtt ctagcctggc cttgcttggg  89520
tcggcttcag ctagggcagc gctgctttgg tctgtttcgt ttacgacttc tttctttttt  89580
ttttttcctt cttttttttt ttttttttga gatggagtct cgctttgttg cccaggctgg  89640
agtgcagtgg tatgatctcg gctcactgca acctccacct ccagggttca agctattctc  89700
ctgcctcagc ctcccatgta gctgggacta caggcacgtg cccccacgcc tggctaattt  89760
ttgtattttt agtagagacg gggtttcacc atgttggcta ggctggtctc gaactcctca  89820
tcgcaggtga tctgcctgcc tcggcctccc aaagtgctgg aattacaggt gtgagccacc  89880
```

-continued atgcccagcc tgttttgttt attatttctg aagagatttc atttgaaaga aggtaacaag 89940
atcaaacaca agtataaaaa ccactgggtg cttgggccgg gcctggtctc atgcctgcac 90000
cgacacacac tgcatcccac cagtgactgc tccactcatg gacagcctct accaagcctg 90060
ctccaggcca taggcaggag cttcattaga ccaccttcct actcatactt cctttcccaa 90120
acttagcctc acattgccca ggagcctccc agggtccttc tccaagtttc ccccgcaggg 90180
tccccttttc tgcctgctct cccaggaccc ctctgctgcg aggaagggaa atgggcaata 90240
ctggggctca agactctggg tgccttttgg ttggaggaga acagaaggag gctagggaca 90300
gagggaaggg gtagagagct gagtgggagg ggcctctctg cctctctcac cccttcccca 90360
ttaacagggg cttaatgcag gctgcacagg atggcattaa tgtggtggat tagcctagat 90420
tgagatgtgt gtcacttggc tgctctggat ttattaggag cctttctcag ggaggtgcag 90480
atgggcagca gcctgtattt gcacatggta atgccccctt caacagctca gagatcacag 90540
ctgtgccccc actccccacc ccacctctca agccaggttg ggagtggaac cgaggtcaag 90600
gcaggaggtt gagaaagagt ccctgctctt tccacaggca gaggggtcta gatcttggac 90660
cttttattgg gtgtgaagag acagggctgg agggaaccca ggacaggaga aaagtcaggc 90720
cagaactgga ggtgtgctca gcttacttcc ccttccaggt cgggtcaggt caggggggttt 90780 ggagctggaa aactttggcc aacaatgctc tgatggaagg gagatgtccc tgagaaggaa 90840
ctatggtagc cttggctggg aagatgaggg aggaagggtt agaactgaga gttggaaaaa 90900
ggggtgctct gaagtctccc cttacttcat accccttact tcatacccaa gatgcccttg 90960
aaatgcaaat catccccctg acttttccag aggccatgga agcaacatgg agctgggaaa 91020
aaacccagag aggggtttac ctgtgggaaa agcagtccca cccttgccac ctagccttcc 91080
agtcagcttt ggctcccgac ttgcagtttt ccaaattacc ctgtccccgg cattccatac 91140
ctgcatcttg ctttcacttt atttcagcag agggaggcag ggtgagaagg gatatgggcg 91200
aggaaaagcc gaggccagaa agccgagttc aggctgcgtg ttcccagaga cagacagaca 91260
catgtgcaga cacacacagg cccccactca gacataataa gcacttggac ttggagctag 91320
gggcacacaa acacacactc tcccacacat gcgctgccac atccaggcag acagacacgt 91380
accgtcacac agtctcctct ctgtgacagg gacagctgcc ggggctgttt tggagctagc 91440
cattattacc cttcccccac cccccacccc cccaccgcct ccctggcccc tctgaacctc 91500
agctctcagt cccaggagct aaggactctg tgtgggggag gagcaggcca aggggccagg 91560
ggagtgttct gcactggatg ctgctgagtg aggagaaggc atgagaatgc tggagctaga 91620
ggatggggtg gggaggaggg gcagaaagtg cccaggcccc tctcaggaaa gtcatctggt 91680
atagcccaaa gaaattaggt ttagagtcag cagatctaga ttcacgtcct ggctgtacaa 91740
cttactagct gtgtgtcctc ggcaagttac tttacctctc tgagcacatt tcttcatctc 91800
cgaaaggaag ttcatgatcc cttccctact tgccttcagt gttgttataa ggtttagata 91860
aaaacataaa catgtaaata tgagtaggga taaaactcta cctgagtagt ttttttttcct 91920 cactcattaa acaaatgttt atttagcaca ttctatgagc tgggcattga gttaggcact 91980
gagggtggag tggtggctaa gatctcatcc ctgtgtctgc ccttccttga gtgagtcatc 92040
tgcccagact ctgtatcctc cagtgaagtg tttccctggt gaatgaaggt gagtacgctg 92100
cattactgag agataggcaa cacatgctgt gaacactctg tcctgagcat aggtgaccca 92160
gtcaacaagg taacagcaaa atgggcagag taacccaagc tgggagccac tttggggaca 92220
agggactggt agaggaaaga atgaagcctt taggctcttg catgggctag taacagcaga 92280
gagaggagcc acagctgaga agggacctga ccgtgaaact gaagagagaa ggaaagaaca 92340
gtaaagccag gcaggcaata gagagatgga agggtggggg catagacctc tagccgactc 92400
acgtccgggt gggctggtca ggcaaaggct gggggcgcca agctgttgtc tgagctggag 92460
acaggctggc tgaagattaa gctcccccaa actgctggag gtcaggaagc tagggagttg 92520
ggactgaggc cagggacttc gcctcactca gtggataggg aagaacaagc agtaggtctg 92580
gaagccgcag gattggttga tgctagtaag aaatgcccag gcagggacag agagagtcag 92640
aagataacag tgatggtgag tccagctctg gaagggggct gccggcccca cccctagact 92700
ttttgccaca ccctgctagg gatgtgaggg atgtgtggcc cagtcccact ggtatcaggg 92760
tggcaatccc aggcccaggg agtacagagg gcctacaggt atgctctgat tctgtagtac 92820
aggctggaat tacaggaagc ctggtcatgg actgcagcaa gaatgaaata tccaggacat 92880
atgaaggtgg agagcagatc ccaggccagg gaggccacag tggggaggcc atggtttcca 92940
agagacacaa ccccatggca ataagtcagc tgtcatgtgg acccacttaa gtcctgaagc 93000
cagagaggta gaccagggac atagtgagag cccacaatcg gttgcaataa taatgcctga 93060
ggctggaggc ataacctgga actcaaatag gagaaaacct ttctcattca ggggctaaat 93120
ggagagatga gaggagctgg agttgtgatg ttttcatctt ataaacatga aactgaagtg 93180
aggtccttaa gtggacatgg ctgcatgttc attagggacg ctgagcaccc agactctatg 93240
gtttgctgaa ctgcagtgtg caaatgggag caaatcgaga cacatttgca gcaaagattt 93300
gaagcactca agttattaag ggacgattcg gggatcagag aaatgactcc acagtcttcc 93360
tgctcttcct tgcttccttc cttcagcaag tattaggtgt taagagggat cccaagaaca 93420
gtaaggcaga gaccctatct tgtaggagtc tgcagtgtag ggaggcaaac agagcacagg 93480
atggaaagat ggaccgcatg ggtctgactc ccagactgtg ggagatcaga gagagggaag 93540
cccatggaag gtggtaccga gtgttgggag ctcagagaat ataggcacgt gactgaattg 93600
ggagttcaag aggaagagaa ggggtatggc attctaaata atcagcagtg ttgggaataa 93660
gctggcaggc tgggagggca gtggtgagcc taggttagtc agagtctcag tgtaggccac 93720
gggagatctg cagagagaaa cgagtcaaac cgagggggcc tccaatgggg gacaaggggc 93780
agtggttcag atttgacaaa gtctaggcta cagtatgtcc agctttttca tcaaaaaccg 93840
ctaagattca cactgagcaa cagccctgaa taaagaaaaa aaccctaaga ccagtcaaaa 93900
acaacatcta ctagaaaaca gaagcatgac ctgaaacagc tgccactagt atgaaattgt 93960
tttgaggtca ccagctttat gttaaaaatg caaacaaatt tttcgttcta ttccatactt 94020
tagtcatgga ttataaaata ttttaatata aaaataaagc ttttttttaat ataaaacccc 94080 ccaatcttca agtgatatca ccacaccagg aagatgggcc ctgtttagac tgtgtgtcat 94140
gcctcctcca ctcccgtact gccctcctcc cccgcccacc ccactatgag aagcaatgca 94200
ccaagcagta ggggtcactg gaggcttgta tccaggggtg tgacaaaaaa cagcatcttt 94260
gtgaccttta tttgaccatg gtgagcataa agggttgggc agggaagaaa taggaaagga 94320
gaaactatta actgaaaggt gtaaaaaagg ccccggggca ggacaatggg aaaggagaga 94380
tagagttttg aaagttattc ctctctgtct tcccccaact cttaccccac tgatgatctt 94440
ttccttttcc tccccatcat tcttttcatg agtccctggc agtggccatg gacaccctag 94500
acaccccaaa gctcaggacc taatggatcc ttcaggttag tctaggaggc atcatttagt 94560
gtgaatggag aagaaaagat tctactggcc ccatccttca gtcaccacaa gtcagctcta 94620
gcctgctgcg tttgccctcc cgtcctgaac ctgagtcctg ggccaatgtt cccatccctg 94680
agcaggaggc aggcagagat atttggcctg gtagacaggc tgagcatttg gggagctccc 94740
cagagttctc agacagcggc aggggtagtg gccagcatct gaagtccacg atagggtggc 94800
ccgtctgtca ttaagatccc tcctatggct gcatcaggga tgagattagg ctgctctaag 94860
tctcagcccc acttttccaa acaaagattc tgcagcttgg gcataataat agcagtgctt 94920
cttatttata tgatgctcct ccatttgcag agggccttca cagacataat ttcatttaac 94980
tcgcacaact gccctgcatg gctggagtgc ctatccccat tacacctcta agaaggcagg 95040
atgcaaggtt acacagtttg aagagatttg aagagattca aaccatctag ttctgctctt 95100
tccatgcctc actccctcca ccctgtagcc atttgtgact ctgacatgtg ctgatccttc 95160
caaaccctga aggattccat ttctacttcc tgcctctatc atctctctgg aaatgagctc 95220
tggaagtatg ctgcccactg tgtgccaaag aacatttttc tattcatcct gagcttgcat 95280
cactccagtt ctaaaaggcc ccctcatctc cagtttcaag atttggggag caagcaattc 95340
ttctgcatat ctaggtcttt tattatgctg tagatttcca tcctgtctca ccttccagag 95400
gactaaactt tgaaatttgc cctcaccagc aacccctggc tccccattct gccaatcatt 95460
ctctgaccct actctaggcc catgacattc ttcctaagag ccagtgacca ggcatgcgtt 95520
cagttacaag gctttatgca agggtgggaa aaggttctgt cttttgtttc caatcacctt 95580
cattatgata ccacctcttt ggcctttttg gcaaaagcca actttgagct aaagtcttca 95640
gggaaccatc tgtaatgctt tccctgttcc tttcctgaca cagagtcctt catttcacct 95700
ataatttcag tgattttatg ggagcacagc aatgggagca caagcccctg aaaagtgtat 95760
cagaatgtga tggggataat tgtggtgtgt ctttatattg atcaaaatag ggcaaatgaa 95820
aaacaaaagt tgagaatcct agccagtaat aagcaaactt tagaactgag gaatggacat 95880
gggagtatgg ggaatacgta ttgtatgtca ctcacaggtg aagggtaaga aaggttgaaa 95940
ccactgttta gattactcat tgctaaatac aatgccttgc acttgtcctt gtgaaaactc 96000
agtccccagc tgggctatct tgctcactta tatggactcg ttctccctgt tctgtcctct 96060
tcagcataat tgagctgtgg ttagaattgg ggtcagggtg gatggtcact gtatgggccc 96120
agcagagtca gggctgtatc ccagctgcag ggaaagtaaa cccggctgtt aggtagggcc 96180
aagatatcct tcccaaccag actgagaggg ccagatagcc ccctgttgga ctccagagtc 96240
tggattccat gagcctcctt cccacctccg ctcagccacc agggtggtgt tgggactggt 96300
agggctgagg aagaaaaagg gaaacaggac cacaggattt gctttgctaa tggggctgta 96360
gttttctctt ctggcctggg ctcctgccca ctgtagggaa ggagccattg gtcgcctgat 96420
actccagcaa ggagtctggg gggtgtctgg ttaattgtat tggaattagg gggcaactga 96480
ggctgccagg ggcttgtacc cagctccttc ctgttttccc attgcctttt gtcacctatt 96540
ccttcctttc ctggtcttga ttcccactag caggctcctc attggccttc tgtcctcaaa 96600
tttggattct ggaagtacag agtgatgctc tgatctattc tgaattgaag ggggcatgtg 96660
tcccagccca cctcacccca aggccaggtt gtagccttta ctctcgctcc ctgctcacag 96720
cttcgcagcc cgaaggagct gaaacaagtt tgcaaagtgt gagctgggat ttgaggtgac 96780
ccaccgcagc cgaccccatc gcacacgcag cagctgggca ggcgctgctg ggtagacgga 96840
catgccaccc agccagggac attctgtccg ccactgccag acacaactcc cgctccggag 96900
agacccactt cgctacccgg acattctgtc cgctccgagc cccatgcacc gcggacattc 96960

```
tgtccgattc tgaggcggcc tcaagtcagg acccttctgg gcccagacac cccaagccag  97020
atccactata cccgccgcct ggtcactctg atccgcacag cggccatctg actcagtcgc  97080
ggccgggctc tcacaacaca gctcctattc caactgcgga gcagctggga agagaagcgt  97140
gtgcgaccag gcgcaccccg gctcccagcc ccaggagtct gagcctaggc cgaggggcat  97200
cgggcgccgt caactgcccc cacactgggg gccgccccgc cagctccccc gctggccagg  97260
gcctctgtaa cccctttcgc tccctggccg cctgccccgt gccctgggat tccagggcgc  97320
tttctggtaa tggtttccag actccctact ccctgcctcg cgaagcccct atcctggttt  97380
caagtctccg gcttcgttcc ggatcctctg agtctccccc ttccctatcc cctggttctt  97440
accctgagtt tccctttcc caagtcctgg ccccaggtct gcagtccgcc ctcccattct  97500
cgacctgttc ccaaggcacc ggagttcagc tgccccaggt ctcgttttag ggattccaag  97560
gtccagcaat agctcctcgg ccccatgagc ccctgtcctt agaatggtca aacactcaca  97620
gtgcgtcctg caacaggcag actcccagta gcggcggctg cggcggcgat ctagagggca  97680
ggcaggggcc aggggccggg cacccggccg gagtgggggc cgccccccctg ctcccgggcc  97740
gcctctccgc tcgggcgctc ctggactctc ggagggagtg agcctcaccg cgtactgcca  97800
cccccagccg gcgcccattc actttatggc agaccagggc gcccccagcc cgccgcggcg  97860
agccgcgcgc gtcaggcccc gcccctttcc agctgccctg ctggggctcc gccctttcca  97920
gctgtggatc tccaggcccc gcctttgagg gaggggtctg gccggcgaga cgccaagaac  97980
cccgccctct ggccaatcag aagcgctctt cagcaactcg gccgcgcccc tccccacgtg  98040
gcagagaccg cgctccggct aggacgctta ggcagagcca agtgggcgag agtagagtgg  98100
tcccggtagc cacgggtaaa agggatcggc tggcagcgaa gtgggttggg ccgctacccc  98160
gaggaaagtg gatcggcgcc aggtgggaag gcgcacgggg ccgccgggtc tcagcgctca  98220
gacttctctg ccactcaagt ttcgccgatt ttctccactt gtcgctgtcc gtctctcctc  98280
ccttttgtct ctgttccaat cctcccacgt ctcgcctttc tttcctcttc tttctcctca  98340
gccgcttcgc tcctgctgtt taccattctc cttcctctgc cactttaaaa gactcatttc  98400
tctttctctc tgctcctctt tcctcatatc tttcctcttc ttcatttccc ccttcttctc  98460
caaggaaggt gacttcgtgg agacagcagg gtttggaatg atacaaacca aagtagtatt  98520
ccaacgctgc cacgaactgc accatcactg agtgaacttg gacgagtaac tatcatctcc  98580
ctccccgcgc aaaacaatta agaggaggtt cctgctggat ctcagggctt gggctgggca  98640
ctccaaaggc attgcctttc agtctgtacc cttgtcttgc ttaggctgtg ctctccctcc  98700
ttcagcaggg ctggtttccc gctggtggta ccaggttaag tcctgtgggc aaggtgtggc  98760
cttggtgcct gctggttagg aatttgcaag ggacaggaca gatgaccaag gaacatcctg  98820
gcagactgtg acttcggccc tctctgactt aggcctcaat ttccaggaaa caggctcctt  98880
ctcttctccc agttaggcta tgttgcttgg gtgctccgaa gagcctaagc ccaggccaaa  98940
cactgtggct catgcctgta atcccagcac tttgggaggc cgaggcgggc ggatcacaag  99000
gtcaggagat tgagaccacc ctggctaaca cggtgaaacc ccatctctac taaaaaatac  99060
aaaaaattag ccgggcttgg tggcgggtgc ctgtagtctc agctactggg gaggctgagg  99120
aagaagaatg gcgtgaaccc aggaggcaga gcttgcagtg agctgagatc gcgccactgc  99180
actccagact gggcgacaga gcaagactct gtctcaaaaa aaaaaaaaaa aaagagccta  99240
agcccagtca cacaatatgc ccctaaggca aatctgagca gtcatgtctt gactgttcag  99300
tgactcccat tgcccttagg ataaaggtca agctccctag cctggcatac aagaccttca  99360
```

-continued

```
ggacctgacc ttgtcttcat ctccaatttc ctagtagtgt cctgcacacc tctggccctt  99420
cctgtgaaag taacccatct ttatattgtc aattcctact cctccaatgt tccactcaag  99480
tcttattttc tctgggaagc cttttctgaa ctctcagttt agccccttgc tctcatgacc  99540
ctcagtgtat accttctatt acaccaccca ccatattgaa gggatcagct tatgtgttgt  99600
ctgctatgat aataaaattt aggagggtaa ggaccatgtc tgttattccc aggcataatg  99660
tagaatctca ataaatgtca cactgaaatc tatgaggaag atgttctgcc tggtaagatg  99720
atgattagtg gttaggaggg actagggaat tgtcatctct ctcctcccca tctctattgc  99780
acaatcacat gcttttagaa tgatgaattt ctggaggtat gtagaagtag atattggcga  99840
gcagaaattt ttggcccact tagaggattt tccaatcggc tttccaggac ctctcaatct  99900
gagacaggcc caggacacca actctcagtt ttcaaatgaa gaggaaaatg gctttgaggt  99960
aatgtggaaa gaggtgctat gatggtatat cctctttccc tgactctctt tgggtgatag 100020
aggctagatc ctcagctgga cccaccgacc agaagcccaa tgtgcaggtg taggaagtta 100080
ctgaggggtt cttcacgtct gatatctgat gggtgcttta cactagagca tcgtggccag 100140
gtgtggtggc tcacacctgt aatctcaaca ctttgggagg ctgaggcggg tggatcacct 100200
gaggtcagga gttcgagacc agcctgtcca acatggtgaa accccatctc tactaaaaat 100260
acaaaaatta gcctggtgtg gtggcagatg cctgtaatcc cagctacttg ggaggctgag 100320
gcaggagaat cacttgaacc caggaggtgg aggttgcagt gagccaagat cacagcactg 100380
cactccatcc tggatgacaa agcaagactc tctcaaaaca aacaaacaaa caaaagacaa 100440
aaaaacaaaa caaaacaaaa aaatagcgca tcgtagcaca cggatggtct ttggatgtct 100500
ggttttgaga ctactttcct atgtggttag ttatagagct tccctggact tgggtcgtcc 100560
ataattggga ggatgtatgg aaagaattag gtattttttt ttcactgcct cccagcagct 100620
tctccaggtc tgcagggaca ctggggctct agtgtcccaa ataggctggg aatttcatga 100680
ttcagtctcc taggagaaaa cccatcctct tgtcctcttc tcacgcattc tcacttccag 100740
gtaatacagg taattctaaa tagcttagta acctctatca tctcttgcaa ggggaggagg 100800
cagctggggg caagacagtg aaaacaggtg ggcatccaac cctcaggccc cttagcgttt 100860
ctaaggcaaa caagaaagac ttctgtttcc tatcactgat gaggtgggct aagctgcgta 100920
tttagcctgg tggataaggc ccgtcaaagg cttggtatga aaggcagacc gggagtcaaa 100980
gcccgatata ctaaggcata agaggtgaca aaaggcgatg aaaagagttg gcctgggggt 101040
gaggagaccc aggggttcgt ctctctgctc tgctatttac taattatgtg aacatgggcc 101100
cagccttcca ccctggggct gtttcctata atgtaaaatg aagagactta aattagatat 101160
ccagggcttc tgctacgtcc cattttctct atttctggat gatgggagtg gggcagagga 101220
cgctgaaaca gagttgggac gtgacagaca taactgtgag aagccacgac agggaaggtg 101280
gacaagaggg cgaggagagc agggtgtgga atagatcgct ggacttgttt ttagaatgaa 101340
gggagcccag agctgcctcg aaaaggagtg attcctcaag gggcatggtc ttggcccagg 101400
taactttgat aatacgtgga caggggagta gggatgcccg ctcaagttct caaagcggac 101460
cccgcccctt tccagccaat tgtagccttt ttccccataa tgcccagcag ccactgccaa 101520
accgcgcact gcaaccgaac tctacctaac tccacctctc tagccgccca gcccagttcc 101580
tcatttttta ttggtttttt aaactgtcac tcagagagta ctcgtatccg ttggttgtcc 101640
cctaacatac cctttctttc ccttgtaatc gcgcttcttt aggcactacc cgcctcctga 101700
```

agccaatttc ctttattcga ttggatagtc ggaatgctac ttttcacggt gcaaagctat 101760
gattggctgc gcgcggcagg gctcgcgcag ttaccaggca gcgggctaga ctgaggctag 101820
ttaccacgtc agtgagctga cagggaaggt acccggctct actgcccgtc ccggacgact 101880
catcctggcg gactgtgcag tcccaccctg acttcggcct caatttccag gaaacaggct 101940
ccttctcttc tcccatctgc taccagagcc gggagagctg ctcggagacg cctccggggt 102000
gcgggctgga catgagcagc ggctgccggt cctgggacta ggccccgcca ttttggatcc 102060
gctgacaggt cagcgaagtc tcttcctaga gttccggtgt cgtgaaggcc gccctgacat 102120
cgcaataggg aattagtggg aagggccctt aaattgggcg agccaaggtg ggctaaggac 102180
gcagcggaca ggaataagac gagggaaggg ttgttgtggg agggaacagg gaggtatgca 102240
ggggcaaagg tcatgcctct gccgcaggag gggcgatttc tgctctcatt actgatcctt 102300
tgcaggtgcc caaatcttct gttttcccag gcttgaccta gtatttagct tctcctttcc 102360
agcgctttct gcatcctgaa gagcccagta ctcaaaagct gaaagcaaac ctaaggagca 102420
ttgtgtctac ttttatgggt tttcagactt tagatgtgaa agtctctcta gattctgtac 102480
agcgtctact tctttgtgat tgcctcacta atacaaagga actgcttcat taataatgat 102540
gaactagtgc accctagaat caggttgtca gcagagggac gtgtggaagg cttgaggtta 102600
tagcagcgca gggaactggg ctatgagaag gcttccctct tacaggacag ctcagctgcc 102660
agtctgggtc tgtatgtaaa cactatactt atcttctggg cctgtttgtt cctttataca 102720
atctttcaca ggcattcttt tgtagtgtat gtttttgttg acatttttct ctcagatctt 102780
cactaaggag atgaggctta atcataagga aaccactcta ttatgacata tttgactgac 102840
agcagagaga gatatttgaa tactggcaaa gtttggtatt gtcggcctat tatgtttagt 102900
gggcaaaaag agtcatgaga gattttcagc caattgtagg gtcagagccc cagagtgaat 102960
gatggaacat aaccctagag agtagtttat ggcactgtga tgacctttga taaactgctg 103020
tgttgtaaag ctataaaagt ccaccaaggg taacgaatgc ttttagaaat aaggaatagt 103080
gtagatggtg ttttttaatg cacaatgtgg aaacttgtgc attaattcag gtataaaagg 103140
cactctaggc cctgtggagg atacaaatgg aaaggtctgc tttgggactg ctcagttaat 103200
gcacttctta aaagtagtag catgtatgtg cagtggccta gctagagcat gtagtaggtt 103260
aagagcagga tcaacctaat accttttggt atgtagtggg cactcaataa acgttatctc 103320
tatctgggat tagtttcagt atgtgatcag gacttgtggc ctgcttttgg ccctggcagt 103380
caggaacact ttgcactttt gcatgatgag gtagtaacaa ggaggatcaa aacctcatag 103440
tgtcagaaga gaaaactatt taggatcttg gaatgactaa ctcaattttt cctacctttg 103500
tccttatgaa attgaaattt cataatttcc cttttccctt cctaccttcg tccttatgaa 103560
attgaaattt ttgtgtgtgt tgggagaagg gggatggcat tatttatgct tcacctgtgt 103620
tgatttagat ggaaatggta caggaaacta tttgcatttt aacttgctga tctaagttgt 103680
agaattcctc ccctctcccc gcccccaaga aagtagttga acgcagcaaa tgaaatgaca 103740
tacctcagga ggtacccagg tttgatgatc ctgccttgct cacttgggcc attgccctgt 103800
tgagttgata tgctttgcat aacaggcaat ctagtctctg ggtaggcagt gtgatcaatc 103860
caggatccag tcatcctcag ttgagcctaa gggtgactat agaggcatca aaacgttttc 103920
tctttctctc tctttctttt ttttaatcct aaatgtcatt tctagatagg aataattttc 103980
tagataggaa taattcccac tcctacccac aaatcagaaa attcatcctt caaatacaag 104040
tcccaagctt gtatttgagc ttctttttaa tggtgtttgt agacagtatg ttccagtctt 104100

-continued gacagtgatg ctcattggca cagtgggaac tcaggctata gacatatctc ctcagtagct 104160
gggcaccaat cccagtttca gctcagagtt ctcaaagtta cactactatt ttatttccct 104220
cttttccaga agtcaggatg actgccactt tcacataata acctcattga tagggtactt 104280
agactggctg ctgtgggcag ctaaagagga agaagacaca gctcttgctt ttgaggagac 104340
tctatttata gagtactcac tgcaaggatc accctaatct ttgtatgaca cttctcattg 104400
attgatcaca cactatatcc ctgtggctct gtgtgactga ttagaatgat tctgttgttg 104460
ggttaatggt gggattgaat ttaagggtgt atgtttttgt tgacatttta tcctcaggct 104520
agaagagcta tgtaaatata atgagctgct gtttagctgt tactcttttt tttttttaat 104580
atttcagtat gttcaactgc agttgtttaa ctaaatgaaa atataataaa gcagtgtgct 104640
gatttggaac cccaataata atagaagtga tcatagaagt gattatttgt tctagtagta 104700
gtggaaatta cgatagatgc aatagtagtg taaatgatca tggaagtatg atggcaaagt 104760
aatggtttgc caatcatata aaccaggggt tacgagctca tgtgcctaaa tgccaggcag 104820
gtaatgtaaa tgagttaatt gagtcccatg ggaatgtatt aggattagtg gggactgttg 104880
tgtactggac aacccatgcc tttatttttt ttttgtcttt aattttaatt tctttttatt 104940
gagacagggt cttgctctgt caccccggct ggagtgcaga ggaacgatca cagctcactg 105000
cagccttgac ctctgggctc aagtgatctt cctacctcag cctcccaagt agcggggaac 105060
acagatgtgc gccatcatgc ccagctaatt ttttaatatt ttgtagagac aaggtctcac 105120
tgtattgctc aggctggttt cgaactccta gactcaagca gtcctcccac ttttgcctcc 105180
caaagtgctg ggattttagg aatgaaccac catgctcaac ccattccttt atttagaaga 105240
gccaactgct cctttttcag cagattgtta ctgttttaga gtgcaggcac agaatgacca 105300
ctctttctat ttttcaggag aaactggaaa tttagatcat tgtgttttct aattgttgga 105360
aactagttaa aagtattttt aagccttttt caggccaaag aaaatatgtc tgtggactgg 105420
attctgccca atggttactg gatgatgacc ctcaataaac aaaatgggca ggccttatga 105480
gacttaatca ctgcagttct ctatacataa tcacatagac tttttttctt tgtcctactc 105540
tgccagctgt cacctttgta ccttgggtgc cctgagtggc taaaagatgg agtgagatag 105600
agaaggtttg ttttattttt catctccaag ctggcagaag ggacagcttt ggacatatta 105660
gtagcttacc ttgtaaacgg tttttgagat actctcagaa tctccacagg gggaggagat 105720
ggcatgctag agctgaggta ccctggtcac ccgattatca ggtctgggag gattttccag 105780
tgatgcattg tcagggcacc agctttttc ccagtttaac cttcttttac ttccaccctt 105840
taagtaaatt tcttgagctc agtaagttgt ttcctagttt agtaactttg gttattctca 105900
ataaagcaca gaactatgat gtgttcctag gccagctctg gaaatgttaa aagctctgca 105960
tctttagtgt ttctctggct tttttttttt ttttctctga tggagtcttg ctctgttgcc 106020
caggctggag tgcagtggtg tgatcttggc tcactgcaac ctccgcctcc tgggttcaag 106080
caattctcct gccttagcct cccaagtagc tgggactaca ggtgcacgcc accacaccca 106140
gctaattttt gtatttttaa tagagatgtg gtttcaccat attggccagg ctggtcttga 106200
actcttgact tcgtgatccg cccacctcgg cctcccaaag tgctgggatt ataggtgtga 106260
gccaatgcgc ccagccttct ctggctttta aaggtattga gtgaacataa accttagaag 106320
ggcctattgc tggtccttta gctccctact accatctacc ttttcagaaa gtccatcagt 106380
ttttcttggt ttgcccagct ctgtattaga cacaaaggca tcatgaaaaa gaaaaacaaa 106440

-continued

```
attgcgcttt tgcctttgga gaatttattt gctagttgga taagaataat ttttttttga 106500
gacagagtct ctctctgcca cccaagctgg aatgcagtgg tgtgagatct cggctcactg 106560
caacctttgc ctctcaggct gaagtgatcc tcccatctca gcctcctgag tagctgggac 106620
tataggtgcg tgccaccacg cctgcctgat ttttgtgttt tttgtagaca caggatttta 106680
ctatgttgcc cagagtccag tggtgtcatc atagcccatt gcagccttga ttttttttgg 106740
ctcaactgat cctcctacct taggctccct agtggctgga actacaggca tgtatcacta 106800
tgtcccacta attttttttt tttttttttt aatttatgtt gcctaggctg gtctctgact 106860
cctgagctca accattcctc ctgctttggc ctcctaaagt gctgggatta aagatgagag 106920
ctactgcacc tggccaagga aatgtttaaa agtgattaag aggccgggcg tggtagctca 106980
tgcctgtaat gccagcactt tgggaagtca agggaggcag atcacctgag gtcaggagtt 107040
aaaggccagc ctggccaaca tggtgaaacg ctgtctctac taaaaatata aaaattagct 107100
aggcgtggtt gtgggcgcct gtaatcccag ctactcggga ggctgaggca ggagaatcac 107160
ttgaaccctg gaggtggagg ttgcagtgag ccgagattgc gccactgcac tccagcctag 107220
acgacaagag cgaaactctg tctcaaaaca aacaaccaaa caaacacaaa accaaacccc 107280
ataaaagtga ttaagaaaaa aaaaaaaacc acttaaacac tagtgtacta aaaacagcta 107340
tttagagcca aagaaaataa ggcatatatg aagaattgac agttacatta aaaattatat 107400
atttcacaaa aatgtgaatg tgcaaataac acttaaggag atgtcaggaa gatagacgtg 107460
aaaaaagaag cattatgata tggctggtag gtaaatgtgg gttcttttta cctgtatgga 107520
aggtttgtaa cttctggtag agaagcaaat atatattatc aaaaaaaggt ttgccagtgt 107580
ggctcagagt tattgtcttc tatgaagtca tttttctcat gaggtggatg tgtgctgtac 107640
cactcttgaa gagtcagtct tgatgttatt tcatttgttc atctagtatt tattgatcat 107700
ttttcttact atgtgtcagg ctttggagat aaaagggtaa ataaatcatg gtctttcccc 107760
ctgagataga gcctgatagt cccatggtgg tgatacacta aataaataat tataaattag 107820
tataagatgt gtttattttt attttcattt atttatttga ggcagagtct cactctgtca 107880
cccaggctgg agtacagtgg cacgatcata ccgcaaggca acctggaact cctgggctca 107940
agtgatcctc ctgccttagc ctcccaagta gctgggacaa caggtgtgcg ccaccacacc 108000
tggccaattt ttctttatgt tttgtagaga cagggtctcg ccatgttgcc taagctggtc 108060
ttgaacttct aggctcaact gatgctccct ccttggcctc ccaaagtgct gggatcacag 108120
acatcagcca ctgtccccag ccaagatatg tttagagata actacaaagt gctgtgggtg 108180
gccgggcatg gtagttcatg cctataatcc cagcactttg agaggccgag gcaggcagat 108240
cacttgaggt caggagtttg agaccaggag tttgagacca gcctggccaa catggtgaaa 108300
ccccaactct actaaaaata ctctgctaaa aaagtggaaa aaagggctgg gcgcagtggc 108360
tcacacctgt aatcccagca ctttgggagg ccgaggtggg cagatcacct gaggccggga 108420
gtttgagacc agcctgacca acacggagaa acctcatctc tactaaaaat acaaaattgg 108480
cccggcatgg tggcgcatga atgtaatccc agctgctggg aggttgaggc aggagaatcg 108540
cttaaacctg ggaggcagag gttacggtga gccgagattg tgccattgca ctccagcctg 108600
ggcaacaagg gggaaacgct gtctcaaaaa aaaaaaaaaa gtggaaaaat aaataaataa 108660
ataaataagt ggttttaaga ttgttcttag aaccactgtg atattctgac tccctcattg 108720
acttttggat ggaatgagta agggtttatc aggtggacaa gagtgagaaa aaacattcag 108780
aatagaaagg gagcttcata tgcaaaggca aagaggcagc aaagaccatg actttaaaaa 108840
```

gtaggaatga tgtggcgtgg tggcccacac ctataatccc agcattttgg gaggccaagg 108900
caggcagatt gctttgagct ctggagtttg agaccagcct gggcaacatg gcaaaatgtt 108960
gtctctacaa aaaatacaaa aaaattagcc aggcatggtg actcatgcct gtagttccag 109020
ctacttggga ggctgaggtg ggaggatcgc ttgagcctgg gaagcagata ttgcagtgag 109080
tcaagattgt accactgcac tccagcctgg gcgacagaat gagaccctgt ttcaaaaaaa 109140
aaaaaggaac tttttaactt tttagggtct tttattttat tttattatta ttattttttg 109200
agccggtgtc ttgctctgct gcccaggctg gagaccagtg atgcaatctt ggcttactgc 109260
aacctccacc tcctgggttc aagcaatcct cctgcctcag cctcctgagt agctgggatt 109320
acaggcccct gccatcatgc ccagctaatt tttgtatttt tagtagagtg ggggtttcac 109380
catgctggcc aggctggtct caaactcctg acctcagttg atctgcctgc tttggcctcc 109440
caaagtgctg ggattacaag catgagccac tgcccccagc cgaggggcta ttttagacaa 109500
agaatatgtg tagcttatat ggggcaccaa tggctgccac ccagcttgaa aaataacatc 109560
accaaaactg aggctgcatg tatgtatgcc cttccctgtt agttccccca cactccctgc 109620
cgcttgccac tattctcaat ttttttgtgt gagcttctct ggggtatagt cctagaagtg 109680
gaattgctga aatataggat atgaagtgct ttagctttgt aagataatgc caaattgtta 109740
ttcaaattca tattaattta gatacatacc agccacttgg tctgcatttt ttaccaactt 109800
aaaaacaatt tttttttga gacagggtct tactctgttg tccaggctgg agtacagtgg 109860
tgtgatcgtg gctcactgca gccttgacct cctaggctca agtgatcctc ccacttcagc 109920
ctctcaagta gctgggacta caggcacatg ccaccatgcc ctactaattt ttaaattttt 109980
tgtagagatg gagttttgct atgatgccca ggctgttctc aaactccttg gctcaagtga 110040
tcctcctgca tcggcctcct aaaatgctgg attataggcg tgagcacctg gccttttaag 110100
tattatcaga tttaaagtgt tttgctattt caggaatgta aagtggtata tcattataat 110160
cttattttgt aattttcctg attattaatg aagctaataa tcttttcata tatttatttg 110220
ctgtttatgt ttcctattct gtgaaacacc tattcatctc tgttgccaat tttggggagg 110280
ggttatatgt ctagttctta tagttttgta gcagttattg tatactctgg atattactcc 110340
tttatattag ttatatgtgc ctcaaatatt ttcttctggt ttgtgcctta tcttttccct 110400
ctttttatg ttgtcttttg aacaggcatt tttaatttta acatggttga attcaccaat 110460
tttttaaaga ggttttgctt tttgtttctt gtttaggtac ttctccctta tgctgagttt 110520
ataaaaatac tctcctgtag ccaggtgctg tggcacacac ctgttgtccc agctacccaa 110580
gaggctgttg tggaaggatt gcttgagcct aggagtttga gtccagcctg ggcaacatgg 110640
caagacccta tctctaaaaa aaaatcaaaa agaaaatatt ctcatatatt agcttctaag 110700
agatttcaag ttttgctttt catatttaaa taacctgaga tatatttttg gtattccatt 110760
aaataagaat acaatttatt gtttcttttt ctcctgcttt tgttggatat agacagagtt 110820
gccaagtgat acagtgactc ctctttggat cctgttgagg taactgggat gccacaaagc 110880
actaggggaa tgttctagac ccagctttaa atggacagtg gtttcaaggg tacatgttac 110940
tcagagtctc tgggccagtg gcttatctgg ctaagggtgt tagttggtat ttatttagtt 111000
gttccctctc ttatttattt ttttctatta atttttcatt tgtgtgggta cataatgaat 111060
gtatttctct tgttatttct gacacaagat aaatcttaag ttcgtttcta ctatactttt 111120
atgaggtttc tgcaggcctt tatgaccttg tgacaaggga tttcttggcc attggctacc 111180

-continued

```
aggcagcaag tggttcatca gtttcccatc tgaagctgaa gggcacaact gtttggagat 111240
tccctgagtg aggggacata ctcagagacc tagaaggaga ttaggcagct ctgcatagta 111300
cttgaaaata attcctcttc attccctaga tgtttctttt tttttgagac agagtctcac 111360
tctgttgccc aggttggaat gcagtggcgc gatctcggct cactgtaacc tccacctcct 111420
gggttcaagt gattctcctg cctcagcctc ccaagcagct gggattacag gtgtgtgtca 111480
ccacacctgg ctaatttttg tatttttagt tgaggtggcg tttcaccatg ttggccaggc 111540
tggtcttgaa ctcccaacct caggtgatct gcccacctca gcctcccaga gtgctgggat 111600
tataggcgtg aaccactgcg cccagcccta gatgtttctt ttttacaatg atttttttgct 111660
tagacctttg ctgtcttaga aagtggttac ttcttttcta aagggcttat tcatttttag 111720
tcaatcagct gattaaaatt taaaagtagt taataggtaa tatatgtttg tgacacaaaa 111780
ttcaaaaggt aaaaaagaat atacagagaa aagttagtct tcctttcact cctccaccac 111840
tcagttccat agtcatccag tttctttccc tggaggccgt aacctcttag cattttctta 111900
caagtccttc cagagaccta gagcatattc atcttgccta cataatttaa ggaaagggaa 111960
ataccaggaa agatttaatc ttttctcttc tgatacttta aatcattttt gaatatatct 112020
ttcttctatt tctaagttct cctcctcctc agaagagagc gtggttgtac attcatatca 112080
ttgacacttc tcagaagaga acgttgttgt gttcctagag catttggaaa gcagatagtc 112140
ttctgagatt aacctagttt tttaaattgt cattaatata aatcttgtgt tggattccct 112200
tgtggactgg ggagctgtca tgggcatgga cacattatta ttattatttt aagacagagt 112260
ctcgctctgt tgcccaggct tgagtgcagt ggcacgaacg cggttcaccg cagcctcaat 112320
ctaccggcct caagcaatcc tcccaccgca gcctccctgg caactgggac tacaggtgtg 112380
caccaccaca cctggctaat tttgtatttt tttatagaga cagggttcgc catgttgcca 112440
aggctggtct cgaactcctg ggctcaaatg atctgcccac ctcagccttc caaagtgtta 112500
gggattacag gtgtgagcca ctgcgcatgg cccctggaca aaatttgtac cagtttcttt 112560
ttcctttatc atggtggttt tcatgctttt cactttcttg gggggcctca tcttatgcaa 112620
aatatgcaaa ttgagctact tgctaggtac atttctttct ctattatctc tggctgtgtc 112680
tgtttttgta tctattccac taaactgtat aaatgcctca aggacataaa ttatatacct 112740
cttatcatta ttaatgttta attatattga tagtacagta atacattctc tttgtaaaaa 112800
aaaaaaattt ttttttttt gggatggagt ctggctctgt tgcccaggct ggatggagta 112860
cagtggcatg atctcggctc actttaacct ctgcctccca ggttccagcg attcttctgc 112920
ctcagccact cgagtagctg ggattacagg cgccctccac cacacctgcc caatttttgt 112980
attttgagtg gagatgggtt tcaccatgtt ggccaggttg gtctcgagct caggttatct 113040
acctgccttg acactcctga agtgctggga ttacaggcat gagccacagt gcccgacctt 113100
cttgtaaaaa gttaaaatat tacagatcca gcctgggcaa caaagtgaga ccccatctct 113160
acaaaaagta caaaaattag ttgggttggt ggtgtgcgcc tgaagtccct gctactcagg 113220
aggctaaggc aggaggattg cttgagccca agagttcaag tctgcagtga ggcatgacag 113280
tgccacagga ctccaacctg ggtgacagag tgagaccttg tctcaaaaaa accccaaaag 113340
acaaaacgat tacagataag gctcaagtat cctctgattg caccctgttt tcacagcacc 113400
ttctctagga ataattatgg ttataagttt gggtatatta gcacagacct tttattttat 113460
atttacatat catattaatg ctttcttgct gtcagttaat atgagttttc agaacttttc 113520
aaaggtcttg tcactgtcac tgtccagttt tctggagctg actgggcaga ttggatgcag 113580
```

tcatttgttt atatttatat ttatatattt ttagagatag tgtcttgctc tgtgacccag 113640
gctggagtgc agttgtgggg tcatagctca ctgcagcctc gaactcctga gctcaagtga 113700
tcctcccgcc tcagcctccc cagtaactag aactacaggt gtatgccacc atgcctggct 113760
aattttttag ttttgttttt ttggtagaga ctgggtctca ctgtttgccc aggctggtct 113820
caactcctgg gctgaactga ttctcctgcc ttggattccc aaagtgctgg gattgcaggt 113880
gtgagccact tcaccttgtc tggatgcagc ctttacgctg acattgcaac tgtggttcta 113940
aaccaacact atgcttccaa caacctttat tcttttcttt aacttgaatc tttaaattca 114000
agttaaattt ttattgagta gattaaaaag aacaaaggga agactatata cttaggagag 114060
agcgagagag agtgtctcga tatgctgccc aggctggtct taaattcctg ggctcaagca 114120
atcctcccgc ctcgtcctcc caaagtgcta ggattatagg catgagccac catgtctggc 114180
cagaaatatt gtttttaaca agctgacatt acagttgtat ctgtgtactt aaaggcatca 114240
taggactttg ggaacaattg actttgaaga atttgacatg cttcctgagg attgttgagg 114300
tgcctttgaa aaatgttctg gattgactcg ctttgagttg tatcttgaac taccttgaac 114360
ttctaaagac ccccaggaga gccagatagt tggattcata acataagatg gacttcatct 114420
cattttagta ttacagattt tttttttttt tttttttttg aggtggagtt tcactcttgt 114480
tgcccaggct ggagtgcaat ggggcgatct tggctcacac aacctctgcc tcccaggtcc 114540
aagcaattct cccatctcag cctcccgggt ggctgagatt acaggcatgc gccacctcgc 114600
ctggctaatt ttttgtgttt ttagtggaga gagggtttct ccatgttggt caggctggtc 114660
ttgagctccc gacctcaggt gatccacctg cctctgcctc tcaaagtgct gggattacag 114720
gcctgagcca ctgcacctgg ctaacagatt ttatgagtat agaaaatttt ggtactggcc 114780
aggtgcagtg gctcacgcct gtaatcccag cactttggga ggcccaggcg ggtggattac 114840
ctgaggtctg gagctcgaga ccagcctgac caacacagag aaaccccgtc tcttctaaaa 114900
aaaatacaaa attagccaga tatggtggcg catgcctgta atcccagcta ctcaggaggc 114960
tgaggcagga gaattgcttg aactcgggag gcagaggttg tggtgagcca ggatcacgcc 115020
attgcactcc agcctgggca acaagagtga aactctgcct caaaaaaaaa aaaaaaaaaa 115080
agaaagaaag aaagaaaatc ttggtactga aaagttaaat cacaattcta accttatcag 115140
gtactgattt ttaaacttgg gtatgctttg ggtaaccaaa tattaaccag actattatct 115200
taactgtttt ggtaggtttg ccaagatggt ggataagaat atttacatca ttcaagggga 115260
gattaacatt gtggttgggg ccatcaaacg aaatgcccga tggagcaccc atacaccact 115320
ggtaagtggg aaatggataa atagcctggt cactaagttt ttatagggga tctgttggca 115380
tggttaaaag agtaatcaaa ttcctagtaa taatgagaat agtaggaatt cagagttgtt 115440
cttgatatct tgtttttttg tatcccaact agcatcagat atataggcta tctttttttc 115500
tctgggaccc aaaagatgac accattcttc ttctaaatat ttttgtaaac agcttaagct 115560
agtcctgtgc ttgggacctc tttagtatgc ctaaaagtat cagaaagatt ctttattttc 115620
taattcttta gggctataat tagctatcaa atttatttaa atcagggtag ttattgatac 115680
atagaacatg acttagtgat ggtactcctt cttgggggtt cagcaaactt ccatatatag 115740
agtaggccat atcttaccaa tcagatgagt aagaaactta cctgttatac agttggcttt 115800
ctttgctata tatgtttgag gacttttttt tgtagaattg tgtaaaacaa tttttggccc 115860
agttgtaaaa gcaagtttag aaattgccaa cttgggagtt tatatgaaca tagttggtaa 115920

-continued gtgcatttgg aaatttctca agttctttca taaaaatgta ttgatttaaa agtgagcatg 115980
gcatcaggaa tatctttgaa atgaatatgt atgatgacat agtgggtatg aaaagggaga 116040
gaagacagaa taatacacat ataaaggacc tggcaatctg tagtagcttg agtgttatgg 116100
tgatgatata gattagcact taagaattca ctattttgta taagcccaga gtatctctac 116160
gaaataagag attagggtac agaaaaatat gaactatggc taattttctt ttcctcagaa 116220
ggaaaactta aatgattttc tgattggatt catagaaaga gcccttgatc tgtcctttat 116280
tttccttttc ctcttttggc ccaataatga cttactttaa tctatgtgtt ctacaggatg 116340
aagaacggga tcctctgctg catagtttcg gtcatctaaa ggaggtttta aacagtataa 116400
caggtaagtc tccatatgta tgtggattac taatcttggt aaaaaatatg tgtttgattt 116460
attgaaagga tagacaaact ttttgtataa aggactttat agtaaataat ttaggctttg 116520
tgggccatac acaactgcaa ctacttaact ctgcctttgt agctcaaaag cagccataga 116580
taatatataa ataaatgaga aatatatatt ttctttttgt ttatttcata gagacagggt 116640
cttgctatgt tgcccaggct ggtttcaaat gcctgagctc aagcaatcct cctgtcttgg 116700
cctctcaaag tgttgggatt ccaggcttga gccactgtgc ctggcctata ttttcctttc 116760
ttcttttttt tttttttttt tttttgagg tagagtctct gttgcccagg ctggagtgca 116820
gtgtcatgaa ctcagctcac tgcaacctct gcctcctggg tttaagccag tctcctgcct 116880
cagcctccta agtagctggg attacaggcg cgtgccacca cacctgccta atttttgtat 116940
ttttagtaga gacggggttt caccatgttg gccaggctgg tctcaaactc ctggcctcag 117000
gtgatccact gcctcggcct ctgaaagtgc tgggattaca ggaatgagcc actgcgcctg 117060
gcctatattt tctttaaaaa aaagaatctg caagccagat ttggcccatg ggtgcagttt 117120
tccaatcctt ggtttattgc attggtttca gtcttcatga tctttcagtc ttcatgtgtt 117180
ctagaatcat ttgtcccttt gtttgccccc tattttccta atcacggtaa ccttatataa 117240
tatattcata tgtttagaat tttcaaagcc attttcacat ttattacctt attgaacttt 117300
tatacaaccc tgtgagggag gcatggcagc tattgtcccc tttttgtgaa agaagttaaa 117360
gcccagagga gtttaaagtg atttagctga ggtcacacta atcctaagag gtggagtcaa 117420
aactagaatt caggcctctg ttgcctggtt tagggctctt tgctctatat tgcttctgta 117480
catgtgatta gaagagaatg tacacattaa gtaccttata tttgtgtgtg tgtgtgtgtg 117540
tgtgtttatt ttatgtatat atatacacac acacacacac atatacactg gcaggaaagg 117600
aggaaagtgt caaaaccaag ggatgtagaa tacagactga aagggacagc ctcagagcta 117660
tgttcctttg ttgaccacaa agggctcctg cagtgtataa ccctggaatg cttttggcta 117720
gtgacatatg tcagactgta attggatagt gtttaggctt ctgcaaatta aacaaacaat 117780
aagaaaattt cttcttttca ttagaaatat gggagaagat ctggagaaaa aatctatttt 117840
actttcctaa acatgggcta aagttatcta agagttccct acatattttc tttctttctt 117900
tctttttttt tttttttttt gaaacagtgt gtctctctgt tgcctaggct ggagtgcagt 117960
ggtgtgatct cggctcactg caactgcaac ttccgtctcc cagattcaag cgattttcgt 118020
gcctcagcct cccaagtagc tgggattaca gacgtgcacc accacacccg actaattttt 118080
gtatttttac tagagacgga gtttcaccat gttggccagg ctagtctcag actcctgacc 118140
tcagatgatc cacttgcctt ggcctcctaa agtgctagga ttacagacgt gagccaccgt 118200
gctcagccca tattttcttt ttgtgcagtg gcgtgatctc agctcactgt aacttctgct 118260
tcttgggttc aagcaagtct tctgcctcag cctcctgagt aactgggatt ataggcgtgt 118320
gccactatgc ctggctaatt tttgtatttt tagtagagat gatgtttcac cgttttggcc 118380
aggctggtgt tgaacttctg acctcaagtg atccgcccac cttggcctcc caaccatatt 118440
ttctttaaag gagcaaattt cactcaattg aaacagcttg gaaatgttag ctaagaagga 118500
tcaagtatag aggaggcaat tgttgactag ttagcagggc aaatgctgct actaggtggc 118560
atgttcttat tttatggcct gtaccgactg gtacttgagt gctttagaat gttggctact 118620
tgcacagatt ttttttttta attttacaga taaagcttac atatcccaat tagaaaggaa 118680
atataatgaa tggagattta cagttctttt tgtttggttt tgaattcaga gtactgtctt 118740
cttaagagat attaagagga tcaaacaagt taatataatt ggaaacactt ggtaaacatc 118800
ttatacacag tgaaggattg ttgttataag tgactgggaa taccctaaaa tgactgagat 118860
caccctggcc ttgtaggcct tttggtcatt ctgcaaacct tgaggagctg aggtggtgct 118920
gctatcctga cagagccaca tttcctgcct gctactgaat ccagatccca tgcttatttt 118980
cttcatgcta acatgtccca agattttacc tcagagacca tacctgtggt gaatgatgca 119040
gtctaggaat tgtagactat ttaagagcta tcaaagttga gtctgacgcc tgatttcctt 119100
acgtccttgg gtcagaaatc cagccagatt atctgctctt ggaactagta aaaccagagt 119160
gtgttcagga gccatttctc tcattggtgg taggaacatc tctgggtgtt gctaagcttt 119220
cccctggagt gagagggaag ggagtagtgt tttccaaggc caacagctgt ggcatgtctt 119280
gaaatggtgc ctgccaaggt tgctacattg ttcttggttt ttagcatatt acctgcctga 119340
gaaaatgaca gaatagacct aaaatagagc atttatggtc ttcatattgc ttctgacccc 119400
acacacagtg ccggctccca ggagcaggtt tatgggtcag ctgtccctgt ggtcctggac 119460
tctgcaaccc atgactaatt tcttgtttct tttacggaaa caaacagatt tttctgattg 119520
gcagtgtcag gaggactgct ttcctggaag cttattaatg gtaggaggct gggaaagggt 119580
ttttaacttg gagagaaaac tgaagggaat gtgcttgtgt tagatgacca gttaaggtgt 119640
accacttaga ttggaggagg gatagcagga attctaggac ttctacccag tttctcatga 119700
aactgacttg gacatggtcc ttttttgcaa agggtttctg tttgcatttt tctaggcttt 119760
ctgctggctt gattggtaag actatcactg ttggaaatgg gtggttcatt ggacattgtc 119820
agtaaaccaa aatgattttt ttttctcttt ttgtagaaag aatctttaaa atgtataagt 119880
actacctaca ctactcctcc aggaatatta tctcattatt gtgaaggaaa taagtccttt 119940
tctccagtaa ggttggctaa gtccatacta gtttttctca cagatgtatg tcattggacc 120000
acatttacag tcagtatttg cctaaactgt atgatgacta caaggtctat agcatttaga 120060
gtaataagat attctaataa taccaaattt gaaaagaggg ttgctcttgg aagaaaaagg 120120
gtgtccaaga gcaaagtttg catactgtta ctttggataa agctttagct taccaccagt 120180
gagagagact tgactgctgt ccctcatttg gtcttgaagt cctctcagga ctccttttag 120240
attattctga aggagttaaa acagatgtgt ggttaccagg ggctgggagg gggtatggag 120300
agtgactgct aatggctaca gggttccttt ttggggtaat gaaaatgttc tagaattaga 120360
tagtagcgat ggttgcacaa ctttgtgagt atacaagaaa ccactgaatt gtatacttga 120420
aaaggataat tttatagtat gtgaatcata tctcagttta taaaggaggc aaatgtaggc 120480
tgcagaagtg atggatttgc cagttttttc tcaggtctca gaactgtgga gggaagtctc 120540
tgtagtcact gctgtgcttt ggacccatta cccagcaaag gcagcataag gctctgttca 120600
gcttctggcc cagtttgtcc ttttatgtct ctctcattaa ctcaaggaag cacatggctt 120660

-continued ttatatttaa atttattcaa actgtaatct ttgacatttg agttagcttt tagtacagtt 120720
ttgcatttat agtaatatat attatgtatt ttctctatcc ccaaagaatc cgttttaatc 120780
ttttccggat gcaaatttca ggctgtcttg tcccatcttc cctctcttgc tctctttccc 120840
ctccccccac ggagtgtgtt tgatcaggtg tggcaggaat atccactgtc aagctgcgcc 120900
ctttatatta gtcaatatta tccttctccc ccctccctgt ctgtctgccc ctttgggctt 120960
tcccagttga tttataattt tggaattctc attggagtct gtaatacagt ttgttcatta 121020
tttaaccaaa acctgtttaa tgagcagaga gaggcaatgt aaatgttagg catgttgcag 121080
tgatgtacct ttgtgcttct cagagcgggt gggtagttaa ctctgtgctg cctgcagggc 121140
tggggtgtcc tggccttagg ggcagaaggg ccactgcctc tctcttacat ctgcccaagc 121200
cctgccatgg gtttagattc caaagacaca tttcctttta ttcttctaag aatcttttgg 121260
ggctcttgca tatgggagtt atcttcagtc tcgcagctag accttgtggt aggatctgtg 121320
gcatgggatg gggcatggaa gggaaagtga aatatcagga tacttgatat tgctcttggt 121380
tttagatctg acaagagtag acagtttatg ggaatgcttc tagccaatat ggtctgtggt 121440
ctttgatctc tttgttccca gactagataa attcttgcaa gccttagttc ccttcatcca 121500
gtatagcttt atggaaaggg ctatagtcag ttgtgagttg tggtgtttgg ttgtagtcat 121560
ttgcctccag atatagtctg tctttgtcct tggtctttaa acttagatca ttacaaagag 121620
attcttttcc agaaaatttt tggtttaaaa caggagagga acagtctaaa agtatcacaa 121680
ccaggctagg tgcagtgacc cacatctgta atctagcact ttgggtggcc aagacagcag 121740
gattacttga ggctgggagt tcgagaccag catgggcaac ataccaagat tccccccatc 121800
tctacaaaaa taaaaataaa aaaaattagt tgggtatggt ggcgtacaac tgtagttcca 121860
gctacttagg ctgaggcgag aggatcactt gagcccagga gttcgaggtt acagtgaccc 121920
atgattgcgc cactgtactc tagcctgagt gacaagagtg agaccctttc aatgaatgaa 121980
tgaatgaatg aatgaatgaa agaaagtatc acaaccaaaa tcttctctta tgggatcatc 122040
ttttaatgac ttactttaaa gccttcaggg ccagggcttg aggaagactt cttagggtgt 122100
gcgtgtgtct atgtgcgtgt gagggtgtgg tggtgaggag tttgcctttg gagatttagt 122160
cccaggtctt tttagctctg aggacctaat gtccagtttt ggttatcagg actggggttc 122220
tcagtgtaag actaaggtgg agggccgggt gcggtggctc acgcctgtaa tcccagcact 122280
ttgggaggcc gaggcgggca gatcacgagg tcaggagatt gagaccatcc tggcgaacac 122340
ggtgaaaccc cgtctctact aaaaaaatac aaaaaattag tcgggcatgg tggcaggcgc 122400
ctgtagtccc agctactcgg gaggctgagg caggagaatg gcctgaacct gggaggcgca 122460
gcttgcagtg agccgagatc gtgccactgc actccagcct gggtgacaga gcgatactct 122520
gtctcaaaaa aaaaaactaa ggtggtcttg aggcccagta taggtaccca tattaactat 122580
aacattgttc tagcttctta gacctttctt tttggggatt ctccaagatt tggattcctt 122640
cagggcctag cttattgagt tgcttctaac tgatatttat tgactatctg gtatgtgcca 122700
ggcatttttc ttaggtactt aggaagtggg tctgtaatgg taaacaatca gtcagacttc 122760
ctgccctcat agccactggt ttgacaggac taatgactct agctgatcat tccaaagcta 122820
acattttgta gcctctactt tatgctatat ggtccctatc aggcatggaa tggatgacca 122880
tgagtgagag caatctgctg ccagcttttc ttattcctgc tctttcctta aggaacaagc 122940
caaagaaata agtaaaaaca atagctcata tttgcttatt tggctttcac atgtaaagct 123000
gttatggcca gagtttagct attcccaaag acattggtgg gttgcatagc gtaattctgg 123060
gggataggat atttctttac agagcttact gggacagcag gttatggcgt gcttgagttt 123120
aagagggaga agcacgtgcc aggagaaagt ggatgtgtca ggagtttatt taagtatagt 123180
ttatcctgga caaacacacc tgtagggtac tgtctgtctc aagctttgtg aattcagagt 123240
ctgagctagg aggtttgagt ccatctaacc tccagaggtt tgcagagaac atttaaacag 123300
agtctggaag ccaacttggg aggaactatg acttaacacc tgtctggcct gggcctctta 123360
gcagtagccg cttaggtaga aaagaaactg tttgagaatg cctgatacct caagtttaat 123420
ctgtttcatt tggaaaatgg ggaggtgtag agaaaagaga ttttagtagt cattgtcagg 123480
aaaaagattg aataagagta tattatatgt gccaggcatg gtggctcaca cctgtaatcc 123540
cagcactttg ggaggctaag gcgggtggat gacttgaggt cagcagttcg agaccagcct 123600
ggccaacatg gtgaaaccct gtctctacta aaaatacaaa aattagccag gtgcggtggc 123660
gcatgcctgt agtcccagct actcaggagg ctgaagcagg tgaattgctt gaacccagga 123720
ggtgagattg cagtgagctg agatcgtgcc actgcactcc agcctgggtg gcagatcaag 123780
actccatctc aacaacaaca acaacaacaa caacaaaagc gagtatgtta tatgaaaaaa 123840
atttgctgga gtcctattga ttaagtgcct acttttattt tttcctacag gggtctatag 123900
tttagggagt aaagtaatat atcattatta atcagcatga gaagaaggtt gaatgggtca 123960
tcagcttttg ttccacttgg aattgagctt gtgaattgtt caaggcctaa gtaggaacta 124020
aaagaaccaa atgtgataaa atttggcaga caaattttgt gaagggctga gtgttaggaa 124080
aggcaatggg cacacttaaa agtatccatt tcctgtgccc tgttttactt tcttggttta 124140
taatataaaa ctatagttga gtaatacatt agaatgtgac ttgaatttga gtcagactga 124200
ctttggcacc ttagaatctc tgtaacttga gtggccacag acttgtagac atttcagcac 124260
agttagagtg aataaaggta ctgtgattct ttttttcccc agggactatt catattaaaa 124320
gggtagctcc aagaggccta tattttgatg acttgatttt gccatttctt tttactgggg 124380
ccttccccag atgatttatg aatgctcttc atttgacact tttaaaccaa gaagttcttc 124440
caaacatttg tttgtactca aggttaggaa atgaagactc ttgagaagaa acagctctgc 124500
ataatctgtc ctctcatggg ttcagctctc tctttttctc ttcctcatac ccaggcacac 124560
ttagccatca gaactagttt cctggctgtt gagggggcac attttctact gcatgtatca 124620
gaaaaggaat tgtgtaaaaa gagggaaaag cattcttaat agtttagctc tcaaaaacag 124680
agaaacctaa tttctttgta gcaaaggtta gggggcagtg taacagtgtg gtttgtggtg 124740
ggtatcaaag ttgctggtgt ttttattgca tttgtcctct ttagcacagc tacctcttga 124800
ggcctgaaac ttctgagtat atgcccaact taccatgaca gcagtcagat gagtaaaaag 124860
aaagccagct gctgtttttt tttcaaacaa ggaggcaggc agagtccctt cctgcttttc 124920
cacccattca aactcaggac aagtgccaaa agggtttcag aagaagccaa atgcttgaaa 124980
ttcaatgtgt tgttttgatt aggagagata gtgaagagtt tgtctcagcc ttgccccccct 125040
ctgactatct ctctatgttc atagatactt agttgataac ccagtttctg aagtgatagt 125100
ggatatgttt atggaaaggg tgagtacatt tgtcttttct ctcctggcat ctgttagaag 125160
atggagttgg ctatagagca aaatggagat aagatcattt cagctcagat cacttcatta 125220
agaaagggta atagatggag agcaatgact actttaggct ctcagtttta ctctaggaaa 125280
ccaggagata atttgcacct caccagttta ggggccttta ttcctttcct ttattctttg 125340
aagatcctaa agaacttaga tggacaagca cttctggctg tctgttggct gggttctcat 125400
ggcatgtctc ttctgtaaca tcagcattct gttaccactg ttaccactgt aggtcgagtt 125460
gtgaagggct gccacatgtg cacagatcac aactgacctt tccttgttcc acgcttattg 125520
agcaattact tgcccgtttg tggaactcac attattgtct tgcatttctg gcccagtgtg 125580
aagtgggggc atccaggaag tggcctaatg gactgtacat cagagggcaa taaattggca 125640
tatgatttgg tggaaaggca gggccagatg tagtgtggga gctagagttt ttctgcagtc 125700
agccatgcag cttgcttcca ggtgtcctgg aaagcagctt gggaactaga gggtaagagt 125760
agttgaggac attcactggg gaagaaaagg atcaaaagca cttcagtgtt atctgggatt 125820
ggccctgaat tgaaaaaaaa tcctctaaaa gtagagggac aaatgagatt tccctgacac 125880
tgacagggac ttttccacag attatttttt gttttcaagt aaagtgagtt attgtaagaa 125940
aaaaaatcta aaatttgaga gacccttgac aagaggatgt agaatgagaa agcctcattc 126000
caaatgagtt tttgcattta agaaaactgg taccaaattg attaaatgaa atgagagctg 126060
atatggtatt acaactgccc tgggctacag tggtgttttt cagactgtag gttgatttgc 126120
attagtgaat tacatcactg taatgggttg catggcattc tctccaattt tttttttttt 126180
tttgagacgg aatcttgctc tgtcaccgcg gctagagtgc agtggcgcga tctcagctca 126240
ctgccagctc tgccttccgg gttcacgcca ttctcctgcc tcagcctccc aagtagctgg 126300
gactacaggc ggccgccacc atgcccggct aatttttgt atttttagta gagatggcgt 126360
ttcaccatgt tagccaggat ggtcttgatc tcctgacctc atgatctgcc cgtcttggcc 126420
tcccaaagtg ctgggattac aggcgtgaac cactgcaccc ggcctttttt ttttgagacg 126480
gagtctagct ccatcaccca ggctggagtg tagtggcgca atcttggctc actgcaacct 126540
ccgcctcctg ggttcaagca attctcctgc ctcagccttc tgagtagctg ggattacagg 126600
cacgggccac cacgcccagc taatttttgt atttttggta gagacagggt ttcaccatgt 126660
tggccaggtt ggtctcgaac tccctcggcc tcccaaagtg ctgggattac aagtgtgagc 126720
cactgtgccc ggactgctct ccagtttttt atgatgaaaa attttaaact tagcaaaaat 126780
tgaaagaata ccataatgat tacccatatt tcacatttag agtcaaaatt actaacattt 126840
aggcatattt gctttatccg tatatgtgta ttatcatttt tttcatgatc catttgaaaa 126900
taaattgcaa acatgttgac atttcacccc taaatacttc agcatgaatc ctaaataagg 126960
atgttctcct acataatacc attatcacaa ctaagaaaca acaataattt gccaattcta 127020
gttaatatcc agttcatatt aaacattttc cgtttgtccc caaactttta tagctataat 127080
tggttttaga aaccaaaatc caagcacaat tctcatttca ttaggtagtt atgtcttttt 127140
agacgtttta ttttatttat tttagagatg gggtctcac tgtgtcactt agggtggagt 127200
gcagtggtac gatcatagct cccagcagct caagcgatcc tcctgcctca gcctcctgag 127260
tagctgggac tacaggcgca tgccaccaag cctagctaat tttttatttt attttatttt 127320
attattatta ttattatttt ttgagatgga gtcttgctct ttcgcccagg ctggactgca 127380
gtggcgctat ctcagctcac tgcaagctcc gcctcctggg ttcatgccat tctcctgcct 127440
cagcctccca agtagctggg actacaggcg cccgccactg cgcccggcta attttttgta 127500
tttttagtag agatggggtt tcactgtgtt agcccagatg gtctcaatct cctgacctcg 127560
tgatctgccc gcctcggcct ccccaagtgc tggaattaca ggcgtgagcc accgcacctg 127620
gcccatgcct agctaatttt taaaattttt tgtagagaca ggatcttgct gtgtttccca 127680
ggctgttctc aagctcttgg cctcaagcaa tcctcccacc ttaacctccc aaaattgttg 127740
agattacagg tgtgagccac tgcacctggc cctaggcttt taaaagacaa ttttctccac 127800 ctttttttt tttttctttt tgcattggct ttttgaggac accagcccat ttatgtttag 127860
aatgttctac attctggatt tgtctgtgtc cttgtggtat catttaactt gttcctcttt 127920
cccgtatgtt atgtactaaa aggattaaaa gcttgattag attcaggtta aatatttttg 127980
gcaagagtat tttatagatg atactatgta attcatatta ttactattat tattatcatc 128040
attaccatta ttttttgaga cagagtcctg ctctgtcccc caggctggag tacagtggtg 128100
tgatctcagc tcaccacagt ctccacctcc tgggctcaag tgatcctccc acctcagcct 128160
cccaagtagc tgggactaca ggtgcatgcc atcatgccca gccaattttt tgtattcttt 128220
gtagagacag ggtcttgcca tgttgcccag gcctgtcttg aactcctgag ctcaagtgat 128280
ccacccacct cagcctacca aggtacaggg attacaggtg tgagctattg cgcccagcct 128340
tatttcatat tatatcacca caggaagcac atcctgtcag gttgtcctgc aattgttgat 128400 ttttttttt ttagacggag tcttgctctg tcacccaagc tggactgcaa tggtgtgatc 128460
tcagctcact gcaacctcac tcccaggttc aagtgattct cctgcctcag cctccccagt 128520
agctgggatt acaggcaccc accaccgcac atggctaatt tttgtattgt tagtagagac 128580
agagtttcgc catgttggcc aggctggttt cgaactcctg acctcaggtg atctgcccac 128640
cttggcttcc caaaatgctg agattacagg catgagccac tgcacccggc cgcaattgtt 128700
gattttaaca gttttgttac ttgcttctta tggtgactgc catatctcct aattttgaaa 128760
tacgttaatt tttctttttg taattttaag taatctgtga agtaatattt ttgcaccttg 128820
taaatatcct gtcctctaat atccttttac ctaatggtta tccactgatt aatatttgac 128880
tgaatctttt atttcactgg tcacagaatg atttttctaa ttctgtcatt tttttctaca 128940
tttattagct agcattttct gtaaagaact attttccctc atcaactgga ggataaacca 129000
atttcttcta aaaaggcagg ataaatgctt aattcattcc ctttaattgg cagttttcag 129060
attcagaagt gagtgttaat aatgatcact agtggtggca aatgtgggtc tgcctcctcc 129120
taggggcttg tgagtatttt ttagtgtttt acaattaatt acagatatgt ttttttccat 129180
tgttattttt ggtgctcaca ttatttcaag tttggccagt gtgcgtcccc ttcagactgg 129240
ttcctttgtc ttttgacatg acatctttga acacttcctt gctttctggt acaatcaacc 129300
agcaataaag gggaaaaaag aatagaatag aaattatcag tgtatctggc cgagtgtggt 129360
agctcatgcc tgtaatccca gcactttggg aggctgagat gggtgcatca tgaggtcagg 129420
agtttgagac cagcttggcc aacatggtga aaccttgtct ctactaaaaa tacaaaactt 129480
agccaggcat ggtggcacgt gccagctact caggaggctg aggcaggaga attgcttgaa 129540
cccaggaggc agaggttgca gtgagccgaa gtcgcgccac tgcactgcag cctgggcgac 129600
agagcaagac tgtctcaaaa aaataaataa ataaaataaa aaataaaaaa aagaaattat 129660
cagtgtatca tacttaagaa agataagtat tgtttttcgc aacttgtttt agttagaaac 129720
ctgtattttc tgggttgtag cgtaagctgt atcttctcct atccatcatg gtcaaaaaag 129780
tttgaaagca ctggtagaaa gtttgtgatg tactcctgtt ctagcactgg tttgaatttg 129840
tctgtctgca atgttatttc atgggcaagg agtcaaggag gatattgagt cagggtgccc 129900
ttctcaccat tttcttgaca ttctgtgaag gactctgtga ggcaccttag ccccccttgac 129960 ttttgggaat gagtggattc ttcatcccta tcaactttga tttcagtaag acagttctat 130020
ttagatggtt gtttctggat gaatcagctt ttgccaggca gagattaatt tgagcctatt 130080
tgagtcgtta taatcctgga aaatattaga gtaagtattc ttccccaagg aaataagaat 130140

-continued

```
tgtggaagta attatgactg attagtcact ttgcacctta tccctttat gtgatgctat 130200
acagattgtt tagacatatc atgttagaca tggccaccct tttgaatcat cttggtgagc 130260
tgagggaatc atttgtcctc gaaagactcc aaaagagcat cttctccagg aacttttctg 130320
ttagtggaag ttcaacaaat atttgttgat tacttactat gtgccaggaa tggaactagg 130380
ttctagggac ctagttttca aggagactga cacagttcct gttctcatag tttatggtct 130440
agtgggctgg tgatttgaga agctctggaa tttgagcaga caactgggca ctagtttgaa 130500
gtctgccagt ttccacacgt gacctcagga aattgttgta tgctttggtt tgctgaaaga 130560
ggttctagga tggtcaaaag aatagcattg gtgttgtcca cattgtctgt cccacctcca 130620
ccctgtgccc tagccctgcc tgcttggcag tgaccctgga aattctgtgc atggcagctt 130680
cattagctgc ttttagggcc ttgaatgtct tatagttgat tagtctatta aaaaaatttt 130740
tttcacctat aatatgttct atgatatgat tagtctcttt atattggcct ttgattaatc 130800
agtctgtgca tcacagactg accacatcac agacggacca caactgacca cagttgaacc 130860
ataggataag ttatcaatgg ctgattgttt tttctaataa aattcaactt tgcatttgag 130920
tcctctttgg cttgggcttc tgacacaatt tttaggacat tgaagtctac aggtgcaaaa 130980
caaagatttt tttttttttt tttttttttt ttttttgaga gggagtctca ctctgtcgcc 131040
caggctggag tacagtggcg tgatctttgc tcactgcaac ctctgcctcc cgggctcaag 131100
taattatcct gcctcagcct cccaagtagc taggattaca ggcacccacc accacgccag 131160
actaattttt gtatttttag tagtgacagg gtttcaccat gttggccagg ctggtcttga 131220
actcccaacc tcaggtgatc tgcccgcctt ggcctcccaa agtgctggga ttacaggtgt 131280
gatccaccgc gccaggactt tttttttttt ttttttgaga cagaatcttg ctctgttgcc 131340
caggctggag tgcagtggtg caatctcctg ccctcaagtg atccaccggc ctcagcctcc 131400
caaagtgctg ggattacagg catgagccac tgcgcccagc caaaaacaga ttttagtagc 131460
tgtttacctt atgttgctaa aagaatgagg aaagctgttt tttccagcca gggtctaata 131520
gtcccagttc acaaataaca aaagtgtttt ttagtagcag cctactacct ttagcccaag 131580
ggtctcatgt gaggaaagta gtaccaaaac ccttgtaact ttgaacagga tttagcttca 131640
taatcaatag gacatttcat catatatttg tcttttgaat cccagagaaa gcacctagaa 131700
gtagcctttg ggagcattga gacctcagag agaccgtccc cttgtgtagg aatagtattc 131760
ctaggatttt caagggtaga aagaggtggt gaggcagtga aacagttaaa cagtggttaa 131820
gaactttcta aaagagaaag ttggagtgaa tgttggagta caaatgtagt ccacagaaag 131880
acctgtgacc tgtcatttgc ttgaatggct tatcgtgttc tgaatttaaa gtgcaattct 131940
ttctcctttg cctcttttt tctgggatga atctatatcc aagttacatt atttaatacc 132000
tactatagct aaatactttt tgtgaccaga atctgttgac tctgatagga tccttgttcc 132060
ctctggcctg ggaaaaaaag ttcttggttc agtccacctg gacagaagca ttgtagggaa 132120
aatagtcaaa ggaaaatgga cttcggttct cagactccaa gtaggtttca ttaatcctcc 132180
caagtgagcc aagactgcat cttaatcagt ttcatttcag gggttttaaa taatgtttct 132240
gggctgggcg tggtggctca cgcctgtaat cccagcactt tgggaggccg aggcaggtgg 132300
atcacctgag gttaggagtt ctagaccagc ctggccaaca tggtgaaacc tcgtctctat 132360
taaaaatatg aaaattagcc gggcatgggt gtgagcgcct gtaatcccag ctactgggga 132420
ggctgaggca ggagaatcgc ttgaacctgg gaggcagaga ttgctgtgag ctgagatcgc 132480
gccactgcac tccagcctgg gcaacagagg gagactccat ctccaaaaaa aggcctggcg 132540
```

cggtggctca tgcctgtaat cccagcactt tgggaggccg aggcaggcgg atcacgaggt 132600
caggagatcg agaccatcct ggctaacacg gtgaaacccc gtctctacta aaaaaacaaa 132660
aaattagctg ggcatggtgg cgggcgccta tagtcacagc tactcaggag tctgaggcag 132720
gagaatcgct tgaacctggg aggtggaggt tgcagtgagc tgagattgca ccactgcact 132780
ccagcctggg cgacagagct agactctgcc tcaaaaaaaa aaaaaaaaaa aatgtttctg 132840
ttgccaaggt tctataagga agaaaatgag tagtgcttgc ctttggtaga actgcttttt 132900
atttagagaa tgggagatgg tgccagggtc ctaagtaatc ctgggtaggc cgtaggctca 132960
atagtcaaca aaatgggttg tgtgcatgta gtaaaggaag gtagagaatg ggaaatattt 133020
gggttggtaa tagtctaaca aaagctccaa agggaagcaa aaagttggct actagaggtt 133080
gttttactgc tatttagaat gtgaattcat ccctatttcc tttttaccta attggtatca 133140
ggacattgaa tcaaatgaac agatggtgaa ttttcttgaa tttttatttt gaaataattt 133200
caaatttaaa ggtgcaagaa taataggtct cccatatgtc cttttgctac ttacacacac 133260
acacacacac acacacacat gcacacacgt atgtatgtat gtatgtatat atagacataa 133320
aattattttt tggctgggca cagtggttca catatataat tccagcactt tggaaggcca 133380
agatgagagg atcacttgag ctcaggaatt tgagattatc ctgggcaaca taggtagact 133440
ccatctctac aaaaaattaa aaagccaggt gtagtggcat gtgcctgctg ttccagctac 133500
ttgggaggct gaggtaagag gatcacttaa atctgggagg tgaaggctga agtgagctgt 133560
gatcatgcca ctgcattcca ccatgggtga cagagttaga ccctgtctca aaaaaagaaa 133620
agtacataaa taaataaatt tttctaaatc atttgagagt aggttatata cattgtgact 133680
tttttttttt ttttttcaga cagtctcgct ctgtcaccca ggctggagtg caatagcgtg 133740
atctcggctc gcctcccggg ttcaaccgat tctccctgcc tcagcctcct gagtagctag 133800
gattacaggc gcccgccacc acgcccagct aatttttgta tttttagtag agacagggtt 133860
tcgccatgat ggccaggctg gtctcgaact catgaccaca ggtgatccgc ccacctcggc 133920
ctcccaaagt gctaggatta caggcgtgag ccaccgcacc cagcctatca tgatctttta 133980
tcccttaata cttcagtgca tatttcctaa gaacaaggat attctcttac taatttaagt 134040
atagttatca aattcaagaa atttagcatt gatacaataa tttactattc atattccaat 134100
tttgtcaata aacttttatt atttgttttt tttttcccct tcagccaagg atcacaaatt 134160
acattagttg tcatgtttct ttagtctcct ttaatctggg accgttcttt agcttctctt 134220
tatgcttcat gacattagca ttaaaaacat ttttttaaaa ttttttcagc cagtggttta 134280
tgcctgtaat tctagcgttt tgggaggcca aggcaggagg gttgcttgag gccaggagtt 134340
tgagaccagc tttggcaaca tagtgagaac tcattgcttc aaaaaaataaa aaaaattagc 134400 tgggcatggt ggcgtgtgcc tgtagaccca gctacacagg aggctgaggt gggaggactg 134460
cttgagccca ggatttggag gctgcggtga gctatgatca tgccactgca ctccagcctg 134520
ggtgattaag aaaacaaaca aaaaaacatt aaacaaaaac actttttttt ttttttagag 134580
ttatggagtt atctgtaact ccataactgt ttacagagtc tggtggtggg atcgtagctt 134640
actgcagcct agaactccca gcctcaactg gtcctcctgc cttggtcttc caaagtgatg 134700
gaattacagg catgagccac cacagccagc tgacattgac attttttata actacagacc 134760
agttcatgtc tgtgttcttt ctttttaaaa aattgatcca taataattat acttatgtat 134820
tggttacatg tgatattttg atacatgagt acaatgtgta atgattgtat ttaggatatc 134880

```
tatcacctca aacatttgtc gtttctttgt gttgggagca tttcaaatct tctcttatag 134940
ctatttggaa atatacagca aattattgtt aactatagtc tccctaattt atttatttct 135000
ttcaagaata tttctcattt tgggtttgtc tgatgttttc ttatggttag attcaggtgg 135060
tgtgtgtcta tcgtgaatct gtaatatata ccactactga tatagggtcc ttctcagggt 135120
atcacaactg caggtgctgt tcattggtga tactaatttt gatcatctgg tcaagtgtta 135180
atctgattta tttactgtgt agatgttatt tccccttgca actaataagc aatctgtagg 135240
gaaacatttg aagatcatac tcctctttaa actttccctc taatacctaa catacattga 135300
taattcttgc ctgaaccaat ttctggttgc agttatggtg aaatttgagt ggttgcttaa 135360
aatacttgtt cttaggtgga cacaaactgt ctttctagct tgcttctgtt tgtttctctt 135420
cctataagaa acacaattgc ataccctaaa gatctatatt tttttatgtc taaatctaat 135480
aactaaaaag agtttgaaaa ttggaaaaag gtttggctca atgaggcttg acttggaact 135540
tggtaatttc ctagaatggc cacatcaccc agtggaattt gttctccact caaccaacag 135600
cataagtgct ttttctctaa gccagactga caacagccat gtgaagtgga ttcttttttt 135660
aaaatttact ccctctttta ataagtggga tttgctatga attcatcatt atatttcagc 135720
ttttgttctc aaatctattt taatagcttg attcatctta ttaagcactt ccacttaagc 135780
tttaacaaaa tccataaagt ttggaaatgc ccattgtcca ggagctttaa gagagaaaag 135840
gttaggagaa acgttttcct attctccttt tctatcattt ttttctttcc ttccctctta 135900
tttttctgta ttttttcctt gtgcctttcc tttcattcct ttgaagcatg attaggatgc 135960
atgactgagc ctccaaaagc agagagaaaa agaagtattg cttcttgaga ctcaggtttt 136020
ttattgttat tactacggag aataggctaa tgatatgata attatgacca ttactaatga 136080
atgccttatc agctatcagt tgtttcttcg agggaacctt gccctcaaaa aaagtggctt 136140
acgcctgtaa tgaccagcac tttgggaggg cgacgcaaga ggattgcttg agctcaggag 136200
tttgaaacca gcctgagtaa ctagtgagac ctcatctcta ctaaattttt ttttgtttta 136260
attagccagg catggtggca cacaccagta gtcccagcta cttgagaggc taagacagga 136320
ggatctcttg aaccccagaa atcaaggctg cagtgagtaa taatggcacc actgcactct 136380
agcctgggtg acagaggagt ccctgtctta aaaaaaaaga gagagagaga gagagagaga 136440
aataagtaga gacaaaagaa aacaactaga gagtcagaaa gaggaaaggg gcagaagcaa 136500
agaacttggg gatggggagg caagggtagg agagaaggac agagaataca gaactcctaa 136560
aataggaaaa tgggagtcag ctctaacatt tacctttacc cagtccagtg tgtgggtttt 136620
ccccttcag tagaatgttc tatgagatag gatgagatgg ggtgaatgaa attgtcccat 136680
ccttgactcc ttggatctgt ttacatggaa ctgaaggttt taccctgtaa tgtgacttga 136740
tagcctgatc ctagtgggtt gggtaggaag aggctattaa gtgatgtttt ttggcttgct 136800
agcattaaca gagttatttt taacctccca tttcaatctc ttcgttgttc aggttcctct 136860
gctggctacc atgagagcag tcaaaattag caactatata aaatgaagta cctcttgtct 136920
ccccagtcac ttccaaaata aacagggagt aatactgtcc atattttgtc tcactttact 136980
ctgaaggcta gcaatagagg aagcatggat tagtgtgtag tgatttccag gctctgccct 137040
ctggacagat tcccctctga gtgctccagt tgagtgacag gaccatgtgg caggagtgca 137100
gctggaagta tatcatcggc agatttgggt tgggtaaata tagcaggagc aggatgtcag 137160
tgtgggagat ggattgttct gggaaaggaa gtgttgtctt tcgtctgaga aacaatttcc 137220
tgcacttctg ggacttttgc tttcttcttt ttcttttttt tcccagggca gagcaggagt 137280
```

tggcagggga tgggtacact tgctgaattc tatctctgga tgtctgcatg tttctacatt 137340
tgaagttggg agtagagatc agatctgttt cagccagtta ggaaatggac ctaataaatt 137400
atcgtaccca tgccttaagt ttcacttttt gaagttttaa attaaagcac ctatctgctt 137460
aaagcctctt tttaaaaagt tactgttctt ttagtgaaat agacgggttg agaggcaaaa 137520
ataattacgt aaagaaaatc aactctattg caagtcagac atgaggcacc agctggcagg 137580
aaacagctgg gatatttctg ggggctagac tcttccacac cagcacttaa ctcttcaagt 137640
gatctctgtt atctgagcta cttaagatag ctacctacct taccaacaat ctgcataaaa 137700
tactaaatct actaaattat gtgatatttt acaattgact agaactttat aatttataaa 137760
gtggtttttc attatagcct ttcaatttta gaatctataa agcacataaa ttataatcta 137820
taaattatat ttttataaat tatctataaa ttatatttat ataaattgtt atattataac 137880
ttagactcat acataatcta taatagatta tttctataaa catatttata gaagagttgt 137940
aaagaagttc tcatctatcc aatgcccagt ttcccctgtt attaacatct tacattaata 138000
tgacacattt gtcacaatta atgaacaaat attgattcat cattaattaa agtccatact 138060
ttattcagat ttcattaggt ttttacttaa tggccttttt ctgttcaagg attccatcta 138120
ggataccaca ttacatttag tcatcacatc ttgttaggtt ccacttggct gtaacagttt 138180
gcctgtattc tttttctttt ctttttttctt tcttttcttt tttttttttt tgagacagag 138240
tctcgctctg tcgcccaggc tggagtgcag tggcgcgatc ttggctcact gcaagctccg 138300
cctcccaggt tcctgccatt ctcctgcctc agcctcctga gtagctggga ctacaggcgc 138360
ccaccaccac acccggctaa tttttttttt ttttgtattt tttagtagag atggggtttc 138420
accgtgttag ccaggatggt ctcaatctcc tgatcttgtg atccacccgc ctcggcctct 138480
caaagtgctg ggattacagg tgtgagccac cgcgcccggc cgcctgtatt cttttcaagt 138540
ttcacaaaaa ctcacaagat agactgtgcc tttattaata ttccccttt acagataaaa 138600
ctcaggttcc agaaaaatta agtaacattt tcaaggttat acagtaaaag cttcttttaa 138660
agtgtgatta tgatttggaa aaaggcgatg aggttattta tttgcttttc acgtgaataa 138720
gggcagactt acagctaacc ttcaggtggg ccatttactg aagaggaaca agagacagag 138780
gtgagtctag cttgttcctg gactcttctg tcttgctgga gacaaattaa cattattatt 138840
ttaatcacaa ttattttggg aaaacccctt tctctttgat tctgctatgt ctaccaaagg 138900
aactgatggc agaaaatcct gagttagcct tgttccctgg caacagactt caggctgctt 138960
actggtccct gttgttggat accaggttca gtaggaaagt ctgctgagag tatagcatga 139020
acactaaccc aactagccta tttccagcac gtgtggtgtt aactatctgg gaataggaac 139080
atgagttttt aaattccagt ctctaattgg gtaggctgaa gttctggctt ggagtaagga 139140
gattcacaga actgcagtgc taagagatag tagaaaaatt taaaaattca ataagacatg 139200
gcacttaact gactctgaat gctctgtccg gagggatgag taaaggggag aggtgagagg 139260
aggtaaagta gcgggttact aatgatccta gatactatta aaagattatc acaaggaggt 139320
ggaaactatt gaggtacaaa ccatcagatc ttaaggtaag gagtcactca tcttgcccag 139380
agaagtagta gtgaagatag tacctggatc ctaaaaggta acttttaaag tacttcaacc 139440
taagatgaca gagggtaggc agtttattga tacccttaac aaccacttgt tagtagagcc 139500
attttaatta atgggaaagg ggatcattct ccgtttatgc ttttattata tgtagctatg 139560
agcatagaag ctgtgtttgg accctctggt gactattgcc ctcttctagt tgtgtccagg 139620
cacaggtaaa ttcttgaggc caggaagggc ctggctttat ctccaaaagg aagctgtgga 139680
aatagcaatg agcaaaacaa tgagaaagag ctttagaaaa tttgcaaata ttgtgtatct 139740
tcatggcatg atgaagtggg attaggacag gggagaaagt ataaaccacc aattatagga 139800
gtctttaagg gcttgggtga ctgaggcctt ctgctaggag gctgggaggt tgttgatgac 139860
agcaaagatg taacaggtat tgaatactag aggatagacc tcatactctg aaaatgcttt 139920
tgcctcaaca atttgaaaga gaaatatgaa agacaaagtg acaatatgaa gaatgactat 139980
tcaaagtgct tctaccagta agtcttgtct gttggcaagt tttaacctgt aggtagggga 140040
aaaacgtggg aggatctctt attcagaatg caaaacagga gacagtgaag tacctgtgtt 140100
tccaaagaac tccgaattga gctgtggtgg aagaggagga aatttcttac tgtggtcttg 140160
tataatgtga aatctttgtg aagtctcaat agatgttaag tctccaagga ggggagactt 140220
tttagctgct aaagaagctt aggttcagtg agcctccagt gggaatacag acatagacgt 140280
ccactgacat ttctgcaacc agttttggtg agtggaaagc aactaggtaa gtttcacttt 140340
ttgcaagaat cccaagtgac cctttgcact atggactgag gtacctgctt gtctctacaa 140400
aaactataga ggagacacga caggctttaa ctggaaattg ttcatggttt cttagaaggg 140460
aagctcatat cctgttaaag cactttagaa aaataaagtc aaattagaga taagaggatc 140520
tttacttgta ttttcaagag cttttttaaa aaactgaagt gaaatgcata taacataaaa 140580
ttaaccattt taaagtgaaa caatatagtg gcatttagta cattcacaat gtaccctatc 140640
taattccaaa acattttcat cgccccaaaa ggaaatcctg tacccattaa gcagttgctc 140700
cacactttcc cttcccctcc agcccctggt agccatccat ctgcattctg tctctgtaaa 140760
tttacctatt ctggatattt catataaatg gaatcatata atatgtgtcc ttttatgtct 140820
ggcttctttc tcttagcata atgtttttga gggtcatcca tgctgtaaca tgaatcagca 140880
cttcaattct ttttaggatt gaataatatt ccattgtgtg tgtataccac aatttgttca 140940
tccattcatt cgttgatgga catttggacc atttcttcct tttggcaatt atgaatagtg 141000
ctgctaggga catgtgtata catgtatttg agtatctgtt ttcaattcct ttggatatat 141060
acctaggact ggaattgctg ggttgtatgg taattctatg tttaactttt tgagtaactg 141120
ccaaacagtt ttctatagca gctgaaccat actacattcc caccaagaat gcatgagggt 141180
tccagttttt ccgcatcctt accaacactt gttatttgtg tttgttttgt tttatatagc 141240
ttcaaaagct tttgagactg gataggactt tgatgataaa gctcctttca ggtcttatgg 141300
atcttctgac atgcttctct cctgaaataa ctggatggct cttctgggcc aaataaggta 141360
ttgagatttt agcttttata ctaaaggatt actttcttcc aaaatttcca ataaacagcg 141420
aacacagatt ttacagattt tacaggttgc ctagacaggg tcgaattctg acttgccaaa 141480
agaagagtgt cagttacact ttgggtcttg aaagtagatg atggtatttc tggtttcatt 141540
tgccatcaga atcctggacc aggcaatagg ctaggtcttg ctgactatac aggtagctca 141600
gtttgcttac acattaccag cttatcttcc tgctcacaga ataaccttct ggggagggag 141660
ttaactctaa ttcctgataa atgactggct ctttttaagg tgctatataa actgaatttg 141720
gatgttactt cgccactact tacaatgata ctatgtacag atattaaaac tctaatgttc 141780
ccatctcctt actgtgtggc tgggtggttt cttattttga tgtcttctac atcaaactgt 141840
tgagttccta agtgttctct tcttacccct ctctttttta gtctctcagt ttctacttct 141900
tgcatctata tattttgtga tttgtctaat agtcactgtg attaatgttt tagtttgttt 141960
ttcttttgtg aaaattattt tcttcttgtg aaaggtgaaa attagtttct tcttgtgaaa 142020
ggagaaaact ggtacagaaa tctaggacgc tggaacttct agctctctcc gtttttteta 142080
gaattgtagc tttccttctt ttttttctt tgactgtttt ctccagttta tatgttgagt 142140
ggtaggtttt tctaactttt agaaaaaaat tattttgcta tttaatgtgt ttgctgtatc 142200
tccttgaaat attataaatc agaatacatt ttagtgttta ttgctgccat tggttgcttt 142260
aaaaaaaaag gttgaacctg ttttcaaagt aaacaaaatt gtagcctcta cttaccttcc 142320
tcctttcccc accacaatac acagtgttgt tgggtttgca aattcatcct aaccatttga 142380
tcaaagtcag gctttgaaca aggctttata gtgaggtgtg gtgaatgaca ggtatgtctg 142440
gatttggcct tgagagattt ggggatgtaa aagcataagg gttttttttt tttttttttt 142500
ttttctgtct ttctttctct tctcctaatg tactgtggtc tataataggt tgagttgtaa 142560
cattcattaa accactcctc gcattccctg ttttcaaagc ttatcaggat gactttgatt 142620
tagttatttg gaaccaaaaa ggcagtttgt ggagcctggt ctggagctgt gtagcagtaa 142680
tatatcagag atcagactta ggtcccagtg ggattattcc tcgggattta tttgcctgga 142740
agtacacaca ggagccaaat ggtatgtatg gaaagctttg ctggaatgca aattggacac 142800
attttgttgg gacctgtagg ggattttcac tgcttcataa tttttcaaag gtttgttata 142860
catcagacag tcactgcctc ttctttaaat ctttaaatcc cccctctttt tcctgttgta 142920
aaggtcagat ttttttgac aactgtgtgc aggaacaaga tttgctaaat cccttcattt 142980
ttattcatac aaatatcgga attcagtgag catcagttat tccagcattt agaggtaagg 143040
aaaactcagg gagaatcttg tgaatctcag ctttgtgcta gacatatatc tctggggata 143100
aatttgctgc ctcaacttta accccttgac tgctctgatg tgagacgaca cccttacagt 143160
ggctgccttg tatgtgaaac ctacccttaa ctaacccca tttatggctg taggatatgt 143220
aatataatta ctgggagggg actgtgttgg actcttctga tggggccttt ttggctgtga 143280
caagccttag attagtgttg gaagagaagg acaattcatt ccctccagtg gagccccttc 143340
tttaggcata tttagctttt aatggtatca taggcaataa ccacttttaa tttgcagatg 143400
attctttctc aaccagtaga tgaaataatg atatcaaatg gtacatttcc ccatcaaact 143460
tgcttagttt gatgttatgt tattatgtta tcgattgctg ggtaacaaat taccccaaca 143520
aattacctct cctacccatc tattgctggg tagcaaatta cccccaaaa tgtggcagct 143580
taaaattaaa aaacaaaaaa aatttcacac agtttctttt attttatttt cttttttttt 143640
tttttttttt tttttttga gatgaggtct cactgtgttt cccaggctag tctcaaactc 143700
ctgggctcaa gtgatcctcc caccttggcc tcccaaagtg ctgggattac aggcatgagc 143760
cactgcacct ggtctatttc acacaatttc taagggtcag gaatctggga gctgcttagc 143820
tagtggttct ggcttagggt ctctcaagat gtcagccagg gcagcagtca tttgaagggg 143880
tgggctggaa gatccatttc caagttcatt catgtggttg ttggccagag gcctcagttc 143940
ctcacaatgt gggcctctca ataggactgc tcacagcatg gaaactagat tctccatagg 144000
tgaatgatct gagagagagc agaagccaca ctttgttttc tgacccaacc tcagaagtaa 144060
acctcaggag taaccatcac tcctgctata ttatattagt cacatagacc aacctaaata 144120
cataaagatg taatcactgg ggacatcact gggagtcatc ttggaggctg gccttgcagg 144180
aagttaaatg gaaattttta gatgttcact gggacttcaa gattgatttt tttaatttga 144240
aaaattttgt tctccccagt cagccctgtc tccctgtctt ctcccaaacc tttatgtctc 144300
tgaaattgtc caatatgtat atggcaaata tctctttctc ttcctttgct gtctcagcca 144360

-continued taagcgctag taaaaacttt ccgtttttct aaagcaagcc agtaagcatg atcgatctac 144420
ctcctctacc cgttttgctg ggacatccat ggcagctggt caaaggaggc ttctgctcat 144480
gagagcactt caactggatt cagataatcc tttgtggttt ctccacctat ttactactga 144540
tcctctaaaa tttggtgcaa atgaactaga ctgactagag ttacagtgtt accatgtttt 144600
tttcagactg agatatataa tgatataatg atatgagctc tttttggatt ctatccagga 144660
tctccaaaat ggagataaag acctaatgct cgggagtgat ttaaaaacga aattacggcc 144720
gggcgcggtg gctcacgcct gtaatcccag cactttggga ggccgaggcg ggcggatcat 144780
gaggtcagga gatcgagacc atcctggcta acaaggtgaa accccgtctc tactaaaaat 144840
acaaaaaatt agccgggcgc ggtggcgggc gcctgtagtc ccagctactc gagaggctga 144900
ggcaggagaa tggcgtgaac ccgggaagcg gagcttgcag tgagccgaga ttgcgccact 144960
gcagtccgca gtccggcctg ggcgacagag cgagactccg tctcaaagga aaaaaaaaaa 145020
aacaaaaaaa aaaaacgaaa ttacttgtca ctagatagat tcatctggtc ctttgtatac 145080
cagtcagata agagccttag gagttggccg catgtggtgg ctcacgcctg taattgcagc 145140
attttggaac gctgaggcgg gcggattact tgtggccagg agtttgagac cagcctggct 145200
aacacagtga aaccccatct caactgaaaa tacaaaaaaa ttatctgggt gtggtggcac 145260
acgtttgtaa tcccagctac ttggaaggct gaggcatgag aatcacttga acccaggaag 145320
cagaggttac agtgagccaa gatcatgcca ctgcactcca gtctgggtga cagagcaaag 145380
actctgtctc agaaaaaaaa aaaaaaaagc cttaggagtt atttactatt cttcaccttt 145440
ctaggacaag caagtcgata gccacagtga tgaggactgc acaggcagac cctaaagcta 145500
accagggaca ctgtcttgcc tctgtgtttg gtaatcattc cagctatgca gtttcattga 145560
tgtctttccc tccttggtac ataccttact ctatacctga taatagaaat ccttgtgaga 145620
atatacttat tcagctcttg gtgacaggag gtgggtggaa gtgtggggca gagaacaggg 145680
gtgaggttgt tacaatggag aatcagttta ctttttcaaa aattctggaa gccagacatg 145740
gtggcatgcg cctgtaatcc cagctacttg ggaggctaag gcaagaggat catttgagcc 145800
caggtgtttg agactagcct gagcaacata gtgagaccct atctcaaaac aaacaaaaat 145860
tccagagcat ctttggcttc ctaggaaata gcctaaggct gtaaataaac cctggcctca 145920
tattcctgtt gtcatttact ggcgtagtag acaattcata actgggaaaa tcctttgggt 145980
gtttttttga tgtaggtttt atagaatcag agaggttcca aaattgtgtt taactgattc 146040
tatagaagac tataaaagta acaaagcagg caaacaagaa caaaaacctt tgtgccataa 146100
aatcactatt taggccaggt gtggtggctc atgcctgtaa ttccagcact ttgagagagg 146160
cctaggcggg aggattgctt gagcacagga gctcaagacc agcctgggca acatagtggg 146220
accccgtctg tacaaaaaaa aattttaatt agctgggcgt ggtggcaagt gcctgtagtc 146280
ccagctactc aggaggctgt gacaggagga ttgcttgagc ccaggaggtc aagacttcaa 146340
gtgagccata atcatgccac tttccagcct gggcaacaga gtaagaccct ttctcaacaa 146400
aaacacaaaa atcactgttt accttctcta acccttatca ttatgtaaac ataatttaat 146460
agtttaatca gtatgcctta ttattatttt ttcctcttat tcatttagta tcattttttta 146520 aagtatattt ttataggcac tatagaacct tgctgaaatt ggctgaggat actcttcagt 146580
ggggccagaa gttcttagca ttatttcata cagaattttc catgcattta cctaatatat 146640
ttatcatctt taatgacatt ataaaaatac attgaaccag aatgccatag attaactatc 146700
ctttttaaat tttgattcat tatatgtagt agaaccttat ctctgtgttg ataacagttt 146760

-continued ttctttttct ttttatatt tttaattttt aatttaattt aaattttcag acagggtctc 146820
tgtcgcccag gctggagtgc aatagtgtga tcacagctca ctgcagcctt gactgcctgg 146880
gcttaggtga tcctccatct cagcctccct gagtagctgg gactacaggt gtgtgcctcc 146940
actcctggct aatttctata tattaatatt ttgtagagat gggtttttgc catgtttccc 147000
aggctagtct caaactcctg ggctaaagca atccacctgc ctgagcctcc caaagtgttg 147060
ggattacagg cgtgagccac cacacccagc ctgcttttct tttaaattat tttctcgaag 147120
taatagtccc ataagtagag tgggttttgt agctatgctg catcctatat tgagttttct 147180
aacttctctt taattttgct aatttaattg acaaagtgat gcttttataa tttgtttcac 147240
atttctttaa ttactagcat tttctcaagt gttttactgt ttggggtttt tcctattgaa 147300
ttatctgttc ttatctcttg gccacttatt ggacagaagt tggataggaa cctttcggat 147360
ttgtattaca tgtatcaggt tctttcatag ctggatagtg tgttttttat tgccaagtct 147420
cttttttttt ctttctatta ctatgagcta ttcactgctt tgtttgtttg tttgtttgtt 147480
tgtttgtttt aaataatacc cagactggtc tgagactatg ggctatttca aacctaaata 147540
ggtagtggta tttttttatc cttacagaga agtgcatcaa ctagtttatt tgcatttgaa 147600
gtgtagaaac gagaggtcct ggctgaactt ttggcatggg agcagtgtgt gtggagagca 147660
ggctgtccat gataggaggg gagttgagga caaggctgac accaggccta taaataccct 147720
aaggtttagc tttgtacttt gaaataggaa ttaggtcact tttattgtct tccccagact 147780
ttttactggt tggctgtgga gaaaaggcat caggactttt agaggaaatg ttactgtttc 147840
cagctctcag aaaggtggaa agtgctgata ttggtcagct cttactcttg ttttctcatt 147900
tctgttagac tgaggtgacc aaatggaaag cgtgggagtg gagacttgat atttggcttc 147960
ctaagtaaga agtggaattc tgaacagcga aaggccttgc ctgtatccct ttgccgtggc 148020
accatgcctt ggacagatgg atggggagct agttacccag catctgtcat tctccttacc 148080
attgacaaag gttctctttt acctttatca taggctgctg tgtccagtca ttctaactgg 148140
gctttctgca gagggaccca aaccccctaga actttttcttt tttttttttt ttttgagagg 148200
gagtctcgct gtgtcgccca ggctggagtg cagtggcaca atctcagctc actgcaagct 148260
ccacctctcg ggttcatgcc attctcctgc cccagcctcc tgagtagctg ggactacagg 148320
cgcccaccac cacgcccagc taattttttg tatttttagt agagacgggg tttcactgtg 148380
ttagccagga tggtctcgat ctcttgacct cgtgatctgc ccgcctcggc ctcccaaagt 148440
gctgggatta caggcatgag ccaccatgcc cggcccctag aactttttct aaggtcctag 148500
tttctagtat tctctttggc ctttccattt tcttctctaa aataagaaaa ttctggaatc 148560
tctgggacaa acaaacagaa aagaaaaaaa aatttaatga taaaaaaaat aagaaaattg 148620
gaccaaacga tctctcaagt atgatgtatg tatgtacttg ttaattaaag acagggcctt 148680
gctgtgacgc ccaggctgga gtgagttgca caatcgtgca atacttcact acagccttga 148740
actcctgggt tcaagcaatt ctgcttcagc ctctccaata gctggggcta caggtgtgtg 148800
ccaccattct cggctacttt attttttcat atttttagag atggggttct cgccagttct 148860
gcccaggctg gccttgaact cctgcctcaa gttttcttct caccttggtc tcctaaagtg 148920
ctgggattgc aggcatgagc cactatgcct ggctcaaatg atctctaaag tccctaaagt 148980
cctaagattt tttggagttt gatgtcttcc cacacaagtt tggaaatact ttcagaggga 149040
ttctattcca tatgaatgtc attacaattt taatgaaaat tttgatgtag caatattgta 149100
gaatatattt taaagaggta aatatacaca gtcttctgtg cattttgaga tagtctgact 149160
ttataatttt cctttgtctt tctgttgtcc agttgtcagt tttcagataa attctgcttc 149220
aaacttgtta tgtaagtttc tattgggcat ttagtttcaa attactgttt ccaaaatctt 149280
cgtatttctt taaattttca atcattctta aaaatagatt aatattgcat gaatgtcaag 149340
agaacctctt ctattttcat tttaaaattt taatcattaa aatatactgc agtgtctcta 149400
tattaattta tctgaagatg catcagtgta cagtcaggtg ctgcataaca acatttcggt 149460
taacaatgga ccccatacat gatagtgggc ccataagatt ataatggagg taaaaaaatt 149520
cctatcactt agtgatgttg tagccatcat aatgtcatag tataacgtat cactcgtgtt 149580
tgtggtgatg ctgttgtaaa caaacctgtg ctgccagtca tataaaagca tagcacataa 149640
attatgtaca gtatataata cttgataata aatgaccatt actagtttat ctatttcata 149700
tattatatat cattgtttta gaatgtactc tttctactaa tcaagaaaaa gagttaacta 149760
taaaatagct ttagacaggt ctttcaggag gtattccaga aagcattatt atcataggag 149820
atgacagctt catgggtgtt attgccctga agaccttcca gtgggacaag ctgtggaggt 149880
ggaaaccagt gatattgatg atcctgacac tctgtaggcc taggccaatg tgagtgtttg 149940
tggcttagtt tttaacaaaa aagtttaaaa agtacaaaat aaaaaattta aaaatagaag 150000
aaaccttata taataaagat ataagaaaat attttgtaca gctgtagtat gttttgtgtt 150060
tttttttttt tttttttttt ttgagatgga gtctcactct gtcgcccagg ctagagtgca 150120
gtggcgtgat ctctgctcac tgcaagctca acctcccggg ttcacaccat tctcctgcct 150180
cagcttcccg agtagctggg actacaggca cccaccacca cgcccagcta attatttgta 150240 tttttaata gagacggggt ttcaccgtgt tagccaggat ggtctcgatc tcctgacctc 150300
atgatccacc cgcctcggcc tcccaaagtg ctggaattac aggcatgagc caccatgccc 150360
gggctgtagt atgtatgttt taagctaagt attattataa aagtccaaaa gcttaaaaaa 150420
atttaaaagt tataaggtaa attatggtaa gctaaggtta attaatgaag aaagaaaaat 150480
ctttttaaaa ataaatttaa tgtagcctaa gcatagtgtt tataaagttt gcagcagcat 150540
acagcaatgt cctaggcctt cacattcact cactattcac tcactgactt atccagagca 150600
acttccagtc ctgcagggtc cattcattct aagtacccag cacagggttg ccattttctt 150660
tttttctttt ttcttttttt ttttttgaga cagagtcttg ctctgtcgcc caggctggag 150720
tgcagtggcg caatcttggc tcactgcaac cttcgcctcc tgggttcaag ccattctcct 150780
gcctcagcct cctgagtaga tgggactaca ggcgcctgtc accacgcccg gctaattttt 150840
tgtattttta gtagagatgg ggtttcaccg tgttagccag gatggtctcg atttcctgac 150900
catctgccca cctcggcctc ccaaagtgct gggattacag gcgtgagtca ccatgcccgg 150960
cccattttgt atcttttatg cagtattttt actgtacttt ttctgtgttt agatatacaa 151020
atccttacca ttgtgttaaa attgcttaca gtgtatagta ttcaatacag taacaggctg 151080
tacaggtttg tagcctagaa gcaataggct gtaccatata gcctagatat gtagtaggct 151140
ataccacgta ggtttgtgta agcatactct atgatttttg cacaacaatg aaatcaccta 151200
acaatgcatt tcttagaatg tatctctgtc cttaagcaat gaatgcatat cagttaagcc 151260
tgtgaggtag gcctgaggat gtggaatagc agacaccaat atatcctaat cccaagaggc 151320
aacttctttc atctctttta gtagattctt ttggaattta ctcccatatt tctaattaac 151380
aagtgtgtat tgctgcttct tagtttttca gattaaagga tagagctcca ctcatttgtt 151440
ttgtttctct gtcaatattt acaagagtca agttatctta gaactggaag agacttcaga 151500
tcctccagag aactaaactc aaaaactgtc aagggcttgg cagataactt aaatgaaaag 151560
aatagggagt agtatggact gtggcagact agaattctgt gccatctaag gacattcaat 151620
tcagttttaa ctctgcacat atcaaacagt tgcaatatat ggaccttgtt tggatagtga 151680
tttatacaac aaactatctt taaaagttta tggcagttat agaaattgaa taattgcaaa 151740
ttgagcacta actaaaattt ttatattaaa gcaatattac tcttttagat gtgatgataa 151800
tgatattaag gttaaagatg tatgaaatga tatgataggc aagatttgct tcaaaacaat 151860
atgggaatag aagggaatag aagggaaaaa acaagataag ccctaagttg ctaattattg 151920
aggctgggtt tgggatattt gggcgtttgt tagtctgttt acataattta catttatata 151980
attttgaaaa ttttcataag ctttttttaa aagacttatg tgggtaaaac cttgtctcct 152040
tcgaagagga atattagaat gaggagaaaa ggaatccaga ttaagcgaga atagaggcag 152100
ttctgttagc tatactgatt aagggttgtc accagaacct tactagtata ttccattgaa 152160
taaatatgta tttgttatta tacatattta tttgtttggc atattctgtt aagtttattt 152220
gtatactcaa ataaatactt atatcttaag tagcggacaa taacattcat tccaaaatgt 152280
ggtttcactt attctcaata aactcattta ttgctattaa aaaaataaaa cacaatataa 152340
tactaagcaa aacacatcta tggaccagcc caaatttgta agctggcttt cagtttgtga 152400
tttctgagtc tattctcacc agcttgtttc acagaagaaa ctaaaactta aaccaaggtc 152460
acatagctta tcagggggaa agctagaact caggtctcct gattccccat tcattgctgc 152520
tgcttatgaa aaaaactgcc caactgactt aaataagaaa gaagggttat ggttttgcct 152580
ggcaattgtc tcctgtttcc taaccttgac tattttttt agaatatagg tttgagattt 152640
gtcttctctc tttttgtaag atgataggga taagagattc agccttaaac ttctggtaga 152700
aatccaggtc taaggatagt tatatttctt tgaatgataa agaattgtag gccagacgcg 152760
gtggctcacg cctgtaatct cagcactttg ggaggccaag gcgggtagat catgaggtca 152820
ggagttcaag accagcctgg ccaagatggt gaaaccccat ctctactaaa aagacaaaat 152880
tagccgggct tagtggcgga tgcctgtaat cccagctact caggagactg aggcagataa 152940
ttgcttgaac ccgggaggtg gaggttgcag tgagctgaga tcgtgccact gcactccagc 153000
ctaggcgaca gagtgagact ctgtctcaaa aaaaaaaaaa agaattgtag gccaggcaca 153060
gtggctcaca cctgtaattc cagcactttg ggcagccaag gtgggcggat cacttgaggc 153120
tagaagttca agatcaagct ggccaattta gtgaaatccc gtctctacta aaaatacaaa 153180
aattagctgg acctggtggc gcgtgcctat aattccagct acttgggagg ctgaggcaca 153240
aggatcgttt gaacccggga ggcagaggtt gcagtgagcc tacgtcgcac tactgtactc 153300
cagcctgagc aacagagcga gactgtctca aaaaaaaaaa aaggaaaaaa aaggtaattg 153360
tagcatttaa gcaagttata agcataagac ttaagatgag gcaggactgg aaaaatgaac 153420
cccttggttc tatttggtcc ccaagtgaca tttcactgcc actaaaaatt gctgctgtgt 153480
gtgggcttta acatttattt ttaaaattta attcttttct ctaagtccag agcactaagc 153540
aagcagcata gatgtacaga cttgccagct attggggatg tgttgctaag tagctgtgac 153600
agccttcgtt agatgctttg ctgtacagtt atcactagac tttgctccca ggtctaattg 153660
ggaaataagg attcaggcag ttttgtttta tgtatgtttt gttagcatgc ttaatttaaa 153720
agcctaataa acctgagctg acttttgaaa aaccatttct gtactagcaa agattcacat 153780
agcaaacatc agttgaggag agattactag aaagcaccag aagaaattag aatgactctt 153840
gtagatagat ttgaatagtc tttctactat tccagcttat tctcttcttt tttaccttct 153900
tatactactc ctgtttgttt atatattttt ccactcagac caaatggaag cagaagggaa 153960
agaaatgatc ttattgaatt cctttggaca tagaatttga gtccttctgg accttttcat 154020
aacccctttg aagtatactc tgttttccta aagaacttga aaattttata aaccaatcac 154080
tcatcaagta gtataaaact caggcctttt atagaatttt tttcctttca taggtaaaaa 154140
gttgttagaa caaataccac tttgaaattg atgcaggtac ctggaatgaa agagttgaaa 154200
ctagtagttt tgtttttggt ttttggtttt ggttttttg agacagagtc tagctctgtt 154260
acccaggctg gagtgcagtg gtgcaatctc agctcactgc aacctccgcc tcctggtttc 154320
aagtgattct cctgcctcag cctcccgagt agctgggatt acaggcgccc accaccacgc 154380
ccagctaatt tttgtatttt tagtagagac ggggtttcac tgtgttagcc aggccagtct 154440
tgaactcctg acctcgtgat ccccccgcct cagcctccca aagtgctgag attacaagca 154500
tgagccacca tgcccggccg aaactaatag ttttaaaaat gtattctaga tgtcgactag 154560
taaaggcttt gctgttatct atacctaggt aatgttctag actagatgac aagtcgagtc 154620
cacacctgag tgttgatttt gactttaaaa aattaaatag aaagttaaag ctattggcta 154680
aaattgtgag tttatctcta tatttgtaga tccagtcaca cagtttagca tcatattata 154740
tcatgacatt agttctactt ttagaaaagt gtatctttta gctagaatat gtgctctttg 154800
tagtcaggga ccatgccttc taaatctttc agagattaat aaatactcgt atatttcgta 154860
agcattttgg cctctctttt tgtctctact caatataggt ggtaataata ctctgtatca 154920
ggaactttgt atgtatcatc tcattgagtt cccccaagga tatttcaagg taatattatc 154980
cccattgtat agaagaggaa acagaggttc caaaaagtga agaacttgtg taaggtcaca 155040
tacttagtaa gtcacagaag tgggactgta aacctaggcc tgtttcactg attatacctc 155100
ctactcttac ctctacatca agatcccttg agagctttgg aattgtcact agaagtcttg 155160
actattctca tcctcatttt tggtaaatat gaaactcatt tgttctgttg ttctagaaaa 155220
gctcttaatg tttaaatcag gatcatggac tactatcccc ctcttctaag agcttagatt 155280
aataggggca gtataacata gtggttaaga gtgtatatag gttctaaagc catgcagact 155340
ggctttgaat actggcctca ccttgatgac cttgggcagg ttgcataacc ttgctgtact 155400
ttaagtgcct tatgaggcac ttaccataaa atgaggatgg tatggaatac tactcagcaa 155460
taagaaagaa ctattgatac atgcaataac ctaggtggat ctcaaagtca ttctgctgag 155520
tgaatgattc cagttacata gcattctgga aaaggcaaaa ctgtggtgac caggaacaag 155580
catgattgcc aggggttggt ggtggggaaa gcgtgtgact accatggggt agtatgaggt 155640
gatttttgag gagatgaaac tgttctgtat cctcattgtg gtagtggtta catgagttag 155700
tacatgtgtt aaaactcata gataatacgc ttccccaagg aatccattta ctatacatta 155760
atttgttaaa aaaataaatg taaaaagggc caggcgcagt ggctcatgcc tgtaatccca 155820
gcactttggg acgcagaggc gggtggatta cctgagttca ggagttcgag accagcctga 155880
ccaacatgga gaaaccccgt ctctactaaa aatacaaaat tagcagggca tggtggcaca 155940
tgcctgtaat cccagctact tgggaggctg aggcaggaga atcgcttgaa cccgggaggt 156000
ggaggggttg tggtgagcca agatcacgct gttgcactcc agcctgggca acaaaagcga 156060
aactccgtcc caaaaaaatt aaaaaataaa tgtaaaaaat ggggcagtaa caaaacctac 156120
acatacctgt gtactaccta ctatacagta cataactata tactaaatta tttttattat 156180
tgttatttta tcattgttat taaaagtatg atattaaata tggtgacatt catttaaagt 156240

```
aggatagaat aaactttcac accatctgca tgggtatggt cagtaaatgt gagaaaaatg 156300
agtaactgtt gagtcaggtg gagtatgttt tcacatgatt tggcagggga tctgaggttt 156360
tctggacagt ggaggattag gcctagtatt tctggagtat cttgcaactg acttcttgtc 156420
tggctgcata tacagttccc ttgatagtat tcttcaacaa aatagctttg gtcttagaag 156480
ccacagctct tttcactggc ttcagattag atctgaaatt tggactgagc aaactggtca 156540
aagaaggagc tggaagtggt tcttatactt ggaagatggt agctgttctg tataacagct 156600
gtagcttcca gaggcatttc ttcctgccag ccatagtctc tggattagac agtgatagca 156660
gtagggcaag cattattcaa cagctaaaaa aaaagttaag gtcgcagtgg cattgtagtt 156720
acactagcag tgaaaaagag gttctaaagt gaaaccatga cctttccatc aagtggggtg 156780
gtgcttttgt agaggaactc acaacctgaa tcaaaacaag ttaaataaat ggtaaaaagg 156840
attctgacct tagaatgctt gctatgttag ttggcactta ctggtctgta tattcatttt 156900
tacctaatga cgccagaatt caggaagcag gggggaaagg ggaatgtttg tggttcctgg 156960
tacagggcat tggtttagca gtgacttaac ttttcctaat ttctttacaa cagtgacact 157020
aaatttcaag caaagctccg tcgtcattca gtttgcttct tttatagctt gttgtacata 157080
tgtgactaag ttattgattg ctgttgagga acatcactct tttgtggctt tgaggagaca 157140
atgccaaatt gactagccta ttgttttatt ttggttttgt gttttagttc tcgttaatta 157200
tgctaagagt agtttgttag gacagtggtt taaaatatat aagagaatca gtattttctt 157260
ttcttttttt ttttttttta agtatttatt gatcattctt gggtgtttct cgcagagggg 157320
gatttggcag ggtcacagga caatagtgga gggaaggtca gcaaataaac aagtgaacag 157380
aggtctctgg ttttcctagg cagaggaccc tgtggccttc cgcagtgttt gtgtccctgg 157440
gtacttgaga ttagggagtg gtgatgactc ttaatgagca tgctgccttc aagcatctgt 157500
ttaacaaagc acatcttgca ccacccttaa tccatttaac cctgagtgga cacagcacat 157560
gtttcagaga gcacggggtt gggggtaagg ttatagatta acagcatccc aaggcagaag 157620
aatttttctt agtacagaac aaagtggagt ctcctgtgtc tacttctttc tacacagaca 157680
cagcaacaat ctgatttctc tatcttttcc ccacatttcc cccttttcta ttcgacaaaa 157740
ccgccatcgt catcatgacc cgttctcagt gagctgttgg gtacacctcc cagacggggc 157800
ggctgccggg cggaggggct cctcacttct cagactgggc agctgccggg cggaggggct 157860
cctcacttct cagacggggc ggccgggcag agacgctcct cacctcccag acggggtcgc 157920
ggccgggcag aggcgctcct cacatcccag atggggcggc ggggcagagg cgctccccac 157980
atctcagacg atgggcggct gggcagagac gctcctcact tcctagacgg gatggcggcc 158040
gggaagaggc gctcctcact tcccagactg ggcagctggg cagaggggct cctcacatcc 158100
cagacgatgg gcggccaggc agagacgctc ctcacttccc agaaggggtg gcggccgggc 158160
agaggctgca atctcggcac tttgggaggc caaggcaggc ggctgggagg tggaggttgt 158220
agcgagccga gatcacgcca ctgcactcca gcctgggcaa cattgagcat tgagtgaacg 158280
agactccctc tgcaatcccg gcacctcggg aggccgaggc tggcagatca ctcgcggtta 158340
ggagctggag accagcccgg ccaacacagc gaaaccccgt ctccaccaaa aaaatagaaa 158400
aaccagtcag gcgtggcggc gcgcgcctgc aatcccaggc acttggcagg ctgaggcagg 158460
agaatcaggc agggaggttg cagtgagccg agatggcggg agtacagtcc agcttcggct 158520
tggcatcaga gggagactgt ggaaagggag agggaaaggg gagaggggag aggttagtat 158580
```

tttcaaaaat catcatatag tacgtggtta cacaactctg aatatactaa aacacattga 158640
attgtatact ttaaaggagt gaactatatc tcaatatata aggggtgagt tatagctcaa 158700
taaagctgtt aacaacaaaa caaaaatgcc ataccaaaaa aaaaatcatc atactgatct 158760
gtgaccttcc aatggaagga attaaactaa acttttcaaa atggggctac tggcccttag 158820
gcaaggtcct gagattatcc taaaattatg gatttagagt atttaatgac ttttctgaag 158880
aattcttaga attcatctac taagcaaata accattcatg tagttatgat gtagtcattg 158940
tcaattttta caagggagga ggataaggat catcactaag actaaaacaa tgattctgaa 159000
ctgggtgatt ttgcccccca gagaaagtct ggcaatatct ggagacattt ttgattgtca 159060
tatctcaggc atgctactgg tatctagtgg atcaaagcca ggagggatgc tggtaaacat 159120
cctacaatgc ataggacagc cccatgatg aagaattacg tggcccaaac tgtcgttagt 159180
gccaaggttg agaaactctg gtacaaaatg tacatctatg ttttctttca agagttttag 159240
cttttacatt tagatctttg atccatttta agcttttttt ttttttttt tggagacaga 159300 gtctcactct gttgcccagg ctggagtgca gtggtacgat gtcaactcac tgcaacctcc 159360
gcctcctggg ttcaagtgat tctcctgcct ccacctccca agtagctggg attacaggtg 159420
catgccacca cacccagcta atttttgtat tttaggtaga gatggggttt caccatgttg 159480
gccaggctgg tctcaaactc ctgacctcaa gtgatccacc cacctcggcc tcccaaagtg 159540
ctgggattac aggcgtgagc caccatgacc agctttaatt tttgtatatg atatgaggta 159600
ggggtccagt tcattgtttt acatgtgggt atcgagttgt cccagcaaca tttgttgaaa 159660
aggctattcc ccattgcatg gtcttggcat ccttgtcaaa atcaattgac cataaatggc 159720
cctggtgtaa aatggctaat gtctgtacct atttctccta gaaaaagcct tacacagcct 159780
ccctgaggtc ttagaaaatc ttgatgactt tctactgcta tggctgccta aagaataatt 159840
caggttgttt ccatatgaat actgctacac ctgagtgaga acaggttaag gattacagtg 159900
tctgtaagcc tcctgtcata tattcaggca gctcacacca cgcagcttca gttctccagg 159960
ctaaggcatg gcattaaaat tgtgaaggac ttcaaaaatt taatccgact ttctaccaag 160020
tactctaaat tatctcaaat attattgttg ttttatgata aatctcaata tacaaagcag 160080
gtaccctctc agtacttact ttttcaaaaa tttccttagc tattcttatc tgaatgtttt 160140
aaatacatta ttttgtttaa ttatcaagcc gaggaggtag ggttgtgcta ttttctttgt 160200
cattttacag atgcagaaac tgaggcttag agaagtttat ttgctatggt cataccagga 160260
ctgggatttt aatctagttt ttttttact ccaaaggcat tgcctttaga gagcacataa 160320
tgaattatat gtgaagtctc catcttcaca tataattaag ttcttctaat aggaataaaa 160380
taactgcaaa aatatatcca aacagaaaaa tggtacataa ggtttaagct taagccaata 160440
tatacttaag gggaaaatct aaactatatt taagattcat tggcctttta taatctatat 160500
tctgacttag aaaggggata tggaccgttc tttgaatact tacttgtttt atagctaaag 160560
aggtcctcac agtcatgggc cacatcgtat gtaattttga aaacattaca acatgcaaag 160620
acttcgaatg ccgtatgtgg ttctggttgc agcatctaag aaagatatat atattttta 160680 aatctgagaa aattttggag tggtaaaata aaatactttc cagtcttaga atattaggat 160740
ttaggaacat aatcttcaag gtgaaattag gtaaaagggg ccgggcatgg tggctcatgc 160800
ctgtaattct agcactttgg gaagccaggg taggtggatc actgagatca ggagttaaag 160860
accagcctgg ccaacacagt gaaaccccat ctctactaaa aatacaaaaa aattagccag 160920
gtgcggtggc acacgccagt aatcttgcta ctagggaggc tgaggcagga gaattgcttg 160980
aacctgggag gtggaggttg cagtgagctg agattgtgct actccactcc agcctgggca 161040
acagagtgag acttcatctc aaaaaaaaaa gaaagaaaga aagaaagaaa ttaggtaaaa 161100
ggaaaagttc ttccttatgt agtagtaagt aaatttttaa aattttatac aagccgggtg 161160
tggtggtgca agcctgtagt cccagctact cagaagcctg agacaggagg atcgtttgag 161220
ctcaggagtt caagaccagc ctgggcaaca tagcaagacg cacatctctt aaaaaaaaag 161280
aaagaaagaa agaaagaaag aaagaaaaag aataaaaaat tagctgggtg tggtggttca 161340
taccaaaata aaaattttat gtaaaacatt ggttccagaa ggattgagat caggcattct 161400
gatctgggat ccagcaatgg gcttcaggag attaatgaac cttctgaaat tatatgcaga 161460
tttgtgtgtg tgtgtgtgtg tgtgtgtgtg tgtgtgtgtg tgtgtgtact tgatcacctc 161520
agtgaaataa tattaagagg tgaaataata ttaagaggta ccactgtact tctaattctg 161580
gacaaatctt tctcctagct atagaaattg gagtcctggc caggtgcagt ggctcatccc 161640
tgtgatccca gcactttggg aggccaagac aggcagatca cttgaggtca gcagttcaag 161700
actagcctgg ccaacctagt gaaaccccat agtgaaaaat acaaaaatta gctgggtatg 161760
atggcacgtg cctgtagtcc cagctacttg ggaggctgag gcaggagaat cacttgaacc 161820
caggaggcac aggttgaagt gagccaagat catgccactg cactccaggc tgggcaacag 161880
agcaagactc catctccaaa aaaaaaagaa aaaagaaatt ggagtccttt cactgtgttt 161940
cttttgagac ggagttccgt tcttgtcgcc caggctggag tgccatgacg caagactctg 162000
tctccaaaaa aagaaaaaag aaaaaaagaa ataaattcga gtcctttcat tgtgtttctc 162060
tcctaaagag tcatttcaat aaatttgtat tgaatatctt ttgtatgcca gacacttgtg 162120
ggtgctttgt gtaatacaaa catgatcact ttaaatgagt gtgaagtact gttctgggca 162180
ggtgaagggt aaaaggagag catccctctc aaaatgatgg aaataggatg ataggtttgg 162240
gggagagcag ggatctccag agggagagaa tgatgaatag gtaggttgga ttcatgttgt 162300
ggatgccctt aaataccaac tgagcaaggt tactatatat atatacaatt aaaggatacc 162360
taagaagaag cctgaagact tgagatatag actgggcttt atcataatta gctgtgttac 162420
ccttaggtaa gtgattttac ctctcttgac ctcagctgca ctactcaaac acacacataa 162480
acacaaatga gacgggaaat gagctgggtg tctgtttcct tacagctcta aattctgtta 162540
ttccccttaa ttcagtttta atagaagtgg gaaatcattc attgaaggtt tctgagcatg 162600
ggagttctct tcaacagaat tactgctgtt tcactacctg gttgctctat ttattaatgc 162660
tctttcttcc acccttatgt gattgctctg ggagggactg tctctttatt tgtttttttg 162720
tttttttgag atggagttct gctcttgtcg cccaggctgg agtgcaatgg cgcaatcttg 162780
gatcactgca ccctctgcct cccaggttca agcgattctc tggcctcagc ctcccgagta 162840
gctgggatta caggcgcctg acaccaagcc tggcttattt ttgtattttt agtagagacg 162900
gggttttgcc atgttggcca ggttggtctt gatctcctga ctgcaggtga tctgcccacc 162960
tgggcctccc aaagtgctgg gattacaggc gtgagccacc gcacccagcc ggggctgtct 163020
ctttagatag ttactgatgt ggccaaggaa ttggccatta ttattagctt atattattga 163080
gaacatgggg atggtcaggt atctattctt gaattagatc tgaagctggt cttgtttcct 163140
catgttatca gtcactgacc tgtgaactga tccatgtgtc cacaatgtgg gcagcaggta 163200
agtgctgaca ttttgatggc cacatcatat ttcagggatc tatgagaagg tctgtaatga 163260
ccatggaaag ccagccaaga atctccttgc catggacaaa tgggagaagt tactaaattt 163320

```
agcggacatt aagctgtaaa ttatttgaaa ggtggaaaag gattctattc agagactatc 163380
cagaatttcc atttactaat caggccttgt gctgtagagg ctttcatccc aggaaaagta 163440
ttgctttctc tcttcctctt tccccacact tttgttcctg ttatagtggg aggatgattt 163500
tcagctctta ctataacatg gacttcagtg catgttgcta ttagatgcca agagcctcag 163560
gatgataaaa tctgaggatt ctgattctga ttctgctatt taaaaattag aatatgagct 163620
gagtttgaat tttttaacta cagaatgata gagacatata tgaaatacag tacatttttg 163680
ctttttgaaa ggaattgtta tagtgatgtt cacaaatcac caaccttggc aaaaaaaaaa 163740
aaaaaaggtc cctgtgagaa ccggtgtaaa tcaataagaa aaaagcagat ttcccagctg 163800
ggcacagtgg ctcacgcctg taatcccagc actttgggag gccaaggcag gcggatcaca 163860
aggtcaggag attgagacca tcctggctaa cacagggaaa ccccatctct actaaaaata 163920
caaaaaaatt agccgggcgt ggtggcgggt gcctatagtc ccagctgccg gggaggctga 163980
ggcagcagaa tggcgtgaac ccgggaggca gagttgcaac gagccgagat cgcgccattg 164040
cactccagcc tgactgagtg acagagcaag acgccgtctc aaaaaaaaca aaaaaaacaa 164100
aaaatcagat ttcccagtag gaaaatggga gaaagacttg aacagacatt cacaatagag 164160
gatacctaaa taatcagtaa acataagaaa aggtgctcaa cttcattagt cattagggaa 164220
cttcaaaacc accatagaat actactacac atagagcaaa atagcaaaaa tgaaaaagat 164280
acacaatatc aagtgatagc aaggatgtgg agtaactcag actttcatac cctaagggta 164340
aatagggtaa attggaaagc tggctgcatc tacaagagct gatttgccag caattacatt 164400
tctaagaata tgcccagcag gtaatcatat atatgttcac caaaagatgt ttatgagaat 164460
gtttatagca gtgttgttca cagaagctaa aaaaaaaaaa aaaaaagagg aaactgccca 164520
aatctccatc agaaataaaa tggataagta aaatgtgaaa attctcatag tggaatacta 164580
taaataaatg agaattagta aactacaata tcttacaaca cagatgactt tctccagcat 164640
aatattgagt gaaagaagcc aatccatacc caaaagacta taaatcatgc tgctataaag 164700
acacacgcac acgtatgttt attgcggcac tattcccaat agcaaagact tggaaccaac 164760
ccaagtgtcc aacagtgata gaccggatta agaaaatgtg gcacatatac accatggaat 164820
actatgcagc cataaaaaat gatgagttca tgtcctttgt agggacatgg atgaaattgg 164880
aaatcatcat tctcagtaaa ctatcgcaag gacaaaaaac caaacaccac atgttctcac 164940
tcataggtgg gaattgaaca atgagaacac atggacacag gaaggggaac atcacactct 165000
ggggactgtt gtggggtagg gggagggggg agggatagca ttaggagata cacctaatgc 165060
taaatgatga gttaatgggt gcagcacacc agcatggcac atgtatacat atgtaactaa 165120
cctgcacatt gtgcacatgt accctaaaac ttaaagtata ataataataa aattaaaaaa 165180
aaaaagaagc caaaccaaag gagcttctac ttcatgatgc catttatgta aagttcaggc 165240
agagaaaatc agtggtttaa gaagttagaa taatgattat ctttggaggg attgcaactg 165300
gaagaagtca tgattgggat ttctgggtcc taatagtgct ctgtgtcttg atctgagtgc 165360
cgactacatg agtggttagg tttgcaaaat tcattgagtt atgcacttaa tggtgttgtc 165420
ttattagagc tgatggagga gagagggctt caatttgcac aactgagtaa tcagctaggc 165480
ccagtcacta ggtgaacaac ttactgctac caatcagcct tagagcagga atcaaactca 165540
tgtctcagaa aagttattaa ttacagcttg tcttgggact tccttcagag tcactcttga 165600
atagctgaaa tagtaaatgt taaatctgtg gatgcaagtg tgtaaattat tttagtcatc 165660
agctctaata agatggcctt tggggaaatg agtataaggt cacgaaaatg aaatggcaag 165720
```

aaggaggtct actatttctt ctgtaatact gatttttacc ccatcagggt cagtccccag 165780
aggttgtaaa tgtgaagctt gttctttttc tttagtaagc tgagtttgtg gctttttaaa 165840
gctttgcttc actgttctca tttgtaagtg agatattgct tgttcacctc ccatagctga 165900
tgaggagatt cttgtgcact gtatttgttg agataaggct ggtttggggt tttgttttca 165960
tctttgtttt ttagttaaat cataacctag ttatgatttt tgtgtgtcct tgtttatgga 166020
tctggaattt aattcattat tagttgtaga atgaaaggta agattttgtt ttactcttct 166080
cctgaatttt ctccccattc tagatctgtt ggcataaaat tttaaccaga agctaattta 166140
gtgatgctga gttagtccta gaaattagtt tcaattctag tgttaatata gtctgggttt 166200
ctaagttgta gaaaaatctc attttttggt tcttggtttt catttgtata atttagggaa 166260
aatacaacca actgtatttt aaacatatat agtcctcatc ttttctgttg ggcttgaaga 166320
gttgtactgg gtattatgga actggaaaga agccatgtgg atagttacgg tatttaggtg 166380
gatttgttgt tggtagaagt ggtgaattgg aaaagtgata gggtacatat gtttcgcctt 166440
caaggcaagt ctattcttac tgtttgatgt cagagtaaaa agtgtcagta gctgaaaaag 166500
acaaaagaat cttgacagag tggaaaaagt cgtgcctcat gttctattga tcaaaaggag 166560
gttatatttt caaactagct tcctaagatg aaattgaagc tgtacatgtg ccctacttat 166620
ccttgttttt cctgattttg gtttttcaga ttattcctat taaacatgat atgctgatta 166680
gcactgaata ttttaggtct gctacgcctg tattagttga gattcctctt aatttgtgtt 166740
agatctctgt taggtcattt ctactgctgg cattccctag actagaggcc tgcacgcaca 166800
tttgtattct aatgagtata agcactaggt gtttttcttg gcactaagaa aaccttgcag 166860
catcattaac ctaggagaga tttggggttt acacattaac tatgggaggt tgatcagttt 166920
gtggcctata caccaagact gttctttatc acccccaagc cacatttgag cagggattga 166980
ggaaggggtt gatttttctg tttattagag gtgacatgag cagtggggca gcggcaaaga 167040
ggccatgttg ctcttgctaa atatacatcc ctgacagttg gataataggt tccaggaagt 167100
tcagtggaaa attaaaacaa agcaacattt atagctgatt gaacttgaaa agccattttg 167160
gtgttgaatg gcaaatatgt ggacttcagc attcctggag cctgatgcat cccgctggat 167220
ggccctgttc ctgtgtacat gatggcctgg ggactcagca gtgtgcaggg tactctcctt 167280
tagagggtgc tttgaggaaa gaagtttgct gccacttaca gaagtcccct tcccatacag 167340
tgatataaca caagtacccc atgtccaggg agcatctttc ctctgatggc ttgaggactt 167400
atttattaaa aggacaggaa tgtctggcaa gaaacagagg agctcttaag tactgtaaat 167460
actcctagtc actctgcatc agggctgcaa gtttaagcag attgctgtgg tgtatacaca 167520
tgattttagc atgataacac ttctgtttaa tgtccttagt tgttctgggg ccaccactgg 167580
cgtgagcctt aagaaaggct aacgcggctg tgaagaaagg gctttatagt ctgtgtgtgg 167640
agtggttaat tttcttagaa ctaaaagaga agctgcaggg gatgggaagg gaaaatgaag 167700
tcatggtaca ggaaatatag gtgaagagag aattgagcca tttgcaagta tcaagaaaag 167760
ttgctacaca ttcccatctt tttctccagg atgatcttac gctattgctt ctatgtgttt 167820
gtcttttgag aagcaaggcc agggtgtctg atgggaactt acgaaccttg gtttgctaag 167880
ggtgatgaga aaacctctgt catttgaccc tgtcagtccc ttggtgactt catccaaacc 167940
agcttggctg tcaggaaaat atgaattgtg gctatgggcc taatttcttc tgttcccact 168000
caaatgaact gcctttgcta gctgtagaat caactattcc tatgccccat gaatttcccc 168060
aaagttgaac tactccagtg gaactgaggg tttattggtt ccctaccatt tcagggcatt 168120
tccccagcaa ataagagtct ttcatccctt gtgttttaac tgaaaaacag agacccagcc 168180
ataacaattc cctcagctcc tcctttactt aatgaagagc ttgagtaggc cccactttta 168240
aatatctctt ctataagtat ggtgcactgt tcacaaactt agaaaatgtt aaatctcgcc 168300
gggcgtggta gctcacgcct gtaatcccag cactttggga ggtcaaggca ggaggatcac 168360
ctgaggtcag gagtttgaga ccagcctgac cagcatggag aaaccctgtc tctactaaaa 168420
atacaaaatt agctgggcgt ggtggcgcat gcctgtaatc ccatctattc aatggaggcc 168480
gaggcgggag aatggcttga acctcggggg tggaggttgc ggtgagctga gatcttacca 168540
ttgcactcca gcctgggcaa caagagcgta actctgtctc agaaaaaaaa aaaaaaagaa 168600
agaaaatgtt aaatctctct ctgccctact ctgctgtggg gttgaggaac aatccactta 168660
atgggtctct tctcttttgc ttagctgtag ccacggcagc tctatgtgta ggttggttgg 168720
caagcattta taaactttgg ataacctggc acccagccct tggttcactt attttaatgc 168780
tactaaagtt tagttttcaa ttcaataatc tttgttggta gggcgtaact attctagtta 168840
gcaattccat ccgttgtaag ggaatgctga cagctgacct gctgtcgtct atgcaggtta 168900
aaagatctta gttaaaagat cttagttgga gtaagcctat acttttggtg ttcccagact 168960
atgaaactgc tgcaggtaga aacaactgtt tgttttggtt tcttcagcag atagagcttt 169020
gcccatgaga cactgctcct ggtgtttgcc tcgggtacct gtaaagtcac tgaggaagaa 169080
acagatcttc cagtgaattg agcttaattg tggtctgttg ctttctctgt ctgtgtctca 169140
tactggcatc atgagtttcc tttctgagtc agttaaatct gagctgtgcc ttgtcctgtg 169200
gaaatctgag gcttggctag gctcatcttg atggtctcca aatggtgaaa ttggggctaa 169260
ggtgtgtgga aatgcacacc ttagccctgt gtgcagggct gtggtgtctt atagatacag 169320
tactttctag tgagtgctca cttaggcagg gccaagaaag tagttctgaa tgggaactcc 169380
agaggcctaa tccagatata gcatattata ggtgctaatg aagaggaatt gtgctgctga 169440
gcaaaggaaa gcttttgtga cttgaaagca cgttctgtgt atcatggagg ctgggttatt 169500
ttcccagctt taggcgagtg gcactaacta caagtttcat gttcttctga gtacacatga 169560
gtcggtactg cagtcagtat acttcttttc ctgaaataag aaagtgattt acgaggtgtg 169620
ggcccttacg tgaaagaaaa caaaaccagc cgctctgtgg gcctgtaaaa ttcctgtgcc 169680
atctcagtgg tgtgggttac aggaggagaa gatggagagg gctagctggc cctcccttgc 169740
tggggctcag ctgccccaaa tacttgtgat attgcaggtt atttatgagc tcgtctggac 169800
tgggattcac tgccccacac cctggtaggt gaagatttgc aggcagaatg tagaagccct 169860
cattaatctt cctggtcttg ttgaggattt cttgtcggcc tgagctcctg ttggagaatg 169920
aactggcttt tccactgaac tacaatggct cagattaata ttaatcccct taatgctgca 169980
gttcatgata tagtcattag gtgacttgga actaatcctg tccacctaac tagtgtgatt 170040
tattaaatac acatggagat cgagtctgaa tacagctagg cagaatcagc agcaaataaa 170100
tacctctgtg tatctgtatt aatgctggtt gattgggaca caattgcagg ctgggctagg 170160
gagaaacaag ggccaaaagg aggctgagct ctcttaatca acagtatttt cccacctcta 170220
ccctttaatt tagatggcag aaactattaa actcttggta acagttttag gagcagtgat 170280
gagagcgtat gtcaggaaca gggattataa gtaatccagt tctgtgcatg taaagtcaaa 170340
gaagagaaaa aaagaaacca tatatgcatt tgaaaaaatg taaagacata agctcaaact 170400
aaggaagaag aaatccttta aacatatctt tttttttttt tttttttctg gagtcaggat 170460

-continued tacgctcttt tgcccaggct ggagtgcagt ggtgtgaaaa tggctcactg cagcctcaac 170520
ctcctgggct caagtgatcc tcctgtctca gcctcccaac tagcgggacc ataggtgcac 170580
accaccacac ctggctaatt tttaattttt tttgtagaga cagggatctt cctatgttgt 170640
ccaggctggt cttgaactcc tgggctcaag cagtcctccc gcctaggcct cccaaaatgc 170700
tgggattaca ggtatgagcc accgcaccca gcaacctgtc aattatttga gtgacttttc 170760
ctcctatact ttcttccttt aagttttaag agtaacggtt caaatggagc tttctctaca 170820
atttaacttc cttagcttcc tttaaattct ttatcagtag acaccctagg ccaggcaatg 170880
atctcactgt tctattactt ctcctggctt caaggcttga atttttcttt ttgaaatggg 170940
taaggagatg gagtagccat gcctgccata taacagttct cttctctgag atccttgccc 171000
aagttagcag aagcataatt tctttggtaa ataattgatg tttatcgttt ccctttctca 171060
aacctccttt tcttcccctt ctttgctctt tcagcagaga tggcattaat atgaaaaaca 171120
tctacctagc tggcttcatt taatcaggca agtctgacat ttgtgaaacc tctcattaac 171180
attttcccca aagagcacaa aatggcctcc cctccaaata cagccacctc aaagtttagg 171240
cttctttcca tcaccattgg caggctgttc tcagagatgt tacttctcta aactcacact 171300
cctggccaac agccactggt cacatatggg gggaccttct gttcaggtgc tgccctattc 171360
cttgtaaaca tcgcttatta ccaattttcc tggaaataac aagaaatctt tgataggaat 171420
actggagtat aggtttcttc agtacttaca taggaccttt ctccaccaat tcagaaacat 171480
cagttgaaga ctactatgtt catggtcctc tacttcaggg ggtccccaac cccctggcca 171540
cggacccgtt aggaactggg ccgcacagca ggaggtaagt ggtgggcgag caagcattac 171600
tgcctgagct ctgcctcctg tcagttaagc tgcagcatta gattctcata ggagtgtgaa 171660
ccctattgtg aactgcacac atgagggatc taggttacgt gctccttatg agaatgtaac 171720
taacactgta gaacatcggt tccccaacct tttcagcacc agggactggt ttcatggcag 171780
accatttttc cacagacagt ggggctggag ggcaagggag gtgtttggga tgaaagtgtt 171840
cgacctcagc tcatcaggca ttagattctc ataaggagca ccaacctaga tccctcacat 171900
ccctcacatg tgcagttcac aatagggttt gtgctcctat gaaaatctaa tgtcgtcgct 171960
aatctgacag gaggcagagt ttaggtggta atgctcactc gcccgctgct cacctccttc 172020
tgtgtggcct ggttcctaat gggccacaga ctggtagtgg tccatggcct tggggttggg 172080
gacccctgct gtaggtaaca gaaaagcaaa gaagccttgt ccctttctgc tttccaggag 172140
cttgcagact acaatttagc aattccataa accagaatat gctatactaa agcaacagaa 172200
ctctatagaa gttctaagaa ggaagaaatt aattctgata gcagactata taatactaat 172260
actagtaata gtactaatat agtactatta gtgctatatc ctcttaccaa ttcatatcag 172320
gatgaggaca gtagtctctg tcatttacct ttctgttttc cttccctcca cttttttttt 172380
tttttttttt tgagatggag tctcactctg tcgcccaagc tggagtgcag tggtgcaata 172440
tcagctcact gcaacctctg cctcctgggt tcaagcgatt ctcctgcctc agcctcccat 172500
gtagctggga ttacaagcgt gtgccaccac acctggctaa tttttgtatt tttagtagag 172560
atgggatttc accgtcttgg ccaggctggt cttgaacttc tgacctcagg tgatccgccc 172620
gccttagcct cccaaagcgc tgggatttac aggcatgagc caccacgctc ggccttccct 172680
ctactttttg acctgtctag tttttgactg agtacagttt aagtaaggac atggattgct 172740
tatacttctt ggtaatttta gtagtcctct tcctcttacc tgttctccat ctcatcacaa 172800
tattagtgtc tttttaacaa gcattaggaa cagaaccacc atttaggtct tcagtgagtc 172860
acagatataa aactgtgcca cagttaacga gtagaatact tggcatgcct gacaatcaga 172920
aatcatagtc attgaatttc tgagccatat ggccatttcc agtcctatcc ttttagatag 172980
atagacagat agaccaactg ataaaataag acccagaaaa tttgaagttt ggctgtggtc 173040
ataaaagcta gtgtagtcta tagtctgtaa gcaagacttt ggattattct tctttgtata 173100
tccaatggct agcagtgcca ggcccacaga aggtacaaaa taatattcac tgaaggagag 173160
gatgagggat ttgaatgcag gaaggccagt attgtttcag taatcctata aatgccattt 173220
taaataatta ttttaaattc cctaataatg ggagattatg ctaaacatca tttttagcta 173280
ttcatgaaca acaaagcagt gctcatatta agttttggga agtgagtttt actaaaactt 173340
agtaataata gtcttcagac tctgtgattt aggctgccca gtgcccccctt ttttttctta 173400
actggctttt aaaaaataac atttagtagt aatataagcc aggcacagtg gcatgtgttg 173460
gtagtcccag ctactccaga ggctgagatg ggagaatcgc ttagcccaga agtccaagtc 173520
tagcctgggc aacatagtga gaccctgtat ctaaaaaata ataatagccc atgtctacat 173580
agactattat ataaatttag gaagatacaa aaaagtttaa agatgctggg catggtggct 173640
catgcctgta atcccagcag tttgggaggc caaggtgggt ggatcacctg aggtcaggag 173700
ttcgagacca acctggccaa cgtggagaaa ccccatcttt actaaaaata caaaattagc 173760
caggcatggt ggcacatgcc tgtaatccta gctacttgag aaggctgagg caggagaatc 173820
gcttgaaccc aggaggcgga ggttgctgtg gccaaaatca cgtcattgca ctccagcctg 173880
ggcgacaaga gcaagactac atctttaaaa aaataaaaaa gtttaaagag atggaaacaa 173940
gaacctccat agtccaatca cctaaagata actattattt tatctttttt tagcgcacgc 174000
aaacacaata tcacccttag caaaatggga atcatattct atacattttt gcctcttctt 174060
ttatcatgtt atgggcattg tcccacatca ttacacatta gaaaataaga tctaatgata 174120
ttattcattg tatgaatgtt acagaattta tttaagagct tcctgttgtt ggttatttat 174180
ttatttattt ttatttattt atttatttat tttgagacgg agtctcgccc tgtcacccag 174240
gctggagtgc agtggtgtga tctcagctca ctacaagctc tgcctcccgg gttcacgcca 174300
ttctcctgcc tcagcctccc aaatagctgg gactacaggc gcctgccacc acgcctggct 174360
aatttttgt atttttagta gagacaaggt ttcaccgtgg tctcgatctc ctgaccttgt 174420
gatccgcccg gcctcggcct cccaaagtgc tgggattaca ggtgtgagcc accatgccca 174480
gtctatttat ttattttaag atagtgtctc actttgttgc ctaggctaga aggcagtggt 174540
gtggctcact gcaccctcaa cctcctgggc tcaagtgatt ctcctgcctt agccccccaa 174600
gtagctggga ctacaggtgc gcatcatcac acccggctaa tttttgtaat tttttttgt 174660
agagatgggg tttcgccatg ttgccaaggc tggtcttgaa ctcctgggct caagcgatcc 174720
acctaccttg gcctcccaaa gtgctgggat tacaggcatg agcaccgtgc ccagtggtta 174780
tttagattat tcccagtttt tcaatattat aagcaatgtg gtataaatat cttggtacac 174840
gatttttgc ttatcactct taaggatcct tataataaat tccttctatt atttttattt 174900
ctctttaggt aatacatgta catagtttta aaaagtcaaa ttgtgctgca aagtccaact 174960
tccccccctt caaggtcccc tccctaaact cttttagctg tttattcagt tgtttcttt 175020
tctatttcta aataatatgt tgatactaca tttttaaata ggatttttac attttaagca 175080
ttatctattg acttcctact cctacatgta gatatagcac atttgcaata ctcaccaccc 175140
cattctcctt tcctccatcc tcccaatata attatcaccc catttggtta aaccagtact 175200
cattctttac cttattaaga ccttatagct gggcacagtg gctcatgcct gtaatcccag 175260
cattttggga agccaagaca ggaggatctg ttgaggccag aagttcaaga ctagcctggg 175320
taggctgggc gcagtggctc atgcctgtaa tcccagcact ttgggaggct aaggcagatg 175380
gatcacgagg tcaggagatc gtgactatcc tggctaacat ggtgaaaccc cgtctctact 175440
aaaaatacaa aacaaaatta gccgggcgtg gtggcaggtg cctgtagtcc cagctactcg 175500
agaggctaag gcaggagaat ggcatgaacc cgggaggcgg agcttgcagt gagccgagat 175560
cgcgccactg cactccagcc tgggtgacag agtgagactc cgtctcaaca acaacaacaa 175620
caaaaggcta gcctgggtaa catagcagga ctcctgtctc taaaaaaaaa gatctttagt 175680
attattcatt tgaattcatt attcaagttt tcccttcctt ttgaaaatat gctgttttct 175740
gttactatta ctgtttcttc tcaaattcta caagttttaa aaactgaata ttatttttcc 175800
acgtggtcaa acacacagct cttctcttcc atttttatct cttcctagaa actccttctc 175860
agagcctccc atcctcttct tctattctgt attggttact gtctagacct caggcacagc 175920
tgtccttctg gaacttccct tcagttttct ctagatctcc tttttcttgt ttatgctatg 175980
tccatttctt tcttttttct ttttcttttt ctttcttttt tttttttttt ttgagacaga 176040
gtttcactca tgtcgcccag gctggagtgc agtgatgtga tctcggctca ctgcaacctc 176100
cgcctcccaa gttcaagcaa ttttcctgcc tctgcctcct gagtagctgg gattacaggt 176160
gcctgccacc acgcccaact aatttttata tttttagtag agatggggtt tcaccatatt 176220
ggccaggttg atctcaaact cctgacctaa ggtgatgtgc ctctgccttc caaagtgctg 176280
ggattacagg cgtgaaccac tgcacctggc ccatttcttt cttgatttac tgtctcacat 176340
tggtttttta ttttttattt tttacgtcat ccagtagctt ctaggaaagg acacctgggg 176400
atgtatggtt tttttagaca ttgcttatct gaagctatct ttttattcta tactgacact 176460
aattgaaggt tttaccggat atagaattct agtttggaaa tagttttcct tcgaaacttg 176520
atggctctgc ttctttttct tctcatttcc agtgttgatc ttgagtagtc tgatgccata 176580
ttgaatctca gtcctttata tttaaactgg agttcttaca atttctttat cctcattatt 176640
ctgaaacact tggtgtgggt ctcttttagt tattctgcta ggttcttagt aagggtcttt 176700
ttgatctgca aaattatatc atttgatttt gggaaatgat cttatattag ttcctcaata 176760
atttcccctt ttccccttc tccatttttt ctgttttctc aattagtccc cctgttttct 176820
gttccatgtc tcaccttcta cctggtgcct ccttccagag cttgtttctt attggtactt 176880
ccttctaaag caacttgctc ttcagccttt tctgctctgc ttatatttcc ttttcttctg 176940
ctaagaatct gttaatgaat ctatgcttga ttttagctga aaggctgaga agcaatctgt 177000
taatgaatct cagacagttt tcttttcacc tcaagatcat tttattctac ttattatata 177060
ttttagtttt tatttttaat tctttttttt tttaaatgga gtctgactct gtcgcccaga 177120
ctggagtgca gtggtgcagt ctcggagtct cggctcacta caacctccac ctcctagatt 177180
caagtgattc tcaagcgtca gcctcccgag tagctgggat tacaggtgtg caccaccacg 177240
cccggctagt tttgtattt ttagtagaga tggggtttca ccatgttggc caagctggtc 177300
tcaaactcct gacctcaagt gatccaccca ccttggcctc ccgaagtgct gggattacag 177360
gcataagcca cggtgcccag cctatattta attcttaacc actctgaaca ccttgtattt 177420
cttcataaca cttacaatta gtgttaaaat cataacttat aattagtcac aattataatt 177480
agttaattgt gtgatccctt gcctaatgtc tttcccacta cacaggaaac tccatgagga 177540

-continued caaggattgt gttgcattgt tcaccatcat atatctatta tctagcctgg tgactggcac 177600
aaagttggca ctcataaata tttaataagt gtattaattt gcatctttct ttaatcaata 177660
taatttattc tgtcaagtgg actgaaatag gaatttaact tttcccacct aacatcccat 177720
ttattgaatg ctctttatca tatatcatat actacatatt gtcctaccta ttcttttgcc 177780
aatagtatac tgatttattt gttgtagtat tataagacat tttaaaatga tactgcagac 177840
ttcctgaaat tagtttttg tttgtttttg ttttgagacg gagtctcgct ctactaccca 177900
ggctggagta taatggcacg atctcagctc actgcaacct ccacctcctg ggctcaagca 177960
atattcctgt ctcagcctcc cgagtagctg ggaccacagg tgtgtgccac cacacctggc 178020
taattttttg tagagacggg gtttcgccat gttgcccaag ctggccttaa actcctgaac 178080
tcaagtgatc tgcccacctt ggcctcccaa agtgccagga ttacaggtgt gagtgagcca 178140
ctgcacccag cctgtttgtt tttgagacag ggtcttgctc tgtcacccag gctggagtac 178200
agtggtgcag tcacagctca ctctagcctc aacctcctgg gctgaagcaa tcctcccagc 178260
tcagcctcca gagtagttgg gactacaggc ctgcaacacc acgcccaggt aattttttgt 178320
attttttgta gagacagggt ttcaccatgt tggccaagct ggtcttgaac tcctgggctt 178380
aagcaatcca cccacctcgg cttcccacag tgctgggatt acaggcgcaa gccaagccac 178440
catgcctggc ctcattagtt gtttgaaaaa atattctggc tatcttcatc tggttcttct 178500
ttcacatgaa gtacagagtc acttattcaa gttcttttc aaagaccttt aagattttga 178560
ttcaaaaaca taaattagta tggagagaat tgacatcttt ataatatatt tggcctccct 178620
aaccaggaac atgttatggc ttctccattt agtcaagact tctctggtga ccttggtaaa 178680
gtttgtagat tcttctttcc ccagtttatg tccatttctt gttagattta ttcctaaata 178740
tgtgtatgtt caattgctaa aggaaatagg atttctcccc actataaatt ccttttatct 178800
cacctaaaac tgggtaagtt tccctttatt cctacaatac agtttacatt atatgcccat 178860
gacaaaatac tagtgttagt agttctcctt acatgtggtg tctcatgcct gtaattctag 178920
cactttggga ggccgaggca ggaggatctc ttgaatccag gagtttgaga ccagcctggg 178980
caacatagtg agatctcatc tctacaaaaa aaaaaaaaaa aaaaaaaaaa attgctgggt 179040
atggtggtgc atgtctgtag tcccagtttc ctaagttagc ttcattttta ataagagcca 179100
gttgtttcag caagaatcgc ttgaacccag gaagcagagg ttgcagtgag ctgagatcac 179160
accactgtag tccagcctgg gtgacagagc aagactgtct caaagtaata ataataataa 179220
gaagaagaca aagaagagcc agccatttca atgatctatt actgtgtaac catttccaaa 179280
ctttgtggct taaaccgaca accattttat tgtatcacaa ttttgtgggt tgtccagggc 179340
ccagctgaac acctcttctc acagtctctc ctgtggttgc agtcagctgc ggctgtggtt 179400
tggatgtctg gtaccatgtg gcttcctttg acatgatacc tcaatctcca gggcttttcc 179460
tcatgaccta gctctcctgc agggtagctt agactgtgta catggcagtt tagatctcca 179520
aaattgaaaa aaaaaaaaaa aaaaaaaaga agaagaagaa gcttcaaagc ctttttagtg 179580
cctgggcatg gaagtcccag attgtcattt tctctgcatt ccgtatgtca aagcagtcac 179640
agacgagatt caaggggagc agacacaagc tgtacctctt gattggagga ggaacatgtg 179700
aggggtggca ctgtaaggga ctacctttgg agattaactg ccataatggc atttgttcat 179760
tggcccttgt cttcttcctt ttcttctttt attccaggta gctaccctag acttcagtgt 179820
agactaagtt cttttaagca tgtttgcact tttttttctg tcttttttttt tttttttcct 179880
ttatgtggag aacgggacct cgctatattg cccaactcct gggctcaagt tatcctccca 179940

-continued

```
tctctgcctc cctaagagct gggattacag gcgtgagcca ccatgcctgg ccataagctt 180000
gtttaatcca gtcaaatttc agtaccaaat aactatattc attgtcataa ataggaatct 180060
gaagggggta gcaagggaag cctttctttt aatgtttcca tcttcacatt tgttttcctg 180120
gatgaagttt aactcttatg gacagaaata cagagttcac ttgagcatga aataccagac 180180
aaagagacag gtgtaaattg gccctgttct tctgaaccct gcctgcctac tttctaggaa 180240
ggctagcctt cccctctttt ccccagcata agtccaaccc cttccctcat tatggtttgt 180300
cataagaact ctctcttata ctggtgcaag tggaaaaaag agagtattat tccttttctt 180360
tttttcacaa aatacttctt cctaccctgg atttgctaac ctctggctta aatacgcacc 180420
aagcaaagat gtatatatag tcttcctccc ttcctctctc tccccttagt ctgaaggaaa 180480
gcagcaggtg atggaatgca taaaggatcg gggcagggct agagtctttt ctcacacact 180540
atggacgttg ctcaacagaa tgggtgtgaa atttagtcag agccacagca tgtgtttcag 180600
ttttccaggg aatttcctct tcctaactgt aggtttaacc ctttcttctg tgtagggaat 180660
gccaggggct acccaagaaa tatgaaatga gttatttgta agaaggaaaa aatgccaggc 180720
ttttaccagg ctcctttggg atctaggatc tccaacttac ttcttgctaa atgattgtgg 180780
aaaaagacat agactttgga gttggataga cctggcttca tatcccatct ctaccattgg 180840
gtggtcttgg gcagtcattg gtggcagtta cttgatcttt tttttttatt tgagacggag 180900
tttcgctctg tcacccaggc tggagtgcag tggcgcaatc ttggctcact gcagcctcca 180960
ccttccaggt tcaagcgatt ctcctgcctc agccttctga gtagctggga ttacaggcgc 181020
ccgccaccac ggctggctaa tttttgtatt ttttagtaaa gacagggttt caccatgttg 181080
gccaggctga tctcaaactc ttgacctcaa gtgatctgcc tacctctgcc tcccaaagtg 181140
ctgggattac aggcgtgagc cactgtacct ggctgatctt tttgaatctc cattttctca 181200
tctgcaaaat aatataaaaa cttgccttat agtattcttg tgagaattac atgagttgat 181260
gtgtataagg tgcctagtac aatgcatacc ctctccacag tatgcactct acatatgatt 181320
attttcttct ccagtcttta cctctggatt ctgaggctat ctactcttct tttgtgccat 181380
gccatgttgg gtgtttgcca tggtagcagc ttttcactaa agtttgttgc ttttctcccc 181440
gaatctaatt ccctaagtgc gttacaggga ggagttattt cacatgatat gcagaatccc 181500
tcttggggtc ctcattaagc taaaggacaa gtctctatac gaatgctgag aagggctggg 181560
cccagtggct cacgcctgta atcccagcac tttgggaggc caaggcaggc ggatcacctg 181620
aggtcaggag ttcaagacca gcctggccaa caatggtgaa accccgtctc tactaaaaat 181680
gcaaaaatta gctaggcgtg atggtgggca cctgtaatgc cagctccttg ggaggctgag 181740
gcaggagaat tgcttgaact caggagacgg aggttgcagt gagctgagat tgctccactg 181800
cactccaagc ctgagcgaca gagcaagact ccgtctcaaa aaaaaaaaaa aaagaaagaa 181860
aaaatgctga gaaggactat agggctttcc ttgcccgtct catactggaa cccatatgaa 181920
cttacaaaag ttttttttgt ttttgttttt ttttaagaca cagtctcact ctgtcaccca 181980
ggctggagtg cggtggcaca atcttggctc actgcaccct ccgcctcctg agttcaagcg 182040
attctcgtgc ctcagcctcc cgagtaggtg ggattacagg cacatgccac cacacctaac 182100
taatttttgt atttttagta gagatggggt tttgccatgt tggcgaggct ggtcttgaac 182160
tcctgacctc aagtgatcca cctgcctcgg cctcccaaag tgctgggatt ataggtgtga 182220
gccactgcgc ccagcctaca cttataagag ttctaaaatc atacagtgtt agaactgaaa 182280
```

tgaagtatag aggtcacctg gcctatttta tacggaaaga actgtggctc ggaaaaggtc 182340
atgtcatgca aggcctcata acggagtagt ggcagctctg gaactaaaga tctgtcttac 182400
ttgtctatta ctatggttat aatttaattt ttttgaacgc tatctgagtt ctaagtgctc 182460
agggcctagt atgcaagttt acgccaagta tgtaaacttg cttctaaatt ggaatgctga 182520
tcatactttt agcaatgggg aagtaaacac tgttgaagac atttcaatat cattcccttg 182580
gggagtaaca gggcttcaat gagaatatta taagctacca cctgaaaacc tcatttttct 182640
acaaaggttg cccaaggggc actgaggtgg cagttcagct ggctgttgag tctctgctcc 182700
cagactggtg agttgggaag caaacttgtt tcttctgttc tttcttcatt ctcccaaata 182760
ataccaagta ggggaagctc accccaagcc cccatctggc tttccttttt tttcaacttg 182820
aggtataatt aacatacaat aaaatatgca gatgttaggt gttcagttgg taagttttga 182880
taattgtata aaccatgtaa ccagcatgaa taaagaatac acagaacatt tcatctcccc 182940
agaaatatcc cccatgcctc tttgagtccc ccaaccccac acatatatac aaaaccattt 183000
tctatcacta tggataagtt ttgtttttgg atttcatata aatggaatca cacaggatat 183060
actctttcat agctagcttc ttttagctta gcatgttttt ggaatttatc catgttgcat 183120
atatcagtag tttttttctg ttttgctttt ctgagtggta gtcaattgtg tggatatata 183180
aggagaaaag gtagaggttg gtgaagggct ttcatctggc acgtagcctg actacccttt 183240
gctcaagagc atttggacca ccagaggccc ccctccttaa gattaagatg ttcacttacc 183300
tgctttaaat gtaccacgtc acagcatata cactattatg tagctatgtc ttgtaaaagt 183360
ctctaatcgg catccattag atgagccgaa ttctcctggc caagccttag cctctcaggg 183420
ggctggcacc aaacagggag gctggagtag ggtttcaaac acctgtttca gctttttaag 183480
tgtccgattc aggccactgt gctctggcag cagggatcct catgatgtgg cttcttctct 183540
cctgccaaat cctcaactta aagaacctag gcccttaggg gaggaaaata tagagctggt 183600
ggagagggga ggggtgtgca gcaacattga agaactgttt cttttaaagt taaatgcaca 183660
tctaccctgt ggctgagcac tttcgctctt aggtatttag tcaagagaaa caaacacatt 183720
tacaaagaga cttttatagg aatgtataca gcagtaatag taaataactg gaaacaactc 183780
aaatatcctt caataagaga atggataaat tctttgggag tgaaggactt acagaggatt 183840
ctctggcggc cctcctctct ttctaggaat cattcttgtt tctattctta tttctttctg 183900
gatttttctg aatttggttg tgttttaaat gccatgtaat ggaataccca ttatttgtaa 183960
gttgattgag cataaagtat tttattataa agtggtcatc cgtcacaaga aggcatgtgg 184020
ctgtaaaaaa cattaactct gcactctggg ctggaatgca actttaccag aataatggag 184080
cttttgtatt aagtgtgcag ttgggataaa acaagagaca gacagacaga cagtgttggg 184140
gaaacaggtg ttggctgggc ccagcttctg tcccatgttt tgtgaaattg ttttccaacc 184200
ctttgaggat tgctcctcca gattcagctg tcttaaaggt tctgtcagca cctttcgagc 184260
aaataaggtg tgacttttca gggtactgct gcttccataa gctttatttg tttactgtcc 184320
agctcacaga catgtctaga gacagcagtg gcaagtgatt accatactta tcctagctcc 184380
atctattttt gacgcttttg ttttccccat cagtaaaatg ggaaatatcc cttatcataa 184440
agttcttgag ccttttagca tgagggtggc tgaaacagca taaagacttc ttaatctggc 184500
tgggcacagt ggctcatgcc tataatccta gcactttggg aggccaagga aggaggatca 184560
cttgaaccca ggagttcaaa accagcctgg gaaataatag caggacctcg tctctacaaa 184620
gaaaaaattt tttttaatta gccaagtgtg gtggcacacg ctttagtccc agctacttgg 184680
gaggctgagg tggaaggatt acttgagagg ttgcagtgag ccgagactgt gccactgcac 184740
tccagccagg gtgacagagt gaaaccctct ctcaaaaaaa ataaaaataa aaagacccct 184800
tagtcttgtt gtcactaaga atttatgata tgctgctgta gtaactattt ccagctcttg 184860
ggaaaacatt aactctgtac tctgatagta cagtaagtga gagtgaataa gtaaggtcct 184920
atacactgaa gggataggga aaggttactt atcagtcctg ttattgagac tggggactgt 184980
ctgattcttc tccaggagct ttgactatta tctcttcagg ctttttcatc atctgtaaac 185040
tttgctaatg tcagttcaga atttagttct ttttaatttc ctctttgtct ttttcagggc 185100
tggtagagaa gacctgacat agttataatt gataataaac ctataatgct gctgttgaac 185160
aatgaaattt tttactagac tctgaaagga atttgtattg aaaaagctgc tccaagtgta 185220
atgactgcat aaagctgggg taaattgttc tgttgtcaag tataccaaca gaagttttta 185280
atttctcctg ggctttcaga ttgcctgctt aagttggggc ttggtcttct acagtgcatg 185340
cagaaaacaa caaggcagag tgaagggcca cagtagctct ggtttgtctg tatgctatag 185400
ctgaattgct tgcctttcaa tatgtgccaa tttcctctag aaagaagaga actagtattt 185460
aaggttgata cgcatcaaac ttgtgctttc agtaagacag atggatcagt ctgtccttgg 185520
gtctctgaga tatgattgag gccagtccct gtgggcctca tttatccctg ccagccttgt 185580
taaaggggcc tcactctccc tctttggatt aggagggaac ctaggtaaac ctgacactta 185640
atttgtatgg cagtactaca agcaataact aacaatgttt agtcactggt taggagaagg 185700
agaggtgcag aagaaacttc agttctagga tggttgagtt ttaaaatttt ttgttttgtt 185760
ttgtttttga gacggagtct tgctctgtct cccaggctgg agtgcagtgg cacaatctcg 185820
gctcactgca agctccgcct cccaggttca ctccattctc ctgcctcagc ctcctgagta 185880
gctgggacta caggtgcccg ccaccacacc cggctaattt tttgtatttt tagtagagat 185940
agggtttcac cgtgttaacc aggatggtct caatctcctg atctcatgat ccacctgcct 186000
cggcctccca aagtgctggg attacaggtg tgagccacca agcccggcca agttttaaat 186060
ttttgtcatc caagtcatgc agttaatata tctagtagta aacttataca ataggccagg 186120
cacagtggct tatgcctata atcccagcac tttgggaggc tgaggcagga ggatcattta 186180
aggccaggag ttcaagacca gcctgggcaa catagcaaga ccccctatct acaaaaaatt 186240
taaaaaatta gctgggcatg gtggcacatg ccagtagtct tagccactca ggagttggta 186300
gtcttagcca ctcaggagtc tgaggcagaa ggattgcttt tgagcctagg actttgagtt 186360
tgcagtgagc tataattgca ccatggtact ccagcctgag caacagagca agactctgtc 186420
tcaaaacaaa caaacaaaca aaaagccccc tgtaccatag catggtataa tattgaagag 186480
tataatacag tggctttgga gtcacaatag acctggattc aaattttatc tcttccactt 186540
gctgtgtgac cttgggtaag tcacttaacc tcttagagcc tcggtgtcct tatctgtaaa 186600
gtgaggacag taacactatt tcccagagtt attgggagga taaaataaaa ttatatatgg 186660
taattatgtt taataatata atgtagctgg ccgggtgcag tggctcacac ctataatccc 186720
agcactttgg gaggctgagg caggcagatc acctcaggtt aggagttcaa gaccagcctg 186780
gccaacatgg cgaaaccccg tctctactaa aaatacaaaa attagctggg tgtggtagta 186840
cacgcctgta atcccagcta cactcaggag gctgaggcag gagaatcgct tgaactctgg 186900
aggtggaggt tgcagtgagc tgaaatcacg ccattgcact ccagcctggg caacaagagc 186960
aaaattccat ctcaaaaaaa aaataaataa aaataatata atgtagctgt tgctgatgtc 187020
tgaggcaaat taaggttgtt gttctggcaa tgaaatggga ttcttgtgag ggtggtagat 187080
agcagctcct agcaacaagt taatctggct atttagcagg aatgcccaag gtaggaaact 187140
cattcctctt ctaatcagga ttcatacatc atattggaca aaatcataca ataaactatt 187200
ttcccatgtg tatgctgcct ttaagtgcct gtcttatctt ttgaaagtgg aggctaaatc 187260
tgacctgagg cagaccaggg cagcctcact cagcaaggag acgatggcaa aaatgacgat 187320
ttcaggagca gagatttacg gaaagcagcc tgctctgaga tacacatgct gttagggatt 187380
ttgaccctga aaaaatatat cctcttccta tcctctctct aaggagaggt tgagctgcta 187440
tagggatgga gatgggggca aggtcctgac aaaggtgttc aagccagaga gcatatatag 187500
atggcaaaaa taattttctg tcatggtcat cttgaacctt tttgcaccag gtatctaggg 187560
aggaggagtt cttacataat ctctgggtta ggttggggcc tcatgaacat gatgctccat 187620
aaagtactta tcagtggcag ttttggagaa aatataaaat tatgatttct aatccctggg 187680
gttttcagac tttaaatgta acctcaaggt gtatacattc aggaactcct catgtttaat 187740
cagagagtta aggtttgggg ttttgattca ttaaaaaaaa cagattgggg ctgggcacgg 187800
tgtctcaagc ctgtagtccc atcactttga gggccaaggt gggtggactg cttgagccca 187860
ggagttcaag accagcctgg gcaagagaga gagaagaaaa acagggtggg ttgacctttg 187920
agggattgat cagccagaaa agtgaacact ttccaaaggg tttgtttttg ttgttgttgt 187980
cttttgagac agggcctcac tctgtcgccc agactggaat gcagtggtgc catcatggct 188040
cactccagcc atgacatccc tgggctcaag tgatccaccc cacacgtcag cctccctagt 188100
agttgggact acaggcgcac gccaccatac ctggctaatt tttttttttt tttttttttt 188160
ttttgagaca gcgtctggct ctgtcgccca ggctggagtg cagtggcgca gtcttggctc 188220
actgcaacct ttgcctcctg ggttcaagcg attcttctgc ctcagcctcc tgaatagctg 188280
ggattacagg cgtctgccat cacgcccagc taatctttgt atttttagta gggacagggt 188340
ttcgccatgt tggccaggct ggtttcgaac tcctgacctc aagtgatcta cccgcctccg 188400
cctcccaaag tgctgggatt acaggtgtga gccaccgcac ccagccttcc cctatacttt 188460
aaatcatctc tagattactt gtaatgccta actcaatata aatactatgt aaatagttat 188520
accatattta gggaataatg acaagggaaa aagtttgtag atgttcagta cagatgcaac 188580
catccactta atttttctga atatttttga tctgtggttg atcgtgtaca ctgatgttgg 188640
atccacagac acagagggtc aactgtaatt tgcctttttt ttttttgaa acagagtctt 188700
gctgtgtcac ccaggctgga gtaaaaatgt tatgatctcg gctaactgca acttctgcct 188760
ccccggctca agcgattctc gtgcctcagc taccagagta gctgggatta caggtgcgca 188820
ccaccatgcc caactaattt ttatattttt tgtagagaca gtgtttcacc atgttggtca 188880
ggctggtatc taacttctga cctcaagtga ttcgcccacc tttgcctacc aaagtgctgg 188940
gataacaagc gtgagccacc aagcccagcc taatttgcct ttttcaatgt aagtggttgg 189000
taccattatc ttctactgct ggccctaagt ggatctatgg atcctgattt ttaccttgat 189060
gcagcaatga ttaagccata atcatacttt gtctcttaaa aatcataatg tcaaagttaa 189120
tagcccccta agtctagaag catcctgaga agctaagaat gtgtttgata aaaagaagca 189180
gatctgagaa actgttgtgt gatagctgag aaaagagcca ctgtgaagag cttagacaaa 189240
caaacaggac ttgccttccc tccaggctag actgtctgca ttcatgtgca tttacttcca 189300
aatggtactt tgcatttaga atcataagtt ttagggacct taaagaatct agttaaatta 189360
ctatcaccac caccaccttc cccaggaaat cccaatggat gaggaaacta tggcccagag 189420
aaatgaggtg tttttgccca aggtcacaca gttaatgaca gaatcagaat tgggcctagt 189480
gcatttcttt atttcatatc tcctgttgta tagggcaggg tctatctggg tttgaccctt 189540
aagcccaggc taggaaatac aggtatggga cctgtccgtt gacagtgttt tctggaatcc 189600
gttcctgaac caagcctaaa ttcccacctg tccattcata ggtctggaaa actttgaagc 189660
tgataaacga aggtatggga ggtttggcag ttattccaga ggcttctggc tttgccaaag 189720
tttagctttg attattcttt ggaccactac ccctcttttt ttttttttc tttttgaaac 189780
agggttccac tctgttgctc agggtagaat gcaatggtat gatcagggct cacctcagct 189840
tcctgagtag ccaggaccac aggtgcgcat gcctggctaa tttttcata ttttgtgcag 189900
ctgaagtctc actatgtcgc ccaggctggt ctcgaactgc tgggctcaag tgattctccc 189960
acctcagcct cccaaagtgc tgggattaca ggtgtaagcc accacacctg gcctggacca 190020
ctactcttga tgtcctctag tgaccaaaaa gaacacagct tcttcctacg gagcttacca 190080
tacatcagac atttttgtag atcactatca atcttgactt ttgcaagaaa tatattcctg 190140
gggtgtacag catagtcaga aaagtagcat atgagaccta acactttctc ctaaaatgga 190200
atgtacagat acagacagaa aagcctaaaa ccaaaaagct tttgtcgtct gtctctggat 190260
acagaaatgt tagaggggta aatgaactaa tttctttttt tatcatgcta tgatttatta 190320
gtctgttata catgatccat cttgtgaatg atggcattct gtctccagga acatgggcca 190380
atatttgcag ggtaaagaac atgcatggga gcaggctggt gaccctctag aaagcaagaa 190440
gagagaagta gactctgagg gcaaaaaggt cgagacaggc atttctgaag ccaaatggtg 190500
ttgaaataac ataccgcagg ccttttctt tgtcagcgta atccaattga gaatgcccaa 190560
ctgcccctga taagagtcac tcaggagtga agagctttgc taccagggaa agcagcttat 190620
gtgtgcattt tggctcagga atgtgccagc ccaatgctgg ccaaatgaga aaaggctgct 190680
gcggcctgga gaacacagcc tcctgggagg atggtggctg ttcccttgta gcttaggaga 190740
gtattctgtt ttgtccaagg gcagtgcttg aggccacatg ttgaggcctt tgacatagat 190800
tatcagagat ggtagcagct ctgacatgag aagagaaaat aatgtcaaga ttcagctggg 190860
cgcagtggtt catccctgta atcccagcac tttgggaggc cgaggcgggc acatcacgag 190920
gtcaggagat cgagaccatc ctagctaata acggtgaaac cccgtctcta ctgaaaatac 190980
aaaaaattag ccaggcgtgg tggcttgcgc ctgtagtccc agctactcgg gaggctgtgg 191040
caggagaatt gcttgaaccg gagaggcgga ggttacagtg agccaaaatt gcaccattgc 191100
actccaggct gggtgacaga gcgagacttc gtctcaaaaa aaaaaaaaaa agtcaagatt 191160
catccccatt ttggagaggt cacctcatca tttgggaaga caagaggtgt gggacatctg 191220
cagattctca gacagacatt gggccaaatt gacacttctg ttttaatgtc ataatatggg 191280
gagtgaagca ccctgcccag tcgtattgag tacagtatga gcagaccacc accaagacat 191340
ctccaaaggg cttcactttg ctttgggttg aagtgactca tgagcctctc cagaaataat 191400
ttaataattc ttgttgtaat ttgtcactga ctgtccagaa attggatccg gatttgattc 191460
tggaaggatc cgaagtgttt tctccaatgg ggggttagat ttcccctcct tgtgcccttt 191520
ttcccccaga tgactggctc atcttagaac atggaccagt caccttcaga gcacctctct 191580
acctaatctg cactctgtgt ttactggact gtttgtgcct tgaggttgac agtcttccag 191640
ggcgggaatt ttggctgctt ggctggggtg tcagatgtct ccttggttgt gaaattattc 191700
agcctgctta ctatgagcag aatcatggca cttttctcct gaaggactca ggcagttttc 191760
actcttctgg agaagatcca gacaattgaa tctcagttcc cagccaggct gaaccgtgag 191820
ataggacacc agaaaccttt ctgttctagc cttgtaggaa gcagtaaagt cggatggcta 191880
cgagcagagc ttttggagtt ggatggacct ggatttgatt cctgtttcca ctactagcta 191940
gtgctatgat cttagctggt ggggacatct cgttatcctt tccaagcctc atttttatct 192000
tcaaaatggg gttaattatg aagagtgaag gtatgtaaag tgcatagcac ttggcatggc 192060
gcaggtaata aatgttaatg agtactttaa taattcattt tattaaaagg aagcctgttc 192120
tttctctgat accttggaga aagctgaagc cctcagaaat taaaagtgct atcccaaatt 192180
gtaccgtaaa tatcaaccac ccgttatctc agtatttatc cttaacttgt gtttgtttta 192240
tggtttagga gtcaaaggta gaatttttat atatatattt acttaaatct taagaaatga 192300
actggtggcc aggtgcagtg gctcatgcct gtaatcccag cactttggga ggccgaggca 192360
ggcagatcac aaggtcagga gatcaaaacc atcttggcca acatggtgaa atcccatctc 192420
tactagaaaa tacaaaaatt agctgggtgt ggtggcatgt gcctgtagtc ccagctactc 192480
gggaggctga gccaggagaa ttacttgaac cggggaggtg gaggttgcag tgagccaaga 192540
tcactccact gcactctagc ctggtgacag agcgagactt tgtctcaaaa aaaaaaaaaa 192600
agaaaaaaaa aaaagaaaga aatgaactgg tatacaatat agagaacact ggactgctgt 192660
gactctagag ctaaaaacta gaacaatatc ttagttatct ttattataca ctttattcca 192720
tgcattgtac caagtgtttt acatgcatca aatgagatag tgtgtaaatt gcttaatacc 192780
atgcctggca catagtatac gctcagtgaa tgttagttgc tattattatt tattttaaat 192840
gtaatttatt taaattatct aatacccatt tacaagtaat aaaattagag acccagaaca 192900
cttaagtaat taaagtcaca tagctattaa gttgcagaac tgggatttga atcgtccacg 192960
aaagcccatg attctaccta gagcccttag cttctagtcc tggttccaat actaactggc 193020
cttgtacaaa ttacttaact tccctaaatc tcagttacct cattataaat tattttcagg 193080
ccctatttta gctgtaatat cctaggattt ggaggatttt cctgaacagt caaaaattat 193140
gacttatttt tgtagggtat ggtttaatct ctgagtaaca gttccctaga aaactgatgc 193200
agcctacaaa ctgctgctta tacacaaaga gatatataca gaagttgaaa gtattttaaa 193260
aattttataa caatgtgaca gtagttacat gtatgttgat tctagtaata aaaaaattgg 193320
actttatgtt tttaaaattt ttctagtaat taactgtatt ttataaaact atgggtctgc 193380
acgggctggg cgaggtggct cacgtctgta atcccagcac tttgggaggc cgaggtgggc 193440
ggatcacgag gtcaggaggt cgagaccatc ctggctaacg cggcgaaacc ccatctctac 193500
taaaaataca aaaagttagc cgggcatggt ggtgggcgcc tgtagtccca ggtactcggg 193560
gggctgaggt ggaagaatgg tgcgtggggg agcttgcagt gagccaagat ctcgccactg 193620
cactccagcc tgggcgacag agcgagactc cgcctcaaaa aaaaaaaaaa aaactatggg 193680
tctgcagtgg attgacataa agaagaaaaa actgctcttc atcacagata atttgacaag 193740
cactattcta gataaccatc tgaacatctc accaggatta taaattcaaa tttgtttgtt 193800
tttaaattac atgtttacaa aaagttaccc cttaaattag aaatatcctt actaaaggct 193860
ggacgtggag actcacgcct gtaatcacag cactttggga ggctgagaca ggtggaccac 193920
ctgaggtcag gagtgcagtt tgagaccagc ctggccaaca tgaagaaacc ccatctctac 193980
taaaaatata aaaattagct gggcctggtg gtacatgcct gtaatcccag ctacctggga 194040
ggctgaggca ggagaatcgc ttgaacccag gaggcagagg ttgcagtgaa ccgagatcac 194100
accactgcac tccagcctgg gtgacagagc aagactctgt ctcaaaaaga aagaaagaaa 194160
gaaagaaata tccttactag tgatgcccca ctaggagttc aacttgcccc caacccccact 194220 tgttgcagag ttgctcctgt tagagcttct cttatgctcc tggcaatcaa cagttgaacc 194280
tagagagcaa aactcttgtt ctccctagac aaaactcttt aaggaaagtt aactttatat 194340
atcatgattc tctttttgg aagaggtagg gaagtgacat gataatgaag gttcctggtg 194400
ggctcattaa aaagtttaac ccttctagtt tttcatcagt aggtttctat aaagcactga 194460
cttaccaaat gaaagtactg gaatgaacat atcttagcag tcatagattc caacaacctt 194520 cttcttttt tttttttttt tttttgagac agagtctcct tctgtcaccc aggctggagt 194580
gcagtggtgc agtctcggct cactgtagcc tctgcctccc aggttgaagc aattctcatg 194640
cctcagcctc caaagtagct gagattacag gcacgtgcca ccacaccagg ctaatttttt 194700
ttgtattttt attagagaca tggtttcact atgttggcca ggctgatctg aaactcgtga 194760
cctcaagtga tccactcacc tcggcctccc aaagtgctgg gattagaggt gtgagccact 194820
gcgcccagcc gatttcaact atctaatttg acagatgaag gtcttgggta tcatatatct 194880
ggctattgat aggagtgaga ctagtccatt gactgaattg tatgctgtgt gagggttaca 194940
cacagagcct cggctgggtg cggtggctta cacctgtaat cccagcactt tggtaggcca 195000
aggcaggcgg attacctgag gttgggagtt tgagaccagc ctgacaaaca tggagatacc 195060
ccgtctctac taaaaataca aaattagctg ggcgtggtgg cgctcatcag tacagtgatg 195120
agagaaacca agaagatctg aataatggag agacatacca agttcatgaa ttggtaggca 195180
caacatagca aagatatcat gtctccccaa attgatctat agactcaatg caattccttt 195240
caaacttcca acaaggcaag tttgtcttaa attgaaatgg aaaggcaaag gaattggaac 195300
actgaatgat attggaaaaa aaaatgaagt tggaggaatc acaccactgt tattaagact 195360
tagtataagc cgggcatggt ggctcacgcc tataatccca gcactttgga aggccgagac 195420
gggtggatca cctgaggtca ggagttcaag accagcctgg ccaacatggc aaaatctcgt 195480
ctatactaaa aatacaaaaa ttagccagac gaggtggtgt gtgcctgtaa tcccaactac 195540
tcaggaggct gaggcatgag aatcacttga acccgggagg tagaggttgc agtgagccga 195600
gatcatgcca ctgcactcca gcctgggtga cagagcgaga ctctgtctca aaaaaagact 195660
tagtatatat cggcagggca cagtggctta tgcctgtaat gccagcactt tgggaggctg 195720
aggcggacag atcacagggt caagagatcg agaccatcct ggccaacatg gtgaaacccc 195780
gtctctacta aaagtacaaa aaaattaact gggcgtggtg gcacgttcct gtagtcccag 195840
ctactcagga ggctgaggca ggagaatcgc ttgaacccag gaggcaaggt tgcagtgagc 195900
caagatcgag ccactgcact ctagcctggg taacagagca agactccgtc tcaaaaaaaa 195960
aaagacttag tatatattta taataattaa cacagtgtcg tgttgtcaga cttagacaca 196020
tagatcaatg aaacagaaca gaacccagaa gagactcaca aaaatatggc caatttaatt 196080
tttatttttt ggaacagggt cttactctgt caccccaggc tggagtgcag tggtatgatc 196140
acagttcact gcagcctcag cctcccaggc tcaagcaatc ctctcacctc agcctcctga 196200
gtcgctggga ctacaggcac atgccatcat acctggttaa tttttttttt ttttttttga 196260
gacaggatct cactttgtca cccaggctgg agtgcagtgg cacgatctca gctcactgca 196320
gcctctacct cctgggttca agatattctt tcacctcagc ctccccagta gctgggacta 196380
caggtgcgcg ccaccatgcc ccactaattt ttgtattttt tggtagagat ggggtttcac 196440
catgtttgcc aggctggtct tgaactcctg acctcaggtg atccacccac ctcagcctcc 196500
caaagtgctg ggattatagg catgaggcat gagccactgc tcctggtcca tgcctttttt 196560
tttttttttt tttttttgag acagagtctc gctgtgttgc ccaggctgga gtgcagtggc 196620
acgatctccg ctcactgcaa gctctgcctc ccaggttcac gccattctcc tgcctcagcc 196680
ttcctgagta gctgggacta caggctcccg ccaccacgcc tggctaattt tttgtatttt 196740
tagtagagac ggggtttcac cgtgttagcc aggatggtct cgatctcctg accttgtgat 196800
ccgcctgcct cggcctccca aagtgctggg attacaggcg tgagccacca cgcctggccg 196860
ttttttaat tattttctgt agagatgatc tcactatgtt gcccaggctg gtctcgaact 196920
cctagactca agggatccac ccacctcagt cttccaaagt gctgggacca gtgcccaacc 196980
tggtcaattt atttttgaca aaggtgcaaa gacaacttaa tgagatatgt tggaaacagt 197040
aggaaattct taggcaaagg aaaaatgagc ctcaatctaa acctcacacc ttatgcaaaa 197100
attaactgaa aatagatcat aggtgaaaaa cataaatctg taaacatttt aggagaaaat 197160
gggagggtgg aaatctttgt gacttggaat taggcagagt caatttagac attaaaccaa 197220
aacacaatcc ataaaatatt aataagttgg acttcatcaa gagtaaaagt gtctgttcta 197280
tgaaagatgt taagggaatg aaaaaataag cttaagactg ggagaaaata cttagaaata 197340
actgtatcac tactgaagga cttgaattca gaataaagaa gtctccaaac tcaatagtaa 197400
gaaaacaatt tagtttaata atggataaaa gacttgagca gacatgtcac ccaaaaggat 197460
atacagacgg caaataagca catgaaaaga tgttcaacat aattagtcat tagagaaatg 197520
caaatttaaa ccacatggag ctactattac atacatactt gaatcgctta agtaaaaaca 197580
ctgaaataca aagtactgaa gaggatgtgg agaaactaga attcttattg ctagtgggaa 197640
tacaaagtga taaaatgaca ttggaaaaga gtttgacagt aaagctaacc acacctttac 197700
cttttgaccc aggaatccta cccctgggta cttaccctaa agaagtggaa acctgtgttc 197760
acacaaacac tgatacacaa atgtttatag cagctccatt cataattgcc ccaaactgga 197820
gatcccacat gtccttcaac cagtgaatgg ataaagaaac tgatacatac aggcaatgaa 197880
tactactcag cagtaaaaag aaacaagcta ttgatatatg caatagcttg gaaaaatttc 197940
agtcatcatg ttgaatgaag gaagccagtc tgaaaattgg ctgtaaaatt acatgctgta 198000
taaatcattc atttaaagaa aagaattaat tttaccaaat tagcaaaaag aggctgaatg 198060
cacatcaccc tagaagtgtg gaccccatat ataaaactgc cctactcttt taccgtgaag 198120
gaagacatga agcaagtata tagttgtagc aactaaatga aatcacagaa aatctgtacc 198180
tgtcccgatt ctcaaagatt tttttcctct agacttttat atgtcaaata tacctcatga 198240
ccacttttaa gataacaaac caaattgtac ataattcatg ctcctaaagc agcaagacta 198300
gatgacttta catttttta tgtacttttt tttttttttt tgagtcggag tcttgttctg 198360
tcacccaggc tggagtgcag tggcgtgacc tcagctcact gaaagctctg cctcctgggt 198420
tcacaccatt ctcctgcctc agcctcccga gtagctggga ctacaggtgc ccaccaccac 198480
acccagctaa tttttttgta tttttagtag agaccaggtt tcaccatgtt agccaggatg 198540
gtctcgatct cctgacctcg tgatgcgccc gcctcggcct cccaaagtgc taggattaca 198600
ggcatgagcc accgtgcccg gcccttttat gtgcttttta aaagtacgtt atgtatttca 198660
gtttttcaca cacacgcaca cacacacaca cacactcaca cacagacaca cacacacgtt 198720
cttctctagg ttttttctgt aaattttaca tctctaggtg ggggtagtag gggaagagaa 198780
gcaggttttt tttacagctg atgtgatcac tgtacagaca agcttggaaa atgctaccca 198840
atctgccaat taattaaagc gttaatctga ggagcagccg ggcccaggga atgtttaccc 198900
agggaggagt gggggtggta ggaactgagt aggcagctcc ctatatttgc atgaaaatga 198960
aggtgcttag gaaaccctgc ttccttttgt ctctaaaggt ggggcagcct agatcacatc 199020
cctaaacact tttggtctct ttaggaagcc ttttagggag ctggtctctg aaagatgaaa 199080
gcacagcaca atctagaaaa acaaatttaa attctggtca gagtaaggta gggagtaagt 199140
acagtgtagt attctttgac ctagaatgga atcttctaaa ttcaggagta aaatttcatc 199200
tatttaggta gaatagatga aggggtttta caagttttaa aaccacatag gctgggttca 199260
aatcccagct ctgcatatta gttgtgtgat ttgggactaa tcatgtatct tatctgagcc 199320
ttttctcatc tgtaaaataa agattatcaa ttgccccttc atctcagagc agttagttct 199380
ctgctaactc taggcaggaa acaggccgga cagtggttac gaacttccaa gattacagac 199440
tgcctccatg actaagagac tgctcagcct tttgttcttg ttaaactttt ttctcagcaa 199500
gggattataa acctcagagt ttcctctcac cctcctggaa tatgctgcac tctttctcta 199560
agagaagtga ccctgaccat aacagcaaag gacataaaga caggagccca ccttgggacc 199620
taagggtcgc attggctcta cccaagatga cgttacctat ttatatcaca ggggagggtg 199680
gtgaaatggg catggaaaat tgactcacaa tatttgatga tattgaaaaa ttattgttaa 199740
tttttaaaaa ttgtgataaa atacatataa tgcaaaattt accattttaa ctgtttgtta 199800
actctttaag cataatattg tgggccaggc acggtggctc gcgcctgtaa tcctagctct 199860
ttgggagggc aaggcaggga caattgcttg agctcaggag ttcgagacca acctgggcaa 199920
catggtgtaa ccccatctct actaaaaata caaaattagc cgggcatggt gacagacgcc 199980
tatagtccca gctactgagg aggctgaggg gcttgagccc tggaggtgga ggtttgcagt 200040
gagctgagat catgccactg cactccaaag caggactctg tctgacaaaa aaaaaaaaaa 200100
aaagataata ttgtgttttt gttctttttt taagattcct aatcttttag atctacatgc 200160
tgaaaatttt acagataaaa tgatacagtg tctgggattt gattcaaggt aatccagagg 200220
gaagaagatt gacccaacaa caaagacctc tagcctcatg gcacaaacaa gaaacttttt 200280
ccagggttta gttttctctt agatgatacc tcttcatttc tgtgtatttt cttgcagaac 200340
tctcagaaat tgagcccaat gtattccttc gaccttttct ggaagtgatt cgctctgaag 200400
ataccactgg ccctatcact ggactggcac tcacctctgt caacaagttc ctgtcctatg 200460
cactcatagg taagagctca ggctttgttg catgaccaca gcacttcatt tcccaccttt 200520
cctggggtgc ccaggcctta ggcaatgagc tggtgatagt gggaaatttt ttccagtcac 200580
ctcttttctt gtagaagaga aataggattg ttgttggtta ttcatcatgc tagctgactc 200640
acgttgtaca gggtgggaag ggcaagagaa gaagttttcc ttggcactct ggcttctcta 200700
tgctttggaa agagttaagg gtatggtacc ttactcttgg aagtttggtt aggtttgttt 200760
gtttgtttgt ttgtttgttt agttagagat ggagtctcac tctgtcgccc aggctggagt 200820
gcagtggtgt gatctcggct cactgcaagc tccacctccc gggttcatgc cagtctcctg 200880
cctcagcctc ccgaggagct gggactacag gcgcccacca ccacgcccag ctaatttttt 200940
gtatttttag taaagacggg gtttcaccat gttagccagg atggtttcga tctcctgacc 201000
tcatgatctg cccgccttgg cctcccaaag tgctgggatt acaggtgtga gccactgtgc 201060
ctggcctggt taggtttatt tttaaagtta ttttttcaaa cataatgcat gcacattata 201120
agaagacaga caatagagat gttcaaaaga aaagttaatt gtccttcctg tactttctca 201180
atgttcctcc tccttcttta ggcaaatagt gtgaacagcc tagtttgaat ctttatgttt 201240
ttctatgtct ttataaatga agtaccattc ctttttaaaa tgaaataagg ccgggtgcgg 201300
tggctcacgc ctgtaagcct agcactttgg gtggccaagg cgggtggatc acgaggtcag 201360
gagtttgaga ccagcctggc caacatggtg aaaccccgta tctactaaaa atacaaatat 201420
tagccaggcg tggtggcggg cttctgtaac cccagctact ggggaggctg aggcaggtga 201480
atcgcttgaa cccgggaggc ggagtttgca gagagcagag atcgcgccac tgtactctaa 201540
cctgagcaac agagcgagac tctgtctcaa aaaaaaaaaa aaaagaatag aataaaatga 201600
aataaaaata ggattatgtg ctacatattt tctttttca tttaatggta ttaacttgac 201660
caggcacagt ggctcatgcc tgtaatccca gcactttttg aggccgaggc ggacggatca 201720
tgaggtcagg agtttgagac cagcctaaca tggtgaaacc ccatctctac taaaaataca 201780
aaaattagcc aggcagggtg gtacgtgcct gtaatcccag ctactcagga ggctgaggca 201840
ggagaatcac ttgaacccgg gaggcggaag ttacagtgag ccaagatcac accattgcac 201900
tccagcctgg gtgacagagc aagactccgt ctcaaaaaaa aaaaaaaaaa aaaaaaaaag 201960
cagatagtat taacttaaat gtacatgata taactattca tctgatttat tcttttatat 202020
tgtagaaaat atatataaaa cttgctattt ccatcagttt cagtttacaa ttcattggca 202080
ttaattacac tcacaatgtt gtgcagccgt caccaccatc tatttcccaa acatttttat 202140
taccccaaat agaaacttaa cataatgggg agttaacatt aaccaataac tccccatttc 202200
tctctcccct cagcccttg tatgattttt tttactagct ctataatttc catagtgtaa 202260
tatagatata acacaattca tgtgctcatt cttaatattt aagattgttt cctattgaag 202320
tcataaataa tgctaatata agcatccttg atcacatgtc cttattaata attttttaa 202380 tttttatttt tagtagagac ggggtttcac cattttgtgc caccacgccc ggctaatttt 202440
tgtattttta gtagagacag ggtttcacca tattggccag gctggtctca aactcctgac 202500
cttgtgatcc acccgcctcg gcttcccaaa gtgctgggat tataggcatg agccaccatg 202560
cccggcccct tattgctaat tttactcttg tatgaaagat ttctgaactt ggaatttctg 202620
gattaaagac cacgtgcata ttgcattttt atagctatta ccaggttgct tccccaaaag 202680
gttacatcat ttatacttcc accagcagtg attgagaatt tctacttcct taccctgtca 202740
tcagcactga atattatcag ttttatttgt gccaacttgg taagtaaaaa atgatatttt 202800
gtttttattt tttgagacag ggtcttgctc tgtcacccag actggagtgc agtggcacaa 202860
tcacggctca ctgcagcctt gaccttcggg ctcaggtgat cctcccacct ccgcctccca 202920
agtagctggg actataggca cacgccacca cacccagcta gtttttgtac ttttagtaga 202980
agtggagttt ctccatgttg cccaggctgg tcttgaactc ctgagctcaa gaaatccacc 203040
accttggcct cccaaagtgc taggattacg gatgtgagcc attgcactca gccttttgtt 203100
gcttttattt cctggaggct gaacatttga atttcctgtc cttcacttct ttttttaatt 203160
gagttgggtt tgtttttcat gtcaatttgt aggagttctt tgtatggtag gaatattaac 203220
ccattgcctt tcatagcatt acaattattt gctcctaatc taggccaaat atttccctta 203280
atctgtagtt tatctctaaa tttcttcatg gtgtctttct ttggatttct tttttagttg 203340
gtcttgacac tcaatttggg aattcatttt ccctgattgg cagcccatgt acaaggatga 203400
agaatataga aaacaggcag ctgtctttgt ttcttaagca gggagacaag aaaagataag 203460
gctcaggctt tagctagcca gaaaagaaaa tagtcttcag ttcagagcaa gaaaaccctt 203520
tattctagaa atgttggatt tgcttagctg atgcattcag gatcctgagc aggaatcctg 203580
ggtaccaact agcttctgaa caggtgcatc agcctctccg acaccctagt cccagcttca 203640
tacttttcct aaacaaaatc aggcccagcc acttccagcc ttgccctgag caccacctgc 203700
aggtcatctt tcttcacagc ctccagtggc tgccgctgct gtgccttttc cctctgctgt 203760
cttgttggtg ttactctttc ctcttcctgg acttggcaga caggctggtc attggagacc 203820
tcaggccacc tggtcattgg agtttcctgt ggtgggaaag gagaatgctg gaggtggtta 203880
ttgcagtggg catgagaaaa ggagcaggaa ggagtgtatg aaagccaaga aagcaaagga 203940
gatgggattg gcagatttcc ctgaagttgg ttccagagta gccagaagag gaggacattt 204000
taaagaaggg tttaggctgc tcttctagaa gaaaactcct gtctcttgct cctatgatcc 204060
aaggtttcag ggattatttt agatcctcca aggactagcc ttttgtttgg ccccatacag 204120
ctgccagacc agaatttttg tgccatggat ttcatgggtt gctagcaagc cttgcctatg 204180
gttcttgtca aagacctgtc actctagtct gccttttttat ttttattttt tattggtttt 204240
tattgagaca gttcgctctg ttgcccaggt tggagtgcac tggtgtgatc ttggctcact 204300
gcaacctcca tttcctgagt tcaagcaatt ctcatgcctc agcctcccaa gtagctggga 204360
ccacaggcat gcaccaccac gcccggctaa tttttgtatt tttagtagag atggggtctc 204420
gctgtattgg ccaggctggt ctcgaactcc tgagctccgg caatctgccc acctcagcct 204480
cccaaaatgc tgggattaca ggcatgagcc accgtgccca gcccataact gcctgtttag 204540
aaaattaact ttgctacttc attcaacctc aggggacaag aactacaaag agatcagtag 204600
agcttaaacc ccattaatgg agtctctctg aatctattct ggttggggga tggaaggagt 204660
gtctgattca aagtaataat ttaaaagaca ccttaacaag agagattact gaaagagagg 204720
aagaaatgga tccccaggag ccttgtgaga tgggaacaag gctactattc acttatctct 204780
gaaatgctac acaacactga gaaggacctg ggtttcctat gtgggccctg gtggcctggg 204840
tagggactgt caggcagggc tatgagatag aggccctgag agtatgggat ttttttgtgc 204900
tgatcgggag aaacgtggag aggtggtgtg ataggaggag ctgggtcacc ccattttatt 204960
atatgtcatg aaactggctt ccttctgcat gacctctaaa gtaactactc ccagtgctga 205020
gtagaaggac actgtaaata ggacaaagaa agtcttgatg tggtgtcgga ggctaatgag 205080
gacagaagaa aaagaggaaa cattcacaat tagtaaaaga cttctggctt atcattgcaa 205140
gagaaatgtt tgggggccag gcacagtggc tcacacctgt aatcccagca ctttgggggt 205200
ccaggcaggc agatcacttg agcccaggag ttcaagacca gcctggacaa tatggggaaa 205260
ccccatgtct ataaaaaata caaaaattct cctggcatgt tagcacacat ctgtagtcct 205320
agctactaag gaggcttagg taggaggatc acttgagccc cagaggtcga ggcagcagtg 205380
agccatgatt gcaccactgc accccagcct gggcgataga gcaagaccct gtctatttaa 205440
aaacaaaaaa agaaaaaaaa aagtttaggt tctcagccat cccctgagct ttaggctcag 205500
gaactctctg atttcaggta ccaagaaaga gaaaatgggc tgggcacagt ggcccaagcc 205560
tgtaatccca gtactttggg aggccaaggt gggtgaatca cctgaggtca ggagtttgtg 205620
accagcctgg ccaacatggt gaaaccccat ctctactaaa aatacaaaaa ttgctgggtg 205680
tggtggcagg cacctgtaat cccagctact caggaggctg aggcaggaga attgcttgaa 205740
cccaggaggc agaggttgca gtgatccgag atcatgccac tggactccat ctggcctgga 205800
tgacagagtg agactctgtc tcaattcaaa agaaagagag agaaaaaata acaacaatct 205860
tataattcct gtgactaaaa ttagggggtg ttcctgcatt acaccatgcc acctctggag 205920
caactttctc tgtcactcac aaagcttttt catatgcctg ccctttcccc ctacttaggc 205980 tccccccttta gaactaaaca gctctggaaa ggatccttca gagcagacct agggcaggag 206040
ctaggcaaga cccttgatgg tgacaactta tttggctatt tctcgtggct atttaataca 206100
tgaatgggag ctgagttccc tgcttaatag catttgtgtt catttccagc gtggtgccgg 206160
ttgtctgacc tctagcttct cccctcttat tctgtacagc tgaaattctc cctcctgcct 206220
accccccagc tagtcagcct ccagtcctgt ttagtttatc ttttttctct cctaatgcct 206280
gttaagctgg aaacaggatt cttgctcgtc gtcatattat tttaaataag aatgaaacta 206340
aagaagaggt ctttgggcca ggcatggtag ctcacacctg taatcccagc actttgggag 206400
gccgaggctg gcagatacct gaggtcggga gttcgagacc agcctgacca acatggagaa 206460
accctgtctc tactaaaaat acaaaattag ccaggcgtgg cggcgcatgc ctgtaatccc 206520
agctactcgg gaagcctcag gcaggagaat cgcttgaacc taggagacgg aggttgcagt 206580
gagccaggat ctcaccatag cactccagcc tgccaacaag agcgaaactc catctccaaa 206640
aaaaaaaaaa aagtcttcaa tctgctgtaa tgtggcactc agatatgagt attggcggca 206700
gtgagtgttc atttcctcct cctgctcccc taattcagtt gcgcctgaac acaaaactcc 206760
aaaagcaacc agagagagaa gctgtgttga aagatgaaag gagaaaaggc cacaagcttt 206820
ggccctacct ggttcttgtt ctgagtcaaa aactcttgtt tccaggcccc tcgtctatga 206880
aattagtaga tttatactag tgattcccag agtatggtcc cctgctcggt ggtgtttaac 206940
ttcaactggg gtcttgttag aaacacaaat tctcaggccc cactctgggc atacaaaatc 207000
aaaactttgt ggtatgggtc cagcaattga gaaccacagt tttacccagt ggattttgtg 207060
ttgaggagct cattaaaacc agttatgggg ccgggtgcag tggctcacat ctgtaatccc 207120
agcactttgg gaggccgagg caggtggatc acctgaggtc aggagttcaa gaccagccta 207180
gccaacatgg caaaacccca tctctactaa aagtacaaaa aaaattagct gggcatggtg 207240
gtgggcgcct gtaatgccag ctactcggga ggctaaggca ggaaaatcgc ttgaacccaa 207300
gaggcggagg ttgcagtaag ctgagatcac gtcattgcac tccagcctgg gccacaaagt 207360
gagactctgt ctcaaaaaaa aaaaaaaaaa atcagttgtg ggcaaaaatt ctcaggtagc 207420
tcaaggagcc acgggttagg gaactgaaga ggaaaaactg tctctcaaag ctagacaggc 207480
tgccttacct tttatctctc tcctctccac atcacttaat ctttcctttt tcgctggagc 207540
agatcccacc catgagggca cagcagaggg catggagaac atggcagatg ctgtcaccca 207600
tgctcgtttt gtgggcacgg atcctgccag tgatgaagtt gtcctgatga aaatccttca 207660
ggtaagcgag agggaaatag caattaggct aatggccagg ggctggtgcc gcagactcta 207720
cttactctgc ccacagcatg aaactgtgtt ttgactccac tggggcttag gggagctact 207780
ttgtttccag acaagcagct ggggtaccca aagtaaaagc tttttctaag gaaaatcagt 207840
aaaagcttta tatgaagtga tgtcaaatac cagaagcctt aaatacactt gtacctctgg 207900
ccgactgtat ttgtgccgtc catctcttgg gctcatgggc tagggctaga atcagttctg 207960
aaatatgtca gggtcataaa aagtgaagaa acaattccaa ggacaagctt cttggagacc 208020
tctctaccaa gctgaggtga ggtcagcatt cttgctaacc cctctctctt acccttgagt 208080
acctctcagt accttgttta tcacagtaat tcctttttct tcctgatagg ttctacggac 208140
tctgctgcta accccagtgg gtgcccacct aaccaatgaa tctgtgtgtg agattatgca 208200
gtcttgcttc cggatctgct ttgaaatgag gctcagtggt aggtgcttgg atattagccc 208260
cttcaccatt cctggggcca gtgtctgagt atgaatacag gaggctgtct tcccagagag 208320
atggaaaatt caggacttct ccatcatcta tctcatgcga tcataggggt ctagaagaaa 208380
tgtctgtact tggctattgt gaagctagaa tagagacctc agcccattat gccagggcag 208440
gagttgggat ggatcccaga ttgacttagc ccaggcacca aatcaccctc tcttggggtt 208500
tctgggattg acaccaacct gcaacccccct agaacacatc tatacctccc cttttttccc 208560
tgactcagta gtgccaccta gtgggccagt gaagttctgg ctgccaggct gagctggagc 208620
tggttttaat aagtttggca taatccttgg taaacaaggt ttggagggga gtctgctctg 208680
agaaccctct tgataatagc acagcaagta atgacacctg tgttatttgt ttttgcctgt 208740
gcagagttat tgagaaaatc cgcagagcac actctcgtag acatggtgca gctgctcttc 208800
acaaggtaaa cctgctgctg tttgcttcag cccggctgcc caggcctctt gagtctgcct 208860
gcttccacac agccacgtca gggacctggc caaccccaca gccgcatcag aggccactgg 208920
gattatggat ggggggtagt tctctgggcc cagggttact gagcaaggga gaaggaggag 208980
ggagctgatt tggcctcacg gggaggcaga gggttattta atataggcca gcagacctca 209040
ttctgcttcc caaatttgtg tctgtttctg tgcaggtagc agctgggaaa gggaacccag 209100
agaggaagcc aaactcaagg gatcatgatt tctgtgggag agggccaaaa ttagggtgac 209160
tagcaattgt gaattgcctg ggactgtcct gatttcagca ctaaaagttc tgcatcctgg 209220
caaacccccc tcagtcccag gcaaaccaag atggttggtt accctttggt aaggccctta 209280
gcctagggcc taggaggcct tttcatacta ggcctgtttc ctgcacctcc tttcaacaga 209340
ctcacagaag agctgaggca atggctttaa accttcctct gggatttctt tttgctctca 209400
aatctataga taataatcct tattatctac agactagact gcccttggat cctgctgcaa 209460
agaatttttt gctcctcagg ctcaaattta ctggtttcaa aacttcaacc tgcctgttaa 209520
ttcttctctt ttgcccactc tcctagggtt ttgatagact gccctccccc catctcttgg 209580
cagcagtatt tgccaagtaa atataagcag gaaggaatca gtctcaggat aaaaagagcc 209640
tccacactcc aagggcactt accttgctct cacaactacc tccttttgtc catgtcacac 209700
atcccccgat tcctgtggct ctttgatgaa gctctgaaaa ggatgaaatt agtctgcttc 209760
tcttttgtag ccttttctaa gacacagggc atgctctggc tcagagcacc tttggtttgt 209820
ggctggcatg gagggagaca tttgtcatta tccctaatga cagttgatgg attttctatc 209880
ttataggtta cctcagttta aagaagaacc caagaactat gtggggacca acatgaagaa 209940
ggtatgatct gagagctgat ctgctgtccc tcatccaaac cttaatctcc caacttcagt 210000
gccttggggt aaccttgctt agcaaagata tgcttttgcc taaacaggtc tgcttggaat 210060
ctagaagtag ctctcactcc tttcgtgaga aatgtattct cttccagata tatcccttcc 210120
tcagcttttc tgctctggcc tatctttgaa ccaccatgta agctggtgag ccagttcttc 210180
atggaaactg catggtaccc atcagtcttg gctaaaaatg tctgttgaca aagatgaaag 210240
tcctgccatc ccctcaagac ttagccttat ccgcaggtag aaggcctaga gaggctatgt 210300
cccaaatcct acctcaatgc tgaattagac tgggctcttg cttgtgctag tctgtattga 210360
agagattagt caagttaaga accaaagggt tcttaaactg ctaggagaag aatagtggtc 210420
aaaagaatgg cttctttcta tcttgaactg aagccctgga cttcacgggc ctctgatgag 210480
gattccgctt gcagccctaa gagggtctac ctatggagat gacccttagc tgtgtgatgc 210540
atgcacctga ccttctcctc tcccctgtca tccatcccca ttcctgccct gttccctgtt 210600
ggtatgtgtc tgagtttatt tcactgttaa atcgtgcgtt tgcctgtctt tcgcagatat 210660
ctccatgtct cctcaacaaa ctggagctaa gtagtgggga gcagaccaaa gccctgaacc 210720

-continued

```
agttagagag ggtactactc tttaagaacc tcaaggtctc tctccctctc tttcccttcc 210780

ccttttttatt tctttcaatg tttatttttt atatataaca cctgggtccc atttccattg 210840

tgtagagcac aacttactcc tccctagtaa cacagcacgg ctttggaaga gttgcacgtg 210900

attgtagctt tgcagtg                                                210917


<210> SEQ ID NO 12
<211> LENGTH: 21
<212> TYPE: DNA
<213> ORGANISM: Artificial sequence
<220> FEATURE:
<223> OTHER INFORMATION: Synthetic Construct

<400> SEQUENCE: 12

gctgctaaat gctgctcaga a                                          21
```